(12) United States Patent
Bennett et al.

US007960355B2

(10) Patent No.: US 7,960,355 B2
(45) Date of Patent: Jun. 14, 2011

(54) COMPOSITIONS AND METHODS FOR THE MODULATION OF THE EXPRESSION OF B7 PROTEIN

(75) Inventors: C. Frank Bennett, Carlsbad, CA (US); Susan M. Freier, San Diego, CA (US)

(73) Assignee: Isis Pharmaceuticals, Inc., Carlsbad, CA (US)

( * ) Notice: Subject to any disclaimer, the term of this patent is extended or adjusted under 35 U.S.C. 154(b) by 471 days.

(21) Appl. No.: 10/558,216

(22) PCT Filed: May 19, 2004

(86) PCT No.: PCT/US2004/015880
§ 371 (c)(1),
(2), (4) Date: May 18, 2006

(87) PCT Pub. No.: WO2005/000202
PCT Pub. Date: Jan. 6, 2005

(65) Prior Publication Data
US 2007/0135364 A1    Jun. 14, 2007

Related U.S. Application Data

(60) Provisional application No. 60/510,614, filed on Oct. 10, 2003, provisional application No. 60/520,401, filed on Nov. 13, 2003, provisional application No. 60/537,291, filed on Jan. 16, 2004.

(51) Int. Cl.
*C07H 21/04* (2006.01)
*C07H 21/02* (2006.01)
*C12N 15/11* (2006.01)

(52) U.S. Cl. .................. 514/44 A; 536/23.1; 536/24.3; 536/24.31; 536/24.5

(58) Field of Classification Search .......... None
See application file for complete search history.

(56) References Cited

U.S. PATENT DOCUMENTS

| | | |
|---|---|---|
| 4,689,320 A | 8/1987 | Kaji |
| 4,806,463 A | 2/1989 | Goodchild et al. |
| 5,004,810 A | 4/1991 | Draper |
| 5,034,506 A | 7/1991 | Summerton et al. |
| 5,087,617 A | 2/1992 | Smith |
| 5,098,890 A | 3/1992 | Gewirtz et al. |
| 5,135,917 A | 8/1992 | Burch |
| 5,138,045 A | 8/1992 | Cook et al. |
| 5,166,195 A | 11/1992 | Ecker |
| 5,194,428 A | 3/1993 | Agrawal et al. |
| 5,218,105 A | 6/1993 | Cook et al. |
| 5,242,906 A | 9/1993 | Pagano et al. |
| 5,264,423 A | 11/1993 | Cohen et al. |
| 5,276,019 A | 1/1994 | Cohen et al. |
| 5,286,717 A | 2/1994 | Cohen et al. |
| 5,434,131 A | 7/1995 | Linsley et al. |
| 5,459,255 A | 10/1995 | Cook et al. |
| 5,512,438 A | 4/1996 | Ecker |
| 5,514,788 A | 5/1996 | Bennett et al. |
| 5,539,082 A | 7/1996 | Nielsen et al. |
| 5,667,998 A | 9/1997 | Dougherty et al. |
| 5,801,154 A | 9/1998 | Baracchini et al. |
| 5,877,021 A | 3/1999 | Stinchcomb et al. |
| 5,883,082 A | 3/1999 | Bennett et al. |
| 5,942,607 A | 8/1999 | Freeman et al. |
| 5,998,148 A | 12/1999 | Bennett et al. |
| 6,077,833 A | 6/2000 | Bennett et al. |
| 6,319,906 B1 * | 11/2001 | Bennett et al. .................. 514/44 |
| 6,582,908 B2 | 6/2003 | Fodor et al. |
| 7,115,580 B1 * | 10/2006 | Bennett et al. .............. 514/44 A |
| 2001/0053519 A1 | 12/2001 | Fodor et al. |
| 2003/0228597 A1 | 12/2003 | Cowsert et al. |

FOREIGN PATENT DOCUMENTS

| | | |
|---|---|---|
| EP | 0 643 077 A1 | 9/1993 |
| EP | 0 600 591 B1 | 5/2003 |
| WO | WO 92/20823 | 11/1992 |
| WO | WO 93/24134 | 12/1993 |
| WO | WO 94/17773 | 8/1994 |
| WO | WO 95/03408 | 2/1995 |
| WO | WO 95/05464 | 2/1995 |
| WO | WO 95/06738 | 3/1995 |
| WO | WO 95/07358 | 3/1995 |
| WO | WO 95/22619 | 8/1995 |
| WO | WO 95/32734 | 12/1995 |
| WO | WO 95/34320 | 12/1995 |
| WO | WO 96/11279 | 4/1996 |
| WO | WO 96/15780 | 5/1996 |
| WO | WO 96/18736 | 6/1996 |
| WO | WO 99/01579 | 1/1999 |
| WO | WO 00/74687 | 12/2000 |
| WO | WO 00/074687 | 12/2000 |
| WO | WO 0074687 A1 * | 12/2000 |
| WO | WO0074687 A2 * | 12/2000 |
| WO | WO 03/083089 | 10/2003 |

OTHER PUBLICATIONS

Vester et al. Biochemistry, 2004, 43 (42), 13233-13241.*
Kurreck et al. (Nucleic Acids Research, 2002, vol. 30, No. 9, pp. 1911-1918).*
Alberts, B. et al., *Molecular Biology of the Cell* (1983) Garland Publishing, Inc., New York, pp. 411-415.
Allison, J. P., "CD28-B7 interactions in T-cell activation," *Curr. Opin. Immunol.* (1994) 6:414-419.
Allison, J. P. et al., "The Yin and Yang of T Cell Costimulation," *Science* (1995) 270:932-3.
Azuma, M. et al., "B70 antigen is a second ligand for CTLA-4 and CD28," *Nature* (1993) 366:76-79.
Berkow et al., eds., *The Merck Manual of Diagnosis and Therapy* (1987) 15th Ed., Rahway, NJ, pp. 302-336 and 2516-2522.
Borriello F. et al., "Characterization of the Murine B7-1 Genomic Locus Reveals an Additional Exon Encoding an Alternative Cytoplasmic Domain and a Chromosomal Location of Chromosome 16, Band B5," *J. Immunol.* (1994) 153:5038-5048.
Borriello, F. et al., "Differential Expression of Alternate mB7-2 Transcripts," *J. Immunol.* (1995) 155:5490-5497.
Brigstock, D. R. et al., "Species-Specific High Molecular Weight Forms of Basic Fibroblast Growth Factor," *Growth Factors* (1990) 4:45-52.

(Continued)

*Primary Examiner* — Janet L Epps-Smith
(74) *Attorney, Agent, or Firm* — Knobbe, Martens, Olson & Bear, LLP

(57) ABSTRACT

Antisense oligonucleotide compositions which specifically hybridize with nucleic acids encoding B7 proteins, and use of these compositions for inhibiting expression of B7 mRNA.

15 Claims, 28 Drawing Sheets

OTHER PUBLICATIONS

Charachon, G. et al., "Phosphorothioate Analogues of (2'-5')(A)$_4$: Agonist and Antagonist Activities in Intact Cells," *Biochem.* (1990) 29(10):2550-2556.

Chen, C. et al., "Monoclonal Antibody 2D10 Recognizes a Novel T Cell Costimulatory Molecule on Activated Murine B Lymphocytes," *J. Immunol.* (1994) 152:2105-2114.

Chen, C. et al., "Molecular Cloning and Expression of Early T Cell Costimulatory Molecule-1 and Its Characterization as B7-2 Molecule," *J. Immunol.* (1994) 152:4929-4936.

Cook, P. D., "Medicinal Chemistry Strategies for Antisense Research," *Antisense Research and Applications* (1993) CRC Press, Boca Raton, pp. 171-172.

Crooke, S. T. et al., "Pharmacokinetic Properties of Several Novel Oligonucleotide Analogs in mice,"*J. Pharmacol. Exp. Ther.* (1996) 277(2):923-937.

De Virgilio, C. et al., "Cloning and Disruption of a Gene Required for Growth on Acetate but not on Ethanol: the Acetyl-Coenzyme A Synthetase Gene of *Saccharomyces cerevisiae*,"*Yeast* (1992) 8:1043-1051.

Dulbecco, R. et al., "Plaque Production by the Polyoma Virus," *Virol.* (1959) 8:396-397.

Freeman, G. J. et al. "B7, A New Member of the Ig Superfamily with Unique Expression on Activated and Neoplastic B Cells," *J. Immunol.* (1989) 143(8):2714-2722.

Freeman, G. J. et al., "Structure, Expression, and T Cell Costimulatory Activity of the Murine Homologue of the Human B Lymphocyte Activation Antigen B7,"*J. Exp. Med.* (1991) 174:625-631.

Freeman, G. J. et al., "Cloning of B7-2: A CTLA-4 Counter-Receptor That Costimulates Human T Cell Proliferation," *Science* (1993) 262:909-911.

French, T. J. et al., "Expression of Two Related Nonstructural Proteins of Bluetongue Virus (BTV) Type 10 in Insect Cells by a Recombinant Baculovrus: Production of Polyclonal Ascitic Fluid and Characterization of the Gene Product in BTV-Infected BHK Cells," *J. Virol.* (1989) 63(8):3270-3278.

Gao, J. et al., "Cloning and Characterization of a Mouse Gene with Homology to the Human von Hippel-Lindau Disease Tumor Suppressor Gene: Implications for the Potential Organization of the Human von Hippel-Lindau Diesease Gene," *Cancer Res.* (1995) 55:743-747.

Gebeyehu, G. et al., "Novel biotinylated nucleotide—analogs for labeling and colorimetric detection of DNA," *Nucleic Acids Res.* (1987) 15(11):4513-4534.

Gelbert, L. M. et al., "Analysis of GPT Activity in Mammalian Cells with a Chromosomally Integrated Shuttle Vector Containing Altered *gpt* Genes," *Somat. Cell. Mol. Genet.* (1990) 16(2):173-184.

Gold, L. et al., "Translation Initiation," *Escherichia coli and Salmonella typhimuium: Cellular and Molecular Biology* (1987) 2:1302-1307.

Hakim, F. T. et al., "Acute Graft-Versus-Host Reaction Can Be Aborted by Blockade of Costimulatory Molcules,"*J. Immunol.* (1995) 155:1757-1766.

Harlan, D. M. et al., "Mice expression both B7-1 and viral glycoprotein on pancreatic beta cells along with glycoprotein-specific transgenic T cells develop diabetes due to a breakdown of T-lymphocyte unresponsiveness," *Proc. Natl. Acad. Sci. USA* (1994) 91:3137-3141.

Hathcock, K. S. et al., "Identification of an Alternative CTLA-4 Ligand Costimulatory for T Cell Activation," *Science* (1993) 262:905-907.

Inobe, M. et al., "The Role of the B7-1a Molecule, an Altneratively Spliced Form of Murine B7-1 (CD80), on T Cell Activation," *J Immunol.* (1996) 157:582-588.

Jellis, C. L. et al., "Genomic organization of the gene coding for the costimulatory human B-lymphocyte antigen B7-2 (CD86)," *Immunogenet.* (1995) 42:85-89.

June, C. H. et al., "The B7 and CD28 receptor families," *Immunol. Today* (1994) 15(7):321-331.

Kabanov, A. V. et al., "A new class of antivirals: antisense oligonucleotides combined with a hydrophobic substituent effectively inhibit influenza virus reproduction and synthesis of virus-specific proteins in MDCK cells," *FEBS Lett.* (1990) 259(2):327-330.

Kanagasundaram, V. et al., "Isolation of characterization of the gene encoding gluconolactonase from *Zymomonas mobilis*," *Biochint. Biophs. Acta* (1992) 1171:198-200.

Kornberg, A., *DNA Replication* (1974) W. H. Freeman & Co., San Francisco, pp. 75-77.

Lenschow, D. J. et al., "Long-Term Survival of Xenogenic Pancreatic Islet Grafts Induced by CTLA4Ig," *Science* (1992) 257:789-792.

Lenschow, D. J. et al., "T cell co-stimulation and in vivo tolerance," *Curr. Opin. Immunol.* (1993) 5:747-752.

Lenschow, D. J. et al., "Expression and functional significance of an additional ligand for CTLA-4," *Proc. Natl. Acad. Sci. USA* (1993) 90:11054-11058.

Letsinger, R. L. et al., "Cholesteryl-conjugated oligonucleotides: Synthesis, properties, and activity as inhibitors of replication of human immunodeficiency virus in cell culture," *Proc. Natl. Acad. Sci. USA* (1989) 86:6553-6556.

Levine, B. L. et al., "Antiviral Effect and Ex Vivo CD4+ T Cell Proliferation in HIV-Positive Patients as a Result of CD28 Costimulation," *Science* (1996) 272:1939-1943.

Lin, H. et al., "Long-Term Acceptance of Major Histocompatibility Complex Mismatched Cardiac Allografts Induced by CTLA4Ig Plus Donor-specific Transfusion," *J. Exp. Med.* (1993) 178:1801-1806.

Linsley, P. S. et al., "CTLA-4 Is a Second Receptor for the B Cell Activation Antigen B7,"*J. Exp. Med.* (1991) 174:561-569.

Linsley, P. S. et al., "Immunosuppression in Vivo by a Soluble Form of the CTLA-4 T Cell Activation Molecule," *Science* (1992) 257:792-795.

Linsley, P. S. et al., "The Role of the CD28 Receptor During T Cell Responses to Antigen," *Annu. Rev. Immunol.* (1993) 11:191-212.

Liu, Y. et al., "Costimulation of T-cell growth," *Curr. Opin. Immunol.* (1992) 4:265-270.

Manoharan, M. et al., "Chemical Modifications to Improve Uptake and Bioavailability of Antisense Oligonucleotides," *Ann. N.Y. Acad. Sci.* (1992) 660:306-309.

Manoharan, M. et al., "Introduction of a Lipophilic Thioether Tether in the Minor Groove of Nucleic Acids for Antisense Applications," *Bioorg. Med. Chem. Lett.* (1993) 3(12):2765-2770.

Manoharan, M. et al., "Cholic Acid-Oligonucleotide Conjugates for Antisense Applications," *Bioorg. Med. Chem. Lett.* (1994) 4(8):1053-1060.

Manoharan, M. et al., "Oligonucleotide Conjugates: Alteration of the Pharmacokinetic Properties of Antisense Agents," *Nucleosides Nucleotides* (1995) 14(3-5):969-973.

Manoharan, M. et al., "Lipidic Nucleic Acids," *Tetrahedron Lett.* (1995): 36(21):3651-3654.

Markussen, F.-H. et al., "Translational control of *oskar* generates Short OSK, the isoform that induces pole plasm assembly," *Development* (1995) 12:3723-3732.

Martin, P. et al., "Ein neuer Zugang zu 2'-O-Alkylribonucleosiden and Eigenschaften deren Oligonucleotide," *Helv. Chim. Acta* (1995) 78:486-504.

McDermott, J. B. et al., "Structure and lens expression of the gene encoding chicken βA3/A1-crystallin," *Gene* (1992) 117:193-200.

Mishra, R. K. et al., "Improved leishmanicidal effect of phosphorothioate antisense oligonucleotides by LDL-mediated delivery," *Biochim. Biophys. Acta* (1995) 1264:229-237.

Monaco, L. et al., "Structure of Two Rat Genes Coding for Closely Related Rolipram-sensitive cAMP Phosphodiesterases,"*J Biol. Chem.* (1994) 269(1):347-357.

Moore, G. E. et al., "Cell Line Derived from Patient with Myeloma," *N. Y. State J. Med.* (1968) Aug. 1: 2054-2060.

Nabavi, N. et al., "Signalling through the MHC class II cytoplasmic domain is required for antigen presentation and induces B7 expression," *Nature* (1992) 360:266-268.

Nielsen, P. E. et al., "Sequence-Selective Recognition of DNA by Strand Displacement with a Thymine-Substituted Polyamide," *Science* (1991) 254:1497-1500.

Oberhauser, B. et al., "Effective incorporation of 2'-O-methyl-oligoribonucleotides into liposomes and enhanced cell association through modification with thiocholesterol," *Nucleic Acids Res.* (1992) 20(3):533-538.

Olsen, S. R. et al., "Inhibition of Protein Kinase-A by Overexpression of the Cloned Human Protein Kinase Inhibitor," *Mol. Endocrinol.* (1991) 5:1246-1256.

Perri, S. et al., "Interactions of Plasmid-encoded Replication Initiation Proteins with the Origin of DNA Replication in the Broad Host Range Plasmid RK2," *J. Biol. Chem.* (1991) 266(19):12536-12543.

Pushpa-Rekha, T. R. et al., "Rat Phospholipid-hydroperoxide Glutathione Peroxidase," *J. Biol. Chem.* (1995) 270(45):26993-26999.

Reiser, H. et al., "Murine B7 antigen provides an efficient costimulatory signal for activation of murine T lymphocytes via the T-cell receptor/CD3 complex," *Proc. Natl. Acad. Sci. USA* (1992) 89:271-275.

Rogers, R. P. et al., "Alternative splicing dictates translational start in Epstein-Barr virus transcripts," *EMBO J.* (1990) 9(7):2273-2277.

Romani, N. et al., "Proliferating Dendritic Cell Progenitors in Human Blood," *J. Exp. Med.* (1994) 180:83-93.

Saison-Behmoaras, T. et al., "Short modified antisense oligonucleotides directed against Ha-*ras* point mutation induce selective cleavage of the mRNA and inhibit T24 cells proliferation," *EMBO J.* (1991) 10(5):1111-1118.

Sambrook, J. et al., *Molecular Cloning. A Laboratory Manual* (1989) Cold Spring Harbor Laboratory Press, vol. 2, pp. 10.59-10.61.

Sambrook, J. et al., *Molecular Cloning. A Laboratory Manual* (1989) Cold Spring Harbor Laboratory Press, vol. 2, pp. 11.31-11.32.

Saul, D. J. et al., "*celB*, a Gene Coding for a Bifunctional Cellulase from the Extreme Theromphile "*Caldocellum saccharolyticum*"," *Appl. Environ. Microbiol.* (1990) 56(10):3117-3124.

Sawai, H. et al., "Synthesis and Properties of Some New 2-5A Analogues," *Chemica Scripta* (1986) 26:169-172.

Shea, R. G. et al., "Synthesis, hybridization properties and antiviral activity of lipid-oligodeoxynucleotide conjugates," *Nucleic Acids Res.* (1990) 18(13):3777-3783.

Smith, J. D. et al., "The Nucleic Acid of Polyoma Virus," *Virol.* (1960) 12:185-196.

Stepkowski, S. M. et al., "Blocking of Heart Allograft Rejection by Intercellular Adhesion Molecule-1 Antisense Oligonucleotides Alone or in Combination with Other Immunosuppressive Modalities," *J. Immunol.* (1994) 153:5336-5346.

Svinarchuk, F. P. et al., "Inhibition of HIV proliferation in MT-4 cells by antisense oligonucleotide conjugated to lipophilic groups," *Biochimie* (1993) 75:49-54.

Wu, Y. et al., "A Major Costimulatory Molecule on Antigen-presenting Cells, CTLA4 Ligand A, Is Distinct from B7,"*J. Exp. Med.* (1993): 178:1789-1793.

Yang, Y. et al., "CD40 Ligand-Dependent T Cell Activation: Requirement of B7-CD28 Signaling Through CD40," *Science* (1996) 273:1862-1864.

Yaoita, Y. et al., "*Xenopus laevis* α and β thyroid hormone receptors," *Proc. Natl. Acad. Sci. USA* (1990) 87:7090-7094.

Brand et al., "Transdermal delivery of antisense compounds" Advanced Drug Delivery Review (2000) 44:51-57.

Database WPI, Section Ch, Week 199804, XP002230059, Derwent Publications Ltd. (1997).

European Search Report for Application #97953268.6 dated Dec. 10, 2001.

European Search Report for Application #00939350.5 dated Mar. 13, 2003.

European Search Report for Application #04752823.7 dated Apr. 17, 2008.

International Search Report for Application # PCT/US97/23270 dated Mar. 26, 1998.

International Search Report for Application # PCT/US00/14471 dated Aug. 14, 2000.

International Search Report for Application # PCT/US2004/015880 dated Nov. 22, 2005.

Lenschow et al., "CD28/B7 System of T-Cell Costimulation" Annual Review of Immunology (1996) 14:233-258.

Liang et al., "Phenotype and allostimulatory function of dendritic cells treated with antisense oligodeoxyribonucleotides targeting CD80 or CD86 mRNA" Transplantation Proceedings (2001) 33:235.

Liang et al., "Administration of dendritic cells transduced with antisense oligodeoxyribonucleotides targeting CD80 or CD86 prolongs allograft survival." Transplantation (2003) 76:721-729.

Ly et al., "Expression of insulin-like growth factor-I in rat glioma cells is associated with change in both immunogenicity and apoptosis" Neuroscience Letters (2000) 281:13-16.

Qian et al., "Administration of antisense oligodeoxyribonucleotides against mRNA of CD80 or CD86 prolongs survival of cardiac allografts by inhibition of CTL activity" Transplantation Proceedings (2001) 33:235.

Revision History for GenBank Accession No. M27533.

Revision History for GenBank Accession No. L25259.

Branch et al., "A good antisense molecule is hard to find," TIBS (1998) 23:45-50.

Chin "On the Preparation and Utilization of Isolated and Purified Oligonucleotides" Document purportedly located on a CD-ROM and contributed to the public collection of the Katherine R. Everett Law Library of the University of North Carolina on Mar. 14, 2002.

Crooke et al., "Basic Principles of Antisense Therapeutics" Antisense Research and Application (1998) Chapter 1:1-50.

New England Biolabs 1998/99 Catalog (cover page and pp. 121 and 284).

Reynolds et al., "Rational siRNA design for RNA interference" Nature Biotechnology (2004) 22(3):326-330.

Sanghvi et al., "Heterocyclic Base Modifications in Nucleic Acids and Their Applications in Antisense Oligonucleotides" Antisense Research and Applications (1993) pp. 273-288.

Bennett et al., "Antisense oligonucleotides as a tool for gene functionalization and target validation" Biochimica et Biophysica Acta (1999) 1489:19-30.

Gewirtz et al., "Facilitating oligonucleotide delivery: Helping antisense deliver on its promise" Proc. Natl. Acad. Sci. USA (1996) 3161:3163.

Monia et al., "Antitumor activity of a phosphorothioate antisense oligodeoxyribonucleotide targeted against c-raf kinase" Nature Medicine (1996) 2:668-675.

\* cited by examiner

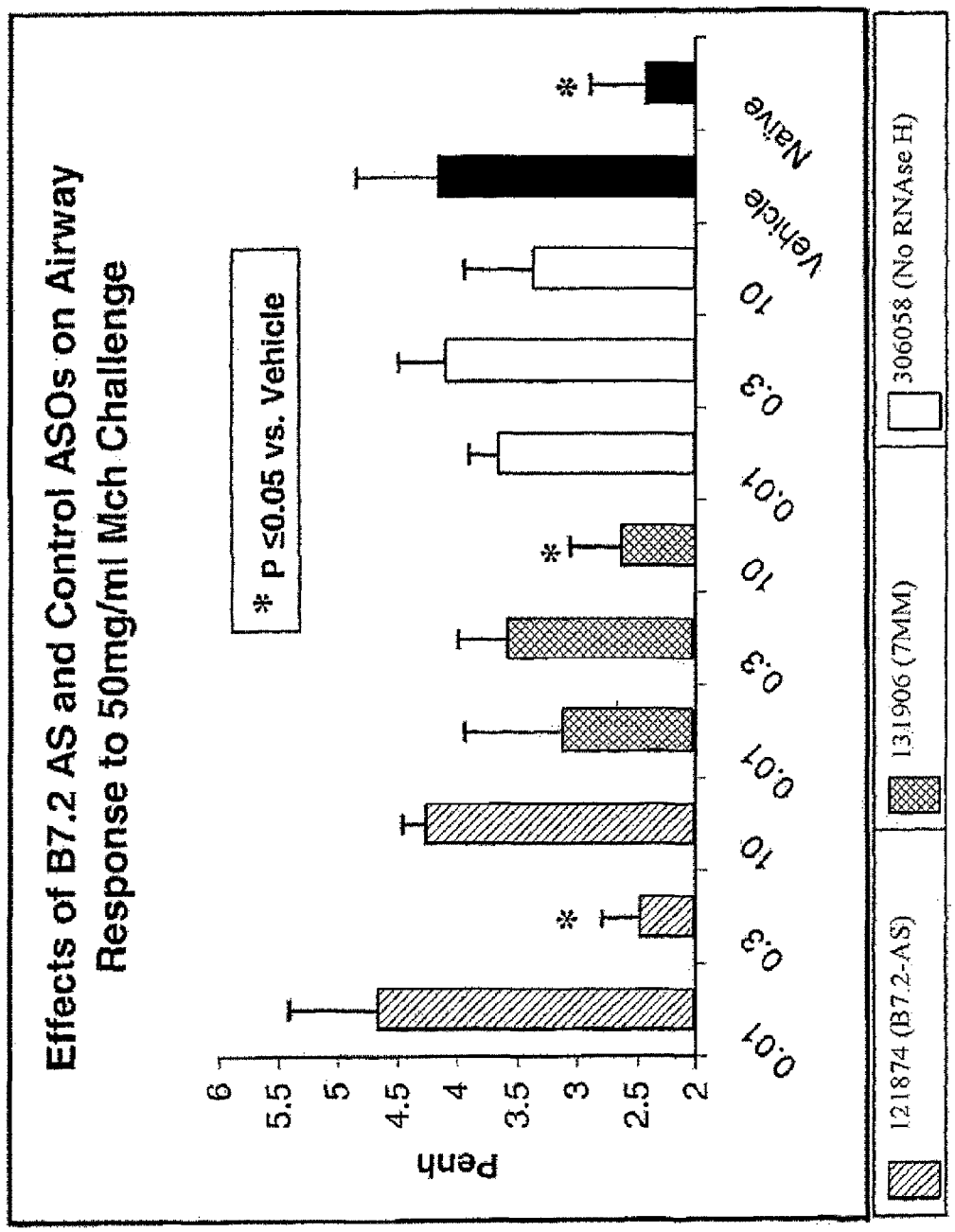

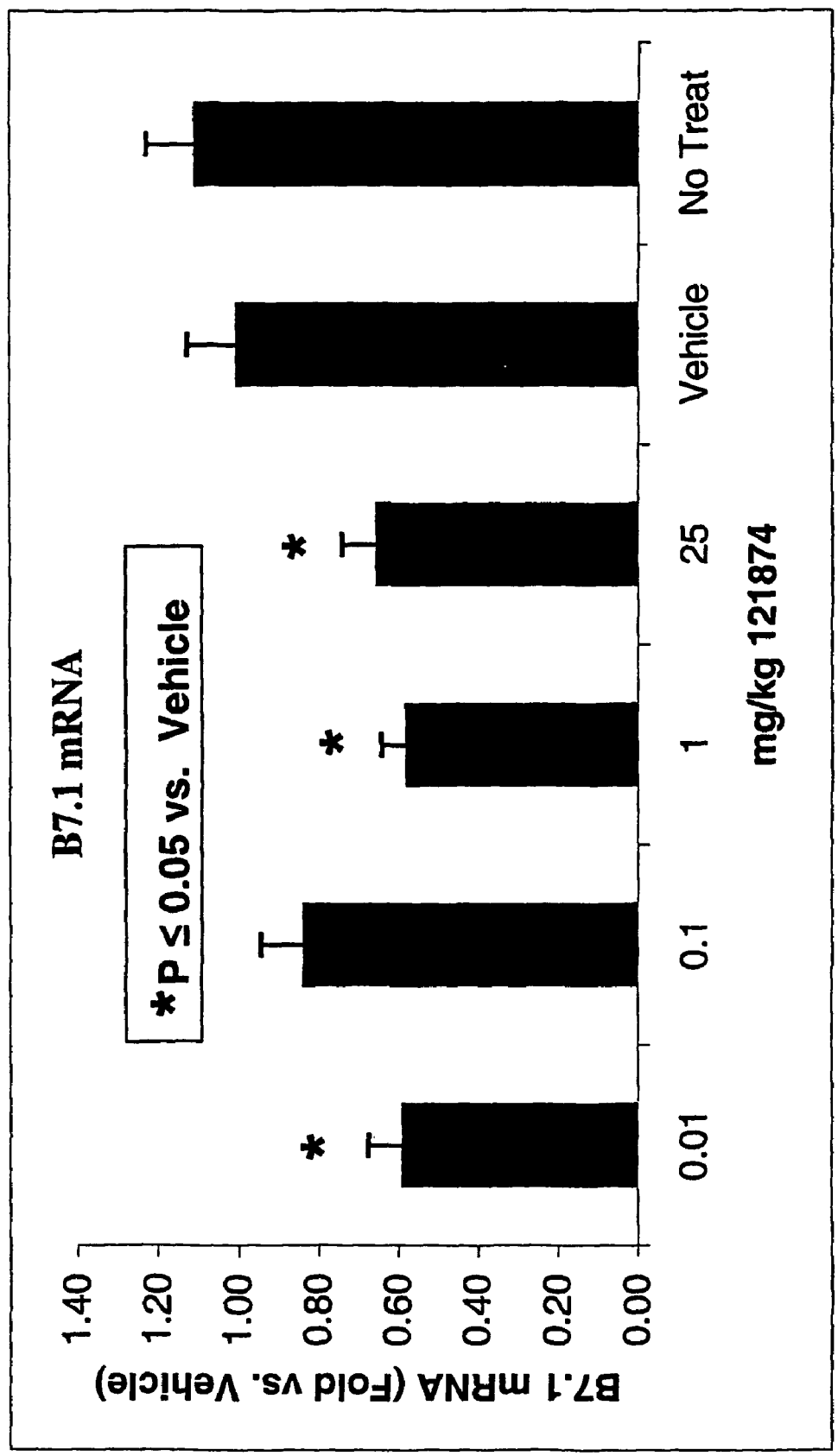

Treatment with ISIS 121844 Reduces the Levels of B7.1 and B7.2 mRNA in Mouse Lung

Figure 23

Aerosol #8: Effects of Aerosolized B7.2 (ISIS 121874) and 7bpMM (ISIS 131906) on Eosinophil Recruitment in an OVA Model of Asthma  N = 7/Group

*P ≤ 0.05 vs. Vehicle

COMPOSITIONS AND METHODS FOR THE MODULATION OF THE EXPRESSION OF B7 PROTEIN

RELATED APPLICATIONS

This application is a U.S. National Phase application of PCT/US2004/015880 filed on May 19, 2004 which claims priority to four U.S. patent applications: Ser. No. 60/651,504, filed May 23, 2003; Ser. No. 60/510,614 filed, Oct. 10, 2003; Ser. No. 60/520,401, filed Nov. 13, 2003; and Ser. No. 60/537, 291, filed Jan. 16, 2004, all of which are incorporated herein by reference in their entirety.

SEQUENCE LISTING

A sequence listing is filed herewith in accordance with CFR 1.821 and is hereby incorporated by reference.

FIELD OF THE INVENTION

This invention relates to diagnostics, research reagents and therapeutics for disease states which respond to modulation of T cell activation. In particular, this invention relates to antisense oligonucleotide interactions with certain messenger ribonucleic acids (mRNAs) or DNAs involved in the synthesis of proteins that modulate T cell activation. Antisense oligonucleotides designed to hybridize to nucleic acids encoding B7 proteins are provided. These oligonucleotides have been found to lead to the modulation of the activity of the RNA or DNA, and thus to the modulation of T cell activation. Palliative, therapeutic and prophylactic effects result.

BACKGROUND OF THE INVENTION

Inflammation is a localized protective response mounted by tissues in response to injury, infection, or tissue destruction resulting in the destruction of the infectious or injurious agent and isolation of the injured tissue. A typical inflammatory response proceeds as follows: recognition of an antigen as foreign or recognition of tissue damage, synthesis and release of soluble inflammatory mediators, recruitment of inflammatory cells to the site of infection or tissue damage, destruction and removal of the invading organism or damaged tissue, and deactivation of the system once the invading organism or damage has been resolved. In many human diseases with an inflammatory component, the normal, homeostatic mechanisms which attenuate the inflammatory responses are defective, resulting in damage and destruction of normal tissue.

Cell-cell interactions are involved in the activation of the immune response at each of the stages described above. One of the earliest detectable events in a normal inflammatory response is adhesion of leukocytes to the vascular endothelium, followed by migration of leukocytes out of the vasculature to the site of infection or injury. In general, the first inflammatory cells to appear at the site of inflammation are neutrophils, followed by monocytes and lymphocytes. Cell-cell interactions are also critical for activation of both B-lymphocytes (B cells) and T-lymphocytes (T cells) with resulting enhanced humoral and cellular immune responses, respectively.

The hallmark of the immune system is its ability to distinguish between self (host) and nonself (foreign invaders). This remarkable specificity exhibited by the immune system is mediated primarily by T cells. T cells participate in the host's defense against infection but also mediate organ damage of transplanted tissues and contribute to cell attack in graft-versus-host disease (GVHD) and some autoimmune diseases. In order to induce an antigen-specific immune response, a T cell must receive signals delivered by an antigen-presenting cell (APC). T cell-APC interactions can be divided into three stages: cellular adhesion, T cell receptor (TCR) recognition, and costimulation. At least two discrete signals are required from an APC for induction of T cell activation. The first signal is antigen-specific and is provided when the TCR interacts with an antigen in the context of a major histocompatibility complex (MHC) protein, or an MHC-related CD1 protein, expressed on the surface of an APC ("CD," standing for "cluster of differentiation," is a term used to denote different T cell surface molecules). The second (costimulatory) signal involves the interaction of the T cell surface antigen, CD28, with its ligand on the APC, which is a member of the B7 family of proteins.

CD28, a disulfide-linked homodimer of a 44 kilodalton polypeptide and a member of the immunoglobulin superfamily, is one of the major costimulatory signal receptors on the surface of a resting T cell for T cell activation and cytokine production (Allison, *Curr. Opin. Immunol.*, 1994, 6, 414; Linsley and Ledbetter, *Annu. Rev. Immunol.*, 1993, 11, 191; June et al., *Immunol. Today*, 1994, 15, 321). Signal transduction through CD28 acts synergistically with TCR signal transduction to augment both interleukin-2 (IL-2) production and proliferation of naive T cells. B7-1 (also known as CD80) was the first ligand identified for CD28 (Liu and Linsley, *Curr. Opin. Immunol.*, 1992, 4, 265). B7-1 is normally expressed at low levels on APCs, however, it is upregulated following activation by cytokines or ligation of cell surface molecules such as CD40 (Lenschow et al., *Proc. Natl. Acad. Sci. U.S.A.*, 1993, 90, 11054; Nabavi et al., *Nature*, 1992, 360, 266). Initial studies suggested that B7-1 was the CD28 ligand that mediated costimulation (Reiser et al., *Proc. Natl. Acad. Sci. U.S.A.*, 1992, 89, 271; Wu et al., *J. Exp. Med.*, 1993, 178, 1789; Harlan et al., *Proc. Natl. Acad. Sci. U.S.A.*, 1994, 91, 3137). However, the subsequent demonstration that anti-B7-1 monoclonal antibodies (mAbs) had minimal effects on primary mixed lymphocyte reactions and that B7-1-deficient mice responded normally to antigens (Lenschow et al., *Proc. Natl. Acad. Sci. U.S.A.*, 1993, 90, 11054; Freeman et al., *Science*, 1993, 262, 909) resulted in the discovery of a second ligand for the CD28 receptor, B7-2 (also known as CD86). In contrast with anti-B7-1 mAbs, anti-B7-2 mAbs are potent inhibitors of T cell proliferation and cytokine production (Wu et al., *J. Exp. Med.*, 1993, 178, 1789; Chen et al., *J. Immunol.*, 1994, 152, 2105; Lenschow et al., *Proc. Natl. Acad. Sci. U.S.A.*, 1993, 90, 11054). B7:CD28 signaling may be a necessary component of other T cell costimulatory pathways, such as CD40:CD40L (CD40 ligand) signaling (Yang et al., *Science*, 1996, 273, 1862).

In addition to binding CD28, B7-1 and B7-2 bind the cytolytic T-lymphocyte associated protein CTLA4. CTLA4 is a protein that is structurally related to CD28 but is expressed on T cells only after activation (Linsley et al., *J. Exp. Med.*, 1991, 174, 561). A soluble recombinant form of CTLA4, CTLA4-Ig, has been determined to be a more efficient inhibitor of the B7:CD28 interaction than monoclonal antibodies directed against CD28 or a B7 protein. In vivo treatment with CTLA4-Ig results in the inhibition of antibody formation to sheep red blood cells or soluble antigen (Linsley et al., *Science*, 1992, 257, 792), prolongation of cardiac allograft and pancreatic islet xenograft survival (Lin et al., *J. Exp. Med.*, 1993, 178, 1801; Lenschow et al., *Science*, 1992, 257, 789; Lenschow et al., *Curr. Opin. Immunol.*, 1991, 9, 243), and significant suppression of immune responses in GVHD (Hakim et al., *J. Immun.*, 1995, 155, 1760). It has been proposed that CD28 and CTLA4, although both acting through common B7 receptors, serve opposing costimulatory and inhibitory functions, respectively (Allison et al., *Science*, 1995, 270, 932). CTLA4Ig, which binds both B7-1 and B7-2 molecules on antigen-presenting cells, has been shown to block T-cell costimulation in patients with stable psoriasis vulgaris, and to cause a 50% or greater sustained improvement in clinical disease activity in 46% of the patients to which it was administered. This result was dose-dependent. Abrams et al., *J. Clin. Invest.*, 1999, 9, 1243-1225.

SUMMARY OF THE INVENTION

In accordance with the present invention, oligonucleotides are provided which specifically hybridize with nucleic acids encoding B7-1 or B7-2. These oligonucleotides may be chemically modified or unmodified. Certain oligonucleotides of the invention are designed to bind either directly to mRNA transcribed from, or to a selected DNA portion of, the B7-1 or B7-2 gene, thereby modulating the amount of protein translated from a B7-1 or B7-2 mRNA or the amount of mRNA transcribed from a B7-1 or B7-2 gene, respectively.

Oligonucleotides may comprise nucleotide sequences sufficient in identity and number to effect specific hybridization with a particular nucleic acid. Such oligonucleotides are commonly described as "antisense." Antisense oligonucleotides are commonly used as research reagents, diagnostic aids, and therapeutic agents.

It has been discovered that the B7-1 and B7-2 genes, encoding B7-1 and B7-2 proteins, respectively, are particularly amenable to this approach. As a consequence of the association between B7 expression and T cell activation and proliferation, inhibition of the expression of B7-1 or B7-2 leads to inhibition of the synthesis of B7-1 or B7-2, respectively, and thereby inhibition of T cell activation and proliferation. Additionally, the oligonucleotides of the invention may be used to inhibit the expression of one of several alternatively spliced mRNAs of a B7 transcript, resulting in the enhanced expression of other alternatively spliced B7 mRNAs. Such modulation is desirable for treating various inflammatory or autoimmune disorders or diseases, or disorders or diseases with an inflammatory component such as asthma, juvenile diabetes mellitus, myasthenia gravis, Graves' disease, rheumatoid arthritis, allograft rejection, inflammatory bowel disease, multiple sclerosis, psoriasis, lupus erythematosus, systemic lupus erythematosus, diabetes, multiple sclerosis, contact dermatitis, rhinitis, various allergies, and cancers and their metastases. Such modulation is further desirable for preventing or modulating the development of such diseases or disorders in an animal suspected of being, or known to be, prone to such diseases or disorders.

In one embodiment, the invention provides methods of inhibiting the expression of a nucleic acid molecule encoding B7-1 or B7-2 in an individual, comprising the step of administering to said individual a compound of the invention targeted to a nucleic acid molecule encoding B7-1 or B7-2, wherein said compound specifically hybridizes with and inhibits the expression of a nucleic acid molecule encoding B7-1 or B7-2.

The invention further provides methods of inhibiting expression of a nucleic acid molecule encoding B7-1 or B7-2 in an individual, comprising the step of administering to an individual a compound of the invention which specifically hybridizes with at least an 8-nucleobase portion of an active site on a nucleic acid molecule encoding B7-1 or B7-2. Regions in the nucleic acid which when hybridized to a compound of the invention effect significantly lower B7-1 or B7-2 expression compared to a control, are referred to as active sites.

In another aspect, the invention provides methods of inhibiting the expression of a nucleic acid molecule encoding B7-1 or B7-2 in an individual comprising the step of administering a compound of the invention target to a nucleic acid encoding B7-1 or B7-2, wherein the compound inhibits B7-1 or B7-2 mRNA expression by at least 5% in 80% confluent HepG2 cells in culture at an optimum concentration compared to a control. In yet another aspect, the compounds inhibit expression of mRNA encoding B7-1 or B7-2 in 80% confluent HepG2 cells in culture at an optimum concentration by at least 10%, at least 15%, at least 20%, at least 25%, at least 30%, at least 35%, at least 40%, or at least 50%, compared to a control.

In one embodiment, there is provided a pharmaceutical composition comprising, as an active ingredient, a modified or unmodified antisense oligonucleotide, or a pharmaceutically acceptable salt thereof, in combination with one or more pharmaceutically acceptable carriers, diluents or excipients.

The invention also relates to pharmaceutical compositions which comprise an antisense oligonucleotide to a B7 protein in combination with a second anti-inflammatory agent, such as a second antisense oligonucleotide to a protein which mediates intercellular interactions, e.g., an intercellular adhesion molecule (ICAM) protein.

Methods comprising contacting animals with oligonucleotides specifically hybridizable with nucleic acids encoding B7 proteins are herein provided. These methods are useful as tools, for example, in the detection and determination of the role of B7 protein expression in various cell functions and physiological processes and conditions, and for the diagnosis of conditions associated with such expression. Such methods can be used to detect the expression of B7 genes (i.e., B7-1 or B7-2) and are thus believed to be useful both therapeutically and diagnostically. Methods of modulating the expression of B7 proteins comprising contacting animals with oligonucleotides specifically hybridizable with a B7 gene are herein provided. These methods are believed to be useful both therapeutically and diagnostically as a consequence of the association between B7 expression and T cell activation and proliferation. The present invention also comprises methods of inhibiting B7-associated activation of T cells using the oligonucleotides of the invention. Methods of treating conditions in which abnormal or excessive T cell activation and proliferation occurs are also provided. These methods employ the oligonucleotides of the invention and are believed to be useful both therapeutically and as clinical research and diagnostic tools. The oligonucleotides of the present invention may also be used for research purposes. Thus, the specific hybridization exhibited by the oligonucleotides of the present invention may be used for assays, purifications, cellular product preparations and in other methodologies which may be appreciated by persons of ordinary skill in the art.

The methods disclosed herein are also useful, for example, as clinical research tools in the detection and determination of the role of B7-1 or B7-2 expression in various immune system functions and physiological processes and conditions, and for the diagnosis of conditions associated with their expression. The specific hybridization exhibited by the oligonucleotides of the present invention may be used for assays, purifications, cellular product preparations and in other methodologies which may be appreciated by persons of ordinary skill in the art. For example, because the oligonucleotides of this invention specifically hybridize to nucleic acids encoding B7 proteins, sandwich and other assays can easily be constructed to exploit this fact. Detection of specific hybridization of an oligonucleotide of the invention with a nucleic acid encoding a B7 protein present in a sample can routinely be accomplished. Such detection may include detectably labeling an oligonucleotide of the invention by enzyme conjugation, radiolabeling or any other suitable detection system. A number of assays may be formulated employing the present invention, which assays will commonly comprise contacting a tissue or cell sample with a detectably labeled oligonucleotide of the present invention under conditions selected to permit hybridization and measuring such hybridization by detection of the label, as is appreciated by those of ordinary skill in the art.

In another embodiment, the invention provides methods of treating a condition associated with an increase in the expression of B7.1 or B7.2 protein comprising administering to an individual in need of such treatment an effective amount of an antisense oligonucleotide of the present invention, or a pharmaceutically acceptable salt thereof. That is, the present invention provides for the use of an antisense oligonucleotide of the present invention, or a pharmaceutical composition thereof, for the treatment of a disorder associated with increased expression of B7-1 or B7-2 proteins.

In another aspect, the present invention provides for the use of an antisense oligonucleotide, or a pharmaceutically acceptable salt thereof, in the manufacture of a medicament for inhibiting the expression of B7-1 or B7-2. Thus, the present invention provides for the use of an antisense oligonucleotide, or a pharmaceutically acceptable salt thereof, in the manufacture of a medicament for the treatment of a disorder associated with expression of B7-1 or B7-2 by means of the methods described above.

In a preferred embodiment, the present invention provides a method for treating asthma comprising administering to a patient an individual in need of such treatment an effective amount of an antisense oligonucleotide of the present invention, or a pharmaceutically acceptable salt thereof.

BRIEF DESCRIPTION OF THE DRAWINGS

FIG. 17 is a graph showing the effects of ISIS 121874, a 7 base pair mismatched control oligonucleotide (ISIS 131906) and a gap ablated control oligonucleotide which does not promote cleavage by RNase H (ISIS 306058).

FIGS. 19A-B is a graph showing the effect of ISIS 121874 on B7.2 (FIG. 19A) and B7.1 (FIG. 19B) mRNA in draining lymph nodes of ovalbumin-challenged mice.

FIG. 23 is a graph 'showing that aerosolized B7-2 antisense oligonucleotide (ISIS 121874), but not a mismatch-control oligonucleotide (ISIS 131906), reduces airway eosinophilia in ovalbumin-challenged mice.

DETAILED DESCRIPTION OF THE INVENTION

Figure 1:
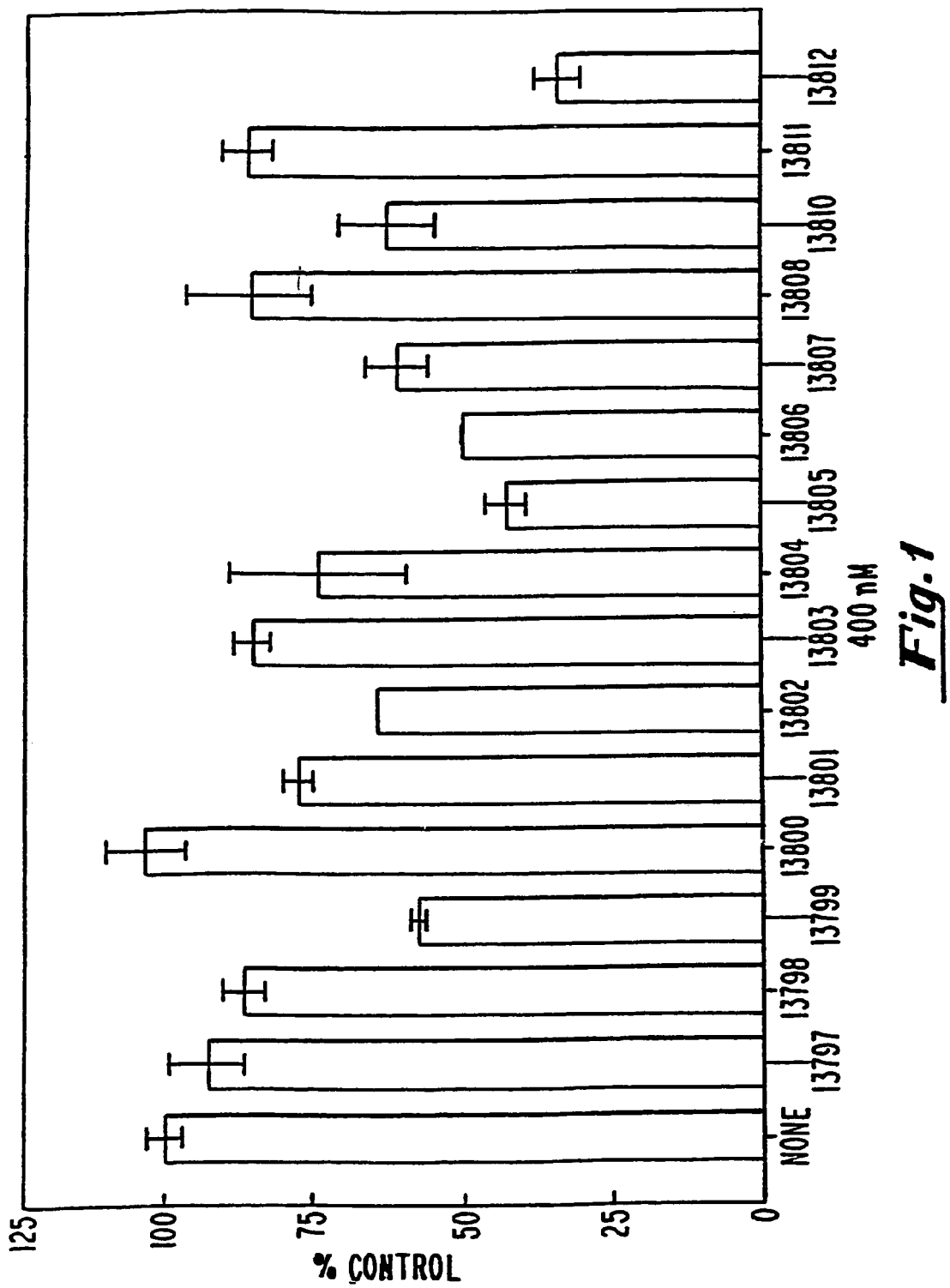
FIG. 1 is a bar graph showing the inhibitory effect of the indicated oligonucleotides on B7-1 protein expression in COS-7 cells.

The present invention employs oligonucleotides for use in antisense inhibition of the function of RNA and DNA encoding B7 proteins including B7-1 and B7-2. The present invention also employs oligonucleotides which are designed to be specifically hybridizable to DNA or messenger RNA (mRNA) encoding such proteins and ultimately to modulate the amount of such proteins transcribed from their respective genes. Such hybridization with mRNA interferes with the normal role of mRNA and causes a modulation of its function in cells. The functions of mRNA to be interfered with include all vital functions such as translocation of the RNA to the site for protein translation, actual translation of protein from the RNA, splicing of the RNA to yield one or more mRNA species, and possibly even independent catalytic activity which may be engaged in by the RNA. The overall effect of such interference with mRNA function is modulation of the expression of a B7 protein, wherein "modulation" means either an increase (stimulation) or a decrease (inhibition) in the expression of a B7 protein. In the context of the present invention, inhibition is the preferred form of modulation of gene expression.

Oligonucleotides may comprise nucleotide sequences sufficient in identity and number to effect specific hybridization with a particular nucleic acid. Such oligonucleotides which specifically hybridize to a portion of the sense strand of a gene are commonly described as "antisense." Antisense oligonucleotides are commonly used as research reagents, diagnostic aids, and therapeutic agents. For example, antisense oligonucleotides, which are able to inhibit gene expression with exquisite specificity, are often used by those of ordinary skill to elucidate the function of particular genes, for example to distinguish between the functions of various members of a biological pathway. This specific inhibitory effect has, therefore, been harnessed by those skilled in the art for research uses.

Antisense compounds include antisense oligomeric compounds, antisense oligonucleotides, ribozymes, external guide sequence (EGS) oligonucleotides, alternate splicers, primers, probes, and other short oligomeric compounds which hybridize to at least a portion of the target nucleic acid.

While oligonucleotides are a preferred form of the antisense compounds of this invention, the present invention comprehends other families of antisense compounds as well, including but not limited to oligonucleotide analogs and mimetics such as locked nucleic acids (LNA), peptide nucleic acids (PNA), cyclohexynyl nucleic acids (CeNA) ethyloxy nucleic acids (ENA) which are described in more detail herein.

"Hybridization", in the context of this invention, means hydrogen bonding, which may be Watson-Crick, Hoogsteen or reversed Hoogsteen hydrogen bonding, between complementary bases, usually on opposite nucleic acid strands or two regions of a nucleic acid strand. Guanine and cytosine are examples of complementary bases which are known to form three hydrogen bonds between them. Adenine and thymine are examples of complementary bases which form two hydrogen bonds between them. "Specifically hybridizable" and "complementary" are terms which are used to indicate a sufficient degree of complementarity such that stable and specific binding occurs between the DNA or RNA target and the oligonucleotide. It is understood that an oligonucleotide need not be 100% complementary to its target nucleic acid sequence to be specifically hybridizable. An oligonucleotide is specifically hybridizable when binding of the oligonucleotide to the target interferes with the normal function of the target molecule to cause a loss of activity, and there is a sufficient degree of complementarity to avoid non-specific binding of the oligonucleotide to non-target nucleic acid sequences under conditions in which specific binding is desired, i.e., under physiological conditions in the case of in vivo assays or therapeutic treatment or, in the case of in vitro assays, under conditions in which the assays are conducted.

It is understood in the art that the sequence of the oligomeric compound need not be 100% complementary to that of its target nucleic acid to be specifically hybridizable. Moreover, an oligomeric compound may hybridize over one or more segments such that intervening or adjacent segments are not involved in the hybridization event (e.g., a loop structure or hairpin structure). It is preferred that the oligomeric compounds of the present invention comprise at least 70% sequence complementarity to a target region within the target nucleic acid, more preferably that they comprise 90% sequence complementarity and even more preferably comprise 95% sequence complementarity to the target region within the target nucleic acid sequence to which they are targeted. For example, an oligomeric compound in which 18 of 20 nucleobases of the oligomeric compound are complementary to a target region, and would therefore specifically hybridize, would represent 90 percent complementarity. In this example, the remaining noncomplementary nucleobases may be clustered or interspersed with complementary nucleobases and need not be contiguous to each other or to complementary nucleobases. As such, an oligomeric compound which is 18 nucleobases in length having 4 (four) noncomplementary nucleobases which are flanked by two regions of complete complementarity with the target nucleic acid would have 77.8% overall complementarity with the target nucleic acid and would thus fall within the scope of the present invention. Percent complementarity of an oligomeric compound with a region of a target nucleic acid can be determined routinely using BLAST programs (basic local alignment search tools) and PowerBLAST programs known in the art (Altschul et al., J. Mol. Biol., 1990, 215, 403-410; Zhang and Madden, Genome Res., 1997, 7, 649-656).

In the present invention the phrase "stringent hybridization conditions" or "stringent conditions" refers to conditions under which an oligomeric compound of the invention will hybridize to its target sequence, but to a minimal number of other sequences. Stringent conditions are sequence-dependent and will vary with different circumstances and in the context of this invention; "stringent conditions" under which oligomeric compounds hybridize to a target sequence are determined by the nature and composition of the oligomeric compounds and the assays in which they are being investigated.

Oligonucleotides capable of modulating the expression of B7 proteins represent a novel therapeutic class of anti-inflammatory agents with activity towards a variety of inflammatory or autoimmune diseases, or disorders or diseases with an inflammatory component such as asthma, juvenile diabetes mellitus, myasthenia gravis, Graves' disease, rheumatoid arthritis, allograft rejection, inflammatory bowel disease, multiple sclerosis, psoriasis, lupus erythematosus, systemic lupus erythematosus, diabetes, multiple sclerosis, contact dermatitis, eczema, atopic dermatitis, seborrheic dermatitis, nummular dermatitis, generalized exfoliative dermatitis, rhinitis and various allergies. In addition, oligonucleotides capable of modulating the expression of B7 proteins provide a novel means of manipulating the proliferation of T cells.

It is preferred to target specific genes for antisense attack. "Targeting" an oligonucleotide to the associated nucleic acid, in the context of this invention, is a multistep process. The process usually begins with the identification of a nucleic acid sequence whose function is to be modulated. This may be, for example, a cellular gene (or mRNA transcribed from the gene) whose expression is associated with a particular disorder or disease state, or a foreign nucleic acid from an infectious agent. In the present invention, the target is a cellular gene associated with several immune system disorders and diseases (such as inflammation and autoimmune diseases), as well as with ostensibly Anormal@ immune reactions (such as a host animal's rejection of transplanted tissue), for which modulation is desired in certain instances. The targeting process also includes determination of a region (or regions) within this gene for the oligonucleotide interaction to occur such that the desired effect, either detection or modulation of expression of the protein, will result. Once the target region have been identified, oligonucleotides are chosen which are sufficiently complementary to the target, i.e., hybridize sufficiently well and with sufficient specificity to give the desired effect.

Generally, there are five regions of a gene that may be targeted for antisense modulation: the 5' untranslated region (hereinafter, the A5'-UTR@), the translation initiation codon region (hereinafter, the AtIR@), the open reading frame (hereinafter, the AORF@), the translation termination codon region (hereinafter, the AtTR@) and the 3' untranslated region (hereinafter, the A3'-UTR@). As is known in the art, these regions are arranged in a typical messenger RNA molecule in the following order (left to right, 5' to 3'): 5'-UTR, tIR, ORF, tTR, 3'-UTR. As is known in the art, although some eukaryotic transcripts are directly translated, many ORFs contain one or more sequences, known as Aintrons,@ which are excised from a transcript before it is translated; the expressed (unexcised) portions of the ORF are referred to as Aexons@ (Alberts et al., Molecular Biology of the Cell, 1983, Garland Publishing Inc., New York, pp. 411-415). Furthermore, because many eukaryotic ORFs are a thousand nucleotides or more in length, it is often convenient to subdivide the ORF into, e.g., the 5' ORF region, the central ORF region, and the 3' ORF region. In some instances, an ORF contains one or more sites that may be targeted due to some functional significance in vivo. Examples of the latter types of sites include intragenic stem-loop structures. (see, e.g., U.S. Pat. No. 5,512,438) and, in unprocessed mRNA molecules, intron/exon splice sites. Within the context of the present invention, one preferred intragenic site is the region encompassing the translation initiation codon of the open reading frame (ORF) of the gene. Because, as is known in the art, the translation initiation codon is typically 5'-AUG (in transcribed mRNA molecules; 5'-ATG in the corresponding DNA molecule), the translation initiation codon is also referred to as the AAUG codon,@ the Astart codon@ or the AAUG start codon.@ A minority of genes have a translation initiation codon having the RNA sequence 5'-GUG, 5'-UUG or 5'-CUG, and 5'-AUA, 5'-ACG and 5'-CUG have been shown to function in vivo. Furthermore, 5'-UUU functions as a translation initiation codon in vitro (Brigstock et al., Growth Factors, 1990, 4, 45; Gelbert et al., Somat. Cell. Mol. Genet., 1990, 16, 173; Gold and Stormo, in: Escherichia coli and Salmonella typhimurium: Cellular and Molecular Biology, Vol. 2, 1987, Neidhardt et al., eds., American Society for Microbiology, Washington, D.C., p. 1303). Thus, the terms Atranslation initiation codon@ and Astart codon@ can encompass many codon sequences, even though the initiator amino acid in each instance is typically methionine (in eukaryotes) or formylmethionine (prokaryotes). It is also known in the art that eukaryotic and prokaryotic genes may have two or more alternative start codons, any one of which may be preferentially utilized for translation initiation in a particular cell type or tissue, or under a particular set of conditions, in order to generate related polypeptides having different amino terminal sequences (Markussen et al., Development, 1995, 121, 3723; Gao et al., Cancer Res., 1995, 55, 743; McDermott et al., Gene, 1992, 117, 193; Perri et al., J. Biol. Chem., 1991, 266, 12536; French et al., J. Virol., 1989, 63, 3270; Pushpa-Rekha et al., J. Biol. Chem., 1995, 270, 26993; Monaco et al., J. Biol. Chem., 1994, 269, 347; DeVirgilio et al., Yeast, 1992, 8, 1043; Kanagasundaram et al., Biochim. Biophys. Acta, 1992, 1171, 198; Olsen et al., Mol. Endocrinol., 1991, 5, 1246; Saul et al., Appl. Environ. Microbiol., 1990, 56, 3117; Yaoita et al., Proc. Natl. Acad. Sci. USA, 1990, 87, 7090; Rogers et al., EMBO J., 1990, 9, 2273). In the context of the invention, Astart codon@ and Atranslation initiation codon@ refer to the codon or codons that are used in vivo to initiate translation of an mRNA molecule transcribed from a gene encoding a B7 protein, regardless of the sequence(s) of such codons. It is also known in the art that a translation termination codon (or Astop codon@) of a gene may have one of three sequences, i.e., 5'-UAA, 5'-UAG and 5'-UGA (the corresponding DNA sequences are 5'-TAA, 5'-TAG and 5'-TGA, respectively). The terms Astart codon region@ and Atranslation initiation region@ refer to a portion of such an mRNA or gene that encompasses from about 25 to about 50 contiguous nucleotides in either direction (i.e., 5' or 3') from a translation initiation codon. Similarly, the terms Astop codon region@ and Atranslation termination region@ refer to a portion of such an mRNA or gene that encompasses from about 25 to about 50 contiguous nucleotides in either direction (i.e., 5' or 3') from a translation termination codon.

In the context of this invention, the term "oligonucleotide" refers to an oligomer or polymer of ribonucleic acid or deoxyribonucleic acid. This term includes oligonucleotides composed of naturally-occurring nucleobases, sugars and covalent intersugar (backbone) linkages as well as oligonucleotides having non-naturally-occurring portions which function similarly. Such modified or substituted oligonucleotides are often preferred over native forms because of desirable properties such as, for example, enhanced cellular uptake, enhanced binding to target and increased stability in the presence of nucleases.

While the preferred form of antisense compound is a single-stranded antisense oligonucleotide, in many species the introduction of double-stranded structures, such as double-stranded RNA (dsRNA) molecules, has been shown to induce potent and specific antisense-mediated reduction of the function of a gene or its associated gene products. This phenomenon occurs in both plants and animals and is believed to have an evolutionary connection to viral defense and transposon silencing.

The first evidence that dsRNA could lead to gene silencing in animals came in 1995 from work in the nematode, Caenorhabditis elegans (Guo and Kempheus, Cell, 1995, 81, 611-620).

Montgomery et al. have shown that the primary interference effects of dsRNA are posttranscriptional (Montgomery et al., Proc. Natl. Acad. Sci. USA, 1998, 95, 15502-15507). The posttranscriptional antisense mechanism defined in Caenorhabditis elegans resulting from exposure to double-stranded RNA (dsRNA) has since been designated RNA interference (RNAi). This term has been generalized to mean antisense-mediated gene silencing involving the introduction of dsRNA leading to the sequence-specific reduction of endogenous targeted mRNA levels (Fire et al., *Nature*, 1998, 391, 806-811). Recently, it has been shown that it is, in fact, the single-stranded RNA oligomers of antisense polarity of the dsRNAs which are the potent inducers of RNAi (Tijsterman et al., *Science*, 2002, 295, 694-697).

Oligomer and Monomer Modifications

As is known in the art, a nucleoside is a base-sugar combination. The base portion of the nucleoside is normally a heterocyclic base. The two most common classes of such heterocyclic bases are the purines and the pyrimidines. Nucleotides are nucleosides that further include a phosphate group covalently linked to the sugar portion of the nucleoside. For those nucleosides that include a pentofuranosyl sugar, the phosphate group can be linked to either the 2', 3' or 5' hydroxyl moiety of the sugar. In forming oligonucleotides, the phosphate groups covalently link adjacent nucleosides to one another to form a linear polymeric compound. In turn, the respective ends of this linear polymeric compound can be further joined to form a circular compound, however, linear compounds are generally preferred. In addition, linear compounds may have internal nucleobase complementarity and may therefore fold in a manner as to produce a fully or partially double-stranded compound. Within oligonucleotides, the phosphate groups are commonly referred to as forming the internucleoside linkage or in conjunction with the sugar ring the backbone of the oligonucleotide. The normal internucleoside linkage that makes up the backbone of RNA and DNA is a 3' to 5' phosphodiester linkage.

Modified Internucleoside Linkages

Specific examples of preferred antisense oligomeric compounds useful in this invention include oligonucleotides containing modified e.g. non-naturally occurring internucleoside linkages. As defined in this specification, oligonucleotides having modified internucleoside linkages include internucleoside linkages that retain a phosphorus atom and internucleoside linkages that do not have a phosphorus atom. For the purposes of this specification, and as sometimes referenced in the art, modified oligonucleotides that do not have a phosphorus atom in their internucleoside backbone can also be considered to be oligonucleosides.

Antisense oligonucleotides of the present invention that further comprise modified internucleoside linkages are preferred, particularly one in which one of the oxygen atoms of the phosphate group in the phosphodiester bond is replaced with a sulfur atom to form a phosphorothioate linkage.

In the *C. elegans* system, modification of the internucleotide linkage (phosphorothioate) did not significantly interfere with RNAi activity. Based on this observation, it is suggested that certain preferred oligomeric compounds of the invention can also have one or more modified internucleoside linkages. A preferred phosphorus containing modified internucleoside linkage is the phosphorothioate internucleoside linkage.

Preferred modified oligonucleotide backbones containing a phosphorus atom therein include, for example, phosphorothioates, chiral phosphorothioates, phosphoro-dithioates, phosphotriesters, aminoalkylphosphotriesters, methyl and other alkyl phosphonates including 3'-alkylene phosphonates, 5'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, selenophosphates and borano-phosphates having normal 3'-5' linkages, 2'-5' linked analogs of these, and those having inverted polarity wherein one or more internucleotide linkages is a 3' to 3', 5' to 5' or 2' to 2' linkage. Preferred oligonucleotides having inverted polarity comprise a single 3' to 3' linkage at the 3'-most internucleotide linkage i.e. a single inverted nucleoside residue which may be abasic (the nucleobase is missing or has a hydroxyl group in place thereof). Various salts, mixed salts and free acid forms are also included.

Representative United States patents that teach the preparation of the above phosphorus-containing linkages include, but are not limited to, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; 5,194,599; 5,565,555; 5,527,899; 5,721,218; 5,672,697 and 5,625,050, certain of which are commonly owned with this application, and each of which is herein incorporated by reference.

In more preferred embodiments of the invention, oligomeric compounds have one or more phosphorothioate and/or heteroatom internucleoside linkages, in particular —CH$_2$—NH—O—CH$_2$—, —CH$_2$—N(CH$_3$)—O—CH$_2$— [known as a methylene (methylimino) or MMI backbone], —CH$_2$—O—N(CH$_3$) —CH$_2$—, —CH$_2$—N(CH$_3$) —N(CH$_3$) —CH$_2$— and —O—N(CH$_3$) —CH$_2$—CH$_2$— [wherein the native phosphodiester internucleotide linkage is represented as —O—P(=O)(OH)—O—CH$_2$—]. The MMI type internucleoside linkages are disclosed in the above referenced U.S. Pat. No. 5,489,677. Preferred amide internucleoside linkages are disclosed in the above referenced U.S. Pat. No. 5,602,240.

Preferred modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; riboacetyl backbones; alkene containing backbones; sulfamate backbones; methyleneimino and methylenehydrazino backbones; sulfonate and sulfonamide backbones; amide backbones; and others having mixed. N, O, S and CH$_2$ component parts.

Representative United States patents that teach the preparation of the above oligonucleosides include, but are not limited to, U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; 5,792,608; 5,646,269 and 5,677,439, certain of which are commonly owned with this application, and each of which is herein incorporated by reference.

Oligomer Mimetics

Another preferred group of oligomeric compounds amenable to the present invention includes oligonucleotide mimetics. The term mimetic as it is applied to oligonucleotides is intended to include oligomeric compounds wherein only the furanose ring or both the furanose ring and the internucleotide linkage are replaced with novel groups, Replacement of only the furanose ring is also referred to in the art as being a sugar surrogate. The heterocyclic base moiety or a modified heterocyclic base moiety is maintained for hybridization with an appropriate target nucleic acid. One such oligomeric compound, an oligonucleotide mimetic that has been shown to have excellent hybridization properties, is referred to as a peptide nucleic acid (PNA). In PNA oligomeric compounds, the sugar-backbone of an oligonucleotide is replaced with an amide containing backbone, in particular an aminoethylglycine backbone. The nucleobases are retained and are bound directly or indirectly to aza nitrogen atoms of the amide portion of the backbone. Representative United States patents that teach the preparation of PNA oligomeric compounds include, but are not limited to, U.S. Pat. Nos. 5,539,082; 5,714,331; and 5,719,262, each of which is herein incorporated by reference. Further teaching of PNA oligomeric compounds can be found in Nielsen et al., *Science*, 1991, 254, 1497-1500.

PNA has been modified to incorporate numerous modifications since the basic PNA structure was first prepared. The basic structure is shown below:

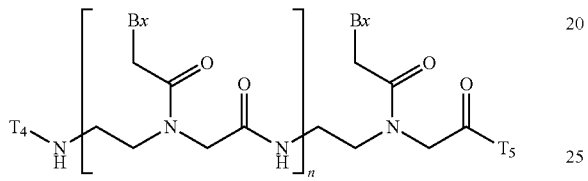

wherein
Bx is a heterocyclic base moiety;
$T_4$ is hydrogen, an amino protecting group, —C(O)$R_5$, substituted or unsubstituted $C_1$-$C_{10}$ alkyl, substituted or unsubstituted $C_2$-$C_{10}$ alkenyl, substituted or unsubstituted $C_2$-$C_{10}$ alkynyl, alkylsulfonyl, arylsulfonyl, a chemical functional group, a reporter group, a conjugate group, a D or L α-amino acid linked via the α-carboxyl group or optionally through the ω-carboxyl group when the amino acid is aspartic acid or glutamic acid or a peptide derived from D, L or mixed D and L amino acids linked through a carboxyl group, wherein the substituent groups are selected from hydroxyl, amino, alkoxy, carboxy, benzyl, phenyl, nitro, thiol, thioalkoxy, halogen, alkyl, aryl, alkenyl and alkynyl;
$T_5$ is —OH, —N($Z_1$)$Z_2$, $R_5$, D or L α-amino acid linked via the α-amino group or optionally through the (ω-amino group when the amino acid is lysine or ornithine or a peptide derived from D, L or mixed D and L amino acids linked through an amino group, a chemical functional group, a reporter group or a conjugate group;
$Z_1$ is hydrogen, $C_1$-$C_6$ alkyl, or an amino protecting group;
$Z_2$ is hydrogen, $C_1$-$C_6$ alkyl, an amino protecting group, —C(=O)—(CH$_2$)$_n$-J-$Z_3$, a D or L α-amino acid linked via the α-carboxyl group or optionally through the ω-carboxyl group when the amino acid is aspartic acid or glutamic acid or a peptide derived from D, L or mixed D and L amino acids linked through a carboxyl group;
$Z_3$ is hydrogen, an amino protecting group, —$C_1$-$C_6$ alkyl, —C(=O)—CH$_3$, benzyl, benzoyl, or —(CH$_2$)$_n$—N(H)$Z_1$;
each J is O, S or NH;
$R_5$ is a carbonyl protecting group; and
n is from 2 to about 50.

Another class of oligonucleotide mimetic that has been studied is based on linked morpholino units (morpholino nucleic acid) having heterocyclic bases attached to the morpholino ring. A number of linking groups have been reported that link the morpholino monomeric units in a morpholino nucleic acid. A preferred class of linking groups have been selected to give a non-ionic oligomeric compound. The non-ionic morpholino-based oligomeric compounds are less likely to have undesired interactions with cellular proteins. Morpholino-based oligomeric compounds are non-ionic mimics of oligonucleotides which are less likely to form undesired interactions with cellular proteins (Dwaine A. Braasch and David R. Corey, *Biochemistry*, 2002, 41(14), 4503-4510). Morpholino-based oligomeric compounds are disclosed in U.S. Pat. No. 5,034,506, issued Jul. 23, 1991. The morpholino class of oligomeric compounds have been prepared having a variety of different linking groups joining the monomeric subunits.

Morpholino nucleic acids have been prepared having a variety of different linking groups ($L_2$) joining the monomeric subunits. The basic formula is shown below:

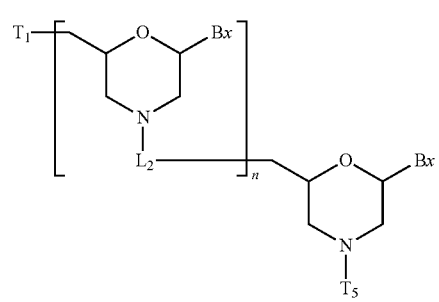

wherein
$B_x$ is a heterocyclic base moiety;
$T_1$ is hydroxyl or a protected hydroxyl;
$T_5$ is hydrogen or a phosphate or phosphate derivative;
$L_2$ is a linking group; and
n is from 2 to about 50.

A further class of oligonucleotide mimetic is referred to as cyclohexenyl nucleic acids (CeNA). The furanose ring normally present in an DNA/RNA molecule is replaced with a cyclohenyl ring. CeNA DMT protected phosphoramidite monomers have been prepared and used for oligomeric compound synthesis following classical phosphoramidite chemistry. Fully modified CeNA oligomeric compounds and oligonucleotides having specific positions modified with CeNA have been prepared and studied (see Wang et al., *J. Am. Chem. Soc.*, 2000, 122, 8595-8602). In general the incorporation of CeNA monomers into a DNA chain increases its stability of a DNA/RNA hybrid. CeNA oligoadenylates formed complexes with RNA and DNA complements with similar stability to the native complexes. The study of incorporating CeNA structures into natural nucleic acid structures was shown by NMR and circular dichroism to proceed with easy conformational adaptation. Furthermore the incorporation of CeNA into a sequence targeting RNA was stable to serum and able to activate *E. Coli* RNase resulting in cleavage of the target RNA strand.

The general formula of CeNA is shown below:

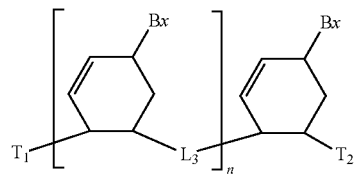

wherein
each Bx is a heterocyclic base moiety;
$T_1$ is hydroxyl or a protected hydroxyl;

$T_2$ is hydroxyl or a protected hydroxyl;
$L_3$ is a linking group; and
n is from 2 to about 50

Another class of oligonucleotide mimetic (anhydrohexitol nucleic acid) can be prepared from one or more anhydrohexitol nucleosides (see, Wouters and Herdewijn, *Bioorg. Med. Chem. Lett.*, 1999, 9, 1563-1566) and would have the general formula:

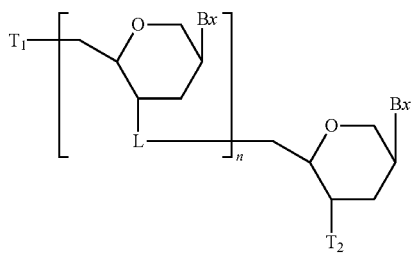

wherein
$B_x$ is a heterocyclic base moiety;
$T_1$ is a hydroxyl or a protected hydroxyl;
$T_2$ is a hydroxyl or a protected hydroxyl;
L is a linking group; and
n is from 2 to about 50

A further preferred modification includes Locked Nucleic Acids (LNAs) in which the 2'-hydroxyl group is linked to the 4' carbon atom of the sugar ring thereby forming a 2'-C,4'-C-oxymethylene linkage thereby forming a bicyclic sugar moiety. The linkage is preferably a methylene ($-CH_2-$)$_n$ group bridging the 2' oxygen atom and the 4' carbon atom wherein n is 1 or 2 (Singh et al., Chem. Commun., 1998, 4, 455-456). LNA and LNA analogs display very high duplex thermal stabilities with complementary DNA and RNA (Tm=+3 to +10 C), stability towards 3'-exonucleolytic degradation and good solubility properties. The basic structure of LNA showing the bicyclic ring system is shown below:

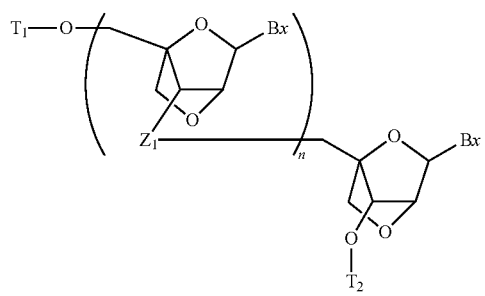

wherein
$B_x$ is a heterocyclic base moiety;
$T_1$ is a hydroxyl or a protected hydroxyl;
$T_2$ is a hydroxyl or a protected hydroxyl;
$Z_1$ is a linking group; and
n is from 2 to about 50;

The conformations of LNAs determined by 2D NMR spectroscopy have shown that the locked orientation of the LNA nucleotides, both in single-stranded LNA and in duplexes, constrains the phosphate backbone in such a way as to introduce a higher population of the N-type conformation (Petersen et al., J. Mol. Recognit., 2000, 13, 44-53). These conformations are associated with improved stacking of the nucleobases (Wengel et al., Nucleosides Nucleotides, 1999, 18, 1365-1370).

LNA has been shown to form exceedingly stable LNA:LNA duplexes (Koshkin et al., J. Am. Chem. Soc., 1998, 120, 13252-13253). LNA:LNA hybridization was shown to be the most thermally stable nucleic acid type duplex system, and the RNA-mimicking character of LNA was established at the duplex level. Introduction of 3 LINA monomers (T or A) significantly increased melting points (Tm=+15/+11) toward DNA complements. The universality of LNA-mediated hybridization has been stressed by the formation of exceedingly stable LNA:LNA duplexes. The RNA-mimicking of LNA was reflected with regard to the N-type conformational restriction of the monomers and to the secondary structure of the LNA:RNA duplex.

LNAs also form duplexes with complementary DNA, RNA or LNA with high thermal affinities. Circular dichroism (CD) spectra show that duplexes involving fully modified LNA (esp. LNA:RNA) structurally resemble an A-form RNA:RNA duplex. Nuclear magnetic resonance (NMR) examination of an LNA:DNA duplex confirmed the 3'-endo conformation of an LNA monomer. Recognition of double-stranded DNA has also been demonstrated suggesting strand invasion by LNA. Studies of mismatched sequences show that LNAs obey the Watson-Crick base pairing rules with generally improved selectivity compared to the corresponding unmodified reference strands.

Novel types of LNA-oligomeric compounds, as well as the LNAs, are useful in a wide range of diagnostic and therapeutic applications. Among these are antisense applications, PCR applications, strand-displacement oligomers, substrates for nucleic acid polymerases and generally as nucleotide based drugs. Potent and nontoxic antisense oligonucleotides containing LNAs have been described (Wahlestedt et al., Proc. Natl. Acad. Sci. U. S. A., 2000, 97, 5633-5638.) The authors have demonstrated that LNAs confer several desired properties to antisense agents. LNA/DNA copolymers were not degraded readily in blood serum and cell extracts. LNA/DNA copolymers exhibited potent antisense activity in assay systems as disparate as G-protein-coupled receptor signaling in living rat brain and detection of reporter genes in *Escherichia coli*. Lipofectin-mediated efficient delivery of LNA into living human breast cancer cells has also been accomplished.

The synthesis and preparation of the LNA monomers adenine, cytosine, guanine, 5-methyl-cytosine, thymine and uracil, along with their oligomerization, and nucleic acid recognition properties have been described (Koshkin et al., Tetrahedron, 1998, 54, 3607-3630). LNAs and preparation thereof are also described in WO 98/39352 and WO 99/14226.

The first analogs of LNA, phosphorothioate-LNA and 2'-thio-LNAs, have also been prepared (Kumar et al., Bioorg. Med. Chem. Lett., 1998, 8, 2219-2222). Preparation of locked nucleoside analogs containing oligodeoxyribonucleotide duplexes as substrates for nucleic acid polymerases has also been described (Wengel et al., PCT International Application WO 98-DK393 19980914). Furthermore, synthesis of 2'-amino-LNA, a novel conformationally restricted high-affinity oligonucleotide analog with a handle has been described in the art (Singh et al., J. Org. Chem., 1998, 63, 10035-10039). In addition, 2'-Amino- and 2'-methylamino-LNA's have been prepared and the thermal stability of their duplexes with complementary RNA and DNA strands has been previously reported.

Further oligonucleotide mimetics have been prepared to include bicyclic and tricyclic nucleoside analogs having the formulas (amidite monomers shown):

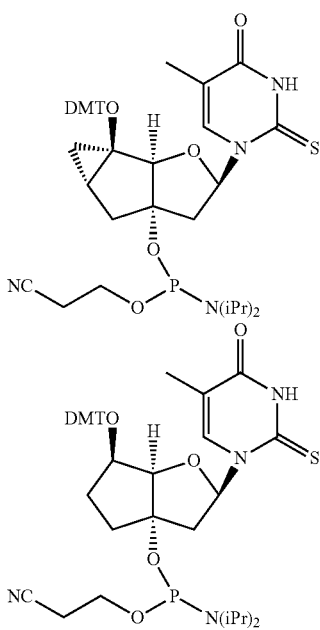

DMT=dimethoxytrityl. (see Steffens et al., *Helv. Chim. Acta*, 1997, 80, 2426-2439; Steffens et al., *J. Am. Chem. Soc.*, 1999, 121, 3249-3255; and Renneberg et al., *J. Am. Chem. Soc.*, 2002, 124, 5993-6002). These modified nucleoside analogs have been oligomerized using the phosphoramidite approach and the resulting oligomeric compounds containing tricyclic nucleoside analogs have shown increased thermal stabilities (Tm's) when hybridized to DNA, RNA and itself. Oligomeric compounds containing bicyclic nucleoside analogs have shown thermal stabilities approaching that of DNA duplexes.

Another class of oligonucleotide mimetic is referred to as phosphonomonoester nucleic acids incorporate a phosphorus group in the backbone. This class of olignucleotide mimetic is reported to have useful physical and biological and pharmacological properties in the areas of inhibiting gene expression (antisense oligonucleotides, ribozymes, sense oligonucleotides and triplex-forming oligonucleotides), as probes for the detection of nucleic acids and as auxiliaries for use in molecular biology.

The general formula (for definitions of Markush variables see: U.S. Pat. Nos. 5,874,553 and 6,127,346 herein incorporated by reference in their entirety) is shown below.

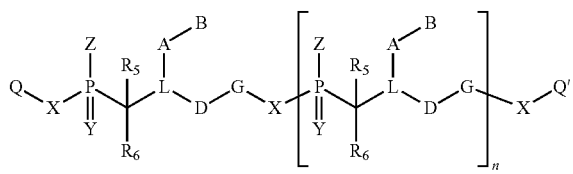

Another oligonucleotide mimetic has been reported wherein the furanosyl ring has been replaced by a cyclobutyl moiety.

Modified Sugars

Oligomeric compounds of the invention may also contain one or more substituted sugar moieties. Preferred oligomeric compounds comprise a sugar substituent group selected from: OH; F; O-, S-, or N-alkyl; O-, S-, or N-alkenyl; O-, S- or N-alkynyl; or O-alkyl-O-alkyl, wherein the alkyl, alkenyl and alkynyl may be substituted or unsubstituted $C_1$ to $C_{10}$ alkyl or $C_2$ to $C_{10}$ alkenyl and alkynyl. Particularly preferred are $O[(CH_2)_nO]_mCH_3$, $O(CH_2)_nOCH_3$, $O(CH_2)_nNH_2$, $O(CH_2)_nCH_3$, $O(CH_2)_nONH_2$, and $O(CH_2)_nON[(CH_2)_nCH_3]_2$, where n and m are from 1 to about 10. Other preferred oligonucleotides comprise a sugar substituent group selected from: $C_1$ to $C_{10}$ lower alkyl, substituted lower alkyl, alkenyl, alkynyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. A preferred modification includes 2'-methoxyethoxy (2'-O—$CH_2CH_2OCH_3$, also known as 2'-O-(2-methoxyethyl) or 2'-MOE) (Martin et al., *Helv. Chim. Acta*, 1995, 78, 486-504) i.e., an alkoxyalkoxy group. Especially preferred compounds of the invention comprise 2'-MOE modifications.

A further preferred modification includes 2'-dimethylaminooxyethoxy, i.e., a $O(CH_2)_2ON(CH_3)_2$ group, also known as 2'-DMAOE, as described in examples hereinbelow, and 2'-dimethylaminoethoxyethoxy (also known in the art as 2'-O-dimethyl-amino-ethoxy-ethyl or 2'-DMAEOE), i.e., 2'-O—$CH_2$—O—$CH_2$—$N(CH_3)_2$.

Other preferred sugar substituent groups include methoxy (—O—$CH_3$), aminopropoxy (—$OCH_2CH_2CH_2NH_2$), allyl (—$CH_2$—CH=$CH_2$), —O-allyl (—O—$CH_2$—CH=$CH_2$) and fluoro (F). 2'-Sugar substituent groups may be in the arabino (up) position or ribo (down) position. A preferred 2'-arabino modification is 2'-F. Similar modifications may also be made at other positions on the oligomeric compound, particularly the 3' position of the sugar on the 3' terminal nucleoside or in 2'-5' linked oligonucleotides and the 5' position of 5' terminal nucleotide. Oligomeric compounds may also have sugar mimetics such as cyclobutyl moieties in place of the pentofuranosyl sugar. Representative United States patents that teach the preparation of such modified sugar structures include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; 5,792,747; and 5,700,920, certain of which are commonly owned with the instant application, and each of which is herein incorporated by reference in its entirety.

Further representative sugar substituent groups include groups of formula $I_a$ or $II_a$:

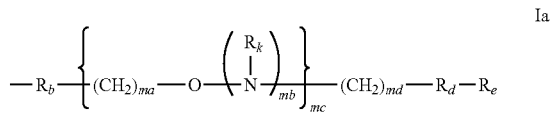

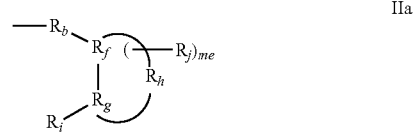

wherein:
$R_b$ is O, S or NH;
$R_d$ is a single bond, O, S or C(=O);

$R_e$ is $C_1$-$C_{10}$ alkyl, $N(R_k)$ $(R_m)$, $N(R_k)$ $(R_n)$, $N\!=\!C(R_p)$ $(R_q)$, $N\!=\!C(R_p)$ $(R_r)$ or has formula $III_a$;

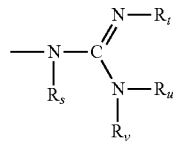

$R_p$ and $R_q$ are each independently hydrogen or $C_1$-$C_{10}$ alkyl;

$R_r$ is —$R_x$—$R_y$;

each $R_s$, $R_t$, $R_u$ and $R_v$ is, independently, hydrogen, C(O)$R_w$, substituted or unsubstituted $C_1$-$C_{10}$ alkyl, substituted or unsubstituted $C_2$-$C_{10}$ alkenyl, substituted or unsubstituted $C_2$-$C_{10}$ alkynyl, alkylsulfonyl, arylsulfonyl, a chemical functional group or a conjugate group, wherein the substituent groups are selected from hydroxyl, amino, alkoxy, carboxy, benzyl, phenyl, nitro, thiol, thioalkoxy, halogen, alkyl, aryl, alkenyl and alkynyl;

or optionally, $R_u$ and $R_v$, together form a phthalimido moiety with the nitrogen atom to which they are attached;

each $R_w$ is, independently, substituted or unsubstituted $C_1$-$C_{10}$ alkyl, trifluoromethyl, cyanoethyloxy, methoxy, ethoxy, t-butoxy, allyloxy, 9-fluorenylmethoxy, 2-(trimethylsilyl)-ethoxy, 2,2,2-trichloroethoxy, benzyloxy, butyryl, isobutyryl, phenyl or aryl;

$R_k$ is hydrogen, a nitrogen protecting group or —$R_x$—$R_y$;

$R_p$ is hydrogen, a nitrogen protecting group or —$R_x$—$R_y$;

$R_x$ is a bond or a linking moiety;

$R_y$ is a chemical functional group, a conjugate group or a solid support medium;

each $R_m$ and $R_n$ is, independently, H, a nitrogen protecting group, substituted or unsubstituted $C_1$-$C_{10}$ alkyl, substituted or unsubstituted $C_2$-$C_{10}$ alkenyl, substituted or unsubstituted $C_2$-$C_{10}$ alkynyl, wherein the substituent groups are selected from hydroxyl, amino, alkoxy, carboxy, benzyl, phenyl, nitro, thiol, thioalkoxy, halogen, alkyl, aryl, alkenyl, alkynyl; $NH_3^+$, $N(R_u)$ $(R_v)$, guanidino and acyl where said acyl is an acid amide or an ester;

or $R_m$ and $R_n$ together, are a nitrogen protecting group, are joined in a ring structure that optionally includes an additional heteroatom selected from N and O or are a chemical functional group;

$R_i$ is $OR_z$, $SR_z$, or $N(R_z)_2$;

each $R_z$ is, independently, H, $C_1$-$C_8$ alkyl, $C_1$-$C_8$ haloalkyl, C($=$NH)N(H)$R_u$, C($=$O)N(H)$R_u$ or OC($=$O)N(H)$R_u$;

$R_f$, $R_g$ and $R_h$ comprise a ring system having from about 4 to about 7 carbon atoms or having from about 3 to about 6 carbon atoms and 1 or 2 heteroatoms wherein said heteroatoms are selected from oxygen, nitrogen and sulfur and wherein said ring system is aliphatic, unsaturated aliphatic, aromatic, or saturated or unsaturated heterocyclic;

$R_j$ is alkyl or haloalkyl having 1 to about 10 carbon atoms, alkenyl having 2 to about 10 carbon atoms, alkynyl having 2 to about 10 carbon atoms, aryl having 6 to about 14 carbon atoms, $N(R_k)$ $(R_m)$ $OR_k$, halo, $SR_k$ or CN;

$m_a$ is 1 to about 10;

each mb is, independently, 0 or 1;

mc is 0 or an integer from 1 to 10;

md is an integer from: 1 to 10;

me is from 0, 1 or 2; and provided that when mc is 0, md is greater than 1.

Representative substituents groups of Formula I are disclosed in U.S. Pat. No. 6,172,209, hereby incorporated by reference in its entirety.

Representative cyclic substituent groups of Formula II are disclosed in United States Pat. No. 6,217,358, hereby incorporated by reference in its entirety.

Particularly preferred sugar substituent groups include $O[(CH_2)_nO]_mCH_3$, $O(CH_2)_nOCH_3$, $O(CH_2)_nNH_2$, $O(CH_2)_nCH_3$, $O(CH_2)_nONH_2$, and $O(CH_2)_nON[(CH_2)_nCH_3]_2$, where n and m are from 1 to about 10.

Representative guanidino substituent groups that are shown in formula III and IV are disclosed in co-owned U.S. Pat. No. 6,593,466, entitled "Functionalized Oligomers", filed Jul. 7, 1999, hereby incorporated by reference in its entirety.

Representative acetamido substituent groups are disclosed in U.S. Pat. No. 6,147,200 which is hereby incorporated by reference in its entirety.

Representative dimethylaminoethyloxyethyl substituent groups are disclosed in International Patent Publication WO 00/08044, entitled "2'-O-Dimethylaminoethyloxyethyl-Oligomeric compounds", filed Aug. 6, 1999, hereby incorporated by reference in its entirety.

Modified Nucleobases/Naturally Occurring Nucleobases

Oligomeric compounds may also include nucleobase (often referred to in the art simply as "base" or "heterocyclic base moiety") modifications or substitutions. As used herein, "unmodified" or "natural" nucleobases include the purine bases adenine (A) and guanine (G), and the pyrimidine bases thymine (T), cytosine (C) and uracil (U). Modified nucleobases also referred herein as heterocyclic base moieties include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—C≡C—$CH_3$) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine and 3-deazaguanine and 3-deazaadenine. Particularly preferred base modifications of the present invention are 5-methyl cytosine modifications.

Heterocyclic base moieties may also include those in which the purine or pyrimidine base is replaced with other heterocycles, for example 7-deaza-adenine, 7-deazaguanosine, 2-aminopyridine and 2-pyridone. Further nucleobases include those disclosed in U.S. Pat. No. 3,687,808, those disclosed in *The Concise Encyclopedia Of Polymer Science And Engineering*, pages 858-859, Kroschwitz, J. I., ed. John Wiley & Sons, 1990, those disclosed by Englisch et al., *Angewandte Chemie*, International Edition 1991, 30, 613, and those disclosed by Sanghvi, Y. S., Chapter 15, *Antisense Research and Applications*, pages 289-302, Crooke, S. T. and Lebleu, B., ed., CRC Press, 1993. Certain of these nucleobases are particularly useful for increasing the binding affinity of the oligomeric compounds of the invention. These include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6-1.2° C. (Sanghvi, Y. S., Crooke, S. T. and Lebleu, B., eds., *Antisense Research and Applications*, CRC Press, Boca Raton, 1993, pp. 276-278) and are presently preferred base substitutions.

In one aspect of the present invention oligomeric compounds are prepared having polycyclic heterocyclic compounds in place of one or more heterocyclic base moieties. A number of tricyclic heterocyclic compounds have been previously reported. These compounds are routinely used in antisense applications to increase the binding properties of the modified strand to a target strand. The most studied modifications are targeted to guanosines hence they have been termed G-clamps or cytidine analogs. Many of these polycyclic heterocyclic compounds have the general formula:

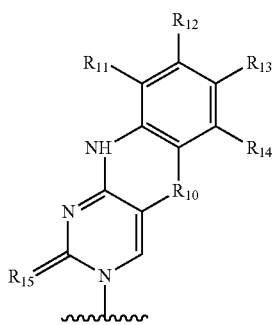

Representative cytosine analogs that make 3 hydrogen bonds with a guanosine in a second strand include 1,3-diazaphenoxazine-2-one (R10=O,R11-R14=H) [Kurchavov, et al., Nucleosides and Nucleotides, 1997, 16, 1837-1846], 1,3-diazaphenothiazine-2-one (R10=S, R11-R14=H), [Lin, K.-Y.; Jones, R. J.; Matteucci, M. J. Am. Chem. Soc. 1995, 117, 3873-3874] and 6,7,8,9-tetrafluoro-1,3-diazaphenoxazine-2-one (R10=O, R11-R14=F) [Wang, J.; Lin, K.-Y., Matteucci, M. Tetrahedron Lett. 1998, 39, 8385-8388]. Incorporated into oligonucleotides these base modifications were shown to hybridize with complementary guanine and the latter was also shown to hybridize with adenine and to enhance helical thermal stability by extended stacking interactions (also see Publication No. US2003-0207804 entitled "Modified Peptide Nucleic Acids"; and Publication No. US2003-0185906 entitled "Nuclease Resistant Chimeric Oligonucleotides", both of which are commonly owned with this application and are herein incorporated by reference in their entirety).

Further helix-stabilizing properties have been observed when a cytosine analog/substitute has an aminoethoxy moiety attached to the rigid 1,3-diazaphenoxazine-2-one scaffold ($R_{10}$=O, $R_{11}$=—O—$(CH_2)_2$—$NH_2$, $R_{12-14}$=H) [Lin, K.-Y.; Matteucci, M. J. Am. Chem. Soc. 1998, 120, 8531-8532]. Binding studies demonstrated that a single incorporation could enhance the binding affinity of a model oligonucleotide to its complementary target DNA or RNA with a $\Delta T_m$ of up to 18° relative to 5-methyl cytosine (dC5$^{me}$), which is the highest known affinity enhancement for a single modification, yet. On the other hand, the gain in helical stability does not compromise the specificity of the oligonucleotides. The $T_m$ data indicate an even greater discrimination between the perfect match and mismatched sequences compared to dC5$^{me}$. It was suggested that the tethered amino group serves as an additional hydrogen bond donor to interact with the Hoogsteen face, namely the O6, of a complementary guanine thereby forming 4 hydrogen bonds. This means that the increased affinity of G-clamp is mediated by the combination of extended base stacking and additional specific hydrogen bonding.

Further tricyclic heterocyclic compounds and methods of using them that are amenable to the present invention are disclosed in U.S. Pat. No. 6,028,183, which issued on May 22, 2000, and U.S. Pat. No. 6,007,992, which issued on Dec. 28, 1999, the contents of both are commonly assigned with this application and are incorporated herein in their entirety.

The enhanced binding affinity of the phenoxazine derivatives together with their uncompromised sequence specificity makes them valuable nucleobase analogs for the development of more potent antisense-based drugs. In fact, promising data have been derived from in vitro experiments demonstrating that heptanucleotides containing phenoxazine substitutions are capable to activate RNaseH, enhance cellular uptake and exhibit an increased antisense activity [Lin, K-Y; Matteucci, M. J. Am. Chem. Soc; 1998, 120, 8531-8532]. The activity enhancement was even more pronounced in case of G-clamp, as a single substitution was shown to significantly improve the in vitro potency of a 20 mer 2'-deoxyphosphorothioate oligonucleotides [Flanagan, W. M.; Wolf, J. J.; Olson, P.; Grant, D.; Lin, K.-Y.; Wagner, R. W.; Matteucci, M. Proc. Natl. Acad. Sci. USA, 1999, 96, 3513-3518]. Nevertheless, to optimize oligonucleotide design and to better understand the impact of these heterocyclic modifications on the biological activity, it is important to evaluate their effect on the nuclease stability of the oligomers.

Further modified polycyclic heterocyclic compounds useful as heterocyicic bases are disclosed in but not limited to, the above noted U.S. Pat. No. 3,687,808, as well as U.S. Pat. Nos. 4,845,205; 5,130,302; 5,134,066; 5,175,273; 5,367,066; 5,432,272; 5,434,257; 5,457,187; 5,459,255; 5,484,908; 5,502,177; 5,525,711; 5,552,540; 5,587,469; 5,594,121, 5,596,091; 5,614,617; 5,645,985; 5,646,269; 5,750,692; 5,830,653; 5,763,588; 6,005,096; and 5,681,941, and Publication No. US 2003-0158403, certain of which are commonly owned with the instant application, and each of which is herein incorporated by reference.

The oligonucleotides of the present invention also include variants in which a different base is present at one or more of the nucleotide positions in the oligonucleotide. For example, if the first nucleotide is an adenosine, variants may be produced which contain thymidine, guanosine or cytidine at this position. This may be done at any of the positions of the oligonucleotide. Thus, a 20-mer may comprise 60 variations (20 positions×3 alternates at each position) in which the original nucleotide is substituted with any of the three alternate nucleotides. These oligonucleotides are then tested using the methods described herein to determine their ability to inhibit expression of HCV mRNA and/or HCV replication.

Conjugates

A further preferred substitution that can be appended to the oligomeric compounds of the invention involves the linkage of one or more moieties or conjugates which enhance the activity, cellular distribution or cellular uptake of the resulting oligomeric compounds. In one embodiment such modified oligomeric compounds are prepared by covalently attaching conjugate groups to functional groups such as hydroxyl or amino groups. Conjugate groups of the invention include intercalators, reporter molecules, polyamines, polyamides, polyethylene glycols, polyethers, groups that enhance the pharmacodynamic properties of oligomers, and groups that enhance the pharmacokinetic properties of oligomers. Typical conjugates groups include cholesterols, lipids, phospholipids, biotin, phenazine, folate, phenanthridine, anthraquinone, acridine, fluoresceins, rhodamines, coumarins, and dyes. Groups that enhance the pharmacodynamic properties, in the context of this invention, include groups that improve oligomer uptake, enhance oligomer resistance to degradation, and/or strengthen sequence-specific hybridization with RNA. Groups that enhance the pharmacokinetic properties, in the context of this invention, include groups that improve oligomer uptake, distribution, metabolism or excretion. Representative conjugate groups are disclosed in International Patent Application PCT/US92/09196, filed Oct. 23, 1992 the entire disclosure of which is incorporated herein by reference. Conjugate moieties include but are not limited to lipid moieties such as a cholesterol moiety (Letsinger et al., *Proc. Natl. Acad. Sci. USA*, 1989, 86, 6553-6556), cholic acid (Manoharan et al., *Bioorg. Med. Chem. Let.*, 1994, 4, 1053-1060), a thioether, e.g., hexyl-S-tritylthiol (Manoharan et al., *Ann. N.Y. Acad. Sci.*, 1992, 660, 306-309; Manoharan et al., *Bioorg. Med. Chem. Let.*, 1993, 3, 2765-2770), a thiocholesterol (Oberhauser et al., *Nucl. Acids Res.*, 1992, 20, 533-538), an aliphatic chain, e.g., dodecandiol or undecyl residues (Saison-Behmoaras et al., *EMBO J.*, 1991, 10, 1111-1118; Kabanov et al., *FEBS Lett.*, 1990, 259, 327-330; Svinarchuk et al., *Biochimie*, 1993, 75, 49-54), a phospholipid, e.g., di-hexadecyl-rac-glycerol or triethyl-ammonium 1,2-di-O-hexadecyl-rac-glycero-3-H-phosphonate (Manoharan et al., *Tetrahedron Lett.*, 1995, 36, 3651-3654; Shea et al., *Nucl. Acids Res.*, 1990, 18, 3777-3783), a polyamine or a polyethylene glycol chain (Manoharan et al., *Nucleosides & Nucleotides*, 1995, 14, 969-973), or adamantane acetic acid (Manoharan et al., *Tetrahedron Lett.*, 1995, 36, 3651-3654), a palmityl moiety (Mishra et al., *Biochim. Biophys. Acta*, 1995, 1264, 229-237), or an octadecylamine or hexylamino-carbonyl-oxycholesterol moiety (Crooke et al., *J. Pharmacol. Exp. Ther.*, 1996, 277, 923-937.

The oligomeric compounds of the invention may also be conjugated to active drug substances, for example, aspirin, warfarin, phenylbutazone, ibuprofen, suprofen, fenbufen, ketoprofen, (S)-(+)-pranoprofen, carprofen, dansylsarcosine, 2,3,5-triiodobenzoic acid, flufenamic acid, folinic acid, a benzothiadiazide, chlorothiazide, a diazepine, indomethicin, a barbiturate, a cephalosporin, a sulfa drug, an antidiabetic, an antibacterial or an antibiotic. Oligonucleotide-drug conjugates and their preparation are described in U.S. Pat. No. 6,656,730 which is incorporated herein by reference in its entirety.

Representative United States patents that teach the preparation of such oligonucleotide conjugates include, but are not limited to, U.S. Pat. Nos. 4,828,979; 4,948,882; 5,218,105; 5,525,465; 5,541,313; 5,545,730; 5,552,538; 5,578,717; 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241; 5,391,723; 5,416,203; 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941, certain of which are commonly owned with the instant application, and each of which is herein incorporated by reference.

Chimeric Oligomeric Compounds

It is not necessary for all positions in an oligomeric compound to be uniformly modified, and in fact more than one of the aforementioned modifications may be incorporated in a single oligomeric compound or even at a single monomeric subunit such as a nucleoside within a oligomeric compound.

The present invention also includes oligomeric compounds which are chimeric oligomeric compounds. "Chimeric" oligomeric compounds or "chimeras," in the context of this invention, are oligomeric compounds that contain two or more chemically distinct regions, each made up of at least one monomer unit, i.e., a nucleotide in the case of a nucleic acid based oligomer.

Chimeric oligomeric compounds typically contain at least one region modified so as to confer increased resistance to nuclease degradation, increased cellular uptake, and/or increased binding affinity for the target nucleic acid. An additional region of the oligomeric compound may serve as a substrate for enzymes capable of cleaving RNA:DNA or RNA:RNA hybrids. By way of example, RNase H is a cellular endonuclease which cleaves the RNA strand of an RNA:DNA duplex. Activation of RNase H, therefore, results in cleavage of the RNA target, thereby greatly enhancing the efficiency of inhibition of gene expression. Consequently, comparable results can often be obtained with shorter oligomeric compounds when chimeras are used, compared to for example phosphorothioate deoxyoligonucleotides hybridizing to the same target region. Cleavage of the RNA target can be routinely detected by gel electrophoresis and, if necessary, associated nucleic acid hybridization techniques known in the art.

Chimeric oligomeric compounds of the invention may be formed as composite structures of two or more oligonucleotides, oligonucleotide analogs, oligonucleosides and/or oligonucleotide mimetics as described above. Such oligomeric compounds have also been referred to in the art as hybrids hemimers, gapmers or inverted gapmers. Representative United States patents that teach the preparation of such hybrid structures include, but are not limited to, U.S. Pat. Nos. 5,013,830; 5,149,797; 5,220,007; 5,256,775; 5,366,878; 5,403,711; 5,491,133; 5,565,350; 5,623,065; 5,652,355; 5,652,356; and 5,700,922, certain of which are commonly owned with the instant application, and each of which is herein incorporated by reference in its entirety.

3'-endo Modifications

In one aspect of the present invention oligomeric compounds include nucleosides synthetically modified to induce a 3'-endo sugar conformation. A nucleoside can incorporate synthetic modifications of the heterocyclic base, the sugar moiety or both to induce a desired 3'-endo sugar conformation. These modified nucleosides are used to mimic RNA like nucleosides so that particular properties of an oligomeric compound can be enhanced while maintaining the desirable 3'-endo conformational geometry. There is an apparent preference for an RNA type duplex (A form helix, predominantly 3'-endo) as a requirement (e.g. trigger) of RNA interference which is supported in part by the fact that duplexes composed of 2'-deoxy-2'-F-nucleosides appears efficient in triggering RNAi response in the *C. elegans* system. Properties that are enhanced by using more stable 3'-endo nucleosides include but aren't limited to modulation of pharmacokinetic properties through modification of protein binding, protein off-rate, absorption and clearance; modulation of nuclease stability as well as chemical stability; modulation of the binding affinity and specificity of the oligomer (affinity and specificity for enzymes as well as for complementary sequences); and increasing efficacy of RNA cleavage. The present invention provides oligomeric triggers of RNAi having one or more nucleosides modified in such a way as to favor a C3'-endo type conformation.

SCHEME 1

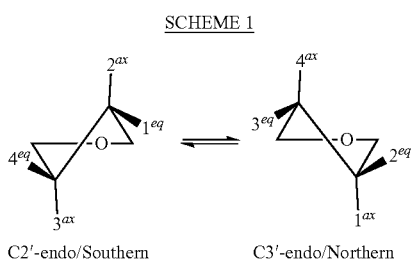

C2'-endo/Southern     C3'-endo/Northern

Figure 2:
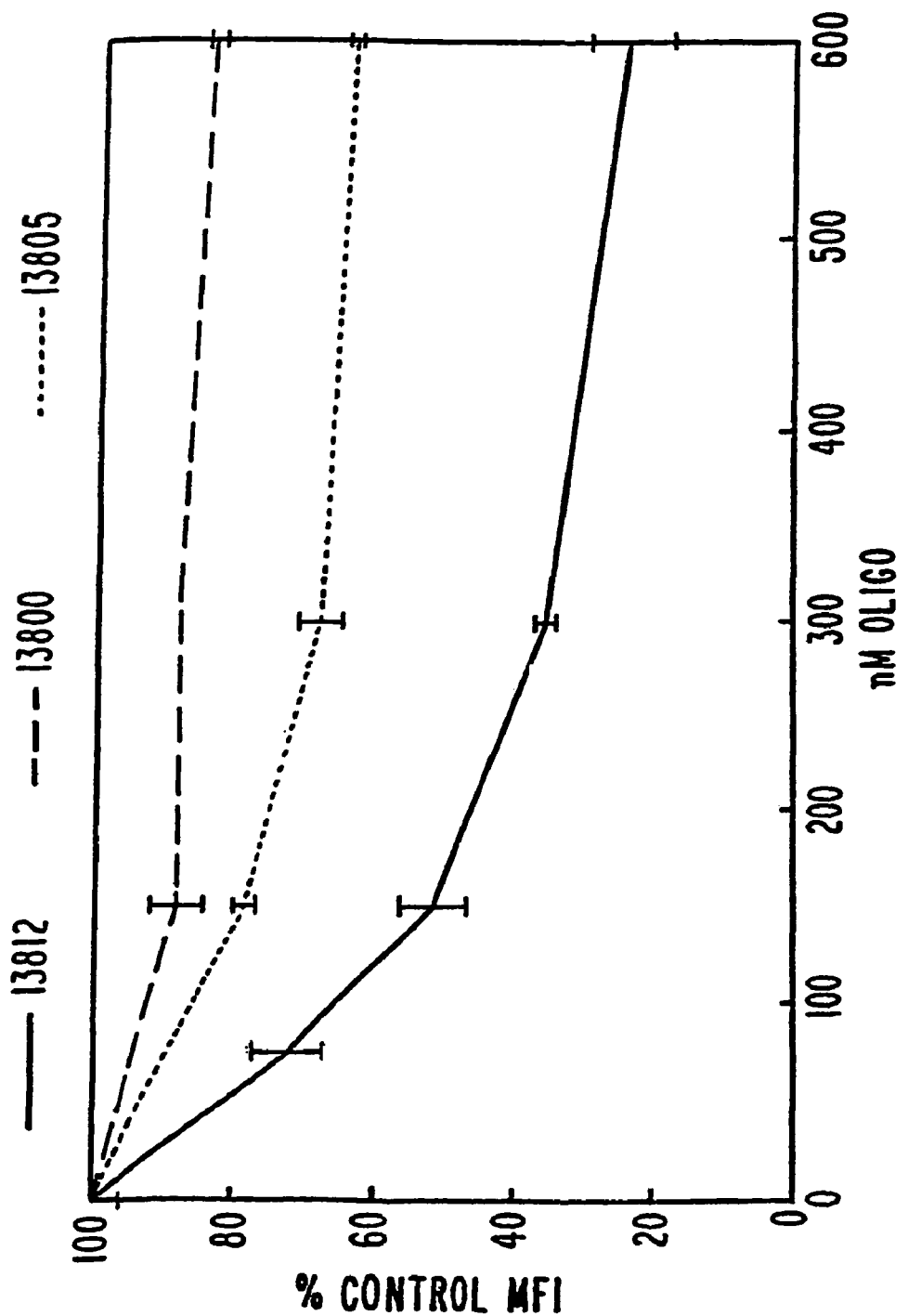
FIG. 2 is a dose-response curve showing the inhibitory effect of oligonucleotides on cell surface expression of B7-1 protein. Solid line, ISIS 13812; dashed line, ISIS 13800; dotted line, ISIS 13805.

Nucleoside conformation is influenced by various factors including substitution at the 2', 3' or 4'-positions of the pentofuranosyl sugar. Electronegative substituents generally prefer the axial positions, while sterically demanding substituents generally prefer the equatorial positions (Principles of Nucleic Acid Structure, Wolfgang Sanger, 1984, Springer-Verlag.) Modification of the 2' position to favor the 3'-endo conformation can be achieved while maintaining the 2'-OH as a recognition element, as illustrated in FIG. 2, below (Gallo et al., Tetrahedron (2001), 57, 5707-5713. Harry-O'kuru et al., J. Org. Chem., (1997), 62(6), 1754-1759 and Tang et al., J. Org. Chem. (1999), 64, 747-754.) Alternatively, preference for the 3'-endo conformation can be achieved by deletion of the 2'-OH as exemplified by 2'deoxy-2°F-nucleosides (Kawasaki et al., J. Med. Chem. (1993), 36, 831-841), which adopts the 3'-endo conformation positioning the electronegative fluorine atom in the axial position. Other modifications of the ribose ring, for example substitution at the 4'-position to give 4'-F modified nucleosides (Guillerm et al., Bioorganic and Medicinal Chemistry Letters (1995), 5, 1455-1460 and Owen et al., J. Org. Chem. (1976), 41, 3010-3017), or for example modification to yield methanocarba nucleoside analogs (Jacobson et al., J. Med. Chem. Lett. (2000), 43, 2196-2203 and Lee et al., Bioorganic and Medicinal Chemistry Letters (2001), 11, 1333-1337) also induce preference for the 3'-endo conformation. Along similar lines, oligomeric triggers of RNAi response might be composed of one or more nucleosides modified in such a way that conformation is locked into a C3'-endo type conformation, i.e. Locked Nucleic Acid (LNA, Singh et al, Chem. Commun. (1998), 4, 455-456), and ethylene bridged Nucleic Acids (ENA, Morita et al, Bioorganic & Medicinal Chemistry Letters (2002); 12, 73-76.) Examples of modified nucleosides amenable to the present invention are shown below in Table I. These examples are meant to be representative and not exhaustive.

TABLE I

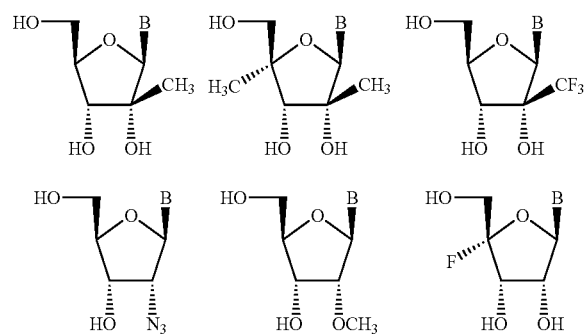

TABLE I-continued

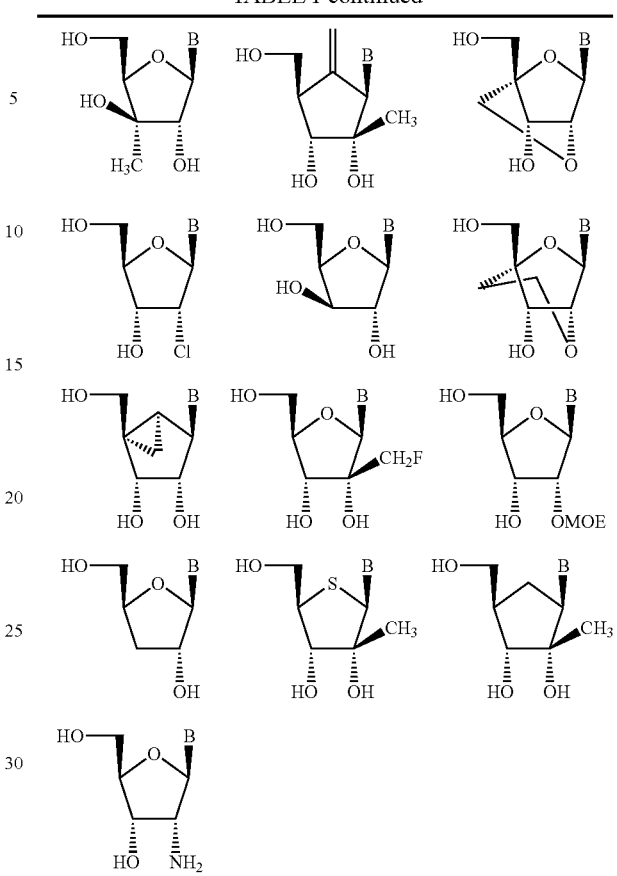

The preferred conformation of modified nucleosides and their oligomers can be estimated by various methods such as molecular dynamics calculations, nuclear magnetic resonance spectroscopy and CD measurements. Hence, modifications predicted to induce RNA like conformations, A-form duplex geometry in an oligomeric context, are selected for use in the modified oligoncleotides of the present invention. The synthesis of numerous of the modified nucleosides amenable to the present invention are known in the art (see for example, Chemistry of Nucleosides and Nucleotides Vol 1-3, ed. Leroy B. Townsend, 1988, Plenum press., and the examples section below.) Nucleosides known to be inhibitors/substrates for RNA dependent RNA polymerases (for example HCV NS5B).

In one aspect, the present invention is directed to oligonucleotides that are prepared having enhanced properties compared to native RNA against nucleic acid targets. A target is identified and an oligonucleotide is selected having an effective length and sequence that is complementary to a portion of the target sequence. Each nucleoside of the selected sequence is scrutinized for possible enhancing modifications. A preferred modification would be the replacement of one or more RNA nucleosides with nucleosides that have the same 3'-endo conformational geometry. Such modifications can enhance chemical and nuclease stability relative to native RNA while at the same time being much cheaper and easier to synthesize and/or incorporate into an oligonulceotide. The selected sequence can be further divided into regions and the nucleosides of each region evaluated for enhancing modifications that can be the result of a chimeric configuration. Consideration is also given to the 5' and 3'-termini as there are often advantageous modifications that can be made to one or more of the terminal nucleosides. The oligomeric compounds of the present invention include at least one 5'-modified phosphate group on a single strand or on at least one 5'-position of a double stranded sequence or sequences. Further modifications are also considered such as internucleoside linkages, conjugate groups, substitute sugars or bases, substitution of one or more nucleosides with nucleoside mimetics and any other modification that can enhance the selected sequence for its intended target. The terms used to describe the conformational geometry of homoduplex nucleic acids are "A Form" for RNA and "B Form" for DNA. The respective conformational geometry for RNA and DNA duplexes was determined from X-ray diffraction analysis of nucleic acid fibers (Arnott and Hukins, *Biochem. Biophys. Res. Comm.*, 1970, 47, 1504.) In general, RNA:RNA duplexes are more stable and have higher melting temperatures (Tm's) than DNA:DNA duplexes (Sanger et al., Principles of Nucleic Acid Structure, 1984, Springer-Verlag; New York, N.Y.; Lesnik et al., Biochemistry, 1995, 34, 10807-10815; Conte et al., Nucleic Acids Res., 1997, 25, 2627-2634). The increased stability of RNA has been attributed to several structural features, most notably the improved base stacking interactions that result from an A-form geometry (Searle et al., Nucleic Acids Res., 1993, 21, 2051-2056). The presence of the 2' hydroxyl in RNA biases the sugar toward a C3' endo pucker, i.e., also designated as Northern pucker, which causes the duplex to favor the A-form geometry. In addition, the 2' hydroxyl groups of RNA can form a network of water mediated hydrogen bonds that help stabilize the RNA duplex (Egli et al., Biochemistry, 1996, 35, 8489-8494). On the other hand, deoxy nucleic acids prefer a C2' endo sugar pucker, i.e., also known as Southern pucker, which is thought to impart a less stable B-form geometry (Sanger, W. (1984) Principles of Nucleic Acid Structure, Springer-Verlag, New York, N.Y.). As used herein, B-form geometry is inclusive of both C2'-endo pucker and O4'-endo pucker. This is consistent with Berger, et. al., *Nucleic Acids Research*, 1998, 26, 2473-2480, who pointed out that in considering the furanose conformations which give rise to B-form duplexes consideration should also be given to a O4'-endo pucker contribution.

DNA:RNA hybrid duplexes, however, are usually less stable than pure RNA:RNA duplexes, and depending on their sequence may be either more or less stable than DNA:DNA duplexes (Searle et al., *Nucleic Acids Res.*, 1993, 21, 2051-2056). The structure of a hybrid duplex is intermediate between A- and B-form geometries, which may result in poor stacking interactions (Lane et al., *Eur. J. Biochem.*, 1993, 215, 297-306; Fedoroff et al., *J. Mol. Biol.*, 1993, 233, 509-523; Gonzalez et al., *Biochemistry*, 1995, 34, 4969-4982; Horton et al., *J. Mol. Biol.*, 1996, 264, 521-533). The stability of the duplex formed, between a target RNA and a synthetic sequence is central to therapies such as but not limited to antisense and RNA interference as these mechanisms require the binding of a synthetic oligonucleotide strand to an RNA target strand. In the case of antisense, effective inhibition of the mRNA requires that the antisense DNA have a very high binding affinity with the mRNA. Otherwise the desired interaction between the synthetic oligonucleotide strand and target mRNA strand will occur infrequently, resulting in decreased efficacy.

One routinely used method of modifying the sugar puckering is the substitution of the sugar at the 2'-position with a substituent group that influences the sugar geometry. The influence on ring conformation is dependent on the nature of the substituent at the 2'-position. A number of different substituents have been studied to determine their sugar puckering effect. For example, 2'-halogens have been studied showing that the 2'-fluoro derivative exhibits the largest population (65%) of the C3'-endo form, and the 2'-iodo exhibits the lowest population (7%). The populations of adenosine (2'-OH) versus deoxyadenosine (2'-H) are 36% and 19%, respectively. Furthermore, the effect of the 2'-fluoro group of adenosine dimers (2'-deoxy-2'-fluoroadenosine-2'-deoxy-2'-fluoro-adenosine) is further correlated to the stabilization of the stacked conformation.

As expected, the relative duplex stability can be enhanced by replacement of 2'-OH groups with 2'-F groups thereby increasing the C3'-endo population. It is assumed that the highly polar nature of the 2'-F bond and the extreme preference for C3'-endo puckering may stabilize the stacked conformation in an A-form duplex. Data from UV hypochromicity, circular dichroism, and $^1$H NMR also indicate that the degree of stacking decreases as the electronegativity of the halo substituent decreases. Furthermore, steric bulk at the 2'-position of the sugar moiety is better accommodated in an A-form duplex than a B-form duplex. Thus, a 2'-substituent on the 3'-terminus of a dinucleoside monophosphate is thought to exert a number of effects on the stacking conformation: steric repulsion, furanose puckering preference, electrostatic repulsion, hydrophobic attraction, and hydrogen bonding capabilities. These substituent effects are thought to be determined by the molecular size, electronegativity, and hydrophobicity of the substituent. Melting temperatures of complementary strands is also increased with the 2'-substituted adenosine diphosphates. It is not clear whether the 3'-endo preference of the conformation or the presence of the substituent is responsible for the increased binding. However, greater overlap of adjacent bases (stacking) can be achieved with the 3'-endo conformation.

One synthetic 2'-modification that imparts increased nuclease resistance and a very high binding affinity to nucleotides is the 2'-MOE modification (Baker et al., *J. Biol. Chem.*, 1997, 272, 11944-12000). One of the immediate advantages of the 2'-MOE substitution is the improvement in binding affinity, which is greater than many similar 2' modifications such as O-methyl, O-propyl, and O-aminopropyl. Oligonucleotides having the 2'-MOE substituent also have been shown to be antisense inhibitors of gene expression with promising features for in vivo use (Martin, P., *Hel V. Chim. Acta*, 1995, 78, 486-504; Altmann et al., *Chimia*, 1996, 50, 168-176; Altmann et al., *Biochem. Soc. Trans.*, 1996, 24, 630-637; and Altmann et al., *Nucleosides Nucleotides*, 1997, 16, 917-926). Relative to DNA, the oligonucleotides having the 2'-MOE modification displayed improved RNA affinity and higher nuclease resistance. Chimeric oligonucleotides having 2'-MOE substituents in the wing nucleosides and an internal region of deoxy-phosphorothioate nucleotides (also termed a gapped oligonucleotide or gapmer) have shown effective reduction in the growth of tumors in animal models at low doses. 2'-MOE substituted oligonucleotides have also shown outstanding promise as antisense agents in several disease states. One such MOE substituted oligonucleotide is on the market for the treatment of CMV retinitis.

Chemistries Defined

Unless otherwise defined herein, alkyl means $C_1$-$C_{12}$, preferably $C_1$-$C_8$, and more preferably $C_1$-$C_6$, straight or (where possible) branched chain aliphatic hydrocarbyl.

Unless otherwise defined herein, heteroalkyl means $C_1$-$C_{12}$, preferably $C_1$-$C_8$, and more preferably $C_1$-$C_6$, straight or (where possible) branched chain aliphatic hydrocarbyl containing at least one, and preferably about 1 to about 3, heteroatoms in the chain, including the terminal portion of the chain. Preferred heteroatoms include N, O and S.

Unless otherwise defined herein, cycloalkyl means $C_3$-$C_{12}$, preferably $C_3$-$C_8$, and more preferably $C_3$-$C_6$, aliphatic hydrocarbyl ring.

Unless otherwise defined herein, alkenyl means $C_2$-$C_{12}$, preferably $C_2$-$C_8$, and more preferably $C_2$-$C_6$ alkenyl, which may be straight or (where possible) branched hydrocarbyl moiety, which contains at least one carbon-carbon double bond.

Unless otherwise defined herein, alkynyl means $C_2$-$C_{12}$, preferably $C_2$-$C_8$, and more preferably $C_2$-$C_6$ alkynyl, which may be straight or (where possible) branched hydrocarbyl moiety, which contains at least one carbon-carbon triple bond.

Unless otherwise defined herein, heterocycloalkyl means a ring moiety containing at least three ring members, at least one of which is carbon, and of which 1, 2 or three ring members are other than carbon. Preferably the number of carbon atoms varies from 1 to about 12, preferably 1 to about 6, and the total number of ring members varies from three to about 15, preferably from about 3 to about 8. Preferred ring heteroatoms are N, O and S. Preferred heterocycloalkyl groups include morpholino, thiomorpholino, piperidinyl, piperazinyl, homopiperidinyl, homopiperazinyl, homomorpholino, homothiomorpholino, pyrrolodinyl, tetrahydrooxazolyl, tetrahydroimidazolyl, tetrahydrothiazolyl, tetrahydroisoxazolyl, tetrahydropyrrazolyl, furanyl, pyranyl, and tetrahydroisothiazolyl.

Unless otherwise defined herein, aryl means any hydrocarbon ring structure containing at least one aryl ring. Preferred aryl rings have about 6 to about 20 ring carbons. Especially preferred aryl rings include phenyl, napthyl, anthracenyl, and phenanthrenyl.

Unless otherwise defined herein, hetaryl means a ring moiety containing at least one fully unsaturated ring, the ring consisting of carbon and non-carbon atoms. Preferably the ring system contains about 1 to about 4 rings. Preferably the number of carbon atoms varies from 1 to about 12, preferably 1 to about 6, and the total number of ring members varies from three to about 15, preferably from about 3 to about 8. Preferred ring heteroatoms are N, O and S. Preferred hetaryl moieties include pyrazolyl, thiophenyl, pyridyl, imidazolyl, tetrazolyl, pyridyl, pyrimidinyl, purinyl, quinazolinyl, quinoxalinyl, benzimidazolyl, benzothiophenyl, etc.

Unless otherwise defined herein, where a moiety is defined as a compound moiety, such as hetarylalkyl (hetaryl and alkyl), aralkyl (aryl and alkyl), etc., each of the sub-moieties is as defined herein.

Unless otherwise defined herein, an electron withdrawing group is a group, such as the cyano or isocyanato group that draws electronic charge away from the carbon to which it is attached. Other electron withdrawing groups of note include those whose electronegativities exceed that of carbon, for example halogen, nitro, or phenyl substituted in the ortho- or para-position with one or more cyano, isothiocyanato, nitro or halo groups.

Unless otherwise defined herein, the terms halogen and halo have their ordinary meanings. Preferred halo (halogen) substituents are Cl, Br, and I.

The aforementioned optional substituents are, unless otherwise herein defined, suitable substituents depending upon desired properties. Included are halogens (Cl, Br, I), alkyl, alkenyl, and alkynyl moieties, $NO_2$, $NH_3$ (substituted and unsubstituted), acid moieties (e.g. —$CO_2H$, —$OSO_3H_2$, etc.), heterocycloalkyl moieties, hetaryl moieties, aryl moieties, etc.

In all the preceding formulae, the squiggle (~) indicates a bond to an oxygen or sulfur of the 5'-phosphate.

Phosphate protecting groups include those described in U.S. Pat. Nos. 5,760,209, 5,614,621, 6,051,699, 6,020,475, 6,326,478, 6,169,177, 6,121,437, 6,465,628 each of which is expressly incorporated herein by reference in its entirety.

The oligonucleotides in accordance with this invention (single stranded or double stranded) preferably comprise from about 8 to about 80 nucleotides, more preferably from about 8 to about 50, even more preferably from about 12-50 nucleotides and most preferably from about 15 to 30 nucleotides. As is known in the art, a nucleotide is a base-sugar combination suitably bound to an adjacent nucleotide through a phosphodiester, phosphorothioate or other covalent linkage.

The oligonucleotides of the present invention also include variants in which a different base is present at one or more of the nucleotide positions in the oligonucleotide. For example, if the first nucleotide is an adenosine, variants may be produced which contain thymidine, guanosine or cytidine at this position. This may be done at any of the positions of the oligonucleotide. Thus, a 20-mer may comprise 60 variations (20 positions×3 alternates at each position) in which the original nucleotide is substituted with any of the three alternate nucleotides. These oligonucleotides are then tested using the methods described herein to determine their ability to inhibit expression of B7.1 or B7.2 mRNA.

The term "pharmaceutically acceptable salts" refers to physiologically and pharmaceutically acceptable salts of the compounds of the invention: i.e., salts that retain the desired biological activity of the parent compound and do not impart undesirable toxicological effects thereto.

Pharmaceutically acceptable base addition salts are formed with metals or amines, such as alkali and alkaline earth metals or organic amines. Examples of metals used as cations are sodium, potassium, magnesium, calcium and the like. Examples of suitable amines are N,N'-dibenzylethylenediamine, chloroprocaine, choline, diethanolamine, dicyclohexylamine, ethylenediamine, N-methylglucamine and procaine (see, for example, Berge et al., "Pharmaceutical Salts," J. of Pharma Sci., 1977, 66, 1-19). Sodium salts are especially preferred pharmaceutically acceptable salts of the compounds of the present invention.

The oligonucleotides used in accordance with this invention may be conveniently and routinely made through the well-known technique of solid phase synthesis. Equipment for such synthesis is sold by several vendors including, for example, Applied Biosystems (Foster City, Calif.). Any other means for such synthesis known in the art may additionally or alternatively be employed. It is also known to use similar techniques to prepare other oligonucleotides such as the phosphorothioates and alkylated derivatives.

The oligonucleotides of the present invention can be utilized as therapeutic compounds, diagnostic tools and as research reagents and kits. The term Atherapeutic uses@ is intended to encompass prophylactic, palliative and curative uses wherein the oligonucleotides of the invention are contacted with animal cells either in vivo or ex vivo. When contacted with animal cells ex vivo, a therapeutic use includes incorporating such cells into an animal after treatment with one or more oligonucleotides of the invention. While not intending to be bound to a particular utility, the ex vivo modulation of, e.g., T cell proliferation by the oligonucleotides of the invention can be employed in, for example, potential therapeutic modalities wherein it is desired to modulate the expression of a B7 protein in APCs.

As an example, oligonucleotides that inhibit the expression of B7-1 proteins are expected to enhance the availability of B7-2 proteins on the surface of APCs, thus increasing the costimulatory effect of B7-2 on T cells ex vivo (Levine et al., *Science,* 1996, 272, 1939).

For therapeutic uses, an animal suspected of having a disease or disorder which can be treated or prevented by modulating the expression or activity of a B7 protein is, for example, treated by administering oligonucleotides in accordance with this invention. The oligonucleotides of the invention can be utilized in pharmaceutical compositions by adding an effective amount of an oligonucleotide to a suitable pharmaceutically acceptable diluent or carrier. Workers in the field have identified antisense, triplex and other oligonucleotide compositions which are capable of modulating expression of genes implicated in viral, fungal and metabolic diseases. Antisense oligonucleotides have been safely administered to humans and several clinical trials are presently underway. It is thus established that oligonucleotides can be useful therapeutic instrumentalities that can be configured to be useful in treatment regimes for treatment of cells, tissues and animals, especially humans.

The oligonucleotides of the present invention can be further used to detect the presence of B7-specific nucleic acids in a cell or tissue sample. For example, radiolabeled oligonucleotides can be prepared by $^{32}$P labeling at the 5' end with polynucleotide kinase (Sambrook et al., *Molecular Cloning. A Laboratory Manual,* Cold Spring Harbor Laboratory Press, 1989, Volume 2, pg. 10.59). Radiolabeled oligonucleotides are then contacted with cell or tissue samples suspected of containing B7 message RNAs (and thus B7 proteins), and the samples are washed to remove unbound oligonucleotide. Radioactivity remaining in the sample indicates the presence of bound oligonucleotide, which in turn indicates the presence of nucleic acids complementary to the oligonucleotide, and can be quantitated using a scintillation counter or other routine means. Expression of nucleic acids encoding these proteins is thus detected.

Radiolabeled oligonucleotides of the present invention can also be used to perform autoradiography of tissues to determine the localization, distribution and quantitation of B7 proteins for research, diagnostic or therapeutic purposes. In such studies, tissue sections are treated with radiolabeled oligonucleotide and washed as described above, then exposed to photographic emulsion according to routine autoradiography procedures. The emulsion, when developed, yields an image of silver grains over the regions expressing a B7 gene. Quantitation of the silver grains permits detection of the expression of mRNA molecules encoding these proteins and permits targeting of oligonucleotides to these areas.

Analogous assays for fluorescent detection of expression of B7 nucleic acids can be developed using oligonucleotides of the present invention which are conjugated with fluorescein or other fluorescent tags instead of radiolabeling. Such conjugations are routinely accomplished during solid phase synthesis using fluorescently-labeled amidites or controlled pore glass (CPG) columns. Fluorescein-labeled amidites and CPG are available from, e.g., Glen Research, Sterling Va.

The present invention employs oligonucleotides targeted to nucleic acids encoding B7 proteins and oligonucleotides targeted to nucleic acids encoding such proteins. Kits for detecting the presence or absence of expression of a B7 protein may also be prepared. Such kits include an oligonucleotide targeted to an appropriate gene, i.e., a gene encoding a B7 protein. Appropriate kit and assay formats, such as, e.g., "sandwich" assays, are known in the art and can easily be adapted for use with the oligonucleotides of the invention.

Hybridization of the oligonucleotides of the invention with a nucleic acid encoding a B7 protein can be detected by means known in the art. Such means may include conjugation of an enzyme to the oligonucleotide, radiolabelling of the oligonucleotide or any other suitable detection systems. Kits for detecting the presence or absence of a B7 protein may also be prepared.

The formulation of therapeutic compositions and their subsequent administration is believed to be within the skill of those in the art. In general, for therapeutics, a patient in need of such therapy is administered an oligonucleotide in accordance with the invention, commonly in a pharmaceutically acceptable carrier, in doses ranging from 0.01 ug to 100 g per kg of body weight depending on the age of the patient and the severity of the disorder or disease state being treated. Further, the treatment regimen may last for a period of time which will vary depending upon the nature of the particular disease or disorder, its severity and the overall condition of the patient, and may extend from once daily to once every 20 years. Following treatment, the patient is monitored for changes in his/her condition and for alleviation of the symptoms of the disorder or disease state. The dosage of the oligonucleotide may either be increased in the event the patient does not respond significantly to current dosage levels, or the dose may be decreased if an alleviation of the symptoms of the disorder or disease state is observed, or if the disorder or disease state has been ablated.

In some cases, it may be more effective to treat a patient with an oligonucleotide of the invention in conjunction with other therapeutic modalities in order to increase the efficacy of a treatment regimen. In the context of the invention, the term Atreatment regimen@ is meant to encompass therapeutic, palliative and prophylactic modalities. In one embodiment, the oligonucleotides of the invention are used in conjunction with an anti-inflammatory and/or immunosuppressive agent, preferably one or more antisense oligonucleotides targeted to an intercellular adhesion molecule (ICAM) (E.g., ICAM-1). Other anti-inflammatory and/or immunosuppressive agents that may be used in combination with the oligonucleotides of the invention include, but are not limited to, soluble ICAM proteins (e.g., sICAM-1), antibody-toxin conjugates, prednisone, methylprednisolone, azathioprine, cyclophosphamide, cyclosporine, interferons, sympathomimetics, conventional antihistamines (histamine $H_1$ receptor antagonists, including, for example, brompheniramine maleate, chlorpheniramine maleate, dexchlorpheniramine maleate, tripolidine HCl, carbinoxamine maleate, clemastine fumarate, dimenhydrinate, diphenhydramine HCl, diphenylpyraline HCl, doxylamine succinate, tripelennamine citrate, tripelennamine HCl, cyclizine HCl, hydroxyzine HCl, meclizine HCl, methdilazine HCl, promethazine HCl, trimeprazine tartrate, azatadine maleate, cyproheptadine HCl, terfenadine, etc.), histamine $H_2$ receptor antagonists (e.g., ranitidine). See, generally, *The Merck Manual of Diagnosis and Therapy,* 15th Ed., Berkow et al., eds., 1987, Rahway, N.J., pages 302-336 and 2516-2522). When used with the compounds of the invention, such agents may be used individually, sequentially, or in combination with one or more other such agents.

In another preferred embodiment of the invention, an antisense oligonucleotide targeted to one B7 mRNA species (e.g., B7-1) is used in combination with an antisense oligonucleotide targeted to a second B7 mRNA species (e.g., B7-2) in order to inhibit the costimulatory effect of B7 molecules to a more extensive degree than can be achieved with either oligonucleotide used individually. In a related version of this embodiment, two or more oligonucleotides of the invention, each targeted to an alternatively spliced B7-1 or B7-2 mRNA, are combined with each other in order to inhibit expression of both forms of the alternatively spliced mRNAs. It is known in the art that, depending on the specificity of the modulating agent employed, inhibition of one form of an alternatively spliced mRNA may not result in a sufficient reduction of expression for a given condition to be manifest. Thus, such combinations may, in some instances, be desired to inhibit the expression of a particular B7 gene to an extent necessary to practice one of the methods of the invention.

Following successful treatment, it may be desirable to have the patient undergo maintenance therapy to prevent the recurrence of the disease state, wherein the oligonucleotide is administered in maintenance doses, ranging from 0.01 Φg to 100 g per kg of body weight, once or more daily, to once every 20 years. In the case of in individual known or suspected of being prone to an autoimmune or inflammatory condition, prophylactic effects may be achieved by administration of preventive doses, ranging from 0.01 Φg to 100 g per kg of body weight, once or more daily. In like fashion, an individual may be made less susceptible to an inflammatory condition that is expected to occur as a result of some medical treatment, e.g., graft versus host disease resulting from the transplantation of cells, tissue or an organ into the individual.

The pharmaceutical compositions of the present invention may be administered in a number of ways depending upon whether local or systemic treatment is desired and upon the area to be treated. Administration may be topical (including ophthalmic and to mucous membranes including vaginal and rectal delivery), pulmonary, e.g., by inhalation or insufflation of powders or aerosols, including by nebulizer, dry powder inhaler, or metered dose inhaler; intratracheal, intranasal, epidermal and transdermal, oral or parenteral. Pulmonary administration methods are described in more detail below.

Metered Dose Inhalers, MDI or pMDI.

This delivery system is the most widely used, and accounts for about 70-80% of the pulmonary delivery systems used worldwide and have been approved since the 1950's. MDI is based typically (except for QVARS which is a solution of beclomethasone DP in a mixture of ethanol and HFA 134a) on a suspension of a micronized drug in a CFC or HFA liquid under high pressure. The drug is metered through a small chamber in the valve (typically 25-150 μL, most common 50 μL) and the suspension/HFA is aerosolized from the valve upon actuation and delivered as a dry powder, due to the evaporation of the propellant. This device typically can have suspension concentrations of up to 2% solids in suspension, which will be able to deliver about 1 mg/puff of active to the airways.

Nebulization—Continuous Nebulizers (Jet and Ultrasonic)

This delivery system typically comprises a continuous generation of an aerosol cloud from a solution or a suspension in water by a stream of compressed air (jet nebulizers) or by a ultrasound energy (ultrasonic nebulizers). Dosing is based on the time that the individual is exposed to the aerosol cloud and on the concentration of the drug in the solution or suspension. The patient or clinician is responsible for the preparation of the unit before and after dosing. Nebulizers continuously release drug throughout the respiratory cycle, but output is increased during inspiration in response to the patient's breathing. Large amounts of drug can be delivered to the airways. Some nebulizera detect pressure changes during breathing and constantly adapt to the inspiratory and expiratory flow pattern of the patient.

Dry Powder Inhaler, DPI

Dry powder inhalers consist of a finely divided dry powder contained in a reservoir or in a metered unit dose that upon actuation (by inspiratory force—these devices are called passive DPI, or by energy provided by the device—these devices are called active DPI) will generate a plume of aerosolized powder particles that will be inhaled. The DPI available can deliver up to a dose of 20-30 mg of active to the airways (Nektar and Alkermes) per puff.

Single Dose Nebulizers.

These devices have the way of metering the dose or have the doses pre-metered in unit dosage packages. The aerosol is generated from an aqueous solution or suspension by energy provided by the device and some of them are breath actuated, which means that the dosing will only occur when the right inspiratory flow rate is achieve to ensure proper dosing. The unit doses are typically 50-150 μL per dose, so depending on the solution concentration a dose of 10 to 20 mg per puff to the airways based on a solution concentration of around 150 mg/mL and a efficiency of around 60%.

Parenteral administration includes intravenous, intraarterial, subcutaneous, intraperitoneal or intramuscular injection or infusion; or intracranial, e.g., intrathecal or intraventricular, administration. Oligonucleotides with at least one 2'-MOE modification are believed to be particularly useful for oral administration.

Formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable. Coated condoms, gloves and the like may also be useful.

Compositions for oral administration include powders or granules, suspensions or solutions in water or non-aqueous media, capsules, sachets or tablets. Thickeners, flavoring agents, diluents, emulsifiers, dispersing aids or binders may be desirable. Compositions for oral administration also include pulsatile delivery compositions and bioadhesive composition as described in Publication Numbers US2003-124196 and US2003-0083286, the entire disclosures of which are incorporated herein by reference.

Compositions for parenteral, intrathecal or intraventricular administration may include sterile aqueous solutions which may also contain buffers, diluents and other suitable additives.

Dosing is dependent on severity and responsiveness of the disease state to be treated, with the course of treatment lasting from several days to several months, or until a cure is effected or a diminution of the disease state is achieved. Optimal dosing schedules can be calculated from measurements of drug accumulation in the body of the patient. Persons of ordinary skill can easily determine optimum dosages, dosing methodologies and repetition rates. Optimum dosages may vary depending on the relative potency of individual oligonucleotides, and can generally be estimated based on $EC_{50}$s found to be effective in in vitro and in vivo animal models. In general, dosage is from 0.01 ug to 100 g per kg of body weight, and may be given once or more daily, weekly, monthly or yearly, or even once every 2 to 20 years.

The following examples illustrate the invention and are not intended to limit the same. Those skilled in the art will recognize, or be able to ascertain through routine experimentation, numerous equivalents to the specific substances and procedures described herein. Such equivalents are considered to be within the scope of the present invention.

The following examples are provided for illustrative purposes only and are not intended to limit the invention.

EXAMPLES

Example 1

Synthesis of Nucleic Acids Oligonucleotides

Oligonucleotides were synthesized on an automated DNA synthesizer using standard phosphoramidite chemistry with oxidation using iodine. β-Cyanoethyldiisopropyl phosphoramidites were purchased from Applied Biosystems (Foster City, Calif.). For phosphorothioate oligonucleotides, the standard oxidation bottle was replaced by a 0.2 M solution of 3H-1,2-benzodithiole-3-one,1,1-dioxide in acetonitrile for the stepwise thiation of the phosphite linkages. The thiation cycle wait step was increased to 68 seconds and was followed by the capping step.

The 2'-fluoro phosphorothioate oligonucleotides of the invention were synthesized using 5'-dimethoxytrityl-3'-phosphoramidites and prepared as disclosed in U.S. patent application Ser. No. 463,358, filed Jan. 11, 1990, and Ser. No. 566,977, filed Aug. 13, 1990, which are assigned to the same assignee as the instant application and which are incorporated by reference herein. The 2'-fluoro oligonucleotides were prepared using phosphoramidite chemistry and a slight modification of the standard DNA synthesis protocol: deprotection was effected using methanolic ammonia at room temperature.

The 2'-methoxy (2'-O-methyl) oligonucleotides of the invention were synthesized using 2'-methoxy β-cyanoethyldiisopropyl-phosphoramidites (Chemgenes, Needham Mass.) and the standard cycle for unmodified oligonucleotides, except the wait step after pulse delivery of tetrazole and base is increased to 360 seconds. Other 2'-alkoxy oligonucleotides are synthesized by a modification of this method, using appropriate 2'-modified amidites such as those available from Glen Research, Inc., Sterling, Va. The 3'-base used to start the synthesis was a 2'-deoxyribonucleotide. The 2'-O-propyl oligonucleotides of the invention are prepared by a slight modification of this procedure.

The 2'-MOE oligonucleotides of the invention were synthesized according to the method of Martin, *Helv. Chim. Acta* 1995, 78, 486. For ease of synthesis, the last nucleotide was a deoxynucleotide. All 2'-MOE cytosines were 5-methyl cytosines, which were synthesized according to the following procedures.

Synthesis of 5-Methyl Cytosine Monomers:

2,2'-Anhydro[-(β-D-arabinofuranosyl)-5-methyluridine]

5-Methyluridine (ribosylthymine, commercially available. through Yamasa, Choshi, Japan) (72.0 g, 0.279 M), diphenylcarbonate (90.0 g, 0.420 M) and sodium bicarbonate (2.0 g, 0.024 M) were added to DMF (300 mL). The mixture was heated to reflux, with stirring, allowing the evolved carbon dioxide gas to be released in a controlled manner. After 1 hour, the slightly darkened solution was concentrated under reduced pressure. The resulting syrup was poured into diethylether (2.5 L), with stirring. The product formed a gum. The ether was decanted and the residue was dissolved in a minimum amount of methanol (ca. 400 mL). The solution was poured into fresh ether (2.5 L) to yield a stiff gum. The ether was decanted and the gum was dried in a vacuum oven (60° C. at 1 mm Hg for 24 h) to give a solid which was crushed to a light tan powder (57 g, 85% crude yield). The material was used as is for further reactions.

2'-O-Methoxyethyl-5-methyluridine 2,2'-Anhydro-5-methyluridine (195 g, 0.81 M), tris(2-methoxyethyl)borate (231 g, 0.98 M) and 2-methoxyethanol (1.2 L) were added to a 2 L stainless steel pressure vessel and placed in a pre-heated oil bath at 160° C. After heating for 48 hours at 155-160° C., the vessel was opened and the solution evaporated to dryness and triturated with MeOH (200 mL). The residue was suspended in hot acetone (1 L). The insoluble salts were filtered, washed with acetone (150 mL) and the filtrate evaporated. The residue (280 g) was dissolved in $CH_3CN$ (600 mL) and evaporated. A silica gel column (3 kg) was packed in $CH_2Cl_2$/acetone/MeOH (20:5:3) containing 0.5% $Et_3NH$. The residue was dissolved in $CH_2Cl_2$ (250 mL) and adsorbed onto silica (150 g) prior to loading onto the column. The product was eluted with the packing solvent to give 160 g (63%) of product.

2'-O-Methoxyethyl-5'-O-dimethoxytrityl-5-methyluridine

2'-O-Methoxyethyl-5-methyluridine (160 g, 0.506 M) was co-evaporated with pyridine (250 mL) and the dried residue dissolved in pyridine (1.3 L). A first aliquot of dimethoxytrityl chloride (94.3 g, 0.278 M) was added and the mixture stirred at room temperature for one hour. A second aliquot of dimethoxytrityl chloride (94.3 g, 0.278 M) was added and the reaction stirred for an additional one hour. Methanol (170 mL) was then added to stop the reaction. HPLC showed the presence of approximately 70% product. The solvent was evaporated and triturated with $CH_3CN$ (200 mL). The residue was dissolved in $CHCl_3$ (1.5 L) and extracted with 2×500 mL of saturated $NaHCO_3$ and 2×500 mL of saturated NaCl. The organic phase was dried over $Na_2SO_4$, filtered and evaporated. 275 g of residue was obtained. The residue was purified on a 3.5 kg silica gel column, packed and eluted with EtOAc/Hexane/Acetone (5:5:1) containing 0.5% $Et_3NH$. The pure fractions were evaporated to give 164 g of product. Approximately 20 g additional was obtained from the impure fractions to give a total yield of 183 g (57%).

3'-O-Acetyl-2'-O-methoxyethyl-5'-O-dimethoxytrityl-5-methyluridine

2'-O-Methoxyethyl-5'-O-dimethoxytrityl-5-methyluridine (106 g, 0.167 M), DMF/pyridine (750 mL of a 3:1 mixture prepared from 562 mL of DMF and 188 mL of pyridine) and acetic anhydride (24.38 mL, 0.258 M) were combined and stirred at room temperature for 24 hours. The reaction was monitored by tlc by first quenching the tlc sample with the addition of MeOH. Upon completion of the reaction, as judged by tlc, MeOH (50 mL) was added and the mixture evaporated at 35° C. The residue was dissolved in $CHCl_3$ (800 mL) and extracted with 2×200 mL of saturated sodium bicarbonate and 2×200 mL of saturated NaCl. The water layers were back extracted with 200 mL of $CHCl_3$. The combined organics were dried with sodium sulfate and evaporated to give 122 g of residue (approx. 90% product). The residue was purified on a 3.5 kg silica gel column and eluted using EtOAc/Hexane (4:1). Pure product fractions were evaporated to yield 96 g (84%).

3'-O-Acetyl-2'-O-methoxyethyl-5'-O-dimethoxytrityl-5-methyl-4-triazoleuridine A first solution was prepared by dissolving 3'-O-acetyl-2'-O-methoxyethyl-5'-O-dimethoxytrityl-5-methyluridine (96 g, 0.144 M) in $CH_3CN$ (700 mL) and set aside. Triethylamine (189 mL, 1.44 M) was added, to a solution of triazole (90 g, 1.3 M) in $CH_3CN$ (1 L), cooled to −5° C. and stirred for 0.5 h using an overhead stirrer. $POCl_3$ was added dropwise, over a 30 minute period, to the stirred solution maintained at 0-10° C., and the resulting mixture stirred for an additional 2 hours. The first solution was added to the later solution dropwise, over a 45 minute period. The resulting reaction mixture was stored overnight in a cold room. Salts were filtered from the reaction mixture and the solution was evaporated. The residue was dissolved in EtOAc (1 L) and the insoluble solids were removed by filtration. The filtrate was washed with 1×300 mL of NaHCO$_3$ and 2×300 mL of saturated NaCl, dried over sodium sulfate and evaporated. The residue was triturated with EtOAc to give the title compound.

2'-O-Methoxyethyl-5-O-dimethoxytrityl-5-methylcytidine

A solution of 3'-O-acetyl-2'-O-methoxyethyl-5'-O-dimethoxytrityl-5-methyl-4-triazoleuridine (103 g, 0.141 M) in dioxane (500 mL) and NH$_4$OH (30 mL) was stirred at room temperature for 2 hours. The dioxane solution was evaporated and the residue azeotroped with MeOH (2×200 mL). The residue was dissolved in MeOH (300 ml) and transferred to a 2 liter stainless steel pressure vessel. MeOH (400 mL) saturated with NH$_3$ gas was added and the vessel heated to 100° C. for 2 hours (tlc showed complete conversion). The vessel contents were evaporated to dryness and the residue was dissolved in EtOAc (500 mL) and washed once with saturated NaCl (200 mL). The organics were dried over sodium sulfate and the solvent was evaporated to give 85 g (95%) of the title compound.

N$^4$-Benzoyl-2'-O-methoxyethyl-5'-O-dimethoxytrityl-5-methylcytidine

2'-O-Methoxyethyl-5'-O-dimethoxytrityl-5-methylcytidine (85 g, 0.134 M) was dissolved in DMF (800 mL) and benzoic anhydride (37.2 g, 0.165 M) was added with stirring. After stirring for 3 hours, tlc showed the reaction to be approximately 95% complete. The solvent was evaporated and the residue azeotroped with MeOH (200 mL). The residue was dissolved in CHCl$_3$ (700 mL) and extracted with saturated NaHCO$_3$ (2×300 mL) and saturated NaCl (2×300 mL), dried over MgSO$_4$ and evaporated to give a residue (96 g). The residue was chromatographed on a 1.5 kg silica column using EtOAc/Hexane (1:1) containing 0.5% Et$_3$NH as the eluting solvent. The pure product fractions were evaporated to give 90 g (90%) of the title compound.

N$^4$-Benzoyl-2'-O-methoxyethyl-5'-O-dimethoxytrityl-5-methylcytidine-3'-amidite N$^4$-Benzoy-2'-O-methoxyethyl-5'-O-dimethoxytrityl-5-methylcytidine (74 g, 0.10 M) was dissolved in CH$_2$Cl$_2$ (1 L). Tetrazole diisopropylamine (7.1 g) and 2-cyanoethoxy-tetra-(isopropyl)phosphite (40.5 mL, 0.123 M) were added with stirring, under a nitrogen atmosphere. The resulting mixture was stirred for 20 hours at room temperature (tlc showed the reaction to be 95% complete). The reaction mixture was extracted with saturated NaHCO$_3$ (1×300 mL) and saturated NaCl (3×300 mL). The aqueous washes were back-extracted with CH$_2$Cl$_2$ (300 mL), and the extracts were combined, dried over MgSO$_4$ and concentrated. The residue obtained was chromatographed on a 1.5 kg silica column using EtOAc\Hexane (3:1) as the eluting solvent. The pure fractions were combined to give 90.6 g (87%) of the title compound.

2'-O-(Aminooxyethyl) Nucleoside Amidites and 2'-O-(dimethylaminooxyethyl) Nucleoside Amidites

2'-(Dimethylaminooxyethoxy) Nucleoside Amidites

2'-(Dimethylaminooxyethoxy) nucleoside amidites [also known in the art as 2'-O-(dimethylaminooxyethyl) nucleoside amidites] are prepared as described in the following paragraphs. Adenosine, cytidine and guanosine nucleoside amidites are prepared similarly to the thymidine (5-methyluridine) except the exocyclic amines are protected with a benzoyl moiety in the case of adenosine and cytidine and with isobutyryl in the case of guanosine.

5'-O-tert-Butyldiphenylsilyl-O2-2'-anhydro-5-methyluridine

O$^2$-2'-anhydro-5-methyluridine (Pro. Bio. Sint., Varese, Italy, 100.0 g, 0.416 mmol), dimethylaminopyridine (0.66 g, 0.013 eq, 0.0054 mmol) were dissolved in dry pyridine (500 ml) at ambient temperature under an argon atmosphere and with mechanical stirring. tert-Butyldiphenylchlotosilane (125.8 g, 119.0 mL, 1.1 eq, 0.458 mmol) was added in one portion. The reaction was stirred for 16 h at ambient temperature. TLC (Rf 0.22, ethyl acetate) indicated a complete reaction. The solution was concentrated under reduced pressure to a thick oil. This was partitioned between dichloromethane (1 L) and saturated sodium bicarbonate (2×1 L) and brine (1 L). The organic layer was dried over sodium sulfate and concentrated under reduced pressure to a thick oil. The oil was dissolved in a 1:1 mixture of ethyl acetate and ethyl ether (600 mL) and the solution was cooled to −10° C. The resulting crystalline product was collected by filtration, washed with ethyl ether (3×200 mL) and dried (40° C., 1 mm Hg, 24 h) to 149 g (74.8%) of white solid. TLC and NMR were consistent with pure product.

5'-O-tert-Butyldiphenylsilyl-2'-O-(2-hydroxyethyl)-5-methyluridine

In a 2 L stainless steel, unstirred pressure reactor was added borane in tetrahydrofuran (1.0 M, 2.0 eq, 622 mL). In the fume hood and with manual stirring, ethylene glycol (350 mL, excess) was added cautiously at first until the evolution of hydrogen gas subsided. 5'-O-tert-Butyldiphenylsilyl-O$^2$-2'-anhydro-5-methyluridine (149 g, 0.311 mol) and sodium bicarbonate (0.074 g, 0.003 eq) were added with manual stirring. The reactor was sealed and heated in an oil bath until an internal temperature of 160° C. was reached and then maintained for 16 h (pressure<100 psig). The reaction vessel was cooled to ambient and opened. TLC (Rf 0.67 for desired product and Rf 0.82 for are-T side product, ethyl acetate) indicated about 70% conversion to the product. In order to avoid additional side product formation, the reaction was stopped, concentrated under reduced pressure (10 to 1 mm Hg) in a warm water bath (40-100° C.) with the more extreme conditions used to remove the ethylene glycol.

[Alternatively, once the low boiling solvent is gone, the remaining solution can be partitioned between ethyl acetate and water. The product will be in the organic phase.] The residue was purified by column chromatography (2 kg silica gel, ethyl acetate-hexanes gradient 1:1 to 4:1). The appropriate fractions were combined, stripped and dried to product as a white crisp foam (84 g, 50%), contaminated starting mate-

2'-O-([2-phthalimidoxy)ethyl]-5'-t-butyldiphenylsilyl-5-methyluridine

5=-O-tert-Butyldiphenylsilyl-2'-O-(2-hydroxyethyl)-5-methyluridine (20 g, 36.98 mmol) was mixed with triphenylphosphine (11.63 g, 44.36 mmol) and N-hydroxyphthalimide (7.24 g, 44.36 mmol). It was then dried over $P_2O_5$ under high vacuum for two days at 40 EC. The reaction mixture was flushed with argon and dry THF (369.8 mL, Aldrich, sure seal bottle) was added to get a clear solution. Diethyl-azodicarboxylate (6.98 mL, 44.36 mmol) was added dropwise to the reaction mixture. The rate of addition is maintained such that resulting deep red coloration is just discharged before adding the next drop. After the addition was complete, the reaction was stirred for 4 hrs. By that time TLC showed the completion of the reaction (ethylacetate:hexane, 60:40). The solvent was evaporated in vacuum. Residue obtained was placed on a flash column and eluted with ethyl acetate:hexane (60:40), to get 2'-O-([2-phthalimidoxy)ethyl]-5'-t-butyldiphenylsilyl-5-methyluridine as white foam (21.819 g, 86%).

5'-O-tert-butyldiphenylsilyl-2'-O-[(2-formadoximinooxy)ethyl]-5-methyluridine 2'-O-([2-phthalimidoxy)ethyl]-5'-t-butyldiphenylsilyl-5-methyluridine (3.1 g, 4.5 mmol) was dissolved in dry $CH_2Cl_2$ (4.5 mL) and methylhydrazine (300 mL, 4.64 mmol) was added dropwise at –10 EC to 0 EC. After 1 h the mixture was filtered, the filtrate was washed with ice cold $CH_2Cl_2$ and the combined organic phase was washed with water, brine and dried over anhydrous $Na_2SO_4$. The solution was concentrated to get 2'-O-(aminooxyethyl) thymidine, which was then dissolved in MeOH (67.5 mL). To this formaldehyde (20% aqueous solution, w/w, 1.1 eq.) was added and the resulting mixture was stirred for 1 h. Solvent was removed under vacuum; residue chromatographed to get 5'-O-tert-butyldiphenylsilyl-2'-O-[(2-formadoximinooxy) ethyl]-5-methyluridine as white foam (1.95 g, 78%).

5'-O-tert-Butyldiphenylsilyl-2'-O-[N,N-dimethylaminooxyethyl]-5

5'-O-tert-butyldiphenylsilyl-2'-O-[(2-formadoximinooxy) ethyl]-5-methyluridine (1.77 g, 3.12 mmol) was dissolved in a solution of 1M pyridinium p-toluenesulfonate (PPTS) in dry MeOH (30.6 mL). Sodium cyanoborohydride (0.39 g, 6.13 mmol) was added to this solution at 10 EC under inert atmosphere. The reaction mixture was stirred for 10 minutes at 10 EC. After that the reaction vessel was removed from the ice bath and stirred at room temperature for 2 h, the reaction monitored by TLC (5% MeOH in $CH_2Cl_2$). Aqueous $NaHCO_3$ solution (5%, 10 mL) was added and extracted with ethyl acetate (2×20 mL). Ethyl acetate phase was dried over anhydrous $Na_2SO_4$, evaporated to dryness. Residue was dissolved in a solution of 1M PPTS in MeOH (30.6 mL). Formaldehyde (20% w/w, 30 mL, 3.37 mmol) was added and the reaction mixture was stirred at room temperature for 10 minutes. Reaction mixture cooled to 10 EC in an ice bath, sodium cyanoborohydride (0.39 g, 6.13 mmol) was added and reaction mixture stirred at 10 EC for 10 minutes. After 10 minutes, the reaction mixture was removed from the ice bath and stirred at room temperature for 2 hrs. To the reaction mixture 5% $NaHCO_3$ (25 mL) solution was added and extracted with ethyl acetate (2×25 mL). Ethyl acetate layer was dried over anhydrous Na2SO4 and evaporated to dryness. The residue obtained was purified by flash column chromatography and eluted with 5% MeOH in $CH_2Cl_2$ to get 5'-O-tert-butyldiphenylsilyl-2'-O-[N,N-dimethylaminooxyethyl]-5-methyluridine as a white foam (14.6 g, 80%).

2'-O-(dimethylaminooxyethyl)-5-methyluridine

Triethylamine trihydrofluoride (3.91 mL, 24.0 mmol) was dissolved in dry THF and triethylamine (1.67 mL, 12 mmol, dry, kept over KOH). This mixture of triethylamine-2HF was then added to 5'-O-tert-butyldiphenylsilyl-2'-O-[N,N-dimethylaminooxyethyl]-5-methyluridine (1.40 g, 2.4 mmol) and stirred at room temperature for 24 hrs. Reaction was monitored by TLC (5% MeOH in $CH_2Cl_2$). Solvent was removed under vacuum and the residue placed on a flash column and eluted with 10% MeOH in $CH_2Cl_2$ to get 2'-O-(dimethylaminooxyethyl)-5-methyluridine (766 mg, 92.5%).

5'-O-DMT-2'-O-(dimethylaminooxyethyl)-5-methyluridine

2'-O-(dimethylaminooxyethyl)-5-methyluridine (750 mg, 2.17 mmol) was dried over $P_2O_5$ under high vacuum overnight at 40 EC. It was then co-evaporated with anhydrous pyridine (20 mL). The residue obtained was dissolved in pyridine (11 mL) under argon atmosphere. 4-dimethylaminopyridine (26.5 mg, 2.60 mmol), 4,4'-dimethoxytrityl chloride (880 mg, 2.60 mmol) was added to the mixture and the reaction mixture was stirred at room temperature until all of the starting material disappeared. Pyridine was removed under vacuum and the residue chromatographed and eluted with 10% MeOH in $CH_2Cl_2$ (containing a few drops of pyridine) to get 5'-O-DMT-2'-O-(dimethylamino-oxyethyl)-5-methyluridine (1.13 g, 80%).

5'-O-DMT-2'-O-(2-N,N-dimethylaminooxyethyl)-5-methyluridine-3'-[(2-cyanoethyl)-N,N-diisopropylphosphoramidite]

5'-O-DMT-2'-O-(dimethylaminooxyethyl)-5-methyluridine (1.08 g, 1.67 mmol) was co-evaporated with toluene (20 mL). To the residue N,N-diisopropylamine tetrazonide (0.29 g, 1.67 mmol) was added and dried over P205 under high vacuum overnight at 40 EC. Then the reaction mixture was dissolved in anhydrous acetonitrile (8.4 mL) and 2-cyanoethyl-N,N,N1,N1-tetraisopropylphosphoramidite (2.12 mL, 6.08 mmol) was added. The reaction mixture was stirred at ambient temperature for 4 hrs under inert atmosphere. The progress of the reaction was monitored by TLC (hexane:ethyl acetate 1:1). The solvent was evaporated, then the residue was dissolved in ethyl acetate (70 mL) and washed with 5% aqueous NaHCO3 (40 mL). Ethyl acetate layer was dried over anhydrous Na2SO4 and concentrated. Residue obtained was chromatographed (ethyl acetate as eluent) to get 5'-O-DMT-2'-O-(2-N,N-dimethylaminooxyethyl)-5-methyluridine-3'-[(2-cyanoethyl)-N,N-diisopropylphosphoramidite] as a foam (1.04 g, 74.9%).

2'-(Aminooxyethoxy) nucleoside amidites

2'-(Aminooxyethoxy) nucleoside amidites [also known in the art as 2'-O-(aminooxyethyl) nucleoside amidites] are prepared as described in the following paragraphs. Adenosine, cytidine and thymidine nucleoside amidites are prepared similarly.

N2-isobutyryl-6-O-diphenylcarbamoyl-2'-O-(2-ethylacetyl)-5'-O-(4,4'-dimethoxytrityl)guanosine-3'-[(2-cyanoethyl)-N,N-diisopropylphosphoramidite]

The 2'-O-aminooxyethyl guanosine analog may be obtained by selective 2'-O-alkylation of diaminopurine riboside. Multigram quantities of diaminopurine riboside may be purchased from Schering AG (Berlin) to provide 2'-O-(2-ethylacetyl) diaminopurine riboside along with a minor amount of the 3'-O-isomer. 2'-O-(2-ethylacetyl) diaminopurine riboside may be resolved and converted to 2'-O-(2-ethylacetyl)guanosine by treatment with adenosine deaminase. (PCT WO94/02501). Standard protection procedures should afford 2'-O-(2-ethylacetyl)-5'-O-(4,4'-dimethoxytrityl)guanosine and 2-N-isobutyryl-6-O-diphenylcarbamoyl-2'-O-(2-ethylacetyl)-5'-O-(4,4'-dimethoxytrityl)guanosine which may be reduced to provide 2-N-isobutyryl-6-O-diphenylcarbamoyl-2'-O-(2-ethylacetyl)-5'-O-(4,4'-dimethoxytrityl) guanosine. As before the hydroxyl group may be displaced by N-hydroxyphthalimide via a Mitsunobu reaction, and the protected nucleoside may phosphitylated as usual to yield 2-N-isobutyryl-6-O-diphenylcarbamoyl-2'-O-(2-ethylacetyl)-5'-O-(4,4'-dimethoxytrityl)guanosine-3'-[(2-cyanoethyl)-N,N-diisopropylphosphoramidite].

2'-dimethylaminoethoxyethoxy (2'-DMAEOE) nucleoside amidites

2'-dimethylaminoethoxyethoxy nucleoside amidites (also known in the art as 2'-O-dimethylaminoethoxyethyl, i.e., 2'-O—CH$_2$—O—CH$_2$—N(CH$_2$)$_2$, or 2'-DMAEOE nucleoside amidites) are prepared as follows. Other nucleoside amidites are prepared similarly.

2'-O-[2(2-N,N-dimethylaminoethoxy)ethyl]-5-methyl uridine

2[2-(Dimethylamino)ethoxy]ethanol (Aldrich, 6.66 g, 50 mmol) is slowly added to a solution of borane in tetra-hydrofuran (1 M, 10 mL, 10 mmol) with stirring in a 100 mL bomb. Hydrogen gas evolves as the solid dissolves. O2-,2'-anhydro-5-methyluridine (1.2 g, 5 mmol), and sodium bicarbonate (2.5 mg) are added and the bomb is sealed, placed in an oil bath and heated to 155 C for 26 hours. The bomb is cooled to room temperature and opened. The crude solution is concentrated and the residue partitioned between water (200 mL) and hexanes (200 mL). The excess phenol is extracted into the hexane layer. The aqueous layer is extracted with ethyl acetate (3×200 mL) and the combined organic layers are washed once with water, dried over anhydrous sodium sulfate and concentrated. The residue is columned on silica gel using methanol/methylene chloride 1:20 (which has 2% triethylamine) as the eluent. As the column fractions are concentrated a colorless solid forms which is collected to give the title compound as a white solid.

5'-O-dimethoxytrityl-2'-O-[2(2-N,N-dimethyl-aninoethoxy)ethyl]-5-methyl uridine

To 0.5 g (1.3 mmol) of 2'-O-[2(2-N,N-dimethylaminoethoxy)ethyl]-5-methyl uridine in anhydrous pyridine (8 mL), triethylamine (0.36 mL) and dimethoxytrityl chloride (DMT-Cl, 0.87 g, 2 eq.) are added and stirred for 1 hour. The reaction mixture is poured into water (200 mL) and extracted with CH2Cl2 (2×200 mL). The combined CH2Cl2 layers are washed with saturated NaHCO3 solution, followed by saturated NaCl solution and dried over anhydrous sodium sulfate. Evaporation of the solvent followed by silica gel chromatography using MeOH:CH2Cl2:Et3N (20:1, v/v, with 1% triethylamine) gives the title compound.

5'-O-Dimethoxytrityl-2'-O-[2(2-N,N-dimethylaminoethoxy)-ethyl)]-5-methyl uridine-3'-O-(cyanoethyl-N,N-diisopropyl)phosphoramidite Diisopropylaminotetrazolide (0.6 g) and 2-cyanoethoxy-N,N-diisopropyl phosphoramidite (1.1 mL, 2 eq.) are added to a solution of 5'-O-dimethoxytrityl-2'-O-[2(2-N,N-dimethylaminoethoxy)ethyl)]-5-methyluridine (2.17 g, 3 mmol) dissolved in CH2Cl2 (20 mL) under an atmosphere of argon. The reaction mixture is stirred overnight and the solvent evaporated. The resulting residue is purified by silica gel flash column chromatography with ethyl acetate as the eluent to give the title compound.

Purification:

After cleavage from the controlled pore glass column (Applied Biosystems) and deblocking in concentrated ammonium hydroxide at 55° C. for 18 hours, the oligonucleotides were purified by precipitation twice out of 0.5 M NaCl with 2.5 volumes ethanol. Analytical gel electrophoresis was accomplished in 20% acrylamide, 8 M urea, 45 mM Tris-borate buffer, pH 7.0. Oligodeoxynucleotides and their phosphorothioate analogs were judged from electrophoresis to be greater than 80% full length material.

B7 Antisense Oligonucleotides

A series of oligonucleotides with sequences designed to hybridize to the published human B7-1 (hB7-1) and murine (mB7-1) mRNA sequences (Freeman et al., *J. Immunol.*, 1989, 143, 2714,. and Freeman et al., *J. Exp. Med.*, 1991, 174, 625 respectively). The sequences of and modifications to these oligonucleotides, and the location of each of their target sites on the hB7-1 mRNA, are given in Tables 1 and 2. Similarly, a series of oligonucleotides with sequences designed to hybridize to the human B7-2 (hB7-2) and murine B7-2 (mB7-2) mRNA published sequences (respectively, Azuma et al., *Nature*, 1993, 366, 76; Chen et al., *J. Immunol.*, 1994, 152, 4929) were synthesized. The sequences of and modifications to these oligonucleotides and the location of each of their target sites on the hB7-2 mRNA are described in Tables 3 and 4. Antisense oligonucleotides targeted to ICAM-1, including ISIS 2302 (SEQ ID NO: 17), have been described in U.S. Pat. No. 5,514,788, which issued May 7, 1996, hereby incorporated by reference. ISIS 1082 (SEQ ID NO: 102) and ISIS 3082 (SEQ ID NO: 101) have been previously described (Stepkowski et al., *J. Immunol.*, 1994, 153, 5336).

Subsequent to their initial cloning, alternative splicing events of B7 transcripts have been reported. The reported alternative splicing for B7-1 is relatively simple, in that it results in messages extended 5' relative to the 5' terminus of the human and murine B7-1 cDNA sequences originally reported (Borriello et al., J. Immunol., 1994, 153, 5038; Inobe et al., *J. Immunol.*, 1996, 157, 588). In order to retain the numbering of the B7-1 sequences found in the references initially reporting B7-1 sequences, positions within these 5' extensions of the initially reported sequences have been given negative numbers (beginning with position -1, the most 3' base of the 5' extension) in Tables 1 and 2. The processing of murine B7-2 transcripts is considerably more complex than that so far reported for B7-1; for example, at least five distinct murine B7-2 mRNAs, and at least two distinct human B7-2 mRNAs, can be produced by alternative splicing events (Borriello et al., *J. Immunol.*, 1995, 155, 5490; Freeman et al., WO 95/03408, published Feb. 2, 1995; see also Jellis et al., Immunogenet., 1995, 42, 85). The nature of these splicing events is such that different 5' exons are used to produce distinct B7-2 mRNAs, each of which has a unique 5' sequence but which share a 3' portion consisting of some or all of the B7-2 sequence initially reported. As a result, positions within the 5' extensions of B7-2 messages cannot be uniquely related to a position within the sequence initially reported. Accordingly, in Table 3, a different set of coordinates (corresponding to those of SEQ ID NO: 1 of WO 95/03408) and, in Table 4, the exon number (as given in Borriello et al., *J. Immunol.*, 1995, 155, 5490) is used to specify the location of targeted sequences which are not included in the initially reported B7-2 sequence. Furthermore, although these 5' extended messages contain potential in-frame start codons upstream from the ones indicated in the initially published sequences, for simplicity's sake, such additional potential start codons are not indicated in the description of target sites in Tables 1-4.

In Tables 1-4, the following abbreviations are used: UTR, untranslated region; ORF, open reading frame; tIR, translation initiation region; tTR, translation termination region; FITC, fluorescein isothiocyanate. Chemical modifications are indicated as follows. Residues having 2' fluoro (2'F), 2'-methoxy (2'MO) or 2'-methoxyethoxy (2'ME) modification are emboldened, with the type of modification being indicated by the respective abbreviations. Unless otherwise indicated, interresidue linkages are phosphodiester linkages; phosphorothioate linkages are indicated by an AS@ in the superscript position (e.g., $T^sA$) Target positions are numbered according to Freeman et al., J. Immunol., 1989, 143:2714 (human B7-1 cDNA sequence; Table 1), Freeman et al., *J. Exp. Med.*, 1991, 174, 625 (murine B7-1 cDNA sequence; Table 2), Azuma et al., *Nature*, 1993, 366:76 (human B7-2 cDNA sequence; Table 3) and Chen et al., *J. Immunol.*, 1994, 152:4929 (murine B7-2 cDNA sequence; Table 4). Nucleotide base codes are as given in 37 C.F.R. '1.822(b)(1).

TABLE 1

Sequences of Oligonucleotides Targeted to Human B7-1 mRNA

| ISIS # | Target Position; Site (and/or Description) | Oligonucleotide Sequence (5' -> 3') and Chemical Modifications | SEQ ID NO: |
|---|---|---|---|
| 13797 | 0053-0072; 5' UTR | $G^sG^sG^sT^sA^sA^sG^sA^sC^sT^sC^sC^sA^sC^sT^sT^sT^sC^sT^sG^sA$ | 22 |
| 13798 | 0132-0151; 5' UTR | $G^sG^sG^sT^sC^sT^sC^sC^sA^sA^sA^sG^sG^sT^sT^sG^sT^sG^sG^sA$ | 23 |
| 13799 | 0138-0157; 5' UTR | $G^sT^sT^sC^sC^sT^sG^sG^sG^sT^sC^sT^sC^sC^sA^sA^sA^sG^sG^sT$ | 24 |
| 13800 | 0158-0177; 5' UTR | $A^sC^sA^sC^sA^sC^sA^sG^sA^sG^sA^sT^sT^sG^sG^sA^sG^sG^sG^sT$ | 25 |
| 13801 | 0193-0212; 5' UTR | $G^sC^sT^sC^sA^sC^sG^sT^sA^sG^sA^sA^sG^sA^sC^sC^sC^sT^sC^sC$ | 26 |
| 13802 | 0217-0236; 5' UTR | $G^sG^sC^sA^sG^sG^sG^sC^sT^sG^sA^sT^sG^sA^sC^sA^sA^sT^sC^sC$ | 27 |
| 13803 | 0226-0245; 5' UTR | $T^sG^sC^sA^sA^sA^sA^sC^sA^sG^sG^sC^sA^sG^sG^sG^sC^sT^sG^sA$ | 28 |
| 13804 | 0246-0265; 5' UTR | $A^sG^sA^sC^sC^sA^sG^sG^sG^sC^sA^sC^sT^sT^sC^sC^sC^sA^sG^sG$ | 29 |
| 13805 | 0320-0339; tIR | $C^sC^sT^sG^sC^sC^sT^sC^sC^sG^sT^sG^sT^sG^sT^sG^sG^sC^sC^sC$ | 30 |
| 13806 | 0380-0399; 5' ORF | $G^sA^sC^sC^sA^sG^sC^sC^sA^sG^sC^sA^sC^sC^sA^sA^sG^sA^sG^sC$ | 31 |
| 13807 | 0450-0469; 5' ORF | $C^sC^sA^sC^sA^sG^sG^sA^sC^sA^sG^sC^sG^sT^sT^sG^sC^sC^sA^sC$ | 32 |
| 13808 | 0568-0587; 5' ORF | $C^sC^sG^sG^sT^sT^sC^sT^sT^sG^sT^sA^sC^sT^sC^sG^sG^sG^sC^sC$ | 33 |
| 13809 | 0634-0653; central ORF | $G^sC^sC^sC^sT^sC^sG^sT^sC^sA^sG^sA^sT^sG^sG^sG^sC^sG^sC^sA$ | 51 |
| 13810 | 0829-0848; central ORF | $C^sC^sA^sA^sC^sC^sA^sG^sG^sA^sG^sA^sG^sG^sT^sG^sA^sG^sG^sC$ | 34 |
| 13811 | 1102-1121; 3' ORF | $G^sG^sC^sA^sA^sA^sG^sC^sA^sG^sT^sA^sG^sG^sTCA^sG^sG^sC$ | 35 |
| 13812 | 1254-1273; 3'-UTR | $G^sC^sC^sT^sC^sA^sT^sG^sA^sT^sC^sC^sC^sC^sA^sC^sG^sA^sT^sC$ | 36 |
| 13872 | (scrambled # 13812) | $A^sG^sT^sC^sC^sT^sA^sC^sT^sA^sC^sC^sA^sG^sC^sC^sG^sC^sC^sT$ | 52 |
| 12361 | 0056-0075; 5' UTR | $T^sC^sA^sG^sG^sG^sT^sA^sA^sG^sA^sC^sT^sC^sC^sA^sC^sT^sT^sC$ | 38 |
| 12348 | 0056-0075; 5' UTR | T C A G G $G^sT^sA^sA^sG^sA^sC^sT^sC^sC$ A C T T C (2'ME) | 38 |
| 12473 | 0056-0075; 5' UTR | $T^sC^sA^sG^sG^sG^sT^sA^sA^sG^sA^sC^sT^sC^sC$C$^s$A$^s$C$^s$T$^s$T$^s$C (2'F1) | 38 |
| 12362 | 0143-0162; 5' UTR | $A^sG^sG^sG^sT^sG^sT^sT^sC^sC^sT^sG^sG^sG^sT^sC^sT^sC^sC^sA$ | 39 |
| 12349 | 0143-0162; 5' UTR | A G G G T $G^sT^sT^sC^sC^sT^sG^sG^sG^sT$ C T C C A (2'ME) | 39 |
| 12474 | 0143-0162; 5' UTR | $A^sG^sG^sG^sT^sG^sT^sT^sC^sC^sT^sG^sG^sG^sT$T$^s$C$^s$T$^s$C$^s$C$^s$A (2'F1) | 39 |

TABLE 1-continued

Sequences of Oligonucleotides Targeted to Human B7-1 mRNA

| ISIS # | Target Position; Site (and/or Description) | Oligonucleotide Sequence (5' -> 3') and Chemical Modifications | SEQ ID NO: |
|---|---|---|---|
| 12363 | 0315-0334; tIR | C$^S$T$^S$C$^S$C$^S$G$^S$T$^S$G$^S$T$^S$G$^S$T$^S$G$^S$G$^S$C$^S$C$^S$C$^S$A$^S$T$^S$G$^S$G$^S$C | 40 |
| 12350 | 0315-0334; tIR | C T C C G T$^S$G$^S$T$^S$G$^S$T$^S$G$^S$G$^S$C$^S$C C A T G G C (2'ME) | 40 |
| 12475 | 0315-0334; tIR | C$^S$T$^S$C$^S$C$^S$G$^S$T$^S$G$^S$T$^S$G$^S$T$^S$G$^S$G$^S$CC$^S$A$^S$T$^S$G$^S$G$^S$C (2'F1) | 40 |
| 12364 | 0334-0353; 5' ORF | G$^S$A$^S$T$^S$G$^S$G$^S$T$^S$G$^S$A$^S$T$^S$G$^S$T$^S$T$^S$C$^S$C$^S$C$^S$T$^S$G$^S$C$^S$C | 41 |
| 12351 | 0334-0353; 5' ORF | G G A T G G$^S$T$^S$G$^S$A$^S$T$^S$G$^S$T$^S$T$^S$C C C T G C C (2'ME) | 41 |
| 12476 | 0334-0353; 5' ORF | G$^S$A$^S$T$^S$G$^S$G$^S$T$^S$G$^S$A$^S$T$^S$G$^S$T$^S$T$^S$C$^S$C$^S$C$^S$T$^S$G$^S$C$^S$C (2'F1) | 41 |
| 12365 | 0387-0406; 5' ORF | T$^S$G$^S$A$^S$G$^S$A$^S$A$^S$A$^S$A$^S$G$^S$A$^S$C$^S$C$^S$A$^S$G$^S$C$^S$C$^S$A$^S$G$^S$C$^S$A$^S$C | 42 |
| 12352 | 0387-0406; 5' ORF | T G A G A A$^S$A$^S$G$^S$A$^S$C$^S$C$^S$A$^S$G$^S$C C A G C A C (2'ME) | 42 |
| 12477 | 0387-0406; 5' ORF | T$^S$G$^S$A$^S$G$^S$A$^S$A$^S$A$^S$A$^S$G$^S$A$^S$C$^S$C$^S$A$^S$G$^S$C$^S$C$^S$A$^S$G$^S$C$^S$A$^S$C (2'F1) | 42 |
| 12366 | 0621-0640; central ORF | G$^S$G$^S$G$^S$C$^S$G$^S$C$^S$A$^S$G$^S$A$^S$A$^S$G$^S$C$^S$C$^S$A$^S$G$^S$G$^S$A$^S$T$^S$C$^S$A$^S$C | 43 |
| 12353 | 0621-0640; central ORF | G G G C G C$^S$A$^S$G$^S$A$^S$G$^S$C$^S$A$^S$A$^S$G G A T C A C (2'ME) | 43 |
| 12478 | 0621-0640; central ORF | G$^S$G$^S$G$^S$C$^S$G$^S$C$^S$A$^S$G$^S$A$^S$A$^S$G$^S$C$^S$C$^S$A$^S$G$^S$G$^S$A$^S$T$^S$C$^S$A$^S$C (2'F1) | 43 |
| 12367 | 1042-1061; 3' ORF | G$^S$G$^S$C$^S$C$^S$C$^S$A$^S$G$^S$G$^S$A$^S$T$^S$G$^S$G$^S$G$^S$A$^S$G$^S$C$^S$A$^S$G$^S$G$^S$T | 44 |
| 12354 | 1042-1061; 3' ORF | G G C C C A$^S$G$^S$G$^S$A$^S$T$^S$G$^S$G$^S$G$^S$A G C A G G T (2'ME) | 44 |
| 12479 | 1042-1061; 3' ORF | G$^S$G$^S$C$^S$C$^S$C$^S$A$^S$G$^S$G$^S$A$^S$T$^S$G$^S$G$^S$G$^S$A$^S$G$^S$C$^S$A$^S$G$^S$G$^S$T (2'F1) | 44 |
| 12368 | 1069-1088; tTR | A$^S$G$^S$G$^S$C$^S$G$^S$T$^S$A$^S$C$^S$A$^S$C$^S$T$^S$T$^S$T$^S$C$^S$C$^S$C$^S$T$^S$T$^S$C | 45 |
| 12355 | 1069-1088; tTR | A G G G C G$^S$T$^S$A$^S$C$^S$A$^S$C$^S$T$^S$T$^S$T C C C T T C (2'ME) | 45 |
| 12480 | 1069-1088; tTR | A$^S$G$^S$G$^S$C$^S$G$^S$T$^S$A$^S$C$^S$A$^S$C$^S$T$^S$T$^S$T$^S$C$^S$C$^S$C$^S$T$^S$T$^S$C (2'F1) | 45 |
| 12369 | 1100-1209; tTR | C$^S$A$^S$G$^S$C$^S$C$^S$C$^S$C$^S$T$^S$T$^S$G$^S$C$^S$T$^S$T$^S$C$^S$T$^S$G$^S$C$^S$G$^S$G$^S$A | 46 |
| 12356 | 1100-1209; tTR | C A G C C C$^S$C$^S$T$^S$T$^S$G$^S$C$^S$T$^S$T$^S$C$^S$T G C G G A (2'ME) | 46 |
| 12481 | 1100-1209; tTR | C$^S$A$^S$G$^S$C$^S$C$^S$C$^S$C$^S$T$^S$T$^S$G$^S$C$^S$T$^S$T$^S$C$^S$T$^S$G$^S$C$^S$G$^S$G$^S$A (2'F1) | 46 |
| 12370 | 1360-1380; 3' UTR | A$^S$A$^S$G$^S$G$^S$A$^S$G$^S$A$^S$G$^S$G$^S$G$^S$A$^S$T$^S$G$^S$C$^S$C$^S$A$^S$G$^S$C$^S$C$^S$A | 47 |
| 12357 | 1360-1380; 3' UTR | A A G G A G$^S$G$^S$G$^S$G$^S$A$^S$T$^S$G$^S$C C A G C C A (2'ME) | 47 |
| 12482 | 1360-1380; 3' UTR | A$^S$A$^S$G$^S$G$^S$A$^S$G$^S$A$^S$G$^S$G$^S$G$^S$A$^S$T$^S$G$^S$C$^S$C$^S$A$^S$G$^S$C$^S$C$^S$A (2'F1) | 47 |
| 12914 | (-0038 to -0059; 5' UTR of alternative mRNA) | C$^S$T$^S$G$^S$T$^S$T$^S$A$^S$C$^S$T$^S$T$^S$T$^S$T$^S$A$^S$C$^S$A$^S$G$^S$A$^S$G$^S$G$^S$G$^S$T$^S$T$^S$G (2'40 MO) | 48 |
| 12915 | (-0035 to -0059; 5' UTR of alternative mRNA) | C$^S$T$^S$T$^S$C$^S$T$^S$G$^S$T$^S$T$^S$A$^S$C$^S$T$^S$T$^S$T$^S$T$^S$A$^S$C$^S$A$^S$G$^S$A$^S$G$^S$G$^S$G$^S$T$^S$T$^S$T$^S$G (2'MO) | 49 |
| 13498 | (-0038 to -0058; 5' UTR of alternative mrNA) | C$^S$T$^S$G$^S$T$^S$T$^S$A$^S$C$^S$T$^S$T$^S$T$^S$T$^S$A$^S$C$^S$A$^S$G$^S$A$^S$G$^S$G$^S$G$^S$T$^S$T$^S$T (2'ME) | 50 |

TABLE 1-continued

Sequences of Oligonucleotides Targeted to Human B7-1 mRNA

| Target Position; Site ISIS # (and/or Description) | Oligonucleotide Sequence (5' -> 3') and Chemical Modifications | SEQ ID NO: |
|---|---|---|
| 13499 (-0038 to -0058; 5' UTR of alternative mRNA) | C T G T T A C T T T A C A G A G G G T T T (2'ME) | 50 |

TABLE 2

Sequences of Oligonucleotides Targeted to Murine B7-1 mRNA

| ISIS # | Target Position; Site | Oligonucleotide Sequence (5' -> 3') and Chemical Modifications | SEQ ID NO: |
|---|---|---|---|
| 14419 | 0009-0028; 5' UTR | $A^SG^ST^SA^SA^SG^SA^SG^ST^SC^ST^SA^ST^ST^SG^SA^SG^SG^ST^SA$ | 53 |
| 14420 | 0041-0060; 5' UTR | $G^SG^ST^ST^SG^SA^SG^ST^ST^ST^SC^SA^SC^SA^SA^SC^SC^ST^SG^SA$ | 54 |
| 14421 | 0071-0091; 5' UTR | $G^ST^SC^SC^SA^SC^SA^SG^SA^SA^ST^SG^SG^SA^SA^SC^SA^SG^SA^SG$ | 55 |
| 14422 | 0109-0128; 5' UTR | $G^SG^SC^SA^ST^SC^SC^SA^SC^SC^SC^SG^SG^SC^SA^SG^SA^ST^SG^SC$ | 56 |
| 14423 | 0114-0133; 5' UTR | $T^SG^SG^SA^ST^SG^SG^SC^SA^ST^SC^SC^SA^SC^SC^SC^SG^SG^SC^SA$ | 57 |
| 14424 | 0168-0187; 5' UTR | $A^SG^SG^SC^SA^SC^SC^ST^SC^SC^ST^SA^SG^SG^SC^ST^SC^SA^SC^SA$ | 58 |
| 14425 | 0181-0200; 5' UTR | $G^SC^SC^SA^SA^ST^SG^SG^SA^SG^SC^ST^ST^SA^SG^SG^SC^SA^SC^SC$ | 59 |
| 14426 | 0208-0217; 5' UTR | $C^SA^ST^SG^SA^ST^SG^SG^SG^SG^SA^SA^SA^SG^SC^SC^SA^SG^SG^SA$ | 60 |
| 14427 | 0242-0261; tIR | $A^SA^ST^ST^SG^SC^SA^SA^SG^SC^SC^SA^ST^SA^SG^SC^ST^ST^SC^SA$ | 61 |
| 14428 | 0393-0412; 5' ORF | $C^SG^SG^SC^SA^SA^SG^SG^SC^SA^SG^SC^SA^SA^ST^SA^SC^SC^ST^ST$ | 62 |
| 14909 | 0478-0497; 5' ORF | $C^SC^SC^SA^SG^SC^SA^SA^ST^SG^SA^SC^SA^SG^SA^SC^SA^SG^SC^SA$ | 63 |
| 14910 | 0569-0588; central ORF | $G^SG^ST^SC^ST^SG^SA^SA^SA^SG^SA^SC^SC^SA^SG^SG^SC^SC^SC$ | 64 |
| 14911 | 0745-0764; central ORF | $T^SG^SG^SA^SA^SA^SC^SC^SC^SC^SC^SG^SG^SA^SA^SG^SC^SA^SA$ | 65 |
| 14912 | 0750-0769; central ORF | $G^SG^SC^ST^ST^ST^SG^SG^SG^SA^SA^SA^SC^SC^SC^SC^SC^SG^SG^SA$ | 66 |
| 14913 | 0825-0844; 3' ORF | $T^SC^SA^SG^SA^ST^ST^SC^SA^SG^SG^SA^ST^SC^SC^ST^SG^SG^SG^SA$ | 67 |
| 14914 | 0932-0951; 3' ORF | $C^SC^SC^SA^SG^SG^ST^SG^SA^SA^SG^ST^SC^SC^ST^SC^ST^SG^SA^SC$ | 68 |
| 14915 | 1001-1020; 3' ORF | $C^ST^SG^SC^SG^SC^SC^SG^SA^SA^ST^SC^SC^ST^SG^SC^SC^SC^SC^SA$ | 69 |
| 14916 | 1125-1144; tTR | $C^SA^SG^SG^SC^SC^SC^SG^SA^SA^SG^SG^ST^SA^SA^SG^SG^SC^ST^SG$ | 70 |
| 14917 | 1229-1248; 3' UTR | $T^SC^SA^SG^SC^ST^SA^SG^SC^SA^SC^SG^SG^ST^SG^SC^ST^SG^SA^SA$ | 71 |
| 14918 | 1329-1348; 3' UTR | $G^SG^SC^SC^SC^SA^SG^SC^SA^SA^SA^SC^ST^ST^SG^SC^SC^SC^SG^ST$ | 72 |
| 14919 | 1377-1393; 3' UTR | $C^SC^SA^SC^SA^SC^SA^SG^ST^SG^SG^SC^ST^SC^SA^SG^SC^SC$ | 73 |
| 12912 | -0067 to -0049; 5' UTR | $G^SG^SC^SC^SA^ST^SG^SA^SG^SG^SG^SC^SA^SA^ST^SC^ST^SA^SA$ (2'MO) | 74 |
| 12913 | -0067 to -0047; 5' UTR | $G^ST^SG^SG^SC^SC^SA^ST^SG^SA^SG^SG^SG^SC^SA^SA^ST^SC^ST^SA^SA$ (2'MO) | 75 |
| 13496 | -0067 to -0047; 5' UTR | $G^ST^SG^SG^SC^SC^SA^ST^SG^SA^SG^SG^SG^SC^SA^SA^ST^SC^ST^SA^SA$ (2'ME) | 75 |
| 13497 | -0067 to -0047; 5' UTR | G T G G C C A T G A G G G C A A T C T A A (2'ME) | 75 |

TABLE 3

Sequences of Oligonucleotides Targeted to Human B7-2 mRNA

| ISIS # | Target Position*; Site** | Oligonucleotide Sequence (5' -> 3') | SEQ ID NO: |
|---|---|---|---|
| 9133 | 1367-1386; 3'-UTR | T$^S$T$^S$C$^S$C$^S$A$^S$G$^S$G$^S$T$^S$C$^S$A$^S$T$^S$G$^S$A$^S$G$^S$C$^S$C$^S$A$^S$T$^S$T$^S$A | 3 |
| 10715 | scrambled control of # 9133 | G$^S$A$^S$T$^S$T$^S$T$^S$A$^S$A$^S$C$^S$A$^S$T$^S$T$^S$T$^S$G$^S$G$^S$C$^S$C$^S$G$^S$C$^S$C$^S$A | 76 |
| 9134 | 1333-1352; 3'-UTR | C$^S$A$^S$T$^S$A$^S$A$^S$G$^S$G$^S$T$^S$G$^S$T$^S$G$^S$C$^S$T$^S$C$^S$T$^S$T$^S$G$^S$A$^S$A$^S$G$^S$T$^S$G | 4 |
| 9135 | 1211-1230; 3'-UTR | T$^S$T$^S$A$^S$C$^S$T$^S$C$^S$A$^S$T$^S$G$^S$G$^S$T$^S$A$^S$A$^S$T$^S$G$^S$T$^S$C$^S$T$^S$T$^S$T$^S$ | 5 |
| 9136 | 1101-1120; tTR | A$^S$T$^S$T$^S$A$^S$A$^S$A$^S$A$^S$C$^S$A$^S$T$^S$G$^S$T$^S$A$^S$T$^S$C$^S$A$^S$C$^S$T$^S$T$^S$ | 6 |
| 10716 | (scrambled # 9136) | A$^S$A$^S$A$^S$G$^S$T$^S$T$^S$A$^S$C$^S$A$^S$A$^S$C$^S$A$^S$T$^S$T$^S$A$^S$T$^S$A$^S$T$^S$C$^S$T | 77 |
| 9137 | 0054-0074; 5'-UTR | G$^S$G$^S$A$^S$A$^S$C$^S$A$^S$C$^S$A$^S$G$^S$A$^S$A$^S$G$^S$C$^S$A$^S$A$^S$G$^S$G$^S$T$^S$G$^S$G$^S$T | 7 |
| 9138 | 0001-0020; 5'-UTR | C$^S$C$^S$G$^S$T$^S$A$^S$C$^S$C$^S$T$^S$C$^S$C$^S$T$^S$A$^S$A$^S$G$^S$G$^S$C$^S$T$^S$C$^S$C$^S$T | 8 |
| 9139 | 0133-0152; tIR | C$^S$C$^S$C$^S$A$^S$T$^S$A$^S$G$^S$T$^S$G$^S$C$^S$T$^S$G$^S$T$^S$C$^S$A$^S$C$^S$A$^S$A$^S$A$^S$T | 9 |
| 10877 | (scrambled # 9139) | A$^S$G$^S$T$^S$G$^S$C$^S$G$^S$A$^S$T$^S$T$^S$C$^S$T$^S$C$^S$A$^S$A$^S$A$^S$C$^S$C$^S$T$^S$A$^S$C | 78 |
| 10367 | 0073-0092; 5'-UTR | G$^S$C$^S$A$^S$C$^S$A$^S$G$^S$C$^S$A$^S$G$^S$C$^S$A$^S$T$^S$T$^S$C$^S$C$^S$C$^S$A$^S$A$^S$G$^S$G | 10 |
| 10368 | 0240-0259; 5' ORF | T$^S$T$^S$G$^S$C$^S$A$^S$A$^S$A$^S$T$^S$T$^S$G$^S$G$^S$C$^S$A$^S$T$^S$G$^S$G$^S$C$^S$A$^S$G$^S$G | 11 |
| 10369 | 1122-1141; 3'-UTR | T$^S$G$^S$G$^S$T$^S$A$^S$T$^S$G$^S$G$^S$G$^S$C$^S$T$^S$T$^S$T$^S$A$^S$C$^S$T$^S$C$^S$T$^S$T$^S$T | 12 |
| 10370 | 1171-1190; 3'-UTR | A$^S$A$^S$A$^S$A$^S$G$^S$G$^S$T$^S$T$^S$G$^S$C$^S$C$^S$C$^S$A$^S$G$^S$G$^S$A$^S$A$^S$C$^S$G$^S$G | 13 |
| 10371 | 1233-1252; 3'-UTR | G$^S$G$^S$G$^S$A$^S$G$^S$T$^S$C$^S$C$^S$T$^S$G$^S$G$^S$A$^S$G$^S$C$^S$C$^S$C$^S$C$^S$C$^S$T$^S$T | 14 |
| 10372 | 1353-1372; 3'-UTR | C$^S$C$^S$A$^S$T$^S$T$^S$A$^S$A$^S$G$^S$C$^S$T$^S$G$^S$G$^S$G$^S$C$^S$T$^S$T$^S$G$^S$G$^S$C$^S$C | 15 |
| 11149 | 0019-0034; 5'-UTR | T$^S$A$^S$T$^S$T$^S$T$^S$G$^S$C$^S$G$^S$A$^S$G$^S$C$^S$T$^S$C$^S$C$^S$C$^S$C | 79 |
| 11151 | 0020-0034; 5'-UTR | T$^S$A$^S$T$^S$T$^S$T$^S$G$^S$C$^S$G$^S$A$^S$G$^S$C$^S$T$^S$C$^S$C$^S$C | 80 |
| 11150 | 0021-0034; 5'-UTR | T$^S$A$^S$T$^S$T$^S$T$^S$G$^S$C$^S$G$^S$A$^S$G$^S$C$^S$T$^S$C$^S$C | 81 |
| 10373 | 0011-0030; 5'-UTR | T$^S$G$^S$C$^S$G$^S$A$^S$G$^S$C$^S$T$^S$C$^S$C$^S$C$^S$C$^S$G$^S$T$^S$A$^S$C$^S$C$^S$T$^S$C$^S$C | 16 |
| 10721 | (scrambled # 10373) | C$^S$G$^S$A$^S$C$^S$A$^S$G$^S$C$^S$T$^S$C$^S$C$^S$T$^S$G$^S$C$^S$G$^S$C$^S$T$^S$C$^S$C$^S$T$^S$C | 82 |
| 10729 | (5'FITC # 10373) | T$^S$G$^S$C$^S$G$^S$A$^S$G$^S$C$^S$T$^S$C$^S$C$^S$C$^S$C$^S$G$^S$T$^S$A$^S$C$^S$C$^S$T$^S$C$^S$C | 16 |
| 10782 | (5'cholesterol # 10373) | T$^S$G$^S$C$^S$G$^S$A$^S$G$^S$C$^S$T$^S$C$^S$C$^S$C$^S$C$^S$G$^S$T$^S$A$^S$C$^S$C$^S$T$^S$C$^S$C | 16 |
| | #10373 Deletion Derivatives: | | |
| 10373 | 0011-0030; 5'-UTR | T$^S$G$^S$C$^S$G$^S$A$^S$G$^S$C$^S$T$^S$C$^S$C$^S$C$^S$C$^S$G$^S$T$^S$A$^S$C$^S$C$^S$T$^S$C$^S$C | 16 |
| 10888 | 0011-0026; 5'-UTR | A$^S$G$^S$C$^S$T$^S$C$^S$C$^S$C$^S$C$^S$G$^S$T$^S$A$^S$C$^S$C$^S$T$^S$C$^S$C | 83 |
| 10889 | 0015-0030; 5'-UTR | T$^S$G$^S$C$^S$G$^S$A$^S$G$^S$C$^S$T$^S$C$^S$C$^S$C$^S$C$^S$G$^S$T$^S$A$^S$C | 84 |
| 10991 | 0015-0024; 5'-UTR | C$^S$T$^S$C$^S$C$^S$C$^S$C$^S$G$^S$T$^S$A$^S$C | 85 |
| 10992 | 0015-0025; 5'-UTR | G$^S$C$^S$T$^S$C$^S$C$^S$C$^S$C$^S$G$^S$T$^S$A$^S$C | 86 |
| 10993 | 0015-0026; 5'-UTR | A$^S$G$^S$C$^S$T$^S$C$^S$C$^S$C$^S$C$^S$G$^S$T$^S$A$^S$C | 87 |
| 10994 | 0015-0027; 5'-UTR | G$^S$A$^S$G$^S$C$^S$T$^S$C$^S$C$^S$C$^S$C$^S$G$^S$T$^S$A$^S$C | 88 |
| 10995 | 0015-0028; 5'-UTR | C$^S$G$^S$A$^S$G$^S$C$^S$T$^S$C$^S$C$^S$C$^S$C$^S$G$^S$T$^S$A$^S$C | 89 |
| 10996 | 0015-0029; 5'-UTR | G$^S$C$^S$G$^S$A$^S$G$^S$C$^S$T$^S$C$^S$C$^S$C$^S$C$^S$G$^S$T$^S$A$^S$C | 90 |
| 11232 | 0017-0029; 5' UTR | G$^S$C$^S$G$^S$A$^S$G$^S$C$^S$T$^S$C$^S$C$^S$C$^S$C$^S$G$^S$T | 91 |
| | # 10996 Derivatives: | | |
| 10996 | 0015-002 9; 5'-UTR | G$^S$C$^S$G$^S$A$^S$G$^S$C$^S$T$^S$C$^S$C$^S$C$^S$C$^S$G$^S$T$^S$A$^S$C | 90 |
| 11806 | (scrambled # 10996) | G$^S$C$^S$C$^S$G$^S$C$^S$C$^S$G$^S$C$^S$C$^S$A$^S$A$^S$G$^S$T$^S$C$^S$T | 92 |
| 11539 | (fully 2' MO # 10996) | G$^S$C$^S$G$^S$A$^S$G$^S$C$^S$T$^S$C$^S$C$^S$C$^S$C$^S$G$^S$T$^S$A$^S$C (2' MO) | 90 |

TABLE 3-continued

Sequences of Oligonucleotides Targeted to Human B7-2 mRNA

| ISIS # Target Position*; Site** | Oligonucleotide Sequence (5' -> 3') | SEQ ID NO: |
|---|---|---|
| 11540 (control for # 11539) | $G^SC^SC^SG^SC^SC^SG^SC^SC^SA^SA^SG^ST^SC^ST$ (2' MO) | 92 |
| 11541 (# 10996 7-base Agapmer@) | $G^SC^SG^SA^SG^SC^ST^SC^SC^SC^SC^SG^ST^SA^SC$ (2' MO) | 90 |
| 11542 (control for # 11541) | $G^SC^SC^SG^SC^SC^SG^SC^SC^SA^SA^SG^ST^SC^ST$ (2' MO) | 92 |
| 11543 (# 109969-base Agapmer@) | $G^SC^SG^SA^SG^SC^ST^SC^SC^SC^SC^SG^ST^SA^SC$ (2' MO) | 90 |
| 11544 (control for # 11543) | $G^SC^SC^SG^SC^SC^SG^SC^SC^SA^SA^SG^ST^SC^ST$ (2' MO) | 92 |
| 11545 (# 10996 5' Awingmer@) | $G^SC^SG^SA^SG^SC^ST^SC^SC^SC^SC^SG^ST^SA^SC$ (2' MO) | 90 |
| 11546 (control for # 11545) | $G^SC^SC^SG^SC^SC^SG^SC^SC^SA^SA^SG^ST^SC^ST$ (2' MO) | 92 |
| 11547 (# 10996 3' Awingmer@) | $G^SC^SG^SA^SG^SC^ST^SC^SC^SC^SC^SG^ST^SA^SC$ (2' MO) | 90 |
| 11548 (control for # 11547) | $G^SC^SC^SG^SC^SC^SG^SC^SC^SA^SA^SG^ST^SC^ST$ (2' MO) | 92 |
| 12496 ((2'-5')A₄ # 10996) | G C G A G C T C C C G T A C | 90 |
| 13107 ((2'-5')A₄ # 10996) | $G^SC^SG^SA^SG^SC^ST^SC^SC^SC^SC^SG^ST^SA^SC$ | 90 |
| 12492 ((2'-5')A₄ # 10996) | $G^SC^SG^SA^SG^SC^ST^SC^SC^SC^SC^SG^ST^SA^SC$ (2' MO) | 90 |
| 12495 ((2'-5')A₄ # 10996) | $G^SC^SG^SA^SG^SC^ST^SC^SC^SC^SC^SG^ST^SA^SC$ (2' MO) | 90 |
| 12887 (1-24 of SEQ ID NO: 1 of WO 95/03408; alternative mrNA) | $G^SA^SG^SA^SA^SG^SC^SA^SA^SA^SG^SC^ST^ST^ST^SC^SA^SC^SC^SC^S-T^SG^ST^SG$ (2' MO) | 93 |
| 12888 (1-22 of SEQ ID NO: 1 of WO 95/03408; alternative mRNA) | $G^SA^SA^SG^SC^SA^SA^SA^SG^SC^ST^ST^ST^SC^SA^SC^SC^SC^ST^SG^ST^SG$ (2' MO) | 94 |
| 12889 (1-19 of SEQ ID NO: 1 of WO 95/03408; alternative mRNA) | $G^SC^SA^SA^SA^SG^SC^ST^ST^ST^SC^SA^SC^SC^SC^ST^SG^ST^SG$ (2' MO) | 95 |
| 12890 0001-0024 | $C^ST^SC^SC^SC^SC^SG^ST^SA^SC^SC^ST^SC^SC^ST^SA^SA^SG^SG^SC^S-T^SC^SC^ST$ (2' MO) | 96 |
| 12891 0001-0022 | $C^SC^SC^SC^SG^ST^SA^SC^SC^ST^SC^SC^ST^SA^SA^SG^SG^SC^ST^SC^SC^ST$ (2' MO) | 97 |
| 12892 0001-0020 | $C^SC^SG^ST^SA^SC^SC^ST^SC^SC^ST^SA^SA^SG^SG^SC^ST^SC^SC$ (2' MO) | 98 |

TABLE 4

Sequences of Oligonucleotides Targeted to Murine B7-2 mRNA

| ISIS # Target Position; Site | Oligonucleotide Sequence (5' -> 3') | SEQ ID NO: |
|---|---|---|
| 11347 1094-1113; 3' UTR | $A^SG^SA^SA^ST^ST^SC^SC^SA^SA^ST^SC^SA^SG^SC^ST^SG^SA^SG^SA$ | 121 |
| 11348 1062-1081; 3' UTR | $T^SC^ST^SG^SA^SG^SA^SA^SA^SC^ST^SC^ST^SG^SC^SA^SC^ST^ST^SC$ | 122 |
| 11349 1012-1031; 3' UTR | $T^SC^SC^ST^SC^SA^SG^SG^SC^ST^SC^ST^SC^SA^SC^ST^SG^SC^SC^ST$ | 123 |
| 11350 0019-1138; 5' UTR | $G^SG^ST^ST^SG^ST^ST^SC^SA^SA^SG^ST^SC^SC^SG^ST^SG^SC^ST^SG$ | 124 |
| 11351 0037-0056; 5' UTR | $A^SC^SA^SC^SG^ST^SC^ST^SA^SC^SA^SG^SG^SA^SG^ST^SC^ST^SG^SG$ | 103 |
| 11352 0089-0108; tIR | $C^SA^SA^SG^SC^SC^SC^SA^ST^SG^SG^ST^SG^SC^SA^ST^SC^ST^SG^SG$ | 104 |
| 11353 0073-0092; tIR | $C^ST^SG^SG^SG^SG^ST^SC^SC^SA^ST^SC^SG^ST^SG^SG^SG^ST^SG^SC$ | 105 |
| 11354 0007-0026; 5' UTR | $C^SC^SG^ST^SG^SC^ST^SG^SC^ST^SA^SC^SA^SG^SA^SG^SA^SG^SC^SC$ | 106 |
| 11695 0058-0077; 5' UTR | $G^SG^ST^SG^SC^ST^ST^SC^SC^SG^ST^SA^SA^SG^ST^ST^SC^ST^SG^SG$ | 107 |
| 11696 0096-0117; tIR | $G^SG^SA^ST^ST^SG^SC^SC^SA^SA^SG^SC^SC^SC^SA^ST^SG^SG^ST^SG$ | 108 |

TABLE 4-continued

Sequences of Oligonucleotides Targeted to Murine B7-2 mRNA

| ISIS # | Target Position; Site | Oligonucleotide Sequence (5' -> 3') | SEQ ID NO: |
|---|---|---|---|
| 11866 | (Scrambled # 11696) | $C^sT^sA^sA^sG^sT^sA^sG^sT^sG^sC^sT^sA^sG^sC^sC^sG^sG^sG^sA$ | 109 |
| 11697 | 0148-0167; 5' ORF | $T^sG^sC^sG^sT^sC^sT^sC^sC^sA^sC^sG^sG^sA^sA^sA^sC^sA^sG^sC$ | 110 |
| 11698 | 0319-0338; 5' ORF | $G^sT^sG^sC^sG^sG^sC^sC^sC^sA^sG^sG^sT^sA^sC^sT^sT^sG^sG^sC$ | 111 |
| 11699 | 0832-0851; 3' ORF | $A^sC^sA^sA^sG^sG^sA^sG^sG^sA^sG^sG^sG^sC^sC^sA^sC^sA^sG^sT$ | 112 |
| 11700 | 0753-0772; 3' ORF | $T^sG^sA^sG^sA^sG^sG^sT^sT^sT^sG^sG^sA^sG^sG^sA^sA^sA^sT^sC$ | 113 |
| 11701 | 0938-0957; 3' ORF | $G^sA^sT^sA^sG^sT^sC^sT^sC^sT^sT^sG^sT^sC^sA^sG^sC^sG^sT$ | 114 |
| 11702 | 0890-0909; 3' ORF | $G^sT^sT^sG^sC^sT^sG^sG^sG^sC^sC^sT^sG^sC^sT^sA^sG^sG^sC^sT$ | 115 |
| 11865 | (scrambled # 11702) | $C^sT^sA^sG^sG^sT^sC^sT^sC^sG^sT^sC^sG^sT^sC^sG^sG^sT^sG^sG$ | 116 |
| 11703 | 1003-1022; tTR | $T^sC^sT^sC^sA^sC^sT^sG^sC^sC^sT^sT^sC^sA^sC^sT^sC^sT^sG^sC$ | 117 |
| 13100 | Exon 1 (Borriello et al., J. Immun., 1995, 155, 5490; 5' UTR of alternative mRNA). | $G^sT^sA^sC^sC^sA^sG^sA^sT^sG^sA^sA^sG^sG^sT^sT^sA^sT^sC^sA^sA$ (2' MO) | 118 |
| 13101 | Exon 4 (Borriello et al.; 5' UTR of alternative mRNA) | $C^sT^sT^sT^sG^sG^sA^sG^sA^sT^sT^sA^sT^sT^sC^sG^sA^sG^sT^sT$ (2' MO) | 119 |
| 13102 | Exon 5 (Borriello et al.; 5' UTR of alternative mRNA) | $G^sC^sA^sA^sG^sT^sG^sT^sA^sA^sA^sG^sC^sC^sC^sT^sG^sA^sG^sT$ (2' MO) | 120 | cDNA Clones:

A cDNA encoding the sequence for human B7-1 was isolated by using the reverse transcription/polymerase chain reaction (RT-PCR). Poly A+RNA from Daudi cells (ATCC accession No. CCL 213) was reverse transcribed using oligo-dT primer under standard conditions. Following a 30 minute reaction at 42° C. and heat inactivation, the reaction mixture (20 uL) was brought to 100 uL with water. A 10 uL aliquot from the RT reaction was then amplified in a 50 uL PCR reaction using the 5' primer,

5'-GAT-CAG-GGT-ACC-CCA-AAG-AAA-AAG-TGA-TTT-GTC-ATT-GC-3'

(sense, SEQ ID NO: 20), and the 3' primer,

5'-GAT-AGC-CTC-GAG-GAT-AAT-GAA-TTG-GCT-GAC-AAG-AC-3'

(antisense, SEQ ID NO: 21)

The primers included unique restriction sites for subcloning of the PCR product into the vector pcDNA-3 (Invitrogen, San Diego, Calif.). The 5' primer was designed to have identity with bases 1 to 26 of the published human B7-1 sequence (Freeman et al., *J. Immunol.*, 1989, 143, 2714; positions 13-38 of the primer) and includes a Kpn I restriction site (positions 7-12 of the primer) for use in cloning. The 3' primer was designed to be complementary to bases 1450 to 1471 of the published sequence for B7-1 (positions 14-35 of the primer) and includes a Xho I restriction site (positions 7-12 of the primer). Following PCR, the reaction was extracted with phenol and precipitated using ethanol. The product was digested with the appropriate restriction enzymes and the full-length fragment purified by agarose gel and ligated into the vector pcDNA-3 (Invitrogen, San Diego, Calif.) prepared by digesting with the same enzymes. The resultant construct, pcB7-1, was confirmed by restriction mapping and DNA sequence analysis using standard procedures. A mouse B7-1 clone, pcmB7-1, was isolated in a similar manner by RT-PCR of RNA isolated from a murine B-lymphocyte cell line, 70Z3.

A cDNA encoding the sequence for human B7-2, position 1 to 1391, was also isolated by RT-PCR. Poly A+RNA from Daudi cells (ATCC accession No. CCL 213) was reverse transcribed using oligo-dT primer under standard conditions. Following a 30 minute reaction at 42° C. and heat inactivation, the reaction mixture (20 uL) was brought to 100 uL with water. A 10 uL aliquot from the RT reaction was then amplified in a 50 uL PCR reaction using the 5' primer,

5'-GAT-CAG-GGT-ACC-AGG-AGC-CTT-AGG-AGG-TAC-GG-3'

(sense, SEQ ID NO: 1), and the 3' primer,

5'-GAT-AGC-CTC-GAG-TTA-TTT-CCA-GGT-CAT-GAG-CCA-3'

(antisense, SEQ ID NO: 2).

The 5' primer was designed to have identity with bases 1-20 of the published B7-2 sequence (Azuma et al., *Nature*, 1993, 366, 76 and Genbank Accession No. L25259; positions 13-32 of the primer) and includes a Kpn I site (positions 7-12 of the primer) for use in cloning. The 3' primer was designed to have complementarity to bases 1370-1391 of the published sequence for B7-2 (positions 13-33 of the primer) and includes an Xho I restriction site (positions 7-12 of the primer). Following PCR, the reaction was extracted with phenol and precipitated using ethanol. The product was digested with Xho I and Kpn I, and the full-length fragment purified by agarose gel and ligated into the vector pcDNA-3 (Invitrogen, San Diego, Calif.) prepared by digesting with the same enzymes. The resultant construct, pcB7-2, was confirmed by restriction mapping and DNA sequence analysis using standard procedures.

A mouse B7-2 clone, pcmB7-2, was isolated in a similar manner by RT-PCR of RNA isolated from P388D1 cells using the 5' primer,

5'-GAT-CAG-GGT-ACC-AAG-AGT-GGC-TCC-TGT-AGG-CA (Sense, SEQ ID NO: 99), and the 3' primer,

5'-GAT-AGC-CTC-GAG-GTA-GAA-TTC-CAA-TCA-GCT-GA (antisense, SEQ ID NO: 100).

The 5' primer has identity with bases 1-20, whereas the 3' primer is complementary to bases 1096-1115, of the published murine B7-2 sequence (Chen et al., *J. Immun.*, 1994, 152, 4929). Both primers incorporate the respective restriction enzyme sites found in the other 5' and 3' primers used to prepare cDNA clones. The RT-PCR product was restricted with Xho I and Kpn I and ligated into pcDNA-3 (Invitrogen, Carlsbad, Calif.).

Other cDNA clones, corresponding to mRNAs resulting from alternative splicing events, are cloned in like fashion, using primers containing the appropriate restriction sites and having identity with (5' primers), or complementarity to (3' primers), the selected B7 mRNA.

Example 2

Modulation of hB7-1 Expression by Oligonucleotides

The ability of oligonucleotides to inhibit B7-1 expression was evaluated by measuring the cell surface expression of B7-1 in transfected COS-7 cells by flow cytometry.

Methods:

A T-175 flask was seeded at 75% confluency with COS-7 cells (ATCC accession No. CRL 1651). The plasmid pcB7-1 was introduced into cells by standard calcium phosphate transfection. Following a 4 hour transfection, the cells were trypsinized and seeded in 12-well dishes at 80% confluency. The cells were allowed to adhere to the plastic for 1 hour and were then washed with phosphate-buffered saline (PBS). OptiMEM™ (GIBCO-BRL, Gaithersburg, Md.) medium was added along with 15 Φg/mL of Lipofectin™ (GIBCO-BRL, Gaithersburg, Md.) and oligonucleotide at the indicated concentrations. After four additional hours, the cells were washed with phosphate buffered saline (PBS) and incubated with fresh oligonucleotide at the same concentration in DMEM (Dulbecco et al., *Virol.*, 1959, 8, 396; Smith et al., *Virol.*, 1960, 12, 185) with 10% fetal calf sera (FCS).

In order to monitor the effects of oligonucleotides on cell surface expression of B7-1, treated COS-7 cells were harvested by brief trypsinization 24-48 hours after oligonucleotide treatment. The cells were washed with PBS, then resuspended in 100 ΦL of staining buffer (PBS, 0.2% BSA, 0.1% azide) with 5 Φ L conjugated anti-B7-1-antibody (i.e., anti-hCD80-FITC, Ancell, Bayport, Minn.; FITC: fluorescein isothiocyanate). The cells were stained for 30 minutes at 4° C., washed with PBS, resuspended in 300 ΦL containing 0.5% paraformaldehyde. Cells were harvested and the fluorescence profiles were determined using a flow cytometer.

Results:

The oligonucleotides shown in Table 1 were evaluated, in COS-7 cells transiently expressing B7-1 cDNA, for their ability to inhibit B7-1 expression. The results (FIG. 1) identified ISIS 13805, targeted to the translation initiation codon region, and ISIS 13812, targeted to the 3' untranslated region (UTR), as the most active oligonucleotides with greater than 50% inhibition of B7-1 expression. These oligonucleotides are thus highly preferred. ISIS 13799 (targeted to the 5' untranslated region), ISIS 13802 (targeted to the 5' untranslated region), ISIS 13806 and 13807 (both targeted to the 5' region of the ORF), and ISIS 13810 (targeted to the central portion of the ORF) demonstrated 35% to 50% inhibition of B7-1 expression. These sequences are therefore also preferred. Oligonucleotide ISIS 13800, which showed essentially no inhibition of B7-1 expression in the flow cytometry assay, and ISIS Nos. 13805 and 13812 were then evaluated for their ability to inhibit cell surface expression of B7-1 at various concentrations of oligonucleotide. The results of these assays are shown in FIG. 2. ISIS 13812 was a superior inhibitor of B7-1 expression with an IC$_{50}$ of approximately 150 nM. ISIS 13800, targeted to the 5' UTR, was essentially inactive.

Example 3

Modulation of hB7-2 Protein by Oligonucleotides

In an initial screen, the ability of hB7-2 oligonucleotides to inhibit B7-2 expression was evaluated by measuring the cell surface expression of B7-2 in transfected COS-7 cells by flow cytometry. The methods used were similar to those given in Example 2, with the exceptions that (1) COS-7 cells were transfected with the plasmids pbcB7-2 or BBG-58, a human ICAM-1 (CD54) expression vector (R&D Systems, Minneapolis, Minn.) introduced into cells by standard calcium phosphate transfection, (2) the oligonucleotides used were those described in Table 2, and (3) a conjugated anti-B7-2 antibody (i.e., anti-hCD86-FITC or anti-CD86-PE, PharMingen; San Diego, Calif.; PE: phycoerythrin) was used during flow cytometry.

Figure 3:
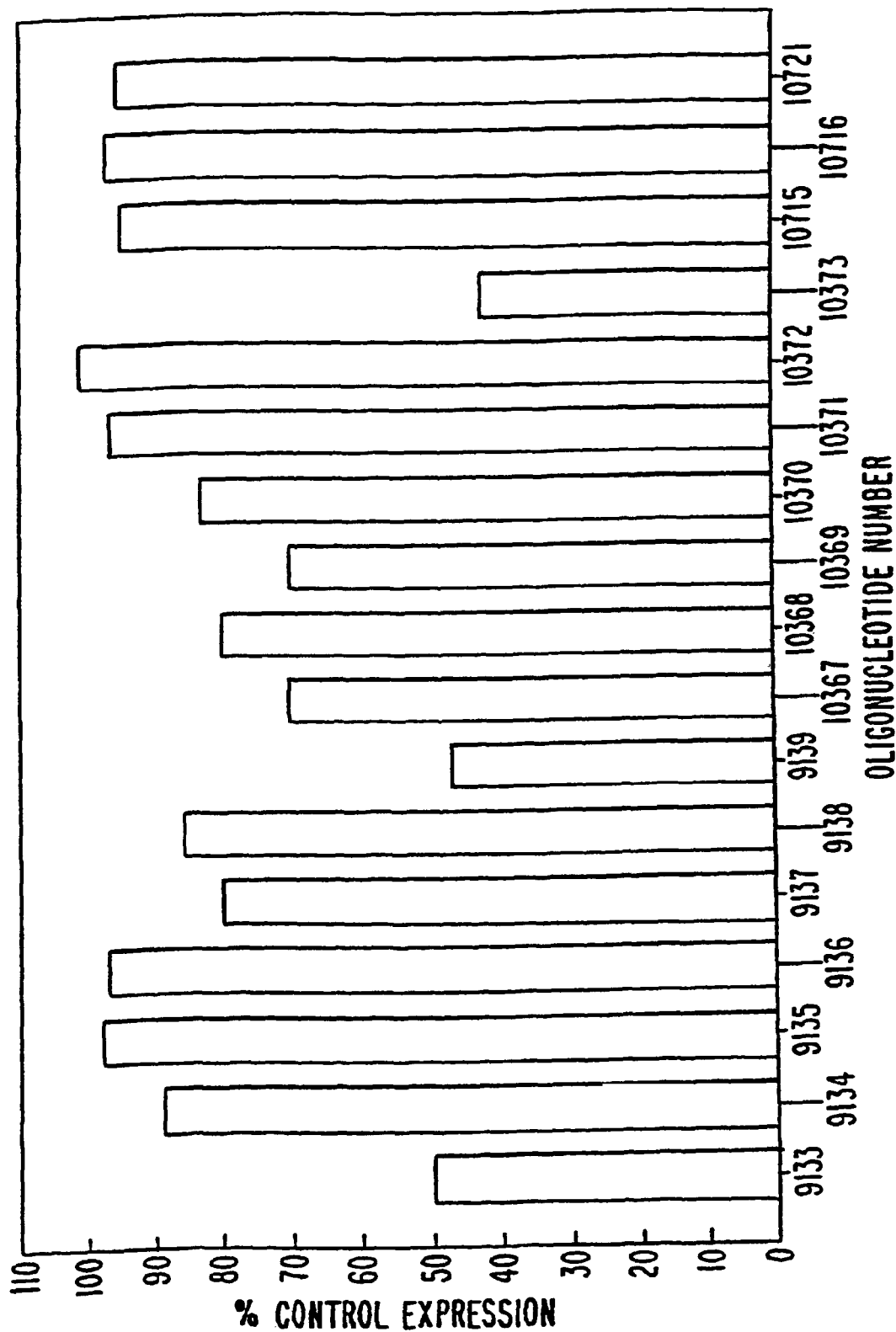
FIG. 3 is a bar graph showing the inhibitory effect of the indicated oligonucleotides on cell surface expression of B7-2 in COS-7 cells.

Results:

The results are shown in FIG. 3. At a concentration of 200 nM, ISIS 9133, ISIS 9139 and ISIS 10373 exhibited inhibitory activity of 50% or better and are therefore highly preferred. These oligonucleotides are targeted to the 3' untranslated region (ISIS 9133), the translation initiation codon region (ISIS 9139) and the 5' untranslated region (ISIS 10373). At the same concentration, ISIS 10715, ISIS 10716 and ISIS 10721, which are scrambled controls for ISIS 9133, ISIS 9139 and ISIS 10373, respectively, showed no inhibitory activity. Treatment with ISIS 10367 and ISIS 10369 resulted in greater than 25% inhibition, and these oligonucleotides are thus also preferred. These oligonucleotides are targeted to the 5' (ISIS 10367) and 3' (ISIS 10369) untranslated regions.

Example 4

Modulation of hB7-2 mRNA by Oligonucleotides

Methods:

For ribonuclease protection assays, cells were harvested 18 hours after completion of oligonucleotide treatment using a Totally RNA™ kit (Ambion, Austin, Tex.). The probes for the assay were generated from plasmids pcB7-2 (linearized by digestion with Bgl II) and pTRI-b-actin (Ambion Inc., Austin, Tex.). In vitro transcription of the linearized plasmid from the SP6 promoter was performed in the presence of a-$^{32}$P-UTP (800 ci/mmole) yielding an antisense RNA complementary to the 3' end of B7-2 (position 1044-1391). The probe was gel-purified after treatment with DNase I to remove DNA template. Ribonuclease protection assays were carried out using an RPA II™ kit (Ambion) according to the manufacturer's directions. Total RNA (5 Φg) was hybridized overnight, at 42° C., with $10^5$ cpm of the B7-2 probe or a control beta-actin probe. The hybridization reaction was then treated, at 37° C. for 30 minutes, with 0.4 units of RNase A and 2 units of RNase T1. Protected RNA was precipitated, resuspended in 10 Φ L of gel loading buffer and electrophoresed on a 6% acrylamide gel with 50% w/v urea at 20 W. The gel was then exposed and the lanes quantitated using a PhosphorImager (Molecular Dynamics, Sunnyvale, Calif.) essentially according to the manufacturer's instructions.

Results:

The extent of oligonucleotide-mediated hB7-2 mRNA modulation generally paralleled the effects seen for hB7-2 protein (Table 5). As with the protein expression (flow cytometry assays, the most active oligonucleotides were ISIS 9133, ISIS 9139 and 10373. None of the oligonucleotides tested had an inhibitory effect on the expression of b-actin mRNA in the same cells.

TABLE 5

Activities of Oligonucleotides Targeted to hB7-2 mRNA

| ISIS NO. | SEQ ID NO. | % Control Protein | % Control RNA Expression |
|---|---|---|---|
| 9133 | 3 | 70.2 | 46.0 |
| 9134 | 4 | 88.8 | 94.5 |
| 9135 | 5 | 98.2 | 83.4 |
| 9136 | 6 | 97.1 | 103.1 |
| 9137 | 7 | 80.5 | 78.1 |
| 9138 | 8 | 86.4 | 65.9 |
| 9139 | 9 | 47.9 | 32.6 |
| 10367 | 10 | 71.3 | 52.5 |
| 10368 | 11 | 81.0 | 84.5 |
| 10369 | 12 | 71.3 | 81.5 |
| 10370 | 13 | 84.3 | 83.2 |
| 10371 | 14 | 97.3 | 92.9 |
| 10372 | 15 | 101.7 | 82.5 |
| 10373 | 16 | 43.5 | 32.7 |

Example 5

Additional hB7-1 and hB7-2 Oligonucleotides

Figure 4:
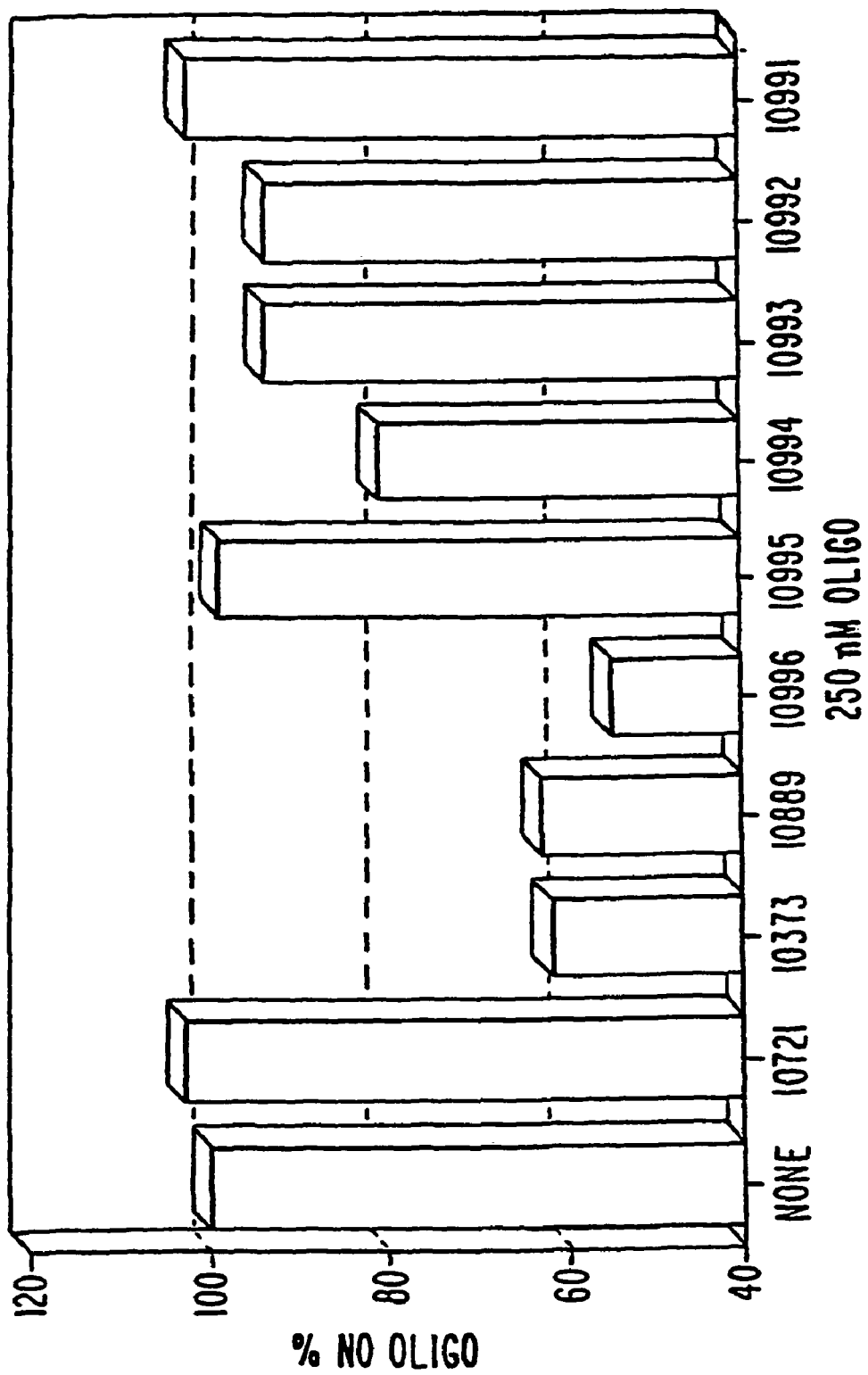
FIG. 4 is a bar graph showing the inhibitory effect of the indicated oligonucleotides, including ISIS 10373 (a 20-mer) and ISIS 10996 (a 15-mer) on cell surface expression of B7-2 in COS-7 cells.

Oligonucleotides having structures and/or sequences that were modified relative to the oligonucleotides identified during the initial screening were prepared. These oligonucleotides were evaluated for their ability to modulate human B7-2 expression using the methods described in the previous examples. ISIS 10996, an oligonucleotide having a 15 nucleotide sequence derived from the 20 nucleotide sequence of ISIS 10373, was also prepared and evaluated. ISIS 10996 comprises 15 nucleotides, 5'-GCG-AGC-TCC-CCG-TAC (SEQ ID NO: 90) contained within the sequence of ISIS 10373. Both ISIS 10373 and 10996 overlap a potential stem-loop structure located within the B7-2 message comprising bases 1-67 of the sequence of hB7-2 presented by Azuma et al. (*Nature,* 1993, 366, 76). While not intending to be bound by any particular theory regarding their mode(s) of action, ISIS 10373 and ISIS 10996 have the potential to bind as loop 1 pseudo-half-knots at a secondary structure within the target RNA. U.S. Pat. No. 5,5152,438, the contents of which are hereby incorporated by reference, describes methods for modulating gene expression by the formation of pseudo-half-knots. Regardless of their mode(s) of action, despite having a shorter length than ISIS 10373, the 15-mer ISIS 10996 is as (or more) active in the B7-2 protein expression assay than the 20-mer from which it is derived (FIG. 4; ISIS 10721 is a scrambled control for ISIS 10373). A related 16-mer, ISIS 10889, was also active in the B7-2 protein expression assay. However, a structurally related 14-mer (ISIS 10995), 13-mer (ISIS 10994), 12-mer (ISIS 10993), 11-mer (ISIS 10992) and 10-mer (ISIS 10991) exhibited little or no activity in this assay. ISIS 10996 was further derivatized in the following ways.

ISIS 10996 derivatives having 2' methoxethoxy substitutions were prepared, including a fully substituted derivative (ISIS 11539), Agapmers@ (ISIS 11541 and 11543) and Awingmers@ (ISIS 11545 and 11547). As explained in Example 5, the 2'-MOE substitution prevents the action of some nucleases (e.g., RNase H) but enhances the affinity of the modified oligonucleotide for its target RNA molecule. These oligonucleotides are tested for their ability to modulate hB7-2 message or function according to the methods of Examples 3, 4, 7 and 8.

ISIS 10996 derivatives were prepared in order to be evaluated for their ability to recruit RNase L to a target RNA molecule, e.g., hB7-2 message. RNase L binds to, and is activated by, $(2'-5')(A)_n$, which is in turn produced from ATP by $(2'-5')(A)_n$ synthetase upon activation by, e.g., interferon. RNase L has been implicated in antiviral mechanisms and in the regulation of cell growth as well (Sawai, *Chemica Scripta,* 1986, 21, 169; Charachon et al., *Biochemistry,* 1990, 29, 2550). The combination of anti-B7 oligonucleotides conjugated to $(2'-5')(A)_n$ is expected to result in the activation of RNase L and its targeting to the B7 message complementary to the oligonucleotide sequence. The following oligonucleotides have identical sequences (i.e., that of ISIS 10996) and identical $(2'-5')(A)_4$ "caps" on their 5' termini: ISIS 12492, 12495, 12496 and 13107. The adenosyl residues have 3' hydroxyl groups and are linked to each other by phosphorothioate linkages. The (3'-5') portion of the oligonucleotide, which has a sequence complementary to a portion of the human B7-2 RNA, is conjugated to the $(2'-5')(A)_4$ "caps" via a phosphorothioate linkage from the 5' residue of the (3'-5') portion of the oligonucleotide to an n-aminohexyl linker which is bonded to the "caps" via another phosphorothioate linkage. In order to test a variety of chemically diverse oligonucleotides of this type for their ability to recruit RNase L to a specific message, different chemical modifications were made to this set of four oligonucleotides as follows. ISIS 12496 consists of unmodified oligonucleotides in the (3'-5') portion of the oligonucleotide. In ISIS 13107, phosphorothioate linkages replace the phosphate linkages found in naturally occurring nucleic acids. Phosphorothioate linkages are also employed in ISIS 12492 and 12495, which additionally have 2'-methoxyethoxy substitutions. These oligonucleotides are tested for their ability to modulate hB7-2 message or function according to the methods of Examples 3, 4, 7 and 8.

Derivatives of ISIS 10996 having modifications at the 2' position were prepared and evaluated. The modified oligonucleotides included ISIS 11539 (fully 2'-O-methyl), ISIS 11541 (having 2'-O-methyl "wings" and a central 7-base "gap", ISIS 11543 (2'-O-methyl wings with a 9-base gap), ISIS 11545 (having a 5'2'-O-methyl wing) and ISIS 11547 (having a 3'2'-O-methyl wing). The results of assays of 2'-O-methyl oligonucleotides were as follows. ISIS 11539, the fully 2'O-methyl version of ISIS 10996, was not active at all in the protein expression assay. The gapped and winged oligonucleotides (ISIS 11541, 11543, 11545 and 11547) each showed some activity at 200 nM (i.e., from 60 to 70% expression relative to untreated cells), but less than that demonstrated by the parent compound, ISIS 10996 (i.e., about 50% expression). Similar results were seen in RNA expression assays.

ISIS 10782, a derivative of ISIS 10373 to which cholesterol has been conjugated via a 5' n-aminohexyl linker, was prepared. Lipophilic moieties such as cholesterol have been reported to enhance the uptake by cells of oligonucleotides in some instances, although the extent to which uptake is enhanced, if any, remains unpredictable. ISIS 10782, and other oligonucleotides comprising lipophilic moieties, are tested for their ability to modulate B7-2 message or function according to the methods of Examples 3, 4, 7 and 8.

A series of 2'-methoxyethoxy (herein, "2'ME") and 2'-fluoride (herein, "2'F") "gapmer" derivatives of the hB7-1 oligonucleotides ISIS 12361 (ISIS Nos. 12348 and 12473, respectively), ISIS 12362 (ISIS Nos. 12349 and 12474), ISIS 12363 (ISIS Nos. 12350 and 12475), ISIS 12364 (ISIS Nos. 12351 and 12476), ISIS 12365 (ISIS Nos. 12352 and 12477), ISIS 12366 (ISIS Nos. 12353 and 12478), ISIS 12367(ISIS Nos. 12354 and 12479), ISIS 12368 (ISIS Nos. 12355 and 12480), ISIS 12369 (ISIS Nos. 12356 and 12481) and ISIS 12370 (ISIS Nos. 12357 and 12482) were prepared. The central, non-2'-modified portions ("gaps")of these derivatives support RNase H activity when the oligonucleotide is bound to its target RNA, even though the 2'-modified portions do not. However, the 2'-modified "wings" of these oligonucleotides enhance their affinity to their target RNA molecules (Cook, Chapter 9 In: *Antisense Research and Applications*, Crooke et al., eds., CRC Press, Boca Raton, 1993, pp. 171-172).

Another 2' modification is the introduction of a methoxy (MO) group at this position. Like 2'ME- and 2'F-modified oligonucleotides, this modification prevents the action of RNase H on duplexes formed from such oligonucleotides and their target RNA molecules, but enhances the affinity of an oligonucleotide for its target RNA molecule. ISIS 12914 and 12915 comprise sequences complementary to the 5' untranslated region of alternative hB7-1 mRNA molecules, which arise from alternative splicing events of the primary hB7-1 transcript. These oligonucleotides include 2' methoxy modifications, and the enhanced target affinity resulting therefrom may allow for greater activity against alternatively spliced B7-1 mRNA molecules which may be present in low abundance in some tissues (Inobe et al., *J. Immun.*, 1996, 157, 582). Similarly, ISIS 13498 and 13499, which comprise antisense sequences to other alternative hB7-1 mRNAs, include 2'-MOE modifications in order to enhance their affinity for their target molecules, and 2'-MOE or 2'methoxy substitutions are incorporated into the hB7-2 oligonucleotides ISIS 12912, 12913, 13496 and 13497. These oligonucleotides are tested for their ability to modulate hB7-1 essentially according to the methods of Example 2 or hB7-2 according to the methods of Examples 3, 4, 7 and 8, with the exception that, when necessary, the target cells are transfected with a cDNA clone corresponding to the appropriate alternatively spliced B7 transcript.

Example 6

Specificity of Antisense Modulation

Figure 5:
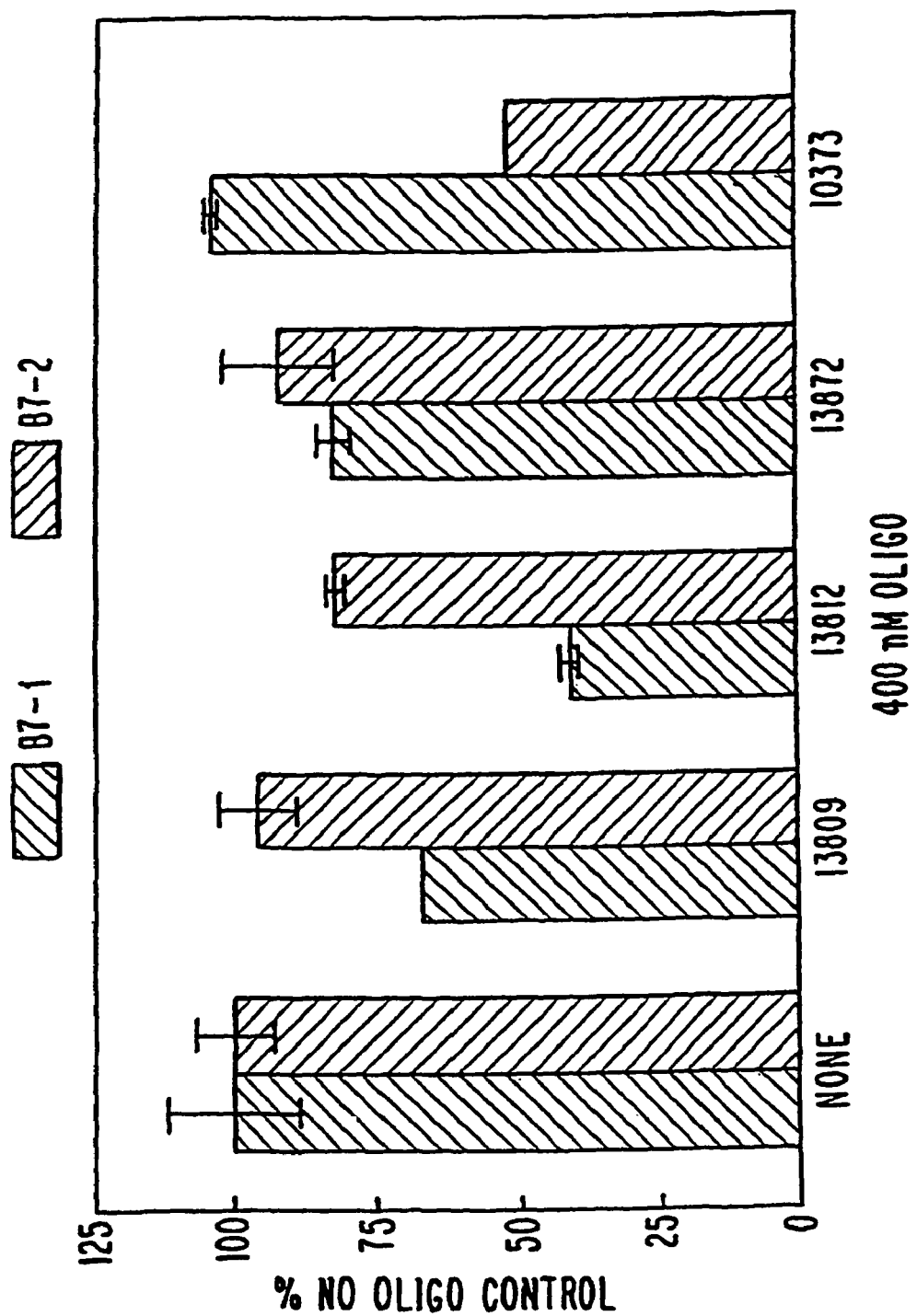
FIG. 5 is a bar graph showing the specificity of inhibition of B7-1 or B7-2 protein expression by oligonucleotides. Crosshatched bars, B7-1 levels; striped bars, B7-2 levels.

Several oligonucleotides of the invention were evaluated in a cell surface expression flow cytometry assay to determine the specificity of the oligonucleotides for B7-1 as contrasted with activity against B7-2. The oligonucleotides tested in this assay included ISIS 13812, an inhibitor of B7-1 expression (FIG. 1; Example 2) and ISIS 10373, an inhibitor of B7-2 expression (FIG. 3; Example 3). The results of this assay are shown in FIG. 5. ISIS 13812 inhibits B7-1 expression with little or no effect on B7-2 expression. As is also seen in FIG. 5, ISIS 10373 inhibits B7-2 expression with little or no effect on B7-1 expression. ISIS 13872 (SEQ ID NO: 37, AGT-CCT-ACT-ACC-AGC-CGC-CT), a scrambled control of ISIS 13812, and ISIS 13809 (SEQ ID NO: 51) were included in these assays and demonstrated essentially no activity against either B7-1 or B7-2.

Example 7

Modulation of hB7-2 Expression by Oligonucleotides in Antigen Presenting Cells

The ability of ISIS 10373 to inhibit expression from the native B7-2 gene in antigen presenting cells (APCs) was evaluated as follows.
Methods:

Monocytes were cultured and treated with oligonucleotides as follows. For dendritic cells, EDTA-treated blood was layered onto Polymorphprep™ (1.113 g/mL; Nycomed, Oslo, Norway) and sedimented at 500× g for 30 minutes at 20° C. Mononuclear cells were harvested from the interface. Cells were washed with PBS, with serum-free RPMI media (Moore et al., N.Y. J. Med., 1968, 68, 2054) and then with RPMI containing 5% fetal bovine serum (FBS). Monocytes were selected by adherence to plastic cell culture cell culture dishes for 1 h at 37° C. After adherence, cells were treated with oligonucleotides in serum-free RPMI containing Lipofectin™ (8 ug/mL). After 4 hours, the cells were washed. Then RPMI containing 5% FBS and oligonucleotide was added to cells along with interleukin-4 (IL-4; R&D Systems, Minneapolis, Minn.) (66 ng/mL) and granulocyte-macrophage colony-stimulating factor (GM-CSF; R&D Systems, Minneapolis, Minn.) (66 ng/mL) to stimulate differentiation (Romani et al., *J. Exp. Med.*, 1994, 180, 83, 1994). Cells were incubated for 48 hours, after which cell surface expression of various molecules was measured by flow cytometry.

Figure 6:
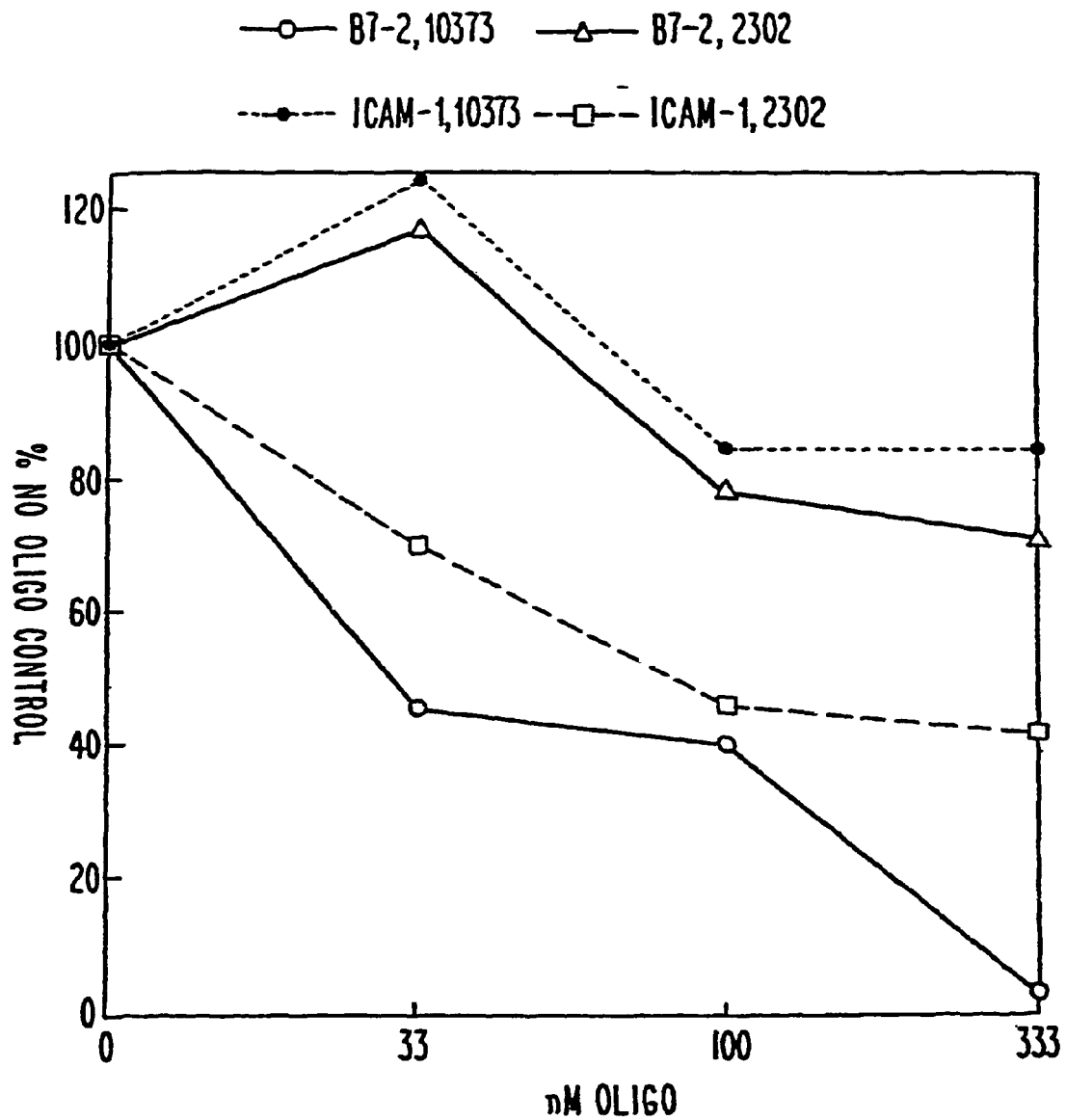
FIG. 6 is a dose-response curve showing the inhibitory effect of oligonucleotides having antisense sequences to ICAM-1 (ISIS 2302) or B7-2 (ISIS 10373) on cell surface expression of the ICAM-1 and B7-2 proteins. Solid line with X's, levels of B7-1 protein on cells treated with ISIS 10373; dashed line with asterisks, levels of ICAM-1 protein on cells treated with ISIS 10373; solid line with triangles, levels of B7-1 protein on cells treated with ISIS 2302; solid line with squares, levels of ICAM-1 protein on cells treated with ISIS 10373.

Mononuclear cells isolated from fresh blood were treated with oligonucleotide in the presence of cationic lipid to promote cellular uptake. As a control oligonucleotide, ISIS 2302 (an inhibitor of ICAM-1 expression; SEQ ID NO: 17) was also administered to the cells. Expression of B7-2 protein was measured by flow cytometry according to the methods of Example 2. Monoclonal antibodies not described in the previous Examples included anti-hCD3 (Ancell, Bayport, Minn.) and anti-HLA-DR (Becton Dickinson, San Jose, Calif.).
Results:

As shown in FIG. 6, ISIS 10373 has a significant inhibitory effect on B7-2 expression with an IC50 of approximately 250 nM. ISIS 10373 had only a slight effect on ICAM-1 expression even at a dose of 1 uM. ISIS 2302 (SEQ ID NO: 17), a control oligonucleotide which has been shown to inhibit ICAM-1 expression, had no effect on B7-2 expression, but significantly decreased ICAM-1 levels with an IC50 of approximately 250 nM. Under similar conditions, ISIS 10373 did not affect the cell surface expression of B7-1, HLA-DR or CD3 as measured by flow cytometry.

Example 8

Modulation of T Cell Proliferation by Oligonucleotides

The ability of ISIS 2302 and ISIS 10373 to inhibit T cell proliferation was evaluated as follows. Monocytes treated with oligonucleotide and cytokines (as in Example 6) were used as antigen presenting cells in a T cell proliferation assay. The differentiated monocytes were combined with CD4+ T cells from a separate donor. After 48 hours, proliferation was measured by [$^3$H] thymidine incorporation.

Methods:

For T cell proliferation assays, cells were isolated from EDTA-treated whole blood as described above, except that a faster migrating band containing the lymphocytes was harvested from just below the interface. Cells were washed as described in Example 6 after which erythrocytes were removed by NH$_4$Cl lysis. T cells were purified using a T cell enrichment column (R&D Systems, Minneapolis, Minn.) essentially according to the manufacturer's directions. CD4+ T cells were further enriched from the entire T cell population by depletion of CD8+ cells with anti-CD8-conjugated magnetic beads (AMAC, Inc., Westbrook, Me.) according to the manufacturer's directions. T cells were determined to be >80% CD4+ by flow cytometry using Cy-chrome-conjugated anti-CD4 mAb (PharMingen, San Diego, Calif.).

Antigen presenting cells (APCs) were isolated as described in Example 6 and treated with mitomycin C (25 ug/mL) for 1 hour then washed 3 times with PBS. APCs (10$^5$ cells) were then combined with 4×10$^4$ CD4+T cells in 350 uL of culture media. Where indicated, purified CD3 mAb was also added at a concentration of 1 ug/mL. During the last 6 hours of the 48 hour incubation period, proliferation was measured by determining uptake of 1.5 uCi of [$^3$H]-thymidine per well. The cells were harvested onto filters and the radioactivity measured by scintillation counting.

Figure 7:
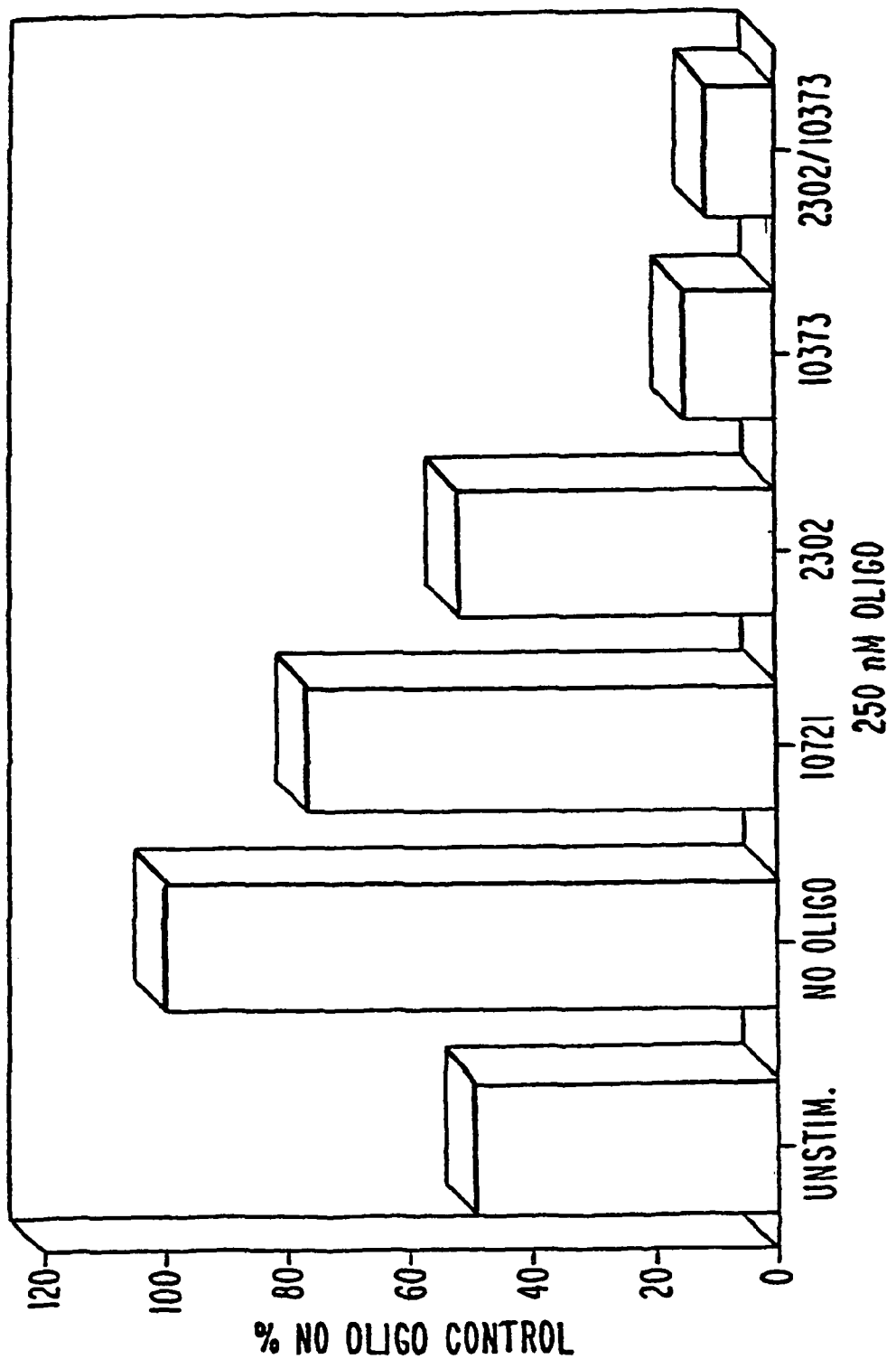
FIG. 7 is a bar graph showing the effect of the indicated oligonucleotides on T cell proliferation.

Results:

As shown in FIG. 7, mononuclear cells which were not cytokine-treated slightly induced T cell proliferation, presumably due to low levels of costimulatory molecules expressed on the cells. However, when the cells were treated with cytokines and induced to differentiate to dendritic-like cells, expression of both ICAM-1 and B7-2 was strongly upregulated. This resulted in a strong T cell proliferative response which could be blocked with either anti-ICAM-1 (ISIS 2302) or anti-B7-2 (ISIS 10373) oligonucleotides prior to induction of the mononuclear cells. The control oligonucleotide (ISIS 10721) had an insignificant effect on T cell proliferation. A combination treatment with both the anti-ICAM-1 (ISIS 2302) and anti-B7-2 (ISIS 10373) oligonucleotides resulted in a further decrease in T cell response.

Example 9

Modulation of Murine B7 Genes by Oligonucleotides

Oligonucleotides (see Table 4) capable of inhibiting expression of murine B7-2 transiently expressed in COS-7 cells were identified in the following manner. A series of phosphorothioate oligonucleotides complementary to murine B7-2 (mB7-2) cDNA were screened for their ability to reduce mB7-2 levels (measured by flow cytometry as in Example 2, except that a conjugated anti-mB7-2 antibody (i.e., anti-mCD86-PE, PharMingen, San Diego, Calif.) in COS-7 cells transfected with an mB7-2 cDNA clone. Anti-mB7-2 antibody may also be obtained from the hybridoma deposited at the ATCC under accession No. HB-253. Oligonucleotides (see Table 2) capable of modulating murine B7-1 expression are isolated in like fashion, except that a conjugated anti-mB7-1 antibody is used in conjunction with COS-7 cells transfected with an mB7-1 cDNA clone.

Figure 8:
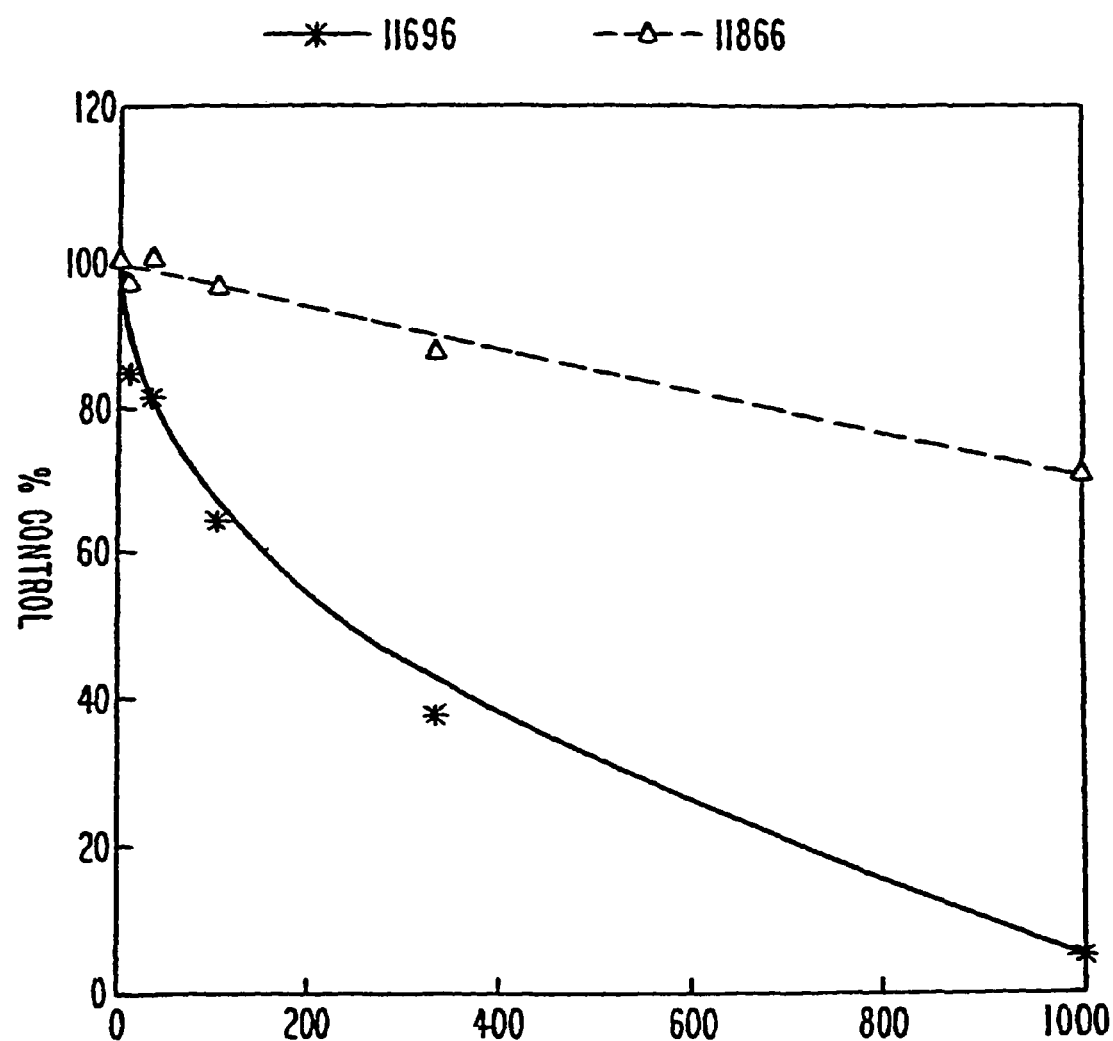
FIG. 8 is a dose-response curve showing the inhibitory effect of oligonucleotides on murine B7-2 protein expression in COS-7 cells. Solid line with asterisks, ISIS 11696; dashed line with triangles, ISIS 11866.

For murine B7-2, the most active oligonucleotide identified was ISIS 11696 (GGA-TTG-CCA-AGC-CCA-TGG-TG, SEQ ID NO: 18), which is complementary to position 96-115 of the cDNA, a site which includes the translation initiation (AUG) codon. FIG. 8 shows a dose-response curve for ISIS 11696 and a scrambled control, ISIS 11866 (CTA-AGT-AGT-GCT-AGC-CGG-GA, SEQ ID NO: 19). ISIS 11696 inhibited cell surface expression of B7-2 in COS-7 cells with an IC$_{50}$ in the range of 200-300 nM, while ISIS 11866 exhibited less than 20% inhibition at the highest concentration tested (1000 nM).

In order to further evaluate the murine B7-2 antisense oligonucleotides, the IC-21 cell line was used. IC-21 monocyte/macrophage cell line expresses both B7-1 and murine B7-2 (mB7-2) constitutively. A 2-fold induction of expression can be achieved by incubating the cells in the presence of lipopolysaccharide (LPS; GIBCO-BRL, Gaithersburg, Md.) (Hathcock et al., *Science*, 1993, 262, 905).

IC-21 cells (ATCC; accession No. TIB 186) were seeded at 80% confluency in 12-well plates in DMEM media with 10% FCS. The cells were allowed to adhere to the plate overnight. The following day, the medium was removed and the cells were washed with PBS. Then 500 uL of OptiMEM™ (GIBCO-BRL, Gaithersburg, Md.) supplemented with 15 ug/mL of Lipofectin™ (GIBCO-BRL, Gaithersburg, Md.) was added to each well. Oligonucleotides were then added directly to the medium at the indicated concentrations. After incubation for 4 hours, the cells were washed with PBS and incubated overnight in culture medium supplemented with 15 ug/mL of LPS. The following day, cells were harvested by scraping, then analyzed for cell surface expression by flow cytometry.

Figure 9:
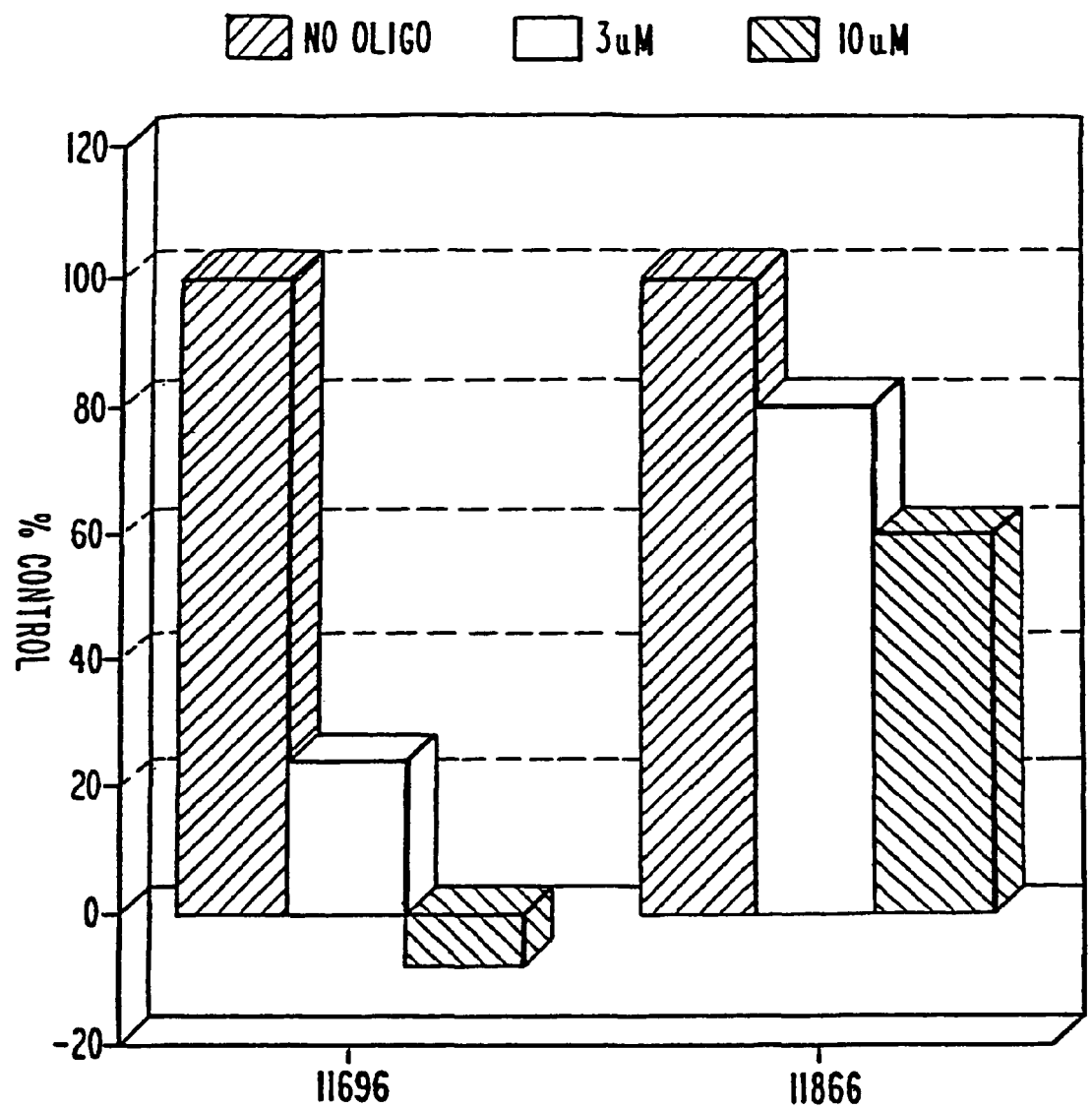
FIG. 9 is a bar graph showing the effect of oligonucleotides ISIS 11696 and ISIS 11866 on cell surface expression of murine B7-2 protein in IC-21 cells. Left (black) bars, no oligonucleotide; middle bars, 3 ΦM indicated oligonucleotide; right bars, 10 ΦM indicated oligonucleotide.
Figure 10:
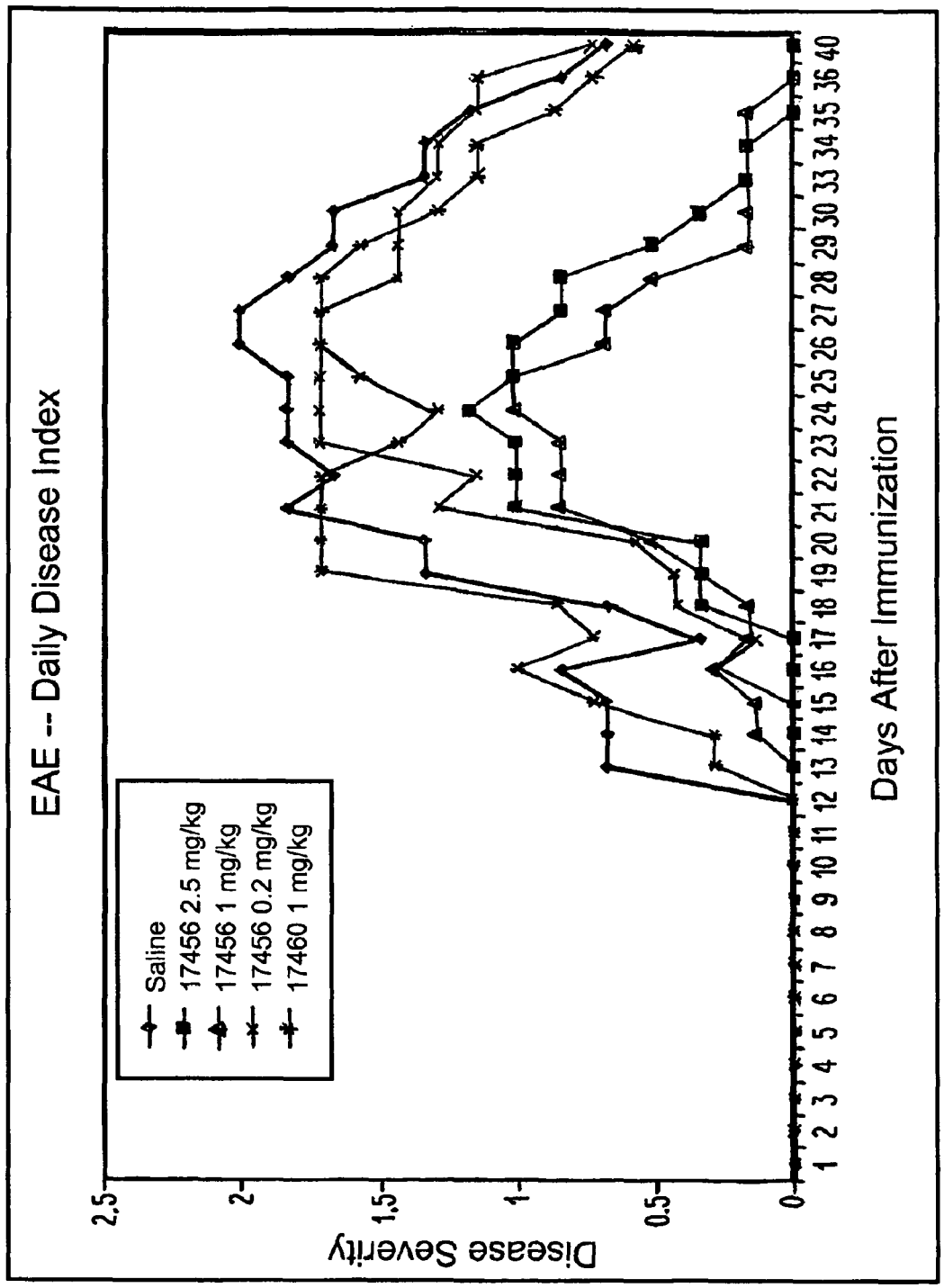
FIG. 10 is a graph showing the effect of ISIS 17456 on severity of EAE at various doses.

ISIS 11696 and ISIS 11866 were administered to IC-21 cells in the presence of Lipofectin™ (GIBCO-BRL, Gaithersburg, Md.). The results are shown in FIG. 9. At a concentration of 10 uM, ISIS 11696 inhibited mB7-2 expression completely (and decreased mB7-2 levels below the constitutive level of expression), while the scrambled control oligonucleotide, ISIS 11866, produced only a 40% reduction in the level of induced expression. At a concentration of 3 uM, levels of induced expression were greatly reduced by ISIS 11696, while ISIS 11866 had little effect.

Example 10

Modulation of Allograft Rejection by Oligonucleotides

A murine model for evaluating compounds for their ability to inhibit heart allograft rejection has been previously described (Stepkowski et al., *J. Immunol.*, 1994, 153, 5336). This model was used to evaluate the immunosuppressive capacity of antisense oligonucleotides to B7 proteins alone or in combination with antisense oligonucleotides to intercellular adhesion molecule-1 (ICAM-1).

Methods:

Heart allograft rejection studies and oligonucleotide treatments of BALB/c mice were performed essentially as previously described (Stepkowski et al., *J. Immunol.*, 1994, 153, 5336). Antisense oligonucleotides used included ISIS 11696, ISIS 3082 (targeted to ICAM-1) and ISIS 1082 (a control oligonucleotide targeted to the herpes virus UL-13 gene sequence). Dosages used were 1, 2, 2.5, 5 or 10 mg/kg of individual oligonucleotide (as indicated below); when combinations of oligonucleotides were administered, each oligonucleotide was given at a dosage of 1, 5 or 10 mg/kg (total oligonucleotide dosages of 2, 10 and 20 mg/kg, respectively). The survival times of the transplanted hearts and their hosts were monitored and recorded.

Results:

The mean survival time for untreated mice was 8.2±0.8 days (7, 8, 8, 8, 9, 9 days). Treatment of the mice for 7 days with ISIS 1082 (SEQ ID NO: 125, unrelated control oligonucleotide) slightly reduced the mean survival times to 7.1±0.7 days (5 mg/kg/day; 6, 7, 7, 7, 8, 8) or 7.0±0.8 days(10 mg/kg/day; 6, 7, 7, 8). Treatment of the mice for seven days with the murine B7-2 oligonucleotide ISIS 11696 (SEQ ID NO: 108) increased the mean survival time to 9.3 days at two doses (2 mg/kg/day, 9.3±0.6 days, 9, 9, 10; 10 mg/kg/day, 9.3±1.3 days, 8, 9, 9, 11). Treatment of mice for seven days with an ICAM-1 oligonucleotide, ISIS 3082, also increased the mean survival of the mice over several doses. Specifically, at 1 mg/kg/day, the mean survival time (MSD) was 11.0±0.0 (11, 11, 11); at 2.5 mg/kg/day, the MSD was 12.0±2.7 (10, 12, 13, 16); at 5 mg/kg/day, the MSD was 14.1±2.7 (10, 12, 12, 13, 16, 16, 17, 17); and, at 10 mg/kg/day, the MSD was 15.3±5.8 (12, 12, 13, 24). Some synergistic effect was seen when the mice were treated for seven days with 1 mg/kg/day each of ISIS 3082 and 11696: the MSD was 13.8±1.0 (13, 13, 14, 15).

Example 11

Detection of Nucleic Acids Encoding B7 Proteins

Oligonucleotides are radiolabeled after synthesis by $^{32}$P-labeling at the 5' end with polynucleotide kinase. Sambrook et al., "Molecular Cloning. A Laboratory Manual," Cold Spring Harbor Laboratory Press, 1989, Volume 2, pg. 11.31. Radiolabeled oligonucleotide capable of hybridizing to a nucleic acid encoding a B7 protein is contacted with a tissue or cell sample suspected of B7 protein expression under conditions in which specific hybridization can occur, and the sample is washed to remove unbound oligonucleotide. A similar control is maintained wherein the radiolabeled oligonucleotide is contacted with a normal tissue or cell sample under conditions that allow specific hybridization, and the sample is washed to remove unbound oligonucleotide. Radioactivity remaining in the samples indicates bound oligonucleotide and is quantitated using a scintillation counter or other routine means. A greater amount of radioactivity remaining in the samples, as compared to control tissues or cells, indicates increased expression of a B7 gene, whereas a lesser amount of radioactivity in the samples relative to the controls indicates decreased expression of a B7 gene.

Radiolabeled oligonucleotides of the invention are also useful in autoradiography. A section of tissues suspected of expressing a B7 gene is treated with radiolabeled oligonucleotide and washed as described above, then exposed to photographic emulsion according to standard autoradiography procedures. A control of a normal tissue section is also maintained. The emulsion, when developed, yields an image of silver grains over the regions expressing a B7 gene, which is quantitated. The extent of B7 expression is determined by comparison of the silver grains observed with control and test samples.

Analogous assays for fluorescent detection of expression of a B7 gene use oligonucleotides of the invention which are labeled with fluorescein or other fluorescent tags. Labeled oligonucleotides are synthesized on an automated DNA synthesizer (Applied Biosystems, Foster City, Calif.) using standard phosphoramidite chemistry. b-Cyanoethyldiisopropyl phosphoramidites are purchased from Applied Biosystems (Foster City, Calif.). Fluorescein-labeled amidites are purchased from Glen Research (Sterling, Va.). Incubation of oligonucleotide and biological sample is carried out as described above for radiolabeled oligonucleotides except that, instead of a scintillation counter, a fluorescence microscope is used to detect the fluorescence. A greater amount of fluorescence in the samples, as compared to control tissues or cells, indicates increased expression of a B7 gene, whereas a lesser amount of fluorescence in the samples relative to the controls indicates decreased expression of a B7 gene.

Example 12

Chimeric (Deoxy Gapped) Human B7-1 Antisense Oligonucleotides

Additional oligonucleotides targeting human B7-1 were synthesized. Oligonucleotides were synthesized as uniformly phosphorothioate chimeric oligonucleotides having regions of five 2'-MOE nucleotides at the wings and a central region of ten deoxynucleotides. Oligonucleotide sequences are shown in Table 6.

Oligonucleotides were screened as described in Example 4. Results are shown in Table 7.

Oligonucleotides 22315 (SEQ ID NO: 128), 22316 (SEQ ID NO: 26), 22317 (SEQ ID NO: 129), 22320 (SEQ ID NO: 132), 22324 (SEQ ID NO: 135), 22325 (SEQ ID NO: 136), 22334 (SEQ ID NO: 145), 22335 (SEQ ID NO: 146), 22337 (SEQ ID NO: 148), and 22338 (SEQ ID NO: 36) resulted in 50% or greater inhibition of B7-1 mRNA in this assay.

TABLE 6

Nucleotide Sequences of Human B7-1 Chimeric (deoxy gapped)

| ISIS NO. | NUCLEOTIDE SEQUENCE[1] (5' -> 3') | SEQ ID NO: | TARGET GENE NUCLEOTIDE CO-ORDINATES[2] | SEQ TARGET REGION |
|---|---|---|---|---|
| 22313 | AGACTCCACTTCTGAGATGT | 126 | 0048-0067 | 5'-UTR |
| 22314 | TGAAGAAAAATTCCACTTTT | 127 | 0094-0113 | 5'-UTR |
| 22315 | TTTAGTTTCACAGCTTGCTG | 128 | 0112-0129 | 5'-UTR |
| 22316 | GCTCACGTAGAAGACCCTCC | 26 | 0193-0212 | 5'-UTR |
| 22317 | TCCCAGGTGCAAAACAGGCA | 129 | 0233-0252 | 5'-UTR |
| 22318 | GTGAAAGCCAACAATTTGGA | 130 | 0274-0293 | 5'-UTR |
| 22319 | CATGGCTTCAGATGCTTAGG | 131 | 0301-0320 | AUG |
| 22320 | TTGAGGTATGGACACTTGGA | 132 | 0351-0370 | coding |
| 22321 | GACCAGCCAGCACCAAGAGC | 31 | 0380-0399 | coding |
| 22322 | GCGTTGCCACTTCTTTCACT | 133 | 0440-0459 | coding |
| 22323 | TTTTGCCAGTAGATGCGAGT | 134 | 0501-0520 | coding |
| 22324 | GGCCATATATTCATGTCCCC | 135 | 0552-0571 | coding |
| 22325 | GCCAGGATCACAATGGAGAG | 136 | 0612-0631 | coding |
| 22326 | GTATGTGCCCTCGTCAGATG | 137 | 0640-0659 | coding |
| 22327 | TTCAGCCAGGTGTTCCCGCT | 138 | 0697-0716 | coding |
| 22328 | GGAAGTCAGCTTTGACTGAT | 139 | 0725-0744 | coding |
| 22329 | CCTCCAGAGGTTGAGCAAAT | 140 | 0798-0817 | coding |
| 22330 | CCAACCAGGAGAGGTGAGGC | 141 | 0827-0846 | coding |
| 22331 | GAAGCTGTGGTTGGTTGTCA | 142 | 0940-0959 | coding |

TABLE 6-continued

Nucleotide Sequences of Human B7-1 Chimeric (deoxy gapped)

| ISIS NO. | NUCLEOTIDE SEQUENCE[1] (5' -> 3') | SEQ ID NO: | TARGET GENE NUCLEOTIDE CO-ORDINATES[2] | SEQ TARGET REGION |
|---|---|---|---|---|
| 22332 | TTGAAGGTCTGATTCACTCT | 143 | 0987-1006 | coding |
| 22333 | AAGGTAATGGCCCAGGTTGG | 144 | 1050-1069 | coding |
| 22334 | AAGCAGTAGGTCAGGCAGCA | 145 | 1098-1117 | coding |
| 22335 | CCTTGCTTCTGCGGACACTG | 146 | 1185-1204 | 3'-UTR |
| 22336 | AGCCCCTTGCTTCTGCGGAC | 147 | 1189-1208 | 3'-UTR |
| 22337 | TGACGGAGGCTACCTTCAGA | 148 | 1216-1235 | 3'-UTR |
| 22338 | GCCTCATGATCCCCACGATC | 36 | 1254-1273 | 3'-UTR |
| 22339 | GTAAACAGCTTAAATTTGT | 149 | 1286-1305 | 3'-UTR |
| 22340 | AGAAGAGGTTACATTAAGCA | 150 | 1398-1417 | 3'-UTR |
| 22341 | AGATAATGAATTGGCTGACA | 151 | 1454-1473 | 3'-UTR |
| 24733 | GCGTCATCATCCGCACCATC | 152 | | control |
| 24734 | CGTTGCTTGTGCCGACAGTG | 153 | | control |
| 24735 | GCTCACGAAGAACACCTTCC | 154 | | control |

[1]Emboldened residues are 2'-MOE residues (others are 2'-deoxy). All 2'-MOE cytosines and 2'-deoxy cytosines residues are 5-methyl-cytosines; all linkages are phosphorothioate linkages.
[2]Co-ordinates from Genbank Accession No. M27533, locus name "HUMIGB7".

TABLE 7

Inhibition of Human B7-1 mRNA Expression by Chimeric (deoxy gapped) Phosphorothioate Oligodeoxynucleotides

| ISIS No: | SEQ ID NO: | GENE TARGET REGION | % mRNA EXPRESSION | % mRNA INHIBITION |
|---|---|---|---|---|
| basal | — | — | 100% | — |
| 13805 | 30 | AUG | 46% | 54% |
| 13812 | 36 | 3'-UTR | 22% | 78% |
| 22313 | 126 | 5'-UTR | 75% | 25% |
| 22314 | 127 | 5'-UTR | 69% | 31% |
| 22315 | 128 | 5'-UTR | 49% | 51% |
| 22316 | 26 | 5'-UTR | 42% | 58% |
| 22317 | 129 | 5'-UTR | 43% | 57% |
| 22318 | 130 | 5'-UTR | 63% | 37% |
| 22319 | 131 | AUG | 68% | 32% |
| 22320 | 132 | coding | 45% | 55% |
| 22321 | 31 | coding | 57% | 43% |
| 22324 | 135 | coding | 46% | 54% |
| 22325 | 136 | coding | 46% | 54% |
| 22326 | 137 | coding | 62% | 38% |
| 22328 | 139 | coding | 64% | 36% |
| 22329 | 140 | coding | 59% | 41% |
| 22330 | 141 | coding | 54% | 46% |
| 22331 | 142 | coding | 62% | 38% |
| 22332 | 143 | coding | 67% | 33% |
| 22333 | 144 | coding | 73% | 27% |
| 22334 | 145 | coding | 43% | 57% |
| 22335 | 146 | 3'-UTR | 43% | 57% |
| 22336 | 147 | 3'-UTR | 55% | 45% |
| 22337 | 148 | 3'-UTR | 42% | 58% |
| 22338 | 36 | 3'-UTR | 40% | 60% |
| 22339 | 149 | 3'-UTR | 69% | 31% |
| 22340 | 150 | 3'-UTR | 71% | 29% |
| 22341 | 151 | 3'-UTR | 59% | 41% |

Dose response experiments were performed on several of the more active oligonucleotides. The oligonucleodides were screened as described in Example 4 except that the concentration of oligonucleotide was varied as shown in Table 8. Mismatch control oligonucleotides were included. Results are shown in Table 8.

All antisense oligonucleotides tested showed a dose response effect with inhibition of mRNA approximately 60% or greater.

TABLE 8

Dose Response of COS-7 Cells to B7-1 Chimeric (deoxy gapped) Antisense Oligonucleotides

| ISIS # | SEQ ID NO: | ASO Gene Target | Dose | % mRNA Expression | % mRNA Inhibition |
|---|---|---|---|---|---|
| basal | — | — | — | 100% | — |
| 22316 | 26 | 5'-UTR | 10 nM | 99% | 1% |
| " | " | " | 30 nM | 73% | 27% |
| " | " | " | 100 nM | 58% | 42% |
| " | " | " | 300 nM | 33% | 67% |
| 24735 | 154 | control | 10 nM | 100% | — |
| " | " | " | 30 nM | 95% | 5% |
| " | " | " | 100 nM | 81% | 19% |
| " | " | " | 300 nM | 75% | 25% |
| 22335 | 146 | 3'-UTR | 10 nM | 81% | 19% |
| " | " | " | 30 nM | 63% | 37% |
| " | " | " | 100 nM | 43% | 57% |
| " | " | " | 300 nM | 35% | 65% |
| 24734 | 153 | control | 10 nM | 94% | 6% |
| " | " | " | 30 nM | 96% | 4% |
| " | " | " | 100 nM | 94% | 6% |
| " | " | " | 300 nM | 84% | 16% |
| 22338 | 36 | 3'-UTR | 10 nM | 68% | 32% |
| " | " | " | 30 nM | 60% | 40% |
| " | " | " | 100 nM | 53% | 47% |
| " | " | " | 300 nM | 41% | 59% |
| 24733 | 152 | control | 10 nM | 90% | 10% |
| " | " | " | 30 nM | 91% | 9% |
| " | " | " | 100 nM | 90% | 10% |
| " | " | " | 300 nM | 80% | 20% |

Example 13

Chimeric (Deoxy Gapped) Mouse B7-1 Antisense Oligonucleotides

Additional oligonucleotides targeting mouse B7-1 were synthesized. Oligonucleotides were synthesized as uniformly phosphorothioate chimeric oligonucleotides having regions of five 2'-MOE nucleotides at the wings and a central region of ten deoxynucleotides. Oligonucleotide sequences are shown in Table 9.

Oligonucleotides were screened as described in Example 4. Results are shown in Table 10.

Oligonucleotides 18105 (SEQ ID NO: 156), 18106 (SEQ ID NO: 157), 18109 (SEQ ID NO: 160), 18110 (SEQ ID NO: 161), 18111 (SEQ ID NO: 162), 18112 (SEQ ID NO: 163), 18113 (SEQ ID NO: 164), 18114 (SEQ ID NO: 165), 18115 (SEQ ID NO: 166), 18117 (SEQ ID NO: 168), 18118 (SEQ ID NO: 169), 18119 (SEQ ID NO: 170), 18120 (SEQ ID NO: 171), 18122 (SEQ ID NO: 173), and 18123 (SEQ ID NO: 174) resulted in greater than approximately 50% inhibition of B7-1 mRNA in this assay.

TABLE 9

Nucleotide Sequences of Mouse B7-1 Chimeric (deoxy gapped) Oligodeoxynucleotides

| ISIS NO. | NUCLEOTIDE SEQUENCE[1] (5' -> 3') | SEQ ID NO: | TARGET GENE NUCLEOTIDE CO-ORDINATES[2] | SEQ TARGET REGION |
|---|---|---|---|---|
| 18104 | AGAGAAACTAGTAAGAGTCT | 155 | 0018-0037 | 5'-UTR |
| 18105 | TGGCATCCACCCGGCAGATG | 156 | 0110-0129 | 5'-UTR |
| 18106 | TCGAGAAACAGAGATGTAGA | 157 | 0144-0163 | 5'-UTR |
| 18107 | TGGAGCTTAGGCACCTCCTA | 158 | 0176-0195 | 5'-UTR |
| 18108 | TGGGGAAAGCCAGGAATCTA | 159 | 0203-0222 | 5'-UTR |
| 18109 | CAGCACAAAGAGAAGAATGA | 160 | 0310-0329 | coding |
| 18110 | ATGAGGAGAGTTGTAACGGC | 161 | 0409-0428 | coding |
| 18111 | AAGTCCGGTTCTTATACTCG | 162 | 0515-0534 | coding |
| 18112 | GCAGGTAATCCTTTTAGTGT | 163 | 0724-0743 | coding |
| 18113 | GTGAAGTCCTCTGACACGTG | 164 | 0927-0946 | coding |
| 18114 | CGAATCCTGCCCCAAAGAGC | 165 | 0995-1014 | coding |
| 18115 | ACTGCGCCGAATCCTGCCCC | 166 | 1002-1021 | coding |
| 18116 | TTGATGATGACAACGATGAC | 167 | 1035-1054 | coding |
| 18117 | CTGTTGTTTGTTTCTCTGCT | 168 | 1098-1117 | coding |
| 18118 | TGTTCAGCTAATGCTTCTTC | 169 | 1134-1153 | coding |
| 18119 | GTTAACTCTATCTTGTGTCA | 170 | 1263-1282 | 3'-UTR |
| 18120 | TCCACTTCAGTCATCAAGCA | 171 | 1355-1374 | 3'-UTR |
| 18121 | TGCTCAATACTCTCTTTTTA | 172 | 1680-1699 | 3'-UTR |
| 18122 | AGGCCCAGCAAACTTGCCCG | 173 | 1330-1349 | 3'-UTR |
| 18123 | AACGGCAAGGCAGCAATACC | 174 | 0395-0414 | coding |

[1] Emboldened residues are 2'-MOE residues (others are 2'-deoxy). All 2'-MOE cytosines and 2'-deoxy cytosines residues are 5-methyl-cytosines; all linkages are phosphorothioate linkages.
[2] Co-ordinates from Genbank Accession No. X60958, locus name "MMB7BLAA".

TABLE 10

Inhibition of Mouse B7-1 mRNA Expression by Chimeric (deoxy gapped) Phosphorothioate Oligodeoxynucleotides

| ISIS No: | SEQ ID NO: | GENE TARGET REGION | % mRNA EXPRESSION | % mRNA INHIBITION |
|---|---|---|---|---|
| basal | — | — | 100.0% | — |
| 18104 | 155 | 5'-UTR | 60.0% | 40.0% |
| 18105 | 156 | 5'-UTR | 32.0% | 68.0% |
| 18106 | 157 | 5'-UTR | 51.0% | 49.0% |
| 18107 | 158 | 5'-UTR | 58.0% | 42.0% |
| 18108 | 159 | 5'-UTR | 82.0% | 18.0% |
| 18109 | 160 | coding | 45.5% | 54.5% |
| 18110 | 161 | coding | 21.0% | 79.0% |
| 18111 | 162 | coding | 38.0% | 62.0% |
| 18112 | 163 | coding | 42.0% | 58.0% |
| 18113 | 164 | coding | 24.6% | 75.4% |
| 18114 | 165 | coding | 25.6% | 74.4% |
| 18115 | 166 | coding | 33.5% | 66.5% |
| 18116 | 167 | coding | 65.6% | 34.4% |
| 18117 | 168 | coding | 46.7% | 53.3% |
| 18118 | 169 | coding | 31.7% | 68.3% |
| 18119 | 170 | 3'-UTR | 24.0% | 76.0% |
| 18120 | 171 | 3'-UTR | 26.7% | 73.3% |
| 18121 | 172 | 3'-UTR | 114.0% | — |
| 18122 | 173 | 3'-UTR | 42.0% | 58.0% |
| 18123 | 174 | coding | 42.0% | 58.0% |

Example 14

Chimeric (Deoxy Gapped) Human B7-2 Antisense Oligonucleotides

Additional oligonucleotides targeting human B7-2 were synthesized. Oligonucleotides were synthesized as uniformly phosphorothioate chimeric oligonucleotides having regions of five 2'-MOE nucleotides at the wings and a central region of ten deoxynucleotides. Oligonucleotide sequences are shown in Table 11.

Oligonucleotides were screened as described in Example 4. Results are shown in Table 12.

Oligonucleotides 22284 (SEQ ID NO: 16), 22286 (SEQ ID NO: 176), 22287 (SEQ ID NO: 177), 22288 (SEQ ID NO: 178), 22289 (SEQ ID NO: 179), 22290 (SEQ ID NO: 180), 22291 (SEQ ID NO: 181), 22292 (SEQ ID NO: 182), 22293 (SEQ ID NO: 183), 22294 (SEQ ID NO: 184), 22296 (SEQ ID NO: 186), 22299 (SEQ ID NO: 189), 22300 (SEQ ID NO: 190), 22301 (SEQ ID NO: 191), 22302 (SEQ ID NO: 192), 22303 (SEQ ID NO: 193), 22304 (SEQ ID NO: 194), 22306 (SEQ ID NO: 196), 22307 (SEQ ID NO: 197), 22308 (SEQ ID NO: 198), 22309 (SEQ ID NO: 199), 22310 (SEQ ID NO: 200), and 22311 (SEQ ID NO: 201) resulted in greater than 50% inhibition of B7-2 mRNA in this assay.

TABLE 11

Nucleotide sequences of Human B7-2 Chimeric (deoxy gapped) Oligodeoxynucleotides

| ISIS NO. | NUCLEOTIDE SEQUENCE[1] (5' -> 3') | SEQ ID NO: | TARGET GENE NUCLEOTIDE CO-ORDINATES[2] | GENE TARGET REGION |
|---|---|---|---|---|
| 22284 | TGCGAGCTCCCCGTACCTCC | 16 | 0011-0030 | 5'-UTR |
| 22285 | CAGAAGCAAGGTGGTAAGAA | 175 | 0049-0068 | 5'-UTR |
| 22286 | GCCTGTCCACTGTAGCTCCA | 176 | 0113-0132 | 5'-UTR |
| 22287 | AGAATGTTACTCAGTCCCAT | 177 | 0148-0167 | AUG |
| 22288 | TCAGAGGAGCAGCACCAGAG | 178 | 0189-0208 | coding |
| 22289 | TGGCATGGCAGGTCTGCAGT | 179 | 0232-0251 | coding |
| 22290 | AGCTCACTCAGGCTTTGGTT | 180 | 0268-0287 | coding |
| 22291 | TGCCTAAGTATACCTCATTC | 181 | 0324-0343 | coding |
| 22292 | CTGTCAAATTTCTCTTTGCC | 182 | 0340-0359 | coding |
| 22293 | CATATACTTGGAATGAACAC | 183 | 0359-0378 | coding |
| 22294 | GGTCCAACTGTCCGAATCAA | 184 | 0392-0411 | coding |
| 22295 | TGATCTGAAGATTGTGAAGT | 185 | 0417-0436 | coding |

TABLE 11-continued

Nucleotide sequences of Human B7-2 Chimeric (deoxy gapped) Oligodeoxynucleotides

| ISIS NO. | NUCLEOTIDE SEQUENCE[1] (5' -> 3') | SEQ ID NO: | TARGET GENE NUCLEOTIDE CO-ORDINATES[2] | GENE TARGET REGION |
|---|---|---|---|---|
| 22296 | AAGCCCTTGTCCTTGATCTG | 186 | 0430-0449 | coding |
| 22297 | TGTGATGGATGATACATTGA | 187 | 0453-0472 | coding |
| 22298 | TCAGGTTGACTGAAGTTAGC | 188 | 0529-0548 | coding |
| 22299 | GTGTATAGATGAGCAGGTCA | 189 | 0593-0612 | coding |
| 22300 | TCTGTGACATTATCTTGAGA | 190 | 0694-0713 | coding |
| 22301 | AAGATAAAAGCCGCGTCTTG | 191 | 0798-0817 | coding |
| 22302 | AGAAAACCATCACACATATA | 192 | 0900-0919 | coding |
| 22303 | AGAGTTGCGAGGCCGCTTCT | 193 | 0947-0968 | coding |
| 22304 | TCCCTCTCCATTGTGTTGGT | 194 | 0979-0998 | coding |
| 22305 | CATCAGATCTTTCAGGTATA | 195 | 1035-1054 | coding |
| 22306 | GGCTTTACTCTTTAATTAAA | 196 | 1115-1134 | stop |
| 22307 | GAAATCAAAAAGGTTGCCCA | 197 | 1178-1197 | 3'-UTR |
| 22308 | GGAGTCCTGGAGCCCCCTTA | 198 | 1231-1250 | 3'-UTR |
| 22309 | TTGGCATACGGAGCAGAGCT | 199 | 1281-1300 | 3'-UTR |
| 22310 | TGTGCTCTGAAGTGAAAAGA | 200 | 1327-1346 | 3'-UTR |
| 22311 | GGCTTGGCCCATAAGTGTGC | 201 | 1342-1361 | 3'-UTR |
| 22312 | CCTAAATTTTATTTCCAGGT | 202 | 1379-1398 | 3'-UTR |
| 24736 | GCTCCAAGTGTCCCAATGAA | 203 | | control |
| 24737 | AGTATGTTTCTCACTCCGAT | 204 | | control |
| 24738 | TGCCAGCACCCGGTACGTCC | 205 | | control |

[1]Emboldened residues are 2'-MOE residues (others are 2'-deoxy). All 2'-MOE cytosines and 2'-deoxy cytosines residues are 5-methyl-cytosines; all linkages are phosphorothioate linkages.
[2]Co-ordinates from Genbank Accession No. U04343 locus name "HSU04343".

TABLE 12

Inhibition of Human B7-2 mRNA Expression by Chimeric (deoxy gapped) Phosphorothioate Oligodeoxynucleotides

| ISIS No: | SEQ ID NO: | GENE TARGET REGION | % mRNA EXPRESSION | % mRNA INHIBITION |
|---|---|---|---|---|
| basal | — | — | 100% | 0% |
| 10373 | 16 | 5'-UTR | 24% | 76% |
| 22284 | 16 | 5'-UTR | 30% | 70% |
| 22285 | 175 | 5'-UTR | 74% | 26% |
| 22286 | 176 | 5'-UTR | 39% | 61% |
| 22287 | 177 | AUG | 27% | 73% |
| 22288 | 178 | coding | 38% | 62% |
| 22289 | 179 | coding | 41% | 59% |
| 22290 | 180 | coding | 42% | 58% |
| 22291 | 181 | coding | 41% | 59% |
| 22292 | 182 | coding | 39% | 61% |
| 22293 | 183 | coding | 43% | 57% |
| 22294 | 184 | coding | 21% | 79% |
| 22295 | 185 | coding | 66% | 34% |
| 22296 | 186 | coding | 42% | 58% |
| 22297 | 187 | coding | 54% | 46% |
| 22298 | 188 | coding | 53% | 47% |
| 22299 | 189 | coding | 46% | 54% |
| 22300 | 190 | coding | 39% | 61% |
| 22301 | 191 | coding | 51% | 49% |
| 22302 | 192 | coding | 41% | 59% |
| 22303 | 193 | coding | 46% | 54% |
| 22304 | 194 | coding | 41% | 59% |
| 22305 | 195 | coding | 57% | 43% |
| 22306 | 196 | stop | 44% | 56% |
| 22307 | 197 | 3'-UTR | 45% | 55% |
| 22308 | 198 | 3'-UTR | 40% | 60% |
| 22309 | 199 | 3'-UTR | 42% | 58% |
| 22310 | 200 | 3'-UTR | 41% | 59% |
| 22311 | 201 | 3'-UTR | 49% | 51% |
| 22312 | 202 | 3'-UTR | 83% | 17% |

Dose response experiments were performed on several of the more active oligonucleotides. The oligonucleotides were screened as described in Example 4 except that the concentration of oligonucleotide was varied as shown in Table 13. Mismatch control oligonucleotides wee included. Results are shown in Table 13.

All antisense oligonucleotides tested showed a dose response effect with maximum inhibition of mRNA approximately 50% or greater.

TABLE 13

Dose Response of COS-7 Cells to B7-2 Chimeric (deoxy gapped) Antisense Oligonucleotides

| ISIS # | SEQ ID NO: | ASO Gene Target | Dose | % mRNA Expression | % mRNA Inhibition |
|---|---|---|---|---|---|
| basal | — | — | — | 100% | — |
| 22284 | 16 | 5'-UTR | 10 nM | 92% | 8% |
| " | " | " | 30 nM | 72% | 28% |
| " | " | " | 100 nM | 59% | 41% |
| " | " | " | 300 nM | 48% | 52% |
| 24738 | 205 | control | 10 nM | 81% | 19% |
| " | " | " | 30 nM | 92% | 8% |
| " | " | " | 100 nM | 101% | — |
| " | " | " | 300 nM | 124% | — |
| 22287 | 177 | AUG | 10 nM | 93% | 7% |
| " | " | " | 30 nM | 79% | 21% |
| " | " | " | 100 nM | 66% | 34% |
| " | " | " | 300 nM | 45% | 55% |
| 24737 | 204 | control | 10 nM | 85% | 15% |
| " | " | " | 30 nM | 95% | 5% |
| " | " | " | 100 nM | 87% | 13% |
| " | " | " | 300 nM | 99% | 1% |
| 22294 | 184 | coding | 10 nM | 93% | 7% |
| " | " | " | 30 nM | 95% | 5% |
| " | " | " | 100 nM | 58% | 42% |
| " | " | " | 300 nM | 45% | 55% |
| 24736 | 203 | control | 10 nM | 102% | — |
| " | " | " | 30 nM | 101% | — |
| " | " | " | 100 nM | 100% | — |
| " | " | " | 300 nM | 107% | — |

Example 15

Chimeric (Deoxy Gapped) Mouse B7-2 Antisense Oligonucleotides

Additional oligonucleotides targeting mouse B7-2 were synthesized. oligonucleotides were synthesized as uniformly phosphorothioate chimeric oligonucleotides having regions of five 2'-MOE nucleotides at the wings and a central region of ten deoxynucleotides. Oligonucleotide sequences are shown in Table 14.

Oligonucleotides were screened as described in Example 4. Results are shown in Table 15.

Oligonucleotides 18084 (SEQ ID NO: 206), 18085 (SEQ ID NO: 207), 18086 (SEQ ID NO: 208), 18087 (SEQ ID NO: 209), 18089 (SEQ ID NO: 211), 18090 (SEQ ID NO: 212), 18091 (SEQ ID NO: 213), 18093 (SEQ ID NO: 215), 18095 (SEQ ID NO: 217), 18096 (SEQ ID NO: 218), 18097 (SEQ ID NO: 219), 18098 (SEQ ID NO: 108), 18102 (SEQ ID NO: 223), and 18103 (SEQ ID NO: 224) resulted in 50% or greater inhibition of B7-2 mRNA expression in this assay.

TABLE 14

Nucleotide Sequences of Mouse B7-2 Chimeric (deoxy gapped) Oligodeoxynucleotides

| ISIS NO. | NUCLEOTIDE SEQUENCE[1] (5' -> 3') | SEQ ID NO: | TARGET GENE NUCLEOTIDE CO-ORDINATES[2] | GENE TARGET REGION |
|---|---|---|---|---|
| 18084 | GCTGCCTACAGGAGCCACTC | 206 | 0003-0022 | 5'-UTR |
| 18085 | TCAAGTCCGTGCTGCCTACA | 207 | 0013-0032 | 5'-UTR |
| 18086 | GTCTACAGGAGTCTGGTTGT | 208 | 0033-0052 | 5'-UTR |
| 18087 | AGCTTGCGTCTCCACGGAAA | 209 | 0152-0171 | coding |
| 18088 | TCACACTATCAAGTTTCTCT | 210 | 0297-0316 | coding |
| 18089 | GTCAAAGCTCGTGCGGCCCA | 211 | 0329-0348 | coding |
| 18090 | GTGAAGTCGTAGAGTCCAGT | 212 | 0356-0375 | coding |
| 18091 | GTGACCTTGCTTAGACGTGC | 213 | 0551-0570 | coding |
| 18092 | CATCTTCTTAGGTTTCGGGT | 214 | 0569-0588 | coding |
| 18093 | GGCTGTTGGAGATACTGAAC | 215 | 0663-0682 | coding |
| 18094 | GGGAATGAAAGAGAGAGGCT | 216 | 0679-0698 | coding |
| 18095 | ACATACAATGATGAGCAGCA | 217 | 0854-0873 | coding |
| 18096 | GTCTCTCTGTCAGCGTTACT | 218 | 0934-0953 | coding |
| 18097 | TGCCAAGCCCATGGTGCATC | 219 | 0092-0111 | AUG |
| 18098 | GGATTGCCAAGCCCATGGTG | 108 | 0096-0115 | AUG |
| 18099 | GCAATTTGGGGTTCAAGTTC | 220 | 0967-0986 | coding |
| 18100 | CAATCAGCTGAGAACATTTT | 221 | 1087-1106 | 3'-UTR |
| 18101 | TTTTGTATAAAACAATCATA | 222 | 0403-0422 | coding |
| 18102 | CCTTCACTCTGCATTTGGTT | 223 | 0995-1014 | stop |
| 18103 | TGCATGTTATCACCATACTC | 224 | 0616-0635 | coding |

[1]Emboldened residues are 2'-MOE residues (others are 2'-deoxy). All 2'-MOE cytosines and 2'-deoxy cytosines residues are 5-methyl-cytosines; all linkages are phosphorothioate linkages.
[2]Co-ordinates from Genbank Accession No. S70108 locus name "S70108".

TABLE 15

Inhibition of Mouse B7-2 mRNA Expression by Chimeric (deoxy gapped) Phosphorothioate Oligodeoxynucleotides

| ISIS No: | SEQ ID NO: | GENE TARGET REGION | % mRNA EXPRESSION | % mRNA INHIBITION |
|---|---|---|---|---|
| basal | — | — | 100.0% | 0.0% |
| 18084 | 206 | 5'-UTR | 36.4% | 63.6% |
| 18085 | 207 | 5'-UTR | 35.0% | 65.0% |
| 18086 | 208 | 5'-UTR | 40.1% | 59.9% |
| 18087 | 209 | coding | 42.1% | 57.9% |
| 18088 | 210 | coding | 52.3% | 47.7% |
| 18089 | 211 | coding | 20.9% | 79.1% |
| 18090 | 212 | coding | 36.6% | 63.4% |
| 18091 | 213 | coding | 37.1% | 62.9% |
| 18092 | 214 | coding | 58.9% | 41.1% |
| 18093 | 215 | coding | 32.7% | 67.3% |
| 18094 | 216 | coding | 63.8% | 36.2% |
| 18095 | 217 | coding | 34.3% | 65.7% |
| 18096 | 218 | coding | 32.3% | 67.7% |
| 18097 | 219 | AUG | 24.5% | 75.5% |
| 18098 | 108 | AUG | 32.2% | 67.8% |
| 18099 | 220 | coding | 66.8% | 33.2% |
| 18100 | 221 | 3'-UTR | 67.2% | 32.8% |
| 18101 | 222 | coding | 88.9% | 11.1% |
| 18102 | 223 | stop | 33.8% | 66.2% |
| 18103 | 224 | coding | 30.2% | 69.8% |

Example 16

Effect of B7 Antisense Oligonucleotides on Cell Expression

B7 antisense oligonucleotides were tested for their effect on cell surface expression of both B7-1 and B7-2. Cell surface expression was measured as described in Example 2. Experiments were done for both human B7 and mouse B7. Results for human B7 are shown in Table 16. Results for mouse B7 are shown in Table 17.

In both species, B7-1 antisense oligonucleotides were able to specifically reduce the cell surface expression of B7-1. B7-2 antisense oligonucleotides were specific for the B7-2 family member. These oligonucleotides were also specific for their effect on B7-1 and B7-2 mRNA levels.

TABLE 16

Inhibition of Human B7 Cell Surface Expression by Chimeric (deoxy gapped) Phosphorothioate Oligodeoxynucleotides

| ISIS No: | SEQ ID NO: | GENE TARGET | % B7-1 EXPRESSION | % B7-2 EXPRESSION |
|---|---|---|---|---|
| basal | — | — | 100% | 100% |
| 22316 | 26 | B7-1 | 31% | 100% |
| 22317 | 129 | B7-1 | 28% | 91% |
| 22320 | 132 | B7-1 | 37% | 86% |
| 22324 | 135 | B7-1 | 37% | 91% |
| 22325 | 136 | B7-1 | 32% | 89% |
| 22334 | 145 | B7-1 | 28% | 92% |
| 22335 | 146 | B7-1 | 23% | 95% |
| 22337 | 148 | B7-1 | 48% | 101% |
| 22338 | 36 | B7-1 | 22% | 96% |
| 22284 | 16 | B7-2 | 88% | 32% |
| 22287 | 177 | B7-2 | 92% | 35% |
| 22294 | 184 | B7-2 | 77% | 28% |

TABLE 17

Inhibition of Mouse B7 Cell Surface Expression by Chimeric (deoxy gapped) Phosphorothioate Oligodeoxynucleotides

| ISIS No: | SEQ ID NO: | GENE TARGET REGION | % B7-1 EXPRESSION | % B7-2 EXPRESSION |
|---|---|---|---|---|
| basal | — | — | 100% | 100% |
| 18089 | 211 | B7-2 | 85% | 36% |
| 18097 | 219 | B7-2 | 87% | 28% |
| 18110 | 161 | B7-1 | 31% | 93% |
| 18113 | 164 | B7-1 | 25% | 91% |
| 18119 | 170 | B7-1 | 27% | 98% |

Dose response experiments were performed on several of the more active human B7-1 antisense oligonucleotides. The oligonucleotides were screened as described in Example 2 except that the concentration of oligonucleotide was varied as shown in Table 18. Results are shown in Table 18.

All antisense oligonucleotides tested showed a dose response effect with inhibition of cell surface expression approximately 60% or greater.

TABLE 18

Dose Response of COS-7 Cells to B7-1 Chimeric (deoxy gapped) Antisense Oligonucleotides

| ISIS # | SEQ ID NO: | ASO Gene Target | Dose | % Surface Expression | % Surface Inhibition |
|---|---|---|---|---|---|
| basal | — | — | — | 100% | — |
| 22316 | 26 | 5'-UTR | 10 nM | 74% | 26% |
| " | " | " | 30 nM | 74% | 26% |
| " | " | " | 100 nM | 47% | 53% |
| " | " | " | 300 nM | 34% | 66% |
| 22335 | 146 | 3'-UTR | 10 nM | 81% | 19% |
| " | " | " | 30 nM | 69% | 31% |
| " | " | " | 100 nM | 47% | 53% |
| " | " | " | 300 nM | 38% | 62% |
| 22338 | 36 | 3'-UTR | 10 nM | 78% | 22% |
| " | " | " | 30 nM | 65% | 35% |
| " | " | " | 100 nM | 50% | 50% |
| " | " | " | 300 nM | 40% | 60% |

Dose response experiments were performed on several of the more active human B7-2 antisense oligonucleotides. The oligonucleotides were screened as described in Example 2 except that the concentration of oligonucleotide was varied as shown in Table 19. Results are shown in Table 19.

All antisense oligonucleotides tested showed a dose response effect with maximum inhibition of cell surface expression 85% or greater.

TABLE 19

Dose Response of COS-7 Cells to B7-2 Chimeric (deoxy gapped) Antisense Oligonucleotides

| ISIS # | SEQ ID NO: | ASO Gene Target | Dose | % Surface Expression | % Surface Inhibition |
|---|---|---|---|---|---|
| basal | — | — | — | 100% | — |
| 22284 | 16 | 5'-UTR | 10 nM | 63% | 37% |
| " | " | " | 30 nM | 60% | 40% |
| " | " | " | 100 nM | 37% | 63% |
| " | " | " | 300 nM | 15% | 85% |
| 22287 | 177 | AUG | 10 nM | 93% | 7% |
| " | " | " | 30 nM | 60% | 40% |
| " | " | " | 100 nM | 32% | 68% |
| " | " | " | 300 nM | 15% | 85% |
| 22294 | 184 | coding | 10 nM | 89% | 11% |
| " | " | " | 30 nM | 62% | 38% |
| " | " | " | 100 nM | 29% | 71% |
| " | " | " | 300 nM | 12% | 88% |

Example 17

Effect of B7-1 Antisense Oligonucleotides in a Murine Model for Rheumatoid Arthritis Collagen-induced arthritis (CIA) was used as a murine model for arthritis (Mussener, A., et al., Clin. Exp. Immunol., 1997, 107, 485-493). Female DBA/1LacJ mice (Jackson Laboratories, Bar Harbor, Me.) between the ages of 6 and 8 weeks were used to assess the activity of B7-1 antisense oligonucleotides.

On day 0, the mice were immunized at the base of the tail with 100 μg of bovine type II collagen which is emulsified in Complete Freund's Adjuvant (CFA). On day 7, a second booster dose of collagen was administered by the same route. On day 14, the mice were injected subcutaneously with 100 μg of LPS. Oligonucleotide was administered intraperitoneally daily (10 mg/kg bolus) starting on day −3 (three days before day 0) and continuing for the duration of the study. Oligonucleotide 17456 (SEQ ID NO. 173) is a fully phosphorothioated analog of 18122.

Weights were recorded weekly. Mice were inspected daily for the onset of CIA. Paw widths are rear ankle widths of affected and unaffected joints were measured three times a week using a constant tension caliper. Limbs were clinically evaluated and graded on a scale from 0-4 (with 4 being the highest).

Results are shown in Table 20. Treatment with B7-1 and B7-2 antisense oligonucleotides was able to reduce the incidence of the disease, but had modest effects on severity. The combination of 17456 (SEQ ID NO. 173) and 11696 (SEQ ID NO. 108) was able to significantly reduce the incidence of the disease and its severity.

TABLE 20

Effect of B7 antisense oligonucleotide on CIA

| ISIS # (s) | SEQ ID NO | Dose mg/kg | % Incidence | Peak day[1] | Severity[2] |
|---|---|---|---|---|---|
| control | — | — | 70% | 6.7 ± 2.9 | 3.2 ± 1.1 |
| 17456 (B7-1) | 173 | 10 | 50% | 12.1 ± 4.6 | 2.7 ± 1.3 |
| 11696 (B7-2) | 108 | 10 | 37.5% | 11.6 ± 4.5 | 3.4 ± 1.8 |
| 17456/11696 | | 10 | 30% | 1.0 ± 0.6 | 0.7 ± 0.4 |
| 18110 (B7-1) | 161 | 10 | 55.6% | 2.0 ± 0.8 | 2.0 ± 1.3 |
| 18089 (B7-2) | 211 | 10 | 44.4% | 6.8 ± 2.2 | 2.3 ± 1.3 |
| 18110/18089 | | 10 | 60% | 11.6 ± 0.7 | 4.5 ± 1.7 |

[1]Peak day is the day from onset of maximum swelling for each joint measure.
[2]Severity is the total clinical score divided by the total number of mice in the group.

Example 18

Effect of B7-1 Antisense Oligonucleotides in a Murine Model for Multiple Sclerosis Experimental autoimmune encephalomyelitis (EAE) is a commonly accepted murine model for multiple sclerosis (Myers, K. J., et al., J. Neuroimmunol., 1992, 41, 1-8). SJL/H, PL/J, (SJLxPL/J)F1, (SJLxBalb/c)F1 and Balb/c female mice between the ages of 6 and 12 weeks are used to test the activity of a B7-1 antisense oligonucleotide.

The mice are immunized in the two rear foot pads and base of the tail with an emulsion consisting of encephalitogenic protein or peptide (according to Myers, K. J., et al., J. of Immunol., 1993, 151, 2252-2260) in Complete Freund's Adjuvant supplemented with heat killed *Mycobacterium tuberculosis*. Two days later, the mice receive an intravenous injection of 500 ng *Bordetella pertussis* toxin and additional adjuvant.

Alternatively, the disease may also be induced by the adoptive transfer of T-cells. T-cells are obtained from the draining of the-lymph nodes of mice immunized with encephalitogenic protein or peptide in CFA. The T cells are grown in tissue culture for several days and then injected intravenously into naive syngeneic recipients.

Mice are monitored and scored daily on a 0-5 scale for signals of the disease, including loss of tail muscle tone, wobbly gait, and various degrees of paralysis.

Oligonucleotide 17456 (SEQ ID NO. 173), a fully phosphorothioated analog of 18122, was compared to a saline control and a fully phosphorothioated oligonucleotide of random sequence (Oligonucleotide 17460). Results of this experiment are shown in FIG. 11.

As shown in FIG. 11, for all doses of oligonucleotide 17456 tested, there is a protective effect, i.e. a reduction of disease severity. At 0.2 mg/kg, this protective effect is greatly reduced after day 20, but at the higher doses tested, the protective effect remains throughout the course of the experiment (day 40). The control oligonucleotide gave results similar to that obtained with the saline control.

Example 19

Additional Antisense Oligonucleotides Targeted to Human B7-1

Additional oligonucleotides targeting human B7-1 were synthesized. Oligonucleotides were synthesized as uniformly phosphorothioate chimeric oligonucleotides having regions of five 2'-MOE nucleotides at the wings and a central region of ten deoxynucleotides. All cytidines shown in Table 21 are 5-methyl cytidines. Oligonucleotide sequences are shown in Table 21.

The human promonocytic leukaemia cell line, THP-1 (American Type Culture Collection, Manassas, Va.) was maintained in RPMI 1640 growth media supplemented with 10% fetal calf serum (FCS; Life Technologies, Rockville, Md.). A total of 1×10$^7$ cells were electroporated at an oligonucleotide concentration of 10 micromolar in 2 mm cuvettes, using an Electrocell Manipulator 600 instrument (Biotechnologies and Experimental Research, Inc.) employing 200 V, 1000 μF. Electroporated cells were then transferred to petri dishes and allowed to recover for 16 hrs. Cells were then induced with LPS at a final concentration of 1 Φg/ml for 16 hours. RNA was isolated and processed as described in previous examples. Results are shown in Table 22.

Oligonucleotides 113492, 113495, 113498, 113499, 113501, 113502, 113504, 113505, 113507, 113510, 113511, 113513 and 113514 (SEQ ID NO: 228, 231, 234, 235, 237, 238, 240, 241, 243, 246, 247, 249 and 250) resulted in 50% or greater inhibition of B7-1 mRNA expression in this assay.

TABLE 21

Nucleotide Sequences of Human B7-1 Chimeric (deoxy gapped) Oligodeoxynucleotides

| ISIS NO. | NUCLEOTIDE SEQUENCE[1] (5' -> 3') | SEQ ID NO: | TARGET GENE NUCLEOTIDE CO-ORDINATES[2] | GENE TARGET REGION |
|---|---|---|---|---|
| 113489 | CCCTCCAGTGATGTTTACAA | 225 | 179 | 5' UTR |
| 113490 | GAAGACCCTCCAGTGATGTT | 226 | 184 | 5' UTR |
| 113491 | CGTAGAAGACCCTCCAGTGA | 227 | 188 | 5' UTR |
| 113492 | TTCCCAGGTGCAAAACAGGC | 228 | 234 | 5' UTR |
| 113493 | TGGCTTCAGATGCTTAGGGT | 229 | 299 | 5' UTR |
| 113494 | CCTCCGTGTGTGGCCCATGG | 230 | 316 | AUG |
| 113495 | GGTGATGTTCCCTGCCTCCG | 231 | 330 | Coding |
| 113496 | GATGGTGATGTTCCCTGCCT | 232 | 333 | Coding |
| 113497 | AGGTATGGACACTTGGATGG | 233 | 348 | Coding |
| 113498 | GAAAGACCAGCCAGCACCAA | 234 | 384 | Coding |
| 113499 | CAGCGTTGCCACTTCTTTCA | 235 | 442 | Coding |
| 113500 | GTGACCACAGGACAGCGTTG | 236 | 454 | Coding |
| 113501 | AGATGCGAGTTTGTGCCAGC | 237 | 491 | Coding |
| 113502 | CCTTTTGCCAGTAGATGCGA | 238 | 503 | Coding |
| 113503 | CGGTTCTTGTACTCGGGCCA | 239 | 567 | Coding |
| 113504 | CGCAGAGCCAGGATCACAAT | 240 | 618 | Coding |
| 113505 | CTTCAGCCAGGTGTTCCCGC | 241 | 698 | Coding |
| 113506 | TAACGTCACTTCAGCCAGGT | 242 | 706 | Coding |
| 113507 | TTCTCCATTTTCCAACCAGG | 243 | 838 | Coding |
| 113508 | CTGTTGTGTTGATGGCATTT | 244 | 863 | Coding |
| 113509 | CATGAAGCTGTGGTTGGTTG | 245 | 943 | Coding |
| 113510 | AGGAAAATGCTCTTGCTTGG | 246 | 1018 | Coding |
| 113511 | TGGGAGCAGGTTATCAGGAA | 247 | 1033 | Coding |
| 113512 | TAAGGTAATGGCCCAGGATG | 248 | 1051 | Coding |
| 113513 | GGTCAGGCAGCATATCACAA | 249 | 1090 | Coding |
| 113514 | GCCCCTTGCTTCTGCGGACA | 250 | 1188 | 3' UTR |
| 113515 | AGATCTTTTCAGCCCCTTGC | 251 | 1199 | 3' UTR |
| 113516 | TTTGTTAAGGGAAGAATGCC | 252 | 1271 | 3' UTR |
| 113517 | AAAGGAGAGGGATGCCAGCC | 253 | 1362 | 3' UTR |
| 113518 | CAAGACAATTCAAGATGGCA | 254 | 1436 | 3' UTR |

[1]Emboldened residues are 2'-MOE residues (others are 2'-deoxy). All 2'-MOE cytosines and 2'-deoxy cytosine residues are 5-methyl-cytosines; all linkages are phosphorothioate linkages.
[2]Co-ordinates from Genbank Accession No. M27533 to which the oligonucleotides are targeted.

TABLE 22

Inhibition of Human B7-1 mRNA Expression by Chimeric (deoxy gapped) Phosphorothioate Oligodeoxynucleotides

| ISIS No: | SEQ ID NO: | GENE TARGET REGION | % mRNA EXPRESSION | % mRNA INHIBITION |
|---|---|---|---|---|
| 113489 | 225 | 5' UTR | 122 | — |
| 113490 | 226 | 5' UTR | 183 | — |
| 113491 | 227 | 5' UTR | 179 | — |
| 113492 | 228 | 5' UTR | 27 | 73 |
| 113493 | 229 | 5' UTR | 488 | — |
| 113494 | 230 | AUG | 77 | 23 |
| 113495 | 231 | Coding | 43 | 57 |
| 113496 | 232 | Coding | 71 | 29 |
| 113497 | 233 | Coding | 78 | 22 |
| 113498 | 234 | Coding | 37 | 63 |
| 113499 | 235 | Coding | 25 | 75 |
| 113500 | 236 | Coding | 83 | 17 |
| 113501 | 237 | Coding | 36 | 64 |
| 113502 | 238 | Coding | 26 | 74 |
| 113503 | 239 | Coding | 65 | 35 |
| 113504 | 240 | Coding | 46 | 54 |
| 113505 | 241 | Coding | 40 | 60 |
| 113506 | 242 | Coding | 105 | — |
| 113507 | 243 | Coding | 36 | 64 |
| 113508 | 244 | Coding | 117 | — |
| 113509 | 245 | Coding | 62 | 38 |
| 113510 | 246 | Coding | 43 | 57 |
| 113511 | 247 | Coding | 48 | 52 |
| 113512 | 248 | Coding | 73 | 27 |
| 113513 | 249 | Coding | 48 | 52 |
| 113514 | 250 | 3' UTR | 35 | 65 |
| 113515 | 251 | 3' UTR | 184 | — |
| 113516 | 252 | 3' UTR | 83 | 17 |
| 113517 | 253 | 3' UTR | 201 | — |
| 113518 | 254 | 3' UTR | 97 | 03 |

Example 20

Additional Antisense Oligonucleotides Targeted to Human B7-2

Additional oligonucleotides targeting human B7-2 were synthesized. Oligonucleotides were synthesized as uniformly phosphorothioate chimeric oligonucleotides having regions of five 2'-MOE nucleotides at the wings and a central region of ten deoxynucleotides. All cytidnes shown in Table 23 are 5-methyl cytidines. Oligonucleotide sequences are shown in Table 23.

The human promonocytic leukaemia cell line, THP-1 (American Type Culture Collection, Manassas, Va.) was maintained in RPMI 1640 growth media supplemented with 10% fetal calf serum (FCS; Life Technologies, Rockville, Md.). A total of $1 \times 10^7$ cells were electroporated at an oligonucleotide concentration of 10 micromolar in 2 mm cuvettes, using an Electrocell Manipulator 600 instrument (Biotechnologies and Experimental Research, Inc.) employing 200 V, 1000 μF. Electroporated cells were then transferred to petri dishes and allowed to recover for 16 hrs Cells were then induced with LPS and dibutyryl cAMP (500 ΦM) for 16 hours. RNA was isolated and processed as described in previous examples. Results are shown in Table 24.

Oligonucleotides ISIS 113131, 113132, 113134, 113138, 113142, 113144, 113145, 113146, 113147, 113148, 113149, 113150, 113153, 113155, 113157, 113158, 113159 and 113160 (SEQ ID NO: 255, 256, 258, 262, 266, 268, 269, 270, 271, 272, 273, 274, 277, 279, 281, 282, 283 and 284) resulted in 50% or greater inhibition of B7-2 mRNA expression in this assay.

TABLE 23

Nucleotide Sequences of Human B7-2 Chimeric (deoxy gapped) Oligodeoxynucleotides

| ISIS NO. | NUCLEOTIDE SEQUENCE[1] (5' -> 3') | SEQ ID NO: | TARGET GENE NUCLEOTIDE CO-ORDINATES[2] | GENE TARGET REGION |
|---|---|---|---|---|
| 113131 | CGTGTGTCTGTGCTAGTCCC | 255 | 38 | 5' UTR |
| 113132 | GCTGCTTCTGCTGTGACCTA | 256 | 83 | 5' UTR |
| 113133 | TATTTGCGAGCTCCCCGTAC | 257 | 15 | 5' UTR |
| 113134 | GCATAAGCACAGCAGCATTC | 258 | 79 | 5' UTR |
| 113135 | TCCAAAAAGAGACCAGATGC | 259 | 97 | 5' UTR |
| 113136 | AAATGCCTGTCCACTGTAGC | 260 | 117 | 5' UTR |
| 113137 | CTTCAGAGGAGCAGCACCAG | 261 | 191 | Coding |
| 113138 | GAATCTTCAGAGGAGCAGCA | 262 | 195 | Coding |
| 113139 | CAAATTGGCATGGCAGGTCT | 263 | 237 | Coding |
| 113140 | GCTTTGGTTTTGAGAGTTTG | 264 | 257 | Coding |
| 113141 | AGGCTTTGGTTTTGAGAGTT | 265 | 259 | Coding |
| 113142 | GCTCACTCAGGCTTTGGTTT | 266 | 267 | Coding |
| 113143 | GGTCCTGCCAAAATACTACT | 267 | 288 | Coding |
| 113144 | AGCCCTTGTCCTTGATCTGA | 268 | 429 | Coding |
| 113145 | TGTGGGCTTTTTGTGATGGA | 269 | 464 | Coding |
| 113146 | AATCATTCCTGTGGGCTTTT | 270 | 473 | Coding |
| 113147 | CCGTGTATAGATGAGCAGGT | 271 | 595 | Coding |
| 113148 | ACCGTGTATAGATGAGCAGG | 272 | 596 | Coding |
| 113149 | TCATCTTCTTAGGTTCTGGG | 273 | 618 | Coding |
| 113150 | ACAAGCTGATGGAAACGTCG | 274 | 720 | Coding |
| 113151 | TGCTCGTAACATCAGGGAAT | 275 | 747 | Coding |
| 113152 | AAGATGGTCATATTGCTCGT | 276 | 760 | Coding |
| 113153 | CGCGTCTTGTCAGTTTCCAG | 277 | 787 | Coding |
| 113154 | CAGCTGTAATCCAAGGAATG | 278 | 864 | Coding |
| 113155 | GGGCTTCATCAGATCTTTCA | 279 | 1041 | Coding |
| 113156 | CATGTATCACTTTTGTCGCA | 280 | 1093 | Coding |
| 113157 | AGCCCCCTTATTACTCATGG | 281 | 1221 | 3' UTR |
| 113158 | GGAGTTACAGGGAGGCTATT | 282 | 1261 | 3' UTR |
| 113159 | AGTCTCCTCTTGGCATACGG | 283 | 1290 | 3' UTR |
| 113160 | CCCATAAGTGTGCTCTGAAG | 284 | 1335 | 3' UTR |

[1]Emboldened residues are 2'-MOE residues (others are 2'-deoxy). All 2'-MOE cytosines and 2'-deoxy cytosine residues are 5-methyl-cytosines; all linkages are phosphorothioate linkages.
[2]For ISIS# 113131 and 113132, co-ordinates are from Genbank Accession No. L25259, locus name "HUMB72A". For remaining oigonucleotides, co-ordinates are from Genbank Accession No. U04343, locus name "HSU04343".

TABLE 24

Inhibition of Human B7-2 mRNA Expression by Chimeric (deoxy gapped) Phosphorothioate Oligodeoxynucleotides

| ISIS No: | SEQ ID NO: | GENE TARGET REGION | % mRNA EXPRESSION | % mRNA INHIBITION |
|---|---|---|---|---|
| 113131 | 255 | 5' UTR | 13 | 87 |
| 113132 | 256 | 5' UTR | 17 | 83 |
| 113133 | 257 | 5' UTR | 214 | — |
| 113134 | 258 | 5' UTR | 27 | 73 |
| 113135 | 259 | 5' UTR | 66 | 34 |
| 113136 | 260 | 5' UTR | 81 | 19 |
| 113137 | 261 | Coding | 57 | 43 |
| 113138 | 262 | Coding | 12 | 88 |
| 113140 | 264 | Coding | 214 | — |
| 113141 | 265 | Coding | 126 | — |
| 113142 | 266 | Coding | 35 | 65 |
| 113143 | 267 | Coding | 118 | — |
| 113144 | 268 | Coding | 41 | 59 |
| 113145 | 269 | Coding | 46 | 54 |
| 113146 | 270 | Coding | 32 | 68 |
| 113147 | 271 | Coding | 35 | 65 |
| 113148 | 272 | Coding | 23 | 77 |
| 113149 | 273 | Coding | 29 | 71 |
| 113150 | 274 | Coding | 19 | 81 |
| 113151 | 275 | Coding | 208 | — |
| 113152 | 276 | Coding | 89 | 11 |
| 113153 | 277 | Coding | 19 | 81 |
| 113154 | 278 | Coding | 63 | 37 |
| 113155 | 279 | Coding | 13 | 87 |
| 113156 | 280 | Coding | 83 | 17 |
| 113157 | 281 | 3' UTR | 13 | 87 |
| 113158 | 282 | 3' UTR | 20 | 80 |
| 113159 | 283 | 3' UTR | 43 | 57 |
| 113160 | 284 | 3' UTR | 09 | 91 |

Example 21

Human Skin Psoriasis Model

Animal models of psoriasis based on xenotransplantation of human skin from psoriatic patients are advantageous because they involve the direct study of affected human tissue. Psoriasis is solely a disease of the skin and consequently, engraftment of human psoriatic skin onto SCID mice allows psoriasis to be created with a high degree of fidelity in mice.

BALB/cByJSmn-Prkdcscid/J SCID mice (4-6 weeks old) of either sex (Jackson Laboratory, Bar Harbor, Me.) were maintained in a pathogen free environment. At 6-8 weeks of age, mice were anesthetized by intraperitoneal injection of 30 mg/kg body weight ketamine-HCl and 1 mg/kg body weight acepromazine. After anesthesia, mice were prepared for transplantation by shaving the hair from the dorsal skin, 2 cm away from the head. The area was then sterilized and cleaned with povidone iodide and alcohol. Graft beds of about 1 cm×1 cm were created on the shaved areas by removing full thickness skin down to the fascia. Partial thickness human skin was then orthotopically transferred onto the graft bed. The transplants were held in place by gluing the human skin to mouse to-mouse skin with Nexband liquid, a veterinary bandage (Veterinary Products Laboratories, Phoenix, Ariz.). Finally, the transplant and the wounds were covered with a thick layer of antibiotic ointment. After 4 weeks of transplantation, a 2 mm punch biopsy was obtained to confirm the acceptance of the graft and the origin of the skin in the transplant area. Only mice whose grafts did not show signs of infection were used for the study. Normal human skin was obtained from elective plastic surgeries and psoriatic plaques were obtained from shave biopsies from psoriatic volunteers. Partial thickness skin was prepared by dermatome shaving of the skin and transplanted to the mouse as described above for the psoriatic skin.

Animals (n=5) were topically treated with 2.5% (w/w) of each antisense oligonucleotide in a cream formulation comprising 10% isopropyl myristate, 10% glyceryl monooleate, 3% cetostearyl alcohol, 10% polyoxyl-20-cetyl ether, 6% poloxamer 407, 2.5% phenoxyethanol, 0.5% methylparaben, 0.5% propylparaben and water (final pH about 7.5).

The following oligonucleotides were used: human B7-1 (5=-TTCCCAGGTGCAAAACAGGC-3=; SEQ ID NO: 228) (ISIS 113492) and human B7-2 (5=-CGTGTGTCTGT-GCTAGTCCC-3=; SEQ ID NO: 255) (ISIS 113131). Both sequences contained only phosphorothioate linkages, 2=-MOE modifications at nucleotides 1-5 and 16-20 and all cytidines were 5-methyl cytidines.

Plaques from the same patients were also transplanted onto control mice (n=5) and treated only with the vehicle of the active cream preparation. Both groups received the topical preparation twice a day for 4 weeks. Within 3-4 weeks the animals were sacrificed and 4 mm punch biopsies were taken from each xenograft. Biopsies were fixed in formalin for paraffin embedding and/or transferred to cryotubes and snap-frozen in liquid nitrogen and stored at −80° C.

Significant histological improvement marked by reduction of hyperkeratosis, acanthosis and lymphonuclear cellular infiltrates was observed in mice treated with the antisense oligonucleotides. Rete pegs, finger-like projections of the epidermis into the dermis, were also measured. These are phenotypic markers for psoriasis which lengthen as the disease progresses. The shortening of these rete pegs are a good measure of anti-psoriatic activity. In mice treated with the active agent, the rete pegs changed from $238.56 \pm 98.3$ μm to $168.4 \pm 96.62$ μm (p<0.05), whereas in the control group the rete pegs before and after treatment were $279.93 \pm 40.56$ μm and $294.65 \pm 45.64$ μm, respectively (p>0.1). HLA-DR positive lymphocytic infiltrates and intraepidermal CD8 positive lymphocytes were significantly reduced in the transplanted plaques treated with the antisense oligonucleotide cream. These results show that antisense oligonucleotides to B7 inhibit psoriasis-induced inflammation and have therapeutic efficacy in the treatment of psoriasis.

Example 22

Mouse Model of Allergic Inflammation

In the mouse model of allergic inflammation, mice were sensitized and challenged with aerosolized chicken ovalbumin (OVA). Airway responsiveness was assessed by inducing airflow obstruction with a methacholine aerosol using a non-invasive method. This methodology utilized unrestrained conscious mice that are placed into the main chamber of a plthysmograph (Buxco Electronics, Inc., Troy, N.Y.). Pressure differences between this chamber and a reference chamber were used to extrapolate minute volume, breathing frequency and enhanced pause (Penh). Penh is a dimensionless parameter that is a function of total pulmonary airflow in mice (i.e., the sum of the airflow in the upper and lower respiratory tracts) during the respiratory cycle of the animal. The lower the PENH, the greater the airflow. This parameter closely correlates with lung resistance as measured by traditional invasive techniques using ventilated animals (Hamelmann et al., *Proc. Natl. Acad. Sci. U.S.A.* 94:1350-1355, 1997). Dose-response data were plotted as raw Penh values to increasing concentrations of methacholine. This system was used to test the efficacy of antisense oligonucleotides targeted to human B7-1 and B7-2.

There are several important features common to human asthma and the mouse model of allergic inflammation. One of these is pulmonary inflammation, in which cytokine expression and Th2 profile is dominant. Another is goblet cell hyperplasia with increased mucus production. Lastly, airway hyperresponsiveness (AHR) occurs resulting in increased sensitivity to cholinergic receptor agonists such as acetylcholine or methacholine. The compositions and methods of the present invention may be used to treat AHR and pulmonary inflammation.

Ovalbumin-induced Allergic Inflammation

Female Balb/c mice (Charles Rivers Laboratory, Taconic Farms, N.Y.) were maintained in micro-isolator cages housed in a specific pathogen-free (SPF) facility. The sentinel cages within the animal colony surveyed negative for viral antibodies and the presence of known mouse pathogens. Mice were sensitized and challenged with aerosolized chicken OVA. Briefly, 20 µg alum-precipitated OVA was injected intraperitoneally on days 0 and 14. On day 24, 25 and 26, the animals were exposed for 20 minutes to 1.0% OVA (in saline) by nebulization. The challenge was conducted using an ultrasonic nebulizer (PulmoSonic, The DeVilbiss Co., Somerset, Pa.). Animals were analyzed about 24 hours following the last nebulization using the Buxco electronics Biosystem. Lung function (Penh), lung histology (cell infiltration and mucus production), target mRNA reduction in the lung, inflammation (BAL cell type & number, cytokine levels), spleen weight and serum AST/ALT were determined.

This method has been used to show that prophylactic treatment with an anti-B7.2 monoclonal antibody continued throughout the sensitization and challenge periods decreases OVA-specific serum IgE and IgE levels, IL-4 and IFN-(levels in bronchoalveolar lavage (BAL) fluid, airway eosinophilia and airway hyperresponsiveness (Haczku et al., *Am. J. Respir. Crit. Care Med.* 159:1638-1643, 1999). Treatment during antigen challenge with both anti-B7.1 and anti-B7.2 mAbs is effective; however, either mAb alone is only partially active (Mathur et al., 21:498-509, 1999). However, the anti-B7.2 mAb had no activity when administered after the OVA challenge. The anti-B7.1 monoclonal antibody had no effect, either prophylactically or post-antigen challenge. Thus, there is a need for an effective B7 inhibitor which can be administered after antigen challenge, and which will reduce airway hyperresponsiveness and pulmonary inflammation. As described below, the antisense oligonucleotides of the present inventors fit this description.

Oligonucleotide Administration

Antisense oligonucleotides (ASOs) were dissolved in saline and used to intratracheally dose mice every day, four times per day, from days 15-26 of the OVA sensitization and challenge protocol. Specifically, the mice were anesthetized with isofluorane and placed on a board with the front teeth hung from a line. The nose was covered and the animal's tongue was extended with forceps and 25 µl of various doses of ASO, or an equivalent volume of saline (control) was placed at the back of the tongue until inhaled into the lung. The deposition pattern of an ASO in the lung, ISIS 13920 (5'-TCCGTCATCGCTCCTCAGGG-3'; SEQ ID NO:285) was also examined by immunohistochemical staining using a monoclonal antibody to the oligonucleotide, and showed that the ASO is taken up throughout the lung, most strongly by antigen presenting cells (APCs) and alveolar epithelium.

The B7 oligonucleotides used were:

```
B7-1:   5'-GCTCAGCCTTTCCACTTCAG-3'  (ISIS 121844;
        SEQ ID NO: 286)

B7-2:   5'-GCTCAGCCTTTCCACTTCAG-3'  (ISIS 121874;
        SEQ ID NO: 287)
```

Both of these oligonucleotides are phosphorothioates with 2'-MOE modifications on nucleotides 1-5 and 16-20, and 2'-deoxy at positions 6-15, and all cytidines are 5-methyl cytidines. These ASOs were identified by mouse-targeted ASO screening by target mRNA reduction in mouse cell lines. For B7-2, 19 mouse-targeted ASOs were screened by target mRNA reduction (Northern analysis) in IC-21 macrophages. Dose-response confirmation led to selection of ISIS 121874 (>70% reduction at 25 nM). For B7-1, 22 mouse-targeted ASOs were screened by target mRNA reduction (RT-PCR) in L-929 fibroblasts. Dose-response confirmation led to selection of ISIS 121844 (>70% reduction at 100 nM). No cross hybridization was predicted, and no cross-target reduction was detected in transfected cells.

RT-PCR Analysis

RNA was harvested from experimental lungs removed on day 28 of the OVA protocol. B7.2 and B7.1 levels were measured by quantitative RT-PCR using the Applied Biosystems PRISM 7700 Sequence Detection System (Applied Biosystems, Foster City, Calif.). Primers and probes used for these studies were synthesized by Operon Technologies (Alameda, Calif.). The primer and probe sequences were as follows:

B7-2:

```
forward:
5'-GGCCCTCCTCCTTGTGATG-3'  (SEQ ID NO: 288)

probe:
5'-/56-FAM/TGCTCATCATTGTATGTCACAAGAAGCCG/36-
TAMTph/-3'  (SEQ ID NO: 289)

reverse:
5'-CTGGGCCTGCTAGGCTGAT3'  (SEQ ID NO: 290)

B7-1:
forward:
5'-CAGGAAGCTACGGGCAAGTT3'  (SEQ ID NO: 291)

probe:
5'-/56-FAM/TGGGCCTTTGATTGCTTGATGACTGAA/36-
TAMTph/-3'  (SEQ ID NO: 292)

reverse:
5'-GTGGGCTCAGCCTTTCCA3'  (SEQ ID NO: 293)
```

Collection of Bronchial Alveolar Lavage (BAL) Fluid and Blood Serum for the Determination of Cytokine and Chemokine Levels Animals were injected with a lethal dose of ketamine, the trachea was exposed and a cannula was inserted and secured by sutures. The lungs were lavaged twice with 0.5 ml aliquots of ice cold PBS with 0.2% FCS. The recovered BAL fluid was centrifuged at 1,000 rpm for 10 min at 4° C., frozen on dry ice and stored at −80° C. until used. Luminex was used to measure cytokine levels in BAL fluid and serum.

BAL Cell Counts and Differentials

Cytospins of cells recovered from BAL fluid were prepared using a Shandon Cytospin 3 (Shandon Scientific LTD, Cheshire, England). Cell differentials were performed from slides stained with Leukostat (Fisher Scientific, Pittsburgh Pa.). Total cell counts were quantified by hemocytometer and, together with the percent type bty differential, were used to calculate specific cell number.

Tissue Histology

Before resection, lungs were inflated with 0.5 ml of 10% phosphate-buffered formalin and fixed overnight at 4° C. The lung samples were washed free of formalin with 1× PBS and subsequently dehydrated through an ethanol series prior to equilibration in xylene and embedded in paraffin. Sections (6μ) were mounted on slides and stained with hematoxylin/eosin, massons trichome and periodic acid-schiff (PAS) reagent. Parasagittal sections were analyzed by bright-field microscopy. Mucus cell content was assessed as the airway epithelium staining with PAS. Relative comparisons of mucus content were made between cohorts of animals by counting the number of PAS-positive airways.

Figure 11A:
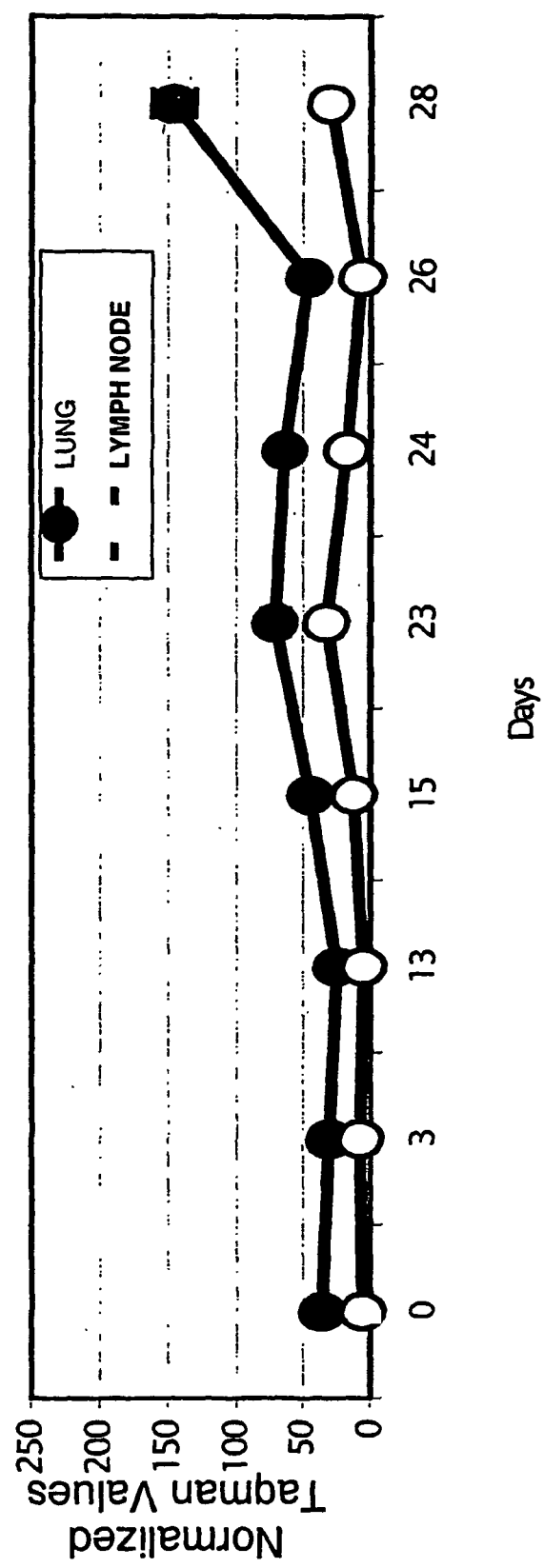
FIG. 11A-B are graphs showing the detection of B7.2 mRNA (FIG. 11A) and B7.1 mRNA (FIG. 11B) during the development of ovalbumin-induced asthma in a mouse model.
Figure 11B:
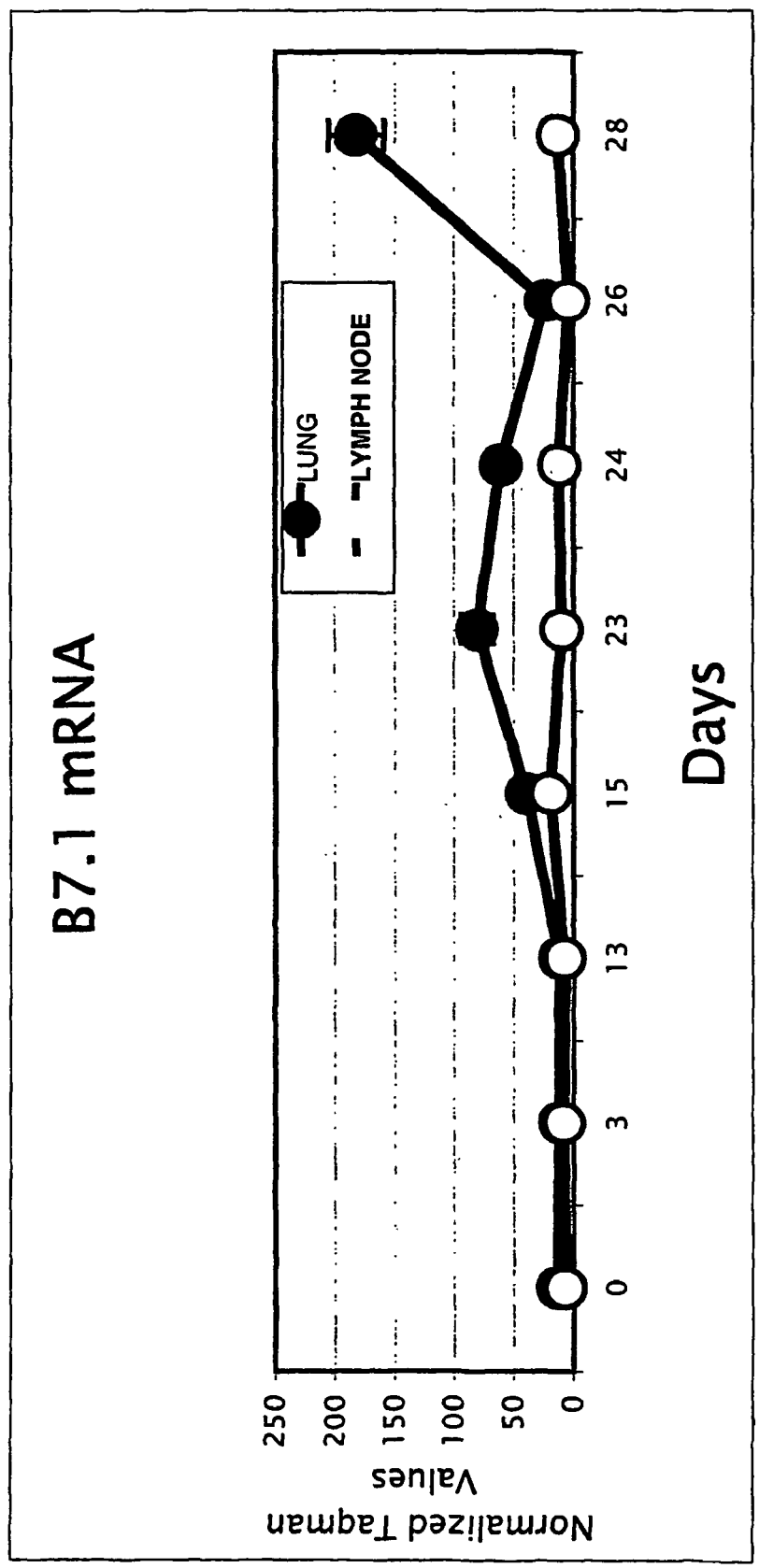
Figure 12:
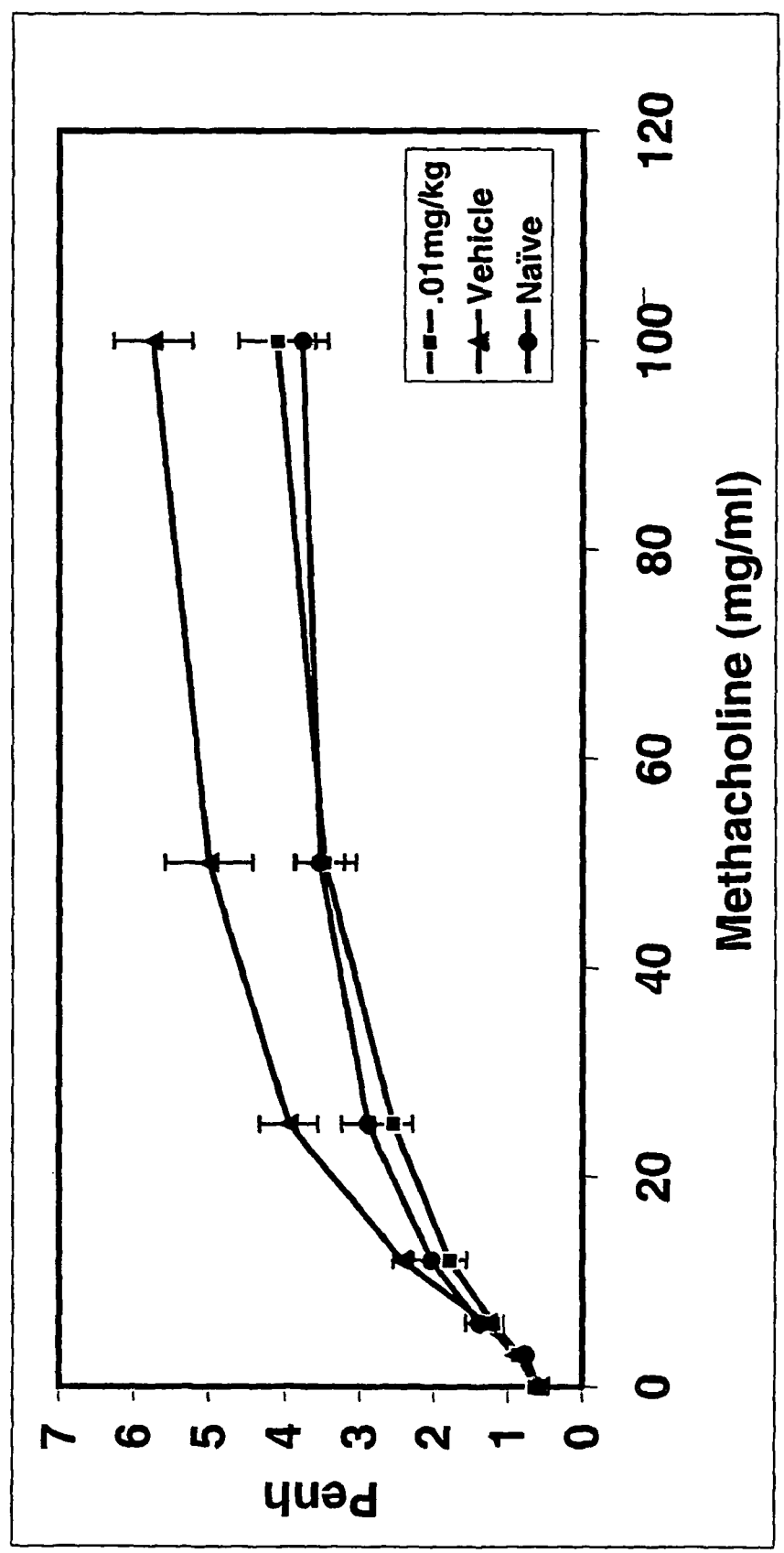
FIG. 12 is a graph showing that intratracheal administration of ISIS 121874, an antisense oligonucleotide targeted to mouse B7.2, following allergen challenge, reduces the airway response to methacholine.
Figure 13:
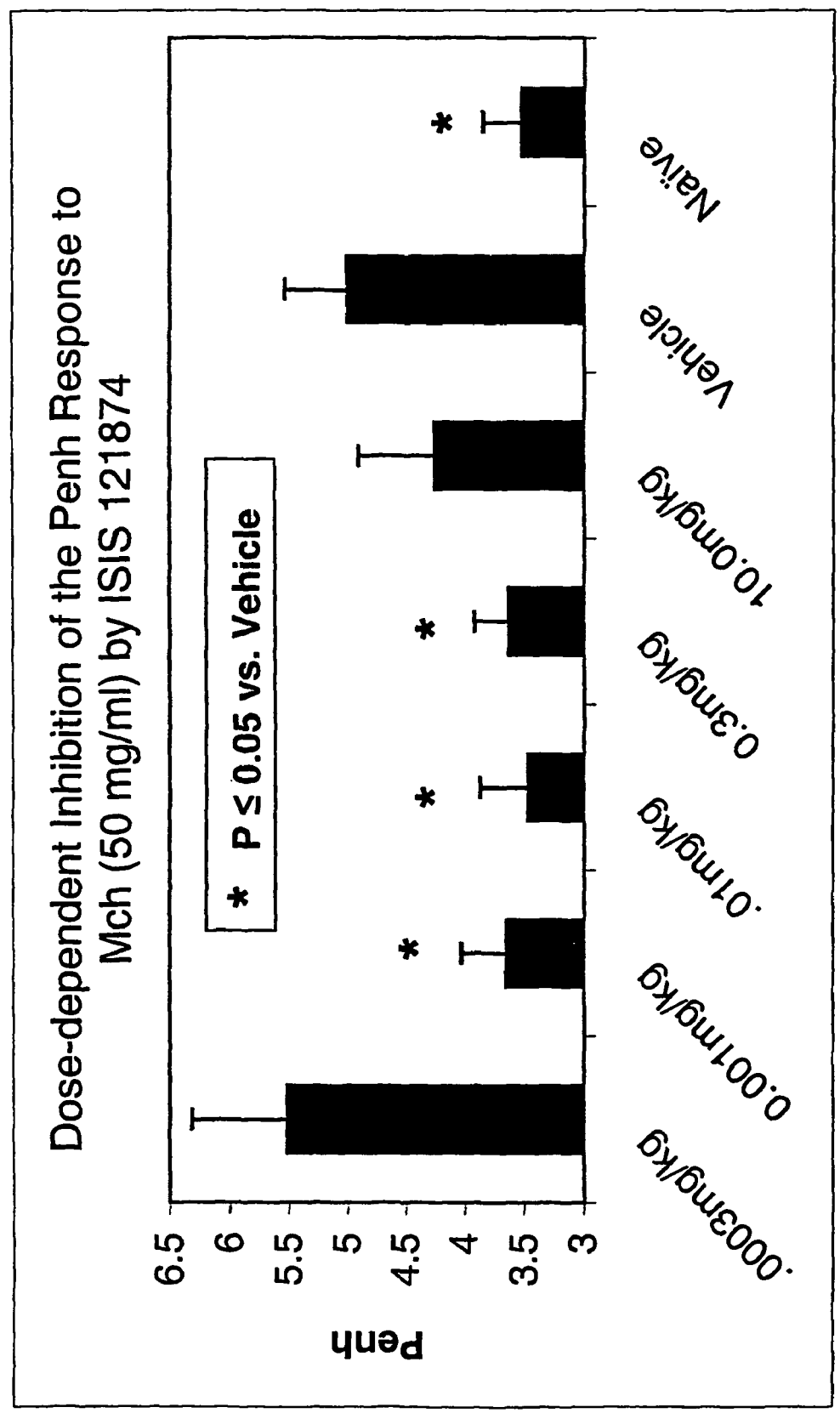
FIG. 13 is a graph showing the dose-dependent inhibition of the Penh response to 50 mg/ml methacholine by ISIS 121874. Penh is a dimensionless parameter that is a function of total pulmonary airflow in mice (i.e., the sum of the airflow in the upper and lower respiratory tracts) during the respiratory cycle of the animal. The lower the PENH, the greater the airflow. The dose of ISIS 121874 is shown on the x-axis.
Figure 14:
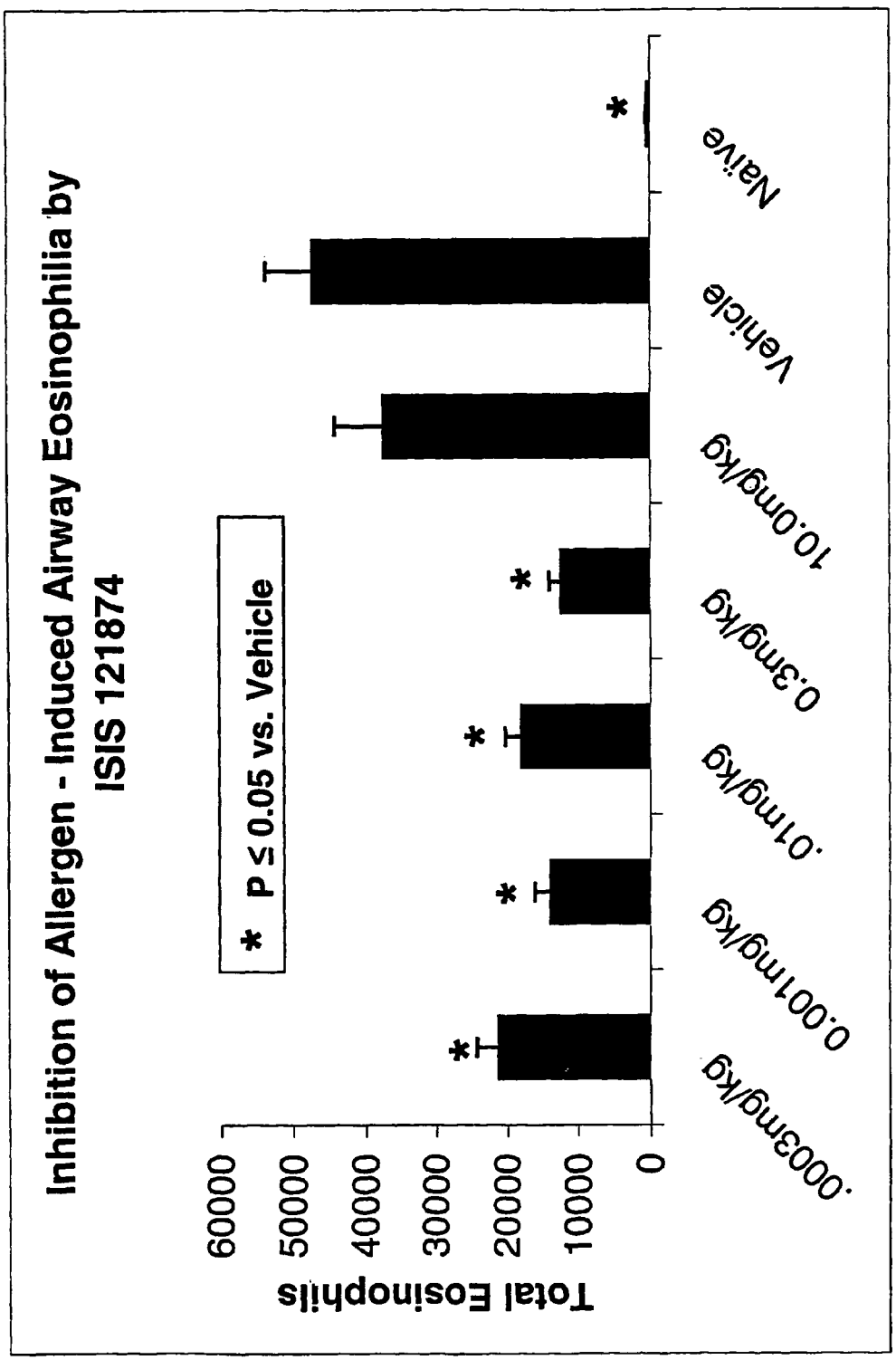
FIG. 14 is a graph showing the inhibition of allergen-induced eosinophilia by ISIS 121874. The dose of ISIS 121874 is shown on the x-axis.
Figure 15:
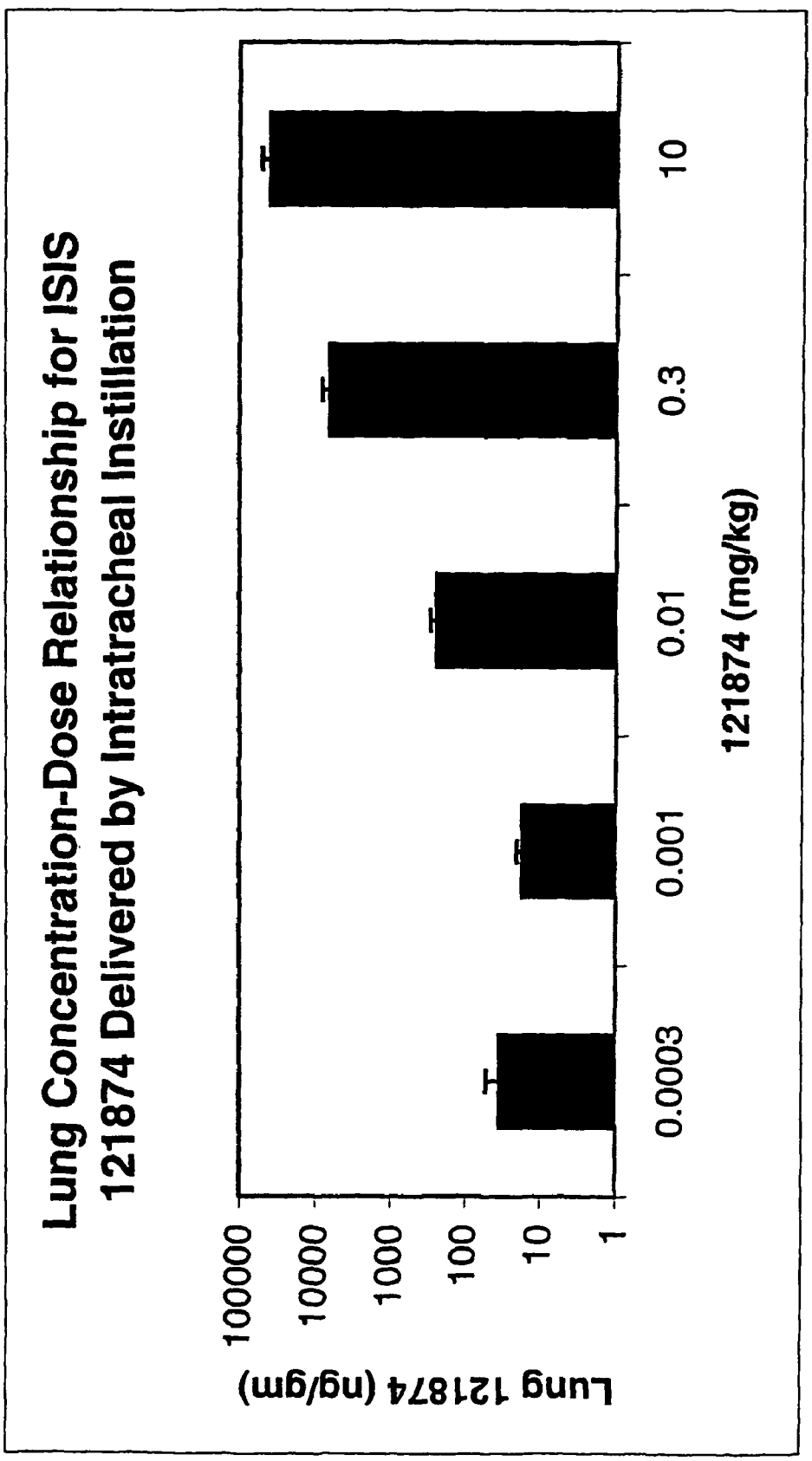
FIG. 15 is a graph showing the lung concentration-dose relationship for ISIS 121874 delivered by intratracheal administration.
Figure 16:
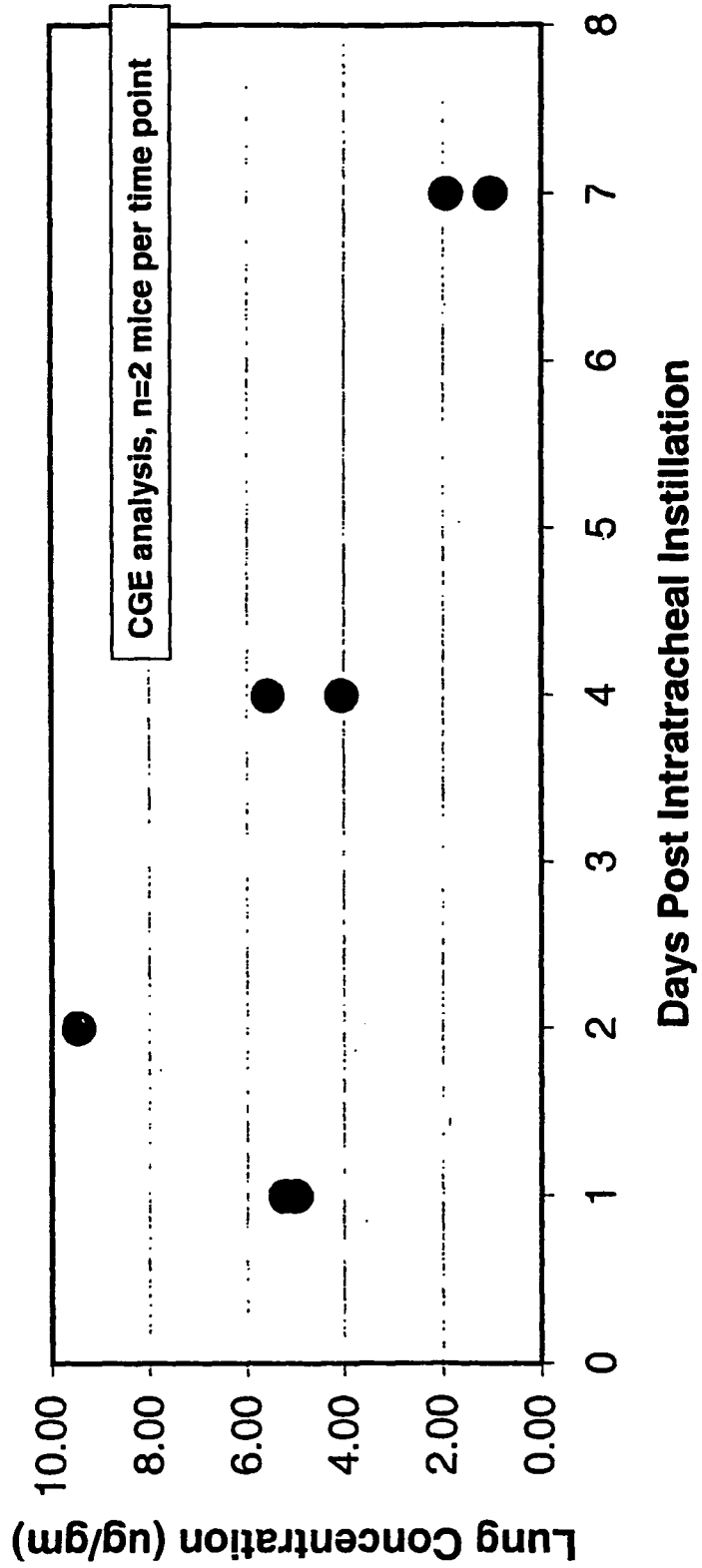
FIG. 16 is a graph showing the retention of ISIS 121874 in lung tissue following single dose (0.3 mg/kg) intratracheal instillation in the ovalbumin-induced mouse model of asthma.

As shown in FIGS. 11A-11B, B7.2 mRNA (FIG. 11A) and B7.1 mRNA (FIG. 11B) were detected in mouse lung and lymph node during the development of ovalbumin-induced asthma. Treatment with ISIS 121874 following allergen challenge reduces the airway response to methacholine (FIG. 12). The Penh value in B7.2 ASO-treated mice was about 40% lower than vehicle-treated mice, and was statistically the same as naive mice which were not sensitized with the allergen or treated with the ASO. This shows that B7.2 ASO-treated mice had significantly better airflow, and less inflammation, than mice which were not treated with the ASO. Treatment with a mismatch control oligonucleotide did not reduce airway hyperresponsiveness. The dose-dependent inhibition of the Penh response to methacholine by ISIS 121874 is shown in FIG. 13. The inhibition of allergen-induced eosinophilia by ISIS 121874 is shown in FIG. 14. ISIS 121874 at 0.3 mg/kg reduced the total number of eosinophils by about 75% compared to vehicle-treated mice. Since increased numbers of eosinophils result from inflammation, this provides further support for the anti-inflammatory properties of the B7.2 ASO. In addition, daily intratracheal delivery of ISIS 121874 does not induce splenomegaly, the concentration of ISIS 121874 achieved in lung tissue via daily intratracheal administration is proportional to the dose delivered (FIG. 15) and ISIS 121874 is retained in lung tissue for at least one week following single dose (0.3 mg/kg) intratracheal administration as determined by capillary gel electrophoresis (CGE) analysis (FIG. 16). There was no increase in inflammatory infiltrates at pharmacologically relevant doses. No increases in spleen weight or AST/ALT levels were observed at dosages up to 10 mg/kg. The observed pharmacology is compatible with daily or weekly dosing in humans.

Example 23

Support for an Antisense Mechanism of Action for ISIS 121874

Two variants of ISIS 121874 were synthesized: a 7 base mismatch 5'-TCAAGTCCTTCCACACCCAA-3' (ISIS 306058; SEQ ID NO: 294) and a gap ablated oligonucleotide ISIS 306058 having the same sequence as ISIS 121874, but with 2'-MOE modifications at nucleotides 1, 2, 3, 6, 9, 13, 16, 18, 19 and 20. Because of the presence of 2'-MOE in the gap, this oligonucleotide is no longer an RNase H substrate and will not recruit RNase H to the RNA-DNA hybrid which is formed.

The results (FIG. 17) show that at 0.3 mg/kg, only. ISIS 121874, and not the mismatch and gap ablated controls, significantly lowered Penh, which supports that ISIS 121874 is working by an antisense mechanism.

Figure 18A:
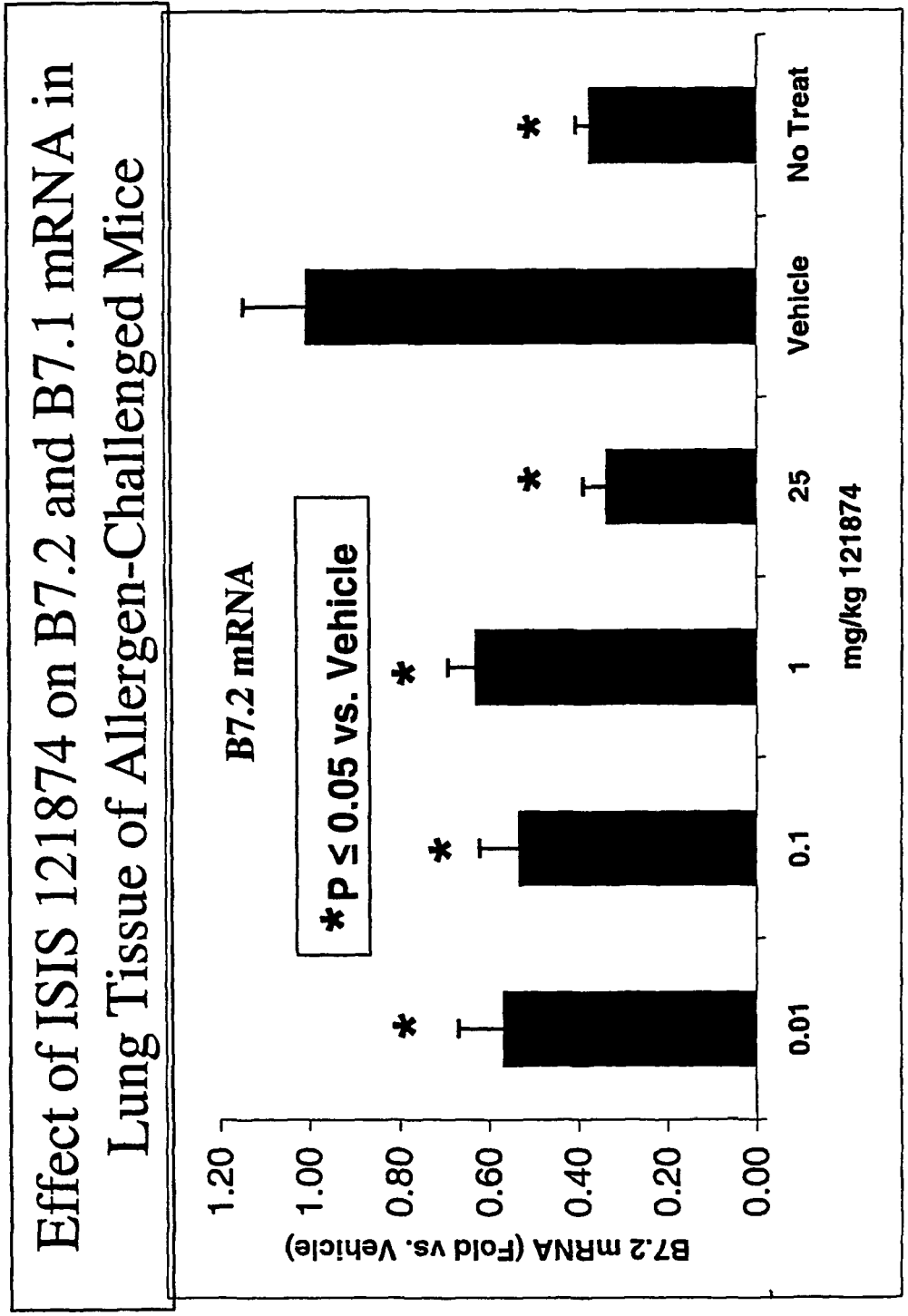
FIGS. 18A-B is a graph showing the effect of ISIS 121874 on B7.2 (FIG. 18A) and B7.1 (FIG. 18B) mRNA in lung tissue of ovalbumin-challenged mice.
Figure 18B:
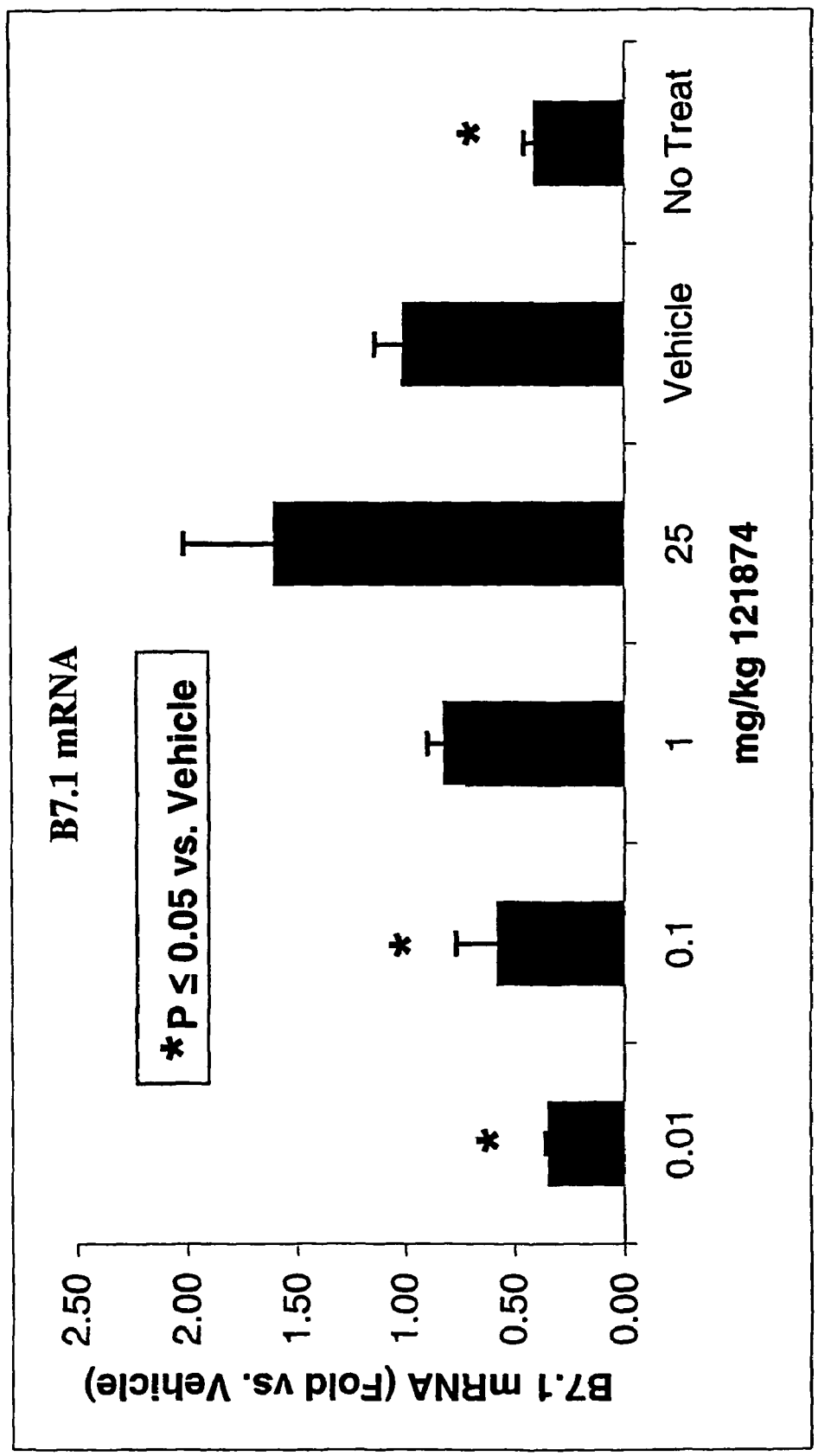

The effects of ISIS 121874 and the control oligonucleotides on airway mucus production in the ovalbumin-induced model were also tested. The results (FIG. 18) show that only ISIS 121874 significantly inhibited mucus production.

Figure 19A:
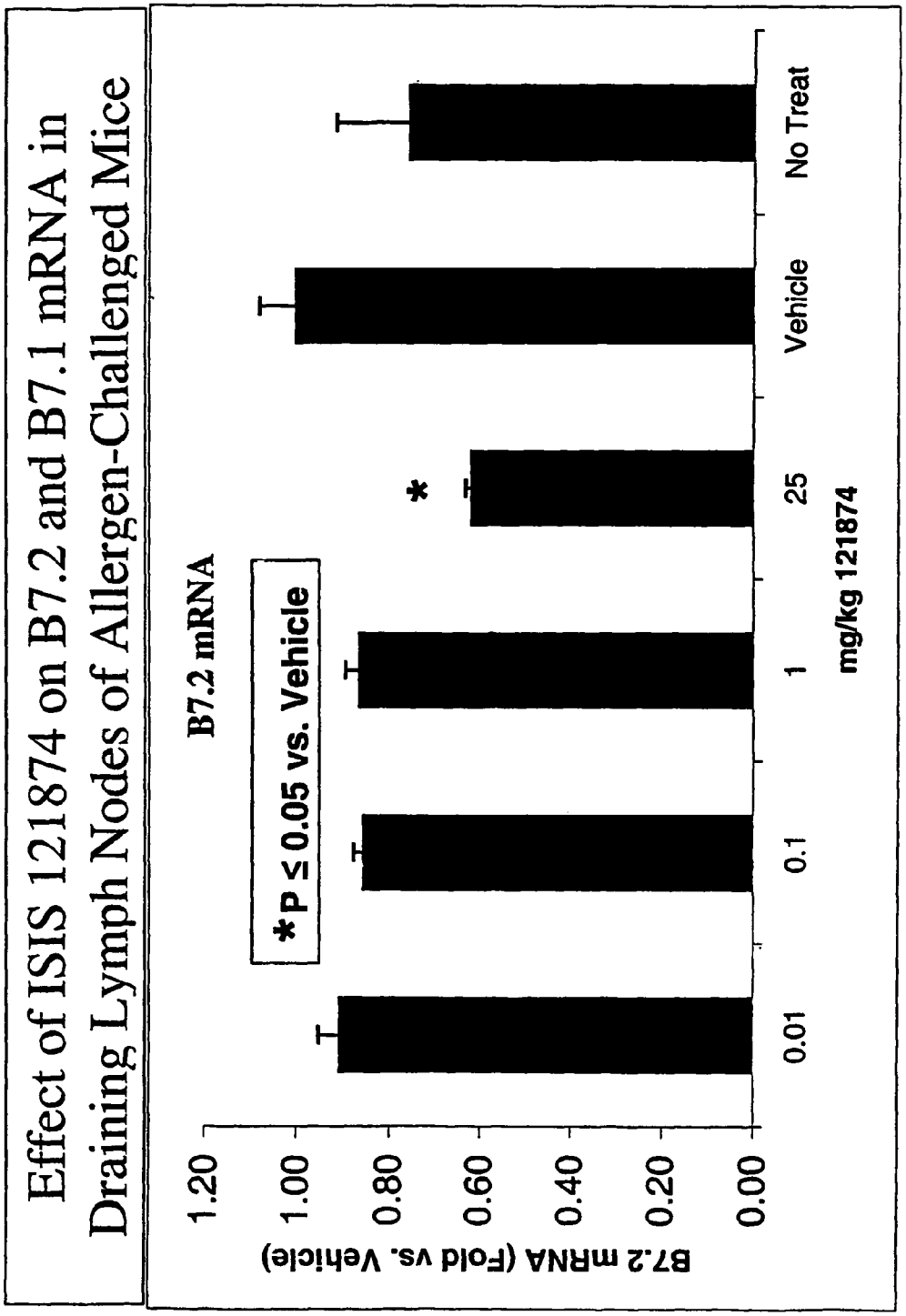
Figure 20:
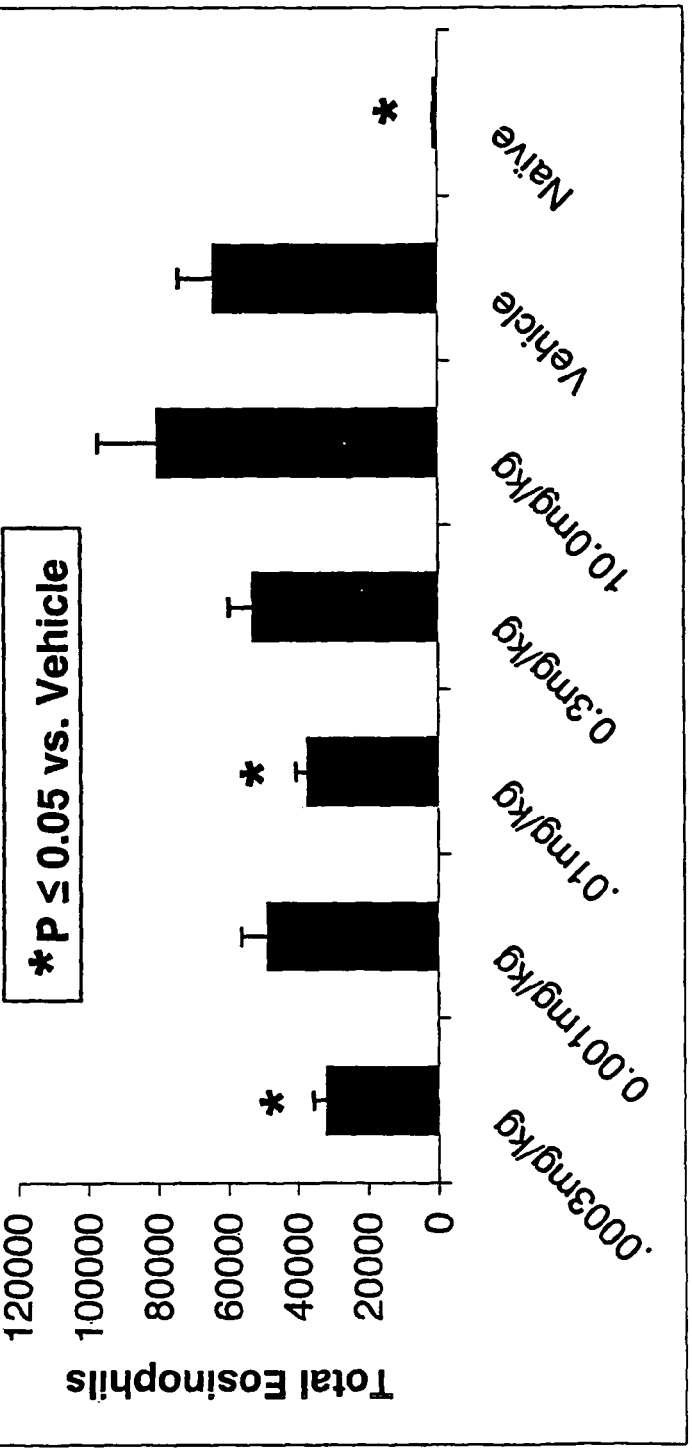
FIG. 20 is a graph showing that treatment with an antisense oligonucleotide targeted to B7.1 (ISIS 121844) reduces allergen-induced eosinophilia in the ovalbumin-induced mouse model of asthma.

The effect of ISIS 121874 on B7.2 and B7.1 mRNA in lung tissue of allergen-challenged mice is shown in FIGS. 19A and 19B, respectively. The effect of ISIS 121874 on B7.2 and B7.1 mRNA in draining lymph nodes of allergen-challenged mice is shown in FIGS. 20A and 20B, respectively. This shows that ISIS 121874 reduces both B7.2 and B7.1 mRNA (greater in lung vs. node).

In summary, ISIS 121874 resulted in a dose-dependent inhibition of airway hypersensitivity, inhibited eosinophilia and reduced B7.1 and B7.2 expression in the lung and lymph nodes. In addition, ISIS 121874 reduced levels of the following inflammatory molecules: IgE mRNA in the lung and IgE protein in the serum; reduced IL-5 mRNA in the lung and IL-5 protein in the BAL fluid; and reduced the serum level of macrophage chemokine (KC).

In the aerosolized ISIS 121874 study, treatment with 0.001, 0.01, 0.1 or 1.0 mg/kg estimated inhaled dose was delivered by nose-only inhalation of an aerosol solution, four times per day, on days 15-26 (n=8 mice per group). The airway response to methacholine was reduced to the level seen in naive mice at 0.001 mg/kg dose (estimated inhaled dose=1 μg/kg). No gross adverse effects were seen.

Figure 22:
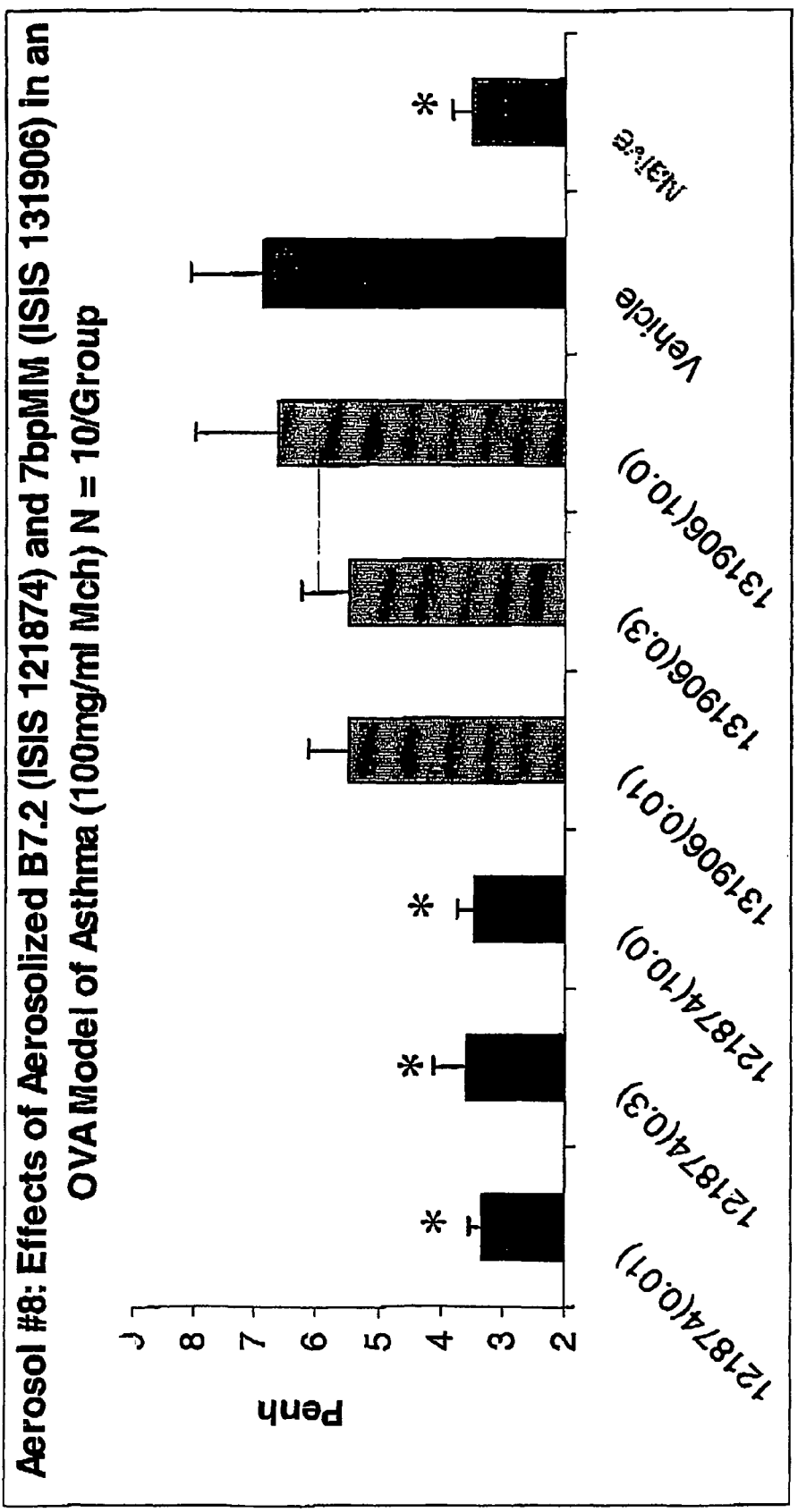
FIG. 22 is a graph showing that aerosolized B7-2 antisense oligonucleotide (ISIS 121874), but not a mismatch control oligonucleotide (ISIS 131906), reduces the airway response to methacholine in an ovalbumin-induced mouse model of asthma.
Figure 24:
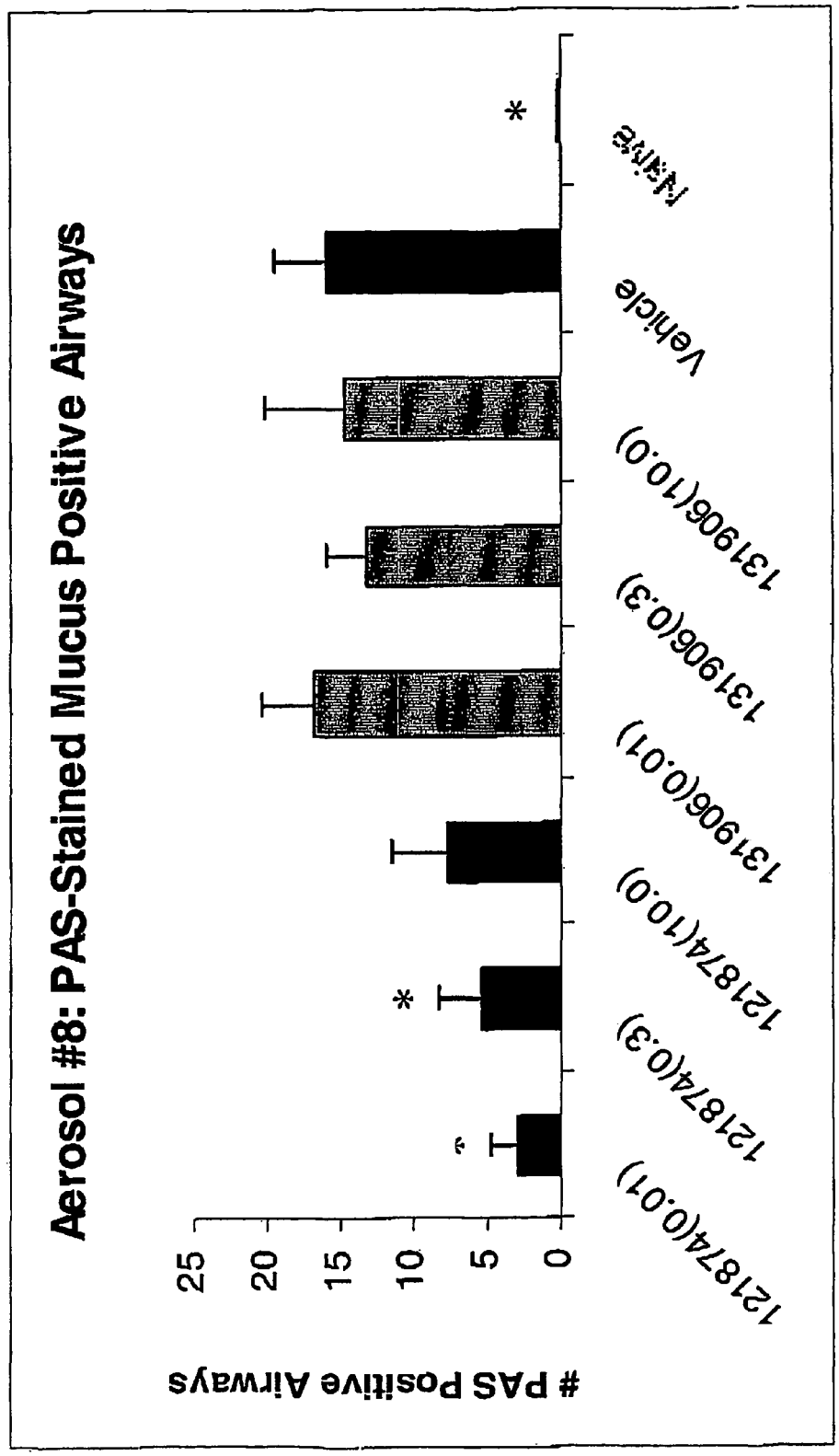
FIG. 24 is a graph showing that aerosolized B7-2 antisense oligonucleotide (ISIS 121874), but not a mismatch control oligonucleotide (ISIS 131906), reduces mucus oveproduction in ovalbumin-challenged mice.

In another aerosolized ISIS 121874 study, mice were treated with 0.01, 0.3 or 10.0 μg/kg estimated inhaled dose (n=10 mice per group), four times per day, or with a 7 base pair mismatched control oligonucleotide. The airway response to methacholine (100 mg/ml) was reduced to the level seen in naive mice at 0.01-0.3 μg/kg dose (FIG. 22). A mismatch control oligonucleotide had no effect on the airway response: to methacholine. In addition, ISIS 121874 reduced airway eosinophilia in a dose-dependent manner (FIG. 23). The mismatch control oligonucleotide had no effect. In addition, aerosolized ISIS 121874, but not a mismatch control oligonucleotide, reduced the percentage,of eosinophils/macrophages in lungs from ovalbumin-challenged mice. Lastly, aerosolized ISIS 121874, but not a mismatched control oligonucleotide, reduced mucus overproduction in a dose-dependent manner in ova-challenged mice (FIG. 24). Thus, both intratracheal and aerosol administration of B7.2 antisense oligonucleotides effectively reduce airway hyperresponsiveness and pulmonary inflammation in a mouse model of allergen-induced asthma, and represents a therapeutically useful treatment of human pulmonary inflammatory disorders, including asthma.

In addition, a dose-dependent increase in lung concentration of ISIS 121874 was observed at 24 hours following single (0.06 mg/kg) or multiple (0.00006, 0.006, 0.005 or 0.06 mg/kg, q2d×5).

Example 24

B7.1 ASO in Ovalbumin Model of Asthma

Figure 21A:
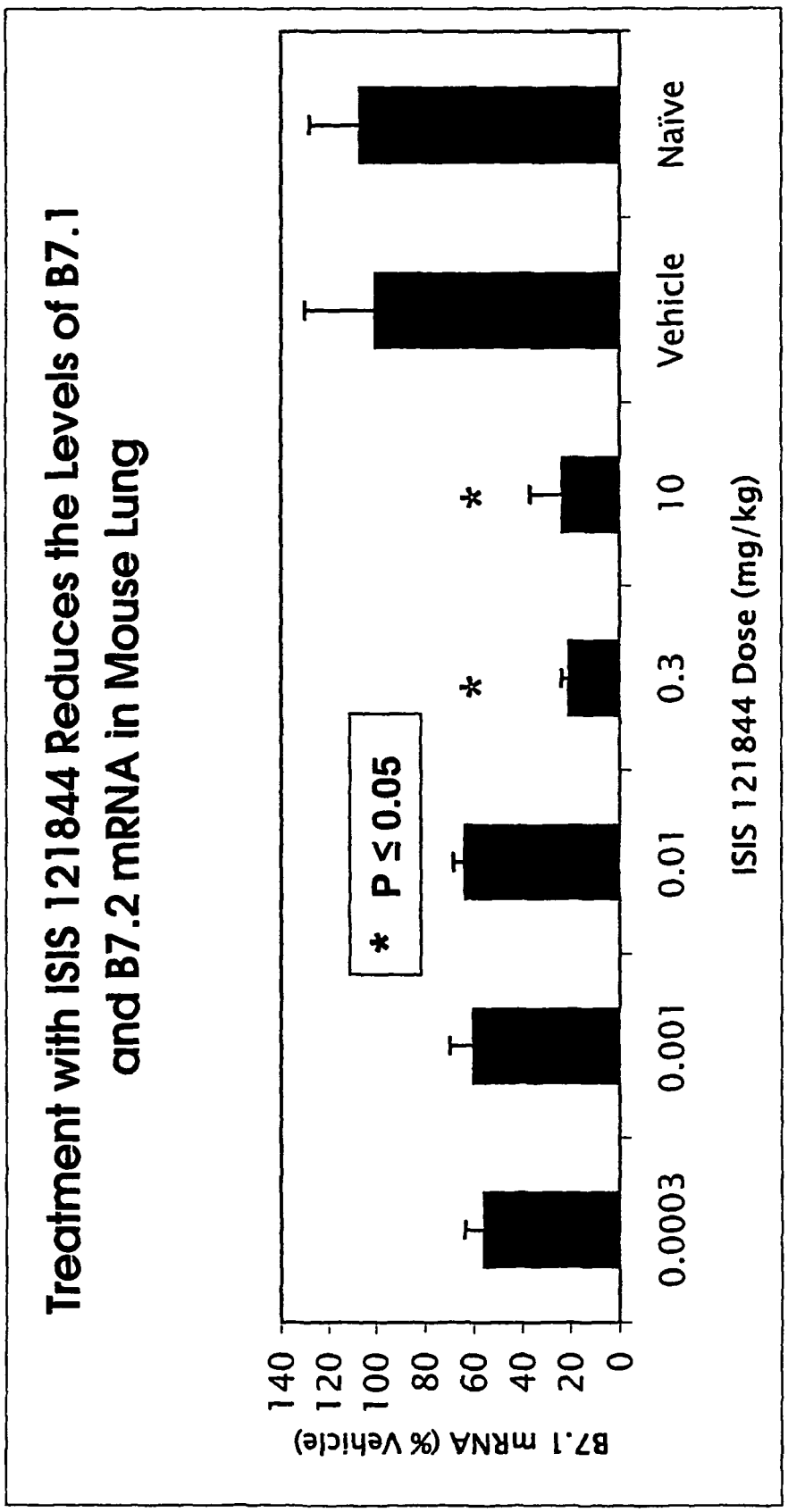
FIGS. 21A-B are graphs showing that treatment with ISIS 121844 reduces the levels of B7.1 mRNA (FIG. 21A) and B7.2 mRNA (FIG. 21B) in the mouse lung.
Figure 21B:
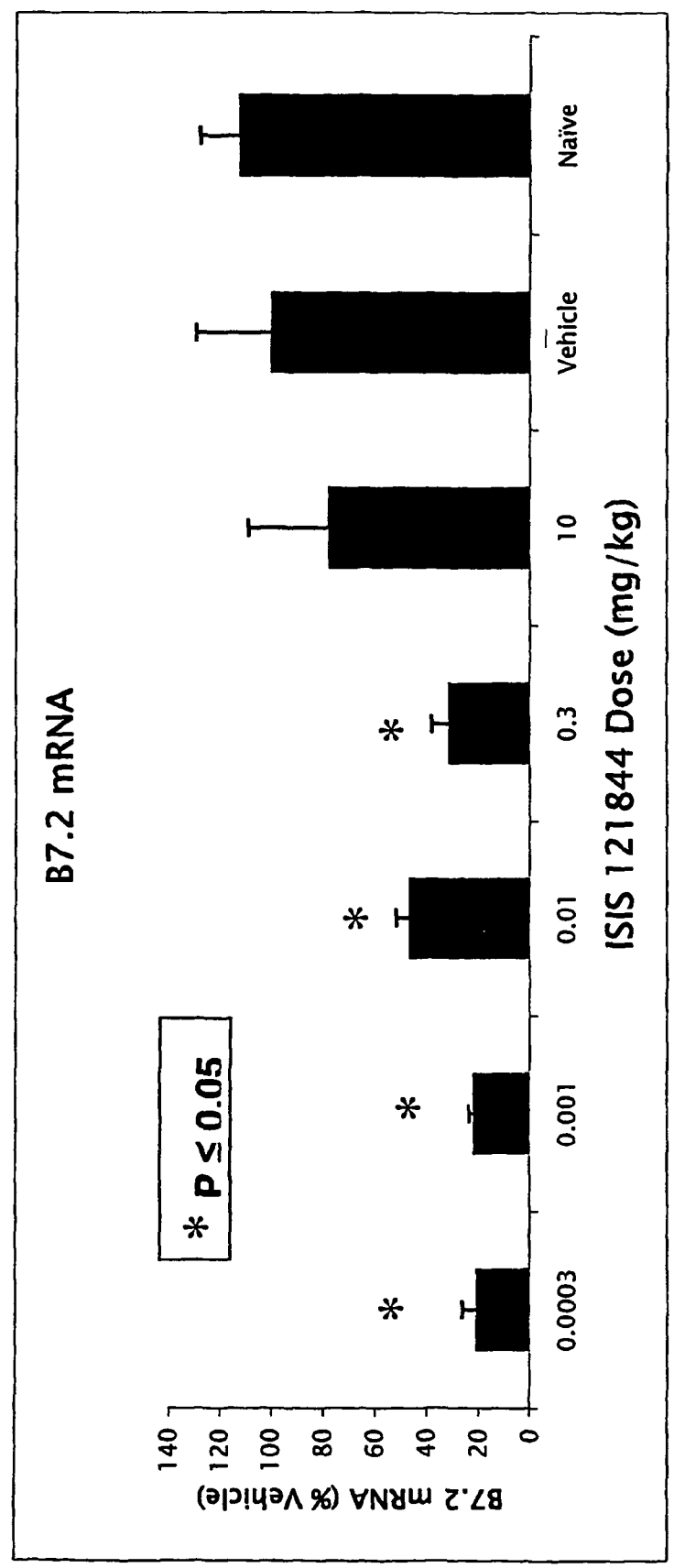

The same protocols described above for the B7.2 ASOs were used to test the effect of the B7.1 ASO ISIS 121844 (SEQ ID NO: 286). In contrast to the B7.2 ASO, ISIS 121844 had no effect on the Penh response in mice challenged with methacholine. Although there was no effect on Penh, ISIS. 121844 reduced allergen-induced airway eosinophilia (FIG. 21) and reduced the levels of B7.1 and B7.2 in the mouse lung. (FIGS. 22A-B). Thus, treatment with B7.1 ASO produced anti-inflammatory effects, but did not prevent airway hyper-responsiveness. There was no effect of ISIS 121844 on the Penh response despite achieving an 80% reduction of B7.2 mRNA in the lung (FIG. 21B). Treatment with ISIS 121844 reduced eosinophil and PMN numbers in BAL fluid. This effect was associated with a reduction in lung B7.2 (not B7.1) mRNA.

The combined use of B7.1 or B7.2 with one or more conventional asthma medications including, but not limited to, montelukast sodium (Singulair™), albuterol, beclomethasone dipropionate, triamcinolone acetonide, ipratropium bromide (Atrovent™), flunisolide, fluticasone propionate (Flovent™) and other steroids is also contemplated. The combined use of oligonucleotides which target both B7.1 and B7.2 for the treatment of asthma is also within the scope of the present invention. B7.1 and B7.2 may also be combined with one or more conventional asthma medications as described above for B7.1 or B7.2 alone.

The tolerability of a 2'-MOE modified antisense oligonucleotide was investigated in an inhalation toxicity study in mice. CD1 mice were exposed to nine lung delivered doses of 1, 3 and 10 mg/kg over 18 days. No effect was seen on survival, clinical signs of toxicity, body weight or clinical pathology parameters. Lung morphology was unaffected except for dose-dependent changes in alveolar macrophages. The treatment doses tested were three orders of magnitude greater than doses with which in vivo efficacy was observed.

Example 25

Design and Screening of Duplexed Antisense Compounds Targeting B7.1 or B7.2

In accordance with the present invention, a series of nucleic acid duplexes comprising the antisense compounds of the present invention and their complements can be designed to target B7.1 or B7.2. The nucleobase sequence of the antisense strand of the duplex comprises at least a portion of an oligonucleotide to B7.1 or B7.2 as described herein. The ends of the strands may be modified by the addition of one or more natural or modified nucleobases to form an overhang. The sense strand of the dsRNA is then designed and synthesized as the complement of the antisense strand and may also contain modifications or additions to either terminus. For example, in one embodiment, both strands of the dsRNA duplex would be complementary over the central nucleobases, each having overhangs at one or both termini.

For example, a duplex comprising an antisense strand having the sequence CGAGAGGCGGACGGGACCG and having a two-nucleobase overhang of deoxythymidine (dT) would have the following structure:

```
cgagaffcggacgggaccgTT  Antisense    (SEQ ID NO 723)
||||||||||||||||||||   Strand
TTgctctccgcctgccctggc  Complement   (SEQ ID NO 724)
```

In another embodiment, a duplex comprising an antisense strand having the same sequence CGAGAGGCGGACGG-GACCG may be prepared with blunt ends (no single stranded overhang) as shown:

```
cgagaggcggacgggaccg  Antisense Strand
|||||||||||||||||||
gctctccgcctgccctggc  Complement
```

RNA strands of the duplex can be synthesized by methods disclosed herein or purchased from Dharmacon Research Inc., (Lafayette, Colo.). Once synthesized, the complementary strands are annealed. The single strands are aliquoted and diluted to a concentration of 50 uM. Once diluted, 30 uL of each strand is combined with 15 uL of a 5× solution of annealing buffer. The final concentration of said buffer is 100 mM potassium acetate, 30 mM HEPES-KOH pH 7.4, and 2 mM magnesium acetate. The final volume is 75 uL. This solution is incubated for 1 minute at 90° C. and then centrifuged for 15 seconds. The tube is allowed to sit for 1 hour at 37° C. at which time the dsRNA duplexes are used in experimentation. The final concentration of the dsRNA duplex is 20 uM. This solution can be stored frozen (−20° C.) and freeze-thawed up to 5 times.

Once prepared, the duplexed antisense compounds are evaluated for their ability to modulate B7.1 or B7.2 expression according to the protocols described herein.

Example 26

Design of Phenotypic Assays and In Vivo Studies for the Use of B7.1 or B7.2 Inhibitors Phenotypic assays Once B7.1 or B7.2 inhibitors have been identified by the methods disclosed herein, the compounds are further investigated in one or more phenotypic assays, each having measurable endpoints predictive of efficacy in the treatment of a particular disease state or condition.

Phenotypic assays, kits and reagents for their use are well known to those skilled in the art and are herein used to investigate the role and/or association of B7.1 or B7.2 in health and disease. Representative phenotypic assays, which can be purchased from any one of several commercial vendors, include those for determining cell viability, cytotoxicity, proliferation or cell survival (Molecular Probes, Eugene, Oreg.; PerkinElmer, Boston, Mass.), protein-based assays including enzymatic assays (Panvera, LLC, Madison, Wis.; BD Biosciences, Franklin Lakes, N.J.; Oncogene Research Products, San Diego, Calif.), cell regulation, signal transduction, inflammation, oxidative processes and apoptosis (Assay Designs Inc., Ann Arbor, Mich.), triglyceride accumulation (Sigma-Aldrich, St. Louis, Mo.), angiogenesis assays, tube formation assays, cytokine and hormone assays and metabolic assays (Chemicon International Inc., Temecula, Calif.; Amersham Biosciences, Piscataway, N.J.).

In one non-limiting example, cells determined to be appropriate for a particular phenotypic assay (i.e., MCF-7 cells selected for breast cancer studies; adipocytes for obesity studies) are treated with B7.1 or B7.2 inhibitors identified from the in vitro studies as well as control compounds at optimal concentrations which are determined by the methods described above. At the end of the treatment period, treated and untreated cells are analyzed by one or more methods specific for the assay to determine phenotypic outcomes and endpoints.

Phenotypic endpoints include changes in cell morphology over time or treatment dose as well as changes in levels of cellular components such as proteins, lipids, nucleic acids, hormones, saccharides or metals. Measurements of cellular status which include pH, stage of the cell cycle, intake or excretion of biological indicators by the cell, are also endpoints of interest.

Analysis of the genotype of the cell (measurement of the expression of one or more of the genes of the cell) after treatment is also used as an indicator of the efficacy or potency of the B7.1 or B7.2 inhibitors. Hallmark genes, or

Example 27

Antisense Inhibition of Human B7.2 Expression by Chimeric Phosphorothioate Oligonucleotides Having 2'-MOE Wings and a Deoxy Gap In accordance with the present invention, an additional series of antisense compounds were designed to target different regions of the human B7.2 RNA, using published sequences (GenBank accession number U04343.1, incorporated herein as SEQ ID NO: 295, GenBank accession number BC040261.1, incorporated herein as SEQ ID NO: 296 and GenBank accession number NT_005543.12, a portion of which is incorporated herein as SEQ ID NO: 297). The compounds are shown in Table 25. "Target site" indicates the first (5'-most) nucleotide number on the particular target sequence to which the compound binds. All compounds in Table 25 are chimeric oligonucleotides ("gapmers") 20 nucleotides in length, composed of a central "gap" region consisting of ten 2'-deoxynucleotides, which is flanked on both sides (5' and 3' directions) by five-nucleotide "wings". The wings are composed of 2'-MOE nucleotides. The internucleoside (backbone) linkages are phosphorothioate (P=S) throughout the oligonucleotide. All cytidine residues are 5-methylcytidines. The compounds were analyzed for their effect on human B7.2 mRNA levels in THP-1 cells by quantitative real-time PCR as described in other examples herein. Data are averages from three experiments. If present, "N.D." indicates "no data".

TABLE 25

Inhibition of human B7.2 mRNA levels by chimeric phosphorothioate oligonucleotides having 2'-MOE wings and a deoxy gap

| Isis Number | Sequence 5' to 3' | SEQ ID NO: | % INHIB | Genbank Accesion Target | Target Site | Region |
|---|---|---|---|---|---|---|
| 322216 | ACCAAAAGGAGTATTTGCGA | 298 | N.D. | U04343.1 | 26 | 5'UTR |
| 322217 | CATTCCCAAGGAACACAGAA | 299 | N.D. | U04343.1 | 64 | 5'UTR |
| 322218 | ACTGTAGTTCCAAAAAGAGA | 300 | N.D. | U04343.1 | 105 | 5'UTR |
| 322219 | CTGTCACAAATGCCTGTCCA | 301 | N.D. | U04343.1 | 124 | 5'UTR |
| 322220 | TCAGTCCCATAGTGCTGTCA | 302 | N.D. | U04343.1 | 138 | START |
| 322221 | CTGTTACAGCAGCAGAGAAG | 303 | N.D. | BC040261.1 | 29 | 5'UTR |
| 322222 | TCCCTGTTACAGCAGCAGAG | 304 | N.D. | BC040261.1 | 32 | 5'UTR |
| 322223 | ATCTGGAAATGACCCCACTC | 305 | N.D. | BC040261.1 | 71 | 5'UTR |
| 322224 | GTGACCTAATATCTGGAAAT | 306 | N.D. | BC040261.1 | 81 | 5'UTR |
| 322225 | CATTTTGGCTGCTTCTGCTG | 307 | N.D. | EC040261.1 | 100 | START |
| 322226 | GGAACTTACAAAGGAAAGGG | 308 | N.D. | BC040261.1 | 1145 | 3'UTR |
| 322227 | AAAAAGGTTGCCCAGGAACT | 309 | N.D. | BC040261.1 | 1159 | 3'UTR |
| 322228 | TGCCTTCTGGAAGAAATCAA | 310 | N.D. | BC040261.1 | 1177 | 3'UTR |
| 322229 | TTTTTGCCTTCTGGAAGAAA | 311 | N.D. | BC040261.1 | 1181 | 3'UTR |
| 322230 | CTATTCCACTTAGAGGGAGT | 312 | N.D. | BC040261.1 | 1233 | 3'UTR |
| 322231 | TCTGATCTGGAGGAGGTATT | 313 | N.D. | BC040261.1 | 1389 | 3'UTR |
| 322232 | AGAAATTGAGAGGTCTATTT | 314 | N.D. | BC040261.1 | 1444 | 3'UTR |
| 322233 | CACCAGCTTAGAATTCTGGG | 315 | N.D. | BC040261.1 | 1484 | 3'UTR |
| 322234 | AGGTAGTTGTTTAGTCACAG | 316 | N.D. | BC040261.1 | 1524 | 3'UTR |
| 322235 | CCAGACTGAGGAGGTAGTTG | 317 | N.D. | BC040261.1 | 1535 | 3'UTR |
| 322236 | CAGTACATAGATCTCTATGT | 318 | N.D. | BC040261.1 | 1599 | 3'UTR |
| 322237 | TTACAGTACATAGATCTCTA | 319 | N.D. | BC040261.1 | 1602 | 3'UTR |
| 322238 | GATGAGAACTCCTTAGCAGG | 320 | N.D. | BC040261.1 | 1657 | 3'UTR |
| 322239 | TAGCAACAGCCCAGATAGAA | 321 | N.D. | BC040261.1 | 1787 | 3'UTR |
| 322240 | TCTGTTGCTTGTTTCAAGAC | 322 | N.D. | BC040261.1 | 2043 | 3'UTR |
| 322241 | TCCATTTGGACAGACTATCC | 323 | N.D. | BC040261.1 | 2064 | 3'UTR |
| 322242 | GGGAAACTGCTGTCTGTCTT | 324 | N.D. | BC040261.1 | 2087 | 3'UTR |

TABLE 25-continued

Inhibition of human B7.2 mRNA levels by chimeric phosphorothioate oligonucleotides having 2'-MOE wings and a deoxy gap

| Isis Number | Sequence 5' to 3' | SEQ ID NO: | % INHIB | Genbank Accesion Target | Target Site | Region |
|---|---|---|---|---|---|---|
| 322243 | TGCTTCCAGGAAGATGACAT | 325 | N.D. | BC040261.1 | 2149 | 3'UTR |
| 322244 | ATTCATCCCATTATCAAGGT | 326 | N.D. | BC040261.1 | 2191 | 3'UTR |
| 322245 | AGCCAGGAGTGGAAAGTCCT | 327 | N.D. | BC040261.1 | 2223 | 3'UTR |
| 322246 | CTTCCTAATTCCGTTGCAGC | 328 | N.D. | BC040261.1 | 2255 | 3'UTR |
| 322247 | CATCTGTAGGCTAAGTAAGC | 329 | N.D. | BC040261.1 | 2297 | 3'UTR |
| 322248 | CCCGTAGGACATCTGTAGGC | 330 | N.D. | BC040261.1 | 2306 | 3'UTR |
| 322249 | GCCCTATGCTGGGCCAGCCC | 331 | N.D. | BC040261.1 | 2331 | 3'UTR |
| 322250 | GTCTCTGTATGCAAGTTTCC | 332 | N.D. | BC040261.1 | 2396 | 3'UTR |
| 322251 | CCAGTATATCTGTCTCTGTA | 333 | N.D. | BC040261.1 | 2407 | 3'UTR |
| 322252 | CCAGGTTTTCAAAGTCATTT | 334 | N.D. | BC040261.1 | 2430 | 3'UTR |
| 322253 | AGCCAGGTTTTCAAAGTCAT | 335 | N.D. | BC040261.1 | 2432 | 3'UTR |
| 322254 | CCCTTAGTGATCCCACCTTA | 336 | N.D. | BC040261.1 | 2453 | 3'UTR |
| 322255 | CTGCCCCATCCCTTAGTGAT | 337 | N.D. | BC040261.1 | 2462 | 3'UTR |
| 322256 | TTTATGTTTGGGCAGAGACT | 338 | N.D. | BC040261.1 | 2480 | 3'UTR |
| 322257 | CATGGCAGTCTATAACCCTT | 339 | N.D. | BC040261.1 | 2556 | 3'UTR |
| 322258 | TAGCATGGCAGTCTATAACC | 340 | N.D. | BC040261.1 | 2559 | 3'UTR |
| 322259 | TCTAGCATGGCAGTCTATAA | 341 | N.D. | BC040261.1 | 2561 | 3'UTR |
| 322260 | TTGTCTAGCATGGCAGTCTA | 342 | N.D. | BC040261.1 | 2564 | 3'UTR |
| 322261 | AAGCTTGTCTAGCATGGCAG | 343 | N.D. | BC040261.1 | 2568 | 3'UTR |
| 322262 | ACATGGACAAGCTTGTCTAG | 344 | N.D. | BC040261.1 | 2576 | 3'UTR |
| 322263 | TTACATGGACAAGCTTGTCT | 345 | N.D. | BC040261.1 | 2578 | 3'UTR |
| 322264 | GAATATTACATGGACAAGCT | 346 | N.D. | BC040261.1 | 2583 | 3'UTR |
| 322265 | AACTAGCCAGGTGCTAGGAG | 347 | N.D. | BC040261.1 | 2636 | 3'UTR |
| 322266 | AATTATTACTCACCACTGGG | 348 | N.D. | NT_005543.12 | 1124 | genomic |
| 322267 | TAATATTTAGGGAAGCATGA | 349 | N.D. | NT_005543.12 | 13890 | genomic |
| 322268 | GGACCCTGGGCCAGTTATTG | 350 | N.D. | NT_005543.12 | 22504 | genomic |
| 322269 | CAAACATACCTGTCACAAAT | 351 | N.D. | NT_005543.12 | 23662 | genomic |
| 322270 | GTGATATCAATTGATGGCAT | 352 | N.D. | NT_005543.12 | 29265 | genomic |
| 322271 | TGCTACATCTACTCAGTGTC | 353 | N.D. | NT_005543.12 | 31796 | genomic |
| 322272 | TGGAACTCTTGCCTTTCGGA | 354 | N.D. | NT_005543.12 | 32971 | genomic |
| 322273 | CCATCCACATTGTAGCATGT | 355 | N.D. | NT_005543.12 | 34646 | genomiC |
| 322274 | TCAGGATGGTATGGCCATAC | 356 | N.D. | NT_005543.12 | 36251 | genomic |
| 322275 | TCCCATAGTGCTAGAGTCGA | 357 | N.D. | NT_005543.12 | 37218 | genomic |
| 322276 | AGGTTCTTACCAGAGAGCAG | 358 | N.D. | NT_005543.12 | 37268 | genomic |
| 322277 | CAGAGGAGCAGCACCTAAAA | 359 | N.D. | NT_005543.12 | 49133 | genomic |
| 322278 | GACCACATACCAAGCACTGA | 360 | N.D. | NT_005543.12 | 49465 | genomic |
| 322279 | ATCTTTCAGAAACCCAAGCA | 361 | N.D. | NT_005543.12 | 51347 | genomic |

TABLE 25-continued

Inhibition of human B7.2 mRNA levels by chimeric phosphorothioate oligonucleotides having 2'-MOE wings and a deoxy gap

| Isis Number | Sequence 5' to 3' | SEQ ID NO: | % INHIB | Genbank Accesion Target | Target Site | Region |
|---|---|---|---|---|---|---|
| 322280 | GAGTCACCAAAGATTTACAA | 362 | N.D. | NT_005543:12 | 51542 | genomic |
| 322281 | CTGAAGTTAGCTGAAAGCAG | 363 | N.D. | NT_005543.12 | 51815 | genomic |
| 322282 | ACAGCTTTACCTATAGAGAA | 364 | N.D. | NT_005543.12 | 52118 | genomic |
| 322283 | TCCTCAAGCTCTACAAATGA | 365 | N.D. | NT_005543.12 | 54882 | genomic |
| 322284 | GACTCACTCACCACATTTAT | 366 | N.D. | NT_005543.12 | 55027 | genomic |
| 322285 | AGTGATAGCAAGGCTTCTCT | 367 | N.D. | NT_005543.12 | 56816 | genomic |
| 322286 | CTTGGAGAGAATGGTTATCT | 368 | N.D. | NT_005543.12 | 61044 | genomic |
| 322287 | GAAGATGTTGATGCCTAAAT | 369 | N.D. | NT_005543.12 | 63271 | genomic |
| 322288 | GTGTTGGTTCCTGAAAGACA | 370 | N.D. | NT_005543.12 | 63665 | genomic |
| 322289 | CAGGATTTACCTTTTCTTGG | 371 | N.D. | NT_005543.12 | 63711 | genomic |
| 322290 | AGGGCAGAATAGAGGTTGCC | 372 | N.D. | NT_005543.12 | 64973 | Genomic |
| 322291 | TTTTTCTCTGGAGAAATAGA | 373 | N.D. | NT_005543.12 | 65052 | genomic |
| 323624 | GTTACTCAGTCCCATAGTGC | 374 | 59 | U04343.1 | 143 | START |
| 323625 | CAAAGAGAATGTTACTCAGT | 375 | 21 | U04343.1 | 153 | Coding |
| 323626 | CCATCACAAAGAGAATGTTA | 376 | 32 | U04343.1 | 159 | Coding |
| 323627 | GGAAGGCCATCACAAAGAGA | 377 | 54 | U04343.1 | 165 | Coding |
| 323628 | GAGCAGGAAGGCCATCACAA | 378 | 44 | U04343.1 | 170 | Coding |
| 323629 | CCAGAGAGCAGGAAGGCCAT | 379 | 36 | U04343.1 | 175 | Coding |
| 323630 | AAATAAGCTTGAATCTTCAG | 380 | 22 | U04343.1 | 205 | Coding |
| 323631 | AGTCTCATTGAAATAAGCTT | 381 | 56 | U04343.1 | 215 | Coding |
| 323632 | AGGTCTGCAGTCTCATTGAA | 382 | 41 | U04343.1 | 223 | Coding |
| 323633 | CTACTAGCTCACTCAGGCTT | 383 | 50 | U04343.1 | 273 | Coding |
| 323634 | AAATACTACTAGCTCACTCA | 384 | 30 | U04343.1 | 278 | Coding |
| 323635 | CTGCCAAAATACTACTAGCT | 385 | 24 | U04343.1 | 284 | Coding |
| 323636 | TTCAGAACCAAGTTTTCCTG | 386 | 23 | U04343.1 | 307 | Coding |
| 323637 | CCTCATTCAGAACCAAGTTT | 387 | 19 | U04343.1 | 312 | Coding |
| 323638 | GTATACCTCATTCAGAACCA | 388 | 20 | U04343.1 | 317 | Coding |
| 323639 | GCCTAAGTATACTTCATTCA | 389 | 55 | U04343.1 | 323 | Coding |
| 323640 | CTCTTTGCCTAAGTATACCT | 390 | 28 | U04343.1 | 329 | Coding |
| 323641 | CCCATATACTTGGAATGAAC | 391 | 88 | U04343.1 | 361 | Coding |
| 323642 | CTTGTGCGGCCCATATACTT | 392 | 27 | U04343.1 | 370 | Coding |
| 323643 | ATCAAAACTTGTGCGGCCCA | 393 | 80 | U04343.1 | 377 | Coding |
| 323644 | CCCTTGTCCTTGATCTGAAG | 394 | 71 | U04343.1 | 427 | Coding |
| 323645 | CAAGCCCTTGTCCTTTGATC | 395 | 56 | U04343.1 | 432 | Coding |
| 323646 | TTGATACAAGCCCTTGTCCT | 396 | 33 | U04343.1 | 437 | Coding |
| 323647 | ATACATTGATACAAGCCCTT | 397 | 41 | U04343.1 | 442 | Coding |
| 323648 | TGGATGATACATTGATACAA | 398 | 31 | U04343.1 | 448 | Coding |

TABLE 25-continued

Inhibition of human B7.2 mRNA levels by chimeric phosphorothioate oligonucleotides having 2'-MOE wings and a deoxy gap

| Isis Number | Sequence 5' to 3' | SEQ ID NO: | % INHIB | Genbank Accesion Target | Target Site | Region |
|---|---|---|---|---|---|---|
| 323649 | GAATTCATCTGGTGGATGCG | 399 | 81 | U04343.1 | 493 | Coding |
| 323650 | GTTCAGAATTCATCTGGTGG | 400 | 92 | U04343.1 | 498 | Coding |
| 323651 | TGACAGTTCAGAATTCATCT | 401 | 64 | U04343.1 | 503 | Coding |
| 323652 | AGCACTGACAGTTCAGAATT | 402 | 87 | U04343.1 | 508 | Coding |
| 323653 | TAGCAAGCACTGACAGTTCA | 403 | 96 | U04343.1 | 513 | Coding |
| 323654 | TGAAGTTAGCAAGCACTGAC | 404 | 87 | U04343.1 | 519 | Coding |
| 323655 | TTGACTGAAGTTAGCAAGCA | 405 | 65 | U04343.1 | 524 | Coding |
| 323656 | CTATTTCAGGTTGACTGAAG | 406 | 76 | U04343.1 | 534 | Coding |
| 323657 | ACTGTTATATTAGAAATTGG | 407 | 43 | U04343.1 | 556 | Coding |
| 323658 | GCAGGTCAAATTTATGTACA | 408 | 36 | U04343.1 | 581 | Coding |
| 323659 | GTATAGATGAGCAGGTCAAA | 409 | 56 | U04343.1 | 591 | Coding |
| 323660 | GGGTAACCGTGTATAGATGA | 410 | 71 | U04343.1 | 601 | Coding |
| 323661 | AGGTTCTGGGTAACCGTGTA | 411 | 68 | U04343.1 | 608 | Coding |
| 323662 | TAGCAAAACACTCATCTTCT | 412 | 22 | U04343.1 | 629 | Coding |
| 323663 | GTTCTTAGCAAAACACTCAT | 413 | 23 | U04343.1 | 634 | Coding |
| 323664 | ATTCTTGGTTCTTAGCAAAA | 414 | 35 | U04343.1 | 641 | Coding |
| 323665 | GATAGTTGAATTCTTGGTTC | 415 | 43 | U04343.1 | 650 | Coding |
| 323666 | ACCATCATACTCGATAGTTG | 416 | 71 | U04343.1 | 662 | Coding |
| 323667 | ATCTTGAGATTTCTGCATAA | 417 | 52 | U04343.1 | 683 | Coding |
| 323668 | ACATTATCTTGAGATTTCTG | 418 | 39 | U04343.1 | 688 | Coding |
| 323669 | CGTACAGTTCTGTGACATTA | 419 | 68 | U04343.1 | 702 | Coding |
| 323670 | AGACAAGCTGATGGAAACGT | 420 | 19 | U04343.1 | 722 | Coding |
| 323671 | GAAACAGACAAGCTGATGGA | 421 | 26 | U04343.1 | 727 | Coding |
| 323672 | GGAATGAAACAGACAAGCTG | 422 | 33 | U04343.1 | 732 | Coding |
| 323673 | CATCAGGGAATGAAACAGAC | 423 | 38 | U04343.1 | 738 | Coding |
| 323674 | CGTAACATCAGGGAATGAAA | 424 | 47 | U04343.1 | 743 | Coding |
| 323675 | AGCTCTATAGAGAAAGGTGA | 425 | 77 | U04343.1 | 817 | Coding |
| 323676 | CCTCAAGCTCTATAGAGAAA | 426 | 24 | U04343.1 | 822 | Coding |
| 323677 | GGAGGCTGAGGGTCCTCAAG | 427 | 55 | U04343.1 | 835 | Coding |
| 323678 | AGTACAGCTGTAATCCAAGG | 428 | 23 | U04343.1 | 868 | Coding |
| 323679 | TTGGAAGTACAGCTGTAATC | 429 | 60 | U04343.1 | 873 | Coding |
| 323680 | ATAATAACTGTTGGAAGTAC | 430 | 51 | U04343.1 | 883 | Coding |
| 323681 | CATCACACATATAATAACTG | 431 | 8 | U04343.1 | 893 | Coding |
| 323682 | TCCATTTCCATAGAATTAGA | 432 | 35 | U04343.1 | 921 | Coding |
| 323683 | TCTTCTTCCATTTCCATAGA | 433 | 16 | U04343.1 | 927 | Coding |
| 323684 | ATTTATAAGAGTTGCGAGGC | 434 | 32 | U04343.1 | 954 | Coding |
| 323685 | TTGGTTWCCACATTATAAGA | 435 | 18 | U04343.1 | 964 | Coding |

TABLE 25-continued

Inhibition of human B7.2 mRNA levels by chimeric phosphorothioate oligonucleotides having 2'-MOE wings and a deoxy gap

| Isis Number | Sequence 5' to 3' | SEQ ID NO: | % INHIB | Genbank Accesion Target | Target Site | Region |
|---|---|---|---|---|---|---|
| 323686 | CTCTCCATTGTGTTGGTTCC | 436 | 53 | U04343.1 | 976 | Coding |
| 323687 | CTTCCCTCTCCATTGTGTTG | 437 | 19 | U04343.1 | 981 | Coding |
| 323688 | TGGTCTGTTCACTCTCTTCC | 438 | 58 | U04343.1 | 996 | Coding |
| 323689 | TTCATCAGATCTTTCAGGTA | 439 | 43 | U04343.1 | 1037 | Coding |
| 323690 | ATCACTTTTGTCGCATGAAG | 440 | 82 | U04343.1 | 1088 | Coding |
| 323691 | GCTTTACTCTTTAATTAAAA | 441 | 40 | U04343.1 | 1114 | STOP |
| 323692 | GTATGGGCTTTACTCTTTAA | 442 | 57 | U04343.1 | 1120 | 3'UTR |
| 323693 | ATACTTGTATGGGCTTTACT | 443 | 62 | U04343.1 | 1126 | 3'UTR |
| 323694 | AATGAATACTTGTATGGGCT | 444 | 71 | U04343.1 | 1131 | 3'UTR |

Example 28

Real-time Quantitative PCR Analysis of B7.2 mRNA Levels

Quantitation of B7.2 mRNA levels was accomplished by real-time quantitative PCR using the ABI PRISM™ 7600, 7700, or 7900 Sequence Detection System (PE-Applied Biosystems, Foster City, Calif.) according to manufacturer's instructions. This is a closed-tube, non-gel-based, fluorescence detection system which allows high-throughput quantitation of polymerase chain reaction (PCR) products in real-time. As opposed to standard PCR in which amplification products are quantitated after the PCR is completed, products in real-time quantitative PCR are quantitated as they accumulate. This is accomplished by including in the PCR reaction an oligonucleotide probe that anneals specifically between the forward and reverse PCR primers, and contains two fluorescent dyes. A reporter dye (e.g., FAM or JOE, obtained from either PE-Applied Biosystems, Foster City, Calif., Operon Technologies Inc., Alameda, Calif. or Integrated DNA Technologies Inc., Coralville, Iowa) is attached to the 5' end of the probe and a quencher dye (e.g., TAMRA, obtained from either PE-Applied Biosystems, Foster City, Calif., Operon Technologies Inc., Alameda, Calif. or Integrated DNA Technologies Inc., Coralville, Iowa) is attached to the 3' end of the probe. When the probe and dyes are intact, reporter dye emission is quenched by the proximity of the 3' quencher dye. During amplification, annealing of the probe to the target sequence creates a substrate that can be cleaved by the 5'-exonuclease activity of Taq polymerase. During the extension phase of the PCR amplification cycle, cleavage of the probe by Taq polymerase releases the reporter dye from the remainder of the probe (and hence from the quencher moiety) and a sequence-specific fluorescent signal is generated. With each cycle, additional reporter dye molecules are cleaved from their respective probes, and the fluorescence intensity is monitored at regular intervals by laser optics built into the ABI PRISM™ Sequence Detection System. In each assay, a series of parallel reactions containing serial dilutions of mRNA from untreated control samples generates a standard curve that is used to quantitate the percent inhibition after antisense oligonucleotide treatment of test samples.

Prior to quantitative PCR analysis, primer-probe sets specific to the target gene being measured are evaluated for their ability to be "multiplexed" with a GAPDH amplification reaction. In multiplexing, both the target gene and the internal standard gene GAPDH are amplified concurrently in a single sample. In this analysis, mRNA isolated from untreated cells is serially diluted. Each dilution is amplified in the presence of primer-probe sets specific for GAPDH only, target gene only ("single-plexing"), or both (multiplexing). Following PCR amplification, standard curves of GAPDH and target mRNA signal as a function of dilution are generated from both the single-plexed and multiplexed samples. If both the slope and correlation coefficient of the GAPDH and target signals generated from the multiplexed samples fall within 10% of their corresponding values generated from the single-plexed samples, the primer-probe set specific for that target is deemed multiplexable. Other methods of PCR are also known in the art.

PCR reagents were obtained from Invitrogen Corporation, (Carlsbad, Calif.). RT-PCR reactions were carried out by adding 20 μL PCR cocktail (2.5× PCR buffer minus MgCl$_2$, 6.6 mM MgCl$_2$, 375 μM each of dATP, dCTP, dCTP and dGTP, 375 nM each of forward primer and reverse primer, 125 nM of probe, 4 Units RNAse inhibitor, 1.25 Units PLATINUM® Taq, 5 Units MuLV reverse transcriptase, and 2.5× ROX dye) to 96-well plates containing 30 μL total RNA solution (20-200 ng). The RT reaction was carried out by incubation for 30 minutes at 48° C. Following a 10 minute incubation at 95° C. to activate the PLATINUM® Taq, 40 cycles of a two-step PCR protocol were carried out: 95° C. for 15 seconds (denaturation) followed by 60° C. for 1.5 minutes (annealing/extension).

Gene target quantities obtained by real time RT-PCR are normalized using either the expression level of GAPDH, a gene whose expression is constant, or by quantifying total RNA using RiboGreen™ (Molecular Probes, Inc. Eugene, Oreg.). GAPDH expression is quantified by real time RT-PCR, by being run simultaneously with the target, multiplexing, or separately. Total RNA is quantified using RiboGreen™ RNA quantification reagent (Molecular Probes, Inc. Eugene, Oreg.). Methods of RNA quantification by RiboGreen™ are taught in Jones, L. J., et al, (Analytical Biochemistry, 1998, 265, 368-374).

In this assay, 170 μL of RiboGreen™ working reagent (RiboGreen™ reagent diluted 1:350 in 10 mM Tris-HCl, 1 mM EDTA, pH 7.5) is pipetted into a 96-well plate containing 30 μL purified, cellular RNA. The plate is read in a CytoFluor 4000 (PE Applied Biosystems) with excitation at 485 nm and emission at 530 nm.

Probes and primers to human B7.2 were designed to hybridize to a human B7.2 sequence, using published sequence information (GenBank accession number U04343.1.1, incorporated herein as SEQ ID NO:295). For human B7.2 the PCR primers were:
forward primer: TGTTTCATTCCCTGATGTTACGA (SEQ ID NO: 445)
reverse primer: AAAAGCCGCGTCTTGTCAGT (SEQ ID NO: 446) and the
PCR probe was: FAM-CAATATGACCATCTTCTGTAT-TCTGGA-TAMRA (SEQ ID NO: 447) where FAM is the fluorescent dye and TAMRA is the quencher dye. For human GAPDH the PCR primers were:
forward primer: GAAGGTGAAGGTCGGAGTC(SEQ ID NO:448)
reverse primer: GAAGATGGTGATGGGATTTC (SEQ ID NO:449) and the
PCR probe was: 5' JOE-CAAGCTTCCCGTTCTCAGCC-TAMRA 3' (SEQ ID NO: 450) where JOE is the fluorescent reporter dye and TAMRA is the quencher dye.

Example 29

Oligonucleotides Targeted to Human B7.2

In accordance with the present invention, an additional series of antisense compounds was designed to target different regions of a human B7.2 RNA, using published sequences (GenBank accession number U04343.1, incorporated herein as SEQ ID NO: 295, GenBank accession number BC040261.1, incorporated herein as SEQ ID NO: 296 and GenBank accession number NT_005543.12, a portion of which is incorporated herein as SEQ ID NO: 297, GenBank accession number BI824940.1, which is incorporated herein as SEQ ID NO: 451). The compounds are shown in Table 26. "Target site" indicates the first (5'-most) nucleotide number on the particular target sequence to which the compound binds. ISIS 331931 through ISIS 332004 (SEQ ID NO: 453 through SEQ ID NO: 526), ISIS 335973 (SEQ ID NO: 544), ISIS 335978 (SEQ ID NO: 549), ISIS 335993 (SEQ ID NO: 723) and ISIS 336004 (SEQ ID NO: 574), in additional to targeting human CD86, are exact matches to CD86 sequences from various other primate species, including Cynomolgous monkey and African Green Monkey.

ISIS 331993 through 332004 (SEQ ID NOS: 515, 516, 517, 518, 519, 520, 521, 522, 523, 524, 525 and 526) are chimeric oligonucleotides 14-20 nucleotides in length, composed of varying combinations of 2'-deoxynucleotides and 2'-MOE nucleotides. The 2'-MOE modifications are at nucleobases 11-18 in 331993; 13-18 in 331994 and 331997; 1-4 and 15-18 in 331995 and 331996; 13-16 in 331998; 1-3 and 14-16 in 331999 and 332000; 1-2 and 13-14 in 332001 and 332002; and 11-20 in 332003 and 332004. The internucleoside (backbone) linkages are phosphorothioate (P=S) throughout the oligonucleotide. All cytidine residues are 5-methylcytidines.

ISIS 336088 through 336096 (SEQ ID NOs: 655, 656, 657, 658, 659, 660, 661, 662 and 663) are 20 nucleotides in length, composed of 2'-MOE nucleotides. The internucleoside (backbone) linkages are phosphorothioate (P=S) throughout the oligonucleotide. All cytidine residues are 5-methylcytidines.

ISIS 336098, 336101 and 336104 (SEQ ID NOs: 664, 665 and 666, respectively) are 20 to 21 nucleotides in length, composed of 2'deoxynucleotides. The internucleoside (backbone) linkages are phosphorophosphate throughout the nucleotdide. All cytidine residues are 5-methylcytidines.

The remaining compounds in Table 26 and ISIS 129686 (CGTTATTAACCTCCGTTGAA, SEQ ID NO: 452) are chimeric oligonucleotides ("gapmers") 20 nucleotides in length, composed of a central "gap" region consisting of ten 2'-deoxynucleotides, which is flanked on both sides (5' and 3' directions) by five-nucleotide "wings". The wings are composed of 2'-MOE nucleotides. The internucleoside (backbone) linkages are phosphorothioate (P=S) throughout the oligonucleotide. All cytidine residues are 5-methylcytidines.

The compounds were analyzed for their effect on human B7.2 mRNA levels in THP-1 cells. THP-1 cells were electroporated in 1 mm cuvettes at a density of $1 \times 10^7$ cells/mL, a voltage of 75V and pulse length of 6 ms, in the presense of 10 ΦM oligonucleotide. Cells were immediately treated with 1 Φg/ml LPS and 0.5 mM dbcAMP, as described in other examples herein. Target mRNA was measured by quantitative real-time PCR as described in other examples herein. ISIS 129686 (SEQ ID NO: 452) was used as a scrambled control oligonucleotide. Data are averages from two experiments and are shown in Table 26. If present, "N.D." indicates "no data".

TABLE 26

Inhibition of human B7.2 mRNA levels by oligonucleotides

| ISIS # | Sequence | SEQ ID NO | % Inhib | GenBank Accession Target | Target Site | Region |
|---|---|---|---|---|---|---|
| 331931 | CAGTCCCATAGTGCACTGGG | 453 | 77 | BC040261.1 | 124 | Coding |
| 331932 | ACTCAGTCCCATAGTGCACT | 454 | 70 | BC040261.1 | 127 | Coding |
| 331933 | TTGAAATAAGCTTGAATCTT | 455 | 37 | BC040261.1 | 195 | Coding |
| 331934 | CATTGAAATAAGCTTGAATC | 456 | 46 | BC040261.1 | 197 | Coding |
| 331935 | CTCATTGAAATAAGCTTGAA | 457 | 56 | BC040261.1 | 199 | Coding |
| 331936 | TGCAGTCTCATTGAAATAAG | 458 | 60 | BC040261.1 | 205 | Coding |
| 331937 | TCTGCAGTCTCATTGAAATA | 459 | 32 | BC040261.1 | 207 | Coding |
| 331938 | GGCAGGTCTGCATTCTCATT | 460 | 83 | BC040261.1 | 213 | Coding |

TABLE 26-continued

Inhibition of human B7.2 mRNA levels by oligonucleotides

| ISIS # | Sequence | SEQ ID NO | % Inhib | GenBank Accession Target | Target Site | Region |
|---|---|---|---|---|---|---|
| 331939 | CATGGCAGGTCTGCAGTCTC | 461 | 74 | BC040261.1 | 216 | Coding |
| 331940 | AATTGGCATGGCAGGTCTGC | 462 | 82 | BC040261.1 | 222 | Coding |
| 331941 | GCAAATTGGCATGGCAGGTC | 463 | 89 | BC040261.1 | 225 | Coding |
| 331942 | TTTGCAAATTGGCATGGCAG | 464 | 60 | BC040261.1 | 228 | Coding |
| 331943 | GAGTTTGCAAATTGGCATGG | 465 | 66 | BC040261.1 | 231 | Coding |
| 331944 | TGAGAGTTTGCAAATTGGCA | 466 | 77 | BC040261.1 | 234 | Coding |
| 331945 | TTTTGAGAGTTTGCAAATTG | 467 | 32 | BC040261.1 | 237 | Coding |
| 331946 | GGTTTTGAGAGTTTGCAAAT | 468 | 63 | BC040261.1 | 239 | Coding |
| 331947 | CCAAATACTACTAGCTCAC | 469 | 75 | BC040261.1 | 268 | Coding |
| 331948 | TAAGTATACCTCATTCAGAA | 470 | 41 | BC040261.1 | 307 | Coding |
| 331949 | TTTGCCTAAGTATACCTCAT | 471 | 85 | BC040261.1 | 313 | Coding |
| 331950 | AATTTCTCTTTGCCTAAGTA | 472 | 47 | BC040261.1 | 321 | Coding |
| 331951 | TCAAATTTCTCTTTGCCTAA | 473 | 45 | BC040261.1 | 324 | Coding |
| 331952 | GTGCGGCCCATATACTTGGA | 474 | 77 | BC040261.1 | 354 | Coding |
| 331953 | AAACTTGTGCGGCCCATATA | 475 | 61 | BC040261.1 | 360 | Coding |
| 331954 | ATGATACATTGATACAAGCC | 476 | 71 | BC040261.1 | 432 | Coding |
| 331955 | AGTTAGCAAGCACTGACAGT | 477 | 36 | BC040261.1 | 503 | Coding |
| 331956 | AGGTTGACTGAAGTTAGCAA | 478 | 56 | BC040261.1 | 514 | Coding |
| 331957 | TTTCAGGTTGACTGAAGTTA | 479 | 54 | BC040261.1 | 518 | Coding |
| 331958 | CGTGTATAGATGAGCAGGTC | 480 | 64 | BC040261.1 | 581 | Coding |
| 331959 | TAACCGTGTATAGATGAGCA | 481 | 63 | BC040261.1 | 585 | Coding |
| 331960 | TCTGGGTAACCGTGTATAGA | 482 | 75 | BC040261.1 | 591 | Coding |
| 331961 | TTGGTTCTTAGCAAAACACT | 483 | 56 | BC040261.1 | 624 | Coding |
| 331962 | TGAATTCTTGGTTCTTAGCA | 484 | 57 | BC040261.1 | 631 | Coding |
| 331963 | CTCGATAGTTGAATTCTTGG | 485 | 37 | BC040261.1 | 640 | Coding |
| 331964 | ATACTCGATAGTTGAATTCT | 486 | 33 | BC040261.1 | 643 | Coding |
| 331965 | ATCATACTCGATAGTTGAAT | 487 | 72 | BC040261.1 | 646 | Coding |
| 331966 | GTGACATTATCTTGAGATTT | 488 | 70 | BC040261.1 | 678 | Coding |
| 331967 | GGTCCTCAAGCTCTATAGAG | 489 | 25 | BC040261.1 | 812 | Coding |
| 331968 | GAGGGTCCTCAAGCTCTATA | 490 | 74 | BC040261.1 | 815 | Coding |
| 331969 | CTGAGGGTCCTCAAGCTCTA | 491 | 66 | BC040261.1 | 817 | Coding |
| 331970 | GGCTGAGGGTCCTCAAGCTC | 492 | 71 | BC040261.1 | 819 | Coding |
| 331971 | TTCCATAGAATTAGACAGAA | 493 | 55 | BC040261.1 | 903 | Coding |
| 331972 | ATTTCCATAGAATTAGACAG | 494 | 31 | BC040261.1 | 905 | Coding |
| 331973 | TCTTCCATTTCCATAGAATT | 495 | 42 | BC040261.1 | 911 | Coding |
| 331974 | CACATTTATAAGAGTTGCGA | 496 | 28 | BC040261.1 | 944 | Coding |
| 331975 | TCCACATTTATAAGAGTTGC | 497 | 67 | BC040261.1 | 946 | Coding |

TABLE 26-continued

Inhibition of human B7.2 mRNA levels by oligonucleotides

| ISIS # | Sequence | SEQ ID NO | % Inhib | GenBank Accession Target | Target Site | Region |
|---|---|---|---|---|---|---|
| 331976 | GTTCCACATTTATAAGAGTT | 498 | 36 | BC040261.1 | 948 | Coding |
| 331977 | GTGTTGGTTCCACATTTATA | 499 | 22 | BC040261.1 | 954 | Coding |
| 331978 | CATTGTGTTGGTTCCACATT | 500 | 38 | BC040261.1 | 958 | Coding |
| 331979 | TCCATTGTGTTGGTTCCACA | 501 | 76 | BC040261.1 | 960 | Coding |
| 331980 | TGTTCACTCTCTTCCCTCTC | 502 | 70 | BC040261.1 | 978 | Coding |
| 331981 | TGAATACTTGTATGGGCTTT | 503 | 62 | BC040261.1 | 1116 | 3' UTR |
| 331982 | GCAGCACCAGAGAGCAGGAA | 504 | 48 | BC040261.1 | 168 | Coding |
| 331983 | GCTTCTTCTTCTTCCATTTC | 505 | 32 | BC040261.1 | 920 | Coding |
| 331984 | ATAGTGCACTGGGGATCCAT | 506 | 38 | BC040261.1 | 117 | Start Codon |
| 331985 | GCCCATATACTTGGAATGAA | 507 | 84 | BC040261.1 | 349 | Coding |
| 331986 | GGCCCATATACTTGGAATGA | 508 | 61 | BC040261.1 | 350 | Coding |
| 331987 | CGGCCCATATACTTGGAATG | 509 | 69 | BC040261.1 | 351 | Coding |
| 331988 | GCGGCCCATATACTTGGAAT | 510 | 49 | BC040261.1 | 352 | Coding |
| 331989 | TGCGGCCCATATACTTGGAA | 511 | 74 | BC040261.1 | 353 | Coding |
| 331990 | TATCACTTTTGTCGCATGAA | 512 | 71 | BC040261.1 | 1076 | Coding |
| 331991 | GTATCACTTTTGTCGCATGA | 513 | 38 | BC040261.1 | 1077 | Coding |
| 331992 | TGTATCACTTTTGTCGCATG | 514 | 87 | BC040261.1 | 1078 | Coding |
| 331993 | CGGCCCATATACTTGGAA | 515 | 52 | 5C040261.1 | 353 | Coding |
| 331994 | TATCACTTTTGTCGCATG | 516 | 80 | BC040261.1 | 1078 | Coding |
| 331995 | CCATATACTTGGAATGAA | 517 | 75 | BC040261.1 | 349 | Coding |
| 331996 | TCACTTTTGTCGCATGAA | 518 | 90 | BC040261.1 | 1076 | Coding |
| 331997 | GCCCATATACTTGGAA | 519 | 46 | BC040261.1 | 353 | Coding |
| 331998 | TCACTTTTGTCGCATG | 520 | 46 | BC040261.1 | 1078 | Coding |
| 331999 | CATATACTTGGAATGA | 521 | 10 | BC040261.1 | 350 | Coding |
| 332000 | CACTTTTGTCGCATGA | 522 | 80 | BC040261.1 | 1077 | Coding |
| 332001 | ATATACTTGGAATG | 523 | 0 | BC040261.1 | 351 | Coding |
| 332002 | ACTTTTGTCGCATG | 524 | 33 | BC040261.1 | 1078 | Coding |
| 332003 | TGCGGCCCATATACTTGGAA | 525 | 43 | BC040261.1 | 353 | Coding |
| 332004 | TGTATCACTTTTGTCGCATG | 526 | 74 | BC040261.1 | 1078 | Coding |
| 335956 | CAAAAGGAGTATTTGCGAGC | 527 | 20 | U04343.1 | 24 | 5' UTR |
| 335957 | AACCAAAAGGAGTATTTGCG | 528 | 14 | U04343.1 | 27 | 5' UTR |
| 335958 | CAAGGTGGTAAGAATAAACC | 529 | 15 | U04343.1 | 43 | 5' UTR |
| 335959 | GAACACAGAAGCAAGGTGGT | 530 | 26 | U04343.1 | 54 | 5' UTR |
| 335960 | AGCATTCCCAAGGAACACAG | 531 | 17 | U04343.1 | 66 | 5' UTR |
| 335961 | CACAGCAGCATTCCCAAGGA | 532 | 25 | U04343.1 | 72 | 5' UTR |
| 335962 | AAGAGACCAGATGCATAAGC | 533 | 10 | U04343.1 | 91 | 5' UTR |
| 335963 | AGAAGCAAAGCTTTCACCCT | 534 | 51 | BC040261.1 | 14 | 5' UTR |
| 335964 | CAGCAGAGAAGCAAAGCTTT | 535 | 46 | BC040261.1 | 20 | 5' UTR |

TABLE 26-continued

Inhibition of human B7.2 mRNA levels by oligonucleotides

| ISIS # | Sequence | SEQ ID NO | % Inhib | GenBank Accession Target | Target Site | Region |
|---|---|---|---|---|---|---|
| 335965 | TTACAGCAGCAGAGAAGCAA | 536 | 20 | BC040261.1 | 26 | 5' UTR |
| 335966 | ACCCCACTCATCCGTGTGTC | 537 | 86 | BC040261.1 | 60 | 5' UTR |
| 335967 | AATGACCCCACTCATCCGTG | 538 | 32 | BC040261.1 | 64 | 5' UTR |
| 335968 | GGAAATGACCCCACTCATCC | 539 | 45 | BC040261.1 | 67 | 5' UTR |
| 335969 | TCTGGAAATGACCCCACTCA | 540 | 32 | BC040261.1 | 70 | 5' UTR |
| 335970 | ATATCTGGAAATGACCCCAC | 541 | 71 | BC040261.1 | 73 | 5' UTR |
| 335971 | GACCTAATATCTGGAAATGA | 542 | 28 | BC040261.1 | 79 | 5' UTR |
| 335972 | GGGATCCAITFTGGCTGCTT | 543 | 27 | BC040261.1 | 106 | Start Codon |
| 335973 | AGGCCATCACAAAGAGAATG | 544 | 18 | BC040261.1 | 149 | Coding |
| 335974 | ATCTTCAGAGGAGCAGCACC | 545 | 36 | BC040261.1 | 180 | Coding |
| 335975 | CTTGAATCITCAGAGGAGCA | 546 | 38 | BC040261.1 | 185 | Coding |
| 335976 | AAGCTTGAATCTTCAGAGGA | 547 | 50 | BC040261.1 | 188 | Coding |
| 335977 | ATATACTTGGAATGAACACT | 548 | 19 | BC040261.1 | 345 | Coding |
| 335978 | TTTTGTGATGGATGATACAT | 549 | 17 | BC040261.1 | 443 | Coding |
| 335979 | GCTTTTTGTGATGGATGATA | 550 | 41 | BC040261.1 | 446 | Coding |
| 335980 | AAATTTATGTACACATTTTC | 551 | 58 | BC040261.1 | 561 | Coding |
| 335981 | CTTCTTAGGTTCTGGGTAAC | 552 | 35 | BC040261.1 | 601 | Coding |
| 335982 | AAAACACTCATCTTCTTAGG | 553 | 25 | BC040261.1 | 612 | Coding |
| 335983 | GCATAATACCATCATACTCG | 554 | 43 | BC040261.1 | 656 | Coding |
| 335984 | TCTGCATAATACCATCATAC | 555 | 66 | BC040261.1 | 659 | Coding |
| 335985 | GATTTTCTGCATAATACCAT | 556 | 26 | BC040261.1 | 664 | Coding |
| 335986 | CTATAGAGAAAGGTGAAGAT | 557 | 21 | BC040261.1 | 800 | Coding |
| 335987 | TCTATAGAGAAAGGTGAAGA | 558 | 10 | BC040261.1 | 801 | Coding |
| 335988 | GTAATCCAAGGAATGTGGTC | 559 | 52 | BC040261.1 | 846 | Coding |
| 335989 | GTTGCGAGGCCGCTTCTTCT | 560 | 35 | BC040261.1 | 931 | Coding |
| 335990 | TAAGAGTTGCGAGGCCGCIT | 561 | 42 | BC040261.1 | 936 | Coding |
| 335991 | AGATCTTTCAGGTATATGGA | 562 | 24 | BC040261.1 | 1018 | Coding |
| 335992 | ATCAGATCTTTCAGGTATAT | 563 | 29 | BC040261.1 | 1021 | Coding |
| 335993 | GGGTTTCATCAGATCTTTCA | 723 | 56 | BC040261.1 | 1028 | Coding |
| 335994 | CACGCTGGGTTTCATCAGAT | 564 | 43 | BC040261.1 | 1034 | Coding |
| 335995 | AAACACGCTGGGTTTCATCA | 565 | 23 | BC040261.1 | 1037 | Coding |
| 335996 | CGAACTTTTAAAAACACGCT | 566 | 62 | BC040261.1 | 1048 | Coding |
| 335997 | GTCTTCGAACTTTTAAAAAC | 567 | 79 | BC040261.1 | 1053 | Coding |
| 335998 | AGATGTCTTCGAACTTTTAA | 568 | 21 | BC040261.1 | 1057 | Coding |
| 335999 | CGCATGAAGATGTCTTCGAA | 569 | 47 | BC040261.1 | 1064 | Coding |
| 336000 | TTGTCGCATGAAGATGTCTT | 570 | 29 | BC040261.1 | 1068 | Coding |
| 336001 | AACATGTATCACTTTTGTCG | 571 | 22 | BC040261.1 | 1082 | Coding |

TABLE 26-continued

Inhibition of human B7.2 mRNA levels by oligonucleotides

| ISIS # | Sequence | SEQ ID NO | % Inhib | GenBank Accession Target | Target Site | Region |
|---|---|---|---|---|---|---|
| 336002 | AAAAACATGTATCACTTTTG | 572 | 24 | BC040261.1 | 1085 | Coding |
| 336003 | CTCTTTAATTAAAAACATGT | 573 | 21 | BC040261.1 | 1095 | Stop Codon |
| 336004 | ACTTACAAAGGAAAGGGTAG | 574 | 16 | BC040261.1 | 1142 | 3' UTR |
| 336005 | TTGCCCAGGAACTTACAAAG | 575 | 31 | BC040261.1 | 1152 | 3' UTR |
| 336006 | GCCTTCTGGAAGAAATCAAA | 576 | 66 | BC040261.1 | 1176 | 3' UTR |
| 336007 | TGGGCTTGGCCCATAAGTGT | 577 | 26 | BC040261.1 | 1331 | 3' UTR |
| 336008 | AGCCATTAAGCTGGGCTTGG | 578 | 30 | BC040261.1 | 1342 | 3' UTR |
| 336009 | TTATTTCCAGGTCATGAGCC | 579 | 69 | BC040261.1 | 1358 | 3' UTR |
| 336010 | AAGAATCTGATCTGGAGGAG | 580 | 52 | BC040261.1 | 1394 | 3' UTR |
| 336011 | GATAAAAGGCAGTTTTCCAG | 581 | 22 | BC040261.1 | 1462 | 3' UTR |
| 336012 | TGGGCAGATAAAAGGCAGTT | 582 | 39 | BC040261.1 | 1468 | 3' UTR |
| 336013 | GCACCAGCTTAGAATTCTGG | 583 | 48 | BC040261.1 | 1485 | 3' UTR |
| 336014 | CCCACCCAGACTGAGGAGGT | 584 | 44 | BC040261.1 | 1540 | 3' UTR |
| 336015 | TATTAACACTATAAGGTCAT | 585 | 2 | BC040261.1 | 1572 | 3' UTR |
| 336016 | TAGATCTCTATGTTTCAAGA | 586 | 38 | BC040261.1 | 1592 | 3' UTR |
| 336017 | ACTATTACAGTACATAGATC | 587 | 47 | BC040261.1 | 1606 | 3' UTR |
| 336018 | AGAGCATAGTAATCACACTA | 588 | 43 | BC040261.1 | 1622 | 3' UTR |
| 336019 | TCTCTAGAGCATAGTAATCA | 589 | 39 | BC040261.1 | 1627 | 3' UTR |
| 336020 | TGACAGAGGGATGAGAACTC | 590 | 43 | BC040261.1 | 1666 | 3' UTR |
| 336021 | TTTCCTTACTGACCCTGACA | 591 | 34 | BC040261.1 | 1681 | 3' UTR |
| 336022 | AGGCCACCGTTTTCCTTACT | 592 | 65 | BC040261.1 | 1691 | 3' UTR |
| 336023 | TTGGTCTGCTCATTGTTGCC | 593 | 48 | BC040261.1 | 1719 | 3' UTR |
| 336024 | CAGCCCAGATAGAAGTGGCT | 594 | 39 | BC040261.1 | 1781 | 3' UTR |
| 336025 | AGCAACAGCCCAGATAGAAG | 595 | 17 | BC040261.1 | 1786 | 3' UTR |
| 336026 | AGTTCTTCAAGAGAAACAGG | 596 | 1 | BC040261.1 | 1886 | 3' UTR |
| 336027 | TAGTCAGTTCTTCAAGAGAA | 597 | 3 | BC040261.1 | 1891 | 3' UTR |
| 336028 | TGTTTCAAGACTTGTTGATG | 598 | 0 | BC040261.1 | 2034 | 3' UTR |
| 336029 | GTTGCTTGTTTCAAGACTTG | 599 | 27 | BC040261.1 | 2040 | 3' UTR |
| 336030 | CTTGGGTATCACCAAAACCC | 600 | 39 | BC040261.1 | 2121 | 3' UTR |
| 336031 | CCCAGCTCTGCTTCCAGGAA | 601 | 45 | BC040261.1 | 2157 | 3' UTR |
| 336032 | CTCTCAGCCAGGAGTGGAAA | 602 | 0 | BC040261.1 | 2228 | 3' UTR |
| 336033 | AATTGCTAGCCCTATGCTG | 603 | 34 | BC040261.1 | 2340 | 3' UTR |
| 336034 | GAGCCAGGTTTTCAAAGTCA | 604 | 59 | BC040261.1 | 2433 | 3' UTR |
| 336035 | GATCCCACCTTAGAGCCAGG | 605 | 73 | BC040261.1 | 2445 | 3' UTR |
| 336036 | CCTTAGTGATCCCACCTTAG | 606 | 49 | BC040261.1 | 2452 | 3' UTR |
| 336037 | CATCCCTTAGTGATCCCACC | 607 | 61 | BC040261.1 | 2456 | 3' UTR |
| 336038 | ATGGGAATATTACATGGACA | 608 | 39 | BC040261.1 | 2587 | 3' UTR |
| 336039 | CTAGCCAGGTGCTAGGAGTC | 609 | 50 | BC040261.1 | 2634 | 3' UTR |

TABLE 26-continued

Inhibition of human B7.2 mRNA levels by oligonucleotides

| ISIS # | Sequence | SEQ ID NO | % Inhib | GenBank Accession | Target Site | Region |
|---|---|---|---|---|---|---|
| 336040 | AAACTAGCCAGGTGCTAGGA | 610 | 53 | BC040261.1 | 2637 | 3' UTR |
| 336041 | TTAGAAACTAGCCAGGTGCT | 611 | 50 | BC040261.1 | 2642 | 3' UTR |
| 336042 | AACATGTTAGAAACTAGCCA | 612 | 49 | BC040261.1 | 2647 | 3' UTR |
| 336043 | CCAGACAAATCATTTTGAAC | 613 | 0 | NT_005543.12 | 245 | intron |
| 336044 | CAGAGAAGCAAAGCTTTCAC | 614 | 49 | NT_005543.12 | 1017 | Coding |
| 336045 | AGCAGCAGAGAAGCAAAGCT | 615 | 23 | NT_005543.12 | 1022 | Coding |
| 336046 | AAGAATTATTACTCACCACT | 616 | 33 | NT_005543.12 | 1127 | exon:intron |
| 335047 | CCCTCTATGGTACCACAAAA | 617 | 64 | NT_005543.12 | 2463 | intron |
| 336048 | GAACAGACATTGTTTAATGG | 618 | 31 | NT_005543.12 | 2610 | intron |
| 336049 | TCTTAGCAAGATAGAGGGTT | 619 | 22 | NT_005543.12 | 2730 | intron |
| 336050 | AGCACAACAATTGTCTTGGA | 620 | 61 | NT_005543.12 | 5446 | intron |
| 336051 | GGTTGTGAGGAAAGAATCTG | 621 | 9 | NT_005543.12 | 5561 | intron |
| 336052 | TCTGGTCTGGATGGTGCAGA | 622 | 30 | NT_005543.12 | 9759 | intron |
| 336053 | TCAATCAAGAGGTAACTACT | 623 | 26 | NT_005543.12 | 9923 | intron |
| 336054 | CCTGCTCAGCAGAGCAATGT | 624 | 15 | NT_005543.12 | 10002 | intron |
| 336055 | TCTTGAAATATAAGACTTGG | 625 | 4 | NT_005543.12 | 10252 | intron |
| 336056 | CTGAACCTCTGATGCATTAA | 626 | 0 | NT_005543.12 | 10379 | intron |
| 336057 | TCGCTCTGACTCACTAAAGC | 627 | 30 | NT_005543.12 | 10455 | intron |
| 336058 | AAAGCTCTTAGATTCAAGCA | 628 | 27 | NT_005543.12 | 11268 | intron |
| 336059 | AATCTCAGAACTTCTTCTGA | 629 | 38 | NT_005543.12 | 14386 | intron |
| 336060 | TAAGTATAGCCTTCAGATGT | 630 | 0 | NT_005543.12 | 15560 | intron |
| 336061 | ATTTGCTTATATTAAAAGGT | 631 | 23 | NT_005543.12 | 15656 | intron |
| 33T062 | GATTCTACAAGTGAATGCAG | 632 | 13 | NT_005543.12 | 15756 | intron |
| 336063 | GTTCCACAAAGGGAGTAGAT | 633 | 57 | NT_005543.12 | 16658 | intron |
| 336064 | CACAGTTCCTGAATTATTCT | 634 | 42 | NT_005543.12 | 19375 | intron |
| 336065 | TGCAGGAAAGGAAGGAGACT | 635 | 34 | NT_005543.12 | 19577 | intron |
| 336066 | AAAGCCCATGGAAGAGATGA | 636 | 29 | NT_005543.12 | 19972 | intron |
| 336067 | TACCAGAACATATTATTTTA | 637 | 22 | NT_005543.12 | 21030 | intron |
| 336068 | AGGCCATGTGCTTCACTTCT | 638 | 29 | NT_005543.12 | 23119 | intron |
| 336069 | CCTTCCCTGACAGATTCCCA | 639 | 11 | NT_005543.12 | 23275 | intron |
| 336070 | TGCACCAGTCCTACCCTGCT | 640 | 42 | NT_005543.12 | 25661 | intron |
| 336071 | GTGCTAAGTAGGTGAAGGGC | 641 | 27 | NT_005543.12 | 29098 | intron |
| 336072 | CTATCTCATACATTTGAAAA | 642 | 0 | NT_005543.12 | 33910 | intron |
| 336073 | ATAGATCATGGTACTAAATG | 643 | 0 | NT_005543.12 | 35788 | intron |
| 336074 | GATCTGGCTGCTAAAGTCTC | 644 | 24 | NT_005543.12 | 36943 | intron |
| 336075 | CCCATAGTGCTAGAGTCGAG | 645 | 55 | NT_005543.12 | 37217 | intron:exon |
| 336076 | TATGATGATTATACAATGAC | 646 | 0 | NT_005543.12 | 39043 | intron |

TABLE 26-continued

Inhibition of human B7.2 mRNA levels by oligonucleotides

| ISIS # | Sequence | SEQ ID NO | % Inhib | GenBank Accession Target | Target Site | Region |
|---|---|---|---|---|---|---|
| 336077 | AGTTGTGCGGACTGGTGACA | 647 | 0 | NT_005543.12 | 45144 | intron |
| 336078 | AGTAATCATGCTGAAGAATA | 648 | 5 | NT_005543.12 | 49023 | intron |
| 336079 | ATGTGGGTGTCAAGGTCAGC | 649 | 27 | NT_005543.12 | 53243 | intron |
| 336080 | AAAGTCCCAGGCTCAGGGCC | 650 | 25 | NT_005543.12 | 54727 | intron |
| 336081 | ATGTCGCCTTTCTTTGAAGT | 651 | 29 | NT_005543.12 | 55223 | intron |
| 336082 | TGTGTTGGTTCCTGAAAGAC | 652 | 6 | NT_005543.12 | 63666 | intron:exon |
| 336083 | TGGTCTCTGCTCTTCATAGG | 653 | 53 | NT_005543.12 | 64347 | intron |
| 336084 | AAGCCTTCCATCCCATACCT | 654 | 0 | NT_005543.12 | 20 | intron |
| 336088 | TATTACTCACCACTGGGGAT | 655 | N.D | NT_005543.12 | 1121 | exon:intron |
| 336089 | ACAAACATACCTGTCACAAA | 656 | N.D | NT_005543.12 | 23663 | exon:intron |
| 336090 | CCGTACCTCCTAAGGCTCCT | 657 | N.D | U04343.1 | 1 | 5' UTR |
| 336091 | TACGGGGCGTACAGCCTGC | 658 | N.D | BI824940.1 | 1 | 5' UTR |
| 336092 | TTGGCTGCTTCTGCTGTGAC | 659 | N.D | BC040261.1 | 96 | 5' UTR |
| 336093 | TGTCCACTGTAGCTCCAAAA | 660 | N.D | U04343.1 | 110 | 5' UTR |
| 336094 | TCACCCTGTGCAAGCCTTCC | 661 | N.D | BC040261.1 | 1 | 5' UTR |
| 336095 | CCTAAATTTTATTTCCAGGT | 662 | N.D | U04343.1 | 1379 | 3' UTR |
| 336096 | ACAAGCATTTATTAAAAACT | 663 | N.D | BC040261.1 | 2678 | 3' UTR |
| 336098 | GACCCCACTCATCCGTGTGT | 664 | N.D | BC040261.1 | 61 | 5' UTR |
| 336101 | GCATAAGCACAGCAGCATTCC | 665 | N.D | U04343.1 | 78 | 5' UTR |
| 336104 | ACCAGAGAGCAGGAAGGCC | 666 | N.D | U04343.1 | 177 | Coding |

In one embodiment, the antisense compound is targeted to nucleobases 195-537 of a coding region of a nucleic acid encoding human B7.2 (SEQ ID NO: 296).

Example 30

Antisense Inhibition of Human B7.2 Expression: Dose Response

In accordance with the present invention, several oligonucleotides were tested in a dose response study. ISIS 323624 (SEQ ID NO: 374), ISIS 323641 (SEQ ID NO: 391), ISIS 323690 (SEQ ID NO: 440), ISIS 331941 (SEQ ID NO: 463), ISIS 331949 (SEQ ID NO: 471), ISIS 331985 (SEQ ID NO: 507), ISIS 331992 (SEQ ID NO: 514), ISIS 331996 (SEQ ID NO: 518) were identified as oligonucleotides with good activity based on the results in Examples 27 and 29.

ISIS 13650 (TCCCGCCTGTGACATGCATT, SEQ ID NO: 667) and ISIS 129700 (TAGTGCGGACCTAC-CCACGA, SEQ ID NO: 668), used as control oligonucleotides, are chimeric oligonucleotides ("gapmers") 20 nucleotides in length, composed of a central "gap" region consisting of ten 2'-deoxynucleotides, which is flanked on both sides (5' and 3' directions) by five-nucleotide "wings". The wings are composed of 2'-MOE nucleotides. The internucleoside (backbone) linkages are phosphorothioate (P=S) throughout the oligonucleotide. All cytidine residues are 5-methylcytidines.

Cells were electroporated in 1 mm cuvettes at a density of $1 \times 10^7$ cells/ml, a voltage of 75 V and a pulse length of 6 ms with an oligonucleotide dose of 2.5, 5, 10 or 20 uM. After electroporation, cells wer treated with 1 ug/ml LPS and 0.5 mM dbcAMP for 16 hours to induce B7-2 expression. Control cells were stimulated with 1 ug/ml LPS and 0.5 mM dbcAMP, but not treated with oligonucleotides.

Target mRNA levels were determined by quantitative real-time PCR as described in other examples herein, using two different primer-probe sets to confirm the results of the antisense igonucleotide treatment. The first primer probe set was 1608, consisting of a forward primer (SEQ ID NO: 445), reverse primer (SEQ ID NO: 446) and probe (SEQ ID NO: 447) described in Example 28. The second primer probe set was #1770, consisting of CGCATCCACCAGATGAAT-TCT (forward primer, SEQ ID NO: 669), AATTGGTAC-TATTTCAGGTTGACTGAAG (reverse primer, SEQ ID NO: 670) and AACTGTCAGTGCTTGCT (probe, SEQ ID NO: 671). The data are the average of two experiments and are presented in Table 27. The percent inhibition is expressed relative to the LPS/dbcAMP-stimulated cells that were not exposed to oligonucleotides.

The results demonstrate that the oligonucleotides of the present invention, unlike the control oligonucleotides, inhibit the expression of B7-2 in a dose-dependent manner.

TABLE 27

Antisense inhibition of B7-2 mRNA expression: dose response

% Inhibition of B7-2 mRNA
Primer-Probe set

| | 1680 | | | | 1770 | | | |
|---|---|---|---|---|---|---|---|---|
| | Dose of oligonucleotide | | | | | | | |
| ISIS # | 2.5 uM | 5 uM | 10 uM | 20 uM | 2.5 uM | 5 uM | 10 uM | 20 uM |
| 323624 | 5 | 17 | 41 | 63 | 9 | 22 | 47 | 62 |
| 323641 | 23 | 55 | 74 | 89 | 31 | 59 | 73 | 88 |
| 323690 | 38 | 55 | 71 | 84 | 35 | 58 | 71 | 84 |
| 331941 | 63 | 75 | 87 | 87 | 63 | 76 | 86 | 87 |
| 331949 | 27 | 41 | 63 | 77 | 26 | 45 | 65 | 76 |
| 331985 | 26 | 46 | 62 | 82 | 28 | 49 | 64 | 82 |
| 331992 | 48 | 62 | 79 | 88 | 50 | 65 | 79 | 87 |
| 331996 | 44 | 57 | 80 | 88 | 44 | 59 | 80 | 88 |
| 13650 | 0 | 4 | 4 | 3 | 0 | 8 | 8 | 7 |
| 129700 | 0 | 9 | 0 | 13 | 0 | 1 | 0 | 3 |

Example 31

Inhibition of B7-2 Protein Expression by Antisense Oligonucleotide Treatment: Dose Response In accordance with the present invention, the effects of antisense oligonucleotide treatment on cell surface expression of B7-2 was evaluated in THP-1 cells. The cell surface expression of B7-1 was also measured as a test of the specificity of the B7-2 antisense oligonucleotides.

The oligonucleotides used for this study were ISIS 22300 (SEQ ID NO: 190), ISIS 113131 (SEQ ID NO: 255), ISIS 323641 (SEQ ID NO: 391), ISIS 323643 (SEQ ID NO: 393), ISIS 323653 (SEQ ID NO: 403), ISIS 323660 (SEQ ID NO: 410), ISIS 323661 (SEQ ID NO: 411), ISIS 323675 (SEQ ID NO: 425), ISIS 323690 (SEQ ID NO: 440). ISIS 115675 (SEQ ID NO: 672) and ISIS 129690 (SEQ ID NO: 673), used as control oligonucleotides, are chimeric oligonucleotides ("gapmers") 20 nucleotides in length, composed of a central "gap" region consisting of ten 2'-deoxynucleotides, which is flanked on both sides (5' and 3' directions) by five-nucleotide "wings". The wings are composed of 2'-MOE nucleotides. The internucleoside (backbone) linkages are phosphorothioate (P=S) throughout the oligonucleotide. All cytidine residues are 5-methylcytidines.

THP-1 cells were electroporated in the presence of 2.5, 10, or 20 uM of antisense or control oligonucleotides. The cells were immediately treated with 1 ug/ml LPS and 0.5 mM dbcAMP for 42 hours to induce B7-2 expression. Control cells were stimulated with 1 ug/ml LPS and dbcAMP, but not exposed to oligonucleotides. Cells were harvested by brief trpsinization, washed with PBS, the resuspended in 100 uL of staining buffer (PBS, 0.2% BSA) containing both 10 uL of FITC-conjugated anti-B7-2 antibody (FITC-anti-hCD86; FITC:fluorescien isothiocyanate; BD Biosciences, San Jose, Calif.) and 10 ul of PE-conjugated anti-B7-1 antibody (PE: phycoerythrin; PE-anti-hCD80, BD Biosciences, San Jose, Calif.). The cells were stained for 30 minutes at 4° C., washed with PBS, resuspended in 300 uL PBS containing 0.5% paraformaldehyde. Measurements of mean fluorescence activity were made by flow cytometry using the FL-1 and FL-2 channels of a BD Bioscience FACScan (BD Biosciences, San Jose, Calif.). With this method, both B7-2 and B7-1 protein expression on the surface of the same cell was measured. The data are the average of two electroporation experiments and are presented in Table 28. The dat are expressed as percent inhibition of protein expression relative to LPS/dbcAMP-stimulated cells that were not exposed to oligonucleotides. The data illustrate that the oligonucleotides of the present invention can reduce cell surface expression of B7-2 protein in a dose dependent manner. Furthermore, the antisense inhibition is specific to B7-2, as the cell surface expression of B7-1 is not reduced.

TABLE 28

Inhibition of cell surface B7-2 protein expression with antisense oligonucleotide treatment: dose response

| | % Inhibition of B7-2 expression | | | % Inhibition of B7-1 expression | | |
|---|---|---|---|---|---|---|
| | Dose of oligonucleotide | | | | | |
| ISIS # | 2.5 uM | 10 uM | 20 uM | 2.5 uM | 10 uM | 20 uM |
| 22300 | 2 | 46 | 63 | 0 | 0 | 0 |
| 113131 | 31 | 73 | 83 | 0 | 0 | 0 |
| 323641 | 53 | 85 | 92 | 0 | 0 | 0 |
| 323643 | 16 | 79 | 90 | 0 | 0 | 0 |
| 323653 | 29 | 62 | 83 | 0 | 0 | 0 |
| 323660 | 25 | 74 | 84 | 18 | 0 | 0 |
| 323661 | 38 | 72 | 80 | 9 | 0 | 0 |
| 323675 | 9 | 46 | 72 | 0 | 0 | 0 |
| 323690 | 46 | 85 | 92 | 0 | 0 | 0 |
| 115675 | 0 | 2 | 29 | 0 | 0 | 0 |
| 129690 | 0 | 15 | 0 | 0 | 0 | 0 |

Example 32

Double Stranded RNAs Targeted to B7.2

In a further embodiment of the present invention, a series of blunt-ended nucleic acid duplexes comprising the antisense compounds of the present invention and their complements was designed to target human B7-2 as described in Example 25, using published sequences (GenBank accession number U04343.1, incorporated herein as SEQ ID NO: 295, GenBank accession number BC040261.1, incorporated herein as SEQ ID NO: 296 and GenBank accession number NT_005612.13, a portion of which is incorporated herein as SEQ ID NO: 674, GenBank accession number L25259.1, which is incorporated herein as SEQ ID NO: 675). The sequences of the antisense strands are listed in Table 29 The sense strand of the dsRNA was designed and synthesized as the complement of the antisense strand, making both strands of the dsRNA duplex complementary over the entire length of the oligomeric compound. Target sites are indicated by the first (5' most) nucleotide number, as given in the sequence source reference (indicated by GenBank accession number) to which the oligonucleotide binds. All compounds in Table 29 are oligoribonucleotides, 20 nucleotides in length with phosphodiester internucleoside linkages (backbones) throughout.

RNA strands of the duplex are synthesized by methods disclosed herein or purchased from Dharmacon Research Inc., (Lafayette, Colo.). Once synthesized, the complementary strands are annealed. The single strands are aliquoted and diluted to a concentration of 50 uM. Once diluted, 30 uL of each strand is combined with 15 uL of a 5× solution of annealing buffer. The final concentration of said buffer is 100 mM potassium acetate, 30 mM HEPES-KOH pH 7.4, and 2 mM magnesium acetate. The final volume is 75 uL. This solution is incubated for 1 minute at 90° C. and then centrifuged for 15 seconds. The tube is allowed to sit for 1 hour at 37° C. at which time the dsRNA duplexes are used in experimentation. The final concentration of the dsRNA duplex is 20 uM. This solution can be stored frozen (−20° C.) and freeze-thawed up to 5 times.

Once prepared, the duplexed antisense compounds are evaluated for their ability to modulate B7-2 expression. When cells reached 80% confluency, they are treated with duplexed antisense compounds of the invention. For cells grown in 96-well plates, wells are washed once with 200 μL OPTI-MEM-1 reduced-serum medium. (Gibco BRL) and then treated with 130 μL of OPTI-MEM-1 containing 12 μg/mL LIPOFECTIN (Gibco BRL) and the desired duplex antisense compound at a final concentration of 200 nM. After 5 hours of treatment, the medium is replaced with fresh medium. Cells are harvested 16 hours after treatment, at which time RNA is isolated and target reduction measured by RT-PCR.

TABLE 29

Design of double stranded oligomeric compounds targeting human B7-2

| ISIS # | SEQUENCE | SEQ ID NO | GenBank Accession Number | Target Site | Region |
|---|---|---|---|---|---|
| 341416 | UUGUCGCAUGAAGAUGUCUU | 570 | BC040261.1 | 1068 | Coding |
| 341417 | UUGGCAUACGGAGCAGAGCU | 199 | U04343.1 | 1281 | 3' UTR |
| 341418 | GCUUGGCCCAUAAGUGUGCU | 676 | NT_005612.13 | 65758 | 3' UTR |
| 341419 | GUCAUGAGCCAUUAAGCUGG | 677 | NT_005612.13 | 65778 | 3' UTR |
| 341420 | CUGAUCUGGAGGAGGUAUUG | 678 | NT_005612.13 | 65818 | 3' UTR |
| 341421 | UCCAGAAAUUGAGAGGUCUA | 679 | NT_005612.13 | 65878 | 3' UTR |
| 341422 | GAGGUAGUUGUUUAGUCACA | 680 | NT_005612.13 | 65958 | 3' UTR |
| 341423 | ACUAUAAGGUCAUAAAUACA | 681 | NT_005612.13 | 65998 | 3' UTR |
| 341424 | CUAUGUUUCAAGAUAUUAAC | 682 | NT_005612.13 | 66018 | 3' UTR |
| 341425 | CUAUUACAGUACAUAGAUCU | 683 | NT_005612.13 | 66038 | 3' UTR |
| 341426 | UCUAGAGCAUAGUAAUCACA | 684 | NT_005612.13 | 66058 | 3' UTR |
| 341427 | GACAGAGGGAUGAGAACUCC | 685 | NT_005612.13 | 66098 | 3' UTR |
| 341428 | GUUGCCUGUACCCUAGGCCA | 686 | NT_005612.13 | 66138 | 3' UTR |
| 341429 | UUUAGGUUGGUCUGCUCAUU | 687 | NT_005612.13 | 66158 | 3' UTR |
| 341430 | GGCUCCAGGUUCUAUCUCUG | 688 | NT_005612.13 | 66198 | 3' UTR |
| 341431 | GCAACAGCCCAGAUAGAAGU | 689 | NT_005612.13 | 66218 | 3' UTR |
| 341432 | GGCAAGCCUCCUCAAUAUUA | 690 | NT_005612.13 | 66238 | 3' UTR |
| 341433 | CACUAUGGCUUGUUGGGUGG | 691 | NT_005612.13 | 66258 | 3' UTR |
| 341434 | CCUGUUUAUUCAGUUCUCUC | 692 | NT_005612.13 | 66278 | 3' UTR |
| 341435 | CCAGGCCAUCUCACUAGUCA | 693 | NT_005612.13 | 66338 | 3' UTR |
| 341436 | UUUGAGUAUUGUGAUCUCUU | 694 | NT_005612.13 | 66378 | 3' UTR |
| 341437 | UCUGUGGAUCAAGAUCUCUC | 695 | NT_005612.13 | 66418 | 3' UTR |
| 341438 | GACCAGACAUUUCAUGUAUU | 696 | NT_005612.13 | 66438 | 3' UTR |
| 341439 | CAUCUGUUGCUUGUUUCAAG | 697 | NT_005612.13 | 66478 | 3' UTR |
| 341440 | GUCCAUUUGGACAGACUAUC | 698 | NT_005612.13 | 66498 | 3' UTR |
| 341441 | GAAACUGCUGUCUGUCUUAU | 699 | NT_005612.13 | 66518 | 3' UTR |

TABLE 29-continued

Design of double stranded oligomeric compounds targeting human B7-2

| ISIS # | SEQUENCE | SEQ ID NO | GenBank Accession Number | Target Site | Region |
|---|---|---|---|---|---|
| 341442 | AUAACUUGGGUAUCACCAAA | 700 | NT_005612.13 | 66558 | 3' UTR |
| 341443 | UCCAGGAAGAUGACAUCCCA | 701 | NT_005612.13 | 66578 | 3' UTR |
| 341444 | CCCAUUAUCAAGGUGAUGGC | 702 | NT_005612.13 | 66618 | 3' UTR |
| 341445 | CUAAGCCUCCUUCCAUUCAU | 703 | NT_005612.13 | 66638 | 3' UTR |
| 341446 | UCAGCCAGGAGUGGAUAGUC | 704 | NT_005612.13 | 66658 | 3' UTR |
| 341447 | GUGUCUUGGUCUUCCUAAUU | 705 | NT_005612.13 | 66698 | 3' UTR |
| 341448 | CCGUAGGACAUCUGUAGGCU | 706 | NT_005612.13 | 66738 | 3' UTR |
| 341449 | ACUCAAAUUUGCUAGCCCUA | 707 | NT_005612.13 | 66778 | 3' UTR |
| 341450 | CAAGUUUCCUCUGGUUGCCU | 708 | NT_005612.13 | 66818 | 3' UTR |
| 341451 | GAUCCCACCUUAGAGCCAGG | 605 | BC040261.1 | 2445 | 3' UTR |
| 341452 | AUAACCCUUGAGGGUUUACA | 709 | NT_005612.13 | 66978 | 3' UTR |
| 341453 | CUUGUCUAGCAUGGCAGUCU | 710 | NT_005612.13 | 66998 | 3' UTR |
| 341454 | UGCUAGGAGUCUAAUCAAGG | 711 | NT_005612.13 | 67058 | 3' UTR |
| 341494 | UCACCCUGUGCAAGCCUUCC | 661 | BC040261.1 | 1 | 5' UTR |
| 341495 | GCAGCAGAGAAGCAAAGCUU | 712 | NT_005612.13 | 1396 | 5' UTR |
| 341496 | CUGUGCUAGUCCCUGUUACA | 713 | NT_005612.13 | 1416 | 5' UTR |
| 341497 | GACCCCACUCAUCCGUGUGU | 664 | BC040261.1 | 61 | 5' UTR |
| 341498 | GUGACCUAAUAUCUGGAAAU | 306 | BC040261.1 | 81 | 5' UTR |
| 341499 | CCAUUUGGCUGCUUCUGCU | 714 | NT_005612.13 | 1476 | 5' UTR |
| 341500 | UCCCAUAGUGCACUGGGGAU | 715 | L25259.1 | 111 | Coding |
| 341501 | AUUUGCGAGCUCCCCGUACC | 716 | NT_005612.13 | 23918 | 5' UTR |
| 341502 | AAGGAGUAUUUGCGAGCUCC | 717 | NT_005612.13 | 23925 | 5' UTR |
| 341503 | CACAGAAGCAAGGUGGUAAG | 718 | NT_005612.13 | 23955 | 5' UTR |
| 341504 | GAACACAGAAGCAAGGUGGU | 719 | U04343.1 | 54 | 5' UTR |
| 341505 | AGCACAGCAGCAUUCCCAAG | 530 | NT_005612.13 | 23978 | 5' UTR |
| 341506 | AUGCAUAAGCACAGCAGCAU | 720 | NT_005612.13 | 23985 | 5' UTR |
| 341507 | UGCCUGUCCACUGUAGCUCC | 721 | NT_005612.13 | 24018 | 5' UTR |
| 341508 | UCCCAUAGUGCUGUCACAAA | 722 | U04343.1 | 134 | Start Codon |

What is claimed is:

1. A compound comprising a chimeric gapmer oligonucleotide consisting of 20 to 50 linked nucleosides and having a nucleobase sequence comprising SEQ ID NO:463, wherein the chimeric gapmer oligonucleotide is a single-stranded oligonucleotide, and wherein said chimeric gapmer oligonucleotide is at least 90% complementary to SEQ ID NO:296 as measured over the entirety of said chimeric gapmer oligonucleotide, and wherein said chimeric gapmer oligonucleotide inhibits the expression of human B7-2 mRNA.

2. A compound comprising a chimeric gapmer oligonucleotide consisting of 20 linked nucleosides having SEQ ID NO:463, wherein the chimeric gapmer oligonucleotide comprises:
   a gap segment consisting of ten linked deoxynucleosides;
   a 5' wing segment consisting of five linked nucleosides;
   a 3' wing segment consisting of five linked nucleosides;
   wherein the gap segment is positioned between the 5' wing segment and the 3' wing segment, wherein each nucleoside of each wing segment comprises a 2'-O-methoxyethyl sugar, and wherein each internucleoside linkage of said chimeric gapmer oligonucleotide is a phosphorothioate linkage, and wherein said chimeric gapmer oligonucleotide inhibits the expression of human B7-2 mRNA.

3. The compound of claim 1, wherein at least one internucleoside linkage is a modified internucleoside linkage.

4. The compound of claim 3, wherein each internucleoside linkage is a phosphorothioate internucleoside linkage.

5. The compound of claim 1, wherein at least one nucleoside comprises a modified sugar, and wherein at least one modified sugar is a bicyclic sugar.

6. The compound of claim 1, wherein at least one nucleoside comprises a modified sugar, and wherein at least one modified sugar comprises a 2'-O-methoxyethyl or a 4'-$(CH_2)_n$-O-2' bridge, wherein n is 1 or 2.

7. The compound of claim 1, wherein at least one nucleoside comprises a modified nucleobase.

8. The compound of claim 7, wherein the modified nucleobase is a 5-methylcytosine.

9. The compound of claim 1, wherein each cytosine of said chimeric gapmer oligonucleotide is a 5-methylcytosine.

10. The compound of claim 1, wherein said chimeric gapmer oligonucleotide is at least 95% complementary to SEQ ID NO:296 as measured over the entirety of said chimeric oligonucleotide.

11. The compound of claim 1, wherein said chimeric gapmer oligonucleotide is 100% complementary to SEQ ID NO:296 as measured over the entirety of said chimeric gapmer oligonucleotide.

12. The compound of claim 2, wherein at least one nucleoside comprises a modified nucleobase.

13. The compound of claim 12, wherein the modified nucleobase is a 5-methylcytosine.

14. The compound of claim 2, wherein each cytosine of said chimeric gapmer oligonucleotide is a 5-methylcytosine.

15. The compound of claim 2, wherein the chimeric gapmer oligonucleotide is a single-stranded oligonucleotide.

* * * * *

UNITED STATES PATENT AND TRADEMARK OFFICE
CERTIFICATE OF CORRECTION

PATENT NO. : 7,960,355 B2
APPLICATION NO. : 10/558216
DATED : June 14, 2011
INVENTOR(S) : Bennett et al.

Page 1 of 1

It is certified that error appears in the above-identified patent and that said Letters Patent is hereby corrected as shown below:

On Title Page 1, in the left column, under Related U.S. Application Data at item (60), immediately following "Provisional" please add -- application No. 60/651,504, filed on May 23, 2003, provisional --.

Signed and Sealed this
Eighteenth Day of October, 2011

David J. Kappos
*Director of the United States Patent and Trademark Office*

SEQUENCE LISTING

<160> NUMBER OF SEQ ID NOS: 724

<210> SEQ ID NO 1
<211> LENGTH: 32
<212> TYPE: DNA
<213> ORGANISM: Artificial Sequence
<220> FEATURE:
<223> OTHER INFORMATION: Synthetic

<400> SEQUENCE: 1

```
gatcaggta ccaggagcct taggaggtac gg                               32

<210> SEQ ID NO 2
<211> LENGTH: 33
<212> TYPE: DNA
<213> ORGANISM: Artificial Sequence
<220> FEATURE:
<223> OTHER INFORMATION: Synthetic

<400> SEQUENCE: 2
gatagcctcg agttatttcc aggtcatgag cca                             33

<210> SEQ ID NO 3
<211> LENGTH: 20
<212> TYPE: DNA
<213> ORGANISM: Artificial Sequence
<220> FEATURE:
<223> OTHER INFORMATION: Synthetic

<400> SEQUENCE: 3
ttccaggtca tgagccatta                                            20

<210> SEQ ID NO 4
<211> LENGTH: 21
<212> TYPE: DNA
<213> ORGANISM: Artificial Sequence
<220> FEATURE:
<223> OTHER INFORMATION: Synthetic

<400> SEQUENCE: 4
cataaggtgt gctctgaagt g                                          21

<210> SEQ ID NO 5
<211> LENGTH: 20
<212> TYPE: DNA
<213> ORGANISM: Artificial Sequence
<220> FEATURE:
<223> OTHER INFORMATION: Synthetic

<400> SEQUENCE: 5
ttactcatgg taatgtcttt                                            20

<210> SEQ ID NO 6
<211> LENGTH: 20
<212> TYPE: DNA
<213> ORGANISM: Artificial Sequence
<220> FEATURE:
<223> OTHER INFORMATION: Synthetic

<400> SEQUENCE: 6
attaaaaaca tgtatcactt                                            20

<210> SEQ ID NO 7
<211> LENGTH: 21
<212> TYPE: DNA
<213> ORGANISM: Artificial Sequence
<220> FEATURE:
<223> OTHER INFORMATION: Synthetic

<400> SEQUENCE: 7
ggaacacaga agcaaggtgg t                                          21

<210> SEQ ID NO 8
<211> LENGTH: 20
<212> TYPE: DNA
<213> ORGANISM: Artificial Sequence
<220> FEATURE:
```

<223> OTHER INFORMATION: Synthetic

<400> SEQUENCE: 8
ccgtacctcc taaggctcct                                            20

<210> SEQ ID NO 9
<211> LENGTH: 20
<212> TYPE: DNA
<213> ORGANISM: Artificial Sequence
<220> FEATURE:
<223> OTHER INFORMATION: Synthetic

<400> SEQUENCE: 9
cccatagtgc tgtcacaaat                                            20

<210> SEQ ID NO 10
<211> LENGTH: 20
<212> TYPE: DNA
<213> ORGANISM: Artificial Sequence
<220> FEATURE:
<223> OTHER INFORMATION: Synthetic

<400> SEQUENCE: 10
gcacagcagc attcccaagg                                            20

<210> SEQ ID NO 11
<211> LENGTH: 20
<212> TYPE: DNA
<213> ORGANISM: Artificial Sequence
<220> FEATURE:
<223> OTHER INFORMATION: Synthetic

<400> SEQUENCE: 11
ttgcaaattg gcatggcagg                                            20

<210> SEQ ID NO 12
<211> LENGTH: 20
<212> TYPE: DNA
<213> ORGANISM: Artificial Sequence
<220> FEATURE:
<223> OTHER INFORMATION: Synthetic

<400> SEQUENCE: 12
tggtatgggc tttactcttt                                            20

<210> SEQ ID NO 13
<211> LENGTH: 20
<212> TYPE: DNA
<213> ORGANISM: Artificial Sequence
<220> FEATURE:
<223> OTHER INFORMATION: Synthetic

<400> SEQUENCE: 13
aaaaggttgc ccaggaacgg                                            20

<210> SEQ ID NO 14
<211> LENGTH: 20
<212> TYPE: DNA
<213> ORGANISM: Artificial Sequence
<220> FEATURE:
<223> OTHER INFORMATION: Synthetic

<400> SEQUENCE: 14
gggagtcctg gagcccctt                                             20

<210> SEQ ID NO 15

```
<211> LENGTH: 20
<212> TYPE: DNA
<213> ORGANISM: Artificial Sequence
<220> FEATURE:
<223> OTHER INFORMATION: Synthetic

<400> SEQUENCE: 15
ccattaagct gggcttggcc                                                     20

<210> SEQ ID NO 16
<211> LENGTH: 20
<212> TYPE: DNA
<213> ORGANISM: Artificial Sequence
<220> FEATURE:
<223> OTHER INFORMATION: Synthetic

<400> SEQUENCE: 16
tgcgagctcc ccgtacctcc                                                     20

<210> SEQ ID NO 17
<211> LENGTH: 20
<212> TYPE: DNA
<213> ORGANISM: Artificial Sequence
<220> FEATURE:
<223> OTHER INFORMATION: Synthetic
<300> PUBLICATION INFORMATION:
<310> PATENT DOCUMENT NUMBER: US 5514788
<311> PATENT FILING DATE: 1993-05-17
<312> PUBLICATION DATE: 1996-05-07

<400> SEQUENCE: 17
gcccaagctg gcatccgtca                                                     20

<210> SEQ ID NO 18
<211> LENGTH: 20
<212> TYPE: DNA
<213> ORGANISM: Artificial Sequence
<220> FEATURE:
<223> OTHER INFORMATION: Synthetic

<400> SEQUENCE: 18
ggattgccaa gcccatggtg                                                     20

<210> SEQ ID NO 19
<211> LENGTH: 20
<212> TYPE: DNA
<213> ORGANISM: Artificial Sequence
<220> FEATURE:
<223> OTHER INFORMATION: Synthetic

<400> SEQUENCE: 19
ctaagtagtg ctagccggga                                                     20

<210> SEQ ID NO 20
<211> LENGTH: 38
<212> TYPE: DNA
<213> ORGANISM: Artificial Sequence
<220> FEATURE:
<223> OTHER INFORMATION: Synthetic

<400> SEQUENCE: 20
gatcagggta ccccaaagaa aaagtgattt gtcattgc                                 38

<210> SEQ ID NO 21
<211> LENGTH: 35
<212> TYPE: DNA
<213> ORGANISM: Artificial Sequence
<220> FEATURE:
```

-continued

<223> OTHER INFORMATION: Synthetic

<400> SEQUENCE: 21
gatagcctcg aggataatga attggctgac aagac     35

<210> SEQ ID NO 22
<211> LENGTH: 20
<212> TYPE: DNA
<213> ORGANISM: Artificial Sequence
<220> FEATURE:
<223> OTHER INFORMATION: Synthetic

<400> SEQUENCE: 22
gggtaagact ccacttctga     20

<210> SEQ ID NO 23
<211> LENGTH: 20
<212> TYPE: DNA
<213> ORGANISM: Artificial Sequence
<220> FEATURE:
<223> OTHER INFORMATION: Synthetic

<400> SEQUENCE: 23
gggtctccaa aggttgtgga     20

<210> SEQ ID NO 24
<211> LENGTH: 20
<212> TYPE: DNA
<213> ORGANISM: Artificial Sequence
<220> FEATURE:
<223> OTHER INFORMATION: Synthetic

<400> SEQUENCE: 24
gttcctgggt ctccaaaggt     20

<210> SEQ ID NO 25
<211> LENGTH: 20
<212> TYPE: DNA
<213> ORGANISM: Artificial Sequence
<220> FEATURE:
<223> OTHER INFORMATION: Synthetic

<400> SEQUENCE: 25
acacacagag attggagggt     20

<210> SEQ ID NO 26
<211> LENGTH: 20
<212> TYPE: DNA
<213> ORGANISM: Artificial Sequence
<220> FEATURE:
<223> OTHER INFORMATION: Synthetic

<400> SEQUENCE: 26
gctcacgtag aagaccctcc     20

<210> SEQ ID NO 27
<211> LENGTH: 20
<212> TYPE: DNA
<213> ORGANISM: Artificial Sequence
<220> FEATURE:
<223> OTHER INFORMATION: Synthetic

<400> SEQUENCE: 27
ggcagggctg atgacaatcc     20

<210> SEQ ID NO 28

```
<211> LENGTH: 20
<212> TYPE: DNA
<213> ORGANISM: Artificial Sequence
<220> FEATURE:
<223> OTHER INFORMATION: Synthetic

<400> SEQUENCE: 28
tgcaaaacag gcagggctga                                                 20

<210> SEQ ID NO 29
<211> LENGTH: 20
<212> TYPE: DNA
<213> ORGANISM: Artificial Sequence
<220> FEATURE:
<223> OTHER INFORMATION: Synthetic

<400> SEQUENCE: 29
agaccagggc acttcccagg                                                 20

<210> SEQ ID NO 30
<211> LENGTH: 20
<212> TYPE: DNA
<213> ORGANISM: Artificial Sequence
<220> FEATURE:
<223> OTHER INFORMATION: Synthetic

<400> SEQUENCE: 30
cctgcctccg tgtgtggccc                                                 20

<210> SEQ ID NO 31
<211> LENGTH: 20
<212> TYPE: DNA
<213> ORGANISM: Artificial Sequence
<220> FEATURE:
<223> OTHER INFORMATION: Synthetic

<400> SEQUENCE: 31
gaccagccag caccaagagc                                                 20

<210> SEQ ID NO 32
<211> LENGTH: 20
<212> TYPE: DNA
<213> ORGANISM: Artificial Sequence
<220> FEATURE:
<223> OTHER INFORMATION: Synthetic

<400> SEQUENCE: 32
ccacaggaca gcgttgccac                                                 20

<210> SEQ ID NO 33
<211> LENGTH: 20
<212> TYPE: DNA
<213> ORGANISM: Artificial Sequence
<220> FEATURE:
<223> OTHER INFORMATION: Synthetic

<400> SEQUENCE: 33
ccggttcttg tactcgggcc                                                 20

<210> SEQ ID NO 34
<211> LENGTH: 20
<212> TYPE: DNA
<213> ORGANISM: Artificial Sequence
<220> FEATURE:
<223> OTHER INFORMATION: Synthetic

<400> SEQUENCE: 34
```
ccaaccagga gaggtgaggc                                                20

<210> SEQ ID NO 35
<211> LENGTH: 20
<212> TYPE: DNA
<213> ORGANISM: Artificial Sequence
<220> FEATURE:
<223> OTHER INFORMATION: Synthetic

<400> SEQUENCE: 35
ggcaaagcag taggtcaggc                                                20

<210> SEQ ID NO 36
<211> LENGTH: 20
<212> TYPE: DNA
<213> ORGANISM: Artificial Sequence
<220> FEATURE:
<223> OTHER INFORMATION: Synthetic

<400> SEQUENCE: 36
gcctcatgat ccccacgatc                                                20

<210> SEQ ID NO 37
<211> LENGTH: 20
<212> TYPE: DNA
<213> ORGANISM: Artificial Sequence
<220> FEATURE:
<223> OTHER INFORMATION: Synthetic

<400> SEQUENCE: 37
agtcctacta ccagccgcct                                                20

<210> SEQ ID NO 38
<211> LENGTH: 20
<212> TYPE: DNA
<213> ORGANISM: Artificial Sequence
<220> FEATURE:
<223> OTHER INFORMATION: Synthetic

<400> SEQUENCE: 38
tcagggtaag actccacttc                                                20

<210> SEQ ID NO 39
<211> LENGTH: 20
<212> TYPE: DNA
<213> ORGANISM: Artificial Sequence
<220> FEATURE:
<223> OTHER INFORMATION: Synthetic

<400> SEQUENCE: 39
agggtgttcc tgggtctcca                                                20

<210> SEQ ID NO 40
<211> LENGTH: 20
<212> TYPE: DNA
<213> ORGANISM: Artificial Sequence
<220> FEATURE:
<223> OTHER INFORMATION: Synthetic

<400> SEQUENCE: 40
ctccgtgtgt ggcccatggc                                                20

<210> SEQ ID NO 41
<211> LENGTH: 20
<212> TYPE: DNA
<213> ORGANISM: Artificial Sequence
<220> FEATURE:

<223> OTHER INFORMATION: Synthetic

<400> SEQUENCE: 41
ggatggtgat gttccctgcc                                                    20

<210> SEQ ID NO 42
<211> LENGTH: 20
<212> TYPE: DNA
<213> ORGANISM: Artificial Sequence
<220> FEATURE:
<223> OTHER INFORMATION: Synthetic

<400> SEQUENCE: 42
tgagaaagac cagccagcac                                                    20

<210> SEQ ID NO 43
<211> LENGTH: 20
<212> TYPE: DNA
<213> ORGANISM: Artificial Sequence
<220> FEATURE:
<223> OTHER INFORMATION: Synthetic

<400> SEQUENCE: 43
gggcgcagag ccaggatcac                                                    20

<210> SEQ ID NO 44
<211> LENGTH: 20
<212> TYPE: DNA
<213> ORGANISM: Artificial Sequence
<220> FEATURE:
<223> OTHER INFORMATION: Synthetic

<400> SEQUENCE: 44
ggcccaggat gggagcaggt                                                    20

<210> SEQ ID NO 45
<211> LENGTH: 20
<212> TYPE: DNA
<213> ORGANISM: Artificial Sequence
<220> FEATURE:
<223> OTHER INFORMATION: Synthetic

<400> SEQUENCE: 45
agggcgtaca ctttcccttc                                                    20

<210> SEQ ID NO 46
<211> LENGTH: 20
<212> TYPE: DNA
<213> ORGANISM: Artificial Sequence
<220> FEATURE:
<223> OTHER INFORMATION: Synthetic

<400> SEQUENCE: 46
cagccccttg cttctgcgga                                                    20

<210> SEQ ID NO 47
<211> LENGTH: 20
<212> TYPE: DNA
<213> ORGANISM: Artificial Sequence
<220> FEATURE:
<223> OTHER INFORMATION: Synthetic

<400> SEQUENCE: 47
aaggagaggg atgccagcca                                                    20

<210> SEQ ID NO 48

```
<211> LENGTH: 22
<212> TYPE: DNA
<213> ORGANISM: Artificial Sequence
<220> FEATURE:
<223> OTHER INFORMATION: Synthetic

<400> SEQUENCE: 48
ctgttacttt acagagggtt tg                                              22

<210> SEQ ID NO 49
<211> LENGTH: 25
<212> TYPE: DNA
<213> ORGANISM: Artificial Sequence
<220> FEATURE:
<223> OTHER INFORMATION: Synthetic

<400> SEQUENCE: 49
cttctgttac tttacagagg gtttg                                           25

<210> SEQ ID NO 50
<211> LENGTH: 21
<212> TYPE: DNA
<213> ORGANISM: Artificial Sequence
<220> FEATURE:
<223> OTHER INFORMATION: Synthetic

<400> SEQUENCE: 50
ctgttacttt acagagggtt t                                               21

<210> SEQ ID NO 51
<211> LENGTH: 20
<212> TYPE: DNA
<213> ORGANISM: Artificial Sequence
<220> FEATURE:
<223> OTHER INFORMATION: Synthetic

<400> SEQUENCE: 51
gccctcgtca gatgggcgca                                                 20

<210> SEQ ID NO 52
<211> LENGTH: 20
<212> TYPE: DNA
<213> ORGANISM: Artificial Sequence
<220> FEATURE:
<223> OTHER INFORMATION: Synthetic

<400> SEQUENCE: 52
agtcctacta ccagccgcct                                                 20

<210> SEQ ID NO 53
<211> LENGTH: 20
<212> TYPE: DNA
<213> ORGANISM: Artificial Sequence
<220> FEATURE:
<223> OTHER INFORMATION: Synthetic

<400> SEQUENCE: 53
agtaagagtc tattgaggta                                                 20

<210> SEQ ID NO 54
<211> LENGTH: 20
<212> TYPE: DNA
<213> ORGANISM: Artificial Sequence
<220> FEATURE:
<223> OTHER INFORMATION: Synthetic

<400> SEQUENCE: 54
```
ggttgagttt cacaacctga                                               20

<210> SEQ ID NO 55
<211> LENGTH: 20
<212> TYPE: DNA
<213> ORGANISM: Artificial Sequence
<220> FEATURE:
<223> OTHER INFORMATION: Synthetic

<400> SEQUENCE: 55
gtccacagaa tggaacagag                                               20

<210> SEQ ID NO 56
<211> LENGTH: 20
<212> TYPE: DNA
<213> ORGANISM: Artificial Sequence
<220> FEATURE:
<223> OTHER INFORMATION: Synthetic

<400> SEQUENCE: 56
ggcatccacc cggcagatgc                                               20

<210> SEQ ID NO 57
<211> LENGTH: 20
<212> TYPE: DNA
<213> ORGANISM: Artificial Sequence
<220> FEATURE:
<223> OTHER INFORMATION: Synthetic

<400> SEQUENCE: 57
tggatggcat ccacccggca                                               20

<210> SEQ ID NO 58
<211> LENGTH: 20
<212> TYPE: DNA
<213> ORGANISM: Artificial Sequence
<220> FEATURE:
<223> OTHER INFORMATION: Synthetic

<400> SEQUENCE: 58
aggcacctcc taggctcaca                                               20

<210> SEQ ID NO 59
<211> LENGTH: 20
<212> TYPE: DNA
<213> ORGANISM: Artificial Sequence
<220> FEATURE:
<223> OTHER INFORMATION: Synthetic

<400> SEQUENCE: 59
gccaatggag cttaggcacc                                               20

<210> SEQ ID NO 60
<211> LENGTH: 20
<212> TYPE: DNA
<213> ORGANISM: Artificial Sequence
<220> FEATURE:
<223> OTHER INFORMATION: Synthetic

<400> SEQUENCE: 60
catgatgggg aaagccagga                                               20

<210> SEQ ID NO 61
<211> LENGTH: 20
<212> TYPE: DNA
<213> ORGANISM: Artificial Sequence
<220> FEATURE:

<223> OTHER INFORMATION: Synthetic

<400> SEQUENCE: 61
aattgcaagc catagcttca                                           20

<210> SEQ ID NO 62
<211> LENGTH: 20
<212> TYPE: DNA
<213> ORGANISM: Artificial Sequence
<220> FEATURE:
<223> OTHER INFORMATION: Synthetic

<400> SEQUENCE: 62
cggcaaggca gcaatacctt                                           20

<210> SEQ ID NO 63
<211> LENGTH: 20
<212> TYPE: DNA
<213> ORGANISM: Artificial Sequence
<220> FEATURE:
<223> OTHER INFORMATION: Synthetic

<400> SEQUENCE: 63
cccagcaatg acagacagca                                           20

<210> SEQ ID NO 64
<211> LENGTH: 20
<212> TYPE: DNA
<213> ORGANISM: Artificial Sequence
<220> FEATURE:
<223> OTHER INFORMATION: Synthetic

<400> SEQUENCE: 64
ggtctgaaag gaccaggccc                                           20

<210> SEQ ID NO 65
<211> LENGTH: 20
<212> TYPE: DNA
<213> ORGANISM: Artificial Sequence
<220> FEATURE:
<223> OTHER INFORMATION: Synthetic

<400> SEQUENCE: 65
tgggaaaccc ccggaagcaa                                           20

<210> SEQ ID NO 66
<211> LENGTH: 20
<212> TYPE: DNA
<213> ORGANISM: Artificial Sequence
<220> FEATURE:
<223> OTHER INFORMATION: Synthetic

<400> SEQUENCE: 66
ggctttggga aaccccgga                                            20

<210> SEQ ID NO 67
<211> LENGTH: 19
<212> TYPE: DNA
<213> ORGANISM: Artificial Sequence
<220> FEATURE:
<223> OTHER INFORMATION: Synthetic

<400> SEQUENCE: 67
tcagattcag gatctggga                                            19

<210> SEQ ID NO 68

```
<211> LENGTH: 20
<212> TYPE: DNA
<213> ORGANISM: Artificial Sequence
<220> FEATURE:
<223> OTHER INFORMATION: Synthetic

<400> SEQUENCE: 68
cccaggtgaa gtcctctgac                                              20

<210> SEQ ID NO 69
<211> LENGTH: 20
<212> TYPE: DNA
<213> ORGANISM: Artificial Sequence
<220> FEATURE:
<223> OTHER INFORMATION: Synthetic

<400> SEQUENCE: 69
ctgcgccgaa tcctgcccca                                              20

<210> SEQ ID NO 70
<211> LENGTH: 20
<212> TYPE: DNA
<213> ORGANISM: Artificial Sequence
<220> FEATURE:
<223> OTHER INFORMATION: Synthetic

<400> SEQUENCE: 70
caggcccgaa ggtaaggctg                                              20

<210> SEQ ID NO 71
<211> LENGTH: 20
<212> TYPE: DNA
<213> ORGANISM: Artificial Sequence
<220> FEATURE:
<223> OTHER INFORMATION: Synthetic

<400> SEQUENCE: 71
tcagctagca cggtgctgaa                                              20

<210> SEQ ID NO 72
<211> LENGTH: 20
<212> TYPE: DNA
<213> ORGANISM: Artificial Sequence
<220> FEATURE:
<223> OTHER INFORMATION: Synthetic

<400> SEQUENCE: 72
ggcccagcaa acttgcccgt                                              20

<210> SEQ ID NO 73
<211> LENGTH: 20
<212> TYPE: DNA
<213> ORGANISM: Artificial Sequence
<220> FEATURE:
<223> OTHER INFORMATION: Synthetic

<400> SEQUENCE: 73
ccaccacagt gggctcagcc                                              20

<210> SEQ ID NO 74
<211> LENGTH: 19
<212> TYPE: DNA
<213> ORGANISM: Artificial Sequence
<220> FEATURE:
<223> OTHER INFORMATION: Synthetic

<400> SEQUENCE: 74
```
ggccatgagg gcaatctaa                                            19

<210> SEQ ID NO 75
<211> LENGTH: 21
<212> TYPE: DNA
<213> ORGANISM: Artificial Sequence
<220> FEATURE:
<223> OTHER INFORMATION: Synthetic

<400> SEQUENCE: 75
gtggccatga gggcaatcta a                                         21

<210> SEQ ID NO 76
<211> LENGTH: 20
<212> TYPE: DNA
<213> ORGANISM: Artificial Sequence
<220> FEATURE:
<223> OTHER INFORMATION: Synthetic

<400> SEQUENCE: 76
gatttaacat ttggcgccca                                           20

<210> SEQ ID NO 77
<211> LENGTH: 20
<212> TYPE: DNA
<213> ORGANISM: Artificial Sequence
<220> FEATURE:
<223> OTHER INFORMATION: Synthetic

<400> SEQUENCE: 77
aaagttacaa cattatatct                                           20

<210> SEQ ID NO 78
<211> LENGTH: 20
<212> TYPE: DNA
<213> ORGANISM: Artificial Sequence
<220> FEATURE:
<223> OTHER INFORMATION: Synthetic

<400> SEQUENCE: 78
agtgcgattc tcaaacctac                                           20

<210> SEQ ID NO 79
<211> LENGTH: 16
<212> TYPE: DNA
<213> ORGANISM: Artificial Sequence
<220> FEATURE:
<223> OTHER INFORMATION: Synthetic

<400> SEQUENCE: 79
tatttgcgag ctcccc                                               16

<210> SEQ ID NO 80
<211> LENGTH: 15
<212> TYPE: DNA
<213> ORGANISM: Artificial Sequence
<220> FEATURE:
<223> OTHER INFORMATION: Synthetic

<400> SEQUENCE: 80
tatttgcgag ctccc                                                15

<210> SEQ ID NO 81
<211> LENGTH: 14
<212> TYPE: DNA
<213> ORGANISM: Artificial Sequence
<220> FEATURE:

<223> OTHER INFORMATION: Synthetic

<400> SEQUENCE: 81
tatttgcgag ctcc                                                                  14

<210> SEQ ID NO 82
<211> LENGTH: 20
<212> TYPE: DNA
<213> ORGANISM: Artificial Sequence
<220> FEATURE:
<223> OTHER INFORMATION: Synthetic

<400> SEQUENCE: 82
cgacagctcc tgcgctcctc                                                            20

<210> SEQ ID NO 83
<211> LENGTH: 16
<212> TYPE: DNA
<213> ORGANISM: Artificial Sequence
<220> FEATURE:
<223> OTHER INFORMATION: Synthetic

<400> SEQUENCE: 83
agctccccgt acctcc                                                                16

<210> SEQ ID NO 84
<211> LENGTH: 16
<212> TYPE: DNA
<213> ORGANISM: Artificial Sequence
<220> FEATURE:
<223> OTHER INFORMATION: Synthetic

<400> SEQUENCE: 84
tgcgagctcc ccgtac                                                                16

<210> SEQ ID NO 85
<211> LENGTH: 10
<212> TYPE: DNA
<213> ORGANISM: Artificial Sequence
<220> FEATURE:
<223> OTHER INFORMATION: Synthetic

<400> SEQUENCE: 85
ctccccgtac                                                                       10

<210> SEQ ID NO 86
<211> LENGTH: 11
<212> TYPE: DNA
<213> ORGANISM: Artificial Sequence
<220> FEATURE:
<223> OTHER INFORMATION: Synthetic

<400> SEQUENCE: 86
gctccccgta c                                                                     11

<210> SEQ ID NO 87
<211> LENGTH: 12
<212> TYPE: DNA
<213> ORGANISM: Artificial Sequence
<220> FEATURE:
<223> OTHER INFORMATION: Synthetic

<400> SEQUENCE: 87
agctccccgt ac                                                                    12

<210> SEQ ID NO 88

```
<211> LENGTH: 13
<212> TYPE: DNA
<213> ORGANISM: Artificial Sequence
<220> FEATURE:
<223> OTHER INFORMATION: Synthetic

<400> SEQUENCE: 88
gagctccccg tac                                                      13

<210> SEQ ID NO 89
<211> LENGTH: 14
<212> TYPE: DNA
<213> ORGANISM: Artificial Sequence
<220> FEATURE:
<223> OTHER INFORMATION: Synthetic

<400> SEQUENCE: 89
cgagctcccc gtac                                                     14

<210> SEQ ID NO 90
<211> LENGTH: 15
<212> TYPE: DNA
<213> ORGANISM: Artificial Sequence
<220> FEATURE:
<223> OTHER INFORMATION: Synthetic

<400> SEQUENCE: 90
gcgagctccc cgtac                                                    15

<210> SEQ ID NO 91
<211> LENGTH: 13
<212> TYPE: DNA
<213> ORGANISM: Artificial Sequence
<220> FEATURE:
<223> OTHER INFORMATION: Synthetic

<400> SEQUENCE: 91
gcgagctccc cgt                                                      13

<210> SEQ ID NO 92
<211> LENGTH: 15
<212> TYPE: DNA
<213> ORGANISM: Artificial Sequence
<220> FEATURE:
<223> OTHER INFORMATION: Synthetic

<400> SEQUENCE: 92
gccgccgcca agtct                                                    15

<210> SEQ ID NO 93
<211> LENGTH: 24
<212> TYPE: DNA
<213> ORGANISM: Artificial Sequence
<220> FEATURE:
<223> OTHER INFORMATION: Synthetic

<400> SEQUENCE: 93
gagaagcaaa gctttcaccc tgtg                                          24

<210> SEQ ID NO 94
<211> LENGTH: 22
<212> TYPE: DNA
<213> ORGANISM: Artificial Sequence
<220> FEATURE:
<223> OTHER INFORMATION: Synthetic

<400> SEQUENCE: 94
```
gaagcaaagc tttcaccctg tg                                                  22

<210> SEQ ID NO 95
<211> LENGTH: 19
<212> TYPE: DNA
<213> ORGANISM: Artificial Sequence
<220> FEATURE:
<223> OTHER INFORMATION: Synthetic

<400> SEQUENCE: 95
gcaaagcttt caccctgtg                                                      19

<210> SEQ ID NO 96
<211> LENGTH: 24
<212> TYPE: DNA
<213> ORGANISM: Artificial Sequence
<220> FEATURE:
<223> OTHER INFORMATION: Synthetic

<400> SEQUENCE: 96
ctccccgtac ctcctaaggc tcct                                                24

<210> SEQ ID NO 97
<211> LENGTH: 22
<212> TYPE: DNA
<213> ORGANISM: Artificial Sequence
<220> FEATURE:
<223> OTHER INFORMATION: Synthetic

<400> SEQUENCE: 97
ccccgtacct cctaaggctc ct                                                  22

<210> SEQ ID NO 98
<211> LENGTH: 19
<212> TYPE: DNA
<213> ORGANISM: Artificial Sequence
<220> FEATURE:
<223> OTHER INFORMATION: Synthetic

<400> SEQUENCE: 98
ccgtacctcc taaggctcc                                                      19

<210> SEQ ID NO 99
<211> LENGTH: 32
<212> TYPE: DNA
<213> ORGANISM: Artificial Sequence
<220> FEATURE:
<223> OTHER INFORMATION: Synthetic

<400> SEQUENCE: 99
gatcagggta ccaagagtgg ctcctgtagg ca                                       32

<210> SEQ ID NO 100
<211> LENGTH: 32
<212> TYPE: DNA
<213> ORGANISM: Artificial Sequence
<220> FEATURE:
<223> OTHER INFORMATION: Synthetic

<400> SEQUENCE: 100
gatagcctcg aggtagaatt ccaatcagct ga                                       32

<210> SEQ ID NO 101
<211> LENGTH: 20
<212> TYPE: DNA
<213> ORGANISM: Artificial Sequence
<220> FEATURE:

```
<223> OTHER INFORMATION: Synthetic
<300> PUBLICATION INFORMATION:
<302> TITLE: Blocking of Heart Allograft Rejection by Intercellular
      Adhesion Molecule 1 Synthetic Alone or
      in Combination with Other Immunosupprssive Modalities
<303> JOURNAL: J. Immunol.
<304> VOLUME: 153
<306> PAGES: 5336 5346
<307> DATE: 1994-12-01

<400> SEQUENCE: 101
tgcatccccc aggccaccat                                              20

<210> SEQ ID NO 102
<211> LENGTH: 21
<212> TYPE: DNA
<213> ORGANISM: Artificial Sequence
<220> FEATURE:
<223> OTHER INFORMATION: Synthetic
<300> PUBLICATION INFORMATION:
<302> TITLE: Blocking of Heart Allograft Rejection by Intercellular
      Adhesion Molecule 1 Synthetic Alone or
      in Combination with Other Immunosupprssive Modalities
<303> JOURNAL: J. Immunol.
<304> VOLUME: 153
<306> PAGES: 5336 5346
<307> DATE: 1994-12-01

<400> SEQUENCE: 102
gccgaggtcc atgtcgtacg c                                            21

<210> SEQ ID NO 103
<211> LENGTH: 20
<212> TYPE: DNA
<213> ORGANISM: Artificial Sequence
<220> FEATURE:
<223> OTHER INFORMATION: Synthetic

<400> SEQUENCE: 103
acacgtctac aggagtctgg                                              20

<210> SEQ ID NO 104
<211> LENGTH: 20
<212> TYPE: DNA
<213> ORGANISM: Artificial Sequence
<220> FEATURE:
<223> OTHER INFORMATION: Synthetic

<400> SEQUENCE: 104
caagcccatg gtgcatctgg                                              20

<210> SEQ ID NO 105
<211> LENGTH: 20
<212> TYPE: DNA
<213> ORGANISM: Artificial Sequence
<220> FEATURE:
<223> OTHER INFORMATION: Synthetic

<400> SEQUENCE: 105
ctggggtcca tcgtgggtgc                                              20

<210> SEQ ID NO 106
<211> LENGTH: 20
<212> TYPE: DNA
<213> ORGANISM: Artificial Sequence
<220> FEATURE:
<223> OTHER INFORMATION: Synthetic

<400> SEQUENCE: 106
```

-continued ccgtgctgcc tacaggagcc          20

<210> SEQ ID NO 107
<211> LENGTH: 20
<212> TYPE: DNA
<213> ORGANISM: Artificial Sequence
<220> FEATURE:
<223> OTHER INFORMATION: Synthetic

<400> SEQUENCE: 107
ggtgcttccg taagttctgg          20

<210> SEQ ID NO 108
<211> LENGTH: 20
<212> TYPE: DNA
<213> ORGANISM: Artificial Sequence
<220> FEATURE:
<223> OTHER INFORMATION: Synthetic

<400> SEQUENCE: 108
ggattgccaa gcccatggtg          20

<210> SEQ ID NO 109
<211> LENGTH: 20
<212> TYPE: DNA
<213> ORGANISM: Artificial Sequence
<220> FEATURE:
<223> OTHER INFORMATION: Synthetic

<400> SEQUENCE: 109
ctaagtagtg ctagccggga          20

<210> SEQ ID NO 110
<211> LENGTH: 20
<212> TYPE: DNA
<213> ORGANISM: Artificial Sequence
<220> FEATURE:
<223> OTHER INFORMATION: Synthetic

<400> SEQUENCE: 110
tgcgtctcca cggaaacagc          20

<210> SEQ ID NO 111
<211> LENGTH: 20
<212> TYPE: DNA
<213> ORGANISM: Artificial Sequence
<220> FEATURE:
<223> OTHER INFORMATION: Synthetic

<400> SEQUENCE: 111
gtgcggccca ggtacttggc          20

<210> SEQ ID NO 112
<211> LENGTH: 20
<212> TYPE: DNA
<213> ORGANISM: Artificial Sequence
<220> FEATURE:
<223> OTHER INFORMATION: Synthetic

<400> SEQUENCE: 112
acaaggagga gggccacagt          20

<210> SEQ ID NO 113
<211> LENGTH: 20
<212> TYPE: DNA
<213> ORGANISM: Artificial Sequence
<220> FEATURE:

<223> OTHER INFORMATION: Synthetic

<400> SEQUENCE: 113
tgagaggttt ggaggaaatc                                                    20

<210> SEQ ID NO 114
<211> LENGTH: 20
<212> TYPE: DNA
<213> ORGANISM: Artificial Sequence
<220> FEATURE:
<223> OTHER INFORMATION: Synthetic

<400> SEQUENCE: 114
gatagtctct ctgtcagcgt                                                    20

<210> SEQ ID NO 115
<211> LENGTH: 20
<212> TYPE: DNA
<213> ORGANISM: Artificial Sequence
<220> FEATURE:
<223> OTHER INFORMATION: Synthetic

<400> SEQUENCE: 115
gttgctgggc ctgctaggct                                                    20

<210> SEQ ID NO 116
<211> LENGTH: 20
<212> TYPE: DNA
<213> ORGANISM: Artificial Sequence
<220> FEATURE:
<223> OTHER INFORMATION: Synthetic

<400> SEQUENCE: 116
ctaggtctcg tcgtcggtgg                                                    20

<210> SEQ ID NO 117
<211> LENGTH: 20
<212> TYPE: DNA
<213> ORGANISM: Artificial Sequence
<220> FEATURE:
<223> OTHER INFORMATION: Synthetic

<400> SEQUENCE: 117
tctcactgcc ttcactctgc                                                    20

<210> SEQ ID NO 118
<211> LENGTH: 21
<212> TYPE: DNA
<213> ORGANISM: Artificial Sequence
<220> FEATURE:
<223> OTHER INFORMATION: Synthetic

<400> SEQUENCE: 118
gtaccagatg aaggttatca a                                                  21

<210> SEQ ID NO 119
<211> LENGTH: 20
<212> TYPE: DNA
<213> ORGANISM: Artificial Sequence
<220> FEATURE:
<223> OTHER INFORMATION: Synthetic

<400> SEQUENCE: 119
ctttggagat tattcgagtt                                                    20

<210> SEQ ID NO 120

```
<211> LENGTH: 20
<212> TYPE: DNA
<213> ORGANISM: Artificial Sequence
<220> FEATURE:
<223> OTHER INFORMATION: Synthetic

<400> SEQUENCE: 120
gcaagtgtaa agccctgagt                                               20

<210> SEQ ID NO 121
<211> LENGTH: 20
<212> TYPE: DNA
<213> ORGANISM: Artificial Sequence
<220> FEATURE:
<223> OTHER INFORMATION: Synthetic

<400> SEQUENCE: 121
agaattccaa tcagctgaga                                               20

<210> SEQ ID NO 122
<211> LENGTH: 20
<212> TYPE: DNA
<213> ORGANISM: Artificial Sequence
<220> FEATURE:
<223> OTHER INFORMATION: Synthetic

<400> SEQUENCE: 122
tctgagaaac tctgcacttc                                               20

<210> SEQ ID NO 123
<211> LENGTH: 20
<212> TYPE: DNA
<213> ORGANISM: Artificial Sequence
<220> FEATURE:
<223> OTHER INFORMATION: Synthetic

<400> SEQUENCE: 123
tcctcaggct ctcactgcct                                               20

<210> SEQ ID NO 124
<211> LENGTH: 20
<212> TYPE: DNA
<213> ORGANISM: Artificial Sequence
<220> FEATURE:
<223> OTHER INFORMATION: Synthetic

<400> SEQUENCE: 124
ggttgttcaa gtccgtgctg                                               20

<210> SEQ ID NO 125
<211> LENGTH: 21
<212> TYPE: DNA
<213> ORGANISM: Artificial Sequence
<220> FEATURE:
<223> OTHER INFORMATION: Synthetic

<400> SEQUENCE: 125
gccgaggtcc atgtcgtagc c                                             21

<210> SEQ ID NO 126
<211> LENGTH: 20
<212> TYPE: DNA
<213> ORGANISM: Artificial Sequence
<220> FEATURE:
<223> OTHER INFORMATION: Synthetic

<400> SEQUENCE: 126
```
agactccact tctgagatgt                                              20

<210> SEQ ID NO 127
<211> LENGTH: 20
<212> TYPE: DNA
<213> ORGANISM: Artificial Sequence
<220> FEATURE:
<223> OTHER INFORMATION: Synthetic

<400> SEQUENCE: 127
tgaagaaaaa ttccactttt                                              20

<210> SEQ ID NO 128
<211> LENGTH: 20
<212> TYPE: DNA
<213> ORGANISM: Artificial Sequence
<220> FEATURE:
<223> OTHER INFORMATION: Synthetic

<400> SEQUENCE: 128
tttagtttca cagcttgctg                                              20

<210> SEQ ID NO 129
<211> LENGTH: 20
<212> TYPE: DNA
<213> ORGANISM: Artificial Sequence
<220> FEATURE:
<223> OTHER INFORMATION: Synthetic

<400> SEQUENCE: 129
tcccaggtgc aaaacaggca                                              20

<210> SEQ ID NO 130
<211> LENGTH: 20
<212> TYPE: DNA
<213> ORGANISM: Artificial Sequence
<220> FEATURE:
<223> OTHER INFORMATION: Synthetic

<400> SEQUENCE: 130
gtgaaagcca acaatttgga                                              20

<210> SEQ ID NO 131
<211> LENGTH: 20
<212> TYPE: DNA
<213> ORGANISM: Artificial Sequence
<220> FEATURE:
<223> OTHER INFORMATION: Synthetic

<400> SEQUENCE: 131
catggcttca gatgcttagg                                              20

<210> SEQ ID NO 132
<211> LENGTH: 20
<212> TYPE: DNA
<213> ORGANISM: Artificial Sequence
<220> FEATURE:
<223> OTHER INFORMATION: Synthetic

<400> SEQUENCE: 132
ttgaggtatg gacacttgga                                              20

<210> SEQ ID NO 133
<211> LENGTH: 20
<212> TYPE: DNA
<213> ORGANISM: Artificial Sequence
<220> FEATURE:

<223> OTHER INFORMATION: Synthetic

<400> SEQUENCE: 133
gcgttgccac ttctttcact                                               20

<210> SEQ ID NO 134
<211> LENGTH: 20
<212> TYPE: DNA
<213> ORGANISM: Artificial Sequence
<220> FEATURE:
<223> OTHER INFORMATION: Synthetic

<400> SEQUENCE: 134
ttttgccagt agatgcgagt                                               20

<210> SEQ ID NO 135
<211> LENGTH: 20
<212> TYPE: DNA
<213> ORGANISM: Artificial Sequence
<220> FEATURE:
<223> OTHER INFORMATION: Synthetic

<400> SEQUENCE: 135
ggccatatat tcatgtcccc                                               20

<210> SEQ ID NO 136
<211> LENGTH: 20
<212> TYPE: DNA
<213> ORGANISM: Artificial Sequence
<220> FEATURE:
<223> OTHER INFORMATION: Synthetic

<400> SEQUENCE: 136
gccaggatca caatggagag                                               20

<210> SEQ ID NO 137
<211> LENGTH: 20
<212> TYPE: DNA
<213> ORGANISM: Artificial Sequence
<220> FEATURE:
<223> OTHER INFORMATION: Synthetic

<400> SEQUENCE: 137
gtatgtgccc tcgtcagatg                                               20

<210> SEQ ID NO 138
<211> LENGTH: 20
<212> TYPE: DNA
<213> ORGANISM: Artificial Sequence
<220> FEATURE:
<223> OTHER INFORMATION: Synthetic

<400> SEQUENCE: 138
ttcagccagg tgttcccgct                                               20

<210> SEQ ID NO 139
<211> LENGTH: 20
<212> TYPE: DNA
<213> ORGANISM: Artificial Sequence
<220> FEATURE:
<223> OTHER INFORMATION: Synthetic

<400> SEQUENCE: 139
ggaagtcagc tttgactgat                                               20

<210> SEQ ID NO 140

```
<211> LENGTH: 20
<212> TYPE: DNA
<213> ORGANISM: Artificial Sequence
<220> FEATURE:
<223> OTHER INFORMATION: Synthetic

<400> SEQUENCE: 140
cctccagagg ttgagcaaat                                               20

<210> SEQ ID NO 141
<211> LENGTH: 20
<212> TYPE: DNA
<213> ORGANISM: Artificial Sequence
<220> FEATURE:
<223> OTHER INFORMATION: Synthetic

<400> SEQUENCE: 141
ccaaccagga gaggtgaggc                                               20

<210> SEQ ID NO 142
<211> LENGTH: 20
<212> TYPE: DNA
<213> ORGANISM: Artificial Sequence
<220> FEATURE:
<223> OTHER INFORMATION: Synthetic

<400> SEQUENCE: 142
gaagctgtgg ttggttgtca                                               20

<210> SEQ ID NO 143
<211> LENGTH: 20
<212> TYPE: DNA
<213> ORGANISM: Artificial Sequence
<220> FEATURE:
<223> OTHER INFORMATION: Synthetic

<400> SEQUENCE: 143
ttgaaggtct gattcactct                                               20

<210> SEQ ID NO 144
<211> LENGTH: 20
<212> TYPE: DNA
<213> ORGANISM: Artificial Sequence
<220> FEATURE:
<223> OTHER INFORMATION: Synthetic

<400> SEQUENCE: 144
aaggtaatgg cccaggatgg                                               20

<210> SEQ ID NO 145
<211> LENGTH: 20
<212> TYPE: DNA
<213> ORGANISM: Artificial Sequence
<220> FEATURE:
<223> OTHER INFORMATION: Synthetic

<400> SEQUENCE: 145
aagcagtagg tcaggcagca                                               20

<210> SEQ ID NO 146
<211> LENGTH: 20
<212> TYPE: DNA
<213> ORGANISM: Artificial Sequence
<220> FEATURE:
<223> OTHER INFORMATION: Synthetic

<400> SEQUENCE: 146
```

```
ccttgcttct gcggacactg                                          20

<210> SEQ ID NO 147
<211> LENGTH: 20
<212> TYPE: DNA
<213> ORGANISM: Artificial Sequence
<220> FEATURE:
<223> OTHER INFORMATION: Synthetic

<400> SEQUENCE: 147
agccccttgc ttctgcggac                                          20

<210> SEQ ID NO 148
<211> LENGTH: 20
<212> TYPE: DNA
<213> ORGANISM: Artificial Sequence
<220> FEATURE:
<223> OTHER INFORMATION: Synthetic

<400> SEQUENCE: 148
tgacggaggc taccttcaga                                          20

<210> SEQ ID NO 149
<211> LENGTH: 20
<212> TYPE: DNA
<213> ORGANISM: Artificial Sequence
<220> FEATURE:
<223> OTHER INFORMATION: Synthetic

<400> SEQUENCE: 149
gtaaaacagc ttaaatttgt                                          20

<210> SEQ ID NO 150
<211> LENGTH: 20
<212> TYPE: DNA
<213> ORGANISM: Artificial Sequence
<220> FEATURE:
<223> OTHER INFORMATION: Synthetic

<400> SEQUENCE: 150
agaagaggtt acattaagca                                          20

<210> SEQ ID NO 151
<211> LENGTH: 20
<212> TYPE: DNA
<213> ORGANISM: Artificial Sequence
<220> FEATURE:
<223> OTHER INFORMATION: Synthetic

<400> SEQUENCE: 151
agataatgaa ttggctgaca                                          20

<210> SEQ ID NO 152
<211> LENGTH: 20
<212> TYPE: DNA
<213> ORGANISM: Artificial Sequence
<220> FEATURE:
<223> OTHER INFORMATION: Synthetic

<400> SEQUENCE: 152
gcgtcatcat ccgcaccatc                                          20

<210> SEQ ID NO 153
<211> LENGTH: 20
<212> TYPE: DNA
<213> ORGANISM: Artificial Sequence
<220> FEATURE:
```

<223> OTHER INFORMATION: Synthetic

<400> SEQUENCE: 153
cgttgcttgt gccgacagtg                                                                    20

<210> SEQ ID NO 154
<211> LENGTH: 20
<212> TYPE: DNA
<213> ORGANISM: Artificial Sequence
<220> FEATURE:
<223> OTHER INFORMATION: Synthetic

<400> SEQUENCE: 154
gctcacgaag aacaccttcc                                                                    20

<210> SEQ ID NO 155
<211> LENGTH: 20
<212> TYPE: DNA
<213> ORGANISM: Artificial Sequence
<220> FEATURE:
<223> OTHER INFORMATION: Synthetic

<400> SEQUENCE: 155
agagaaacta gtaagagtct                                                                    20

<210> SEQ ID NO 156
<211> LENGTH: 20
<212> TYPE: DNA
<213> ORGANISM: Artificial Sequence
<220> FEATURE:
<223> OTHER INFORMATION: Synthetic

<400> SEQUENCE: 156
tggcatccac ccggcagatg                                                                    20

<210> SEQ ID NO 157
<211> LENGTH: 20
<212> TYPE: DNA
<213> ORGANISM: Artificial Sequence
<220> FEATURE:
<223> OTHER INFORMATION: Synthetic

<400> SEQUENCE: 157
tcgagaaaca gagatgtaga                                                                    20

<210> SEQ ID NO 158
<211> LENGTH: 20
<212> TYPE: DNA
<213> ORGANISM: Artificial Sequence
<220> FEATURE:
<223> OTHER INFORMATION: Synthetic

<400> SEQUENCE: 158
tggagcttag gcacctccta                                                                    20

<210> SEQ ID NO 159
<211> LENGTH: 20
<212> TYPE: DNA
<213> ORGANISM: Artificial Sequence
<220> FEATURE:
<223> OTHER INFORMATION: Synthetic

<400> SEQUENCE: 159
tggggaaagc caggaatcta                                                                    20

<210> SEQ ID NO 160

```
<211> LENGTH: 20
<212> TYPE: DNA
<213> ORGANISM: Artificial Sequence
<220> FEATURE:
<223> OTHER INFORMATION: Synthetic

<400> SEQUENCE: 160
cagcacaaag agaagaatga                                               20

<210> SEQ ID NO 161
<211> LENGTH: 20
<212> TYPE: DNA
<213> ORGANISM: Artificial Sequence
<220> FEATURE:
<223> OTHER INFORMATION: Synthetic

<400> SEQUENCE: 161
atgaggagag ttgtaacggc                                               20

<210> SEQ ID NO 162
<211> LENGTH: 20
<212> TYPE: DNA
<213> ORGANISM: Artificial Sequence
<220> FEATURE:
<223> OTHER INFORMATION: Synthetic

<400> SEQUENCE: 162
aagtccggtt cttatactcg                                               20

<210> SEQ ID NO 163
<211> LENGTH: 20
<212> TYPE: DNA
<213> ORGANISM: Artificial Sequence
<220> FEATURE:
<223> OTHER INFORMATION: Synthetic

<400> SEQUENCE: 163
gcaggtaatc cttttagtgt                                               20

<210> SEQ ID NO 164
<211> LENGTH: 20
<212> TYPE: DNA
<213> ORGANISM: Artificial Sequence
<220> FEATURE:
<223> OTHER INFORMATION: Synthetic

<400> SEQUENCE: 164
gtgaagtcct ctgacacgtg                                               20

<210> SEQ ID NO 165
<211> LENGTH: 20
<212> TYPE: DNA
<213> ORGANISM: Artificial Sequence
<220> FEATURE:
<223> OTHER INFORMATION: Synthetic

<400> SEQUENCE: 165
cgaatcctgc cccaaagagc                                               20

<210> SEQ ID NO 166
<211> LENGTH: 20
<212> TYPE: DNA
<213> ORGANISM: Artificial Sequence
<220> FEATURE:
<223> OTHER INFORMATION: Synthetic

<400> SEQUENCE: 166
```
actgcgccga atcctgcccc                                      20

<210> SEQ ID NO 167
<211> LENGTH: 20
<212> TYPE: DNA
<213> ORGANISM: Artificial Sequence
<220> FEATURE:
<223> OTHER INFORMATION: Synthetic

<400> SEQUENCE: 167
ttgatgatga caacgatgac                                      20

<210> SEQ ID NO 168
<211> LENGTH: 20
<212> TYPE: DNA
<213> ORGANISM: Artificial Sequence
<220> FEATURE:
<223> OTHER INFORMATION: Synthetic

<400> SEQUENCE: 168
ctgttgtttg tttctctgct                                      20

<210> SEQ ID NO 169
<211> LENGTH: 20
<212> TYPE: DNA
<213> ORGANISM: Artificial Sequence
<220> FEATURE:
<223> OTHER INFORMATION: Synthetic

<400> SEQUENCE: 169
tgttcagcta atgcttcttc                                      20

<210> SEQ ID NO 170
<211> LENGTH: 20
<212> TYPE: DNA
<213> ORGANISM: Artificial Sequence
<220> FEATURE:
<223> OTHER INFORMATION: Synthetic

<400> SEQUENCE: 170
gttaactcta tcttgtgtca                                      20

<210> SEQ ID NO 171
<211> LENGTH: 20
<212> TYPE: DNA
<213> ORGANISM: Artificial Sequence
<220> FEATURE:
<223> OTHER INFORMATION: Synthetic

<400> SEQUENCE: 171
tccacttcag tcatcaagca                                      20

<210> SEQ ID NO 172
<211> LENGTH: 20
<212> TYPE: DNA
<213> ORGANISM: Artificial Sequence
<220> FEATURE:
<223> OTHER INFORMATION: Synthetic

<400> SEQUENCE: 172
tgctcaatac tctctttta                                       20

<210> SEQ ID NO 173
<211> LENGTH: 20
<212> TYPE: DNA
<213> ORGANISM: Artificial Sequence
<220> FEATURE:

<223> OTHER INFORMATION: Synthetic

<400> SEQUENCE: 173
aggcccagca aacttgcccg    20

<210> SEQ ID NO 174
<211> LENGTH: 20
<212> TYPE: DNA
<213> ORGANISM: Artificial Sequence
<220> FEATURE:
<223> OTHER INFORMATION: Synthetic

<400> SEQUENCE: 174
aacggcaagg cagcaatacc    20

<210> SEQ ID NO 175
<211> LENGTH: 20
<212> TYPE: DNA
<213> ORGANISM: Artificial Sequence
<220> FEATURE:
<223> OTHER INFORMATION: Synthetic

<400> SEQUENCE: 175
cagaagcaag gtggtaagaa    20

<210> SEQ ID NO 176
<211> LENGTH: 20
<212> TYPE: DNA
<213> ORGANISM: Artificial Sequence
<220> FEATURE:
<223> OTHER INFORMATION: Synthetic

<400> SEQUENCE: 176
gcctgtccac tgtagctcca    20

<210> SEQ ID NO 177
<211> LENGTH: 20
<212> TYPE: DNA
<213> ORGANISM: Artificial Sequence
<220> FEATURE:
<223> OTHER INFORMATION: Synthetic

<400> SEQUENCE: 177
agaatgttac tcagtcccat    20

<210> SEQ ID NO 178
<211> LENGTH: 20
<212> TYPE: DNA
<213> ORGANISM: Artificial Sequence
<220> FEATURE:
<223> OTHER INFORMATION: Synthetic

<400> SEQUENCE: 178
tcagaggagc agcaccagag    20

<210> SEQ ID NO 179
<211> LENGTH: 20
<212> TYPE: DNA
<213> ORGANISM: Artificial Sequence
<220> FEATURE:
<223> OTHER INFORMATION: Synthetic

<400> SEQUENCE: 179
tggcatggca ggtctgcagt    20

<210> SEQ ID NO 180

```
<211> LENGTH: 20
<212> TYPE: DNA
<213> ORGANISM: Artificial Sequence
<220> FEATURE:
<223> OTHER INFORMATION: Synthetic

<400> SEQUENCE: 180
agctcactca ggctttggtt                                               20

<210> SEQ ID NO 181
<211> LENGTH: 20
<212> TYPE: DNA
<213> ORGANISM: Artificial Sequence
<220> FEATURE:
<223> OTHER INFORMATION: Synthetic

<400> SEQUENCE: 181
tgcctaagta tacctcattc                                               20

<210> SEQ ID NO 182
<211> LENGTH: 20
<212> TYPE: DNA
<213> ORGANISM: Artificial Sequence
<220> FEATURE:
<223> OTHER INFORMATION: Synthetic

<400> SEQUENCE: 182
ctgtcaaatt tctctttgcc                                               20

<210> SEQ ID NO 183
<211> LENGTH: 20
<212> TYPE: DNA
<213> ORGANISM: Artificial Sequence
<220> FEATURE:
<223> OTHER INFORMATION: Synthetic

<400> SEQUENCE: 183
catatacttg gaatgaacac                                               20

<210> SEQ ID NO 184
<211> LENGTH: 20
<212> TYPE: DNA
<213> ORGANISM: Artificial Sequence
<220> FEATURE:
<223> OTHER INFORMATION: Synthetic

<400> SEQUENCE: 184
ggtccaactg tccgaatcaa                                               20

<210> SEQ ID NO 185
<211> LENGTH: 20
<212> TYPE: DNA
<213> ORGANISM: Artificial Sequence
<220> FEATURE:
<223> OTHER INFORMATION: Synthetic

<400> SEQUENCE: 185
tgatctgaag attgtgaagt                                               20

<210> SEQ ID NO 186
<211> LENGTH: 20
<212> TYPE: DNA
<213> ORGANISM: Artificial Sequence
<220> FEATURE:
<223> OTHER INFORMATION: Synthetic

<400> SEQUENCE: 186
```

-continued aagcccttgt ccttgatctg                                          20

<210> SEQ ID NO 187
<211> LENGTH: 20
<212> TYPE: DNA
<213> ORGANISM: Artificial Sequence
<220> FEATURE:
<223> OTHER INFORMATION: Synthetic

<400> SEQUENCE: 187
tgtgatggat gatacattga                                          20

<210> SEQ ID NO 188
<211> LENGTH: 20
<212> TYPE: DNA
<213> ORGANISM: Artificial Sequence
<220> FEATURE:
<223> OTHER INFORMATION: Synthetic

<400> SEQUENCE: 188
tcaggttgac tgaagttagc                                          20

<210> SEQ ID NO 189
<211> LENGTH: 20
<212> TYPE: DNA
<213> ORGANISM: Artificial Sequence
<220> FEATURE:
<223> OTHER INFORMATION: Synthetic

<400> SEQUENCE: 189
gtgtatagat gagcaggtca                                          20

<210> SEQ ID NO 190
<211> LENGTH: 20
<212> TYPE: DNA
<213> ORGANISM: Artificial Sequence
<220> FEATURE:
<223> OTHER INFORMATION: Synthetic

<400> SEQUENCE: 190
tctgtgacat tatcttgaga                                          20

<210> SEQ ID NO 191
<211> LENGTH: 20
<212> TYPE: DNA
<213> ORGANISM: Artificial Sequence
<220> FEATURE:
<223> OTHER INFORMATION: Synthetic

<400> SEQUENCE: 191
aagataaaag ccgcgtcttg                                          20

<210> SEQ ID NO 192
<211> LENGTH: 20
<212> TYPE: DNA
<213> ORGANISM: Artificial Sequence
<220> FEATURE:
<223> OTHER INFORMATION: Synthetic

<400> SEQUENCE: 192
agaaaaccat cacacatata                                          20

<210> SEQ ID NO 193
<211> LENGTH: 20
<212> TYPE: DNA
<213> ORGANISM: Artificial Sequence
<220> FEATURE:

-continued

<223> OTHER INFORMATION: Synthetic

<400> SEQUENCE: 193
agagttgcga ggccgcttct                                          20

<210> SEQ ID NO 194
<211> LENGTH: 20
<212> TYPE: DNA
<213> ORGANISM: Artificial Sequence
<220> FEATURE:
<223> OTHER INFORMATION: Synthetic

<400> SEQUENCE: 194
tccctctcca ttgtgttggt                                          20

<210> SEQ ID NO 195
<211> LENGTH: 20
<212> TYPE: DNA
<213> ORGANISM: Artificial Sequence
<220> FEATURE:
<223> OTHER INFORMATION: Synthetic

<400> SEQUENCE: 195
catcagatct ttcaggtata                                          20

<210> SEQ ID NO 196
<211> LENGTH: 20
<212> TYPE: DNA
<213> ORGANISM: Artificial Sequence
<220> FEATURE:
<223> OTHER INFORMATION: Synthetic

<400> SEQUENCE: 196
ggctttactc tttaattaaa                                          20

<210> SEQ ID NO 197
<211> LENGTH: 20
<212> TYPE: DNA
<213> ORGANISM: Artificial Sequence
<220> FEATURE:
<223> OTHER INFORMATION: Synthetic

<400> SEQUENCE: 197
gaaatcaaaa aggttgccca                                          20

<210> SEQ ID NO 198
<211> LENGTH: 20
<212> TYPE: DNA
<213> ORGANISM: Artificial Sequence
<220> FEATURE:
<223> OTHER INFORMATION: Synthetic

<400> SEQUENCE: 198
ggagtcctgg agccccctta                                          20

<210> SEQ ID NO 199
<211> LENGTH: 20
<212> TYPE: DNA
<213> ORGANISM: Artificial Sequence
<220> FEATURE:
<223> OTHER INFORMATION: Synthetic

<400> SEQUENCE: 199
ttggcatacg gagcagagct                                          20

<210> SEQ ID NO 200

```
<211> LENGTH: 20
<212> TYPE: DNA
<213> ORGANISM: Artificial Sequence
<220> FEATURE:
<223> OTHER INFORMATION: Synthetic

<400> SEQUENCE: 200
tgtgctctga agtgaaaaga                                                     20

<210> SEQ ID NO 201
<211> LENGTH: 20
<212> TYPE: DNA
<213> ORGANISM: Artificial Sequence
<220> FEATURE:
<223> OTHER INFORMATION: Synthetic

<400> SEQUENCE: 201
ggcttggccc ataagtgtgc                                                     20

<210> SEQ ID NO 202
<211> LENGTH: 20
<212> TYPE: DNA
<213> ORGANISM: Artificial Sequence
<220> FEATURE:
<223> OTHER INFORMATION: Synthetic

<400> SEQUENCE: 202
cctaaatttt atttccaggt                                                     20

<210> SEQ ID NO 203
<211> LENGTH: 20
<212> TYPE: DNA
<213> ORGANISM: Artificial Sequence
<220> FEATURE:
<223> OTHER INFORMATION: Synthetic

<400> SEQUENCE: 203
gctccaagtg tcccaatgaa                                                     20

<210> SEQ ID NO 204
<211> LENGTH: 20
<212> TYPE: DNA
<213> ORGANISM: Artificial Sequence
<220> FEATURE:
<223> OTHER INFORMATION: Synthetic

<400> SEQUENCE: 204
agtatgtttc tcactccgat                                                     20

<210> SEQ ID NO 205
<211> LENGTH: 20
<212> TYPE: DNA
<213> ORGANISM: Artificial Sequence
<220> FEATURE:
<223> OTHER INFORMATION: control oligonucleotide

<400> SEQUENCE: 205
tgccagcacc cggtacgtcc                                                     20

<210> SEQ ID NO 206
<211> LENGTH: 20
<212> TYPE: DNA
<213> ORGANISM: Artificial Sequence
<220> FEATURE:
<223> OTHER INFORMATION: Synthetic

<400> SEQUENCE: 206
```
gctgcctaca ggagccactc                                              20

<210> SEQ ID NO 207
<211> LENGTH: 20
<212> TYPE: DNA
<213> ORGANISM: Artificial Sequence
<220> FEATURE:
<223> OTHER INFORMATION: Synthetic

<400> SEQUENCE: 207
tcaagtccgt gctgcctaca                                              20

<210> SEQ ID NO 208
<211> LENGTH: 20
<212> TYPE: DNA
<213> ORGANISM: Artificial Sequence
<220> FEATURE:
<223> OTHER INFORMATION: Synthetic

<400> SEQUENCE: 208
gtctacagga gtctggttgt                                              20

<210> SEQ ID NO 209
<211> LENGTH: 20
<212> TYPE: DNA
<213> ORGANISM: Artificial Sequence
<220> FEATURE:
<223> OTHER INFORMATION: Synthetic

<400> SEQUENCE: 209
agcttgcgtc tccacggaaa                                              20

<210> SEQ ID NO 210
<211> LENGTH: 20
<212> TYPE: DNA
<213> ORGANISM: Artificial Sequence
<220> FEATURE:
<223> OTHER INFORMATION: Synthetic

<400> SEQUENCE: 210
tcacactatc aagtttctct                                              20

<210> SEQ ID NO 211
<211> LENGTH: 20
<212> TYPE: DNA
<213> ORGANISM: Artificial Sequence
<220> FEATURE:
<223> OTHER INFORMATION: Synthetic

<400> SEQUENCE: 211
gtcaaagctc gtgcggccca                                              20

<210> SEQ ID NO 212
<211> LENGTH: 20
<212> TYPE: DNA
<213> ORGANISM: Artificial Sequence
<220> FEATURE:
<223> OTHER INFORMATION: Synthetic

<400> SEQUENCE: 212
gtgaagtcgt agagtccagt                                              20

<210> SEQ ID NO 213
<211> LENGTH: 20
<212> TYPE: DNA
<213> ORGANISM: Artificial Sequence
<220> FEATURE:

<223> OTHER INFORMATION: Synthetic

<400> SEQUENCE: 213
gtgaccttgc ttagacgtgc                                              20

<210> SEQ ID NO 214
<211> LENGTH: 20
<212> TYPE: DNA
<213> ORGANISM: Artificial Sequence
<220> FEATURE:
<223> OTHER INFORMATION: Synthetic

<400> SEQUENCE: 214
catcttctta ggtttcgggt                                              20

<210> SEQ ID NO 215
<211> LENGTH: 20
<212> TYPE: DNA
<213> ORGANISM: Artificial Sequence
<220> FEATURE:
<223> OTHER INFORMATION: Synthetic

<400> SEQUENCE: 215
ggctgttgga gatactgaac                                              20

<210> SEQ ID NO 216
<211> LENGTH: 20
<212> TYPE: DNA
<213> ORGANISM: Artificial Sequence
<220> FEATURE:
<223> OTHER INFORMATION: Synthetic

<400> SEQUENCE: 216
gggaatgaaa gagagaggct                                              20

<210> SEQ ID NO 217
<211> LENGTH: 20
<212> TYPE: DNA
<213> ORGANISM: Artificial Sequence
<220> FEATURE:
<223> OTHER INFORMATION: Synthetic

<400> SEQUENCE: 217
acatacaatg atgagcagca                                              20

<210> SEQ ID NO 218
<211> LENGTH: 20
<212> TYPE: DNA
<213> ORGANISM: Artificial Sequence
<220> FEATURE:
<223> OTHER INFORMATION: Synthetic

<400> SEQUENCE: 218
gtctctctgt cagcgttact                                              20

<210> SEQ ID NO 219
<211> LENGTH: 20
<212> TYPE: DNA
<213> ORGANISM: Artificial Sequence
<220> FEATURE:
<223> OTHER INFORMATION: Synthetic

<400> SEQUENCE: 219
tgccaagccc atggtgcatc                                              20

<210> SEQ ID NO 220

```
<211> LENGTH: 20
<212> TYPE: DNA
<213> ORGANISM: Artificial Sequence
<220> FEATURE:
<223> OTHER INFORMATION: Synthetic

<400> SEQUENCE: 220
gcaatttggg gttcaagttc                                               20

<210> SEQ ID NO 221
<211> LENGTH: 20
<212> TYPE: DNA
<213> ORGANISM: Artificial Sequence
<220> FEATURE:
<223> OTHER INFORMATION: Synthetic

<400> SEQUENCE: 221
caatcagctg agaacatttt                                               20

<210> SEQ ID NO 222
<211> LENGTH: 20
<212> TYPE: DNA
<213> ORGANISM: Artificial Sequence
<220> FEATURE:
<223> OTHER INFORMATION: Synthetic

<400> SEQUENCE: 222
ttttgtataa aacaatcata                                               20

<210> SEQ ID NO 223
<211> LENGTH: 20
<212> TYPE: DNA
<213> ORGANISM: Artificial Sequence
<220> FEATURE:
<223> OTHER INFORMATION: Synthetic

<400> SEQUENCE: 223
ccttcactct gcatttggtt                                               20

<210> SEQ ID NO 224
<211> LENGTH: 20
<212> TYPE: DNA
<213> ORGANISM: Artificial Sequence
<220> FEATURE:
<223> OTHER INFORMATION: Synthetic

<400> SEQUENCE: 224
tgcatgttat caccatactc                                               20

<210> SEQ ID NO 225
<211> LENGTH: 20
<212> TYPE: DNA
<213> ORGANISM: Artificial Sequence
<220> FEATURE:
<223> OTHER INFORMATION: Synthetic

<400> SEQUENCE: 225
ccctccagtg atgtttacaa                                               20

<210> SEQ ID NO 226
<211> LENGTH: 20
<212> TYPE: DNA
<213> ORGANISM: Artificial Sequence
<220> FEATURE:
<223> OTHER INFORMATION: Synthetic

<400> SEQUENCE: 226
```

-continued gaagaccctc cagtgatgtt                          20

<210> SEQ ID NO 227
<211> LENGTH: 20
<212> TYPE: DNA
<213> ORGANISM: Artificial Sequence
<220> FEATURE:
<223> OTHER INFORMATION: Synthetic

<400> SEQUENCE: 227
cgtagaagac cctccagtga                          20

<210> SEQ ID NO 228
<211> LENGTH: 20
<212> TYPE: DNA
<213> ORGANISM: Artificial Sequence
<220> FEATURE:
<223> OTHER INFORMATION: Synthetic

<400> SEQUENCE: 228
ttcccaggtg caaaacaggc                          20

<210> SEQ ID NO 229
<211> LENGTH: 20
<212> TYPE: DNA
<213> ORGANISM: Artificial Sequence
<220> FEATURE:
<223> OTHER INFORMATION: Synthetic

<400> SEQUENCE: 229
tggcttcaga tgcttagggt                          20

<210> SEQ ID NO 230
<211> LENGTH: 20
<212> TYPE: DNA
<213> ORGANISM: Artificial Sequence
<220> FEATURE:
<223> OTHER INFORMATION: Synthetic

<400> SEQUENCE: 230
cctccgtgtg tggcccatgg                          20

<210> SEQ ID NO 231
<211> LENGTH: 20
<212> TYPE: DNA
<213> ORGANISM: Artificial Sequence
<220> FEATURE:
<223> OTHER INFORMATION: Synthetic

<400> SEQUENCE: 231
ggtgatgttc cctgcctccg                          20

<210> SEQ ID NO 232
<211> LENGTH: 20
<212> TYPE: DNA
<213> ORGANISM: Artificial Sequence
<220> FEATURE:
<223> OTHER INFORMATION: Synthetic

<400> SEQUENCE: 232
gatggtgatg ttccctgcct                          20

<210> SEQ ID NO 233
<211> LENGTH: 20
<212> TYPE: DNA
<213> ORGANISM: Artificial Sequence
<220> FEATURE:

<223> OTHER INFORMATION: Synthetic

<400> SEQUENCE: 233
aggtatggac acttggatgg                                          20

<210> SEQ ID NO 234
<211> LENGTH: 20
<212> TYPE: DNA
<213> ORGANISM: Artificial Sequence
<220> FEATURE:
<223> OTHER INFORMATION: Synthetic

<400> SEQUENCE: 234
gaaagaccag ccagcaccaa                                          20

<210> SEQ ID NO 235
<211> LENGTH: 20
<212> TYPE: DNA
<213> ORGANISM: Artificial Sequence
<220> FEATURE:
<223> OTHER INFORMATION: Synthetic

<400> SEQUENCE: 235
cagcgttgcc acttctttca                                          20

<210> SEQ ID NO 236
<211> LENGTH: 20
<212> TYPE: DNA
<213> ORGANISM: Artificial Sequence
<220> FEATURE:
<223> OTHER INFORMATION: Synthetic

<400> SEQUENCE: 236
gtgaccacag gacagcgttg                                          20

<210> SEQ ID NO 237
<211> LENGTH: 20
<212> TYPE: DNA
<213> ORGANISM: Artificial Sequence
<220> FEATURE:
<223> OTHER INFORMATION: Synthetic

<400> SEQUENCE: 237
agatgcgagt tgtgccagc                                           20

<210> SEQ ID NO 238
<211> LENGTH: 20
<212> TYPE: DNA
<213> ORGANISM: Artificial Sequence
<220> FEATURE:
<223> OTHER INFORMATION: Synthetic

<400> SEQUENCE: 238
ccttttgcca gtagatgcga                                          20

<210> SEQ ID NO 239
<211> LENGTH: 20
<212> TYPE: DNA
<213> ORGANISM: Artificial Sequence
<220> FEATURE:
<223> OTHER INFORMATION: Synthetic

<400> SEQUENCE: 239
cggttcttgt actcgggcca                                          20

<210> SEQ ID NO 240

```
<211> LENGTH: 20
<212> TYPE: DNA
<213> ORGANISM: Artificial Sequence
<220> FEATURE:
<223> OTHER INFORMATION: Synthetic

<400> SEQUENCE: 240
cgcagagcca ggatcacaat                                                    20

<210> SEQ ID NO 241
<211> LENGTH: 20
<212> TYPE: DNA
<213> ORGANISM: Artificial Sequence
<220> FEATURE:
<223> OTHER INFORMATION: Synthetic

<400> SEQUENCE: 241
cttcagccag gtgttcccgc                                                    20

<210> SEQ ID NO 242
<211> LENGTH: 20
<212> TYPE: DNA
<213> ORGANISM: Artificial Sequence
<220> FEATURE:
<223> OTHER INFORMATION: Synthetic

<400> SEQUENCE: 242
taacgtcact tcagccaggt                                                    20

<210> SEQ ID NO 243
<211> LENGTH: 20
<212> TYPE: DNA
<213> ORGANISM: Artificial Sequence
<220> FEATURE:
<223> OTHER INFORMATION: Synthetic

<400> SEQUENCE: 243
ttctccattt tccaaccagg                                                    20

<210> SEQ ID NO 244
<211> LENGTH: 20
<212> TYPE: DNA
<213> ORGANISM: Artificial Sequence
<220> FEATURE:
<223> OTHER INFORMATION: Synthetic

<400> SEQUENCE: 244
ctgttgtgtt gatggcattt                                                    20

<210> SEQ ID NO 245
<211> LENGTH: 20
<212> TYPE: DNA
<213> ORGANISM: Artificial Sequence
<220> FEATURE:
<223> OTHER INFORMATION: Synthetic

<400> SEQUENCE: 245
catgaagctg tggttggttg                                                    20

<210> SEQ ID NO 246
<211> LENGTH: 20
<212> TYPE: DNA
<213> ORGANISM: Artificial Sequence
<220> FEATURE:
<223> OTHER INFORMATION: Synthetic

<400> SEQUENCE: 246
```
aggaaaatgc tcttgcttgg                                              20

<210> SEQ ID NO 247
<211> LENGTH: 20
<212> TYPE: DNA
<213> ORGANISM: Artificial Sequence
<220> FEATURE:
<223> OTHER INFORMATION: Synthetic

<400> SEQUENCE: 247
tgggagcagg ttatcaggaa                                              20

<210> SEQ ID NO 248
<211> LENGTH: 20
<212> TYPE: DNA
<213> ORGANISM: Artificial Sequence
<220> FEATURE:
<223> OTHER INFORMATION: Synthetic

<400> SEQUENCE: 248
taaggtaatg gcccaggatg                                              20

<210> SEQ ID NO 249
<211> LENGTH: 20
<212> TYPE: DNA
<213> ORGANISM: Artificial Sequence
<220> FEATURE:
<223> OTHER INFORMATION: Synthetic

<400> SEQUENCE: 249
ggtcaggcag catatcacaa                                              20

<210> SEQ ID NO 250
<211> LENGTH: 20
<212> TYPE: DNA
<213> ORGANISM: Artificial Sequence
<220> FEATURE:
<223> OTHER INFORMATION: Synthetic

<400> SEQUENCE: 250
gccccttgct tgtgcggaca                                              20

<210> SEQ ID NO 251
<211> LENGTH: 20
<212> TYPE: DNA
<213> ORGANISM: Artificial Sequence
<220> FEATURE:
<223> OTHER INFORMATION: Synthetic

<400> SEQUENCE: 251
agatcttttc agccccttgc                                              20

<210> SEQ ID NO 252
<211> LENGTH: 20
<212> TYPE: DNA
<213> ORGANISM: Artificial Sequence
<220> FEATURE:
<223> OTHER INFORMATION: Synthetic

<400> SEQUENCE: 252
tttgttaagg gaagaatgcc                                              20

<210> SEQ ID NO 253
<211> LENGTH: 20
<212> TYPE: DNA
<213> ORGANISM: Artificial Sequence
<220> FEATURE:

<223> OTHER INFORMATION: Synthetic

<400> SEQUENCE: 253
aaaggagagg gatgccagcc                                                    20

<210> SEQ ID NO 254
<211> LENGTH: 20
<212> TYPE: DNA
<213> ORGANISM: Artificial Sequence
<220> FEATURE:
<223> OTHER INFORMATION: Synthetic

<400> SEQUENCE: 254
caagacaatt caagatggca                                                    20

<210> SEQ ID NO 255
<211> LENGTH: 20
<212> TYPE: DNA
<213> ORGANISM: Artificial Sequence
<220> FEATURE:
<223> OTHER INFORMATION: Synthetic

<400> SEQUENCE: 255
cgtgtgtctg tgctagtccc                                                    20

<210> SEQ ID NO 256
<211> LENGTH: 20
<212> TYPE: DNA
<213> ORGANISM: Artificial Sequence
<220> FEATURE:
<223> OTHER INFORMATION: Synthetic

<400> SEQUENCE: 256
gctgcttctg ctgtgaccta                                                    20

<210> SEQ ID NO 257
<211> LENGTH: 20
<212> TYPE: DNA
<213> ORGANISM: Artificial Sequence
<220> FEATURE:
<223> OTHER INFORMATION: Synthetic

<400> SEQUENCE: 257
tatttgcgag ctccccgtac                                                    20

<210> SEQ ID NO 258
<211> LENGTH: 20
<212> TYPE: DNA
<213> ORGANISM: Artificial Sequence
<220> FEATURE:
<223> OTHER INFORMATION: Synthetic

<400> SEQUENCE: 258
gcataagcac agcagcattc                                                    20

<210> SEQ ID NO 259
<211> LENGTH: 20
<212> TYPE: DNA
<213> ORGANISM: Artificial Sequence
<220> FEATURE:
<223> OTHER INFORMATION: Synthetic

<400> SEQUENCE: 259
tccaaaaaga gaccagatgc                                                    20

<210> SEQ ID NO 260

```
<211> LENGTH: 20
<212> TYPE: DNA
<213> ORGANISM: Artificial Sequence
<220> FEATURE:
<223> OTHER INFORMATION: Synthetic

<400> SEQUENCE: 260
aaatgcctgt ccactgtagc                                              20

<210> SEQ ID NO 261
<211> LENGTH: 20
<212> TYPE: DNA
<213> ORGANISM: Artificial Sequence
<220> FEATURE:
<223> OTHER INFORMATION: Synthetic

<400> SEQUENCE: 261
cttcagagga gcagcaccag                                              20

<210> SEQ ID NO 262
<211> LENGTH: 20
<212> TYPE: DNA
<213> ORGANISM: Artificial Sequence
<220> FEATURE:
<223> OTHER INFORMATION: Synthetic

<400> SEQUENCE: 262
gaatcttcag aggagcagca                                              20

<210> SEQ ID NO 263
<211> LENGTH: 20
<212> TYPE: DNA
<213> ORGANISM: Artificial Sequence
<220> FEATURE:
<223> OTHER INFORMATION: Synthetic

<400> SEQUENCE: 263
caaattggca tggcaggtct                                              20

<210> SEQ ID NO 264
<211> LENGTH: 20
<212> TYPE: DNA
<213> ORGANISM: Artificial Sequence
<220> FEATURE:
<223> OTHER INFORMATION: Synthetic

<400> SEQUENCE: 264
gctttggttt tgagagtttg                                              20

<210> SEQ ID NO 265
<211> LENGTH: 20
<212> TYPE: DNA
<213> ORGANISM: Artificial Sequence
<220> FEATURE:
<223> OTHER INFORMATION: Synthetic

<400> SEQUENCE: 265
aggctttggt tttgagagtt                                              20

<210> SEQ ID NO 266
<211> LENGTH: 20
<212> TYPE: DNA
<213> ORGANISM: Artificial Sequence
<220> FEATURE:
<223> OTHER INFORMATION: Synthetic

<400> SEQUENCE: 266
```
gctcactcag gctttggttt                                              20

<210> SEQ ID NO 267
<211> LENGTH: 20
<212> TYPE: DNA
<213> ORGANISM: Artificial Sequence
<220> FEATURE:
<223> OTHER INFORMATION: Synthetic

<400> SEQUENCE: 267
ggtcctgcca aaatactact                                              20

<210> SEQ ID NO 268
<211> LENGTH: 20
<212> TYPE: DNA
<213> ORGANISM: Artificial Sequence
<220> FEATURE:
<223> OTHER INFORMATION: Synthetic

<400> SEQUENCE: 268
agcccttgtc cttgatctga                                              20

<210> SEQ ID NO 269
<211> LENGTH: 20
<212> TYPE: DNA
<213> ORGANISM: Artificial Sequence
<220> FEATURE:
<223> OTHER INFORMATION: Synthetic

<400> SEQUENCE: 269
tgtgggcttt ttgtgatgga                                              20

<210> SEQ ID NO 270
<211> LENGTH: 20
<212> TYPE: DNA
<213> ORGANISM: Artificial Sequence
<220> FEATURE:
<223> OTHER INFORMATION: Synthetic

<400> SEQUENCE: 270
aatcattcct gtgggctttt                                              20

<210> SEQ ID NO 271
<211> LENGTH: 20
<212> TYPE: DNA
<213> ORGANISM: Artificial Sequence
<220> FEATURE:
<223> OTHER INFORMATION: Synthetic

<400> SEQUENCE: 271
ccgtgtatag atgagcaggt                                              20

<210> SEQ ID NO 272
<211> LENGTH: 20
<212> TYPE: DNA
<213> ORGANISM: Artificial Sequence
<220> FEATURE:
<223> OTHER INFORMATION: Synthetic

<400> SEQUENCE: 272
accgtgtata gatgagcagg                                              20

<210> SEQ ID NO 273
<211> LENGTH: 20
<212> TYPE: DNA
<213> ORGANISM: Artificial Sequence
<220> FEATURE:

<223> OTHER INFORMATION: Synthetic

<400> SEQUENCE: 273
tcatcttctt aggttctggg                                           20

<210> SEQ ID NO 274
<211> LENGTH: 20
<212> TYPE: DNA
<213> ORGANISM: Artificial Sequence
<220> FEATURE:
<223> OTHER INFORMATION: Synthetic

<400> SEQUENCE: 274
acaagctgat ggaaacgtcg                                           20

<210> SEQ ID NO 275
<211> LENGTH: 20
<212> TYPE: DNA
<213> ORGANISM: Artificial Sequence
<220> FEATURE:
<223> OTHER INFORMATION: Synthetic

<400> SEQUENCE: 275
tgctcgtaac atcagggaat                                           20

<210> SEQ ID NO 276
<211> LENGTH: 20
<212> TYPE: DNA
<213> ORGANISM: Artificial Sequence
<220> FEATURE:
<223> OTHER INFORMATION: Synthetic

<400> SEQUENCE: 276
aagatggtca tattgctcgt                                           20

<210> SEQ ID NO 277
<211> LENGTH: 20
<212> TYPE: DNA
<213> ORGANISM: Artificial Sequence
<220> FEATURE:
<223> OTHER INFORMATION: Synthetic

<400> SEQUENCE: 277
cgcgtcttgt cagtttccag                                           20

<210> SEQ ID NO 278
<211> LENGTH: 20
<212> TYPE: DNA
<213> ORGANISM: Artificial Sequence
<220> FEATURE:
<223> OTHER INFORMATION: Synthetic

<400> SEQUENCE: 278
cagctgtaat ccaaggaatg                                           20

<210> SEQ ID NO 279
<211> LENGTH: 20
<212> TYPE: DNA
<213> ORGANISM: Artificial Sequence
<220> FEATURE:
<223> OTHER INFORMATION: Synthetic

<400> SEQUENCE: 279
gggcttcatc agatctttca                                           20

<210> SEQ ID NO 280

```
<211> LENGTH: 20
<212> TYPE: DNA
<213> ORGANISM: Artificial Sequence
<220> FEATURE:
<223> OTHER INFORMATION: Synthetic

<400> SEQUENCE: 280
catgtatcac ttttgtcgca                                           20

<210> SEQ ID NO 281
<211> LENGTH: 20
<212> TYPE: DNA
<213> ORGANISM: Artificial Sequence
<220> FEATURE:
<223> OTHER INFORMATION: Synthetic

<400> SEQUENCE: 281 agcccccctta ttactcatgg                                          20

<210> SEQ ID NO 282
<211> LENGTH: 20
<212> TYPE: DNA
<213> ORGANISM: Artificial Sequence
<220> FEATURE:
<223> OTHER INFORMATION: Synthetic

<400> SEQUENCE: 282
ggagttacag ccaggctatt                                           20

<210> SEQ ID NO 283
<211> LENGTH: 20
<212> TYPE: DNA
<213> ORGANISM: Artificial Sequence
<220> FEATURE:
<223> OTHER INFORMATION: Synthetic

<400> SEQUENCE: 283
agtctcctct tggcatacgg                                           20

<210> SEQ ID NO 284
<211> LENGTH: 20
<212> TYPE: DNA
<213> ORGANISM: Artificial Sequence
<220> FEATURE:
<223> OTHER INFORMATION: Synthetic

<400> SEQUENCE: 284
cccataagtg tgctctgaag                                           20

<210> SEQ ID NO 285
<211> LENGTH: 20
<212> TYPE: DNA
<213> ORGANISM: Artificial Sequence
<220> FEATURE:
<223> OTHER INFORMATION: Synthetic

<400> SEQUENCE: 285
tccgtcatcg ctcctcaggg                                           20

<210> SEQ ID NO 286
<211> LENGTH: 20
<212> TYPE: DNA
<213> ORGANISM: Artificial Sequence
<220> FEATURE:
<223> OTHER INFORMATION: Synthetic

<400> SEQUENCE: 286
```
gctcagcctt tccacttcag                                               20

<210> SEQ ID NO 287
<211> LENGTH: 20
<212> TYPE: DNA
<213> ORGANISM: Artificial Sequence
<220> FEATURE:
<223> OTHER INFORMATION: Synthetic

<400> SEQUENCE: 287
gctcagcctt tccacttcag                                               20

<210> SEQ ID NO 288
<211> LENGTH: 19
<212> TYPE: DNA
<213> ORGANISM: Artificial Sequence
<220> FEATURE:
<223> OTHER INFORMATION: Synthetic

<400> SEQUENCE: 288
ggccctcctc cttgtgatg                                                19

<210> SEQ ID NO 289
<211> LENGTH: 29
<212> TYPE: DNA
<213> ORGANISM: Artificial Sequence
<220> FEATURE:
<223> OTHER INFORMATION: Synthetic

<400> SEQUENCE: 289
tgctcatcat tgtatgtcac aagaagccg                                     29

<210> SEQ ID NO 290
<211> LENGTH: 19
<212> TYPE: DNA
<213> ORGANISM: Artificial Sequence
<220> FEATURE:
<223> OTHER INFORMATION: Synthetic

<400> SEQUENCE: 290
ctgggcctgc taggctgat                                                19

<210> SEQ ID NO 291
<211> LENGTH: 20
<212> TYPE: DNA
<213> ORGANISM: Artificial Sequence
<220> FEATURE:
<223> OTHER INFORMATION: Synthetic

<400> SEQUENCE: 291
caggaagcta cgggcaagtt                                               20

<210> SEQ ID NO 292
<211> LENGTH: 27
<212> TYPE: DNA
<213> ORGANISM: Artificial Sequence
<220> FEATURE:
<223> OTHER INFORMATION: Synthetic

<400> SEQUENCE: 292
tgggcctttg attgcttgat gactgaa                                       27

<210> SEQ ID NO 293
<211> LENGTH: 18
<212> TYPE: DNA
<213> ORGANISM: Artificial Sequence
<220> FEATURE:

<223> OTHER INFORMATION: Synthetic

<400> SEQUENCE: 293
gtgggctcag cctttcca                                               18

<210> SEQ ID NO 294
<211> LENGTH: 20
<212> TYPE: DNA
<213> ORGANISM: Artificial Sequence
<220> FEATURE:
<223> OTHER INFORMATION: Synthetic

<400> SEQUENCE: 294
tcaagtcctt ccacacccaa                                             20

<210> SEQ ID NO 295
<211> LENGTH: 1424
<212> TYPE: DNA
<213> ORGANISM: Homo sapiens
<220> FEATURE:
<221> NAME/KEY: CDS
<222> LOCATION: (148)...(1119)

<400> SEQUENCE: 295
aggagcctta ggaggtacgg ggagctcgca aatactcctt ttggtttatt cttaccacct    60
tgcttctgtg ttccttggga atgctgctgt gcttatgcat ctggtctctt tttggagcta   120
cagtggacag gcatttgtga cagcact atg gga ctg agt aac att ctc ttt gtg  174
                              Met Gly Leu Ser Asn Ile Leu Phe Val
                                1               5 atg gcc ttc ctg ctc tct ggt gct gct cct ctg aag att caa gct tat    222
Met Ala Phe Leu Leu Ser Gly Ala Ala Pro Leu Lys Ile Gln Ala Tyr
 10              15                  20                  25 ttc aat gag act gca gac ctg cca tgc caa ttt gca aac tct caa aac    270
Phe Asn Glu Thr Ala Asp Leu Pro Cys Gln Phe Ala Asn Ser Gln Asn
             30                  35                  40 caa agc ctg agt gag cta gta gta ttt tgg cag gac cag gaa aac ttg    318
Gln Ser Leu Ser Glu Leu Val Val Phe Trp Gln Asp Gln Glu Asn Leu
         45                  50                  55 gtt ctg aat gag gta tac tta ggc aaa gag aaa ttt gac agt gtt cat    366
Val Leu Asn Glu Val Tyr Leu Gly Lys Glu Lys Phe Asp Ser Val His
     60                  65                  70 tcc aag tat atg ggc cgc aca agt ttt gat tcg gac agt tgg acc ctg    414
Ser Lys Tyr Met Gly Arg Thr Ser Phe Asp Ser Asp Ser Trp Thr Leu
 75                  80                  85 aga ctt cac aat ctt cag atc aag gac aag ggc ttg tat caa tgt atc    462
Arg Leu His Asn Leu Gln Ile Lys Asp Lys Gly Leu Tyr Gln Cys Ile
 90                  95                 100                 105 atc cat cac aaa aag ccc aca gga atg att cgc atc cac cag atg aat    510
Ile His His Lys Lys Pro Thr Gly Met Ile Arg Ile His Gln Met Asn
             110                 115                 120 tct gaa ctg tca gtg ctt gct aac ttc agt caa cct gaa ata gta cca    558
Ser Glu Leu Ser Val Leu Ala Asn Phe Ser Gln Pro Glu Ile Val Pro
         125                 130                 135 att tct aat ata aca gaa aat gtg tac ata aat ttg acc tgc tca tct    606
Ile Ser Asn Ile Thr Glu Asn Val Tyr Ile Asn Leu Thr Cys Ser Ser
     140                 145                 150 ata cac ggt tac cca gaa cct aag aag atg agt gtt ttg cta aga acc    654
Ile His Gly Tyr Pro Glu Pro Lys Lys Met Ser Val Leu Leu Arg Thr
 155                 160                 165 aag aat tca act atc gag tat gat ggt att atg cag aaa tct caa gat    702
Lys Asn Ser Thr Ile Glu Tyr Asp Gly Ile Met Gln Lys Ser Gln Asp
             170                 175                 180                 185

```
aat gtc aca gaa ctg tac gac gtt tcc atc agc ttg tct gtt tca ttc      750
Asn Val Thr Glu Leu Tyr Asp Val Ser Ile Ser Leu Ser Val Ser Phe
            190                 195                 200 cct gat gtt acg agc aat atg acc atc ttc tgt att ctg gaa act gac      798
Pro Asp Val Thr Ser Asn Met Thr Ile Phe Cys Ile Leu Glu Thr Asp
                205                 210                 215 aag acg cgg ctt tta tct tca cct ttc tct ata gag ctt gag gac cct      846
Lys Thr Arg Leu Leu Ser Ser Pro Phe Ser Ile Glu Leu Glu Asp Pro
            220                 225                 230 cag cct ccc cca gac cac att cct tgg att aca gct gta ctt cca aca      894
Gln Pro Pro Pro Asp His Ile Pro Trp Ile Thr Ala Val Leu Pro Thr
        235                 240                 245 gtt att ata tgt gtg atg gtt ttc tgt cta att cta tgg aaa tgg aag      942
Val Ile Ile Cys Val Met Val Phe Cys Leu Ile Leu Trp Lys Trp Lys
250                 255                 260                 265 aag aag aag cgg cct cgc aac tct tat aaa tgt gga acc aac aca atg      990
Lys Lys Lys Arg Pro Arg Asn Ser Tyr Lys Cys Gly Thr Asn Thr Met
                270                 275                 280 gag agg gaa gag agt gaa cag acc aag aaa aga gaa aaa atc cat ata     1038
Glu Arg Glu Glu Ser Glu Gln Thr Lys Lys Arg Glu Lys Ile His Ile
            285                 290                 295 cct gaa aga tct gat gaa gcc cag cgt gtt ttt aaa agt tcg aag aca     1086
Pro Glu Arg Ser Asp Glu Ala Gln Arg Val Phe Lys Ser Ser Lys Thr
        300                 305                 310 tct tca tgc gac aaa agt gat aca tgt ttt taa ttaaagagta aagcccatac   1139
Ser Ser Cys Asp Lys Ser Asp Thr Cys Phe *
        315                 320 aagtattcat tttttctacc ctttcctttg taagttcctg ggcaaccttt ttgatttctt   1199
ccagaaggca aaaagacatt accatgagta ataaggggc tccaggactc cctctaagtg    1259
gaatagcctc cctgtaactc cagctctgct ccgtatgcca agaggagact ttaattctct   1319
tactgcttct tttcacttca gagcacactt atgggccaag cccagcttaa tggctcatga   1379
cctggaaata aaatttagga ccaataaaaa aaaaaaaaa aaaaa                    1424

<210> SEQ ID NO 296
<211> LENGTH: 2781
<212> TYPE: DNA
<213> ORGANISM: Homo sapiens
<220> FEATURE:
<221> NAME/KEY: CDS
<222> LOCATION: (117)...(1106)

<400> SEQUENCE: 296
ggaaggcttg cacagggtga agctttgct tctctgctgc tgtaacaggg actagcacag     60
acacacggat gagtggggtc atttccagat attaggtcac agcagaagca gccaaa atg   119
                                                                  Met
                                                                   1 gat ccc cag tgc act atg gga ctg agt aac att ctc ttt gtg atg gcc    167
Asp Pro Gln Cys Thr Met Gly Leu Ser Asn Ile Leu Phe Val Met Ala
            5                   10                  15 ttc ctg ctc tct ggt gct gct cct ctg aag att caa gct tat ttc aat    215
Phe Leu Leu Ser Gly Ala Ala Pro Leu Lys Ile Gln Ala Tyr Phe Asn
        20                  25                  30 gag act gca gac ctg cca tgc caa ttt gca aac tct caa aac caa agc    263
Glu Thr Ala Asp Leu Pro Cys Gln Phe Ala Asn Ser Gln Asn Gln Ser
    35                  40                  45 ctg agt gag cta gta gta ttt tgg cag gac cag gaa aac ttg gtt ctg    311
Leu Ser Glu Leu Val Val Phe Trp Gln Asp Gln Glu Asn Leu Val Leu
50                  55                  60                  65
```

```
aat gag gta tac tta ggc aaa gag aaa ttt gac agt gtt cat tcc aag        359
Asn Glu Val Tyr Leu Gly Lys Glu Lys Phe Asp Ser Val His Ser Lys
            70                  75                  80 tat atg ggc cgc aca agt ttt gat tcg gac agt tgg acc ctg aga ctt        407
Tyr Met Gly Arg Thr Ser Phe Asp Ser Asp Ser Trp Thr Leu Arg Leu
        85                  90                  95 cac aat ctt cag atc aag gac aag ggc ttg tat caa tgt atc atc cat        455
His Asn Leu Gln Ile Lys Asp Lys Gly Leu Tyr Gln Cys Ile Ile His
                100                 105                 110 cac aaa aag ccc aca gga atg att cgc atc cac cag atg aat tct gaa        503
His Lys Lys Pro Thr Gly Met Ile Arg Ile His Gln Met Asn Ser Glu
        115                 120                 125 ctg tca gtg ctt gct aac ttc agt caa cct gaa ata gta cca att tct        551
Leu Ser Val Leu Ala Asn Phe Ser Gln Pro Glu Ile Val Pro Ile Ser
130                 135                 140                 145 aat ata aca gaa aat gtg tac ata aat ttg acc tgc tca tct ata cac        599
Asn Ile Thr Glu Asn Val Tyr Ile Asn Leu Thr Cys Ser Ser Ile His
                150                 155                 160 ggt tac cca gaa cct aag aag atg agt gtt ttg cta aga acc aag aat        647
Gly Tyr Pro Glu Pro Lys Lys Met Ser Val Leu Leu Arg Thr Lys Asn
            165                 170                 175 tca act atc gag tat gat ggt att atg cag aaa tct caa gat aat gtc        695
Ser Thr Ile Glu Tyr Asp Gly Ile Met Gln Lys Ser Gln Asp Asn Val
        180                 185                 190 aca gaa ctg tac gac gtt tcc atc agc ttg tct gtt tca ttc cct gat        743
Thr Glu Leu Tyr Asp Val Ser Ile Ser Leu Ser Val Ser Phe Pro Asp
    195                 200                 205 gtt acg agc aat atg acc atc ttc tgt att ctg gaa act gac aag acg        791
Val Thr Ser Asn Met Thr Ile Phe Cys Ile Leu Glu Thr Asp Lys Thr
210                 215                 220                 225 cgg ctt tta tct tca cct ttc tct ata gag ctt gag gac cct cag cct        839
Arg Leu Leu Ser Ser Pro Phe Ser Ile Glu Leu Glu Asp Pro Gln Pro
                230                 235                 240 ccc cca gac cac att cct tgg att aca gct gta ctt cca aca gtt att        887
Pro Pro Asp His Ile Pro Trp Ile Thr Ala Val Leu Pro Thr Val Ile
        245                 250                 255 ata tgt gtg atg gtt ttc tgt cta att cta tgg aaa tgg aag aag aag        935
Ile Cys Val Met Val Phe Cys Leu Ile Leu Trp Lys Trp Lys Lys Lys
                260                 265                 270 aag cgg cct cgc aac tct tat aaa tgt gga acc aac aca atg gag agg        983
Lys Arg Pro Arg Asn Ser Tyr Lys Cys Gly Thr Asn Thr Met Glu Arg
    275                 280                 285 gaa gag agt gaa cag acc aag aaa aga gaa aaa atc cat ata cct gaa        1031
Glu Glu Ser Glu Gln Thr Lys Lys Arg Glu Lys Ile His Ile Pro Glu
290                 295                 300                 305 aga tct gat gaa acc cag cgt gtt ttt aaa agt tcg aag aca tct tca        1079
Arg Ser Asp Glu Thr Gln Arg Val Phe Lys Ser Ser Lys Thr Ser Ser
                310                 315                 320 tgc gac aaa agt gat aca tgt ttt taa ttaaagagta aagcccatac              1126
Cys Asp Lys Ser Asp Thr Cys Phe *
                325 aagtattcat ttttctacc ctttcctttg taagttcctg ggcaaccttt ttgatttctt       1186 ccagaaggca aaaagacatt accatgagta ataaggggggc tccaggactc cctctaagtg     1246 gaatagcctc cctgtaactc cagctctgct ccgtatgcca agaggagact ttaattctct      1306 tactgcttct tttcacttca gagcacactt atgggccaag cccagcttaa tggctcatga     1366 cctggaaata aaatttagga ccaataccctc ctccagatca gattcttctc ttaatttcat    1426 agattgtgtt ttttttaaa tagacctctc aatttctgga aaactgcctt ttatctgccc      1486
```

```
agaattctaa gctggtgccc cactgaatct tgtgtacctg tgactaaaca actacctcct   1546
cagtctgggt gggacttatg tatttatgac cttatagtgt taatatcttg aaacatagag   1606
atctatgtac tgtaatagtg tgattactat gctctagaga aaagtctacc cctgctaagg   1666
agttctcatc cctctgtcag ggtcagtaag gaaaacggtg gcctagggta caggcaacaa   1726
tgagcagacc aacctaaatt tggggaaatt aggagaggca gagatagaac ctggagccac   1786
ttctatctgg gctgttgcta atattgagga ggcttgcccc acccaacaag ccatagtgga   1846
gagaactgaa taaacaggaa aatgccagag cttgtgaacc ctgtttctct tgaagaactg   1906
actagtgaga tggcctgggg aagctgtgaa agaaccaaaa gagatcacaa tactcaaaag   1966
agagagagag agaaaaaaga gagatcttga tccacagaaa tacatgaaat gtctggtctg   2026 tccacccat caacaagtct tgaaacaagc aacagatgga tagtctgtcc aaatggacat   2086
aagacagaca gcagtttccc tggtggtcag ggaggggttt tggtgatacc caagttattg   2146
ggatgtcatc ttcctggaag cagagctggg gaggagagc catcaccttg ataatgggat   2206
gaatggaagg aggcttagga ctttccactc ctggctgaga gaggaagagc tgcaacggaa   2266
ttaggaagac caagcacag atcacccggg gcttacttag cctacagatg tcctacggga   2326
acgtgggctg gcccagcata gggctagcaa atttgagttg gatgattgtt tttgctcaag   2386
gcaaccagag gaaacttgca tacagagaca gatatactgg gagaaatgac tttgaaaacc   2446
tggctctaag gtgggatcac taagggatgg ggcagtctct gcccaaacat aaagagaact   2506
ctggggagcc tgagccacaa aaatgttcct ttattttatg taaaccctca agggttatag   2566
actgccatgc tagacaagct tgtccatgta atattcccat gttttttaccc tgcccctgcc   2626 ttgattagac tcctagcacc tggctagttt ctaacatgtt ttgtgcagca cagtttttaa   2686
taaatgcttg ttacattcaa aaaaaaaaaa aaaaaaaaa aaaaaaaaa aaaaaaaaa   2746 aaaaaaaaa aaaaaaaaa aaaaaaaaa aaaaa                              2781

<210> SEQ ID NO 297
<211> LENGTH: 68001
<212> TYPE: DNA
<213> ORGANISM: Homo sapiens

<400> SEQUENCE: 297
gctgtcttgg tggtggtatt tctgttgcag ttgttgtttt cttgcctgct tggtgacata     60
tttctattga cttgacactt aactggcatc ttatctaggt agataatgct aattcaaaat    120
tctgcagata ttgttctgtt gttttttgcc atttagggtt gagtaagatg ccaagttgtt    180
ttttgtttct ctgtagtcat tctgtttca ttttgttttt agctttgcct ttggaattta    240
aaatgttcaa aatgatttgt ctggatgaga atcgattttc ataactttg ctttgataca    300 ctaaacagtt tgagtttcta gatgatgccc attttaattc atacgaggaa atatcttcta    360
gtatagtttc tgcttgatta attctatgtt tgtctcttag ggacatctat taattttata    420
atgctgcctt ttttcagac ttctgtttca gaatattcgc tttcatcaat gtaatccttg    480
gctatagtag gaatgaaata ataaagcag tagcttctgt ctgccctcct tggttatgca    540
gtccttacag aacatctccc catctcccat ccccccaccc cagctcagtg aaactctcca    600
cactttggtt gtgaaattg gcagggttag gtggctactc actcccaatc cacatccaca    660
ataaatcact ttttattatc ttatcaaaat ctgtagaatg cctctttatt ctattttgtt    720 gctgcgagg tttgttttct ctttctaatt atttttattt ctaggttttt tgagggaatt    780
tcaagagggg agatttttta ttcaggctca tcttaacgtc atgtctggaa ctcaagctac    840
```

```
tgaattatat attctttaat acatatagac ctacgtcaat gagtttaaac tgcaaggaaa    900
gggttaaatt tcttcctcaa gtgtggtcaa aatctgtaga gaaaagagga acagcttctc    960
ttaaagaaag ttagctgggt aggtatacag tcattgccga ggaaggcttg cacagggtga   1020
aagctttgct tctctgctgc tgtaacaggg actagcacag acacacggat gagtggggtc   1080
atttccagat attaggtcac agcagaagca gccaaaatgg atccccagtg gtgagtaata   1140
attcttattc tttgcagaga agttatgagt tgtgactgca gtgaaaggct gaggttgaag   1200
atggtgcttt gatgtgtgtc cttcacttag ttcctaagtg gagaagcttt cttttctac    1260 aaaagatctt tggcacataa aggcaagaat tatttgcaat gcccaaagca gttcattggt   1320
ggtagttata tatattttta ggtgcctaat tttggttttg taaatctgtt attcaaatac   1380
tgaatgttac agtcattgat tttagtgaag aatcaggaat ttttaaaata tctgcataag   1440
aatgacaaat aacagggaat atgttttttg tctaccaggg tcagtttggt ctgagggtgg   1500
aggaatgaga tagagaaggt agagggagag agatcaagaa aaagaaagag aaaaagagg    1560 tataaggaga aaatgcaaaa ctcagttaat atgtcataat caggccatgg gagattctgg   1620
gcagggttgg gtagtggaag gaggtagagt gattaaatta gttaccatgt attgaacatg   1680
catgatgtgc tgggtacttt actagtgcta tttcattgaa ttttattctt cacaatgact   1740
tttggaaaga catcatcatt cttttttgaca gatggggtaa ctgtggctta aaaaacttgc   1800
ccaagttcac actattcata aggggtagag ctaaaatctt tcctgcccgc ttcgtggtgc   1860
gccagaaggt ttctccatgc tgtgagact tcctggaagg agtcacaccc gcccttctct   1920
tgggtggtgg cagctggcgc cagtcactat gtatttattt atttttaatt atttattttt   1980
gaaacagagt ctcgctctgt cgccaagctg gagtgcagtg gcgcaatctc agctcactgc   2040
aacctccgcc tctcggattc aaacgattct ccttcctcag tctcctgagt agctgggact   2100
acaggcgccc accaccacgc ccggctaatt tttgtatttt tggtagagac ggggtccacc   2160
atgttggcca ggatggtctc gatctcttga ccttgtgatc tggccacctc ggcctcccaa   2220
agtgctggga ttacaggcgt gagccaccgc gcacccggcc gtcactatgt atttataatt   2280
actgttcttt gaaaatcgaa gtaactttca tctacccagt gcttactggt ttgagaaaaa   2340
gctttgttgc ttttatttca gaagattaaa atttaatttt ccagtaaaga ttccttttgc   2400
tccagtggaa ttttgaagcg ttatacttgt atgaagaaaa aaagaatttc aaaatttata   2460 attttttgtgg taccatagag gggatactac ttaattatgc tagcactgtc tgcagaggtc   2520
taaaaaacca taggctgctg tctatattga acttgttaag attccttttg tttcacagtg   2580
cctgaagatt ggtcatgaac cagtaatagc cattaaacaa tgtctgttct cataagagat   2640
gaaataaata caaattaaaa caacagtgaa gtatcatttt ttctctatca aagagataaa   2700
tattaagttt taaaaagcaa gcaatcaaga accctctatc ttgctaagaa gggaggatta   2760
tttgtaccct agttgcgcac tagtggtgat atcatctttc tggacaataa tctagtgata   2820
catatcaaaa gcctttaaaa tgtatatgcc ctttaaccaa gcaattcacc ttttaggaat   2880
ttattctaag atataataat acatgttgt aaagttttag tgatggatat ttttcttgct    2940
attgtttcta ataaggaaaa tcttagaaac aatttacgtg tttaaaaaca agtgattgga   3000
tgattatgga acatccataa tggaatacca tgtaattatt taaaattcca ctgtagaaca   3060
attcataatg tgtttagtta aagggggaaaa atgcagaacg aacagtgcta tcactttat    3120 acatgataca tgtatacaaa caatattaat cagaaatata ggtagtttgt attttctact   3180
gtgtgctttt caatttgaat cccatctgta ggcagaaaaa taaagttaaa tatttaagat   3240
```

```
ttaaaaaaaa caatagctgg ttttttttcag agaagtaacc atctagtgat gtgtgataat    3300
ttataagttg tgagattcca tagttagggc tttagcccct tgcatttatc tttcttcatc    3360
tcttgaatcc tcttcaaaat acacccactc tacccataac tcattagatc ttgaaaggca    3420
tgttctgata gaattttata tttagaacag gctgcagcac tcttccctta ttttacagaa    3480
gtgattgcat ggctctctag ggtgagttgc atattgagag ggaggacagt gcagtggcta    3540
agtggccgca cattgaagcc aggctgctgg ggtttgaata ccagttcccc aacttcctag    3600
ctatgtgatt ttggacaagt tgcttaacca ttgtaattcc cagtttcttg tctgtaaaat    3660
gggagtatgg taatatgtcg taaagtagtt gtgagatttt aatgagataa tccatatcct    3720
gctaagtact caggaattgt tagtagtttt tattactatt actgtttgga ttaagaaaca    3780
gaggaaaagt gatttgtcca agattataca accacttaat ggcattacta agaacagaat    3840
ggaggaaggt ttttccagc agaaatgttc agtatcctct gtgcctggca ggacaacccc    3900
aagttgtgct tttgggatgg aggagctgat ctaaaacaag cagtacccag acaaggcca    3960
gcctccaggg agtgactgat gacagtggga agccaaatgg tagaaaggca ggtgaagtta    4020
aggaaactga gagtcaactt aggagcagga atgaagcctg gagcaaagag ctagtgcaag    4080
agagagcaga tgactcagag ctactggggc ttttgtaggc caccagctat gggcttcacg    4140
ggaggttaat gtggtttaaa gtctcaagac ctgggtaatt aaatagacaa atggggtcta    4200
ggtgcatggg ggaattttaa gtatagcttt gagaagatgc ctaatgggga gtaataatag    4260
agaaagaagc tgggtggggc cagaacaagg agcccacagt ccaggcatcc agctatgatc    4320
atcctaaagg aacagcctaa gtttgaagaa tcataaacaa atagagacat gataaaattt    4380
acttaaaaaa aaatcccttg gcagaagaat gaaaactgat ttggagtgac aaggagatca    4440
tttaggagac tattggagta agccaaggag aaatggcgag ggcatgaaac cagggcagtt    4500
atggtgggat cagactggag aggatgcatt taagagatat tttagcacca gaattgacag    4560
aatttggttt ttgacagatg tagacactgg gagaggagga gagatctaag tgcatagtgg    4620
catccttcac aaaatggaag gtataggaag cagagtgggt ttgcgccagg cagagagaaa    4680
agacagatgg tgaattcctt ctctaacatg ttgagtttga ggtgcctgtg gagcagctgg    4740
atagagatgt ccaagcagac aagtagatat ttaggtgcaa gttcaaaaaa gagggatggc    4800
ctggaatgca catgaagagt cttctgcata agtatggttg acagttgaaa ttctcattgt    4860
gggtcaattc agtagcagag aggttggagg attgagagga agccaaggac agaacctgga    4920
aaaccttgac atctaaggag ggagatgagg aagaagaatc tacaatagat actaaggagg    4980
ggctagagag actggagcag cccaggagaa aagtggtgtc atagaaatca agtgggcctg    5040
tagtcccagc tacttgggag actgaggcac gagaatagct tgaacccagg aggcagaggt    5100
tgcagtgagc tgagatagca ccacggcact ccagcctggg tgacagagtg agactccgtc    5160
tcaaaaaaaa aaaaaaaga aagaaatcaa gtggggagat ggatgcaaga aagaggagaa    5220
tgcattcatg gaaagagcat atttaccaag cttttccatgt tgaacacatg agatgtgaca    5280
tgaaaggtaa ctgtagtgac tacatgttaa gcgttgaatt gtggctccct taaaattcat    5340
atgttgaaat cctaactccc agggcttcag gatttgatca tatttggaga tagggtcttt    5400
acagagataa taaatttaa atgaggtcat tagggtgggt cctaatccaa gacaattgtt    5460
gtgcttattg taaggaaggg aaacacacag cggaaaagcg gtgtgaagac acagggcgaa    5520
gacggccatc cacatacaag ccagagagaa aggctcgcaa cagattcttt cctcacaacc    5580
ttcagaaaga accaaccctg tggaaaccct aagtttggac tcctggcttc cagaaaaaaa    5640
```

```
ataaatttttt tttgtttaag ccaccccagt ttgtggtact ttgttaccac agccccagca    5700
aactaataca cttggtgaga gtgcatacag ccagagaaag aagctgtgaa taagtgcatc    5760
agggaggagg gaaagaaacc aaaacaggat tacatcactt aaattaagag tagaaacatt    5820
tcacaaagca gagtgtagtc acaggtcaaa ttctgcagaa aggcgaagta ggagaatgac    5880
tgaaaatgtc agtccagagg ccctcagtga ccttgacctt tgcagaacac tcccagttga    5940
gtggaggcag tagactttgg agagcttgga aaatggaggc agcacagatg gtctcctgca    6000
gaaagtctgg tgataaaatg agacctcctc actggagtaa actcacctct gctgtcggtg    6060
gaaataatct ggagtcaggc cagccagacc cagagttctt ccttcctcca ttttaaaggt    6120
taaacagagc tgaggtcaat ggctcatgcc tgtaatccca gtgactcagg aggcggaggt    6180
gggaggatgc cttgaggcga ggagttccgt tcaagaccag tctgagcaac atagcgagac    6240
tcccattcct aaaaaaattt taatttaaat taaaaaaaaa ggctaaccaa aaataaaatc    6300
caatacttta tttttcccac ccaaaactag tttgggaagg atttctggaa gaaataatt    6360 tttgcagtca ttttacatgt tggattttga gtgcacataa catacagatt ctattctgta    6420
ttatcagttc agaggcaagt tgagatttga ggcttcgcag aggtaaagcc tctggtgaat    6480
ctggtgagat aaagaagaaa acaagcccaa gaggaatttc agggatcatt tataatttac    6540
atcaataaac agaatgggaa aaaaaaccca ttagagtttg gaatagagaa gtattaaaac    6600
actttcttag aaagctttga gtcaaaatta atctttctgt agtggcagga atatgataag    6660
ccaaacaacc ctaatgtcac agctctatat tattaggtgt cgaatcagat ttgcactaaa    6720
acatcaagta aaaataaaag gaatgaacat ttggttaagt gaaccaatta gtcaatacac    6780
gccagaaaat ggtaaaactg gataaaccta aatactcaa ctaccctagat taatcaaggc    6840 caacctagat tatcaccccca atattacaac tattttcaac caactaaaca ataaatcttt    6900
atcaagagcc tgatagttta aggtactgtg atgaatacaa atgaaattgc tgatactttt    6960
tttcaagtct atttagaaat agaaacccac aattatgaaa tgacaaaaac aattaatgca    7020
gttaataatt cagtaacttt taaaagaaa taaacatgac aaaagttca ttctcaccaa    7080 atactaaaga aatgccaatt caaacaccaa tgagatattt tcctgtatca gattagacag    7140
taaaacaaac aatccaatca gaaaatggg caaaagatat aaaagacat ttccccaaag    7200 aaaatataca gatggtgaac aaccatataa gagagtcaac atcatttgcc tttatgaaaa    7260 aattaaaccca ctacctacct ataaaaatgg ttaaaataat aaaagataat gacaacacca    7320
aatgatggca ggatgcggag aaactggatc atgcatacat tgcttgttgg gaatgtacaa    7380
tggtcaagcc actctagaaa acagtttggc agtttcttat aaaaccaaac atgcatttag    7440
tatatgaccc agcaactgca ttcttgggtt ttgatcccag agaataaaaa gcctatgctc    7500
ctgcaaaaat cagtatatga atatttatac cagctttatt cataatagta aaaactggg    7560 gaaaaaagtc cctcagtggg tgaatcgtaa cacaaactgt gtgtgcaaga tgttaccact    7620
gaaggaagct gggtgaaggt acacaggact tccctgtaca tttttttcaac ttcttttgaa    7680 tcaataatta tttaaaaatg aaaagtttaa aaagtaaaaa aaaaaaacaa aaactaaaaa    7740
tgttcatctt cactaaatat taaaaaaat gccaattcaa acacaagata ttctcctttt    7800
acaaattaac aatttatatg gattttggga gggttgggag taatcatgct aataagtatg    7860
caataagagg atactttcgt atactactga ttgtgggaat atgaatgggg agaacatttc    7920
tggaaagcaa tatgtcaaca atatcaagag tcttaaaaat ggttgtacaa gcagacaccc    7980
attctgggca ctgccaattt ctccatgtcc ttagtacatt tttttttcagt tcattcagca    8040
```

```
tctttgttcc aggcactgtg ctaaacatta aaaatacacc aaagatgagt atgagtaaac    8100
atgatttctg ttctcaagaa tttcagtttt gtggtaaata tatcaaaggt gattttttat    8160
aagagttttt tataacaggg tgtgacgttt cataggagca tgaaggtagc tgtttcctat    8220
ttgtctgtag gcagtatgat gtcttagata aatgccaggg ttttgagcta gtttggttgg    8280
tatcaaataa taagtagtta ataaatcatc ttctatttat tagtggtatc actttgggaa    8340
gcctattagc ttcctgaact tcagtgtcct ctgtaagatg aggctactaa gcacttgcca    8400
atgccatgag gaatataaca atttataatg gacaggaagt cctatggata taagatattt    8460
taggactcac attctttgct ttaaaatcta ttatttccta tattttttaat tgtcagagtt    8520 ctttagctct gccttttctg attgatttcc agcagatgga ctcttaccta taacctagaa    8580
gttgctatag tagacctcct aactatagat aagagaaggg catgccaaat gcagttgaat    8640
caggtgaaag tcaagcaaca aagctgccta aaataaattt tatgtaaggt agggtgccaa    8700
aatcattaaa ataaaattct attctataac tgtaatcacg taagtgcttt catgaagttg    8760
tctatgaaaa ctttcttttt cgctttctgg acttcaaata ttttaagttt gcttttcatt    8820
tacaaagatt ttttttgctca ttagtaatca tgaactgtat tcaaacttac acttctaatt    8880
ctagaagata tataaactac cattttttaa ttataaaaat gtttatatat cttgctttaa    8940
taatttcacc tctagggatc tagctagtta ataacaaga gctacggaaa catatttgtg    9000
caccaaaatg tttattacat tatttaatgt aatgaaaaat aagaatcaac ctaaataagt    9060
agaagaatag gtaagtaagt taaaatgaa gttaataatg actccttaat gagagaagac    9120
aacataaggc tacatacaga attgtaaaga aaataatcca cagaatgtgt gttttatttt    9180
ggtaaatggt tcctaaaact aagtaagtac atagaaagat ttttttttttt tttttttaa    9240 agacagagtc tcactcacgt tgtcacctag gctggagtgc agtagtgcaa tctcagttca    9300
ctgcagcctt cacctcccgg gttcaggaca cgccaccaca cccagctaat tttcttgtat    9360
ttttagtaga gacacagttt catcatgggg ctggtctcaa actcctgacc tcaagtgatc    9420
tgcccacctt ggccttctaa agtgctgtat tataggtgtg acccaccgca cctggcctag    9480
gaagaatttt agaaagaaag ctccatatca ggaattgaga agccggtgtt ttaattgaga    9540
atatatttgc acagaaaaat cttggcataa atattggttt acaaaacaaa caaacaaagt    9600
aatgtccttt aatcttggat caggagctgc ccaacaactc caaaaagtca gctcatgcaa    9660
aaccatccaa ggacagatga atcagccaaa caagagagaa aggggaaggg aaagtgtctt    9720
ttcacaggca gcttttgagg cagtgcataa accatgcctc tgcaccatcc agaccagaca    9780
gttgtgacac agggttgaca aagcaggaca acgaagggta gctgctccta aggtggggat    9840
gatgctggag caaggggag caccaagagg aaaaaaaaaa agcataaaaa taagatagca    9900
tagtaaaaaa taagatagtc atagtagtta cctcttgatt gatgggatta tggaaatagg    9960
gttatttctt tgactaaaat tgccagatct tcagtacaat tacattgctc tgctgagcag   10020
gatgaaatca agttgaaaag taatctagta gtgaggtaca gcccgtatgc tgcaaatggc   10080
caacatagat cctcagatga cagaagtgag tgatgcaggc ctgtggttta cgtacagctc   10140
catgacgtat gaatggcaga agctgtgtat gtccacaggc gagccccatt tcaagaagtg   10200
cttctggtca ccactctgtt gtcctgtgta taaggatgtg gttcagaaca gccaagtctt   10260
atatttcaag aggagccaga aagacaaact taccagtgaa atcctaatat ttatataata   10320
gctcaatatc tggagggget ggtttggtat aaatcaccag ttttacctct gacctctgtt   10380
aatgcatcag aggttcagga gagagtgaga aaattgtaaa tggaatattt taggactatt   10440
```

```
atattggggc caggctttta gtgagtcaga gcgagaaagt aggggggctga aactatttga    10500 ctattaattt attcaataaa gttttattta atgttggaaa gatgaagatg aatcagatag    10560
aaatcctgtt tagaagcttc tatgggaaga gatatcacca tagctaatat gtcttagcct    10620
ctaaaaggaa ttatggcaaa ctatattgta tcatatatga tctcatttaa tcatcataac    10680
tgcaggaggt aagtagtatt atccctgatt ttccataagt gaaaactgag tctctcttag    10740
ttacatagct gacaacacaa ccaggattcc aaatgccagt ctgatcccag agccaagcta    10800
tgaacaacca tgctatatat tatggcagat cagggaagga agacattact tctagcagca    10860
agaaacattt gtggatgaaa agatttgagc ttggagagag ctgtgttgag ccatgtccaa    10920
aacaattttt ggcaaccata cgataaaggt aaaagccaga gattgaaaag taaaagctgg    10980
tggactaaaa atggtccata gacagagagt catcaaaaca acaaaacaaa acaaaaacct    11040
taatcataat taattgccaa tatttcaaaa gtctggagaa ttcacataag tttagatttc    11100
cagctcttct ggagaattag aatatctagt aacagtgtgc taataatccc acatggtaac    11160
aactggtgaa tctggcagag gctgcccagc ttccaatggt gtataagctc tcctcttcct    11220
atgcaacctg cctgcctcat ttatatgagc tgcttggatg ctgcagatgc ttgaatctaa    11280
gagctttggt ctggaaagtg aggccctaac aaggaagaag gaataaccta tggatcaagg    11340
agaactggga gtccagaaat gaaggttatt tgtaagtctg gacccagcca ttccaactcc    11400
tttgaggaaa taagattcta aggaaaaggc cgtttgcatt ctgctctcca agatctctgg    11460
gtgttggaag aaactgaatt gggggagagg gggaaacttg actgggggct caatacagac    11520
atgtaaattt gaaggaaaca gagagtttag atgacaggca gtagaaaagt taatgtgtcc    11580
attctatggc tgacccaaga ttctgttttcc agaagacctc tctggcttgt taagtgttca    11640
tggttgcagg ggaaaagtta gaaaaaaaga aaaacaagcc aaaacccagc tccttaaatg    11700
tttctaattt tattttcaaa caatcaggca gagtaatccc tttacacact cttcaggcat    11760
tggctgaggg tcccagtcaa gaaccattca gttttggggg ccttaagaaa aatatttcct    11820
atgattaaag gaacttttgga caggttatta ccttctttga gcctcagttt ctttgtcact    11880
tagaaggttg aatggtttcc acattctgag ggtaaggaat acgagagtga atgaagaaat    11940
atcaagtgca tagctcagag taggaagaaa gaagtgacca gggacaaggc taagaactta    12000
ctcaaaaggt gcccagctgc tcagcattct gtccaaaaaa gggacactga catctctcca    12060
gcattctaac agcagtcaca tagcattatc agctagaaat gaaaacagat tcaattctat    12120
atcctgctaa aagcttgagg gtcacactag ctgtgtgatc tttggcagct ggccaaaacc    12180
ctctgaaagg cagttttcctc acctataaat ttttaaaaa atatttattg tgaagattaa    12240
atgaagtaat gcatttaaaa tacttagggt gccttagagt tccagcacag ttcgtagctc    12300
atagtaatca gttaatagat attgacttta ataaatagat acttaactga gcctccaccc    12360
tgggcctgtt actatgctaa gtaccaggag tgcaaaggga aatgaaacac gttccccaaa    12420
cttgtggaac tcagagcagg ccaactatat gagtagtaga tttttaacac gatgaggaaa    12480
ctgttataat ggaaaaataa atagtgtgaa gagggactaa ggaagataaa gatatggtga    12540
aaaaaagagg gttcaggctc caactgtggc atgatctaga tctgcaagga agagtagaga    12600
attgcagtag agaaagcagg gaagacattc caggcagaaa aaacagcttc cacagaggta    12660
aagaaggcaa aacgttttca aaggttctag gggtggggga tggtgggaa gatggtcacg    12720 gaatagtgaa tggttcaagt gaaactgttg tatgggttgt gagggcagtt ttatgggttg    12780
ggtgataaaa tcagaagaga aaaattgaat tcacgctttg aaaggccttg tgtgtcttgc    12840
```

```
tgagaagcgt gaacactaac tcatgaggag taaggcgcgg gtctttaaag gaaggaagtt    12900
tcataatcaa attgttttcc atgaaagata atgaagggaa ccagccacaa ggctgttgca    12960
atcaatcgtc caaacaagag gtgacaaaga ctctaaaact ggccaccaat gaattgaaag    13020
tggatggtga ggaagaaaga atacaggggtg acataaacac aatatgtaaa atccaaggta   13080
tgaaaatggc ctggtcccct cgtccttacc acagtcatcc caagagacca aaacaaaaac    13140
acagaaaatc tcttttaaaa ataatctctt ttgtttgtat gcaaataggc catccacagt    13200
gaaaatgcaa ctcaaatgca atattttatc tgcagtccac caaatgcaaa gatcaaattg    13260
gtttacaaat gctgtccttc ttaaaaattc caactcctca cattaaaact gtagccagct    13320
agtgcaagtt aagattgttt gcaatcttaa ataagatttg agtaaagctg aaattgagac    13380
acttttcaaa agaggccatc ccttactcac attgctgaag agtagaaaga ttgacaccctt   13440 cttttatcag aaaatttctt tcagggagta atgcctcttg tgtggtggca gacccttcaa    13500
gtcttccaga taaagcatgt gatggaagta gcagggagct gcaaaaattg caactctatg    13560
attctgcatc accgacttga aaactacaag cccaggttga caaatgtaca ttttaagtgt    13620
tcagagaagt cttaagtgcc ttgctttggt cacaaagttg ccacagggaa gtaagttttt    13680
gaatgtgcag tgccccgtcc ccagctctgt tgtgaaatgg aaactttaaa aaaaaaatca    13740
ctgatttaaa aaaccactgg ttttgttttt taacaagttt agtcatattg cctgtgttct    13800 ataccccca atctatttta ttttactttg tagtgtacat ttaatttata ctcaaataaa    13860
tattttacat aaggtgcttt cacggacctt catgcttccc taaatattaa atatgctgcc    13920
catttgttaa aatgtgttag ttttgttatg tattatatcc cttcccctgc acacatagaa    13980
aaaaaaaata tgaacttaac cttcaagcaa gttttacgtt tagaatatta cctcatttta    14040
tttcttctaa ctgaggttat aaagaaaatg gcaaatgtca tgtgctttgt aaagaaatga    14100
cagtttctca gaatacgtaa atgcacaccc ttagacaaat aggccactta aattcagaat    14160
cacagtcttt tgaatattgg tttaatattc tcagataaag attgaaagga taacaagttt    14220
tggaatcagg tgtttacttt gagttctgaa aggtgacatc acaggtgttg gtagtttatt    14280
gatatttaat ttttaaaatgt gctgctgtat atatttcatt tgattagaaa tatgttacat    14340
agttatgtta tttgttaaat aatagaccat cttttgtata acctatcaga agaagttctg    14400
agattgtaag attagattgt aaatcctatt gcataactag aatacagaat tattaaattg    14460
gaaaggaagt taaatcactt agaccgtcct tcccccagga agtcctctct acagtgttat    14520
ccatgacaaa tgtttatgca ggcaccctaa ccatttaaaa tacgaagaga aggagaagag    14580
atatatcgag aaaactattc ctgagacaag agaccagggg aaaacttttc ttagttgtaa    14640
cctacacaac tagctagaat ctacctcatg ctccttaagat ggtgtttaat catgaggata   14700
tcatacataa ctgaaattgt ataatgttga acatcttttg gtggcaagta ccttgacttt    14760
attaaatcag tgtaggtctc ctgcattcaa ctatggtctc taggagggca gggaccacac    14820
ttcttagctc accttggatc tcaagaccag tccaaggcct tcattcagtc agagctagtt    14880
aagcatttgt taattgaatg aaggaaatta aaaaaaaaaa aactagaaat tccaaattgt    14940
gcaattacat ctgtgaattt taaggtgtta ttggaaaatg ggaaaaatta ctgagattcg    15000
aagatggata ggaacaaagg taaagcatga aaatgtgcat atttgtgtgt tgctagagtc    15060
aatagtgatt gccagttcct atgcagccct ggcaccacct ctgaaacctt ggccaacccc    15120
tgccattagg tgttgagata cacgacaggc aggtgaggaa ggaggggtgc tctgatgta     15180 gtcttgccgc tagactgtgg tctttagtgt ccatgtccat ggggtgagtt gtgagcccat    15240
```

```
cagtttccca cactacagtc cttctctggc ttagccttcc ttccctgtcc tgtggtccag    15300 gttaccctg gccctgtgg ccttcctcca gagatggacc ttcctccaca cacttctcag     15360
gagctcctga ttctaggcat gccccagaac accgcaactc cactctgccc tgtctccatc    15420
agaccagaga cctcacttag accctgggta tggggttgtt ggttctccac ttgctgcggt    15480
tgtcactagc ctgagctcta tcctgagctc tgtccatcct tctcatcttc ctcattgccc    15540
tttctgctaa agcaactgca catctgaagg ctatacttat ccctagtaca atggtacttt    15600
ttctaaaatg catacaccct aatgcttacc cttttgacaa tttttttcctg aacctacctt   15660 ttaatataag caaattcagt cttcaattca aataagtgta ttttgctgct gaagccacca    15720
tgtgattttg agagatagtg aagacagaca gtcttctgca ttcacttgta gaatcctgaa    15780
aatacctctt ggtgtccctt gcctttctga cttcttgctt gaagacatct agacaaaaat    15840
gtgtccctgg gtcctagttt ctgggttcag aaattgatcg aatgcaagaa aacaatacac    15900
attgcctctt ccttagcatg catgaatggt aggtgtgaat ttgcatcatg agaaagtaaa    15960
taaaagaaga ttccccaggg cagctaggga ggcagaaaaa gccagcctag gatgggagtg    16020
gaggacatgt tagaggttat gagagtgagg gtccatccta ccccacctcg gtaactcact    16080
ggtatggtat aaatgcaaaa ttttggctca cacaagaaa aatactcaac ttctaatgct     16140
taactatgta aaatttgctt ttaaagtaca agttaaaatt gtatcgcccc tcaaagaaac    16200
aagaaactca ttacatttct aagaatgttc cttcagaaac atggaactga aagctatttt    16260
taaaaattga tctggcccctt agaaaactgg ggccttttct ttaatttacc taaggaattg    16320
acataaaagt ctagggttct gcaccagaaa aatgcagaaa gtgtcaaaat aaaaggcaga    16380
aatacaaaag gagactttt gcagcaacgt tctatgtata gcattgattc caagggtgca     16440
acatagggaa gtgaacatgt ggactgtgaa attgatgcta atttctttc ccactagtct     16500 agcagccctc taaatgtca cattattaat ttagttactt taccagaaat ccgtgtatgt     16560
ggttagcatg tgtgttttt tttaattaac agactttact tattttaga acagttttag      16620 attttcaaaa aattgagcac atagtacgag aattcccatc tactcccttt gtggaacaca    16680
atttccccta tttttaccat cttgcattag tgtgatgtat ttcttacgat caagccattg    16740
ttgcttcatt attattatta tttaaagccc ataatttaca ttaagtttct ctctttgggt    16800
tgtacagttc tatggatttt gacaaataca caatgtcatg tatccaccat tatagtatca    16860
tacagaatag cttcactgcc ctaagaatcc cctgtgctct gcctgttgac ccttcccacc    16920 cctcccaac ccctggaaac cactgatctt tttactgtct ccacagtttt gccttttcca    16980
gaatgttcta tctttggaat catacagtat gtacccttt cagattgact tctttcatta     17040
agcaatatga atttaagttt tctccatgtc ttttcacatc ttgatggctc atttctattt    17100
attaccacat aatattccat tgtctggata taccacagct ttaccaactg aggggcatct    17160
tagttgctaa ttatgaataa agtggctata catattcacg tgtaggtttt gtgtggacat    17220
aagtcttcaa ttcaattgag taaatatacc tagaagtgtg actgctggat catatggtaa    17280
gagtatattt acttttttaa gaaactgcta aactatatcc caaagtagtt ttaccatttt    17340
gcattctttt cttatttttt tttttattat actttaagtt ttagggtatg tgtgcacaat    17400
gtgcaggtta gttacatatg tatacatgtg ccatgttggt gtgctgcacc cattaactca    17460
tcatttagca ttaggaggta aatctcctaa tgctatccct cccccctccc cccaccccac    17520
aacagtcccc agagtgtgat gttccccttc ctgtgtccat gtgttctcat tgttcaactc    17580
ctatctatga gtgagaacat gcggtgtttg gtttttttgtc cttgcggtag tttactgaga    17640
```

```
atgatgattt ccaatttcat ccatgtccct acaaaggaca tgaactcatc atttttatg      17700
gctgcatagt attccatggt gtatatgtgc catattttct taatccagtc tatcattgtt      17760
ggacatttgg gttggttcca agtctttgct attgtgaata gtgccacaat aaacatacgt      17820
gtgcatgtgt ctttatagca gcatgattta tagtcctttg ggtatatacc cagtaatggg      17880
atggctgggt caaatggtat ttctagttct agatccctga ggaatcgcca cactgacttc      17940
cacaatggtt gaactagttt acagtcccac caacagtgta aaagtgttcc tatttctcca      18000
cattctctcc agcacctgtt gtttcctgac ttttaatga ttgccattct aactggtgtg       18060
agatggtatc tcattgtggt tttgatttgc atttgtctga tggccagtga tggtgagcat      18120
ttttcatgt gtcttttggc tgcataaatg tcttcttttg agaagtgtct gttcatatcc       18180
cttgcccact ttttgatggg gttgtttgtt ttttcttgt aaatttgttt gagttcattg       18240
tagattctgg atattagccc tttgtcagat gagtaggttg caaaaatttt ttcccatttt     18300
gtaggttgcc tgttcactct gatggtattt tcttttgctg tgcagaagct ctttagttta     18360
attagatccc atttgtcaat tttggctttg gttgccattg cttttggtgt tttagacatg     18420
aagtccttgc ccatgcctat gtcctgaatg gtaatgtcta ggttttcttc tagggttttt     18480
atggttttag gtctaatgtt taagtctta atccatcttg aattgatttt tgtataaggt      18540
gtaaggaagg gatccagttt cagctttctg catatggcta gccagttttc ccagcaccat     18600
ttattaaaca gggaatcctt tccccattgc ttgttttct caggtttgtc aaagatcaga      18660
tagttgtaga tatgcggcct tatttctgag ggctctgtca ctatacatct actgaatgg      18720
gtaaaatcca aaaatctgac aataccaaat gctgctgagg atgtggagca acaggaagcc     18780
tcattgctcc acatcctcag cagcatttgg tattgtcaga ttttggatt ttagccattc      18840
tactagatgt gtagtggtat cttactgttt taatttgcaa ttctctaatg aggtatgatg     18900
ctgaccacct tttcatatgc ttatttgctg tccgtgtacc ttctttggtg aggtatatgt     18960
tcagatcttt tgctccttat taaattgggc tgtttgttct tttatctttg agttataaga     19020
gttcattgtg tatttggat accagcccct tatcagatat atcttttgca aatatttttt     19080
ccccaatctt tggcgtgtct ttttattcat ataatggttg atacatgttt ctgctttaag    19140
gaggaagggt tttaaaaata caatttacag tagcagtaaa aataaaaatt tattgcaaat    19200
gtcttatgtt cactctcagg tgatgtcagg gaactatgga cccagcaggg tttaattaaa    19260
ggggagtgtc aagtcctggg ggctgtggtt gacaatcctc ctttattggc aattgtgcag   19320
cagggctggg agtaagaaga caacccagtc ctgagctgca tcacttctaa attaagaata    19380
attcaggaac tgtgtttacg gtgaaatcct ggcccttctc acatagatta tattatgcat   19440
aggatatgaa tttctgtcca tgaatccaag tatatatgaa atcatcactt tgaaaatttc    19500
ctttaactca acttaatccc actggtgagc ctcaatcctg ccagttgaaa aagagactgt    19560
aactgggtca tgcaggagtc tccttccttt cctgcagccc agtcagaatt caagaagttc    19620
acctggtaac tggaaaatga tggaagggcc tcaagtccct agtctgtcct ggttgccatt    19680
ggcacccttta ctatctgagc ccatagtggt ctgtgaagtc cggcagctcc ctgcccccat    19740
gccacagtgg ggaatgagaa tatctactga tgctgggccc catgagcaaa gcatgctgcc    19800
tttctaggca tgagccatca cacctgaggt tgctaccccc tcgggagcac tgatggaggg    19860
gcagttgggt ttctactgct cacaggaccc agacaaccat cccctgccct cccttcttct    19920
tgcacttcaa aagcactctc ttcctctctt ttcacctcta agccaccggt atcatctctt   19980
ccatgggctt tcacaaaagt ctggatgaac ctttgaactt gtatctcttc tgctttcccc    20040
```

```
cttgcatcaa gaaagcttag aaaacaaaca ctaattaacg tttcaataaa taatgctgct      20100
ctaattattt gtggaaacta ttctgtatta gaactaccat cagcaccgcc tcctagagtg      20160
cttttagact tgaccactgg ccgcaggagg ccacttccat ataacaacaa acagatggct      20220
gaaattggaa aactcagcta aatgttcaga tgtttctaga ctcccacggg tttctggctc      20280
tggcacatgg agtagatcct gactgtgtgg tcctcagggg actctctctg gtgaagtttg      20340
gtgaggtcaa cttccacacc cacacacacc agctactgtg tgtagcctgt cctcctctgg      20400
ttgcttctac ttgcagcctt ggcctcttca gtcctgagag cgttggagaa tgaggcagtg      20460
gaggaagcag ccccacacag aaagcagttt ctgaagtaac ctcagcaact tcctcctcac      20520
caaacacaag gaactgatct tctccactgg gctcggcctc tggtcagcca aggacaacac      20580
tgttgaccac catcacggtt ggccccactc caccccttggc tctgatgaca tatgtgggag      20640
tcagaggaat tttgattggc tgactgctgg cctgtcacac aaacaagatg gggcaagggg      20700
gttgcgatat gacttgacat gtgaaaaaaa aaaagccgt ggtcagcaac cccctgcaac      20760
tgttgaaagg ctaattcaat ctctgactct ttaacaaaag tgatcttgtt cactgcctgt      20820
tctgccctga gagccttctc tgctaggagg taggttgact gactcaggga aagggtgct      20880 ggtggcagag ctgccaatgg gtgagggtcc tagagactat cgacatgagg ggcagttgag      20940
aacactgtag tatttagctg agaggagaga ctattaataa aatttacaaa atcagctttc      21000
agctatttgg aagggtttat ataaaaggat aaaataatat gttctggtag ttctagaaaa      21060
caggacagag acaagtagct ggtacttatg gattggagga gtgagtggca gtagtttggg      21120
gattatttat aaaaaagaca ttttttctgtt aactctcttt tctaatagtg aatttcccaa      21180
cctgacaagt aagaaagcac aggctagaca cgcatctgtc atgacactga agggtccctt      21240
gcttgagtga gagactggaa tgatgagttt tgaggtccct tacagtccag caactctagc      21300
taagttggag aataagagaa ttccatgaca ccatatcacc ccctcatttc tgctgcctgc      21360
ctcaccattc atctctcttt actccttta atatcattct acgttacagc attggaggag      21420
gctgctctaa ataggaactg aaataagtag attaagaag tgctatggaa gggaaaacaa      21480
taaaacaact tgttttttaa gagcctacta ttgccaggat ctgtgctaag caccatatat      21540
atgccatgtt atttaaccgt catgacatgc ctatgagata tttagtatta cttctgtgag      21600
gaagccaaag ctcagagagg ttaaataact gccccaagaa cacacaggca ttaagtagtg      21660
gagcagggtt tgaacacagg tctctatgac tccaaagtgc agtgtgatat gttattttta      21720
ctgatctgtt tatggaaaat gatactgctt tctaatttag tattaacaca agatttttt      21780 tctaaataga tttacttaaa gtatgttata aaaatactat ataaataatg aaacagattt      21840
tacatgagta tgaagtggta ctagtagcta gaatgatgaa agtttgggga atactactcc      21900 aaatatttg atagctagcc tttcaattta gcctgtctta tatttggact gctgagtaca      21960
aggaaaagaa ggaaacatga aaattaagtg aaatatgagt tacttcccct gtgctctgat      22020
aggtgggtaa ttgatcatat gtcacaataa gaaaatcaaa tgaaccctt caaacaacag      22080 caaaatctgt gattgtaaaa tccagaggaa accccaggt gggatctatc tgtatgaagg      22140
atgaaattcc caaggtctga acatagaatg gctgagagga agtgatgacc ctgtgagtca      22200
agaccctgga ccctggggga gccctgtggg tttgagaagc cctgggtgaa aggtgaaggg      22260
ttttacaggc ctgtttacag acctctgtag tgacagaagg gagatctttg tgcaaaggtc      22320
aaagtaagaa ttgggaaagt ctgaaaagaa aacaggaaag taataatgaa gatgaaataa      22380
ctacttggca tactctgcca catgatttac aggcaaggtt tcctttgttt ttcacaacaa      22440
```

```
tgcagcaaag aagtgattat gagtcacatt tcataagtga gaagactgac attcaaacat   22500
gttcaataac tggcccaggg tccagtggtc aagccaggac tggacttcgg accaccagtt   22560
ccaaacccac accccttccc ttgcaccaca cgcttttgtg tggatgagcc tccccaaccc   22620
tgtcaacaac aaactgtcac tttgtcactt ttaatgtctc ctgcttcaca ggacacagct   22680
agcctccaag agatcaggga ggcatgccca gagggtgctg cttctctctt ttgaagctca   22740
agtgccacag acctcagagg cacataaatg tcccccacac tgagcagagg actttgcagt   22800
gcctgatcag ggcagaaaaa ggaggcatgc acctggggga ggatcacata cgagtgaaac   22860
ctgtccccgc tgaagcacta ggtttggaga aatctactgg gcatttacac acctttccca   22920
cttctgctta tgacttgtag ccaaactcaa gagtaccacc cacttccagg aatagtgtac   22980
caaggtaaca gaaacattct agattcatac aattggggtt agattaggat catctgaaaa   23040
tgaaggttgt gtatgtcaat tgccttctaa caggatgggt ggagagatgt acttaatgaa   23100
tgattttggg gaagggctag aagtgaagca catggcctct ctgccctcac tcattgaagg   23160
ctgtcttctg aagcccgtg gagctcagtg cctgtcacat ggttgcccac atttgttgaa   23220
ctgaactgca ttttcatcta tgggcttcaa aggctgtgtg tactctggga tctctgggaa   23280
tctgtcaggg aaggtgtctt tgtcatgttt gtggatgggg ctccctttgg gggtttccca   23340
gggctttaca ctcatgctcc gagggtacgt ttgtagtcat tctcatcagt ggaaatgccc   23400
acctgccggc agaagttatt tggaaccaag caagagcact gtccctggct gtggtgttgt   23460
ttctctagtc agttcccctt tctgtatttg agttctaccg tcagtcctgg cattatttct   23520
ctctctacaa ggagccttag gaggtacggg gagctcgcaa atactccttt tggtttattc   23580
ttaccacctt gcttctgtgt tccttgggaa tgctgctgtg cttatgcatc tggtctcttt   23640
ttggagctac agtggacagg catttgtgac aggtatgttt gtggaggctc agacgcctag   23700
ggagtggcat gagataaagc tgcaagctgc atctggggca gaaatgctga tgtgctaatg   23760
gccggccaga gaatgagtaa aagggattgc agagagcatg cttaaaacct ctgaccatca   23820
ggtttgcttc tcagattgac tacattggag gtgggatatt acaaaaatct gtctcttcct   23880
gccagatccc ttcatctgtt tttcgtgagc taagagacaa aataggcagg aaatagaagg   23940
tgccacttac caaataattg gcagctgttc ttggctttgg ggtgctgggg tctccgagca   24000
gcctctgctc tagaagaagc agtccaaaga tgtcagctcg cctcgcctga gtcccctgtg   24060
ccagtgggaa atccagagaa ggggggattc ctcctcttgc agcctctctg caatggactt   24120
acttggcttt cctgtttgac cttcccttc tctggtccag agacccttcc ccaatatttc   24180
ttcccatcca agtgccccat cccaatatta gccccacttg gcaccagaga ccaagatcta   24240
atttaaaaag aaatattctt gggtcaaaaa agagcccaag caagtgattg aacataatgt   24300
gtttcacata cggtgaacct atttgcattt gcatttgcaa acgggcttaa aatatcatct   24360
ctattaatag caatttaagg ttctggagag ccaggtgaaa atagttttg acaaagggaa   24420 cttcctactc cccttaaact gtaataatga aggaaatgaa ctgtttatct tacatgtaac   24480
ctcaatcttg ggactaaggc cctgtactaa aatgcgtcta tttatgtgct cagacttgca   24540
gttcgtgtta tgtctgctgc tgcagatacc gttaatatta tttatgtgag ctatcctgtg   24600
tataatggaa gcttttataa atctctattt atttattcct aatatagtta ttaagtgctt   24660
gctatgttcc aggtactagg gacttaacag gtagcataaa agacataagg aaaagctgca   24720 ctcttgttt ctagcctagt ggggaaatca cattaattta atcacactaa acatgactac   24780
atagcaatag tgctttaaag ggaaggaaat tgttctatgt gactatatca gctgattaat   24840
```

```
taccaagcct ttgcatttga tattttggtt agtctattct tcttgaattt catatgcctc   24900
ttcctgggtg ggggtgagga tgggatttta tggagttgag gctagggcag gtagggagaa   24960
aacatgagaa agatgaagag ataagccaag ccagattctt cagcagaaaa atcaaggttg   25020
aaataccatg tttcaaaaat cagactgagg tgggagttga ggttaggggt ccctaggcca   25080
ggggattgaa gcttcaaaga gataaaacta gagcaaaagc aagcacagag agtggcagag   25140
aggtccctgg gcattttcc acagtccatt ctagtgctgg caatccacct ttcatggcca    25200
ggcaggtaag agtatttgtg gggtgggaga aaggacaggg ccataggctg gcacacagc    25260 cctttactgg cccttatctc tcctctcttc tcctatacag tgctgtttcc gaactgtaca   25320
ttggcttaca ctcgggctga ggtttgggaa ataggcgcca ttttgaatat gtgtggagga   25380
agaaaagtgt gtcttcagca cttttccacct ccccatcacg gccctgagac ctcaacaccg  25440
ggaagcatct cgttccctat cggtcctcct ttattcatgg acggatatga ttcctttcta   25500
agttccatgt cctttttaga taaattaact tgaacctaat gcctaatggc ttaaaaacaa   25560
acaaaaaaaa ccctcttcct tccagctagc atttgcattt taacaggggc tttcaaaaaa   25620
tgccttagcc caaggaatga gtaatgtggg aattccaagc agcagggtag gactggtgca   25680
cagtatgggg agagaaggcc cctcaagttg tggccctgaa atgttggctt cctctctttg   25740
accatgatgc tgtttctgag aaaacaagaa tcaggctacc ttaggggacc aggatgggca   25800 tggctcccctt ttagtgagtt ctatgagcct catacctgac agtcagagcc ctcgagtgga  25860
tgagcacaga ctagaagaag cactgtgaaa ctttgcatga tccttacctt tttggcaaaa   25920
aggaaaaaaa atcgttctca aattcatcaa tagtttgaaa tagggtgtgc cttgattcag   25980
aaagtttcga ttctagatac aactcggaga actaggcgtg tcttgtacac agatttgctc   26040
ttgggggacc ggaaaagcta aatgctatcg ccatgctatg ctccttcttc taggccagtg   26100 agggggaacgc attcttcatt ttaatatttc agttgcctac aatattggaa ggtggataaa   26160
agcaccctct gctccttcta aatctgcgaa gacatttctt ctctgcacct actcatcctt   26220
gatgcagctc tcctcatgtc tgtatggaaa cactgtgctc tcaaatgagt ttcagaaaga   26280
acaactcacg aaagaaaaca agcattcggt cagaaaaatc tccacaaatg gggaataagg   26340
gggatttgct ccaaggagag actggaaacc aagtcagaca taaaatccag cctaagctag   26400
aaggagacat ggctggtggg agcttgagga aaacagagct caggatggag gacgtctcca   26460
cctccagtca tgtcctctgt ccaccagaca ccaagaagtg ttcatgttcc atcgaggcag   26520
ccctcacacc catcccttcc tcatcatgcc gactgcctct ttactgcttc aggctcacca   26580
tctcaagtcg acgagcctgt aatactggct ttcttgatca ccctgatacc agccgtcacc   26640
tcttgacagg cttattttct ttaagctgtc attacaccat ttttctgctc ccaaactatt   26700
aattccaaac ttccaatttt ctgttaaatt aaatatgaat tccttatttg actttccatg   26760
ccctattagg ctatcttgct ccttgcttta cttatagaaa ctaatctccc attatttatc   26820
caaagacaac ctctgctgca ggccagtcag cttttcttac tgtcctgtaa aaattccatg   26880
gtcactcctc catttccatg tgtccttaaa aactgttatt tgattgtgtc tcagaaagtc   26940
gtcaaagaat atataccaat gaaaagcatc aaaaaggtta tacttgatgt tatgtgtgta   27000
tcaaaaatat ggctgaaata tttatccagt gaaactcaat caacactaaa aagtggttct   27060
ttcggaagca tcagttcttt gagacccatt aaacagatgc ctcggatgca gggttatata   27120
ttatcaggaa tctgtctagg gaagaattat tggaagcttg caaagccttt caaggacaga   27180
ggacgatagc taccacgttg agttctagga aattaaccat tgttattgtt aaaggaagac   27240
```

```
agcgtttctc agaggaagac tgttaaacag tgcagtggcc caggctaaca gccctcataa    27300
gtgggagtat cagaatgagt ggacttaatt acttaaaacc aatacagggt ggaacttcat    27360
ctgctataac agaaatcaac tcgtgcaagt tctaacatgc agggtacagt tctgagacca    27420
agtctgactc acctgtcaaa gctcagctca actattacca cctttacacc acccttccaa    27480
gctgtaggag tgcttgctgt tctccatgtc ttctgaagcc ctggatcact tgtagccagc    27540
tcagcagact ctacccagac agggatcctt taaatgtacc atattgtcta ctgtgttaaa    27600
aatgagagga actgactcag ggtgagagcg atggagtgtc cagatgttct cctttatttc    27660
tccttattcc tggaaatgta atgagaatct tagaggtgaa ctgaaaagtt atgagttcaa    27720
ccacttactc aattcgagat tcgctcctaa aatgtctctt ctgtgttatc accccccactt    27780 tggtttgaat agtacttgtg acagggagct tatcacctca aagaaaatc cagtcattgc    27840 ttgtagctct ctattaaaag ttttccatca tctggaactg aaatctggct ccctgtaact    27900
tttagttatt ggaactactt gcccttcagc aacagtgtat gtatcctccc atggaagggc    27960
ccttacatat ttgcagacac ccagcatata cttgcaatct tttcttcttc aggttcatta    28020
ccctagtcct tttagttgtt cttcatttga cataatttca ttattcacta gtgaaccttg    28080
ctgcccttcc ccttgataaa ccgaatttgt cagtgtcatt caagtataac tgacctcaca    28140
gaacgtgata ccacaagcga tgtggtctga ttagcacaga gttcagtgaa tgaatcctac    28200
actaggattg gatgaaattt acttagccat accacactaa cacttatgtg attttatgt    28260 ttactatgga tagactattt ctcctgtgtc cacttcttcc tcttacacag ttgttatttc    28320
aaaactgaag tacagattct tacacttacc ctcaggagat tcatcatgtt agtattagtc    28380
tctcttttca ggctttatga atgttaattc agctaactca ttttgagct atctgtctca    28440 ttttgtgcca tctgcacagc ataagtttga tttctgttgc ttttattagt agttttacta    28500
aatacataaa agtgaaatag tgaaacacag agtcttgtag catccactgt gggatcagtc    28560
ttttagacaa gaatgatgca gttgctgagt caaatgaata aatgaataaa tcaaacaata    28620
ctttgtcctc atttcccata ttgatctatc accatatcct gttaattata attctaaata    28680
tttcttgatc tatccacttt tcccttactt cacctgctac tatcccagac caaacagcca    28740
tcttctttca ctcaaacaat tgcagtagcc aactgattgg tcttcctgca tctgtcctgg    28800
cttccctatc atccatttgc tacacagaaa ccatggtcat ctttttcaaaa tgcaaatctg    28860 atgatatcag tctcagctct aatttctttg gtggttcaca tataaagact gaaatctta    28920 actgaccaat aacacacgtg tgatctggcc cctgctcacc tcttcagcct tgtctttcac    28980
ctgtctcttc atttttggcca cagggacctc ctcgtacctt ctctcacgtg ccctcctgcc    29040
tcagcgcctt tgcatatgct gttcccttg ccgagaactc ttcctgtcaa ctcccaagcc    29100
cttcacctac ttagcaccta cctattcaat ctgttctgtt tgcctcttgg tatgttacaa    29160
actgtctcca aacttagcag cttagaacaa tgaatccttt accctctctc acaatgtttg    29220
gggtcaggaa tttgagcggg ccttggctga ttttctgtt cctcatgcca tcaattgata    29280
tcacctgatg ttattaagct gatggatggg ctgatctgga gatgcactgt ccagtttggt    29340
agccactggt tacctgaaat gcagccagtc ctaattgaga tgtgctataa ctataaaaca    29400
cccacatgat tattgaagat ttggtgccac caaaaaattt aaaatattcg ttaataattt    29460
gtattctgat tacatgttga gattataata tttcacatac atcagataac ataaaatgtc    29520
attaaaatta atgtcaccta tttctttta atttctttaa tgtgactact acaagttttc    29580
aaattatatc tgtggcttgt aattgtggct tgtattgtat tcttttttc tgagatggag    29640
```

```
tcttactctg ttgcccaggc tggagtgcag tggcgagatc tctgctcatc gcaagctctg    29700
cctcccaggt tcaagtgatt ctcctgcctc agcctcctga gtagctgaaa ttacaggtgc    29760
ccgccactat gcccagctaa ttttttgtatt tttagtagag acggggtttc cccataatgg    29820
ccaggctggt ctcaaactcc tgacctcagg taatctgccc acctcggcct cccaaagtgc    29880
tgggattaca agcatgagcc accacacctg gcctgtttta tattcttact ggacagtgct    29940
gatctagagc aggagtcaag cagttttttc tatgaaaggc cacatagaaa atgttttcag    30000
ctttgcaggc catgcagtct ccatcatagc tgttcaactc ttccattgca ctgcaaaagc    30060
agccatagat aataatttac aatagacata gcagtgttcc agtacaacta ttaataaaaa    30120
taggtggtag ccagatttgg cctacaggct gtagtttgct gacccctgat ctagaagatc    30180
caagatttta ttcatatgtc tggtggcttg caggggatag gtggaaggct cagctgggac    30240
cattgaccca aacagctata cagtcctctc cagcatgatg gtctcggggt agtgggacat    30300
cttacgtggt ggctcagaac tccagataag gtactcccag agagacaggt agaagctgtg    30360
aggcttctta tgaccaagct ctcgaagtcc cagaatatcc cttgtactgt attctatggt    30420
caaacaggtc actcaggcta gcccagattc aaagagagga gatccaactc tacctcttca    30480
tgggaggagg agtagccaag gatatgtgtt ctttttaat ctattatatc attcttcaga    30540
tctcagttta ggctggtcct gttatgggct ctcaaagtac catgaacctc tcttttgtag    30600
cacttgtcat agctagtttt acatttctct gtatgattac ttgatcacta tcttgctttt    30660
ctactaaact gtaggcaacc acgtgaagag gaactgtttc tggttttgct cattatattc    30720
ctagcaccaa acacaatgct tggttcaata aatatttgtg gaagaaacga atgaatgaat    30780
gaaccaatag caaatgaatg aatgagtaat aactgtatca atattaatcc tacatttctc    30840
catattgctg tcacgtatat cataagatac tctgtcagaa gccttgctaa aattcaaata    30900
tatttgattc ccagtaacct tcttattttg tagttcagaa actttataaa gaaggaaata    30960
agcctatctt actcttccca gtatctcaaa gagggtttct gccctgagct gctcaagagg    31020
gtttctgccc tgagctgctg ttcattctgc aaacactgct cgaatacccca ctgtgtgcca    31080 ggtacagaga gttcttctct gctgtaatct ggacaggcac cagcttccca gcgtgggttt    31140
aggcttcagg tgcacactac tgtgtaccgt ctaagccaca cctagaagag ctctggggaa    31200
atatgactac ttgggcagaa aaggaaggaa ctaagaagag gtatctttgt gtctgaggtc    31260
tgaaggagcg tgtgggctct tgttcaggca aagggcagga tgaggggagg tggggtggca    31320
gcagccagta atgggtggg acagcggaat gcagaggatg aaacttcagg tcctggtgct    31380
ctgagaagta acgctgtgca gcatgtcaca cccagaggca aaccaaggcc cagggagct    31440 gatgttgcac tggagctcta ctctcctctc agcgagctgg tgacgtgcca gtccagcagg    31500
cctggcttat ccaaccacaa gtatgaatcg gcagaaggca atgagctggg ccctgagtgc    31560
tgctgggctg aggccgacct aatccttcct ccacagagac tgtggtgtcc cctgctttgc    31620
tcagggtaag aactcttgta tacctcacaa gaagccaagg actacctacc accttccaca    31680
ctggccctgg agcctgcatt gtagttattt gtggacactg ttttcttctct ttagtgccag    31740 gtggggacc aaggcctaca tgtctttaca accectcaat ctctagaaca agtctgacac    31800
tgagtagatg tagcaaatgt ttgcctgaaa gactacctca ataaataacc ttctgaggca    31860
ccagcaaact tctcagcatt tttcctgata ctccggttac cactaacatt ctacacaaag    31920
ttgtgaaata agtcttttc tttgttgctc tccaacatct actgtggacc ctcctctca    31980 cttcctgttt catcctctct gcactcccct gtcccacccc attactggct gctgccattc    32040
```

```
cacctccctc atcctgccct tgcctgaat gagagcccac atgctccttc agacctcaga    32100
tacaaagata ccccttctta gttccttcct tttctgccca agtagtcata tttccccaga    32160
gctcttctag atatggctta gatggtccac agtagtgtgc acctgaagcc taaatccacg    32220
ctgggaagct ggtgcctgtc caggttaaag tggagaagta ctctctgtac ctggcacaca    32280
gtgggtattc gagcagtgtt tgcagaatga acagcagctc agggcagaaa ccctcttgat    32340
gcaaagggat actttggggc cccttcttct cccaccccag tctgtctctc tgagagtcct    32400
ctcgattcca ggagccacca tcacacctgg ccctaggctg tgctgctccc gtctgtctca    32460
gaggctagat aacatcagag tcctttccac tggctcctgt ggcagagcaa aaactggttg    32520
gcatttttaa acgtgctaca ccagtgtgtg aaagaaacac aggctgcatg ggtttaaatc    32580
tcagctgtac catttactag ctgggcagcc tagggcaagt actgtgacct ctctgagact    32640
ccattccttc atctgtaaca tggggacaaa taatctcacc ctgttgtgag cagtaataat    32700
atgattaatc atttagccaa ctcttattca tgttctctga tgggccagac atacaaagta    32760
agtgaaagtg gattacggca ggtgctcttc ttggtttctg gagtgaacct ccatttacat    32820
ggaggctcct cttttagat ttctgactag ttcacccacc ttattcatag acctattct     32880 gtgcttagct gacagaaatc tcctctcaga gaatcccccc ggtaaattct taggttcttt    32940
cctcttccat tccccttttt gctctctccc tccgaaggca agagtttcca ctttacaggc    33000
ccactggaga aagttatggc ttctggttgt ggttggaggt tcattcctga gggagtgggg    33060
acatttctac acttcttcac ggccaatgac attggagaaa ctggcttcct aacccagccc    33120
acaccctcgc acacacacat cacacatcat ggctagaatg gagagaaatt cttcatatgg    33180
ggcacttgta cttcatgaaa gaaaatcata tcaatcttga gtattttaac atcctattac    33240
agcagggtca ctgataaact aagtgtccag agtgtttttct aggatggtgt gtggtctcca    33300
aattaacatt agtgaagctt actgaaggga ttgttactcc tgggccaggc caggattttg    33360
aggagagatg tgtttgctgt caccaaatcc ttgacagact ttggcagaag tgtgttaggc    33420
ttactctgga tagcttcaga ggacaaaact agtattgacg gaaggaaggt aaggagaagc    33480
agcttctaac ccaggggaag agagagtttc caaactgaga aatcaaaaat ggtactgatt    33540
ccttgtcagg gtcagtgctt ctccccactg tgtgaattac aggggccatt tgtccaagat    33600
tccttagagc aatactgatt tcatgtaatt atttgaatga aggtgattt gttaaattta     33660 tagtaaaata taatttgatt tgtgtccctg tttgtcatgc caccccagaa gaaaaattgt    33720
ctttggttag gtcgaacata atggtttttt ggtttgcaaa ccatgagcga ttcccatatt    33780
aggtgggagt tcagattcaa agggccctct tttttttttt tttttttttg tagtagccag    33840
cctaatgagt aggaagttgt tctcactgtc attttatatt gaatttcttt tatttgagt    33900 atgaccatct tttcaaatgt atgagatagt tatttccagt tccacatact atctgtacat    33960
ttcttttgcc cgctttttagt ttgggtcttt ggccttttc ttattgattt atagaagctc    34020
ttttatacat agaaaattaa tactttgtga ctagttgcaa atattttcag ttgctgaaat    34080
acacagtagg tgttccatgt aagagctgaa cagctggttc ctgattgctg tctccctccc    34140
ttccagccaa tagatttcag agtttgggca ttacctattg agccaaagct gacaccacac    34200
aagcgcagag tatgggaaca gagttctctg tctgattcct gtgagcttcc tcatactaaa    34260
tcaccaacag caacctactt atcacagaat atgagaattg aacaagtgtt ggcaaggatg    34320
tggagaaatt ggagctcttg ttccagttgt cgatgggaat gtaaagtgat gtcgctgcta    34380
tggaaaatag tgtagcagtt cctcagaaaa ttaaaaatag aatgaccaca tgatctagca    34440
```

```
attccccttc tgggtatata cccaaaagaa ctgaaagcag agtcttaaag agatattcat    34500
acagccttgt tcataccagc attatgcaca atagccaaaa ggtggaagca actcaaatgt    34560
ccatcaaaaa tgaatggata aacaaaatgt agtatgtaca tacagtggaa tatcatttag    34620
tcttagaaag aaaggaaatt caaacacatg ctacaatgtg gatggccctt gaatacatta    34680
tactaagtga aataagccag tcacaaaaag acaaatactg tatgagttta cttataccct    34740
aagcagtcaa attcatggaa acagaaggtg gaatggtggt tggcaagagc tgagaggagg    34800
agagaaagaa gagttattgt ttaataggta tagaggctta gttttgcaag atgaaagagt    34860
tctgaagatg gatgtagtga tgactgtaca acaatgtgaa tgtatttcat accactgtac    34920
actcaaaagg tgaagatggc aaattttatg tgtattatgc cacaactaat aaagatttct    34980
aaaacttatg agatctaatt tcaccgtttc ctattgctaa agatcacaaa ttagaaaaca    35040
cgttggcaaa aggtacatga aaataagcac tcttgtgttg atcagagcat aaacgtataa    35100
tctcataaac taataaagat ttctaaataa caaagatttc taaaacttat gagatgtaat    35160
ttcaccattt cctattgcta agatcacaaa attagaaaac atgttggcaa aaggtacatg    35220
aaaataagca ctcttgtgtt gatcagagca taaacgtata atctcagggg agaacaattt    35280
gcaactattc ttcaacccctt tggtcaaacg attctgcttc taggaatata gcttactccc    35340
acctgtgtga tatggcatat aatcaaggtt ttccattgca acaaaagatt ggaaacaacg    35400
ttaagtatcc atcactagtg gtctggaaat atatatatat tattgtcatc caatagaata    35460
caatagacta atatgcaact tttagcatga ggatactcgt tacatgctga tacagaataa    35520
tctccaaggt agtcatatgt gtgcaaaacc gtacatagta tgctaccatt tgtgcttaaa    35580
aataaaaaga aaacagaata tgggtcaatg ttttttgttta gttttgtcta aagtaacttt    35640
aagtagaggc aagaaactgg taacatgtaa cagtgatcac ccctgttacc tctgtggaag    35700
aaaactagac agctaaggga caaggctggg aggcagactt gctttccact atttatcacc    35760
tttatctttc aaatttagta ccatctacat ttagtaccat gatctattca aaaatattta    35820
ttaaaaaaag aaaaggtata gtctagaagg aaaaaaaaca taacagacac ttctagccca    35880
atgtcctgca ctgggtgcta tgagagcaga ggaaagaaac acatatggct tctagacaac    35940
accgtctggg gcatacattt ctgctattcg atcaagaata gttgtgcatc ttttcctgga    36000
aagaattgat tgttttttat caacagacct atgaatttag tggacagacc tgtgaattaa    36060
ttcactggtt aggttttcct ttttacattg gctgttaaaa agctataagc caaatttatg    36120
tccccctcag tgcaaattgg gcagattcct agggcaagca tttagcactg gccttgtcct    36180
tggctctgta tcatattcct gtatttggtt tgcttttcca cctgtttctc atgttggtca    36240
tcttttcctgt gtatgccat accatcctga atgtgcctga tcgcatctaa tgttggtcac    36300
ctctccttat tctttgcttc cttataagcc actaagcagc ctttttggtg ctagttaggg    36360
taagtgcgtg ggtagtgaag gagggaggag ggagaggaag aaagaagata gaggttataa    36420
agcaaagcat atccttttc ttggcttcat catgtagatt aagtgaattg ctctcaaagc    36480
gtggtcctta ggccggcagc attgtcatca ccttatgttg ttaaacataa aaattcatgg    36540
gtttcatccc aacttactaa gccagacttt ctgtggttga ggcccaggaa actctccagg    36600
tgattttttac tcacattcaa gtttgagaac cacaggaaaa caaaggaag gcagatttct    36660
aagcgtaaat gcaatactaa ccgattgccc ccatcatgcc tgttatgttg gtcaagataa    36720
ataatactag ctactgcaat aatcaatccc tcaaatttta tttttgcca atatcacaat    36780
ccattgtaga tcagttgtgg gagaggtgta aagagagctg ctttattagt ttattaagca    36840
```

```
aaccagatct cttccattgt gagactttgc gattttctag gcccttggac atttcctctg   36900 gatccctgc tgctaagaag gcaggagagg gaggaaagag aagagacttt agcagccaga   36960
tctggaagaa acatctttc tgcccacaat tccattggct agaagccagt ctcatggcct    37020
gtataactgc aggggaggct gggaaatgtg acctatcgat ggagctaaga gcaaaaggaa   37080
atggctttga tgaagccctg gcattgtctc tgcacacccg agaacccaag tgaatcccaa   37140
actccacgtc caggtcatgt tttggtgaac atcggttttc agtttccttt tctaatcaag   37200
ttttaccttt ttttttctcg actctagcac tatgggactg agtaacattc tctttgtgat   37260
ggccttcctg ctctctggta agaaccttc agctttgtta agtcctggaa tcctactgtc    37320
tcctgatgag tctgaccaca gcaagcccag gcctgagact tggtgggttt tactcacttt    37380
ctactgagca ttgtacaaga ccacatgcaa aaagacttt cctggagaag aaggaagtgt     37440
tatgattgag agcagctgat ggcaggcagc tgggatggag ctctccccc cgtgtgcttc     37500 ttcctcctct gcagtctcac atcagtgagc ctagatgctc agagtagggt agcctggccc    37560
atcccatggg gatggggaa ggctgctgca ctgaggcccc tgagacttga ctcttttgtt    37620
ccacacatat tctcttctgg tcttctctga ccctgtttct gtctttctca ggctcctagg    37680
aaacaactga cagaattcca aaagtctccc ttcattcgga gcactggctt tcacgtccct    37740
gacttcccta ccctctctca ctcccttccc tacagcccat gcacatacct catggttgcc    37800
acggcttcct gacaactatg gatgttcagc taattgtgtc agctgattta tagtggagcc    37860
aatgaagctg aagcttcaga gccctccatt tgcacaaccc tttctaaatc cccctcaaga   37920
ccctgtgaag ggccccctag cagtgtggtc acctgtctta tgctttggta aaatttgaat   37980
aagtaagata ttgtaaccac aataagttat gaccactgtc tccttcctct gcaacttttc   38040
cctccatgcc attctcctgt ctggtggtgt tagcagtcag gggcattttg tatttgaatt    38100
ctacattctt tttcttaact atccaccacc tcccctcaaa attttaacag catccagcct     38160
cacaaaactc agatcttccc tgtttacagt tccactttga gtttcagttt cttcatctat     38220
aaacaggagt tggctgcggt ccctgccatg tatcctgtga ctcagtgtct cgtagttact    38280 cctgcccac cccttcctgc tgctccttgt ctccacctgc aggcctgaga gggaagccac    38340
cccactaaga cagggaggtg aactgagcct gaagtttggc tacagcaccc acaggccacc   38400
agccatgagt tcacctcctc cagatggcca cacaccaggc ccttggccac tgtccccatg    38460
tctgctgtgg atgatgagga gtcagggaac tacaaagaga tggtccctca gatccatgct    38520
ggctgggata agcctttca gatttctgtt tttctgctta gcaccttgag cttgtgggagt    38580 ccttgagtgc aaggtctgta gatgtgccag ctgatcactg acttaggtaa caacagcagc    38640
ttccaacccc cagggcccat gacctgctac cttagctcct ggggatgtgg gaggtatgtg    38700
tgtgtcagag agcaaggcaa gaagactcta gagaacatta ccagtaaga ttcccttctc     38760 atcccacttc ttatttattt attttatta ttttattttt tgagacagca tctttctctg    38820
tcacccaggc tggagtacag tggcacagtc acagctcact gtggcctcga ttacctgggc   38880
tcaagcaatt ctcccacctc agcctcccca agtgctagaa ttatatgcat gagccatcgc   38940
acatgactta tttattttat ttgataaatg catatataca cacagtcatg aatcgtttaa   39000 caacagggg acgttctgag aaacacatta ttaggcgatt ttgtcattgt ataatcatca    39060
tagggtgtcc ttacacaaaa ctagatagca tagcctgctc catacttagg ctacctggca    39120
cagcctattg ctcctaggct acaagcctgc acagcatgtt actgtgctga atactgtagg    39180
tgttgtaaca caatggtatg tattttgta tctgaacata tctaagcata gaaaagatac     39240
```

```
agtaaaaata tggtgttata atcttatggg accaccattg tatatgactg aaatgtggct   39300
gtgcaataca tgacagtata tgcatatata tatatatccc ttactttgtg cctggtactg   39360
ttctaagtac ctcataaata ttaactcatt tgagcctcac aataactctc tgctttaggt   39420
cttgttgtta tttcccattt taagatgtgg acactaaagc ccagagagat gaagtaattt   39480
acccaagatc gacagagcta ctaagtggca gagcttggat tcacacccag caatgtagat   39540
ttagcattcg ttcacttgac tcttctccta actcttgtgg taaaccatga ataagtggta   39600
agacttcttc catggggcct gaacagcttt ggtggataat atagcttctg cctcatccgt   39660
gttcatccag tgcctcctcc ccatcacctg cagctgacac ctcagttgac ccaagagctt   39720
gggcccaagc ccttctcatc aaagtgacca gcccagctct caagatctgg gagagaagga   39780
agaaaaatgc cctggaaaca catttccaga aaacactaaa ctggaacacc atttcccacc   39840
aaattttctg actccgcaca ctgaaagtga gaaagtaaag ccgagacact ctatgaaaac   39900
tgagttcagg tgtcactttt gcccttgatt tgccattgac acttcttaga agtttcttag   39960
ctcctgagaa aagagttacc aatattgaaa gcaacaacct caaatggtaa ccgtttaagt   40020
tttatggtgg tgagagaata agtgactata tttttggcag tacaattta aagtggaata   40080 gaaagcccat gacatcagat cagaaaataa cattgccagt aattcacaca cgatgaaaag   40140
caacaaaaaa tcagattcta tttgaattct ttcttctcag gcacacctc tgcttactgg   40200 gctggtgaac agtgacctag ccacagggcc ggcttccaaa gggagaaagg agatgcaatt   40260
ggcccacata atccaccctc aaaatgtaga gctgaataat tcatttcatg gcatagaaat   40320
agcaatacag tgaagcaatt ctgtttaact tttccctccc tatattttgt gtcctctgtc   40380
atggaaattt gacacagtag tatttgctgc ccctgctctt gaggataaaa ttggatggga   40440
gtttaagact gaaacgggca cctgtggcct tgcagaatta ggttacagtt tgtgccttgt   40500
atttacaaag cgaaaggaat tcctagtgcc acctgcagag gcacttctaa ctttcaagct   40560
ctgtttgcca ctgtcctggc acctccatca cacttttagg ctggagccag agaggttttt   40620
gaaaaatcag tagctcccac atcaggagga agtatctttc cagtttgagt tttggtagct   40680
gctctctttt tgtctgaggg ttctctgggt cctagggctt tctcatttct cttgaacaac   40740
acctctagtt aatttcatgt acctggagtg gtagttggaa tatttcttca ctttaagatt   40800
tttttttttt tttttgaga tggagtctca ctctgttgcc caggctaaag tgcaatggca   40860
tgatcttggc tcacggcaac ccccgcctcc caggttcaag tgattctctt gcctcagcct   40920
cccaagtagc tgggattaca cctaccacca caaaatacaa aaatacacaa ataatttttg   40980
tatttttggt agagacgggg tttcaccatg ttggccatgc tagtctcgaa ctcctgacct   41040
caggtgatct gcccgcctcg acctcccaaa gtgctgggat tacagacagg catgagccac   41100
tgcgcccggc ccaccttaag atttatgtaa gattggctca aaagctcatt cctgtggaaa   41160
ggtccactgt tttcctccca agatttttgc agatatctgc gtgggtggtt acttttgact   41220
cccatttcct gctgttgttg atagccctca ttaaaccat cacctggagg tgaatagaca   41280
gtcgagacct atcattccca aagaattgtc atggagccta atagttctat tggattcacc   41340
cctttatgtt aagccaccat ttcagtgttt ttcaaaatag atatatgtta tctagtaggg   41400
agtatcttac ccccaaatta gttgattgtt tcaggagggc ttttagtggg ttccagagaa   41460
aatgagcaat cagacaagtt gatttagtgg aagacagtca ctgaatagga tgtgtatagg   41520
gttgtttggg agcaagagtg aaattggtat ggaacagaga ggctcccaag gcaagcagac   41580
attttttttg gaagaagcaa gtgtttgaga gactgtggct tatttttcct tgtgagagg    41640
```

```
ggagttttaa taccatttcc aaaatatgta acctggtatt ttgtcccag aagtactgtt    41700 gagatttatg gaagcaaaaa actctgtcac ccaggctaga ggagtgcagt ggtgctatca    41760
aagcttactg cagcctctaa ttcccaggct caagagatgt ttctgcctca gccacctgaa    41820
tagctggcac tataagtaca tgccaccatg cctggctagt ttttttttgtt gttgttttgt    41880 tttgctttag agacggggtc tcgctttgtg cccaggctgg tcttgaactc cttttaagtg    41940
attatctctt ctcagcttct taaagtcctg ggattatagg catggcctat ctatttttat    42000
gttttataat ttcttgtact ttttgatgtt acttcaaata tcttttttaag tatcctaaat    42060 atacttattt aaatttttt tgagtaaatt tatctataaa ttattgattt tatgtcgata    42120
gacattgttc tctatcatta ataatgttaa aaataaataa aaaacaaaa acaagtaaat    42180 caattaatgc ttaccacagg ccagtatttg atccaacact aactcaaata ttcatttctt    42240
taatcctcac aacaaaccta tgaggtaggt accattattg ttcctgcttt ttgcaagagg    42300
aaactgagac acagggaagt taagtaattt gcctatggta acacaggcag tgagtagttg    42360
agctgagatt gaactcacgc tgtccagaat ccatgctatt agttataata gtgtactgcc    42420
ctatagcttt ctgtttcaca gctacatggc attactttgt atggatgtat cattatttgt    42480
taaaccattt aacttatttc cagtgtattg ttcttataaa caatgaatac ctgtgtacct    42540
ctaattttgt gcacatgtat cttttttgtag aatgaattct taagaaattg agttgctaag    42600
tcaatgctta agcccataat taatttttctt acatattacc aactgtcctc caaaaaggtt    42660
gtaccaattt agaattttac cagcagtaaa ttcagcagtt aggacccatt ttcctaacac    42720
tctcgcggac actgggtatt accagtattt ttttttaatac gtgccaatca aatgggcaaa    42780
aagaatggtt tctcactgag gtttaaattg catttcccta gttattcttg agattttttcc    42840 tttccttttct tcaacaatta cttattgagt gcttcatatt tgtaagggac aattgcaggt    42900
actgaaaatg tcacagtgag gaaaagtgac aaagcccctg ctgtcatgga gcttattcta    42960
atgggagatg tcaggtgctc agctgagctg ggagagagag agctgagttg tcaggtgtca    43020
gaggagccaa ttatagcagc aaaacaaaaa taaaatagtt cagcttttaa tctcttacta    43080
cgacggtata atcaagaggc taaaatggga ggaagggcag actctgcctg ttccatttcc    43140
ccacatagag tgagtatacc agtcgagggt caggtaatca gtgcagactt agggggtcgc    43200
cttaccattg aagaagcccc aaatgaaagg ctctagcagt tttatggacc tggggggtgga    43260 ggaatccaag ggtggggaga attcatgagg aaaatgaggt gagagggcta ggagtggaaa    43320
agtacaaagt actgagttag cgtgggggaat agtgtcttta gggctaggag tggaaaaaat    43380
actaggtact gagtcagagt ggaaaacagt gtcttcaagg cagggagtgg aaaagtgcta    43440
ggtactgagt ccgagtggag aaaagtgtct tctctatgat gaggaggctt cagcagaggt    43500
gcctgaagac ctcaccccag agcctcagat aaagagacct aagaatgagg gtgcctgggc    43560
taagattgca agtatgtgaa aaagcatgac tggcgggagg ctgagatctt gattgcagcc    43620
cccttcagag actgccatgc actgactgtg caccaagtct gctgtagaaa gggcaacttc    43680
ctcagcaagg cttgtcagat taagcctctt taattgcctg tggtcaggtc tgaaaaatca    43740
cacatagatt tttaatcaga acccagacat ctcaggagag acagacaata accaaacata    43800
ccgtgtcatg tcatgtcatg ataagtacca caataaatat aagtcagcat gagggacaga    43860
atgcccagga tgctatcttc aatagaatgg ttagagaaat ctccctggga ggtagcattt    43920
aatgaaagac ctcatgaag tgaaggagaa gctatgagac tgtctggagg aagaaccttc    43980
tggacagagg gaacaacatg agaagaggac ttgagacaga gtgtgtgatc ttttggagga    44040
```

```
atgtcaaggg aggcagtgtg gctggggaga gtaagcaggg gaaagaggcc tgataggtac    44100
tggggaccca attacatgag gtcttgtaag gccaggggag ggactttgga tgtagttctc    44160
agtgtgaggg gaagggatct ggatatattt ttcagtttgg tggaaggcat cagaggcttc    44220
tgaacaggag gattatgtga ttggagctgt attttttaagg gatcattttg gcttgagaaa    44280
ctagacccgg ggacaaggac ggagcaggca gatgagttag gagacaatta cattagtctc    44340 ctctacccttt ttcttaacat attggagttc agctctggct gtagtagttc tagatctcct    44400
cagacacact tgtgtagagc ctctgttggg tattttgggt acacaaatga ttcatcttgg    44460
ttatacagat gatttagatg attgtagaca aagagggtt gtctggtcat cccagacag    44520 gggagcattc cttgagatag agtagaggaa ggctgaaggg gaggaagaca gtacctgttg    44580
ctatctagat agagacatcc agcaggaagt tgaatacagg tatctgaaac tctagtgaaa    44640
gttataggct ggcaataagc acctgggagt tattagcttt tacttgacag ttgaatccgt    44700
ggggctagag gagaaaaacc aggaaagtat ggagaataag aagaccaaga acatgcactc    44760
aaggttacca aaattaaaga gtgatttgag aaaattaaca aggaaatcag agattgggaa    44820
agaatagagc atttcaatga ggagagatgc caacacttgc atttgacaca gcggtcaaat    44880
gagttgagat ctgaaaagag ctcaagcctt ggccatggtg tgaagtcacc aacaaccttt    44940
gtcagggagt ttcagtagag aggtgggggt gggaggctgg gaataaaggc agcaattgct    45000
gcttactctt tcagggagtt tgactccaag ggaaagagaa actaaaagca gtagcacaag    45060
gtttgtgttt gaagtaatgg aggtgaacca ggtgaatagc ctggaggccg agtgaagtga    45120
gacaggacac tgcagatttg gaatgtcacc agtccgcaca actgaataat ttcctccaga    45180
actgctcaat tgcccagttg taagaacaga tatgtagacc aaaagtagag tgtccccagg    45240 gtaaattttta tagagacaaa ggggtgtgtt tattgaagtt gtggaaagga ataattacaa    45300
agacatacta ttgttgcatt gtccaatata ataaccacta gccatatgtg actacttaaa    45360
tttcaattaa ttaaaattaa ataagattaa aaattcatct tctcagtcat actagctatg    45420
tatcaattgc tcaatagcca caggggctgg tggctatcat attgttcagc acagagacag    45480
agcatttcca ttatcactaa gagttcttgt ggaaaacact gcactacagg gtctggataa    45540
agctgaggtc ttgattaagt tgaacaacag ttgtagaagg agtaagcaag agcaaaacct    45600
ggatgaatag gaggttgtgg acggagatta gtatattgag attaagattc tagggactga    45660
gctgctccag gtgaaaagtt tcagggttat gtcataagaa ggtgggggggc agctgctgaa    45720 atagtctgcg ggtgtagacc tgtggagttg acaagatcaa agaaatttga ggcaaggttg    45780
ttagactcat tcatgaagaa gtcacccaaa ttgttagcaa gaccttgcat ctaatgccaa    45840
aatcctcatt tagcaaggtg gtagtgactt agtagctaca agcaatgaga aagtcagaca    45900
cctcaaaagg ggaaggtgtt gctcaaagtc cccacaaagt gtgataaaac aaacagtagc    45960
tggggctgga gcaagtggct tcctttgggt gaagccagat ttcactgaaa taataacctc    46020
agggaaacag tcaatgaagg ggttaaagat gtgggagagt ttccttgtag taagtaatgg    46080
aatgaggctt tcaaagggcc aagtaaaact tggaggaag tttagtaaaa gaaggaatt    46140 tttttagtac agataagcat aggaacataa agaagagata attcttaaac atataagata    46200
tgcatttggg gatagcagcc agggaacact gaagtcccag tggggtcaga gacttcataa    46260
ggctagcaaa ttacagtttt tgagtggcat tccaacagta gagtgtattg ctcaggaagt    46320
ccttaattat cctttgaaac aaattccttc agctgattac gaaggcatct agctggattc    46380
ttgagcgact tgttcctgac atcatagcaa cccattgtaa ctagacttcg accattcctc    46440
```

```
ttacccaagt gctggggaag ggagagattc tcaatgctta cccacctatg gaatcccagt    46500
aagtccagtt gctaggtggc ttgaggtctg gggtcataaa atggaaggcc tgaagtcatt    46560
tggtgatcac agaccttgag ccaaactttc cccatttagt cagagaaagg attagcagca    46620
tcccccatgc ctggctctgt gtgagatcat ggaagccagt ggttggtgag gtgctatgga    46680
gtataaattg caaaatactt tcagttccac tcagaatgga tttcaaagtg atttccaccc    46740
catggggagg agagggagtc tgaggaggga tggatggaaa aaaaattttc atgtcatttt    46800
ctgtgatcca ctctggagac agaggcagag attctctaca acagctgctc aaactatagc    46860
tcttgttaaa atggaggttc tgaatcagta agtcttgggt ggggccagag attccgtgtt    46920
tcagaccagc ccacatgtga cgtgaatctc attggtccat acatcacact ttcagttgct    46980
aggtgaagaa gggagcactc gatgagtgga agagaaagcc gttgtaatct tgggagaag    47040 gggcctgggt cagcggagtt agactggtct gtgagtggac agaatggatg ggaaggaaag    47100
aagatactgt gaggctctac agaaaaaaaa aaaaaaaaaa atatatatat atatatatat    47160
atatatatgt aaatcaagaa gacagaagca gctaaagacg aagtcatttc caggtccaga    47220
aggcacaact gacagctgag taataacata acattgactg ttaattggca gaatttttaa    47280
ctgtgtgttt ggtttctcca tcaggtcatc tgtcctatat tacatgacaa tttagactaa    47340
aaccagtatt tcctcagaga caatgctaga agcttttaca gtaggggca ctcttgcatt    47400 acattaagag ctcagcaaag aagatgcaga agcctcaggt ttgccttgta aggtgattca    47460
taaacacact aaatcttcct taggtctccc tttcactgtc agggtacgca tatagatttt    47520
ccttcctccc tccaataccg gtacgcatcc tctacaggtg gtgcatttta tacctcaagt    47580
acttcacagg gtcctagtga gtgtagtgaa ataggcagtg attcatattt gtgcaaactc    47640
ccactgatgc ctgctgtctg cttccctaag agttcaagac caccaccaac cccttgatta    47700
tgtgttctca ctgggccact ctgtacacag tttagtttga caagtgcatg tcactgttat    47760
ctgtccttct attccctctt tcaagagaaa ccacatcaat ttaattactc ccccacttag    47820
aactcttcaa atgaagctcc tctcatctct ctcatcaacc catctcctcc ctttcctcct    47880
caatgtcaac atgccttcac ataaatcctg aatgatgaaa ttttatttag aacttacact    47940
aacttcctct ccaaggtggc atctaacttc atattaagta agaaacagcc ttcccactct    48000
ccacccccgc acttctcacc caccactgct tacttttttt tttttttttt tttttttttt    48060
gccaagtctc aagtaattct gtaacctaga aaaggtccta cacaaacccc gtgatcattc    48120
acatttaagt agttgggtgg cccacatcct tcccacaaac cccaaagtgt cctcaaggac    48180
taaagccttt ctctcaaccc ttccagcatg atgtctatgg ttgtaaaatt gtccagggtc    48240
agtgcatact gggagcagca agtttgtggt gcctggggtt tccccaatac tcccaaagca    48300
catcctcacc tgcccatcta tgattcattt tcagcatttc actcatgtgc cttaaatggt    48360
cattgaccac cacaatccga aaacagccat caaatttgcc cagttctctt tctgatctct    48420
gaaagagctt agagaggtca ctgaaaataa aggccttggt tcactatcga agtcatttct    48480
aaagcatttg acatccttgg aagtgctggc catgggagca gcagtcatag gggaagttct    48540
gtaaagggag ctatttgaat ttcaaagatg ttactcaacg tgattcccca actaatgaag    48600
tataataaag gggggctata atttattacc attatcagca atcttttcac catagcagac    48660
caaggaatat gtggatggga ggggaggggga aagcttttgg tgatggtgta gaagttatgg    48720
aacctgtaac agctacagtg atgaaaacta aaattaaggt tataggaagg taactggtgg    48780
gtgaatgggt tgtctaactc tactggtttt tccctgtctt gcaatttaaa ttcacagaac    48840
```

```
cacagtacta gaaagaccct tggaacattt agtcaaccac ttcattaatc agatgaggaa    48900
actgaggctc ataaagattg cagtttgtac aaggccacac atttagtcag cggtgaagca    48960
aggacaaagg tcctaatctc cagatgccaa gcagatgtgc acagttccag agcttaatat    49020
cttattcttc agcatgatta ctgataagat agtatctggg tattgtataa agagaaatgg    49080
aggttttttc ccctttcctc ttgtttctcc ctccctaatc cttaaccttc tttttaggt     49140 gctgctcctc tgaagattca agcttatttc aatgagactg cagacctgcc atgccaattt    49200
gcaaactctc aaaaccaaag cctgagtgag ctagtagtat tttggcagga ccaggaaaac    49260
ttggttctga atgaggtata cttaggcaaa gagaaatttg acagtgttca ttccaagtat    49320
atgggccgca caagttttga ttcggacagt tggaccctga gacttcacaa tcttcagatc    49380
aaggacaagg gcttgtatca atgtatcatc catcacaaaa agcccacagg aatgattcgc    49440
atccaccaga tgaattctga actgtcagtg cttggtatgt ggtcaatggt gtgtgttcag    49500
attcttagcc ttctcagatg agactgcaaa tgagttagaa aaacactgga gggggacttg    49560
aggggcccag gggaaaaggg gggtctatag agagaaggca gaggacagcc acttctggga    49620
agtgcatttg aagggagtgt agagtctggg agtagggaac tgaaagtctt ttgtactttt    49680
tatagtctgc ttctgaagga tcagtaaaaa tctgctttgg ggaaaaaata gagctaattg    49740
aacaaagata atatgctaa ttacctatag taaaaaccat ggataatttg gccatcacaa     49800
agtttatata accataaagg cctcagatgt cttacattca tttttttcctt gggtccaaga   49860 tttttcacct actaaatctt tgcctggagc tcctagcaaa gcggacagct gacacatttg    49920
ggttttccct tcagcctcct ctaggttgct tatgagttgt ttgctgccac aaccatgagc    49980
ctggtagaca gaagggaaaa aaacccaaca acataaccc acaaacttac aaaccagctc     50040
ctctgcttca cgagaccttg gaaggcctaa atgccactac agatttttt aaaactatca     50100 cacagtaaaa ttatttttt ttgttttgat atactgttct actgattgta tagatcttgt     50160
atagatttag gtaaccgcca caggacatag agcatttcta tcaccctaaa aatttccctc    50220
aggctgtccc ttcatagagt catacctgt ctgcactcat aaccttgtt gggcatccta      50280 tagttttgtc tttttgacag tgtcacataa gtgaagccac acagtatgta acctttttaag   50340 cctggcttct ttcgtttagc gcgccttcga gattcaccca agttgttgca catatcgagc    50400
ttgtcccttt ttattgctga gtagcatttt attgtttatc cattcaactc agtaaaagac    50460
attgggttgt ttctggtttg gggctcttat gaataaggct gctgtaaacg ttcatgtaca    50520 ggttttgtg tgaacataag ttctcagttc tctagaggaa atacccaggt gtggtattac     50580
tggatccagg ttaatttttg atgaaacttg aaaaggcaga tcaacaccta ttctaaaacc    50640
atagagtaaa acagaagcaa aagtaaaaat agaatggaga gctgctccct ttgaaccctg    50700
tgtgatttaa actaggctgc agggctttag gaatagttaa ccaagtgcta aatccgtgtt    50760
ttcaaaatgt ggtcaggtac cattggaaat gttttaggtg ggacacagat aagcattttg    50820
aaaagccatg ttgtatttgt tttaatgtat attagaaaaa ctctaactta cgcaacatgt    50880
gatttcacag atcttgttaa tgaagctaaa cacggtctgg caattcacct tctacaggcc    50940
acatagactc caagaagact gctcaaatag tacactgata tagcaaaact tataaagatg    51000
acatgcaaat gacagacctt ttagtaagaa tacactaaat tataaattag tttgtagaac    51060
ctgcaaacta cctagtaact ataaaagaac aagggatttt ttctgacaga aggcacatga    51120
cacaggtcta gggactccat gccagtgatc ctgaacagcc agaaaagtga gaatggcaaa    51180
ggcaagagaa acactgtgtt tattaagatc atgtatttttt ccctaaaata gctggatttg   51240
```

```
gccttcttct tagagtatgt tatgaagaca ctttgatgct catgccaaaa atcagtgttc    51300
tgaatttcga attccaaaat atccacccac tcacttacca caatcctgct tgggtttctg    51360
aaagatatga cgcagggcat ctcagcacca tgaactctgt cagttcctgg tgagactcca    51420
gctcaattcc ttcctgctct cttagtctgg ggagctggaa tgtgcccat gggacacctg    51480 ggccctagag tcagaccact tctccttcca aagactctac tccctggaaa cagtggcttc    51540
attgtaaatc tttggtgact caattacagc cctcctgtca cttagagagc accccttga    51600 tttggataag caggaagtaa gcatggctgc aaactctatt gttgaaaaat aaacatgaag    51660
tcattatgtg gcactcacct tgggctgagg gtcacatttt agacaccctg aggctcccag    51720
gtgtgcccca atgagcccca gatcaagtac ccagttattt gctattccct cctagataca    51780
tctaaactta gattgatttt tttttatctc tcttctgctt tcagctaact tcagtcaacc    51840
tgaaatagta ccaatttcta atataacaga aaatgtgtac ataaatttga cctgctcatc    51900
tatacacggt tacccagaac ctaagaagat gagtgttttg ctaagaacca agaattcaac    51960
tatcgagtat gatggtgtta tgcagaaatc tcaagataat gtcacagaac tgtacgacgt    52020
ttccatcagc ttgtctgttt cattccctga tgttacgagc aatatgacca tcttctgtat    52080
tctgaaaact gacaagacgc ggcttttatc ttcaccttc tctataggta aagctgtttt     52140
ccaagactat ttctttcagc aggtattata cacaaatgct taaggcagat catccaatgt    52200
ccccgacttg ctaggaaacc tccaactggg ccattttatg acgctgttag gaaggaccca    52260
gatggaggtc tcctgcttct cctgagtgat gcagggtcca ggaggctacg agcctatgtt    52320
gcacttgaag aaatatgctt ttagccctga aactgactca gtctcttggt ttaccttggg    52380
atggaggatt ctgaagtttt gatttaaaaa tacaggattc ctccaggcta gaattctttc    52440
tttgattaca acacatacat gcgcttgcac acacacacac acacacacac acacacacca    52500
tgcatacatg cagacataca aatgatattt attgtgagta tagaaccatt tgggacatta    52560
ttggtcacag gagtgaaaac aaaaagatat gacaccccct ctgcccttga ggaccttcca    52620
atagaatcag aaccctgtaa tgtgcacaca tgaaaaactg gattttttaaa aggttgaatt    52680 ggaatctaaa ttttattcca tggaaatatc tgactaaatt taaaataaaa gtgactggta    52740
atgagattta tgggcattca gaggtaggca agatccctga gggtcaggga atggttccta    52800
aaggaagggg taccttgtaa catgtaaaat aaattattgg ggttaataaa tgtggtgagg    52860
aggggagggc attctggatg acaggttccc aaaactgtgg tgacttccgt agctgaaaaa    52920
atttgagaca gtatctgggc taagcaggtg agaggaccac agtggatcag ctgtatctga    52980
cgtaagtgca ggaggtatgt caaagaaagc cttggaggca gaaatgcttg tgtgttcaca    53040
agtattcttc agggacaagt tcagtggagg aaaggattga aactaagcag tagccactaa    53100
taggagcctg acattttaaa gtcctggctt tacccaggag ggcatgtgtc tatatttgac    53160
tcctctttta agaagctgta actgcaagat tccctcctgg aataaaggtg gtctgcatct    53220
accctgtccc atcactgcct gtgctgacct tgacaccccac atctgccttc ttcttacctt    53280 gacccccttct ccagcggtga tttcttggct tgcccctcc agtgacatcc atccaactcc    53340
ttgctccata ccctggcttt gtcacctcct ttctcccagt gtcttgttgt tcagatataa    53400
cttggtctgt gaacagccca cggggccagt ccccatgaac caactttaca actgggccaa    53460
tctcatctcc tgctactgac ttcttcctat tcagacactt cagcctctga gaatccagta    53520
aatggtggag ccaactcgtc ctgtcccagt tgcttctcct gtatcctctc ttggccagat    53580
agaagcctct ccaagctatg cctgaagttc agtacctcct tcaatgtgta attagtttga    53640
```

```
ttggtggcca caagatggcc atatatgaca tgccccaggg ccctctgtta cggctcccat    53700
agtctacaaa ttaacagggg cttgccacca ctataacctc atcatggctc accttcctgc    53760
tgcttctcaa ctactgttct gccaaacttc aacaggtacc cccatcttca gaaatgtttc    53820
agctctagct gcctcaggaa gatgggctt gcctctctgg gtttcccatt ctatcgcttg     53880
atcagagata ggttagaccc tgagtcaagg ggccttttttt gcatgttaaa aggtagcagc   53940
ctccacgtta gtaagtataa cccctaaccc cctttactgg gagtgccaaa ctggctcaag    54000
tggaatagac tgggacagac tcaaaaggga ttaaatatgg cctgcaatgc caacaacttc    54060
ttaacatccc agaaacaggg catgtgtcta caaattatag ctaagctaat agatcagctg    54120
gtcctaattt tcctgaaatt tgggattagc taccagaact gttcccaaaa atgtctttaa    54180
agtgggcgac tccgttctaa gttttcccca caaagcctgt tttccaactc cccagaaact    54240
taggagttct catgtaagga agtagttcct gaaggcgtga aggttcctca aggcatgaag    54300
aaacatcaaa ggttttttcag tagatgagat atgctgaaag ccatgcagag gaaacctgct   54360
gtgacctcag taggaaaaaa ctaaacaaac aagcaaatga aaactagagg tagggggcctg 54420 tggaagctgt tccatttgtc caagtgagag gtgtctggag attatagtgg acagaagaat    54480
catcacgaga ggaacttcag ggcctgggaa ctgactgcag aggggggcag gatagcaggc    54540
acggcacaaa tgactgcacg tgcagagcct cagcacagac acctcaccca gattccagaa    54600
tcacgggcca ggctgaccct cttcttcctg atcatggtcg gtgttatccc cacctccatg    54660
aaggcatggc agctcagtcc aggcatttgg ccagaggcat gggctcgatt cttaggtcgc    54720
tgctgaggcc ctgagcctgg gactttctat ggcctcctat tgtggatttc aggcttctct    54780
ggccttagag ccctggggag aggctggcag gtaaataaag agaagagcag ctagcagaaa    54840
ccttttgtaa atgactctcc tggctgattg aaaatttgtg gtcatttgta gagcttgagg    54900
accctcagcc tcccccagac cacattcctt ggattacagc tgtacttcca acagttatta    54960
tatgtgtgat ggttttctgt ctaattctat ggaaatggaa gaagaagaag cggcctcgca    55020
actcttataa atgtggtgag tgagtccttg tcctccccac agactgtcac tttgcaccta    55080
cttcccaatc ggctggctgc cttccggagc ttgttggctg agcctagact ggcaaaaagt    55140
caggaagttg ttgggaaaaa aggttttccc ttggagtttt gagcctatac agactggcag    55200
tagcagataa tgctgctctt ggacttcaaa gaaaggcgac atttctaacc tctggtttac    55260
aaatgtactt ctggtttcca gggaaaactg attattactt gctttatcta cctcacttca    55320
tgaggttact gtgacatata cataaagtaa aatggtgaaa ccactcctaa atgttaaaga    55380
ttgtggacct ggtggtgttt aagcagggat atttgctaaa tgaccacaag aatcagcttc    55440
tcgtctctaa aaaaatctag gtttcttatg aaataagtta gatgaattat tgcccattga    55500
cttataacaa acaatattaa ctttaactaa tttctaagta atacatatcc attatcatat    55560
ataccaaaaa taaataatc tataactcca ctaataagaa aaaatgatta cacaaatatt     55620
tttggtgcct atctttaaga ttttttctgtg tatcaatcta tgttgttttc cataattagg   55680
attatcataa gggttatttt tcacaatttg gataatatat gtactgtgtt ctaatttttgt   55740 tatactaaat gtagcaagac aattttcaat gtcataaata tcattctaca gcatcatttt    55800
taatggctgc aagatattcc cttttgtgga tacaccataa tttatttatt taaccaacct    55860
cattttttgg acacttgagt tagtccaata gttttgttat tataaacacc ctccccactg    55920
acttctgtta taaaaatgtt tcatggggac aaagtggtcc ctaactttat aataatgcca    55980 tgccttttttg tagtttggtc tggttctaag ctaagattgg actttatctc agtaattgcc   56040
```

```
tccagtagta attagtttga ttggtgctaa taattaaggt aaccttctaa ctcacttatg   56100
gtagaaagca caagatgagt attgcctctg gccagcatct tgtttttcag tatactgatt   56160
ttaaaatcta actagaaaat agatggatga cattagcagt cattcaatgc atcctgctgt   56220
actttaaaaa taagaaattg gggagcaacg atcgaattta aataaattaa cacaaagcat   56280
gtggcagagc cattcaaact gccaatgtat ggagtgtgct gcgagatttc tatgatataa   56340 aagtatataaaa ttcctagcac agatgtaaag acatatcatg cttgtccagg ctttgacttt   56400
tcaaggtgag agttttgagc ttcactttct ttcaacctca ttgccattta aaattagtca   56460
aatatgaaga agtgacttac atcttgggaa taagctgttt gctagatttt tcttcacatt   56520
agaatgatca gcttacaaat gaaacaaaga agggttggag aaaaagatta aggatgtttc   56580
ttcctccatg aggcaatcag aaaaaaatca ggagactaga tagggagat aaagaggata   56640 tgtgtgttca catgagagaa gttagaaggt ggttaaataa gctctgtagg tacagatgag   56700
atggtcagat tgggctgagt ggcacataca tgacccctaa gaatgtaatg aagaatattg   56760
gtaagaaaaa gttatttatt cagacagtca tccatgccac tgagtttgat caaagagaga   56820
agccttgcta tcactgtagg gagggaggtg caacaggtat aactatgcca ttatagatat   56880
gatatatttg taaatttgga ttctgtaact tcagcaatat ctgccattgc tttgtgggta   56940
ctcctggcat tggctatgtg ataggtaaaa taatgccccc cacaagacgt ccacctccta   57000
tactccagaa cctgtaatat gttatcttac atggcaaaag gaacttcaca taggtgatta   57060
aggcaccaag cttgagatgg tgagattaac ctggattatc caggtgggcc caatgtaatc   57120
acatgagtca gagaacccttt cctagctggg atggagaaat gaactggaag aaggagagat   57180
ctgaaacttg agaagctcaa cccagcacttt ctagctttga agatggaagg aggaagccat   57240
gagccaagga atgtaagtag cttctagaag ctggaagtgg ctctcagttg acagccagcc   57300
attaaggaaa ttaggatctc agttctgcaa ctataaggag ctgaattctg ccaagagacc   57360
aatgtggaaa cagcagatcc ctccacagag acacaagctt actgataact ggtaggaatt   57420
tctccaaaag tggagcttcc tcctactcca gtgttaatcc ctttctcaga ggagacggtc   57480
ctcaaactaa ctaacttggc accaaaagtc ctatccagtg ttttctcatt atagtttttc   57540
tatgcctcaa ctgtatatat ttacccagtt taggctgttt aaatgaataa aaaggaaatg   57600
ccatagttat tctagccagt ttccaatctc tcttctcttt ttttgttttg tcaaataggg   57660
cagataaggc atgagaattt ataactatga attactgtct tttcccaaac agaaatcacc   57720
ctatcagctt acccattggg agaaaaacta aaatagctcc ccctgaaatt ttacttcctc   57780
atttgggtct tgtgtgactg aaatctgtat acaatgccct agcaacaacg gtttttacag   57840
cttgcctccc tagaacaaac ctaggagtct cagctgtttc aggaatgatt tcttaaaggt   57900
aaagtgcctt tttcaaaaga aattattatt attttttttt aatttttttt ttgtgtgtgt   57960
gtgagacaga gcctcactct gtcaccaggc tggagtgcag tggcacgatc tcagcacact   58020
gcaacctctg cctcccaggt tcaagcgatt ctcctgcctc agcctcccaa gtagctggga   58080
ctacaggcac gtgccaccaa gcccaggtaa ttttttgtatt ttcagtagag atgggttttc   58140
accatgttgg ccaggatggt ctcgatctct tgacctcgtg atccgttttt aaccaacatt   58200
taaacagaaa tattcacagg cttaaagact gaaagttagt gatatcatca catttcccct   58260
tcaaaatgct gaatttgtaa gcaaatttaa aagtttagaa tctacctttt aattgtctgc   58320 tttcatttttt ttgacagtgg ctttttttga tatggtgact attttgtcat gggtataaaa   58380
ggataattca ttttgtgtta atctgaagac atctgaaata ctgtattcaa ctataagtac   58440
```

```
cttttttttac atttataaga ttcttttttca aaatttttat ttgaatagtt ttttgggaac   58500
tactgaacta aactaggtgg ttttttggtta catggataag ttatttagtg gtgatttctg   58560
agactttggt gccacctgtc actcgagcag tgtacactgc accagtgtgt agtctttttat  58620 ctctcacccc tcccactctt tcctctgagt ccccaaagtc cattatatta ttcttatgtc   58680
tttgcatcct catagtttag ctcccactta tcagtgaaaa catacaatat ttgtttctcc   58740
attcttgagt tacttcactt agaataatgg tctctggttc catcaaagtt gctgcaaatg   58800
ccattatttt gtttctttt atggctgagt aatattccat gagggatatt taccacattt    58860
tccttatcca ctcatgggtt gatggacatt taggttggtt ccttattttt ggaattgcaa   58920
attgtgctgc tataaacatg cgtgtgcatg tgtctttttc atataatgaa ttattttcct   58980
ttgggtatat acccagtagt aggattgctg aattaaatag tagagttcta cttttagttc    59040
tttaaggaat ctccatactg ttttccatag tgtttgtact agtttacatt cccaccagca   59100
gtgtaaacat gttcccttttt caccacatcc atgccaacat ctattatttt ttgatttttt   59160
aataatggcc attcttgcag gagtaaggtg gtatctcatg gtggttttaa tttgcatttc    59220
cctgatagtt agtgatattg aacttttttt catgtttgtt ggccatttgt atattttctt   59280
ttcagaattg tctattcatg tccttataaa caccattatt tttaagaaga aactttacaa   59340
aaatagaaca taaccagatt tataaagcat ctgggaactc agtcaattaa gaaatagctc   59400
aagtaactga tgatgcttca cctgaaagaa ggcctggaga gaacagagat actgtcttca   59460
aatatctgaa gagctaccat gggatgcaaa gattgagctt gatggtatga ctctgaaggg   59520
catctctatg aatgaaggtt atgagagggt ataaggaatt aagagagact tttctaacaa   59580
ttaaaaggtc ttttaggcca ggggtggtgg ctcacacctg taatcccagc acttttggag   59640
gctgaggcag gcagatcacc ttagatcagg agttcgagac ccgcctggcc aacatggtga   59700
aaccccattt ctactaaaca tacaaaaatt agctgggtgt ggtggcaggc acctgtaatc   59760
ccagctactt gggaggctga gagaggagaa tcgcttgaac ctgggaggca gaggttgcag   59820
tgagccaaga tcacaccact gcactccagc ctgggtgaca aagatcaag attccgtctt    59880 aaaaaatata aataaataaa taaataaata aatagtcttt aaaattgtat agaagaagta   59940
gacttctgct tcctccaaca aaggattaac tgctatagga attgccctct ttccataaac   60000
aactagaaag cagacaaaat atatgaaaca actgtttttca gagatcggat gacagacagc   60060
agaaaactgt agtccctgag tgaaggaaag aaaaaatgag ataagcccta tgattgctct   60120
agtttgctgc ctggagccag tgtccaggcc cctctgaagg caggggagcc ctgatactga   60180
actaggaaaa gacattgcaa gaaaagaaaa ctacaaacat ctctcgtgaa atgcttaaca   60240
aaattagcaa ctaaaatcta gcaatatgtt aaaagtataa tacatcatga tcaagtgggg   60300
tttattcaag aaacacaggt aagctcaaca ttcaaaaatc aggcaataac ctttactaca   60360
taaataaact aaaaagaaaa aaacatatga tcatgtcaat ggatacagga aaaacttttg   60420
acaaaattaa tacccattca tagtttttaaa tggaagaaaa agctctcata aaaataggaa   60480
tacaagatga cttcctcaac ctgacaaagg acatctacca aaaattcttc tgttagcata   60540
atatttcatg atagaagact gattgctttt accttaagat ggcgaatgtg gggaggatgt   60600
ctactctctc tacttttgtt ccacattgta ctggaggtca tagccagaga aacaagacta   60660 gaaaagaaa taaagacat acagattgga aaggaagtaa aactgtcttt tttcacagat     60720
aatgatcatg cttgtagaaa atcctgagga atctatcaaa aacctattaa aactgataag   60780
tgagtgtagc aaagacacag gatacaaagt caatacacaa aatcaattat ttctatatac   60840
```

-continued

```
taacaaaagc aattgtacat tgaaaaaaat taatagcatt tataatagca tcaaataata   60900
ttaaaaactt ggaaataaat ttaacaaaac aagtacaagg tctatatact gaaaactata   60960
caatattact actggagaaa ttaaagtaaa ccaaaataaa tggagacata ggccatgttt   61020
atgaatcaga agactagatg ttaagataac cattctctcc aagttgatct atggattaaa   61080
tgtaatcaca atcaaaatcc tggtaagctc tctaatagat actaaaaatc ttactcgaaa   61140
agttataggg aaatgcaaag aatctacaat tgccaaaaca attctgaaaa ataagaacaa   61200
aggttaaaaa tacaaaatta gccaggcatg gtggcgcatg cctgtaatcc cagctactct   61260
ggaggctgag gcaggagaat tgcttgaacc cgggaggcag aggttgctgt gagctgagat   61320
cgtgccattg cactccagcc tgggcaacaa gagtgaaact ccctctcaaa aaaaaaaaa    61380
aaaaaaaaaa aaaagaacaa aggtggactt aacctaccta atttcaatat ttactatata   61440
tagtaattaa tacagtgtga tattggtaaa aggacagaca tatcagtcaa tggaacaaaa   61500
tagagagtca aaaatagatt cacactgttg acaaagctac caaggtaatt ccatgcagaa   61560
aggatagtat tttcaacaaa tagtgttggg acaattagat atccacatgg aaaaagtatg   61620
aacctagaca cacacaaagt aacttatata ttaagaatta aaatgaaagg acttccaaaa   61680
gaaacagag gagaaaatct ttgtaacctt aagttaggca agtcttctta gataggacac   61740
agaaagcaaa aaccatatca taaaaagata aaatggatgt catcaatatg gaaaactttt   61800
gttctttgac tttgtttaaa aaacgaaaag tcaaaccaca gacagggaga aaacgtttgc   61860
aaaatatata tctgataaag gacttgtatc cagtatataa ttacatattg ctactcatta   61920
gtaagaagac aatccattta ataaaaggca agaagaagag acttgaacag atacataaca   61980
gaagaagata tacagatggc cgatgagcac agtcacaaca tcattagtca tcagggaagt   62040
acaaattaaa acgataatga gataccactg cacaccctct agaatggcta aaattaaaag   62100
gtctgataaa catcaagtgt tggagaggat atgaagcaac tgaaactctc atatactgct   62160
atacaaccca gaaatcctag acatttacca aacagaaatt ttaaaaaatt taaaaatata   62220
taaagactca tacacaaatg ttcatagcag cttgcttcat aataccaaac ctggcattct   62280
aaattttcat cagttggcgg tggtatattt atacaatgaa atactgcaaa gctatagaaa   62340
ggaatggact actaataata cacaagaaca tagataaatt tcaaaagcat tatgctaagt   62400
gaaacaatcc aggcacaaga agaatacaca ttatacaatt tcatgtatat gaaatttgag   62460
aaaaagcaaa actattttaa gtagattcat ggttatccat gggatggggg aaaggaatca   62520
gctgaaaagc gaactatttt ggcttataaa aatgttctcg atcttgattg tggtggtggt   62580
tacgtgacta tatatattcg ttaaaatcac caaactctaa actgaaaatg attgggtttt   62640
attatttatt aattataccct ccataaagct gattgttttt atcttttatt tttattttat   62700
ttcaatagtt tttggggaac agatggtttt cggttacatg gatgagttct ttagtggtga   62760
tttctgagat tttgatgcac ctgtcacccg agcaatgtcc actgtaccca atgtgtagtc   62820
ttttatcctt catccacctc tctctcactc ttccccccaa gtacccaagt ccattatatc   62880
attcttatga ctttgtggcc tcataaaagc tgattgtttt taaatacaca catcacaca    62940
taaaagagaa cttccagtga caggaagtgt tcaagaatgc tctatttagt aaagacagaa   63000
tcacaaaacc atcagaggta ttgttgagtg gattcttgtg gtctataaat acctccatgg   63060
acacccaggt tagcaacctg ttggagttta cgtgggacaa tagcatcatc acaacagtca   63120
gcctagagaa atttacatcc caagttgtgt cagtagcaag tccctatcaa tagcaactca   63180
ggctttgtga ggtctagctg gctagaaatt tcccacttgg ccttgcccat gcaacattgt   63240
```

```
gtaatattct tagcaccatc tggctagccg atttaggcat caacatcttc aagacttctt   63300
ctcctcctcc ttataaacct tgctttcaga aaaggattag aaactcttcc aatcacaaaa   63360
tgattgctaa aactaaatat attaccccctc ccaatggtat tttttggtta gccaggatag   63420
agatataagt gaaaaatcta tttccagtgt tagaatttaa ggcacagtga gaagggaag   63480 gcatatactt tttgaatgca agaaacttct tcccaatccc cctgaaattg catcatttga   63540
gtaactatct cttccatata taaagtcaca acaatttctc tctcagtccc agaactttga   63600
agccttttca aactttcctt cttttggtat ctaggaggaa tacattttg aagattgttc   63660 ttggtgtctt tcaggaacca acacaatgga gagggaagag agtgaacaga ccaagaaaag   63720
gtaaatcctg accctgagac attgatgaga gagaggtata atccccagag tgcctgttac   63780
ttgaataggc ttatgcctaa catatgttga gacctcagca aacctgaact aatggagagg   63840
gagaggaaaa taaaactagt taagaactgg aagaaaataa cctgataatg gatgacaggg   63900
tatccaatgc acaatgccca gaaagcatga caagctctgt catggtcaag taaaagtcaa   63960
taccaaagac ttcagaggtg gtgaacatgg gcttcatctt atctgccaca gtaaccccag   64020
tacctggcac agtgcctaga ttagtgggca tcctacatgt gtggaatgaa taaatgaaga   64080
agtggggaat gataacatgt ttgcttcagc ctgagcatct tagtatttgc tatggccctg   64140
tttagatgtt cttctgccac ttctttacct cattcttcag atcttgcctc aagcagcact   64200
ttcttaaaaa cccttttccca aactagaaaa tgtcaacttg ttacagtgtc atgtggatcc   64260
cttggctttt tcttaataac accagattat gcttacatat ttgtgtaatt atcttattaa   64320
actctataaa ctagacttaa ctaaatccta tgaagagcag agaccatacc agttaagctc   64380
atcattgtgc tgctagcact tagcatggtg cctggcatat agcaggttct caataaatgt   64440
tgaaagaatg attgatgcat gatgaataca taaaagttcg tggtgatcag tcctttcaca   64500
acgtgaagct atcagatagt ctgtacctct atccctcctg agaaattaag ctctcaggaa   64560
tatcaaggct ctgactgcat acccatagga tcaaagcaac cctcagtcac aagcctggtt   64620
tcagagatag ggtcataacc cccagggtgc agagacaacc gagagtaccc agcactaatc   64680
cagatatacc agccactgtg attctagcaa caaaactaat aattccgggc acccttggac   64740
aatgagaaag ggtgctgaaa tcctgcctac cctgtcacac tcagtttcag aaatggtctg   64800
gaagagcctg cagagggcag gcagcagaga accggcagag ggcatgggaa gggccaggca   64860
gaaataaagg gtagctcttg aagcatagat gacagtgtag accgtggttc ttttctcttg   64920 cttttctccac ctttctcttc aatagtttgt ttctcctcat tgctgttcca atggcaacct   64980
ctattctgcc ctatcattga aatctagaaa aagaaagtag ctcaaatgtg aaatatcacc   65040
taatcttttc ttctatttct ccagagaaaa aatccatata cctgaaagat ctgatgaagc   65100
ccagcgtgtt tttaaaagtt cgaagacatc ttcatgcgac aaaagtgata catgttttta   65160
attaaagagt aaagcccata caagtattca ttttttctac cctttccttt gtaagttcct   65220
gggcaacctt tttgatttct tccagaaggc aaaaagacat taccatgagt aataagggg   65280 ctccaggact ccctctaagt ggaatagcct ccctgtaact ccagctctgc tccgtatgcc   65340
aagaggagac tttaattctc ttactgcttc ttttcacttc agagcacact tatgggccaa   65400
gcccagctta atggctcatg acctggaaat aaaatttagg accaatacct cctccagatc   65460
agattcttct cttaatttca tagattgtgt tttttttta aatagacctc tcaatttctg   65520
gaaaactgcc tttatctgc ccagaattct aagctggtgc cccactgaat tttgtgtgta   65580
cctgtgacta aacaactacc tcctcagtct gggtgggact tatgtattta tgaccttata   65640
```

```
gtgttaatat cttgaaacat agagatctat gtactgtaat agtgtgatta ctatgctcta    65700
gagaaaagtc taccccctgct aaggagttct catccctctg tcagggtcag taaggaaaac    65760
ggtggcctag ggtacaggca acaatgagca gaccaaccta aatttgggga aattaggaga    65820
ggcagagata gaacctggag ccacttctat ctgggctgtt gctaatattg aggaggcttg    65880
ccccacccaa caagccatag tggagagaac tgaataaaca ggaaaatgcc agagcttgtg    65940
aaccctgttt ctcttgaaga actgactagt gagatggcct ggggaagctg tgaaagaacc    66000
aaaagagatc acaatactca aaagagagag agagagaaaa aagagagatc ttgatccaca    66060
gaaatacatg aaatgtctgg tctgtccacc ccatcaacaa gtcttgaaac aagcaacaga    66120
tggatagtct gtccaaatgg acataagaca gacagcagtt tccctggtgg tcagggaggg    66180
gttttggtga tacccaagtt attgggatgt catcttcctg gaagcagagc tggggaggga    66240
gagccatcac cttgataatg ggatgaatgg aaggaggctt aggactttcc actcctggct    66300
gagagaggaa gagctgcaac ggaattagga agaccaagac acagatcacc cggggcttac    66360
ttagcctaca gatgtcctac gggaacgtgg gctggcccag catagggcta gcaaatttga    66420
gttggatgat tgttttttgct caaggcaacc agaggaaact tgcatacaga gacagatata    66480
ctgggagaaa tgactttgaa aacctggctc taaggtggga tcactaaggg atggggcagt    66540
ctctgcccaa acataaagag aactctgggg agcctgagcc acaaaaatgt tcctttattt    66600
tatgtaaacc ctcaagggtt atagactgcc atgctagaca agcttgtcca tgtaatattc    66660
ccatgttttt accctgcccc tgccttgatt agactcctag cacctggcta gtttctaaca    66720
tgttttgtgc agcacagttt ttaataaatg cttgttacat tcatttaaaa gtctacattt    66780
tctgctttgg cttcaagagt actactcaac ccttgtggtc tgatgttccc tgctctgtcc    66840
tctgaatgta cttcctttct ctttacatct ctatggctag aagcctctca cgcatcctgt    66900
atcttctcct cctcccttt ccctaccatt atttgagaaa ggaggcttgt atacttctat     66960
atgtttatct cagtaataag tcataaaaaa tcaagtaaga atggttgttt ttgaggacaa    67020
ctaagaaatc tggaataagg aagggaagct tacttttgag tttgtaacct gtagtgtgta    67080
atttttttaat tatgtactta catgtacatt aaacaaaagc ttaatgtaaa aatattcctt    67140
gaaaacacca tgattataaa ataaatgcat atatacacat acagcatgtg agaggagcca    67200
ggaaaactct ggaaaaaaga aaattaccta gactctgtga gggcaggaat gtgtttaatt    67260
tctctccaat ggatcctcag acaactaaga tagttgtcta ttctattgtc catcttttg    67320
tcttttgttg tatttcttaa agattccctc aactttatct tctaacttct gttgtatttt    67380
tatttctgct atcatgtatt cttttcagaa ttcttttttg ttctctcaaa acatatctgt    67440
ttaaagattg aatgaaatat taacatgccc tttggtgaga acatccctcc tttgtatatt    67500
aaattctctg aactgctgta ttctaagact aggggaaaga aaagaaggt tgaaagaggt     67560
cattaggcag aatagtacta gctaacatta tttcacattt accatatacc cgtcactcat    67620
ctaaaccttt aaactcatta tcctatttaa tcctcacaat gaccctgtga cgtaggtaat    67680
ggaatattat gcccattatg ctgatgagaa aatataaaca cagagataag tcagagtaat    67740
ttacccaaca ttgttaactt tgtaagtggc agagctttgt aacaggcaga ggttggaaca    67800
gtttggaggg ctcagaagaa gacaggaaga tgtaggaaag tttggaactt cccagagcct    67860
tgttgaatgg cttttgaccaa aatgctgata gtaatatgga caatgaaata caggctgagg    67920
tggtctcaga tagagaagag gaacttgttg ggaactggaa taaaggtgac tcttgctatg    67980
ttttagcaaa gacactggtg g                                              68001
```

```
<210> SEQ ID NO 298
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 298
accaaaagga gtatttgcga                                                   20

<210> SEQ ID NO 299
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 299
cattcccaag gaacacagaa                                                   20

<210> SEQ ID NO 300
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 300
actgtagctc caaaaagaga                                                   20

<210> SEQ ID NO 301
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 301
ctgtcacaaa tgcctgtcca                                                   20

<210> SEQ ID NO 302
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 302
tcagtcccat agtgctgtca                                                   20

<210> SEQ ID NO 303
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 303
ctgttacagc agcagagaag                                                   20

<210> SEQ ID NO 304
<211> LENGTH: 20
<212> TYPE: DNA
<213> ORGANISM: Artificial Sequence
<220> FEATURE:
<223> OTHER INFORMATION: Antisense Oligonucleotide
```

```
<400> SEQUENCE: 304
tccctgttac agcagcagag                                              20

<210> SEQ ID NO 305
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 305
atctggaaat gaccccactc                                              20

<210> SEQ ID NO 306
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 306
gtgacctaat atctggaaat                                              20

<210> SEQ ID NO 307
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 307
cattttggct gcttctgctg                                              20

<210> SEQ ID NO 308
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 308
ggaacttaca aaggaaaggg                                              20

<210> SEQ ID NO 309
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 309
aaaaaggttg cccaggaact                                              20

<210> SEQ ID NO 310
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 310
tgccttctgg aagaaatcaa                                              20

<210> SEQ ID NO 311
<211> LENGTH: 20
<212> TYPE: DNA
```

```
<213> ORGANISM: Artificial Sequence
<220> FEATURE:
<223> OTHER INFORMATION: Antisense Oligonucleotide

<400> SEQUENCE: 311
tttttgcctt ctggaagaaa                                              20

<210> SEQ ID NO 312
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 312
ctattccact tagagggagt                                              20

<210> SEQ ID NO 313
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 313
tctgatctgg aggaggtatt                                              20

<210> SEQ ID NO 314
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 314
agaaattgag aggtctattt                                              20

<210> SEQ ID NO 315
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 315
caccagctta gaattctggg                                              20

<210> SEQ ID NO 316
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 316
aggtagttgt ttagtcacag                                              20

<210> SEQ ID NO 317
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 317
ccagactgag gaggtagttg                                              20
```

```
<210> SEQ ID NO 318
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 318
cagtacatag atctctatgt                                               20

<210> SEQ ID NO 319
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 319
ttacagtaca tagatctcta                                               20

<210> SEQ ID NO 320
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 320
gatgagaact ccttagcagg                                               20

<210> SEQ ID NO 321
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 321
tagcaacagc ccagatagaa                                               20

<210> SEQ ID NO 322
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 322
tctgttgctt gtttcaagac                                               20

<210> SEQ ID NO 323
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 323
tccatttgga cagactatcc                                               20

<210> SEQ ID NO 324
<211> LENGTH: 20
<212> TYPE: DNA
<213> ORGANISM: Artificial Sequence
<220> FEATURE:
<223> OTHER INFORMATION: Antisense Oligonucleotide
```

```
<400> SEQUENCE: 324
gggaaactgc tgtctgtctt                                            20

<210> SEQ ID NO 325
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 325
tgcttccagg aagatgacat                                            20

<210> SEQ ID NO 326
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 326
attcatccca ttatcaaggt                                            20

<210> SEQ ID NO 327
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 327
agccaggagt ggaaagtcct                                            20

<210> SEQ ID NO 328
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 328
cttcctaatt ccgttgcagc                                            20

<210> SEQ ID NO 329
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 329
catctgtagg ctaagtaagc                                            20

<210> SEQ ID NO 330
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 330
cccgtaggac atctgtaggc                                            20

<210> SEQ ID NO 331
<211> LENGTH: 20
<212> TYPE: DNA
```

-continued

<213> ORGANISM: Artificial Sequence
<220> FEATURE:
<223> OTHER INFORMATION: Antisense Oligonucleotide

<400> SEQUENCE: 331
gccctatgct gggccagccc                    20

<210> SEQ ID NO 332
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 332
gtctctgtat gcaagtttcc                    20

<210> SEQ ID NO 333
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 333
ccagtatatc tgtctctgta                    20

<210> SEQ ID NO 334
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 334
ccaggttttc aaagtcattt                    20

<210> SEQ ID NO 335
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 335
agccaggttt tcaaagtcat                    20

<210> SEQ ID NO 336
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 336
cccttagtga tcccaccttc                    20

<210> SEQ ID NO 337
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 337
ctgccccatc ccttagtgat                    20

```
<210> SEQ ID NO 338
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 338
tttatgtttg ggcagagact                                               20

<210> SEQ ID NO 339
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 339
catggcagtc tataaccctt                                               20

<210> SEQ ID NO 340
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 340
tagcatggca gtctataacc                                               20

<210> SEQ ID NO 341
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 341
tctagcatgg cagtctataa                                               20

<210> SEQ ID NO 342
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 342
ttgtctagca tggcagtcta                                               20

<210> SEQ ID NO 343
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 343
aagcttgtct agcatggcag                                               20

<210> SEQ ID NO 344
<211> LENGTH: 20
<212> TYPE: DNA
<213> ORGANISM: Artificial Sequence
<220> FEATURE:
<223> OTHER INFORMATION: Antisense Oligonucleotide
```

<400> SEQUENCE: 344
acatggacaa gcttgtctag                                                  20

<210> SEQ ID NO 345
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 345
ttacatggac aagcttgtct                                                  20

<210> SEQ ID NO 346
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 346
gaatattaca tggacaagct                                                  20

<210> SEQ ID NO 347
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 347
aactagccag gtgctaggag                                                  20

<210> SEQ ID NO 348
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 348
aattattact caccactggg                                                  20

<210> SEQ ID NO 349
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 349
taatatttag ggaagcatga                                                  20

<210> SEQ ID NO 350
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 350
ggaccctggg ccagttattg                                                  20

<210> SEQ ID NO 351
<211> LENGTH: 20
<212> TYPE: DNA

```
<213> ORGANISM: Artificial Sequence
<220> FEATURE:
<223> OTHER INFORMATION: Antisense Oligonucleotide

<400> SEQUENCE: 351
caaacatacc tgtcacaaat                                               20

<210> SEQ ID NO 352
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 352
gtgatatcaa ttgatggcat                                               20

<210> SEQ ID NO 353
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 353
tgctacatct actcagtgtc                                               20

<210> SEQ ID NO 354
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 354
tggaaactct tgccttcgga                                               20

<210> SEQ ID NO 355
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 355
ccatccacat tgtagcatgt                                               20

<210> SEQ ID NO 356
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 356
tcaggatggt atggccatac                                               20

<210> SEQ ID NO 357
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 357
tcccatagtg ctagagtcga                                               20
```

<210> SEQ ID NO 358
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 358
aggttcttac cagagagcag                                               20

<210> SEQ ID NO 359
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 359
cagaggagca gcacctaaaa                                               20

<210> SEQ ID NO 360
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 360
gaccacatac caagcactga                                               20

<210> SEQ ID NO 361
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 361
atctttcaga aacccaagca                                               20

<210> SEQ ID NO 362
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 362
gagtcaccaa agatttacaa                                               20

<210> SEQ ID NO 363
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 363
ctgaagttag ctgaaaagcag                                              20

<210> SEQ ID NO 364
<211> LENGTH: 20
<212> TYPE: DNA
<213> ORGANISM: Artificial Sequence
<220> FEATURE:
<223> OTHER INFORMATION: Antisense Oligonucleotide

```
<400> SEQUENCE: 364
acagctttac ctatagagaa                                                  20

<210> SEQ ID NO 365
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 365
tcctcaagct ctacaaatga                                                  20

<210> SEQ ID NO 366
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 366
gactcactca ccacatttat                                                  20

<210> SEQ ID NO 367
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 367
agtgatagca aggcttctct                                                  20

<210> SEQ ID NO 368
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 368
cttggagaga atggttatct                                                  20

<210> SEQ ID NO 369
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 369
gaagatgttg atgcctaaat                                                  20

<210> SEQ ID NO 370
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 370
gtgttggttc ctgaaagaca                                                  20

<210> SEQ ID NO 371
<211> LENGTH: 20
<212> TYPE: DNA
```

```
<213> ORGANISM: Artificial Sequence
<220> FEATURE:
<223> OTHER INFORMATION: Antisense Oligonucleotide

<400> SEQUENCE: 371
caggatttac cttttcttgg                                               20

<210> SEQ ID NO 372
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 372
agggcagaat agaggttgcc                                               20

<210> SEQ ID NO 373
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 373
tttttctctg gagaaataga                                               20

<210> SEQ ID NO 374
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 374
gttactcagt cccatagtgc                                               20

<210> SEQ ID NO 375
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 375
caaagagaat gttactcagt                                               20

<210> SEQ ID NO 376
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 376
ccatcacaaa gagaatgtta                                               20

<210> SEQ ID NO 377
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 377
ggaaggccat cacaaagaga                                               20
```

<210> SEQ ID NO 378
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 378
gagcaggaag gccatcacaa                                               20

<210> SEQ ID NO 379
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 379
ccagagagca ggaaggccat                                               20

<210> SEQ ID NO 380
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 380
aaataagctt gaatcttcag                                               20

<210> SEQ ID NO 381
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 381
agtctcattg aaataagctt                                               20

<210> SEQ ID NO 382
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 382
aggtctgcag tctcattgaa                                               20

<210> SEQ ID NO 383
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 383
ctactagctc actcaggctt                                               20

<210> SEQ ID NO 384
<211> LENGTH: 20
<212> TYPE: DNA
<213> ORGANISM: Artificial Sequence
<220> FEATURE:
<223> OTHER INFORMATION: Antisense Oligonucleotide

```
<400> SEQUENCE: 384
aaatactact agctcactca                                           20

<210> SEQ ID NO 385
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 385
ctgccaaaat actactagct                                           20

<210> SEQ ID NO 386
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 386
ttcagaacca agttttcctg                                           20

<210> SEQ ID NO 387
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 387
cctcattcag aaccaagttt                                           20

<210> SEQ ID NO 388
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 388
gtatacctca ttcagaacca                                           20

<210> SEQ ID NO 389
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 389
gcctaagtat acctcattca                                           20

<210> SEQ ID NO 390
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 390
ctctttgcct aagtatacct                                           20

<210> SEQ ID NO 391
<211> LENGTH: 20
<212> TYPE: DNA
```

```
<213> ORGANISM: Artificial Sequence
<220> FEATURE:
<223> OTHER INFORMATION: Antisense Oligonucleotide

<400> SEQUENCE: 391
cccatatact tggaatgaac                                                    20

<210> SEQ ID NO 392
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 392
cttgtgcggc ccatatactt                                                    20

<210> SEQ ID NO 393
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 393
atcaaaactt gtgcggccca                                                    20

<210> SEQ ID NO 394
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 394
cccttgtcct tgatctgaag                                                    20

<210> SEQ ID NO 395
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 395
acaagccctt gtccttgatc                                                    20

<210> SEQ ID NO 396
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 396
ttgatacaag cccttgtcct                                                    20

<210> SEQ ID NO 397
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 397
atacattgat acaagcccttt                                                   20
```

```
<210> SEQ ID NO 398
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 398
tggatgatac attgatacaa                                                   20

<210> SEQ ID NO 399
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 399
gaattcatct ggtggatgcg                                                   20

<210> SEQ ID NO 400
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 400
gttcagaatt catctggtgg                                                   20

<210> SEQ ID NO 401
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 401
tgacagttca gaattcatct                                                   20

<210> SEQ ID NO 402
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 402
agcactgaca gttcagaatt                                                   20

<210> SEQ ID NO 403
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 403
tagcaagcac tgacagttca                                                   20

<210> SEQ ID NO 404
<211> LENGTH: 20
<212> TYPE: DNA
<213> ORGANISM: Artificial Sequence
<220> FEATURE:
<223> OTHER INFORMATION: Antisense Oligonucleotide
```

```
<400> SEQUENCE: 404
tgaagttagc aagcactgac                                          20

<210> SEQ ID NO 405
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 405
ttgactgaag ttagcaagca                                          20

<210> SEQ ID NO 406
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 406
ctatttcagg ttgactgaag                                          20

<210> SEQ ID NO 407
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 407
tctgttatat tagaaattgg                                          20

<210> SEQ ID NO 408
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 408
gcaggtcaaa tttatgtaca                                          20

<210> SEQ ID NO 409
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 409
gtatagatga gcaggtcaaa                                          20

<210> SEQ ID NO 410
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 410
gggtaaccgt gtatagatga                                          20

<210> SEQ ID NO 411
<211> LENGTH: 20
<212> TYPE: DNA
```

```
<213> ORGANISM: Artificial Sequence
<220> FEATURE:
<223> OTHER INFORMATION: Antisense Oligonucleotide

<400> SEQUENCE: 411
aggttctggg taaccgtgta                                               20

<210> SEQ ID NO 412
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 412
tagcaaaaca ctcatcttct                                               20

<210> SEQ ID NO 413
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 413
gttcttagca aaacactcat                                               20

<210> SEQ ID NO 414
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 414
attcttggtt cttagcaaaa                                               20

<210> SEQ ID NO 415
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 415
gatagttgaa ttcttggttc                                               20

<210> SEQ ID NO 416
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 416
accatcatac tcgatagttg                                               20

<210> SEQ ID NO 417
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 417
atcttgagat ttctgcataa                                               20
```

<210> SEQ ID NO 418
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 418
acattatctt gagatttctg                                            20

<210> SEQ ID NO 419
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 419
cgtacagttc tgtgacatta                                            20

<210> SEQ ID NO 420
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 420
agacaagctg atggaaacgt                                            20

<210> SEQ ID NO 421
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 421
gaaacagaca agctgatgga                                            20

<210> SEQ ID NO 422
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 422
ggaatgaaac agacaagctg                                            20

<210> SEQ ID NO 423
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 423
catcagggaa tgaaacagac                                            20

<210> SEQ ID NO 424
<211> LENGTH: 20
<212> TYPE: DNA
<213> ORGANISM: Artificial Sequence
<220> FEATURE:
<223> OTHER INFORMATION: Antisense Oligonucleotide

```
<400> SEQUENCE: 424
cgtaacatca gggaatgaaa                                            20

<210> SEQ ID NO 425
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 425
agctctatag agaaaggtga                                            20

<210> SEQ ID NO 426
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 426
cctcaagctc tatagagaaa                                            20

<210> SEQ ID NO 427
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 427
ggaggctgag ggtcctcaag                                            20

<210> SEQ ID NO 428
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 428
agtacagctg taatccaagg                                            20

<210> SEQ ID NO 429
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 429
ttggaagtac agctgtaatc                                            20

<210> SEQ ID NO 430
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 430
ataataactg ttggaagtac                                            20

<210> SEQ ID NO 431
<211> LENGTH: 20
<212> TYPE: DNA
```

```
<213> ORGANISM: Artificial Sequence
<220> FEATURE:
<223> OTHER INFORMATION: Antisense Oligonucleotide

<400> SEQUENCE: 431
catcacacat ataataactg                                              20

<210> SEQ ID NO 432
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 432
tccatttcca tagaattaga                                              20

<210> SEQ ID NO 433
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 433
tcttcttcca tttccataga                                              20

<210> SEQ ID NO 434
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 434
atttataaga gttgcgaggc                                              20

<210> SEQ ID NO 435
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 435
ttggttccac atttataaga                                              20

<210> SEQ ID NO 436
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 436
ctctccattg tgttggttcc                                              20

<210> SEQ ID NO 437
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 437
cttccctctc cattgtgttg                                              20
```

<210> SEQ ID NO 438
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 438
tggtctgttc actctcttcc                                               20

<210> SEQ ID NO 439
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 439
ttcatcagat ctttcaggta                                               20

<210> SEQ ID NO 440
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 440 atcactttg tcgcatgaag                                                20

<210> SEQ ID NO 441
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 441
gctttactct ttaattaaaa                                               20

<210> SEQ ID NO 442
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 442
gtatgggctt tactctttaa                                               20

<210> SEQ ID NO 443
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 443
atacttgtat gggctttact                                               20

<210> SEQ ID NO 444
<211> LENGTH: 20
<212> TYPE: DNA
<213> ORGANISM: Artificial Sequence
<220> FEATURE:
<223> OTHER INFORMATION: Antisense Oligonucleotide

```
<400> SEQUENCE: 444
aatgaatact tgtatgggct                                                    20

<210> SEQ ID NO 445
<211> LENGTH: 23
<212> TYPE: DNA
<213> ORGANISM: Artificial Sequence
<220> FEATURE:
<223> OTHER INFORMATION: PCR Primer

<400> SEQUENCE: 445
tgtttcattc cctgatgtta cga                                                23

<210> SEQ ID NO 446
<211> LENGTH: 20
<212> TYPE: DNA
<213> ORGANISM: Artificial Sequence
<220> FEATURE:
<223> OTHER INFORMATION: PCR Primer

<400> SEQUENCE: 446
aaaagccgcg tcttgtcagt                                                    20

<210> SEQ ID NO 447
<211> LENGTH: 27
<212> TYPE: DNA
<213> ORGANISM: Artificial Sequence
<220> FEATURE:
<223> OTHER INFORMATION: PCR Probe

<400> SEQUENCE: 447
caatatgacc atcttctgta ttctgga                                            27

<210> SEQ ID NO 448
<211> LENGTH: 19
<212> TYPE: DNA
<213> ORGANISM: Artificial Sequence
<220> FEATURE:
<223> OTHER INFORMATION: PCR Primer

<400> SEQUENCE: 448
gaaggtgaag gtcggagtc                                                     19

<210> SEQ ID NO 449
<211> LENGTH: 20
<212> TYPE: DNA
<213> ORGANISM: Artificial Sequence
<220> FEATURE:
<223> OTHER INFORMATION: PCR Primer

<400> SEQUENCE: 449
gaagatggtg atgggatttc                                                    20

<210> SEQ ID NO 450
<211> LENGTH: 20
<212> TYPE: DNA
<213> ORGANISM: Artificial Sequence
<220> FEATURE:
<223> OTHER INFORMATION: PCR Probe

<400> SEQUENCE: 450
caagcttccc gttctcagcc                                                    20

<210> SEQ ID NO 451
<211> LENGTH: 655
<212> TYPE: DNA
```

<213> ORGANISM: H. sapiens

<400> SEQUENCE: 451

| | | | | | |
|---|---|---|---|---|---|
| gcaggctgta | cgcccccgta | ggtatgggat | ggaaggcttg | cacaggttga | aatgctttgc | 60 |
| ttctctgctg | ctgtaacagg | aactagcaca | gacacacgga | tgagtggggt | catttccaga | 120 |
| tattaggtca | cagcagaagc | agccaaaatg | gatccccagt | gcactatggg | actgagtaac | 180 |
| attctctttg | tgatggcctt | cctgctctct | ggtgctgctc | ctctgaagat | tcaagcttat | 240 |
| ttcaatgaga | ctgcagacct | gccatgccaa | tttgcaaact | ctcaaaacca | aagcctgagt | 300 |
| gagctagtag | tattttggca | ggaccaggaa | aacttggttc | tgaatgaggt | atacttaggc | 360 |
| aaagagaaat | ttgacagtgt | tcattccaag | tatatgggcc | gcacaagtta | tgattcggac | 420 |
| agttggaccc | tgagacttca | caatcttcag | atcaaggaca | agggcttgta | tcaatgtatc | 480 |
| atccatcaca | aaaagcccac | aggaatgatt | cgcatccacc | agatgaattc | tgaactgtca | 540 |
| gtgcttgcta | acttcagtca | acctgaaata | gtaccaattt | ctaatataac | agaaaatgtg | 600 |
| tacatacatt | tgacctgctc | atctatacac | ggttacccag | aacctaagaa | gatga | 655 |

<210> SEQ ID NO 452
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 452
cgttattaac ctccgttgaa                                          20

<210> SEQ ID NO 453
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 453
cagtcccata gtgcactggg                                          20

<210> SEQ ID NO 454
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 454
actcagtccc atagtgcact                                          20

<210> SEQ ID NO 455
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 455
ttgaaataag cttgaatctt                                          20

<210> SEQ ID NO 456
<211> LENGTH: 20
<212> TYPE: DNA
<213> ORGANISM: Artificial Sequence
<220> FEATURE:

-continued

<223> OTHER INFORMATION: Antisense Oligonucleotide

<400> SEQUENCE: 456
cattgaaata agcttgaatc                                          20

<210> SEQ ID NO 457
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 457
ctcattgaaa taagcttgaa                                          20

<210> SEQ ID NO 458
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 458
tgcagtctca ttgaaataag                                          20

<210> SEQ ID NO 459
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 459
tctgcagtct cattgaaata                                          20

<210> SEQ ID NO 460
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 460
ggcaggtctg cagtctcatt                                          20

<210> SEQ ID NO 461
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 461
catggcaggt ctgcagtctc                                          20

<210> SEQ ID NO 462
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 462
aattggcatg gcaggtctgc                                          20

<210> SEQ ID NO 463

```
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 463
gcaaattggc atggcaggtc                                                    20

<210> SEQ ID NO 464
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 464
tttgcaaatt ggcatggcag                                                    20

<210> SEQ ID NO 465
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 465
gagtttgcaa attggcatgg                                                    20

<210> SEQ ID NO 466
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 466
tgagagtttg caaattggca                                                    20

<210> SEQ ID NO 467
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 467
ttttgagagt ttgcaaattg                                                    20

<210> SEQ ID NO 468
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 468
ggttttgaga gtttgcaaat                                                    20

<210> SEQ ID NO 469
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 469
```
ccaaaatact actagctcac                                          20

<210> SEQ ID NO 470
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 470
taagtatacc tcattcagaa                                          20

<210> SEQ ID NO 471
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 471
tttgcctaag tatacctcat                                          20

<210> SEQ ID NO 472
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 472
aatttctctt tgcctaagta                                          20

<210> SEQ ID NO 473
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 473
tcaaatttct ctttgcctaa                                          20

<210> SEQ ID NO 474
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 474
gtgcggccca tatacttgga                                          20

<210> SEQ ID NO 475
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 475
aaacttgtgc ggcccatata                                          20

<210> SEQ ID NO 476
<211> LENGTH: 20
<212> TYPE: DNA
<213> ORGANISM: Artificial Sequence
<220> FEATURE:

<223> OTHER INFORMATION: Antisense Oligonucleotide

<400> SEQUENCE: 476
atgatacatt gatacaagcc                                                      20

<210> SEQ ID NO 477
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 477
agttagcaag cactgacagt                                                      20

<210> SEQ ID NO 478
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 478
aggttgactg aagttagcaa                                                      20

<210> SEQ ID NO 479
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 479
tttcaggttg actgaagtta                                                      20

<210> SEQ ID NO 480
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 480
cgtgtataga tgagcaggtc                                                      20

<210> SEQ ID NO 481
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 481
taaccgtgta tagatgagca                                                      20

<210> SEQ ID NO 482
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 482
tctgggtaac cgtgtataga                                                      20

<210> SEQ ID NO 483

```
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 483
ttggttctta gcaaaacact                                                   20

<210> SEQ ID NO 484
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 484
tgaattcttg gttcttagca                                                   20

<210> SEQ ID NO 485
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 485
ctcgatagtt gaattcttgg                                                   20

<210> SEQ ID NO 486
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 486
atactcgata gttgaattct                                                   20

<210> SEQ ID NO 487
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 487
atcatactcg atagttgaat                                                   20

<210> SEQ ID NO 488
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 488
gtgacattat cttgagattt                                                   20

<210> SEQ ID NO 489
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 489
```

-continued ggtcctcaag ctctatagag                  20

<210> SEQ ID NO 490
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 490
gagggtcctc aagctctata                  20

<210> SEQ ID NO 491
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 491
ctgagggtcc tcaagctcta                  20

<210> SEQ ID NO 492
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 492
ggctgagggt cctcaagctc                  20

<210> SEQ ID NO 493
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 493
ttccatagaa ttagacagaa                  20

<210> SEQ ID NO 494
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 494
atttccatag aattagacag                  20

<210> SEQ ID NO 495
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 495
tcttccattt ccatagaatt                  20

<210> SEQ ID NO 496
<211> LENGTH: 20
<212> TYPE: DNA
<213> ORGANISM: Artificial Sequence
<220> FEATURE:

-continued

<223> OTHER INFORMATION: Antisense Oligonucleotide

<400> SEQUENCE: 496
cacatttata agagttgcga                                       20

<210> SEQ ID NO 497
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 497
tccacattta taagagttgc                                       20

<210> SEQ ID NO 498
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 498
gttccacatt tataagagtt                                       20

<210> SEQ ID NO 499
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 499
gtgttggttc cacatttata                                       20

<210> SEQ ID NO 500
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 500
cattgtgttg gttccacatt                                       20

<210> SEQ ID NO 501
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 501
tccattgtgt tggttccaca                                       20

<210> SEQ ID NO 502
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 502
tgttcactct cttccctctc                                       20

<210> SEQ ID NO 503

```
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 503
tgaatacttg tatgggcttt                                              20

<210> SEQ ID NO 504
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 504
gcagcaccag agagcaggaa                                              20

<210> SEQ ID NO 505
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 505
gcttcttctt cttccatttc                                              20

<210> SEQ ID NO 506
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 506
atagtgcact ggggatccat                                              20

<210> SEQ ID NO 507
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 507
gcccatatac ttggaatgaa                                              20

<210> SEQ ID NO 508
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 508
ggcccatata cttggaatga                                              20

<210> SEQ ID NO 509
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 509
```
cggcccatat acttggaatg                                              20

<210> SEQ ID NO 510
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 510
gcggcccata tacttggaat                                              20

<210> SEQ ID NO 511
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 511
tgcggcccat atacttggaa                                              20

<210> SEQ ID NO 512
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 512
tatcactttt gtcgcatgaa                                              20

<210> SEQ ID NO 513
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 513
gtatcacttt tgtcgcatga                                              20

<210> SEQ ID NO 514
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 514
tgtatcactt ttgtcgcatg                                              20

<210> SEQ ID NO 515
<211> LENGTH: 18
<212> TYPE: DNA
<213> ORGANISM: Artificial Sequence
<220> FEATURE:
<223> OTHER INFORMATION: Antisense Oligonucleotide

<400> SEQUENCE: 515
cggcccatat acttggaa                                                18

<210> SEQ ID NO 516
<211> LENGTH: 18
<212> TYPE: DNA
<213> ORGANISM: Artificial Sequence
<220> FEATURE:

-continued

<223> OTHER INFORMATION: Antisense Oligonucleotide

<400> SEQUENCE: 516
tatcactttt gtcgcatg                                                 18

<210> SEQ ID NO 517
<211> LENGTH: 18
<212> TYPE: DNA
<213> ORGANISM: Artificial Sequence
<220> FEATURE:
<223> OTHER INFORMATION: Antisense Oligonucleotide

<400> SEQUENCE: 517
ccatatactt ggaatgaa                                                 18

<210> SEQ ID NO 518
<211> LENGTH: 18
<212> TYPE: DNA
<213> ORGANISM: Artificial Sequence
<220> FEATURE:
<223> OTHER INFORMATION: Antisense Oligonucleotide

<400> SEQUENCE: 518
tcacttttgt cgcatgaa                                                 18

<210> SEQ ID NO 519
<211> LENGTH: 16
<212> TYPE: DNA
<213> ORGANISM: Artificial Sequence
<220> FEATURE:
<223> OTHER INFORMATION: Antisense Oligonucleotide

<400> SEQUENCE: 519
gcccatatac ttggaa                                                   16

<210> SEQ ID NO 520
<211> LENGTH: 16
<212> TYPE: DNA
<213> ORGANISM: Artificial Sequence
<220> FEATURE:
<223> OTHER INFORMATION: Antisense Oligonucleotide

<400> SEQUENCE: 520
tcacttttgt cgcatg                                                   16

<210> SEQ ID NO 521
<211> LENGTH: 16
<212> TYPE: DNA
<213> ORGANISM: Artificial Sequence
<220> FEATURE:
<223> OTHER INFORMATION: Antisense Oligonucleotide

<400> SEQUENCE: 521
catatacttg gaatga                                                   16

<210> SEQ ID NO 522
<211> LENGTH: 16
<212> TYPE: DNA
<213> ORGANISM: Artificial Sequence
<220> FEATURE:
<223> OTHER INFORMATION: Antisense Oligonucleotide

<400> SEQUENCE: 522 cactttttgtc gcatga                                                  16

<210> SEQ ID NO 523

```
<211> LENGTH: 14
<212> TYPE: DNA
<213> ORGANISM: Artificial Sequence
<220> FEATURE:
<223> OTHER INFORMATION: Antisense Oligonucleotide

<400> SEQUENCE: 523
atatacttgg aatg                                                        14

<210> SEQ ID NO 524
<211> LENGTH: 14
<212> TYPE: DNA
<213> ORGANISM: Artificial Sequence
<220> FEATURE:
<223> OTHER INFORMATION: Antisense Oligonucleotide

<400> SEQUENCE: 524
acttttgtcg catg                                                        14

<210> SEQ ID NO 525
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 525
tgcggcccat atacttggaa                                                  20

<210> SEQ ID NO 526
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 526
tgtatcactt ttgtcgcatg                                                  20

<210> SEQ ID NO 527
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 527
caaaaggagt atttgcgagc                                                  20

<210> SEQ ID NO 528
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 528
aaccaaaagg agtatttgcg                                                  20

<210> SEQ ID NO 529
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 529
```

-continued caaggtggta agaataaacc                                          20

<210> SEQ ID NO 530
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 530
gaacacagaa gcaaggtggt                                          20

<210> SEQ ID NO 531
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 531
agcattccca aggaacacag                                          20

<210> SEQ ID NO 532
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 532
cacagcagca ttcccaagga                                          20

<210> SEQ ID NO 533
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 533
aagagaccag atgcataagc                                          20

<210> SEQ ID NO 534
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 534
agaagcaaag ctttcaccct                                          20

<210> SEQ ID NO 535
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 535
cagcagagaa gcaaagcttt                                          20

<210> SEQ ID NO 536
<211> LENGTH: 20
<212> TYPE: DNA
<213> ORGANISM: Artificial Sequence
<220> FEATURE:

-continued

<223> OTHER INFORMATION: Antisense Oligonucleotide

<400> SEQUENCE: 536
ttacagcagc agagaagcaa                                        20

<210> SEQ ID NO 537
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 537
accccactca tccgtgtgtc                                        20

<210> SEQ ID NO 538
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 538
aatgacccca ctcatccgtg                                        20

<210> SEQ ID NO 539
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 539
ggaaatgacc ccactcatcc                                        20

<210> SEQ ID NO 540
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 540
tctggaaatg accccactca                                        20

<210> SEQ ID NO 541
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 541
atatctggaa atgaccccac                                        20

<210> SEQ ID NO 542
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 542
gacctaatat ctggaaatga                                        20

<210> SEQ ID NO 543

```
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 543
gggatccatt ttggctgctt                                                 20

<210> SEQ ID NO 544
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 544
aggccatcac aaagagaatg                                                 20

<210> SEQ ID NO 545
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 545
atcttcagag gagcagcacc                                                 20

<210> SEQ ID NO 546
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 546
cttgaatctt cagaggagca                                                 20

<210> SEQ ID NO 547
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 547
aagcttgaat cttcagagga                                                 20

<210> SEQ ID NO 548
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 548
atatacttgg aatgaacact                                                 20

<210> SEQ ID NO 549
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 549
```

-continued ttttgtgatg gatgatacat                                          20

<210> SEQ ID NO 550
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 550 gcttttgtg atggatgata                                           20

<210> SEQ ID NO 551
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 551
aaatttatgt acacattttc                                          20

<210> SEQ ID NO 552
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 552
cttcttaggt tctgggtaac                                          20

<210> SEQ ID NO 553
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 553
aaaacactca tcttcttagg                                          20

<210> SEQ ID NO 554
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 554
gcataatacc atcatactcg                                          20

<210> SEQ ID NO 555
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 555
tctgcataat accatcatac                                          20

<210> SEQ ID NO 556
<211> LENGTH: 20
<212> TYPE: DNA
<213> ORGANISM: Artificial Sequence
<220> FEATURE:

-continued

<223> OTHER INFORMATION: Antisense Oligonucleotide

<400> SEQUENCE: 556
agatttctgc ataataccat                                               20

<210> SEQ ID NO 557
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 557
ctatagagaa aggtgaagat                                               20

<210> SEQ ID NO 558
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 558
tctatagaga aggtgaaga                                                20

<210> SEQ ID NO 559
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 559
gtaatccaag gaatgtggtc                                               20

<210> SEQ ID NO 560
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 560
gttgcgaggc cgcttcttct                                               20

<210> SEQ ID NO 561
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 561
taagagttgc gaggccgctt                                               20

<210> SEQ ID NO 562
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 562
agatctttca ggtatatgga                                               20

<210> SEQ ID NO 563

```
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 563
atcagatctt tcaggtatat                                              20

<210> SEQ ID NO 564
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 564
cacgctgggt ttcatcagat                                              20

<210> SEQ ID NO 565
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 565
aaacacgctg ggtttcatca                                              20

<210> SEQ ID NO 566
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 566
cgaactttta aaacacgct                                               20

<210> SEQ ID NO 567
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 567
gtcttcgaac ttttaaaaac                                              20

<210> SEQ ID NO 568
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 568
agatgtcttc gaacttttaa                                              20

<210> SEQ ID NO 569
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 569
```

-continued cgcatgaaga tgtcttcgaa                                              20

<210> SEQ ID NO 570
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 570
ttgtcgcatg aagatgtctt                                              20

<210> SEQ ID NO 571
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 571
aacatgtatc acttttgtcg                                              20

<210> SEQ ID NO 572
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 572
aaaaacatgt atcacttttg                                              20

<210> SEQ ID NO 573
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 573
ctctttaatt aaaaacatgt                                              20

<210> SEQ ID NO 574
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 574
acttacaaag gaaagggtag                                              20

<210> SEQ ID NO 575
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 575
ttgcccagga acttacaaag                                              20

<210> SEQ ID NO 576
<211> LENGTH: 20
<212> TYPE: DNA
<213> ORGANISM: Artificial Sequence
<220> FEATURE:

```
<223> OTHER INFORMATION: Antisense Oligonucleotide

<400> SEQUENCE: 576
gccttctgga agaaatcaaa                                               20

<210> SEQ ID NO 577
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 577
tgggcttggc ccataagtgt                                               20

<210> SEQ ID NO 578
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 578
agccattaag ctgggcttgg                                               20

<210> SEQ ID NO 579
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 579
ttatttccag gtcatgagcc                                               20

<210> SEQ ID NO 580
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 580
aagaatctga tctggaggag                                               20

<210> SEQ ID NO 581
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 581
gataaaaggc agttttccag                                               20

<210> SEQ ID NO 582
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 582
tgggcagata aaggcagtt                                                20

<210> SEQ ID NO 583
```

```
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 583
gcaccagctt agaattctgg                                              20

<210> SEQ ID NO 584
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 584
cccacccaga ctgaggaggt                                              20

<210> SEQ ID NO 585
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 585
tattaacact ataaggtcat                                              20

<210> SEQ ID NO 586
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 586
tagatctcta tgtttcaaga                                              20

<210> SEQ ID NO 587
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 587
actattacag tacatagatc                                              20

<210> SEQ ID NO 588
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 588
agagcatagt aatcacacta                                              20

<210> SEQ ID NO 589
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 589
```

-continued

```
tctctagagc atagtaatca                                           20

<210> SEQ ID NO 590
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 590
tgacagaggg atgagaactc                                           20

<210> SEQ ID NO 591
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 591
tttccttact gaccctgaca                                           20

<210> SEQ ID NO 592
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 592
aggccaccgt tttccttact                                           20

<210> SEQ ID NO 593
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 593
ttggtctgct cattgttgcc                                           20

<210> SEQ ID NO 594
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 594
cagcccagat agaagtggct                                           20

<210> SEQ ID NO 595
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 595
agcaacagcc cagatagaag                                           20

<210> SEQ ID NO 596
<211> LENGTH: 20
<212> TYPE: DNA
<213> ORGANISM: Artificial Sequence
<220> FEATURE:
```

```
<223> OTHER INFORMATION: Antisense Oligonucleotide

<400> SEQUENCE: 596
agttcttcaa gagaaacagg                                                   20

<210> SEQ ID NO 597
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 597
tagtcagttc ttcaagagaa                                                   20

<210> SEQ ID NO 598
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 598
tgtttcaaga cttgttgatg                                                   20

<210> SEQ ID NO 599
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 599
gttgcttgtt tcaagacttg                                                   20

<210> SEQ ID NO 600
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 600
cttgggtatc accaaaaccc                                                   20

<210> SEQ ID NO 601
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 601
cccagctctg cttccaggaa                                                   20

<210> SEQ ID NO 602
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 602
ctctcagcca ggagtggaaa                                                   20

<210> SEQ ID NO 603
```

```
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 603
aatttgctag ccctatgctg                                               20

<210> SEQ ID NO 604
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 604
gagccaggtt ttcaaagtca                                               20

<210> SEQ ID NO 605
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 605
gatcccacct tagagccagg                                               20

<210> SEQ ID NO 606
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 606
ccttagtgat cccaccttag                                               20

<210> SEQ ID NO 607
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 607
catcccttag tgatcccacc                                               20

<210> SEQ ID NO 608
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 608
atgggaatat tacatggaca                                               20

<210> SEQ ID NO 609
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 609
```

```
ctagccaggt gctaggagtc                                                    20

<210> SEQ ID NO 610
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 610
aaactagcca ggtgctagga                                                    20

<210> SEQ ID NO 611
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 611
ttagaaacta gccaggtgct                                                    20

<210> SEQ ID NO 612
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 612
aacatgttag aaactagcca                                                    20

<210> SEQ ID NO 613
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 613
ccagacaaat cattttgaac                                                    20

<210> SEQ ID NO 614
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 614
cagagaagca aagctttcac                                                    20

<210> SEQ ID NO 615
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 615
agcagcagag aagcaaagct                                                    20

<210> SEQ ID NO 616
<211> LENGTH: 20
<212> TYPE: DNA
<213> ORGANISM: Artificial Sequence
<220> FEATURE:
```

```
<223> OTHER INFORMATION: Antisense Oligonucleotide

<400> SEQUENCE: 616
aagaattatt actcaccact                                              20

<210> SEQ ID NO 617
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 617
ccctctatgg taccacaaaa                                              20

<210> SEQ ID NO 618
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 618
gaacagacat tgtttaatgg                                              20

<210> SEQ ID NO 619
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 619
tcttagcaag atagagggtt                                              20

<210> SEQ ID NO 620
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 620
agcacaacaa ttgtcttgga                                              20

<210> SEQ ID NO 621
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 621
ggttgtgagg aaagaatctg                                              20

<210> SEQ ID NO 622
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 622
tctggtctgg atggtgcaga                                              20

<210> SEQ ID NO 623
```

```
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 623
tcaatcaaga ggtaactact                                                 20

<210> SEQ ID NO 624
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 624
cctgctcagc agagcaatgt                                                 20

<210> SEQ ID NO 625
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 625
tcttgaaata taagacttgg                                                 20

<210> SEQ ID NO 626
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 626
ctgaacctct gatgcattaa                                                 20

<210> SEQ ID NO 627
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 627
tcgctctgac tcactaaagc                                                 20

<210> SEQ ID NO 628
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 628
aaagctctta gattcaagca                                                 20

<210> SEQ ID NO 629
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 629
```

```
aatctcagaa cttcttctga                                              20

<210> SEQ ID NO 630
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 630
taagtatagc cttcagatgt                                              20

<210> SEQ ID NO 631
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 631
atttgcttat attaaaaggt                                              20

<210> SEQ ID NO 632
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 632
gattctacaa gtgaatgcag                                              20

<210> SEQ ID NO 633
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 633
gttccacaaa gggagtagat                                              20

<210> SEQ ID NO 634
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 634
cacagttcct gaattattct                                              20

<210> SEQ ID NO 635
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 635
tgcaggaaag gaaggagact                                              20

<210> SEQ ID NO 636
<211> LENGTH: 20
<212> TYPE: DNA
<213> ORGANISM: Artificial Sequence
<220> FEATURE:
```

<223> OTHER INFORMATION: Antisense Oligonucleotide

<400> SEQUENCE: 636
aaagcccatg gaagagatga                                           20

<210> SEQ ID NO 637
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 637
taccagaaca tattatttta                                           20

<210> SEQ ID NO 638
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 638
aggccatgtg cttcacttct                                           20

<210> SEQ ID NO 639
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 639
ccttccctga cagattccca                                           20

<210> SEQ ID NO 640
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 640
tgcaccagtc ctaccctgct                                           20

<210> SEQ ID NO 641
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 641
gtgctaagta ggtgaagggc                                           20

<210> SEQ ID NO 642
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 642
ctatctcata catttgaaaa                                           20

<210> SEQ ID NO 643

```
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 643
atagatcatg gtactaaatg                                                   20

<210> SEQ ID NO 644
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 644
gatctggctg ctaaagtctc                                                   20

<210> SEQ ID NO 645
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 645
cccatagtgc tagagtcgag                                                   20

<210> SEQ ID NO 646
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 646
tatgatgatt atacaatgac                                                   20

<210> SEQ ID NO 647
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 647
agttgtgcgg actggtgaca                                                   20

<210> SEQ ID NO 648
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 648
agtaatcatg ctgaagaata                                                   20

<210> SEQ ID NO 649
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 649
```

```
atgtgggtgt caaggtcagc                                              20

<210> SEQ ID NO 650
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 650
aaagtcccag gctcagggcc                                              20

<210> SEQ ID NO 651
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 651
atgtcgcctt tctttgaagt                                              20

<210> SEQ ID NO 652
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 652
tgtgttggtt cctgaaagac                                              20

<210> SEQ ID NO 653
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 653
tggtctctgc tcttcatagg                                              20

<210> SEQ ID NO 654
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 654
aagccttcca tcccatacct                                              20

<210> SEQ ID NO 655
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 655
tattactcac cactggggat                                              20

<210> SEQ ID NO 656
<211> LENGTH: 20
<212> TYPE: DNA
<213> ORGANISM: Artificial Sequence
<220> FEATURE:
```

```
<223> OTHER INFORMATION: Antisense Oligonucleotide

<400> SEQUENCE: 656
acaaacatac ctgtcacaaa                                              20

<210> SEQ ID NO 657
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 657
ccgtacctcc taaggctcct                                              20

<210> SEQ ID NO 658
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 658
tacgggggcg tacagcctgc                                              20

<210> SEQ ID NO 659
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 659
ttggctgctt ctgctgtgac                                              20

<210> SEQ ID NO 660
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 660
tgtccactgt agctccaaaa                                              20

<210> SEQ ID NO 661
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 661
tcaccctgtg caagccttcc                                              20

<210> SEQ ID NO 662
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 662
cctaaatttt atttccaggt                                              20

<210> SEQ ID NO 663
```

```
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 663
acaagcattt attaaaaact                                                    20

<210> SEQ ID NO 664
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 664
gaccccactc atccgtgtgt                                                    20

<210> SEQ ID NO 665
<211> LENGTH: 21
<212> TYPE: DNA
<213> ORGANISM: Artificial Sequence
<220> FEATURE:
<223> OTHER INFORMATION: Antisense Oligonucleotide

<400> SEQUENCE: 665
gcataagcac agcagcattc c                                                  21

<210> SEQ ID NO 666
<211> LENGTH: 19
<212> TYPE: DNA
<213> ORGANISM: Artificial Sequence
<220> FEATURE:
<223> OTHER INFORMATION: Antisense Oligonucleotide

<400> SEQUENCE: 666
accagagagc aggaaggcc                                                     19

<210> SEQ ID NO 667
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 667
tcccgcctgt gacatgcatt                                                    20

<210> SEQ ID NO 668
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 668
tagtgcggac ctacccacga                                                    20

<210> SEQ ID NO 669
<211> LENGTH: 21
<212> TYPE: DNA
<213> ORGANISM: Artificial Sequence
<220> FEATURE:
<223> OTHER INFORMATION: PCR Primer

<400> SEQUENCE: 669
```

```
cgcatccacc agatgaattc t                                                  21
```

<210> SEQ ID NO 670
<211> LENGTH: 28
<212> TYPE: DNA
<213> ORGANISM: Artificial Sequence
<220> FEATURE:
<223> OTHER INFORMATION: PCR Primer

<400> SEQUENCE: 670

```
aattggtact atttcaggtt gactgaag                                           28
```

<210> SEQ ID NO 671
<211> LENGTH: 17
<212> TYPE: DNA
<213> ORGANISM: Artificial Sequence
<220> FEATURE:
<223> OTHER INFORMATION: PCR Probe

<400> SEQUENCE: 671

```
aactgtcagt gcttgct                                                       17
```

<210> SEQ ID NO 672
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 672

```
aagatagcac actaattttc                                                    20
```

<210> SEQ ID NO 673
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 673

```
ttagaatacg tcgcgttatg                                                    20
```

<210> SEQ ID NO 674
<211> LENGTH: 31737
<212> TYPE: DNA
<213> ORGANISM: H. sapiens

<400> SEQUENCE: 674

```
atattattgc tgtcttcatt ttttaaaatt ctcaaatcca gatgaaatta tcaaagttga        60
taaaataatc attgttctat cttcttattt gaagattaat aattgtgttg attttgcttc       120
cttgctctag ttagcagtga tgtcatctgc tattttaaaa cttccttgaa ataatatatg       180
taatctactt ctaataagtt tttcttattt agcattttgg tctaaactaa tttataatta       240
tttagcctta tttctccatg tttaacttgc tttaaagctc agcactggtg ttttcagcca       300
tggcttctcc attttaaggc tattttaatt cattattat tctggaatat atccttaaat        360
aatttattta ggaaggctgt cttggtggtg gtatttctgt tgcagttgtt gttttcttgc       420
ctgcttggtg acatatttct attgacttga cacttaactg gcatcttatc taggtagata       480
atgctaattc aaaattctgc agatattgtt ctgttgtttt ttgccattta gggttgagta       540
agatgccaag ttgttttttg tttctctgta gtcattctgt tttcattttg ttttagctt        600
tgcctttgga atttaaaatg ttcaaaatga tttgtctgga tgagaatcga ttttcataac       660
```

```
ttttgctttg atacactaaa cagtttgagt ttctagatga tgcccatttt aattcatacg      720
aggaaatatc ttctagtata gtttctgctt gattaattct atgtttgtct cttagggaca      780
tctattaatt ttataatgct gccttttttt cagacttctg tttcagaata ttcgctttca      840
tcaatgtaat ccttggctat agtaggaatg aaataataaa agcagtagct tctgtctgcc      900
ctccttggtt atgcagtcct tacagaacat ctccccatct cccatccccc caccccagct      960
cagtgaaact ctccacactt tggttgtgga aattggcagg gttaggtggc tactcactcc     1020
caatccacat ccacaataaa tcacttttta ttatcttatc aaaatctgta gaatgcctct     1080
ttattctatt ttgttgctgc ggaggtttgt tttctctttc taattatttt attttctagg     1140 tttttttgagg gaatttcaag aggggagatt ttttattcag gctcatctta acgtcatgtc     1200
tggaactcaa gctactgaat tatatattct ttaatacata tagacctacg tcaatgagtt     1260
taaactgcaa ggaaagggtt aaatttcttc ctcaagtgtg gtcaaaatct gtagagaaaa     1320
gaggaacagc ttctcttaaa gaaagttagc tgggtaggta tacagtcatt gccgaggaag     1380
gcttgcacag ggtgaaagct ttgcttctct gctgctgtaa cagggactag cacagacaca     1440
cggatgagtg gggtcatttc cagatattag gtcacagcag aagcagccaa aatggatccc     1500
cagtggtgag taataattct tattctttgc agagaagtta tgagttgtga ctgcagtgaa     1560
aggctgaggt tgaagatggt gctttgatgt gtgtccttca cttagttcct aagtggagaa     1620
gctttctttt tctacaaaag atctttggca cataaaggca agaattattt gcaatgccca     1680
aagcagttca ttggtggtag ttatatatat ttttaggtgc ctaattttgg ttttgtaaat     1740
ctgttattca aatactgaat gttacagtca ttgattttag tgaagaatca ggaattttta     1800
aaatatctgc ataagaatga caaataacag ggaatatgtt ttttgtctac cagggtcagt     1860
ttggtctgag ggtggaggaa tgagatagag aaggtagagg gagagagatc aagaaaaaga     1920
aagagaaaaa agaggtataa ggagaaaatg caaaactcag ttaatatgtc ataatcaggc     1980
catgggagat tctgggcagg gttgggtagt ggaaggaggt agagtgatta aattagttac     2040
catgtattga acatgcatga tgtgctgggt actttactag tgctatttca ttgaatttta     2100
ttcttcacaa tgacttttgg aaagacatca tcattctttt tgacagatgg ggtaactgtg     2160
gcttaaaaaa cttgcccaag ttcacactat tcataagggg tagagctaaa atctttcctg     2220
cccgcttcgt ggtgcgccag aaggtttctc catgctgtgg agacttcctg gaaggagtca     2280
cacccgccct tctcttgggt ggtggcagct ggcgccagtc actatgtatt tatttatttt     2340
taattattta tttttgaaac agagtctcgc tctgtcgcca agctggagtg cagtggcgca     2400
atctcagctc actgcaacct ccgcctctcg gattcaaacg attctccttc ctcagtctcc     2460
tgagtagctg ggactacagg cgcccaccac cacgcccggc taattttttgt attttttggta     2520 gagacggggt ccaccatgtt ggccaggatg gtctcgatct cttgaccttg tgatctggcc     2580
acctcggcct cccaaagtgc tgggattaca ggcgtgagcc accgcgcacc cggccgtcac     2640
tatgtattta taattactgt tctttgaaaa tcgaagtaac tttcatctac ccagtgctta     2700
ctggtttgag aaaaagcttt gttgctttta tttcagaaga ttaaaattta attttccagt     2760
aaagattcct tttgctccag tggaatttg aagcgttata cttgtatgaa gaaaaaaga     2820 atttcaaaat ttataatttt tgtggtacca tagaggggat actacttaat tatgctagca     2880
ctgtctgcag aggtctaaaa aaccataggc tgctgtctat attgaacttg ttaagattcc     2940
ttttgtttca cagtgcctga agattggtca tgaaccagta atagccatta aacaatgtct     3000
gttctcataa gagatgaaat aaatacaaat taaaacaaca gtgaagtatc attttttctc     3060
```

```
tatcaaagag ataaatatta agttttaaaa agcaagcaat caagaaccct ctatcttgct    3120
aagaagggag gattatttgt accctagttg cgcactagtg gtgatatcat ctttctggac    3180
aataatctag tgatacatat caaaagcctt taaaatgtat atgcccttta accaagcaat    3240 tcaccttttta ggaatttatt ctaagatata ataacatg tttgtaaagt tttagtgatg    3300 gatattttc ttgctattgt ttctaataag gaaaatctta gaaacaattt acgtgtttaa    3360
aaacaagtga ttggatgatt atggaacatc cataatggaa taccatgtaa ttatttaaaa    3420
ttccactgta gaacaattca taatgtgttt agttaaaggg gaaaaatgca gaacgaacag    3480
tgctatcact tttatacatg atacatgtat acaaacaata ttaatcagaa atataggtag    3540
tttgtatttt ctactgtgtg cttttcaatt tgaatcccat ctgtaggcag aaaaataaag    3600
ttaaatattt aagatttaaa aaaaacaata gctggttttt ttcagagaag taaccatcta    3660
gtgatgtgtg ataattata agttgtgaga ttccatagtt agggctttag ccctttgcat    3720
ttatctttct tcatctcttg aatcctcttc aaaatacacc cactctaccc ataactcatt    3780
agatcttgaa aggcatgttc tgatagaatt ttatatttag aacaggctgc agcactcttc    3840 ccttattttta cagaagtgat tgcatggctc tctagggtga gttgcatatt gagagggagg    3900
acagtgcagt ggctaagtgg ccgcacattg aagccaggct gctggggttt gaataccagt    3960
tccccaactt cctagctatg tgattttgga caagttgctt aaccattgta attcccagtt    4020
tcttgtctgt aaaatgggag tatggtaata tgtcgtaaag tagttgtgag attttaatga    4080
gataatccat atcctgctaa gtactcagga attgttagta gtttttatta ctattactgt    4140
ttggattaag aaacagagga aaagtgattt gtccaagatt atacaaccac ttaatggcat    4200
tactaagaac agaatggagg aaggtttttt ccagcagaaa tgttcagtat cctctgtgcc    4260
tggcaggaca acccaagtt gtgctttgg gatggaggag ctgatctaaa acaagcagta    4320
cccaggacaa ggccagcctc cagggagtga ctgatgacag tgggaagcca atggtagaa    4380 aggcaggtga agttaaggaa actgagagtc aacttaggag caggaatgaa gcctggagca    4440
aagagctagt gcaagagaga gcagatgact cagagctact ggggcttttg taggccacca    4500
gctatgggct tcacgggagg ttaatgtggt ttaaagtctc aagacctggg taattaaata    4560
gacaaatggg gtctaggtgc atgggggaat tttaagtata gctttgagaa gatgcctaat    4620
ggggagtaat aatagagaaa gaagctgggt ggggccagaa caaggagccc acagtccagg    4680
catccagcta tgatcatcct aaaggaacag cctaagtttg aagaatcata aacaaataga    4740
gacatgataa aatttactttt aaaaaaaatc ccttggcaga agaatgaaaa ctgatttgga    4800
gtgacaagga gatcatttag gagactattg gagtaagcca aggagaaatg gcgagggcat    4860
gaaaccaggg cagttatggt gggatcgac tggagaggat gcatttaaga gatattttag    4920
caccagaatt gacagaattt ggtttttgac agatgtagac actgggagag gaggagagat    4980
ctaagtgcat agtggcatcc ttcacaaaat ggaaggtata ggaagcagag tgggtttgcg    5040
ccaggcagag agaaaagaca gatggtgaat tccttctcta acatgttgag tttgaggtgc    5100
ctgtggagca gctggataga gatgtccaag cagacaagta gatatttagg tgcaagttca    5160 aaaagaggg atggcctgga atgcacatga agagtcttct gcataagtat ggttgacagt    5220
tgaaattctc attgtgggtc aattcagtag cagagaggtt ggaggattga gaggaagcca    5280
aggacagaac ctggaaaacc ttgacatcta aggagggaga tgaggaagaa gaatctacaa    5340
tagatactaa ggaggggcta gagagactgg agcagcccag gagaaaagtg gtgtcataga    5400
aatcaagtgg gcctgtagtc ccagctactt gggagactga ggcacgagaa tagcttgaac    5460
```

-continued

```
ccaggaggca gaggttgcag tgagctgaga tagcaccacg gcactccagc ctgggtgaca    5520
gagtgagact ccgtctcaaa aaaaaaaaaa aagaaagaa atcaagtggg gagatggatg     5580
caagaaagag gagaatgcat tcatggaaag agcatattta ccaagctttc catgttgaac    5640
acatgagatg tgacatgaaa ggtaactgta gtgactacat gttaagcgtt gaattgtggc    5700
tcccttaaaa ttcatatgtt gaaatcctaa ctcccagggc ttcaggattt gatcatattt    5760
ggagataggg tctttacaga gataataaaa tttaaatgag gtcattaggg tgggtcctaa    5820
tccaagacaa ttgttgtgct tattgtaagg aagggaaaca cacagcggaa aagcggtgtg    5880 aagcacagg gcgaagacgg ccatccacat acaagccaga gagaaaggct cgcaacagat     5940
tctttcctca caaccttcag aaagaaccaa ccctgtggaa accctaagtt tggactcctg    6000
gcttccagaa aaaaaataaa tttttttgt ttaagccacc ccagtttgtg gtactttgtt     6060
accacagccc cagcaaacta atacacttgg tgagagtgca tacagccaga gaaagaagct    6120
gtgaataagt gcatcaggga ggagggaaag aaaccaaaac aggattacat cacttaaatt    6180
aagagtagaa acatttcaca aagcagagtg tagtcacagg tcaaattctg cagaaaggcg    6240
aagtaggaga atgactgaaa atgtcagtcc agaggccctc agtgaccttg acctttgcag    6300
aacactccca gttgagtgga ggcagtagac tttggagagc ttggaaaatg gaggcagcac    6360
agatggtctc ctgcagaaag tctggtgata aaatgagacc tcctcactgg agtaaactca    6420
cctctgctgt cggtggaaat aatctggagt caggccagcc agacccagag ttcttccttc    6480
ctccatttta aaggttaaac agagctgagg tcaatggctc atgcctgtaa tcccagtgac    6540
tcaggaggcg gaggtgggag gatggcttga ggcgaggagt tccgttcaag accagtctga    6600
gcaacatagc gagactccca ttcctaaaaa aatttaatt taaattaaaa aaaaaggcta    6660
accaaaaata aaatccaata ctttattttt cccacccaaa actagtttgg gaaggatttc     6720
tggaagaaaa taattttttgc agtcattta catgttggat tttgagtgca cataacatac    6780
agattctatt ctgtattatc agttcagagg caagttgaga tttgaggctt cgcagaggta    6840
aagcctctgg tgaatctggt gagataaaga agaaaacaag cccaagagga atttcaggga    6900
tcatttataa tttacatcaa taaacagaat gggaaaaaaa acccattaga gtttggaata    6960
gagaagtatt aaaacacttt cttagaaagc tttgagtcaa aattaatctt tctgtagtgg    7020
caggaatatg ataagccaaa caaccctaat gtcacagctc tatattatta ggtgtcgaat    7080
cagatttgca ctaaaacatc aagtaaaaat aaaaggaatg aacatttggt taagtgaacc    7140
aattagtcaa tacacgccag aaaatggtaa aactggataa acctaaaata ctcaactacc    7200
tagattaatc aaggccaacc tagattatca ccccaatatt acaactattt tcaaccaact    7260
aaacaataaa tctttatcaa gagcctgata gtttaaggta ctgtgatgaa tacaaatgaa    7320
attgctgata ctttttttca agtctattta gaaatagaaa cccacaatta tgaaatgaca    7380
aaaacaatta atgcagttaa taattcagta acttttaaaa agaataaaac atgacaaaaa    7440
gttcattctc accaaatact aaagaaatgc caattcaaac accaatgaga tattttcctg    7500
tatcagatta gacagtaaaa caaacaatcc aatcagaaaa atgggcaaaa gatataaaaa    7560
gacatttccc caagaaaat atacagatgg tgaacaacca tataagagag tcaacatcat     7620
ttgcctttat gaaaaaatta aaccactacc tacctataaa aatggttaaa ataataaaag    7680
ataatgacaa caccaaatga tggcaggatg cggagaaact ggatcatgca tacattgctt    7740
gttgggaatg tacaatggtc aagccactct agaaaacagt ttggcagttt cttataaaac    7800
caaacatgca tttagtatat gacccagcaa ctgcattctt gggttttgat cccagagaaa    7860
```

```
taaaagccta tgctcctgca aaaatcagta tatgaatatt tataccagct ttattcataa   7920
tagtaaaaaa ctggggaaaa aagtccctca gtgggtgaat cgtaacacaa actgtgtgtg   7980
caagatgtta ccactgaagg aagctgggtg aaggtacaca ggacttccct gtacattttt   8040
tcaacttctt ttgaatcaat aattatttaa aaatgaaaag tttaaaaagt aaaaaaaaaa   8100
aacaaaaact aaaatgttc atcttcacta aatattaaaa aaatgccaa ttcaaacaca     8160 agatattctc cttttacaaa ttaacaattt atatggattt tgggagggtt gggagtaatc   8220
atgctaataa gtatgcaata agaggatact ttcgtatact actgattgtg ggaatatgaa   8280
tggggagaac atttctggaa agcaaatgt caacaatatc aagagtctta aaaatggttg    8340
tacaagcaga cacccattct gggcactgcc aatttctcca tgtccttagt acatttttt    8400 tcagttcatt cagcatcttt gttccaggca ctgtgctaaa cattaaaaat acaccaaaga   8460
tgagtatgag taaacatgat ttctgttctc aagaatttca gttttgtggt aaatatatca   8520
aaggtgattt tttataagag tttttttataa cagggtgtga cgtttcatag gagcatgaag  8580
gtagctgttt cctatttgtc tgtaggcagt atgatgtctt agataaatgc cagggttttg   8640
agctagtttg gttggtatca aataataagt agttaataaa tcatcttcta tttattagtg   8700
gtatcacttt gggaagccta ttagcttcct gaacttcagt gtcctctgta agatgaggct   8760
actaagcact tgccaatgcc atgaggaata taacaattta taatggacag gaagtccctat  8820 ggatataaga tatttaggag ctcacattct ttgctttaaa atctattatt tcctatattt    8880
ttaattgtca gagttcttta gctctgcctt tctgattga tttccagcag atggactctt    8940
acctataacc tagaagttgc tatagtagac ctcctaacta tagataagag aagggcatgc   9000
caaatgcagt tgaatcaggt gaaagtcaag caacaaagct gcctaaaata aattttatgt    9060
aaggtagggt gccaaaatca ttaaaataaa attctattct ataactgtaa tcacgtaagt   9120
gctttcatga agttgtctat gaaaactttc ttttcgctt tctggacttc aaatattta     9180 agtttgcttt tcatttacaa agatttttt gctcattagt aatcatgaac tgtattcaaa    9240
cttacacttc taattctaga agatatataa actaccattt tttaattata aaaatgttta   9300
tatatcttgc tttaataatt tcacctctag ggatctagct agttaaataa caagagctac   9360
ggaaacatat ttgtgcacca aaatgtttat tacattattt aatgtaatga aaaataagaa   9420
tcaacctaaa taagtagaag aataggtaag taagttaaaa atgaagttaa taatgactcc   9480
ttaatgagag aagacaacat aaggctacat acagaattgt aaagaaaata atccacagaa   9540
tgtgtgtttt atttggtaa atggttccta aaactaagta agtacataga aagatttttt    9600 ttttttttt tttaaagaca gagtctcact cacgttgtca cctaggctgg agtgcagtag    9660
tgcaatctca gttcactgca gccttcacct cccgggttca ggacacgcca ccacacccag   9720
ctaattttct tgtatttta gtagagacac agtttcatca tggggctggt ctcaaactcc    9780
tgacctcaag tgatctgccc accttggcct tctaaagtgc tgtattatag gtgtgaccca   9840
ccgcacctgg cctaggaaga attttagaaa gaaagctcca tatcaggaat tgagaagccg   9900 gtgtttaat tgagaatata tttgcacaga aaaatcttgg cataaatatt ggtttacaaa    9960
acaaacaaac aaagtaatgt cctttaatct tggatcagga gctgcccaac aactccaaaa  10020
agtcagctca tgcaaaacca tccaaggaca gatgaatcag ccaaacaaga gagaagggg   10080 aagggaaagt gtcttttcac aggcagctttt tgaggcagtg cataaaccat gcctctgcac 10140
catccagacc agacagttgt gacacagggt tgacaaagca ggacaacgaa gggtagctgc  10200
tcctaaggtg gggatgatgc tggagcaagg gggagcacca agaggaaaaa aaaaaagcat 10260
```

```
aaaaataaga tagcatagta aaaaataaga tagtcatagt agttacctct tgattgatgg    10320
gattatggaa ataggqttat ttctttgact aaaattgcca gatcttcagt acaattacat    10380
tgctctgctg agcaggatga aatcaagttg aaaagtaatc tagtagtgag gtacagcccg    10440
tatgctgcaa atggccaaca tagatcctca gatgacagaa gtgagtgatg caggcctgtg    10500
gtttacgtac agctccatga cgtatgaatg gcagaagctg tgtatgtcca caggcgagcc    10560
ccatttcaag aagtgcttct ggtcaccact ctgttgtcct gtgtataagg atgtggttca    10620
gaacagccaa gtcttatatt tcaagaggag ccagaaagac aaacttacca gtgaaatcct    10680
aatatttata taatagctca atatctggag gggctggttt ggtataaatc accagttta    10740 cctctgacct ctgttaatgc atcagaggtt caggagagag tgagaaaatt gtaaatggaa    10800
tattttagga ctattatatt ggggcccagg ctttagtgag tcagagcgag aaagtagggg    10860
gctgaaacta tttgactatt aatttattca ataaagtttt atttaatgtt ggaaagatga    10920
agatgaatca gatagaaatc ctgtttagaa gcttctatgg gaagagatat caccatagct    10980
aatatgtctt agcctctaaa aggaattatg gcaaactata ttgtatcata tatgatctca    11040
tttaatcatc ataactgcag gaggtaagta gtattatccc tgattttcca taagtgaaaa    11100
ctgagtctct cttagttaca tagctgacaa cacaaccagg attccaaatg ccagtctgat    11160
cccagagcca agctatgaac aaccatgcta tatattatgg cagatcaggg aaggaagaca    11220
ttacttctag cagcaagaaa catttgtgga tgaaaagatt tgagcttgga gagagctgtg    11280
ttgagccatg tccaaaacaa ttttttggcaa ccatacgata aagqtaaaag ccagagattg    11340 aaaagtaaaa gctggtggac taaaaatggt ccatagacag agagtcatca aaacaacaaa    11400
acaaaacaaa aaccttaatc ataattaatt gccaatattt caaaagtctg gagaattcac    11460
ataagtttag atttccagct cttctggaga attagaatat ctagtaacag tgtgctaata    11520
atcccacatg gtaacaactg gtgaatctgc cagaggctgc ccagcttcca atggtgtata    11580
agctctcctc ttcctatgca acctgcctgc ctcatttata tgagctgctt ggatgctgca    11640
gatgcttgaa tctaagagct ttggtctgga aagtgaggcc ctaacaagga agaaggaata    11700
acctatggat caaggagaac tgggagtcca gaaatgaagg ttatttgtaa gtctggaccc    11760
agccattcca actcctttga ggaaataaga ttctaaggaa aaggccgttt gcattctgct    11820
ctccaagatc tctgggtgtt ggaagaaact gaattggggg agaggggaa acttgactgg    11880 gggctcaata cagacatgta aatttgaagg aaacagagag tttagatgac aggcagtaga    11940
aaagttaatg tgtccattct atggctgacc caagattctg tttccagaag acctctctgg    12000
cttgttaagt gttcatggtt gcaggggaaa agttagaaaa aagaaaaac aagccaaaac    12060 ccagctcctt aaatgtttct aatttattt tcaaacaatc aggcagagta atcccttac    12120 acactcttca ggcattggct gagggtccca gtcaagaacc attcagtttt ggggqccttta   12180 agaaaaatat ttcctatgat taaggaact ttggacaggt tattaccttc tttgagcctc    12240
agtttctttg tcacttagaa ggttgaatgg tttccacatt ctgagggtaa ggaatacgag    12300
agtgaatgaa gaaatatcaa gtgcatagct cagagtagga agaaagaagt gaccagggac    12360
aaggctaaga acttactcaa aaggtgccca gctgctcagc attctgtcca aaaagggac    12420 actgacatct ctccagcatt ctaacagcag tcacatagca ttatcagcta gaaatgaaaa    12480
cagattcaat tctatatcct gctaaaagct tgagggtcac actagctgtg tgatctttgg    12540
cagctggcca aaaccctctg aaaggcagtt tcctcaccta taaattttt aaaaatatt     12600 tattgtgaag attaaatgaa gtaatgcatt taaaatactt agggtgcctt agagttccag    12660
```

```
cacagttcgt agctcatagt aatcagttaa tagatattga ctttaataaa tagatactta  12720
actgagcctc caccctgggc ctgttactat gctaagtacc aggagtgcaa agggaaatga  12780
aacacgttcc ccaaacttgt ggaactcaga gcaggccaac tatatgagta gtagattttt  12840
aacacgatga ggaaactgtt ataatggaaa aataaatagt gtgaagaggg actaaggaag  12900
ataaagatat ggtgaaaaaa agagggttca ggctccaact gtggcatgat ctagatctgc  12960
aaggaagagt agagaattgc agtagagaaa gcagggaaga cattccaggc agaagaaaca  13020
gcttccacag aggtaaagaa ggcaaaacgt tttcaaaggt tctaggggtg ggggatggtg  13080
gggaagatgg tcacggaata gtgaatggtt caagtgaaac tgttgtatgg gttgtgaggg  13140
cagttttatg ggttgggtga taaaatcaga agagaaaaat tgaattcacg ctttgaaagg  13200
ccttgtgtgt cttgctgaga agcgtgaaca ctaactcatg aggagtaagg cgcgggtctt  13260
taaaggaagg aagtttcata atcaaattgt tttccatgaa agataatgaa gggagccagc  13320
cacaaggctg ttgcaatcaa tcgtccaaac aagaggtgac aaagactcta aaactggcca  13380
ccaatgaatt gaaagtggat ggtgaggaag aaagaataca gggtgacata aacacaatat  13440
gtaaaatcca aggtatgaaa atggcctggt cccttcgtcc ttaccacagt catcccaaga  13500
gaccaaaaca aaaacacaga aaatctcttt taaaaataat ctcttttgtt tgtatgcaaa  13560
taggccatcc acagtgaaaa tgcaactcaa atgcaatatt ttatctgcag tccaccaaat  13620
gcaaagatca aattggttta caaatgctgt ccttcttaaa aattccaact cctcacatta  13680
aaactgtagc cagctagtgc aagttaagat tgtttgcaat cttaaataag atttgagtaa  13740
agctgaaatt gagacacttt tcaaaagagg ccatccctta ctcacattgc tgaagagtag  13800
aaagattgac accttctttt atcagaaaat ttctttcagg gagtaatgcc tcttgtgtgg  13860
tggcagaccc ttcaagtctt ccagataaag catgtgatgg aagtagcagg gagctgcaaa  13920
aattgcaact ctatgattct gcatcaccga cttgaaaact acaagcccag gttgacaaat  13980
gtacatttta agtgttcaga gaagtcttaa gtgccttgct ttggtcacaa agttgccaca  14040
gggaagtaag ttttttgaatg tgcagtgccc cgtccccagc tctgttgtga aatggaaact  14100
ttaaaaaaaa aatcactgat ttaaaaaacc actggttttg ttttttaaca agtttagtca  14160
tattgcctgt gttctatata ccccaatcta ttttatttta ctttgtagtg tacatttaat  14220
ttatactcaa ataaatattt tacataaggt gctttcacgg accttcatgc ttccctaaat  14280
attaaatatg ctgcccattt gttaaaatgt gttagttttg ttatgtatta tatcccttcc  14340
cctgcacaca tagaaaaaaa aaatatgaac ttaaccttca agcaagtttt acgtttagaa  14400
tattacctca tttttatttct tctaactgag gttataaaga aaatggcaaa tgtcatgtgc  14460
tttgtaaaga aatgacagtt tctcagaata cgtaaatgca caccettaga caaataggcc  14520
acttaaattc agaatcacag tcttttgaat attggtttaa tattctcaga taaagattga  14580
aaggataaca agtttggaa tcaggtgttt actttgagtt ctgaaaggtg acatcacagg  14640
tgttggtagt ttattgatat ttaatttta aatgtgctgc tgtatatatt tcatttgatt  14700
agaaatatgt tacatagtta tgttatttgt taaataatag accatctttt gtataaccta  14760
tcagaagaag ttctgagatt gtaagattag attgtaaatc ctattgcata actagaatac  14820
agaattatta aattgaaag gaagttaaat cacttagacc gtccttcccc caggaagtcc  14880
tctctacagt gttatccatg acaaatgttt atgcaggcac cctaaccatt taaaatacga  14940
agagaaggag aagagatata tcgagaaaac tattcctgag acaagagacc agggggaaaac  15000
ttttcttagt tgtaacctac acaactagct agaatctacc tcatgctctt aagatggtgt  15060
```

-continued

```
ttaatcatga ggatatcata cataactgaa attgtataat gttgaacatc ttttggtggc  15120
aagtaccttg actttattaa atcagtgtag gtctcctgca ttcaactatg gtctctagga  15180
gggcagggac cacacttctt agctcacctt ggatctcaag accagtccaa ggccttcatt  15240
cagtcagagc tagttaagca tttgttaatt gaatgaagga aattaaaaaa aaaaaaacta  15300
gaaattccaa attgtgcaat tacatctgtg aattttaagg tgttattgga aaatgggaaa  15360
aattactgag attcgaagat ggataggaac aaagtaaag catgaaaatg tgcatatttg  15420
tgtgttgcta gagtcaatag tgattgccag ttcctatgca gccctggcac cacctctgaa  15480
accttggcca accctgcca ttaggtgttg agatacacga caggcaggtg aggaaggagg  15540
ggtgctctgg atgtagtctt gccgctagac tgtggtcttt agtgtccatg tccatggggt  15600
gagttgtgag cccatcagtt tcccacacta cagtccttct ctggcttagc cttccttccc  15660
tgtcctgtgg tccaggttac ccctggcccc tgtggccttc ctccagagat ggaccttcct  15720
ccacacactt tcaggagct cctgattcta ggcatgcccc agaacaccgc aactccactc  15780
tgccctgtct ccatcagacc agagacctca cttagaccct gggtatgggg ttgttggttc  15840
tccacttgct gcggttgtca ctagcctgag ctctatcctg agctctgtcc atccttctca  15900
tcttcctcat tgcccttct gctaaagcaa ctgcacatct gaaggctata cttatcccta  15960
gtacaatggt actttttcta aaatgcatac accctaatgc ttacccttt gacaattttt  16020 tcctgaacct accttttaat ataagcaaat tcagtcttca attcaaataa gtgtattttg  16080
ctgctgaagc caccatgtga ttttgagaga tagtgaagac agacagtctt ctgcattcac  16140
ttgtagaatc ctgaaaatac ctcttggtgt cccttgcctt tctgacttct tgcttgaaga  16200
catctagaca aaaatgtgtc cctgggtcct agtttctggg ttcagaaatt gatcgaatgc  16260
aagaaaacaa tacacattgc ctcttcctta gcatgcatga atggtaggtg tgaatttgca  16320
tcatgagaaa gtaaataaaa gaagattccc cagggcagct aggaggcag aaaaagccag  16380 cctaggatgg gagtggagga catgttagag gttatgagag tgagggtcca tcctaccca  16440 cctcggtaac tcactggtat ggtataaatg caaaattttg gctcacacaa agaaaaatac  16500
tcaacttcta atgcttaact atgtaaaatt tgcttttaaa gtacaagtta aaattgtatc  16560 gccctcaaa gaaacaagaa actcattaca tttctaagaa tgttccttca gaaacatgga  16620
actgaaagct attttaaaa attgatctgg ccctagaaa actggggcct ttctttaat   16680 ttacctaagg aattgacata aaagtctagg gttctgcacc agaaaatgc agaaagtgtc  16740 aaaataaag gcagaaatac aaaaggagac tttttgcagc aacgttctat gtatagcatt  16800
gattccaagg gtgcaacata gggaagtgaa catgtggact gtgaaattga tgctaatttt  16860
ctttcccact agtctagcag ccctctaaaa tgtcacatta ttaatttagt tactttacca  16920
gaaatccgtg tatgtggtta gcatgtgtgt ttttttttaa ttaacagact ttacttattt  16980
ttagaacagt tttagatttt caaaaaattg agcacatagt acgagaattc ccatctactc  17040
cctttgtgga acacaatttc ccctattttt accatcttgc attagtgtga tgtatttctt  17100
acgatcaagc cattgttgct tcattattat tattatttaa agcccataat ttacattaag  17160
tttctctctt tgggttgtac agttctatgg attttgacaa atacacaatg tcatgtatcc  17220
accattatag tatcatacag aatagcttca ctgccctaag aatcccctgt gctctgcctg  17280
ttgacccttc ccaccctcc caaccctg gaaaccactg atctttttac tgtctccaca  17340
gttttgcctt ttcagaatg ttctatcttt ggaatcatac agtatgtacc cttttcagat  17400
tgacttcttt cattaagcaa tatgaattta agttttctcc atgtctttc acatcttgat  17460
```

```
ggctcatttc tatttattac cacataatat tccattgtct ggatatacca cagctttacc   17520
aactgagggg catcttagtt gctaattatg aataaagtgg ctatacatat tcacgtgtag   17580
gttttgtgtg gacataagtc ttcaattcaa ttgagtaaat atacctagaa gtgtgactgc   17640
tggatcatat ggtaagagta tatttacttt tttaagaaac tgctaaacta tatcccaaag   17700
tagttttacc attttgcatt cttttcttta tttttttttt attatacttt aagttttagg   17760
gtatgtgtgc acaatgtgca ggttagttac atatgtatac atgtgccatg ttggtgtgct   17820
gcacccatta actcatcatt tagcattagg aggtaaatct cctaatgcta tccctccccc   17880 ctcccccac cccacaacag tccccagagt gtgatgttcc ccttcctgtg tccatgtgtt    17940
ctcattgttc aactcctatc tatgagtgag aacatgcggt gtttggtttt ttgtccttgc   18000
ggtagtttac tgagaatgat gatttccaat ttcatccatg tccctacaaa ggacatgaac   18060
tcatcatttt ttatggctgc atagtattcc atggtgtata tgtgccatat tttcttaatc   18120
cagtctatca ttgttggaca tttgggttgg ttccaagtct ttgctattgt gaatagtgcc   18180
acaataaaca tacgtgtgca tgtgtctttta tagcagcatg atttatagtc ctttgggtat   18240
atacccagta atgggatggc tgggtcaaat ggtatttcta gttctagatc cctgaggaat   18300
cgccacactg acttccacaa tggttgaact agtttacagt cccaccaaca gtgtaaaagt   18360
gttcctattt ctccacattc tctccagcac ctgttgtttc ctgactttt aatgattgcc    18420 attctaactg gtgtgagatg gtatctcatt gtggttttga tttgcatttg tctgatggcc   18480
agtgatggtg agcattttt catgtgtctt tggctgcat aaatgtcttc ttttgagaag     18540
tgtctgttca tatcccttgc ccacttttg atgggggttgt ttgtttttt cttgtaaatt    18600 tgtttgagtt cattgtagat tctggatatt agcccttttgt cagatgagta ggttgcaaaa   18660 atttttccc attttgtagg ttgcctgttc actctgatgg tattttcttt tgctgtgcag     18720
aagctcttta gtttaattag atcccatttg tcaattttgg ctttggttgc cattgctttt   18780
ggtgttttag acatgaagtc cttgcccatg cctatgtcct gaatggtaat gtctaggtttt  18840 tcttctaggg tttttatggt tttaggtcta atgtttaagt cttaatcca tcttgaattg    18900 attttgtat aaggtgtaag gaagggatcc agtttcagct ttctgcatat ggctagccag    18960
ttttcccagc accatttatt aaacagggaa tcctttcccc attgcttgtt tttctcaggt   19020
ttgtcaaaga tcagatagtt gtagatatgc ggccttattt ctgagggctc tgtcactata   19080
catctactag aatgggtaaa atccaaaaat ctgacaatac caaatgctgc tgaggatgtg   19140
gagcaacagg aagcctcatt gctccacatc ctcagcagca tttggtattg tcagattttt   19200
ggattttagc cattctacta gatgtgtagt ggtatcttac tgttttaatt gcaattctc    19260 taatgaggta tgatgctgac cacctttca tatgcttatt tgctgtccgt gtaccttctt   19320
tggtgaggta tatgttcaga tcttttgctc cttattaaat tgggctgttt gttctttat    19380 ctttgagtta taagagttca ttgtgtattt tggataccag ccctttatca gatatatctt   19440
ttgcaaatat tttttcccca atctttggcg tgtcttttta ttcatataat ggttgataca   19500
tgtttctgct ttaaggagga agggttttaa aaatacaatt tacagtagca gtaaaaataa   19560
aaatttattg caaatgtctt atgttcactc tcaggtgatg tcagggaact atggacccag   19620
cagggtttaa ttaaagggga gtgtcaagtc ctggggctg tggttgacaa tcctcctttta  19680 ttggcaattg tgcagcaggg ctgggagtaa gaagacaacc cagtcctgag ctgcatcact  19740
tctaaattaa gaataattca ggaactgtgt ttacggtgaa atcctggccc ttctcacata   19800
gattatatta tgcataggat atgaatttct gtccatgaat ccaagtatat atgaaatcat   19860
```

```
cactttgaaa atttcctta actcaactta atcccactgg tgagcctcaa tcctgccagt    19920
tgaaaaagag actgtaactg ggtcatgcag gagtctcctt cctttcctgc agcccagtca    19980
gaattcaaga agttcacctg gtaactggaa aatgatggaa gggcctcaag tccctagtct    20040
gtcctggttg ccattggcac ccttactatc tgagcccata gtggtctgtg aagtccggca    20100
gctccctgcc cccatgccac agtggggaat gagaatatct actgatgctg ggccccatga    20160
gcaaagcatg ctgcctttct aggcatgagc catcacacct gaggttgcta ccccctcggg    20220
agcactgatg gaggggcagt tgggtttcta ctgctcacag gacccagaca accatcccct    20280
gccctccctt cttcttgcac ttcaaaagca ctctcttcct ctcttttcac ctctaagcca    20340
ccggtatcat ctcttccatg ggctttcaca aaagtctgga tgaaccttg aacttgtatc     20400 tcttctgctt tcccccttgc atcaagaaag cttagaaaac aaacactaat taacgtttca    20460
ataaataatg ctgctctaat tatttgtgga aactattctg tattagaact accatcagca    20520
ccgcctccta gagtgctttt agacttgacc actggccgca ggaggccact tccatataac    20580
aacaaacaga tggctgaaat tggaaaactc agctaaatgt tcagatgttt ctagactccc    20640
acgggtttct ggctctggca catggagtag atcctgactg tgtggtcctc aggggactct    20700
ctctggtgaa gtttggtgag gtcaacttcc acacccacac acaccagcta ctgtgtgtag    20760
cctgtcctcc tctggttgct tctacttgca gccttggcct cttcagtcct gagagcgttg    20820
gagaatgagg cagtggagga agcagcccca cacagaaagc agtttctgaa gtaacctcag    20880
caacttcctc ctcaccaaac acaaggaact gatcttctcc actgggctcg gcctctggtc    20940
agccaaggac aacactgttg accaccatca cggttggccc cactccaccc ttggctctga    21000
tgacatatgt gggagtcaga ggaattttga ttggctgact gctggcctgt cacacaaaca    21060
agatggggca aggggttgc gatatgactt gacatgtgaa aaaaaaaaa gccgtggtca      21120 gcaaccccct gcaactgttg aaaggctaat tcaatctctg actctttaac aaaagtgatc    21180
ttgttcactg cctgttctgc cctgagagcc ttctctgcta ggaggtaggt tgactgactc    21240
agggagaagg gtgctggtgg cagagctgcc aatgggtgag ggtcctagag actatcgaca    21300
tgaggggcag ttgagaacac tgtagtattt agctgagagg agagactatt aataaaattt    21360
acaaaatcag ctttcagcta tttgaagggg tttatataaa aggataaaat aatatgttct    21420
ggtagttcta gaaaacagga cagagacaag tagctggtac ttatggattg gaggagtgag    21480
tggcagtagt ttggggatta tttataaaaa agacattttt ctgttaactc tctttctaa     21540 tagtgaattt cccaacctga caagtaagaa agcacaggct agacacgcat ctgtcatgac    21600
actgaagggg tccttgcttg agtgagagac tggaatgatg agttttgagg tcccttacag    21660
tccagcaact ctagctaagt tggagaataa gagaattcca tgacaccata tcacccctc     21720 atttctgctg cctgcctcac cattcatctc tctttactcc ttttaatatc attctacgtt    21780
acagcattgg aggaggctgc tctaaatagg aactgaaata agtagattaa agaagtgcta    21840
tggaagggaa acaataaaa caacttgttt tttaagagcc tactattgcc aggatctgtg      21900
ctaagcacca tatatatgcc atgttattta accgtcatga catgcctatg agatatttag    21960
tattacttct gtgaggaagc caaagctcag agaggttaaa taactgcccc aagaacacac    22020
aggcattaag tagtggagca gggttttgaac acaggtctct atgactccaa agtgcagtgt   22080
gatatgttat ttttactgat ctgtttatgg aaaatgatac tgctttctaa tttagtatta    22140
acacaaagat ttttttctaa atagatttac ttaaagtatg ttataaaaat actatataaa    22200
taatgaaaca gattttacat gagtatgaag tggtactagt agctagaatg atgaaagttt    22260
```

```
ggggaatact actccaaata ttttgatagc tagcctttca atttagcctg tcttatattt   22320
ggactgctga gtacaaggaa aagaaggaaa catgaaaatt aagtgaaata tgagttactt   22380
cccctgtgct ctgataggtg ggtaattgat catatgtcac aataagaaaa tcaaatgaac   22440
cctttcaaac aacagcaaaa tctgtgattg taaaatccag aggaaaaccc caggtgggat   22500
ctatctgtat gaaggatgaa atttccaagg tctgaacata gaatggctga gaggaagtga   22560
tgaccctgtg agtcaagacc ctggaccctg ggggagccct gtgggtttga gaagccctgg   22620
gtgaaaggtg aagggtttta caggcctgtt tacagacctc tgtagtgaca aaggagagat   22680
ctttgtgcaa aggtcaaagt aagaattggg aaagtctgaa aagaaaacag gaaagtaata   22740
atgaagatga ataactact tggcatactc tgccacatga tttacaggca aggtttcctt   22800 tgttttcac aacaatgcag caaagaagtg attatgagtc acatttcata agtgagaaga   22860
ctgacattca aacatgttca ataactggcc cagggtccag tggtcaagcc aggactggac   22920
ttcggaccac cagttccaaa cccacacccc ttcccttgca ccacacgctt ttgtgtggat   22980
gagcctcccc aaccctgtca acaacaaact gtcactttgt cacttttaat gtctcctgct   23040
tcacaggaca cagctagcct ccaagagatc agggaggcat gcccagaggg tgctgcttct   23100
ctcttttgaa gctcaagtgc cacagacctc agaggcacat aaatgtcccc cacactgagc   23160
agaggacttt gcagtgcctg atcagggcag aaaaaggagg catgcacctg ggggaggatc   23220
acatacgagt gaaacctgtc cccgctgaag cactaggttt ggagaaatct actgggcatt   23280
tacacacctt tcccacttct gcttatgact tgtagccaaa ctcaagagta ccacccactt   23340
ccaggaatag tgtaccaagg taacagaaac attctagatt catacaattg gggttagatt   23400
aggatcatct gaaaatgaag gttgtgtatg tcaattgcct tctaacagga tgggtggaga   23460
gatgtactta atgaatgatt ttggggaagg gctagaagtg aagcacatgg cctctctgcc   23520
ctcactcatt gaaggctgtc ttctgaagcc ccgtggagct cagtgcctgt cacatggttg   23580
cccacatttg ttgaactgaa ctgcattttc atctatgggc ttcaaaggct gtgtgtactc   23640
tgggatctct gggaatctgt cagggaaggt gtctttgtca tgtttgtgga tggggctccc   23700 tttggggtt tcccagggct ttacactcat gctccgaggg tacgtttgta gtcattctca   23760
tcagtggaaa tgcccacctg ccggcagaag ttatttggaa ccaagcaaga gcactgtccc   23820
tggctgtggt gttgtttctc tagtcagttc cccttctgt atttgagttc taccgtcagt   23880
cctggcatta tttctctctc tacaaggagc cttaggaggt acggggagct cgcaaatact   23940 cctttggtt tattcttacc accttgcttc tgtgttcctt gggaatgctg ctgtgcttat   24000
gcatctggtc tctttttgga gctacagtgg acaggcattt gtgacaggta tgtttgtgga   24060
ggctcagacg cctagggagt ggcatgagat aaagctgcaa gctgcatctg ggcagaaat   24120 gctgatgtgc taatggccgg ccagagaatg agtaaaggg attgcagaga gcatgcttaa   24180
aacctctgac catcaggttt gcttctcaga ttgactacat tggaggtggg atattacaaa   24240
aatctgtctc ttcctgccag atcccttcat ctgttttcg tgagctaaga gacaaaatag   24300
gcaggaaata gaaggtgcca cttaccaaat aattggcagc tgttcttggc tttgggtgc   24360 tggggtctcc gagcagcctc tgctctagaa gaagcagtcc aaagatgtca gctcgcctcg   24420
cctgagtccc ctgtgccagt gggaaatcca gagaaggggg attcctcct cttgcagcct   24480 ctctgcaatg gacttacttg gctttcctgt ttgacctttc ccttctctgg tccagagacc   24540
cttccccaat atttcttccc atccaagtgc cccatcccaa tattagcccc acttggcacc   24600
agagaccaag atctaattta aaaagaaata ttcttgggtc aaaaaagagc ccaagcaagt   24660
```

```
gattgaacat aatgtgtttc acatacggtg aacctatttg catttgcatt tgcaaacggg    24720
cttaaaatat catctctatt aatagcaatt taaggttctg gagagccagg tgaaaatagt    24780
ttttgacaaa gggaacttcc tactcccctt aaactgtaat aatgaaggaa atgaactgtt    24840
tatcttacat gtaacctcaa tcttgggact aaggccctgt actaaaatgc gtctatttat    24900
gtgctcagac ttgcagttcg tgttatgtct gctgctgcag ataccgttaa tattatttat    24960
gtgagctatc ctgtgtataa tggaagcttt tataaatctc tatttattta ttcctaatat    25020
agttattaag tgcttgctat gttccaggta ctagggactt aacaggtagc ataaaagaca    25080
taaggaaaag ctgcactctt gttttctagc ctagtgggga aatcacatta atttaatcac    25140
actaaacatg actacatagc aatagtgctt taaagggaag gaaattgttc tatgtgacta    25200
tatcagctga ttaattacca agcctttgca tttgatattt tggttagtct attcttcttg    25260
aatttcatat gcctcttcct gggtgggggt gaggatggga ttttatggag ttgaggctag    25320
ggcaggtagg gagaaaacat gagaaagatg aagagataag ccaagccaga ttcttcagca    25380
gaaaaatcaa ggttgaaata ccatgtttca aaatcagac tgaggtggga gttgaggtta    25440
ggggtcccta ggccagggga ttgaagcttt aaagagataa aactagagca aaagcaagca    25500
cagagagtgg cagagaggtc cctgggcatt tttccacagt ccattctagt gctggcaatc    25560 caccttttcat ggccaggcag gtaagagtat ttgtggggtg ggagaaagga cagggccata    25620
ggctgggcac acagcccttt actggccctt atctctcctc tcttctcccta tacagtgctg    25680 tttccgaact gtacattggc ttacactcgg gctgaggttt gggaaatagg cgccatttg    25740 aatatgtgtg gaggaagaaa agtgtgtctt cagcactttc cacctcccca tcacggccct    25800
gagacctcaa caccgggaag catctcgttc cctatcggtc ctcctttatt catggacgga    25860
tatgattcct ttctaagttc catgtccttt ttagataaat taacttgaac ctaatgccta    25920
atggcttaaa aacaaacaaa aaaaaccctc ttccttccag ctagcatttg cattttaaca    25980
ggggctttca aaaatgcct tagcccaagg aatgagtaat gtgggaattc caagcagcag    26040
ggtaggactg gtgcacagta tggggagaga aggcccctca agttgtggcc ctgaaatgtt    26100
ggcttcctct ctttgaccat gatgctgttt ctgagaaaac aagaatcagg ctaccttagg    26160
ggaccaggat gggcatggct ccctttagt gagttctatg agcctcatac ctgacagtca    26220
gagccctcga gtggatgagc acagactaga agaagcactg tgaaactttg catgatcctt    26280
acctttttgg caaaaggaa aaaaaatcgt tctcaaattc atcaatagtt tgaaataggg    26340
tgtgccttga ttcagaaagt ttcgattcta gatacaactc ggagaactag gcgtgtcttg    26400
tacacagatt tgctcttggg ggaccggaaa agctaaatgc tatcgccatg ctatgctcct    26460
tcttctaggc cagtgagggg aacgcattct tcattttaat atttcagttg cctacaatat    26520
tggaaggtgg ataaaagcac cctctgctcc ttctaaatct gcgaagacat ttcttctctg    26580
cacctactca tccttgatgc agctctcctc atgtctgtat ggaaacactg tgctctcaaa    26640
tgagtttcag aaagaacaac tcacgaaaga aaacaagcat tcggtcagaa aaatctccac    26700
aaatggggaa taaggggat ttgctccaag gagagactgg aaaccaagtc agacataaaa    26760
tccagcctaa gctagaagga gacatggctg gtgggagctt gaggaaaaca gagctcagga    26820
tggaggacgt ctccacctcc agtcatgtcc tctgtccacc agacaccaag aagtgttcat    26880
gttccatcga ggcagccctc acacccatcc cttcctcatc atgccgactg cctctttact    26940
gcttcaggct caccatctca agtcgacgag cctgtaatac tggcttct gatcaccctg    27000 ataccagccg tcacctcttg acaggcttat tttctttaag ctgtcattac accatttttc    27060
```

```
tgctcccaaa ctattaattc caaacttcca attttctgtt aaattaaata tgaattcctt    27120
atttgacttt ccatgccctc ttaggctatc ttgctccttg ctttacttat agaaactaat    27180
ctcccattat ttatccaaag acaacctctg ctgcaggcca gtcagctttt cttactgtcc    27240
tgtaaaaatt ccatggtcac tcctccattt ccatgtgtcc ttaaaaactg ttatttgatt    27300
gtgtctcaga aagtcgtcaa agaatatata ccaatgaaaa gcatcaaaaa ggttatactt    27360
gatgttatgt gtgtatcaaa aatatggctg aaatatttat ccagtgaaac tcaatcaaca    27420
ctaaaaagtg gttctttcgg aagcatcagt tctttgagac ccattaaaca gatgcctcgg    27480
atgcagggtt atatattatc aggaatctgt ctagggaaga attattggaa gcttgcaaag    27540
cctttcaagg acagaggacg atagctacca cgttgagttc taggaaatta accattgtta    27600
ttgttaaagg aagacagcgt ttctcagagg aagactgtta aacagtgcag tggcccaggc    27660
taacagccct cataagtggg agtatcagaa tgagtggact taattactta aaaccaatac    27720
agggtggaac ttcatctgct ataacagaaa tcaactcgtg caagttctaa catgcagggt    27780
acagttctga gaccaagtct gactcacctg tcaaagctca gctcaactat taccacctt    27840
acaccaccct tccaagctgt aggagtgctt gctgttctcc atgtcttctg aagccctgga    27900
tcacttgtag ccagctcagc agactctacc cagacaggga tccttaaat gtaccatatt    27960
gtctactgtg ttaaaatga gaggaactga ctcagggtga gagcgatgga gtgtccagat    28020
gttctccttt atttctcctt attcctggaa atgtaatgag aatcttagag gtgaactgaa    28080
aagttatgag ttcaaccact tactcaattc gagattcgct cctaaaatgt ctcttctgtg    28140
ttatcacccc cactttggtt tgaatagtac ttgtgacagg gagcttatca cctcacaaga    28200
aaatccagtc attgcttgta gctctctatt aaaagttttc catcatctgg aactgaaatc    28260
tggctccctg taacttttag ttattggaac tacttgccct tcagcaacag tgtatgtatc    28320
ctcccatgga agggccctta catatttgca gacacccagc atatacttgc aatcttttct    28380
tcttcaggtt cattacccta gtccttttag ttgttcttca tttgacataa tttcattatt    28440
cactagtgaa ccttgctgcc cttccccttg ataaaccgaa tttgtcagtg tcattcaagt    28500
ataactgacc tcacagaacg tgataccaca agcgatgtgg tctgattagc acagagttca    28560
gtgaatgaat cctacactag gattggatga aatttactta gccataccac actaacactt    28620
atgtgatttt tatgtttact atggatagac tatttctcct gtgtccactt cttcctctta    28680
cacagttgtt atttcaaaac tgaagtacag attcttacac ttaccctcag gagattcatc    28740
atgttagtat tagtctctct tttcaggctt tatgaatgtt aattcagcta actcattttt    28800
gagctatctg tctcattttg tgccatctgc acagcataag tttgatttct gttgctttta    28860
ttagtagttt tactaaatac ataaaagtga aatagtgaaa cacagagtct tgtagcatcc    28920
actgtgggat cagtcttta gacaagaatg atgcagttgc tgagtcaaat gaataaatga    28980
ataaatcaaa caatactttg tcctcatttc ccatattgat ctatcaccat atcctgttaa    29040
ttataattct aaatatttct tgatctatcc acttttccct tacttcacct gctactatcc    29100
cagaccaaac agccatcttc tttcactcaa acaattgcag tagccaactg attggtcttc    29160
ctgcatctgt cctggcttcc ctatcatcca tttgctacac agaaaccatg gtcatctttt    29220
caaaatgcaa atctgatgat atcagtctca gctctaattt ctttggtggt tcacatataa    29280
agactgaaat ctttaactga ccaataacac acgtgtgatc tggcccctgc tcacctcttc    29340
agccttgtct ttcacctgtc tcttcatttt ggcacaggg acctcctcgt accttctctc    29400
acgtgccctc ctgcctcagc gcctttgcat atgctgttcc ctttgccgag aactcttcct    29460
```

```
gtcaactccc aagcccttca cctacttagc acctacctat tcaatctgtt ctgtttgcct    29520
cttggtatgt tacaaactgt ctccaaactt agcagcttag aacaatgaat cctttaccct    29580
ctctcacaat gtttggggtc aggaatttga gcgggccttg gctgattttt ctgttcctca    29640
tgccatcaat tgatatcacc tgatgttatt aagctgatgg atgggctgat ctggagatgc    29700
actgtccagt ttggtagcca ctggttacct gaaatgcagc cagtcctaat tgagatgtgc    29760
tataactata aaacacccac atgattattg aagatttggt gccaccaaaa aatttaaaat    29820
attcgttaat aatttgtatt ctgattacat gttgagatta taatatttca catacatcag    29880
ataacataaa atgtcattaa aattaatgtc acctatttct ttttaatttc tttaatgtga    29940
ctactacaag ttttcaaatt atatctgtgg cttgtaattg tggcttgtat tgtattcttt    30000
ttttctgaga tggagtctta ctctgttgcc caggctggag tgcagtggcg agatctctgc    30060
tcatcgcaag ctctgcctcc caggttcaag tgattctcct gcctcagcct cctgagtagc    30120
tgaaattaca ggtgcccgcc actatgccca gctaattttt gtattttag tagagacggg    30180 gtttccccat aatggccagg ctggtctcaa actcctgacc tcaggtaatc tgcccacctc    30240
ggcctcccaa agtgctggga ttacaagcat gagccaccac acctggcctg ttttatattc    30300
ttactggaca gtgctgatct agagcaggag tcaagcagtt ttttctatga aaggccacat    30360
agaaaatgtt ttcagctttg caggccatgc agtctccatc atagctgttc aactcttcca    30420
ttgcactgca aaagcagcca tagataataa tttacaatag acatagcagt gttccagtac    30480
aactattaat aaaaataggt ggtagccaga tttggcctac aggctgtagt ttgctgaccc    30540
ctgatctaga agatccaaga ttttattcat atgtctggtg gcttggcagg ataggtgga    30600 aggctcagct gggaccattg acccaaacag ctatacagtc ctctccagca tgatggtctc    30660
ggggtagtgg gacatcttac gtggtggctc agaactccag ataaggtact cccagagaga    30720
caggtagaag ctgtgaggct tcttatgacc aagctctcga agtcccagaa tatcccttgt    30780
actgtattct atggtcaaac aggtcactca ggctagccca gattcaaaga gaggagatcc    30840
aactctacct cttcatggga ggaggagtag ccaaggatat gtgtttcttt ttaatctatt    30900
atatcattct tcagatctca gtttaggctg gtcctgttat gggctctcaa agtaccatga    30960
acctctcttt tgtagcactt gtcatagcta gttttacatt tctctgtatg attacttgat    31020
cactatcttg ctttctact aaactgtagg caaccacgtg aagaggaact gtttctggtt    31080
ttgctcatta tattcctagc accaaacaca atgcttggtt caataaatat ttgtggaaga    31140
aacgaatgaa tgaatgaacc aatagcaaat gaatgaatga gtaataactg tatcaatatt    31200
aatcctacat ttctccatat tgctgtcacg tatatcataa gatactctgt cagaagcctt    31260
gctaaaattc aaatatattt gattcccagt aaccttctta ttttgtagtt cagaaactt    31320 ataaagaagg aaataagcct atcttactct tcccagtatc tcaaagaggg tttctgccct    31380
gagctgctca agagggtttc tgccctgagc tgctgttcat tctgcaaaca ctgctcgaat    31440
acccactgtg tgccaggtac agagagttct tctctgctgt aatctggaca ggcaccagct    31500
tcccagcgtg ggtttaggct tcaggtcac actactgtgt accgtctaag ccacacctag    31560
aagagctctg ggaaatatg actacttggg cagaaaagga aggaactaag aagaggtatc    31620
tttgtgtctg aggtctgaag gagcgtgtgg gctcttgttc aggcaaaggg caggatgagg    31680
ggaggtgggg tggcagcagc cagtaatggg gtgggacagc ggaatgcaga ggatgaa       31737

<210> SEQ ID NO 675
<211> LENGTH: 1112
<212> TYPE: DNA
```

<213> ORGANISM: H. sapiens

<400> SEQUENCE: 675

| | | | | |
|---|---|---|---|---|
| cacagggtga aagctttgct tctctgctgc tgtaacaggg actagcacag acacacggat | | | | 60 |
| gagtggggtc atttccagat attaggtcac agcagaagca gccaaaatgg atccccagtg | | | | 120 |
| cactatggga ctgagtaaca ttctctttgt gatggccttc ctgctctctg gtgctgctcc | | | | 180 |
| tctgaagatt caagcttatt tcaatgagac tgcagacctg ccatgccaat ttgcaaactc | | | | 240 |
| tcaaaaccaa agcctgagtg agctagtagt attttggcag gaccaggaaa acttggttct | | | | 300 |
| gaatgaggta tacttaggca aagagaaatt tgacagtgtt cattccaagt atatgggccg | | | | 360 |
| cacaagtttt gattcggaca gttggaccct gagacttcac aatcttcaga tcaaggacaa | | | | 420 |
| gggcttgtat caatgtatca tccatcacaa aaagcccaca ggaatgattc gcatccacca | | | | 480 |
| gatgaattct gaactgtcag tgcttgctaa cttcagtcaa cctgaaatag taccaatttc | | | | 540 |
| taatataaca gaaaatgtgt acataaattt gacctgctca tctatacacg gttacccaga | | | | 600 |
| acctaagaag atgagtgttt tgctaagaac caagaattca actatcgagt atgatggtat | | | | 660 |
| tatgcagaaa tctcaagata atgtcacaga actgtacgac gtttccatca gcttgtctgt | | | | 720 |
| ttcattccct gatgttacga gcaatatgac catcttctgt attctggaaa ctgacaagac | | | | 780 |
| gcggctttta tcttcacctt tctctataga gcttgaggac cctcagcctc ccccagacca | | | | 840 |
| cattccttgg attacagctg tacttccaac agttattata tgtgtgatgg ttttctgtct | | | | 900 |
| aattctatgg aaatggaaga agaagaagcg gcctcgcaac tcttataaat gtggaaccaa | | | | 960 |
| cacaatggag agggaagaga gtgaacagac caagaaaaga gaaaaaatcc atatacctga | | | | 1020 |
| aagatctgat gaagcccagc gtgtttttaa aagttcgaag acatcttcat gcgacaaaag | | | | 1080 |
| tgatacatgt ttttaattaa agagtaaagc cc | | | | 1112 |

<210> SEQ ID NO 676
<211> LENGTH: 20
<212> TYPE: RNA
<213> ORGANISM: Artificial Sequence
<220> FEATURE:
<223> OTHER INFORMATION: Antisense Oligonucleotide

<400> SEQUENCE: 676
gcuuggccca uaagugugcu                    20

<210> SEQ ID NO 677
<211> LENGTH: 20
<212> TYPE: RNA
<213> ORGANISM: Artificial Sequence
<220> FEATURE:
<223> OTHER INFORMATION: Antisense Oligonucleotide

<400> SEQUENCE: 677
gucaugagcc auuaagcugg                    20

<210> SEQ ID NO 678
<211> LENGTH: 20
<212> TYPE: RNA
<213> ORGANISM: Artificial Sequence
<220> FEATURE:
<223> OTHER INFORMATION: Antisense Oligonucleotide

<400> SEQUENCE: 678
cugaucugga ggagguauug                    20

<210> SEQ ID NO 679

```
<211> LENGTH: 20
<212> TYPE: RNA
<213> ORGANISM: Artificial Sequence
<220> FEATURE:
<223> OTHER INFORMATION: Antisense Oligonucleotide

<400> SEQUENCE: 679
uccagaaauu gagaggucua                                                  20

<210> SEQ ID NO 680
<211> LENGTH: 20
<212> TYPE: RNA
<213> ORGANISM: Artificial Sequence
<220> FEATURE:
<223> OTHER INFORMATION: Antisense Oligonucleotide

<400> SEQUENCE: 680
gagguaguug uuuagucaca                                                  20

<210> SEQ ID NO 681
<211> LENGTH: 20
<212> TYPE: RNA
<213> ORGANISM: Artificial Sequence
<220> FEATURE:
<223> OTHER INFORMATION: Antisense Oligonucleotide

<400> SEQUENCE: 681
acuauaaggu cauaaauaca                                                  20

<210> SEQ ID NO 682
<211> LENGTH: 20
<212> TYPE: RNA
<213> ORGANISM: Artificial Sequence
<220> FEATURE:
<223> OTHER INFORMATION: Antisense Oligonucleotide

<400> SEQUENCE: 682
cuauguuuca agauauuaac                                                  20

<210> SEQ ID NO 683
<211> LENGTH: 20
<212> TYPE: RNA
<213> ORGANISM: Artificial Sequence
<220> FEATURE:
<223> OTHER INFORMATION: Antisense Oligonucleotide

<400> SEQUENCE: 683
cuauuacagu acauagaucu                                                  20

<210> SEQ ID NO 684
<211> LENGTH: 20
<212> TYPE: RNA
<213> ORGANISM: Artificial Sequence
<220> FEATURE:
<223> OTHER INFORMATION: Antisense Oligonucleotide

<400> SEQUENCE: 684
ucuagagcau aguaaucaca                                                  20

<210> SEQ ID NO 685
<211> LENGTH: 20
<212> TYPE: RNA
<213> ORGANISM: Artificial Sequence
<220> FEATURE:
<223> OTHER INFORMATION: Antisense Oligonucleotide

<400> SEQUENCE: 685
```

```
gacagaggga ugagaacucc                                              20

<210> SEQ ID NO 686
<211> LENGTH: 20
<212> TYPE: RNA
<213> ORGANISM: Artificial Sequence
<220> FEATURE:
<223> OTHER INFORMATION: Antisense Oligonucleotide

<400> SEQUENCE: 686
guugccugua cccuaggcca                                              20

<210> SEQ ID NO 687
<211> LENGTH: 20
<212> TYPE: RNA
<213> ORGANISM: Artificial Sequence
<220> FEATURE:
<223> OTHER INFORMATION: Antisense Oligonucleotide

<400> SEQUENCE: 687
uuuagguugg ucugcucauu                                              20

<210> SEQ ID NO 688
<211> LENGTH: 20
<212> TYPE: RNA
<213> ORGANISM: Artificial Sequence
<220> FEATURE:
<223> OTHER INFORMATION: Antisense Oligonucleotide

<400> SEQUENCE: 688
ggcuccaggu ucuaucucug                                              20

<210> SEQ ID NO 689
<211> LENGTH: 20
<212> TYPE: RNA
<213> ORGANISM: Artificial Sequence
<220> FEATURE:
<223> OTHER INFORMATION: Antisense Oligonucleotide

<400> SEQUENCE: 689
gcaacagccc agauagaagu                                              20

<210> SEQ ID NO 690
<211> LENGTH: 20
<212> TYPE: RNA
<213> ORGANISM: Artificial Sequence
<220> FEATURE:
<223> OTHER INFORMATION: Antisense Oligonucleotide

<400> SEQUENCE: 690
ggcaagccuc cucaauauua                                              20

<210> SEQ ID NO 691
<211> LENGTH: 20
<212> TYPE: RNA
<213> ORGANISM: Artificial Sequence
<220> FEATURE:
<223> OTHER INFORMATION: Antisense Oligonucleotide

<400> SEQUENCE: 691
cacuauggcu uguugggugg                                              20

<210> SEQ ID NO 692
<211> LENGTH: 20
<212> TYPE: RNA
<213> ORGANISM: Artificial Sequence
<220> FEATURE:
```

<223> OTHER INFORMATION: Antisense Oligonucleotide

<400> SEQUENCE: 692
ccuguuuauu caguucucuc					20

<210> SEQ ID NO 693
<211> LENGTH: 20
<212> TYPE: RNA
<213> ORGANISM: Artificial Sequence
<220> FEATURE:
<223> OTHER INFORMATION: Antisense Oligonucleotide

<400> SEQUENCE: 693
ccaggccauc ucacuaguca					20

<210> SEQ ID NO 694
<211> LENGTH: 20
<212> TYPE: RNA
<213> ORGANISM: Artificial Sequence
<220> FEATURE:
<223> OTHER INFORMATION: Antisense Oligonucleotide

<400> SEQUENCE: 694
uuugaguauu gugaucucuu					20

<210> SEQ ID NO 695
<211> LENGTH: 20
<212> TYPE: RNA
<213> ORGANISM: Artificial Sequence
<220> FEATURE:
<223> OTHER INFORMATION: Antisense Oligonucleotide

<400> SEQUENCE: 695
ucuguggauc aagaucucuc					20

<210> SEQ ID NO 696
<211> LENGTH: 20
<212> TYPE: RNA
<213> ORGANISM: Artificial Sequence
<220> FEATURE:
<223> OTHER INFORMATION: Antisense Oligonucleotide

<400> SEQUENCE: 696
gaccagacau uucauguauu					20

<210> SEQ ID NO 697
<211> LENGTH: 20
<212> TYPE: RNA
<213> ORGANISM: Artificial Sequence
<220> FEATURE:
<223> OTHER INFORMATION: Antisense Oligonucleotide

<400> SEQUENCE: 697
caucuguugc uuguuucaag					20

<210> SEQ ID NO 698
<211> LENGTH: 20
<212> TYPE: RNA
<213> ORGANISM: Artificial Sequence
<220> FEATURE:
<223> OTHER INFORMATION: Antisense Oligonucleotide

<400> SEQUENCE: 698
guccauuugg acagacuauc					20

<210> SEQ ID NO 699

```
<211> LENGTH: 20
<212> TYPE: RNA
<213> ORGANISM: Artificial Sequence
<220> FEATURE:
<223> OTHER INFORMATION: Antisense Oligonucleotide

<400> SEQUENCE: 699
gaaacugcug ucugucuuau                                               20

<210> SEQ ID NO 700
<211> LENGTH: 20
<212> TYPE: RNA
<213> ORGANISM: Artificial Sequence
<220> FEATURE:
<223> OTHER INFORMATION: Antisense Oligonucleotide

<400> SEQUENCE: 700
auaacuuggg uaucaccaaa                                               20

<210> SEQ ID NO 701
<211> LENGTH: 20
<212> TYPE: RNA
<213> ORGANISM: Artificial Sequence
<220> FEATURE:
<223> OTHER INFORMATION: Antisense Oligonucleotide

<400> SEQUENCE: 701
uccaggaaga ugacauccca                                               20

<210> SEQ ID NO 702
<211> LENGTH: 20
<212> TYPE: RNA
<213> ORGANISM: Artificial Sequence
<220> FEATURE:
<223> OTHER INFORMATION: Antisense Oligonucleotide

<400> SEQUENCE: 702
cccauuauca aggugauggc                                               20

<210> SEQ ID NO 703
<211> LENGTH: 20
<212> TYPE: RNA
<213> ORGANISM: Artificial Sequence
<220> FEATURE:
<223> OTHER INFORMATION: Antisense Oligonucleotide

<400> SEQUENCE: 703
cuaagccucc uuccauucau                                               20

<210> SEQ ID NO 704
<211> LENGTH: 20
<212> TYPE: RNA
<213> ORGANISM: Artificial Sequence
<220> FEATURE:
<223> OTHER INFORMATION: Antisense Oligonucleotide

<400> SEQUENCE: 704
ucagccagga guggaaaguc                                               20

<210> SEQ ID NO 705
<211> LENGTH: 20
<212> TYPE: RNA
<213> ORGANISM: Artificial Sequence
<220> FEATURE:
<223> OTHER INFORMATION: Antisense Oligonucleotide

<400> SEQUENCE: 705
```
gugucuuggu cuuccuaauu                                                       20

<210> SEQ ID NO 706
<211> LENGTH: 20
<212> TYPE: RNA
<213> ORGANISM: Artificial Sequence
<220> FEATURE:
<223> OTHER INFORMATION: Antisense Oligonucleotide

<400> SEQUENCE: 706
ccguaggaca ucuguaggcu                                                       20

<210> SEQ ID NO 707
<211> LENGTH: 20
<212> TYPE: RNA
<213> ORGANISM: Artificial Sequence
<220> FEATURE:
<223> OTHER INFORMATION: Antisense Oligonucleotide

<400> SEQUENCE: 707
acucaaauuu gcuagcccua                                                       20

<210> SEQ ID NO 708
<211> LENGTH: 20
<212> TYPE: RNA
<213> ORGANISM: Artificial Sequence
<220> FEATURE:
<223> OTHER INFORMATION: Antisense Oligonucleotide

<400> SEQUENCE: 708
caaguuuccu cugguugccu                                                       20

<210> SEQ ID NO 709
<211> LENGTH: 20
<212> TYPE: RNA
<213> ORGANISM: Artificial Sequence
<220> FEATURE:
<223> OTHER INFORMATION: Antisense Oligonucleotide

<400> SEQUENCE: 709
auaacccuug aggguuuaca                                                       20

<210> SEQ ID NO 710
<211> LENGTH: 20
<212> TYPE: RNA
<213> ORGANISM: Artificial Sequence
<220> FEATURE:
<223> OTHER INFORMATION: Antisense Oligonucleotide

<400> SEQUENCE: 710 cuugcuagc auggcagucu                                                        20

<210> SEQ ID NO 711
<211> LENGTH: 20
<212> TYPE: RNA
<213> ORGANISM: Artificial Sequence
<220> FEATURE:
<223> OTHER INFORMATION: Antisense Oligonucleotide

<400> SEQUENCE: 711
ugcuaggagu cuaaucaagg                                                       20

<210> SEQ ID NO 712
<211> LENGTH: 20
<212> TYPE: RNA
<213> ORGANISM: Artificial Sequence
<220> FEATURE:

-continued

<223> OTHER INFORMATION: Antisense Oligonucleotide

<400> SEQUENCE: 712
gcagcagaga agcaaagcuu                                           20

<210> SEQ ID NO 713
<211> LENGTH: 20
<212> TYPE: RNA
<213> ORGANISM: Artificial Sequence
<220> FEATURE:
<223> OTHER INFORMATION: Antisense Oligonucleotide

<400> SEQUENCE: 713
cugugcuagu cccuguuaca                                           20

<210> SEQ ID NO 714
<211> LENGTH: 20
<212> TYPE: RNA
<213> ORGANISM: Artificial Sequence
<220> FEATURE:
<223> OTHER INFORMATION: Antisense Oligonucleotide

<400> SEQUENCE: 714
ccauuuuggc ugcuucugcu                                           20

<210> SEQ ID NO 715
<211> LENGTH: 20
<212> TYPE: RNA
<213> ORGANISM: Artificial Sequence
<220> FEATURE:
<223> OTHER INFORMATION: Antisense Oligonucleotide

<400> SEQUENCE: 715
ucccauagug cacugggau                                            20

<210> SEQ ID NO 716
<211> LENGTH: 20
<212> TYPE: RNA
<213> ORGANISM: Artificial Sequence
<220> FEATURE:
<223> OTHER INFORMATION: Antisense Oligonucleotide

<400> SEQUENCE: 716
auuugcgagc uccccguacc                                           20

<210> SEQ ID NO 717
<211> LENGTH: 20
<212> TYPE: RNA
<213> ORGANISM: Artificial Sequence
<220> FEATURE:
<223> OTHER INFORMATION: Antisense Oligonucleotide

<400> SEQUENCE: 717
aaggaguauu ugcgagcucc                                           20

<210> SEQ ID NO 718
<211> LENGTH: 20
<212> TYPE: RNA
<213> ORGANISM: Artificial Sequence
<220> FEATURE:
<223> OTHER INFORMATION: Antisense Oligonucleotide

<400> SEQUENCE: 718
cacagaagca aggugguaag                                           20

<210> SEQ ID NO 719

```
<211> LENGTH: 20
<212> TYPE: RNA
<213> ORGANISM: Artificial Sequence
<220> FEATURE:
<223> OTHER INFORMATION: Antisense Oligonucleotide

<400> SEQUENCE: 719
gaacacagaa gcaagguggu                                              20

<210> SEQ ID NO 720
<211> LENGTH: 20
<212> TYPE: RNA
<213> ORGANISM: Artificial Sequence
<220> FEATURE:
<223> OTHER INFORMATION: Antisense Oligonucleotide

<400> SEQUENCE: 720
augcauaagc acagcagcau                                              20

<210> SEQ ID NO 721
<211> LENGTH: 20
<212> TYPE: RNA
<213> ORGANISM: Artificial Sequence
<220> FEATURE:
<223> OTHER INFORMATION: Antisense Oligonucleotide

<400> SEQUENCE: 721
ugccugucca cuguagcucc                                              20

<210> SEQ ID NO 722
<211> LENGTH: 20
<212> TYPE: RNA
<213> ORGANISM: Artificial Sequence
<220> FEATURE:
<223> OTHER INFORMATION: Antisense Oligonucleotide

<400> SEQUENCE: 722
ucccauagug cugucacaaa                                              20

<210> SEQ ID NO 723
<211> LENGTH: 21
<212> TYPE: DNA
<213> ORGANISM: Artificial Sequence
<220> FEATURE:
<221> NAME/KEY: Antisense Oligonucleotide
<220> FEATURE:
<221> NAME/KEY: misc_feature
<222> LOCATION: (1)...(19)
<223> OTHER INFORMATION: bases at these positions are RNA

<400> SEQUENCE: 723
cgagaggcgg acgggaccgt t                                            21

<210> SEQ ID NO 724
<211> LENGTH: 21
<212> TYPE: DNA
<213> ORGANISM: Artificial Sequence
<220> FEATURE:
<221> NAME/KEY: Antisense Oligonucleotide
<220> FEATURE:
<221> NAME/KEY: misc_feature
<222> LOCATION: (2)...(21)
<223> OTHER INFORMATION: bases at these positions are RNA

<400> SEQUENCE: 724
ttgctctccg cctgccctgg c                                            21
```